(12) United States Patent
Masuda et al.

(10) Patent No.: US 8,383,622 B2
(45) Date of Patent: Feb. 26, 2013

(54) NITROGEN-CONTAINING HETEROCYCLIC DERIVATIVE HAVING 11β-HYDROXYSTEROID DEHYDROGENASE TYPE I INHIBITORY ACTIVITY

(75) Inventors: Koji Masuda, Osaka (JP); Tomoyuki Ogawa, Osaka (JP); Takuji Nakatani, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 282 days.

(21) Appl. No.: 12/599,133

(22) PCT Filed: May 7, 2008

(86) PCT No.: PCT/JP2008/058461
§ 371 (c)(1),
(2), (4) Date: Nov. 6, 2009

(87) PCT Pub. No.: WO2008/142986
PCT Pub. Date: Nov. 27, 2008

(65) Prior Publication Data
US 2010/0240659 A1   Sep. 23, 2010

(30) Foreign Application Priority Data

May 18, 2007   (JP) .................................. 2007-132259
Dec. 19, 2007   (JP) .................................. 2007-327114

(51) Int. Cl.
| | | |
|---|---|---|
| A61K 31/5377 | (2006.01) | |
| A61K 31/415 | (2006.01) | |
| A61K 31/4245 | (2006.01) | |
| A61K 31/421 | (2006.01) | |
| C07D 231/10 | (2006.01) | |
| C07D 271/10 | (2006.01) | |
| C07D 263/04 | (2006.01) | |
| C07D 413/12 | (2006.01) | |
| A61P 3/10 | (2006.01) | |

(52) U.S. Cl. .................. 514/236.5; 548/369.7; 548/143; 548/229; 548/374.1; 544/140; 514/407; 514/364; 514/376; 514/406

(58) Field of Classification Search .................. None
See application file for complete search history.

(56) References Cited

U.S. PATENT DOCUMENTS

| | | | |
|---|---|---|---|
| 4,226,877 A | 10/1980 | Arendsen | |
| 7,728,029 B2 * | 6/2010 | Anderson et al. | ............. 514/406 |
| 2005/0059663 A1 | 3/2005 | Martin et al. | |
| 2005/0245532 A1 | 11/2005 | Hoff et al. | |
| 2005/0245533 A1 | 11/2005 | Hoff et al. | |
| 2005/0261302 A1 | 11/2005 | Hoff et al. | |
| 2005/0277647 A1 | 12/2005 | Link et al. | |
| 2006/0148871 A1 | 7/2006 | Rohde et al. | |
| 2009/0170832 A1 * | 7/2009 | Kurose et al. | ............. 514/217.09 |

FOREIGN PATENT DOCUMENTS

| | | |
|---|---|---|
| EP | 0394043 | 10/1990 |
| EP | 0566138 | 10/1993 |
| EP | 1400516 | 3/2004 |
| EP | 1889842 | 2/2008 |
| EP | 1894919 | 3/2008 |
| EP | 1953145 | 8/2008 |
| EP | 2006286 | 12/2008 |

(Continued)

OTHER PUBLICATIONS

Morissette et al. In Advanced Drug Delivery Reviews 56 (2004) 275-300.*

(Continued)

*Primary Examiner* — Dennis Heyer
(74) *Attorney, Agent, or Firm* — Hamre, Schumann, Mueller & Larson, P.C.

(57) ABSTRACT

Disclosed is a compound which is useful as an 11β-hydroxysteroid dehydrogenase type 1 inhibitor.
A compound represented by the formula:

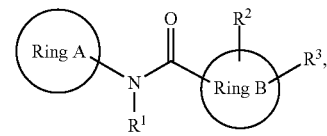

its pharmaceutically acceptable salt, or a solvate thereof, wherein Ring A is a group represented by the formula:

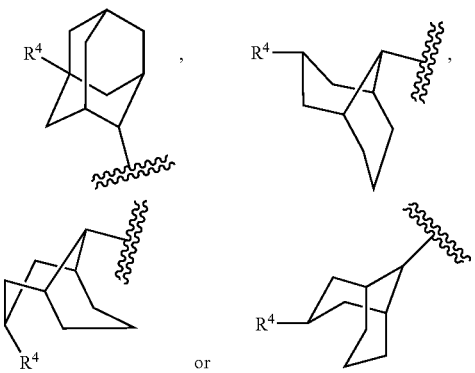

Ring B is optionally substituted heteroaryl, provided that optionally substituted isoxazole is excluded, or optionally substituted heterocycle,
$R^1$ is hydrogen or optionally substituted alkyl,
$R^2$ is —$OR^5$, —$SR^5$, halogen, halogenated alkyl or the like,
$R^3$ is optionally substituted alkyl or the like,
$R^4$ is optionally substituted alkyl or the like,
$R^5$ is optionally substituted alkyl or the like,
$R^6$ is hydrogen or the like,
$R^7$ and $R^8$ are each independently hydrogen or the like,
$R^{10}$ and $R^{11}$ are each independently hydrogen or the like,
$R^{12}$ is optionally substituted alkyl or the like,
m and p are each independently integer of 1 to 3.

46 Claims, No Drawings

FOREIGN PATENT DOCUMENTS

| | | |
|---|---|---|
| EP | 2088136 | 8/2009 |
| JP | 60-214785 | 10/1985 |
| JP | 01-207289 | 8/1989 |
| JP | 2004-065194 | 3/2004 |
| WO | 93/25535 | 12/1993 |
| WO | 97/07789 | 3/1997 |
| WO | 98/41519 | 9/1998 |
| WO | 01/23358 | 4/2001 |
| WO | 02/02797 | 1/2002 |
| WO | 02/076435 | 10/2002 |
| WO | 03/104208 | 12/2003 |
| WO | 2004/056744 | 7/2004 |
| WO | 2004/056745 | 7/2004 |
| WO | 2004/076418 | 9/2004 |
| WO | 2004/089470 | 10/2004 |
| WO | 2005/016877 | 2/2005 |
| WO | 2005/061462 | 7/2005 |
| WO | 2005/070889 | 8/2005 |
| WO | 2005/095350 | 10/2005 |
| WO | 2005/097764 | 10/2005 |
| WO | 2005/108359 | 11/2005 |
| WO | 2005/108361 | 11/2005 |
| WO | 2005/108368 | 11/2005 |
| WO | 2005/112923 | 12/2005 |
| WO | 2006/024627 | 3/2006 |
| WO | 2006/024628 | 3/2006 |
| WO | WO 2006/024627 * | 3/2006 |
| WO | 2006/048750 | 5/2006 |
| WO | 2006/074244 | 7/2006 |
| WO | 2006/074330 | 7/2006 |
| WO | 2006/100502 | 9/2006 |
| WO | 2006/106052 | 10/2006 |
| WO | WO2007/058346 * | 5/2007 |
| WO | 2007/107470 | 9/2007 |
| WO | WO2007/107470 * | 9/2007 |
| WO | 2007/114125 | 10/2007 |
| WO | 2007-262022 | 10/2007 |
| WO | 2007/144394 | 12/2007 |
| WO | 2008/012532 | 1/2008 |
| WO | 2008/044656 | 4/2008 |
| WO | 2008/051875 | 5/2008 |
| WO | 2008/053194 | 5/2008 |
| WO | 2008/099145 | 8/2008 |
| WO | 2008/120655 | 10/2008 |
| WO | 2008/142986 | 11/2008 |
| WO | 2009/001817 | 12/2008 |
| WO | 2009/010416 | 1/2009 |
| WO | 2009/013211 | 1/2009 |
| WO | 2009/056881 | 5/2009 |
| WO | 2009/060232 | 5/2009 |
| WO | 2009/098501 | 8/2009 |
| WO | 2009/130496 | 10/2009 |

OTHER PUBLICATIONS

Vippagunta et al., Crystalline solids, Advanced Drug Delivery Reviews, 48 (2001) 3-26.*
Patani et al. In Chemical Reviews 1996, 3147-3176.*
Barf et al. In the Journal of Medicinal Chemistry 45(18) 3813-3815 (2002).*
Stewart, "11β-Hydroxysteroid dehydrogenase: implications for clinical medicine," Clinical Molecular Endocrinology, vol. 44, 1996, pp. 493-499.
Kotelevtsev et al., "11β-Hydroxysteroid dehydrogenase type 1 knockout mice show attenuated glucocorticoid-inducible responses and resist hyperglycemia on obesity or stress", Proc. Natl. Acad. Sci. USA, vol. 94, Dec. 1997, pp. 14924-14929.
Walker et al., "Carbenoxolone Increases Hepatic Insulin Sensitivity in Man: A Novel Role for 11-Oxosteroid Reductase in Enhancing Glucocorticoid Receptor Activation", Journal of Clinical Endocrinology and Metabolism, vol. 80, No. 11, 1995, pp. 3155-3159.
Bujalska et al., "Does central obesity reflect 'Cushing's disease of the omentum'?", The Lancet, vol. 349, Apr. 26, 1997, pp. 1210-1213.

* cited by examiner

NITROGEN-CONTAINING HETEROCYCLIC DERIVATIVE HAVING 11β-HYDROXYSTEROID DEHYDROGENASE TYPE I INHIBITORY ACTIVITY

FIELD OF THE INVENTION

The present invention relates to a pharmaceutically useful compound having inhibitory activity to 11β-hydroxysteroid dehydrogenase type 1 (hereinafter, referred to as 11β-HSD-1).

BACKGROUND ART

11β-HSD-1 is an enzyme that converts 11β-dehydrosteroid, which is inactive steroid, into an active steroid, and is considered to have great significance in biological basal metabolism (Non-patent document 1). Also, an 11β-HSD-1 knockout mouse has resistance to hyperglycemia induced by obesity and stress (Non-patent document 2). Also in human, a similar phenomenon was observed when carbenoxolone which is an 11β-HSD-1 inhibitor was administered (Non-patent document 3).

These facts suggest the possibility of a selective inhibitor of this enzyme as a therapeutic agent in insulin independent diabetes and obesity (Non-patent document 4).

Patent Document 1 discloses a compound that has the inhibitory activity to 11β-HSD-1, but it is limited to isoxazole derivative and the present compound has not been disclosed.

Patent Document 2, 3 and 4 disclose an adamantane derivative having inhibitory activity to 11β-HSD-1, but the heteroaryl derivative which is substituted with alkyloxy such as the present compound has not been disclosed.

Patent Document 5 discloses an pyrazole derivative having inhibitory activity to 11β-HSD-1, but the present compound has not been disclosed.

Patent Document 6 discloses a pyrazole derivative having inhibitory activity to 11β-HSD-1, but a substituent on 3-position of pyrazole is limited to carbamoyl, and the present compound has not been disclosed.

Patent Document 7 discloses a pyrazole derivative useful as a herbicide, but a substituent on 1-position of pyrazole is limited to hydrogen, alkyl or aralkyl, and the present compound has not been disclosed.

Patent Document 8 discloses a pyrazole derivative having CB2 receptor agonist activity, but a substituent on 2-position of pyrazole is limited to 2-(4-morpholino)ethoxy, 2-(diallylamino)ethoxy, 2-, 3- or 4-pyridylmethoxy, 2-(diethylamino)ethoxy, 1-methylpiperidinyl-2-methoxy, benzyloxy and 4-substituted benzyloxy and the present compound has not been disclosed.

Patent Document 9 discloses a pyrazole derivative having NK-3 receptor modulator activity, but a substituent of carbamoyl group on 4-position of pyrazole is limited to arylalkyl, heteroarylalkyl or phenoxyalkyl and the present compound has not been disclosed.

Patent Document 10 discloses a pyrazole derivative having inhibitory activity to 11β-HSD-1, but a substituent on 1-position of pyrazole is limited to alkyl, hydroxy, hydroxyalkyl or the like, and "optionally substituted alkenyl" such as the present compound has not been disclosed.

[Patent document 1]WO2006/132197
[Patent document 2]WO2006/074330
[Patent document 3]WO2006/024627
[Patent document 4]WO2005/016877
[Patent document 5]WO2007/058346
[Patent document 6]WO2005/016877
[Patent document 7]WO2001/023358
[Patent document 8]WO98/41519
[Patent document 9]WO2005/061462
[Patent document 10]WO2007/107470
[Non-patent document 1] Clin. Endocrinol, 1996, vol. 44, p. 493
[Non-patent document 2] Proc. Nat. Acad. Sci. USA, 1997, vol. 94, p. 14924
[Non-patent document 3] J. Clin. Endocrinol. Metab., 1995, vol. 80, p. 3155
[Non-patent document 4] Lancet, 1997, vol. 349, p. 1210

DISCLOSURE OF INVENTION

Problems To Be Solved By the Invention

The present invention provides a useful 11β-hydroxysteroid dehydrogenase type 1 inhibitor.

The present invention provides:
(1)
A compound represented by the Formula (I):

[Formula 1]

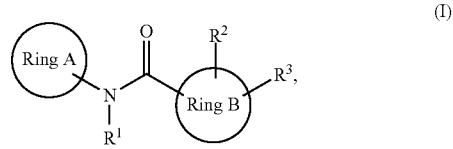

its pharmaceutically acceptable salt, or a solvate thereof, wherein Ring A is a group represented by the formula:

[Formula 2]

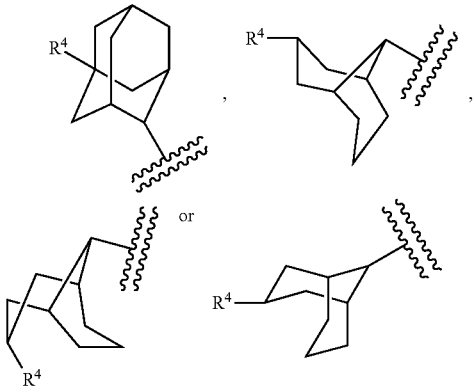

Ring B is optionally substituted heteroaryl, provided that optionally substituted isoxazolyl is excluded, or optionally substituted heterocycle, $R^1$ is hydrogen or optionally substituted alkyl, $R^2$ is —$OR^5$, —$SR^5$, halogen, halogenated alkyl, halogenated alkoxy, hydroxy, cyano, nitro, carboxy, optionally substituted alkyl, optionally substituted alkenyl, optionally substituted alkynyl, optionally substituted aryl, optionally substituted cycloalkyl, optionally substituted cycloalkenyl, optionally substituted heteroaryl, optionally substituted heterocycle, a group represented by the formula: —$NR^{5A}R^{6A}$, wherein $R^{5A}$ and $R^{6A}$ are each independently hydrogen, hydroxy, alkoxy, optionally substituted alkyl, optionally substituted alkenyl, optionally substituted carbamoyl, optionally substituted aryl, optionally substituted cycloalkyl, optionally substituted cycloalkenyl, optionally substituted heteroaryl or optionally substituted heterocycle, or $R^{5A}$ and $R^{6A}$ taken together with the adjacent nitrogen atom to which they are attached may form an optionally substituted ring, a group represented by the formula: $-S(=O)x-R^{7A}$, wherein x is an integer of 1 or 2, $R^{7A}$ is optionally substituted alkyl, optionally substituted alkenyl, optionally substituted aryl, optionally substituted cycloalkyl, optionally substituted cycloalkenyl, optionally substituted heteroaryl or optionally substituted heterocycle, a group represented by the formula: $-C(=O)NR^{5A}R^{6A}$, wherein $R^{5A}$ and $R^{6A}$ are as defined in the above, or a group represented by the formula: $-(CR^{8A}R^{9A})y-O-(CR^{10A}R^{11A})z-CR^{12A}R^{13A}R^{14A}$, wherein y and z are each independently integer of 0 to 5, $R^{8A}$, $R^{9A}$, $R^{10A}$, $R^{11A}$, $R^{12A}$, $R^{13A}$ and $R^{14A}$ are each independently hydrogen, hydroxy, halogen, halogenated alkyl, halogenated alkoxy, alkoxy, cyano, carboxy, optionally substituted alkyl, optionally substituted alkenyl, optionally substituted aryl, optionally substituted cycloalkyl, optionally substituted cycloalkenyl, optionally substituted heteroaryl or optionally substituted heterocycle, $R^3$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: $-CH=CH-C(R^aR^b)-R^c-R^d$ or a group represented by the formula: $-(CR^eR^f)_m-C(R^aR^b)-R^c-R^d$, wherein $R^a$ and $R^b$ are each independently hydrogen, optionally substituted alkyl or halogen, or $R^a$ and $R^b$ taken together with the adjacent carbon atom to which they are attached may form an optionally substituted ring, $R^c$ is $-(CH_2)_n-$, wherein n is an integer of 0 to 3, $R^d$ is hydrogen, halogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: $-C(=O)-NR^gR^h$ or a group represented by the formula: $-NR^iR^j$, $R^e$ and $R^f$ are each independently hydrogen, halogen or optionally substituted alkyl, $R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxy, optionally substituted carbamoyl or $R^g$ and $R^h$ taken together with the adjacent nitrogen atom to which they are attached may form an optionally substituted ring, $R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, optionally substituted sulfamoyl or $R^i$ and $R^j$ taken together with the adjacent nitrogen atom to which they are attached may form an optionally substituted ring, $R^4$ is optionally substituted alkyl, optionally substituted alkenyl, $-OR^6$, $-CONR^7R^8$, $-NR^9CONR^7R^8$, $-NR^9SO_2NR^7R^8$, $-(CR^{10}R^{11})pOH$, $-(CR^{10}R^{11})pOCONR^7R^8$, $-NR^9COR^{12}$, $-NR^9C(=O)OR^{12}$, $-(CR^{10}R^{11})pNR^9COR^{12}$, $-C(=O)NR^9OR^{12}$, $-CONR^9CONR^7R^8$, $-CN$, $-COOH$, halogen or $-NR^7R^8$, $R^5$ is optionally substituted alkyl, optionally substituted alkenyl, optionally substituted cycloalkyl, optionally substituted aryl, optionally substituted heteroaryl or optionally substituted heterocycle, $R^6$ is hydrogen, optionally substituted alkyl, optionally substituted alkenyl, optionally substituted cycloalkyl, optionally substituted aryl, optionally substituted heteroaryl, optionally substituted heterocycle, $-SO_2R^5$, $-SO_2NR^7R^8$ or $-CONR^7R^8$, $R^7$ and $R^8$ are each independently hydrogen, optionally substituted alkyl, optionally substituted cycloalkyl, optionally substituted aryl, optionally substituted heteroaryl, optionally substituted heterocycle or $-SO_2R^5$, or $R^7$ and $R^8$ taken together with the adjacent nitrogen atom to which they are attached may form an optionally substituted ring, $R^9$ is hydrogen or optionally substituted alkyl, $R^{10}$ and $R^{11}$ are each independently hydrogen, halogen or optionally substituted alkyl, $R^{12}$ is optionally substituted alkyl, optionally substituted cycloalkyl, optionally substituted aryl, optionally substituted heteroaryl or optionally substituted heterocycle, m and p are each independently integer of 1 to 3, provided that, when Ring B is pyrazolyl and $R^2$ is halogen, halogenated alkyl, optionally substituted alkyl, optionally substituted heteroaryl, a group represented by the formula: $-NR^{5A}R^{6A}$, wherein $R^{5A}$ and $R^{6A}$ are as defined in the above or a group represented by the formula: $-(CR^{8A}R^{9A})y-O-(CR^{10A}R^{11A})z-CR^{12A}R^{13A}R^{14A}$, wherein $R^{8A}$ to $R^{14A}$, y and z are as defined in the above, $R^3$ is optionally substituted alkenyl or a group represented by the formula: $-CH=CH-C(R^aR^b)-R^c-R^d$, provided that, when Ring B is piperidyl or pyrrolidinyl and $R^2$ is optionally substituted alkyl, $R^3$ is optionally substituted alkenyl or a group represented by the formula: $-CH=CH-C(R^aR^b)-R^c-R^d$, and provided that, the compounds shown as follows are excluded,

[Formula 3]

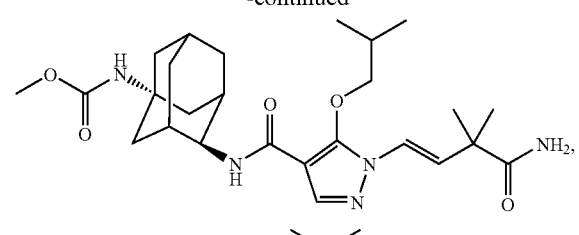
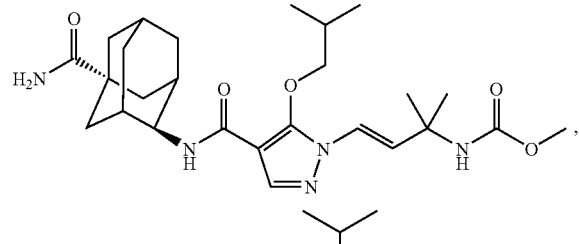
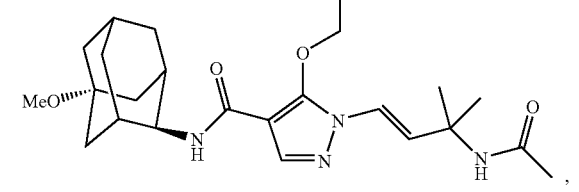
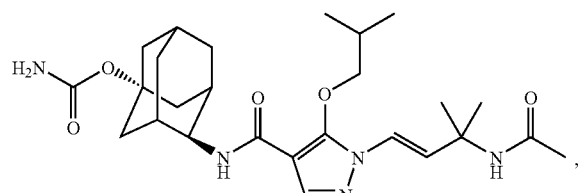
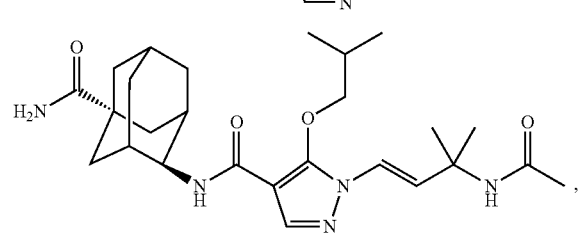
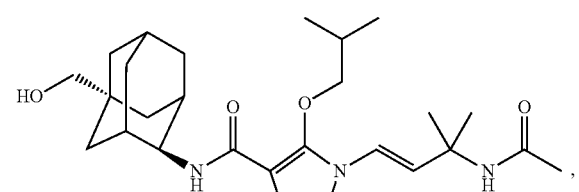
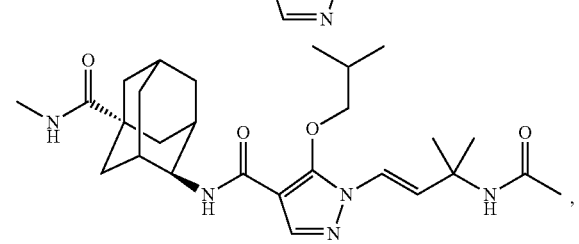
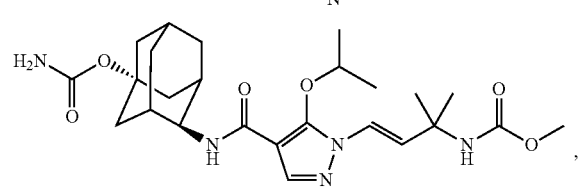
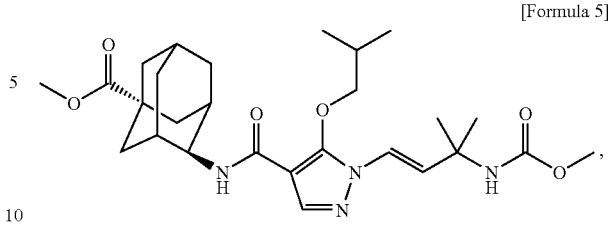
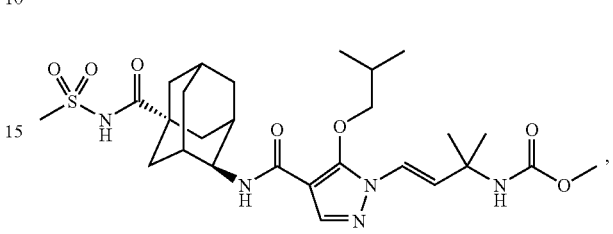
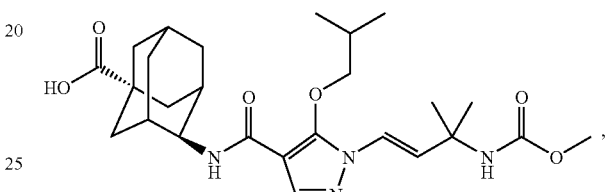
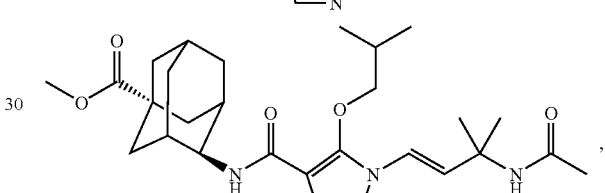
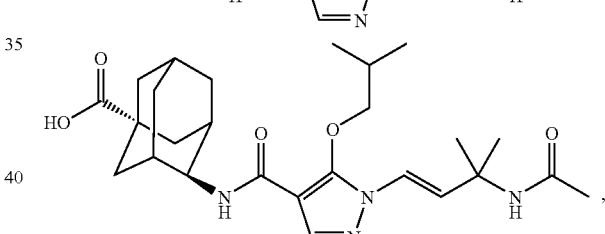
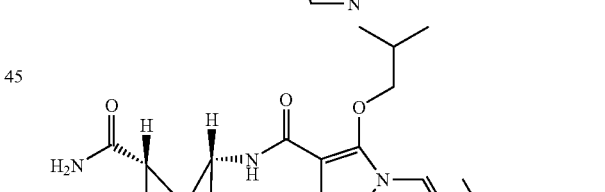
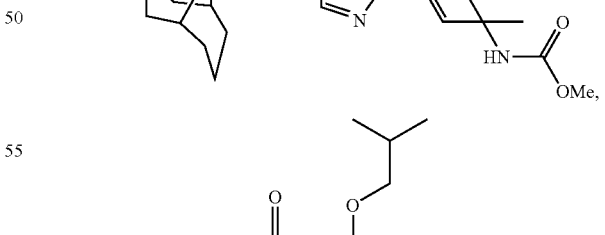
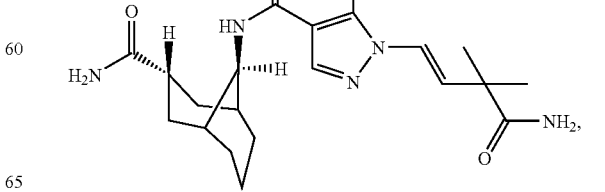
[Formula 5]

-continued

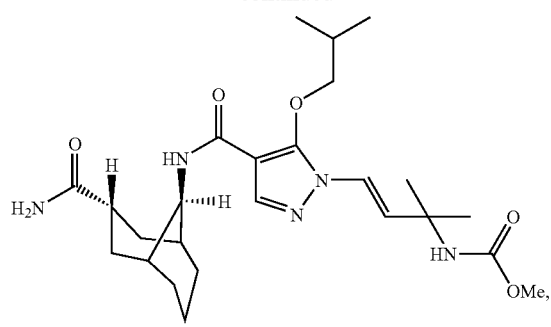

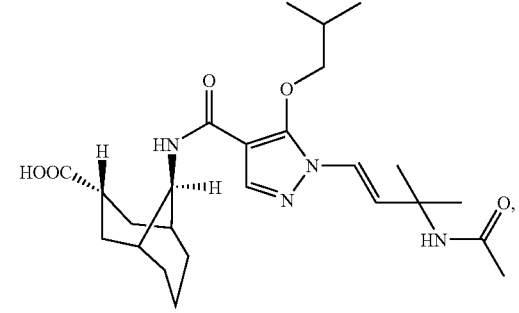

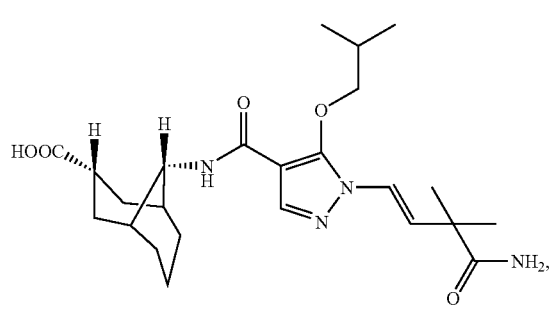

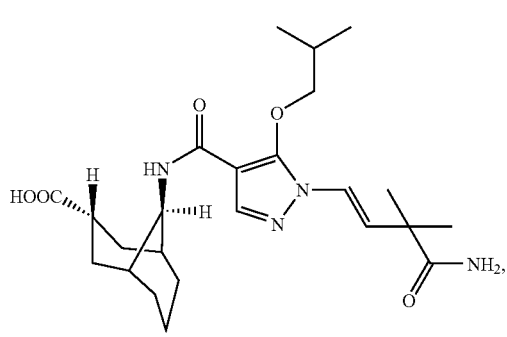

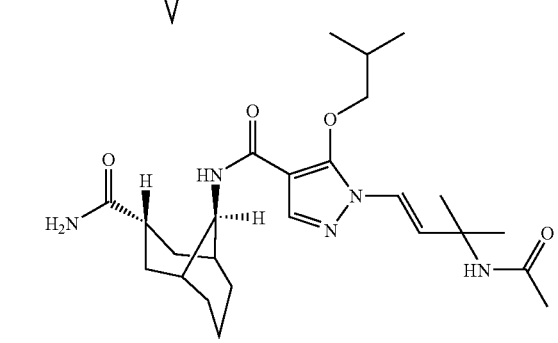

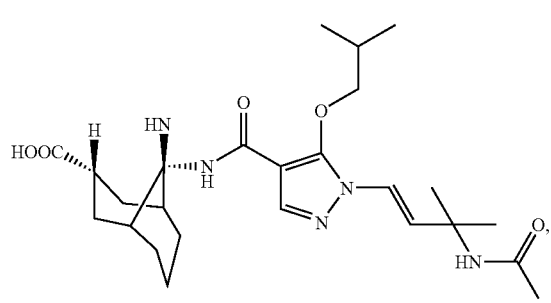

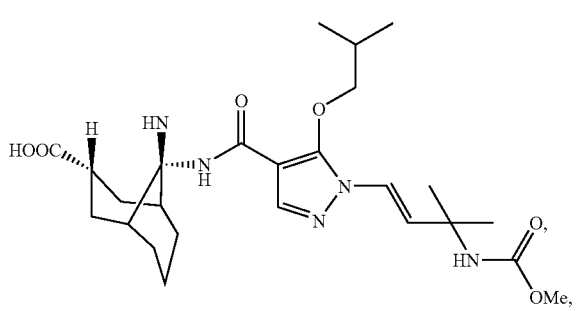

(2) The compound according to the above (1), its pharmaceutically acceptable salt, or a solvate thereof, wherein $R^2$ is —$OR^5$ or —$SR^5$, wherein $R^5$ is as defined in the above (1).

(3) The compound according to the above (2), its pharmaceutically acceptable salt, or a solvate thereof, wherein the compound represented by the formula (I) is a compound represented by the formula (II):

[Formula 7]

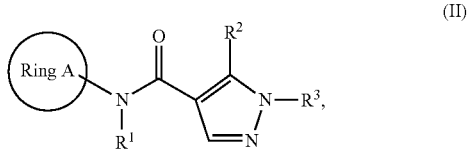

(II)

wherein Ring A, $R^1$, $R^2$ and $R^3$ are as defined in the above (1).

(4) The compound according to any one of the above (1) to (3), its pharmaceutically acceptable salt, or a solvate thereof, wherein $R^6$ is optionally substituted alkyl, optionally substituted alkenyl, optionally substituted cycloalkyl, optionally substituted aryl, optionally substituted heteroaryl, optionally substituted heterocycle or —$CONR^7R^8$, wherein $R^7$ and $R^8$ are as defined in the above (1).

(5)
The compound according to any one of the above (1) to (4), its pharmaceutically acceptable salt, or a solvate thereof, wherein Ring A is a group represented by the formula (III):

[Formula 8]

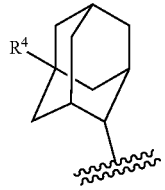

(III)

wherein $R^4$ is as defined in the above (1), $R^6$ is optionally substituted alkyl, optionally substituted alkenyl, optionally substituted cycloalkyl, optionally substituted aryl, optionally substituted heteroaryl, optionally substituted heterocycle or —CONR$^7$R$^8$, wherein $R^7$ and $R^8$ are as defined in the above (1).

(6)
The compound according to the above (1), (2), (4) or (5), its pharmaceutically acceptable salt, or a solvate thereof, wherein Ring B is optionally substituted heteroaryl, provided that optionally substituted isoxazole is excluded.

(7)
The compound according to any one of the above (1) to (6), its pharmaceutically acceptable salt, or a solvate thereof, wherein $R^1$ is hydrogen.

(8)
The compound according to any one of the above (1) to (7), its pharmaceutically acceptable salt, or a solvate thereof, wherein $R^2$ is —OR$^5$, wherein $R^5$ is as defined in the above (1).

(9)
The compound according to any one of the above (1) to (7), its pharmaceutically acceptable salt, or a solvate thereof, wherein $R^2$ is —SR$^5$, wherein $R^5$ is as defined in the above (1).

(10)
The compound according to any one of the above (1) to (9), its pharmaceutically acceptable salt, or a solvate thereof, wherein $R^5$ is optionally substituted alkyl.

(11)
The compound according to any one of the above (1) to (10), its pharmaceutically acceptable salt, or a solvate thereof, wherein $R^3$ is optionally substituted alkyl or optionally substituted alkenyl.

(12)
The compound according to the above (11), its pharmaceutically acceptable salt, or a solvate thereof, wherein $R^3$ is a group represented by the formula: —CH=CH—C(R$^a$R$^b$)—R$^c$—R$^d$ or a group represented by the formula: —(CR$^e$R$^f$)$_m$—C(R$^a$R$^b$)—R$^c$—R$^d$, wherein $R^a$ to $R^f$ and m are as defined in the above (1).

(13)
The compound according to the above (12), its pharmaceutically acceptable salt, or a solvate thereof, wherein $R^a$ and $R^b$ are each independently optionally substituted alkyl.

(14)
The compound according to the above (12) or (13), its pharmaceutically acceptable salt, or a solvate thereof, wherein $R^c$ is —(CH$_2$)n-, wherein n is an integer of 0 or 1.

(15)
The compound according to any one of the above (12) to (14), its pharmaceutically acceptable salt, or a solvate thereof, wherein $R^d$ is halogen, hydroxy, cyano, optionally substituted heteroaryl or optionally substituted heterocycle.

(16)
The compound according to any one of the above (12) to (14), its pharmaceutically acceptable salt, or a solvate thereof, wherein $R^d$ is a group represented by the formula: —C(=O)—NR$^g$R$^h$, wherein $R^g$ and $R^h$ are each independently hydrogen, optionally substituted alkyl, optionally substituted alkyloxy or optionally substituted carbamoyl.

(17)
The compound according to any one of the above (12) to (14), its pharmaceutically acceptable salt, or a solvate thereof, wherein $R^d$ is a group represented by the formula: —NR$^i$R$^j$, wherein $R^i$ and $R^j$ are each independently hydrogen, optionally substituted alkylsulfonyl, optionally substituted alkyloxycarbonyl, optionally substituted alkylcarbonyl or optionally substituted heterocyclecarbonyl.

(18)
The compound according to any one of the above (1) to (17), its pharmaceutically acceptable salt, or a solvate thereof, wherein $R^d$ is —OR$^6$, —CONR$^7$R$^8$, —NR$^9$CONR$^7$R$^8$, —(CR$^{10}$R$^{11}$)$_p$OH, —(CR$^{10}$R$^{11}$)$_p$OCONR$^7$R$^8$, —NR$^9$COR$^{12}$, —NR$^9$C(=O)OR$^{12}$, —(CR$^{10}$R$^{11}$)$_p$NR$^9$COR$^{12}$, —C(=O)NR$^9$OR$^{12}$, —CONR$^9$CONR$^7$R$^8$ or —CN, wherein $R^6$ to $R^{12}$ and p are as defined in the above (1).

(19)
The compound according to the above (18), its pharmaceutically acceptable salt, or a solvate thereof, wherein $R^7$ and $R^8$ are each independently hydrogen or optionally substituted alkyl.

(20)
The compound according to the above (18) or (19), its pharmaceutically acceptable salt, or a solvate thereof, wherein $R^9$ is hydrogen.

(21)
The compound according to any one of the above (18) to (20), its pharmaceutically acceptable salt, or a solvate thereof, wherein $R^{10}$ and $R^{11}$ are each independently hydrogen.

(22)
The compound according to any one of the above (18) to (21), its pharmaceutically acceptable salt, or a solvate thereof, wherein $R^{12}$ is optionally substituted alkyl.

(23)
A compound defined below, its pharmaceutically acceptable salt, or a solvate thereof,

[Formula 9]

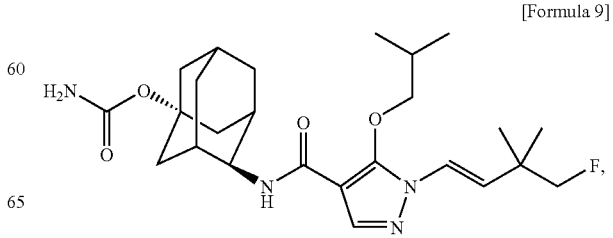

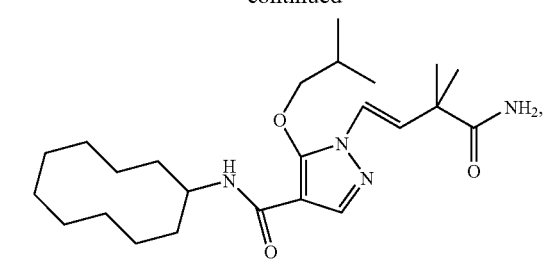
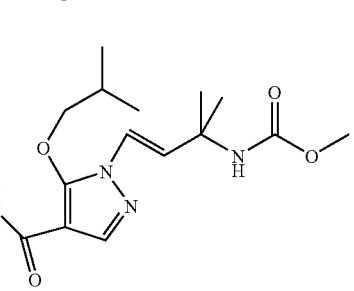
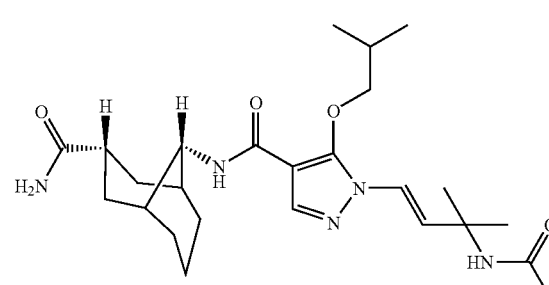
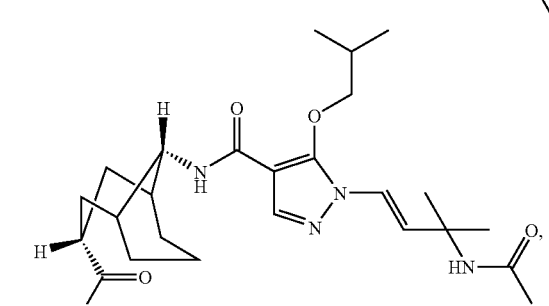
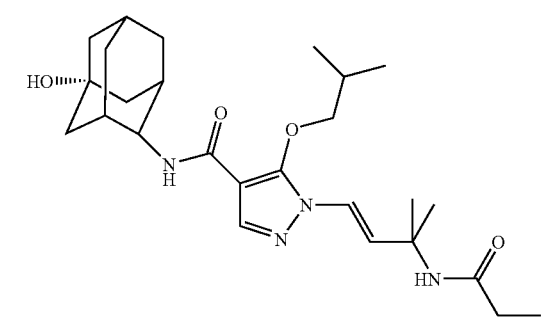
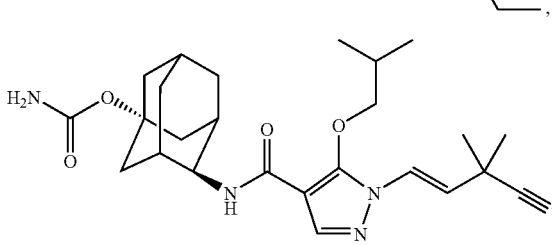
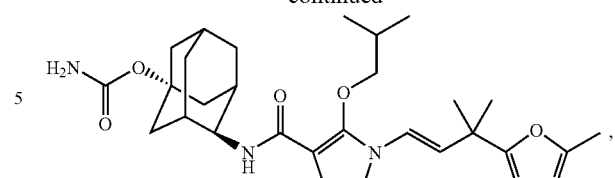
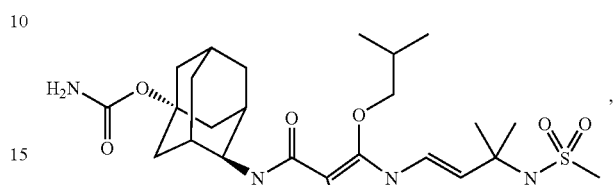
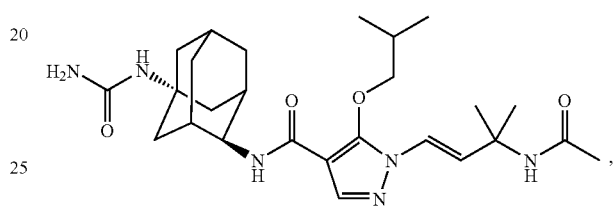
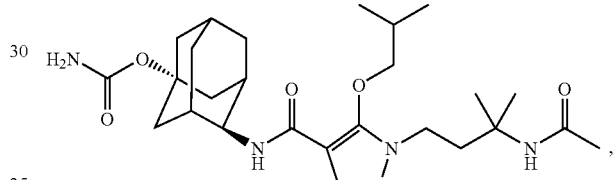
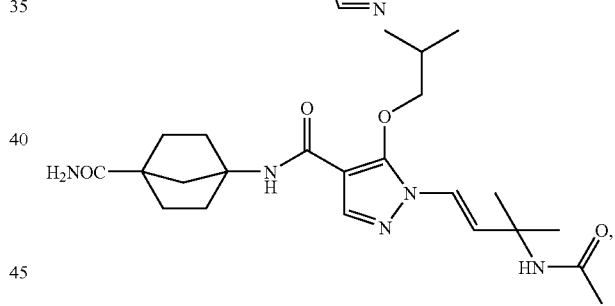
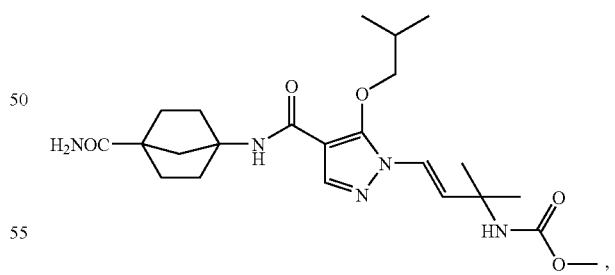
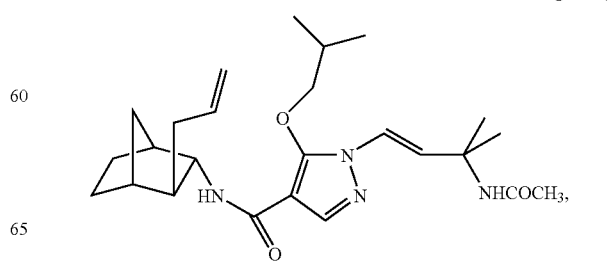

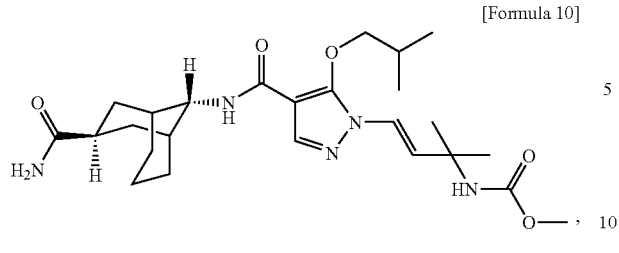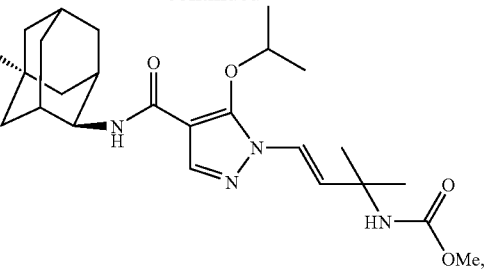

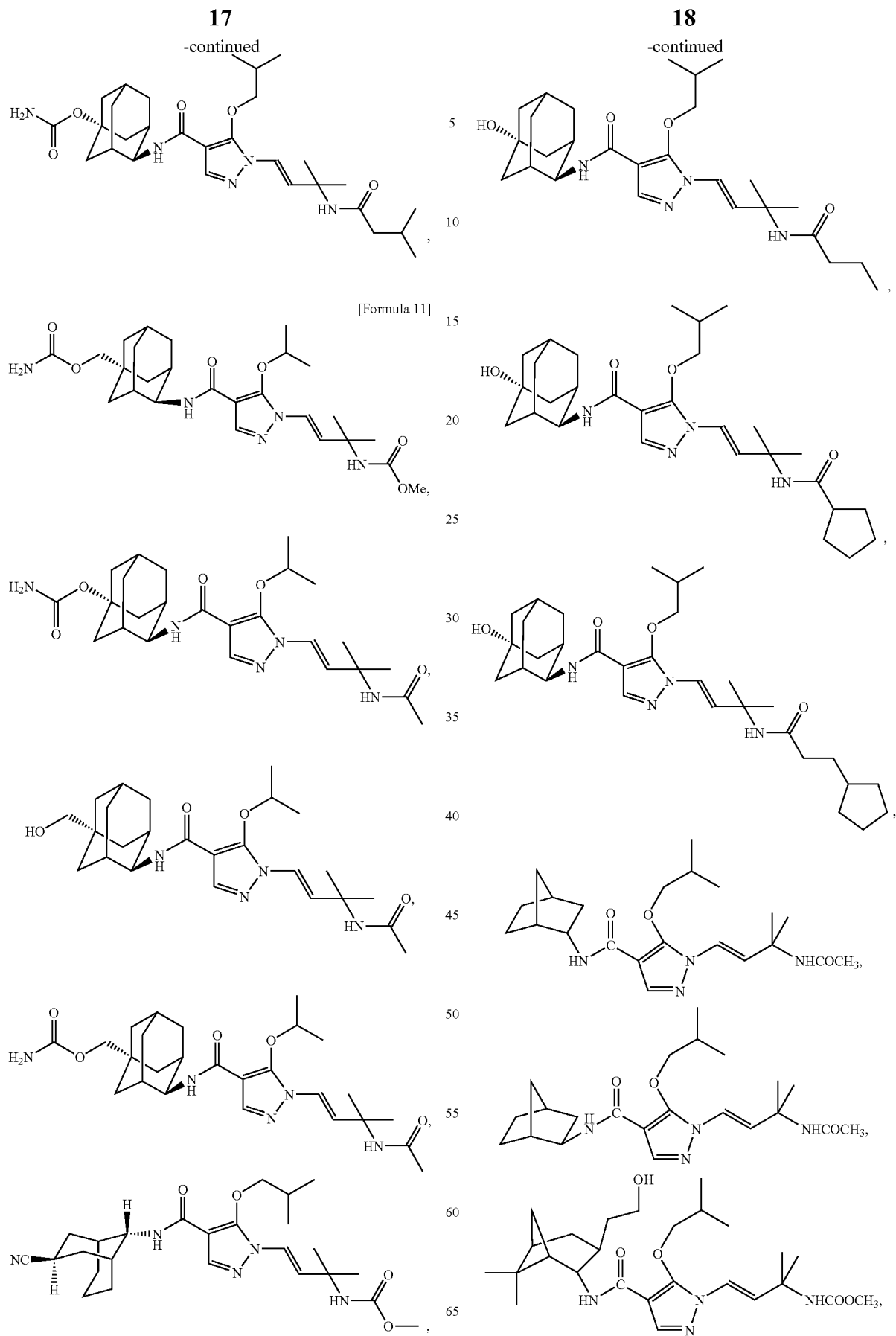

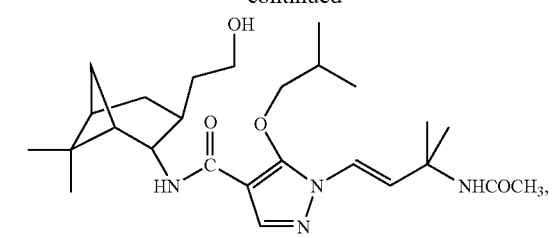
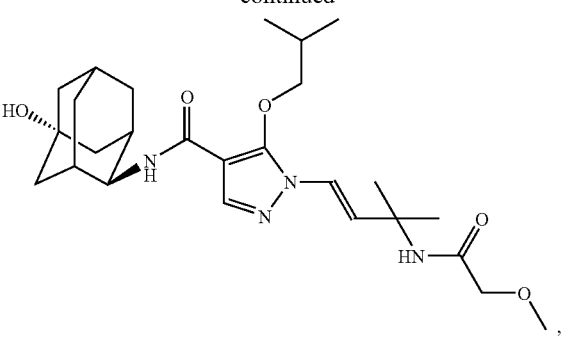
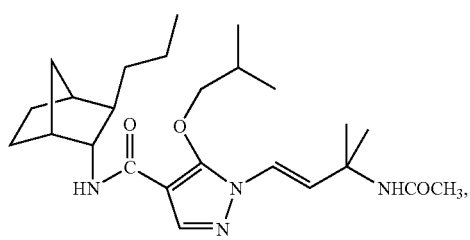
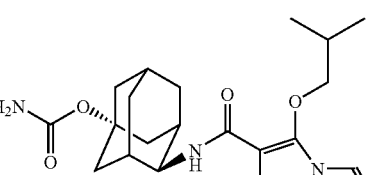
[Formula 12]
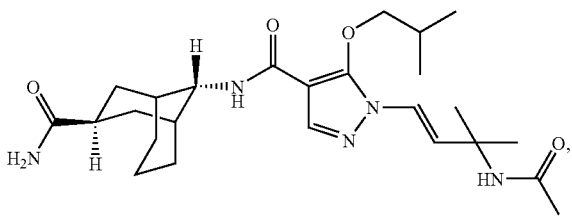
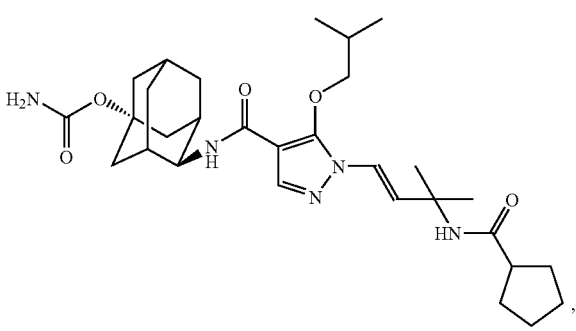
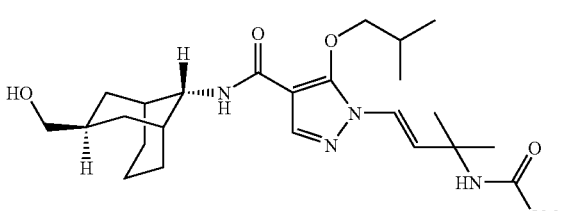
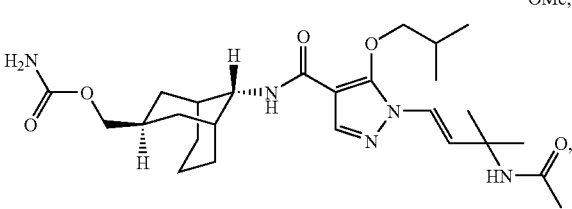
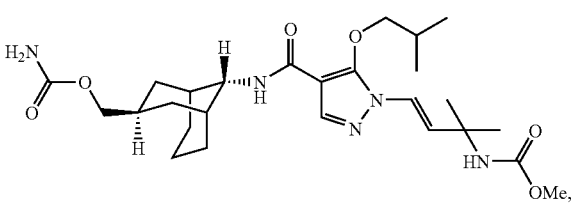
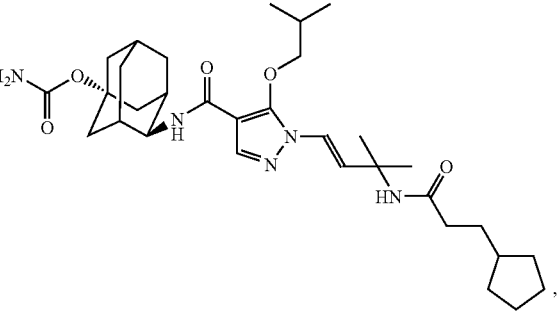
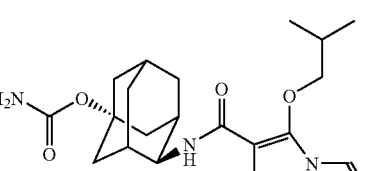

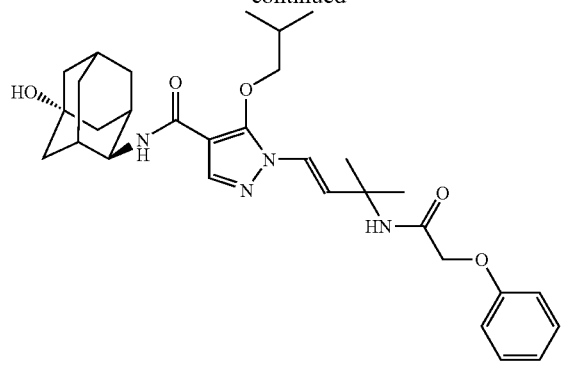
,
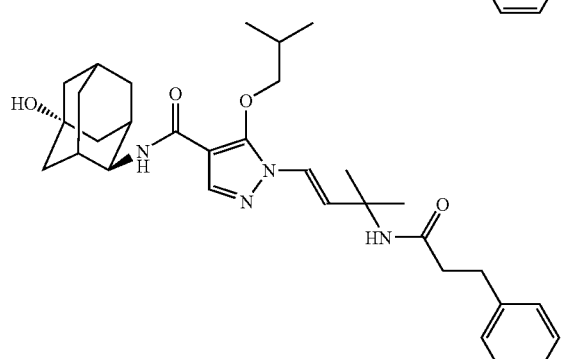
,
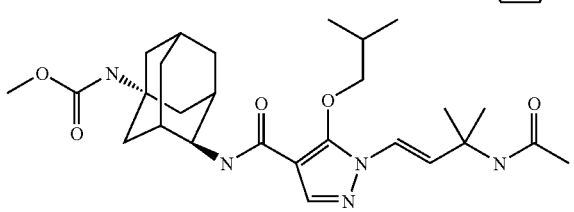
,
[Formula 13]
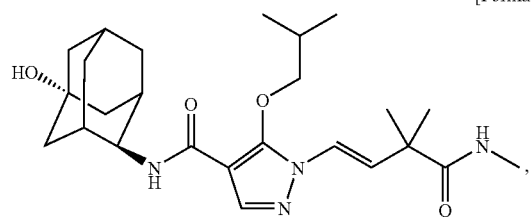
,
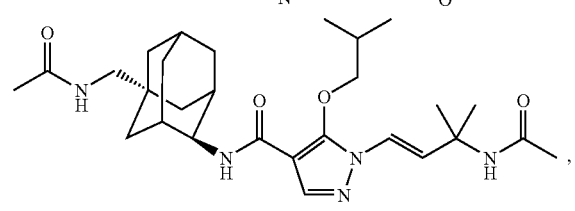
,
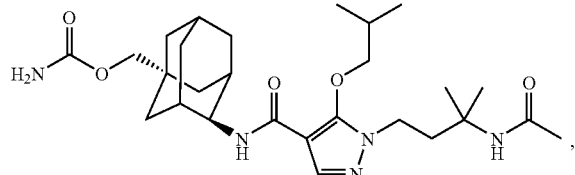
,
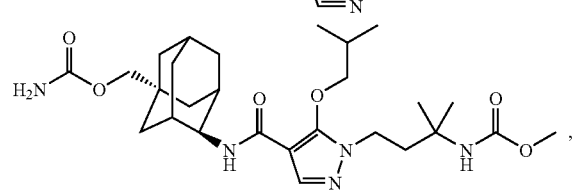
,
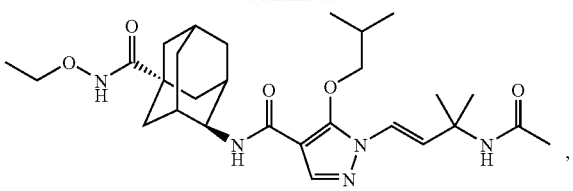
,
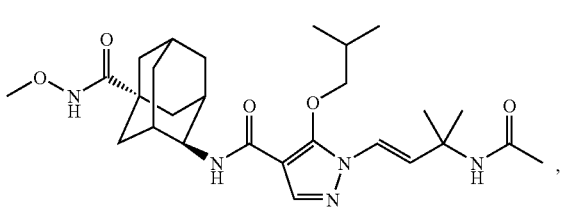
,
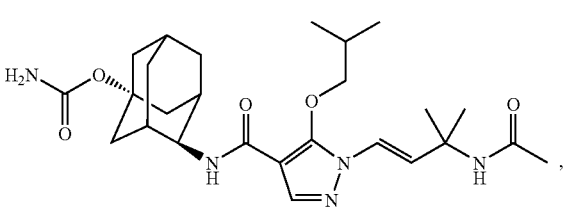
,
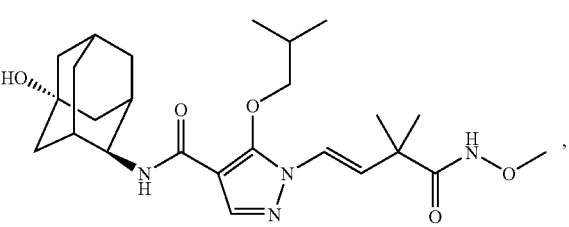
,
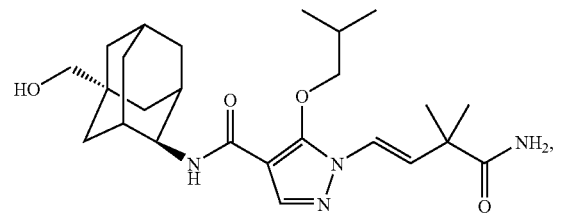
,
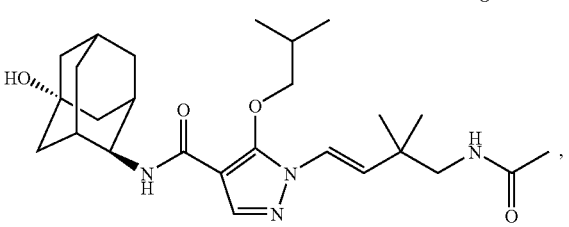
,
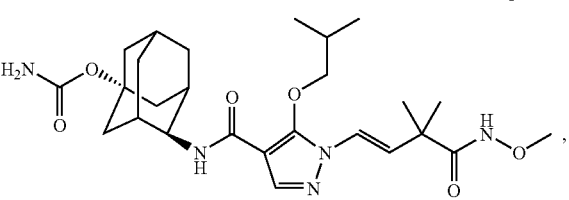
,
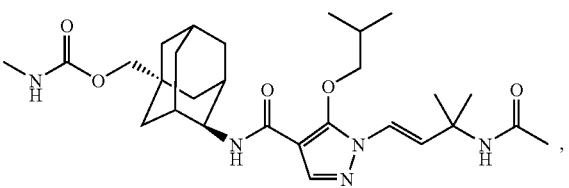
,

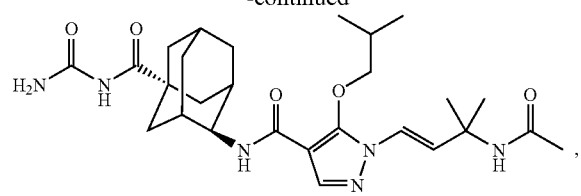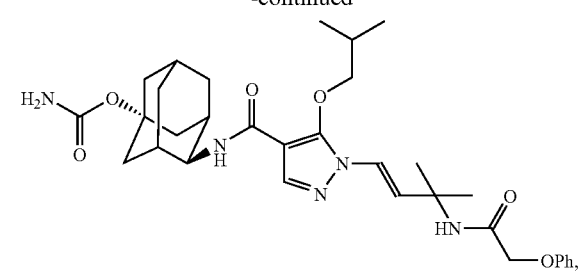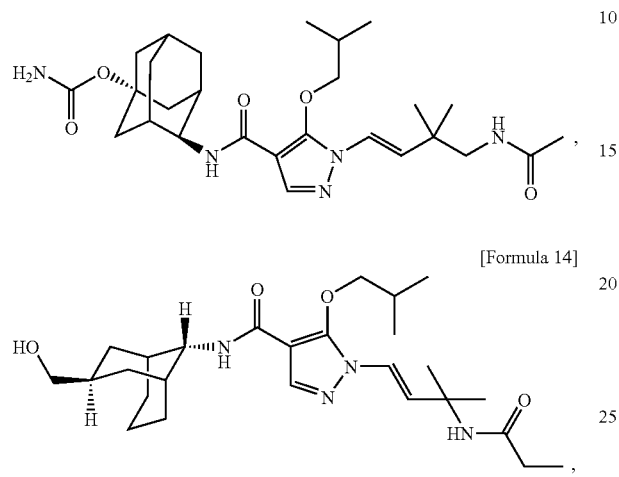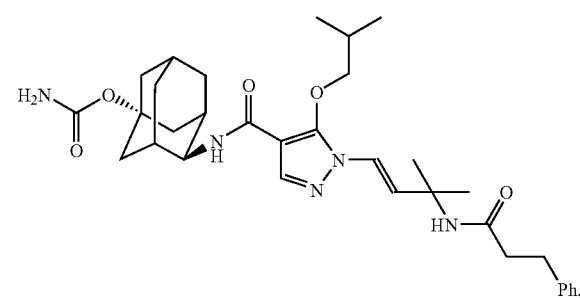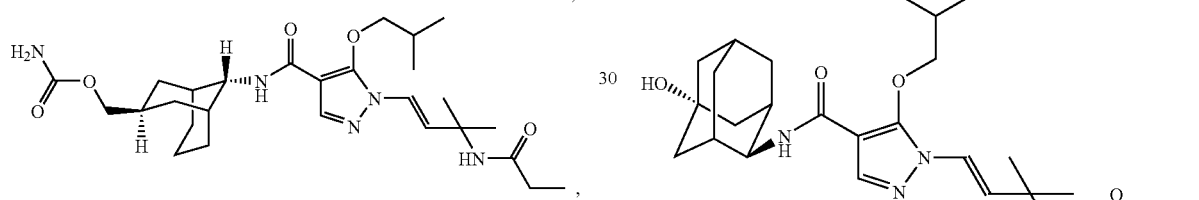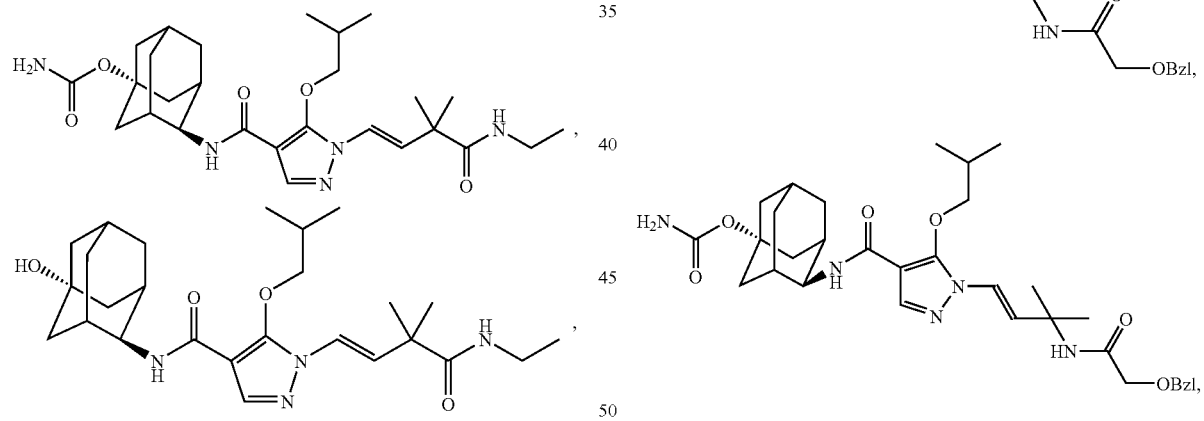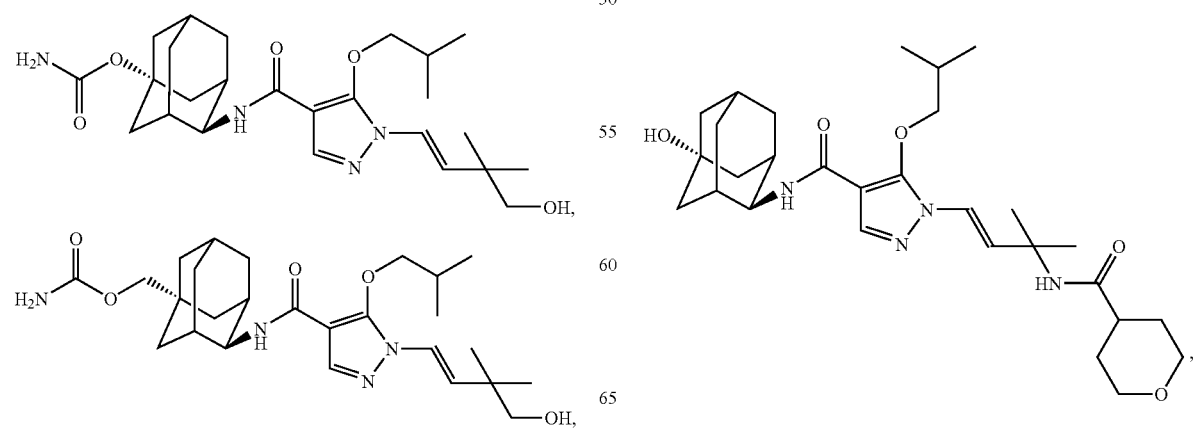

-continued

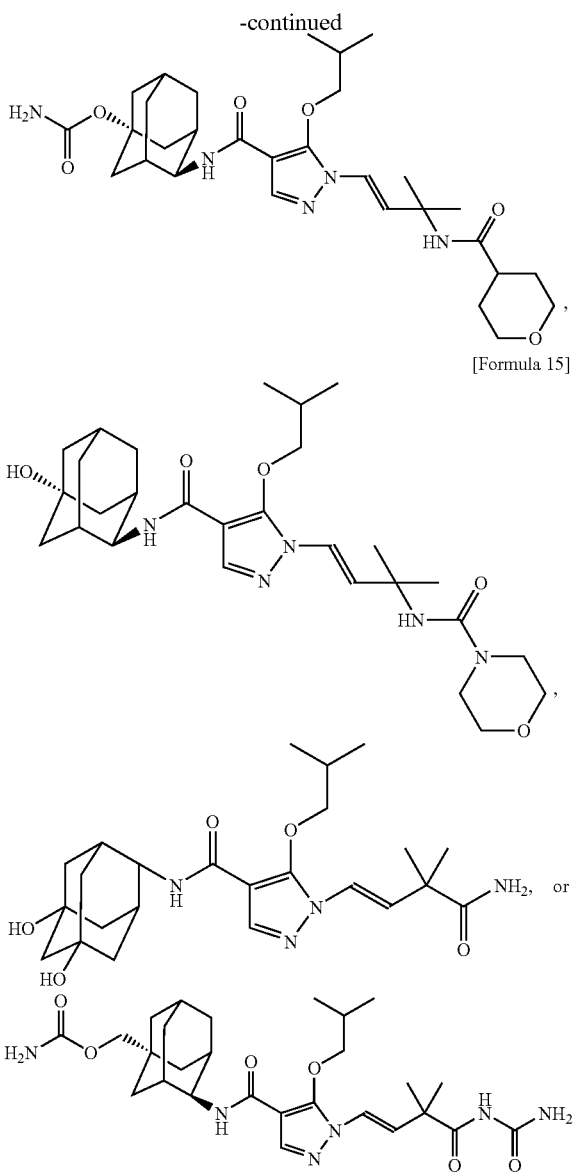

(24)
A pharmaceutical composition comprising the compound according to any one of the above (1) to (23), its pharmaceutically acceptable salt, or a solvate thereof.

(25)
The pharmaceutical composition according to the above (24), which has an 11β-hydroxysteroid dehydrogenase type 1 inhibitory activity.

Further, the present invention includes:

(26)
A method for preventing or treating diabetes, comprising administering the compound according to any one of the above (1) to (23), its pharmaceutically acceptable salt, or a solvate thereof.

(27)
A use of the compound according to any one of the above (1) to (23), its pharmaceutically acceptable salt, or a solvate thereof for manufacturing a medicament of treatment and/or prevention of diabetes.

Further, the present invention includes:

(28)
The compound according to any one of the above (1), (4) to (22), its pharmaceutically acceptable salt, or a solvate thereof, wherein $R^2$ is halogen, halogenated alkyl, halogenated alkoxy, hydroxy, cyano, nitro, carboxy, optionally substituted alkyl, optionally substituted alkenyl, optionally substituted alkynyl, optionally substituted aryl, optionally substituted cycloalkyl, optionally substituted cycloalkenyl, optionally substituted heteroaryl, optionally substituted heterocycle, a group represented by the formula: $-NR^{5A}R^{6A}$,
wherein $R^{5A}$ and $R^{6A}$ are each independently hydrogen, hydroxy, alkoxy, optionally substituted alkyl, optionally substituted alkenyl, optionally substituted carbamoyl, optionally substituted aryl, optionally substituted cycloalkyl, optionally substituted cycloalkenyl, optionally substituted heteroaryl or optionally substituted heterocycle, or $R^{5A}$ and $R^{6A}$ taken together with the adjacent nitrogen atom to which they are attached may form an optionally substituted ring, a group represented by the formula: $-S(=O)_x-R^{7A}$,
wherein x is an integer of 1 or 2, $R^{7A}$ is optionally substituted alkyl, optionally substituted alkenyl, optionally substituted aryl, optionally substituted cycloalkyl, optionally substituted cycloalkenyl, optionally substituted heteroaryl or optionally substituted heterocycle, a group represented by the formula: $-C(=O)NR^{5A}R^{6A}$,
wherein $R^{5A}$ and $R^{6A}$ have the same meaning as defined in the above, or a group represented by the formula: $-(CR^{8A}R^{9A})y-O-(CR^{10A}R^{11A})_z-CR^{12A}R^{13A}R^{14A}$,
wherein y and z are each independently integer of 0 to 5, $R^{8A}$, $R^{9A}$, $R^{10A}$, $R^{12A}$, $R^{13A}$ and $R^{14A}$ are each independently hydrogen, hydroxy, halogen, halogenated alkyl, halogenated alkoxy, alkoxy, cyano, carboxy, optionally substituted alkyl, optionally substituted alkenyl, optionally substituted aryl, optionally substituted cycloalkyl, optionally substituted cycloalkenyl, optionally substituted heteroaryl or optionally substituted heterocycle.

(29)
A pharmaceutical composition comprising the compound according to the above (28), its pharmaceutically acceptable salt, or a solvate thereof.

(30)
The pharmaceutical composition according to the above (29), which has an 11β-hydroxysteroid dehydrogenase type 1 inhibitory activity.

(31)
A method for preventing or treating diabetes, comprising administering the compound according to the above (28), its pharmaceutically acceptable salt, or a solvate thereof.

(32)
A use of the compound according to the above (28), its pharmaceutically acceptable salt, or a solvate thereof for manufacturing a medicament of treatment and/or prevention of diabetes.

(A1)
A compound represented by the Formula (I):

[Formula 16]

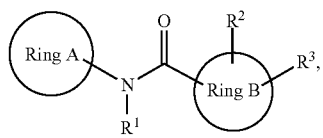

(I)

its pharmaceutically acceptable salt, or a solvate thereof, wherein Ring A is a group of the formula:

[Formula 17]

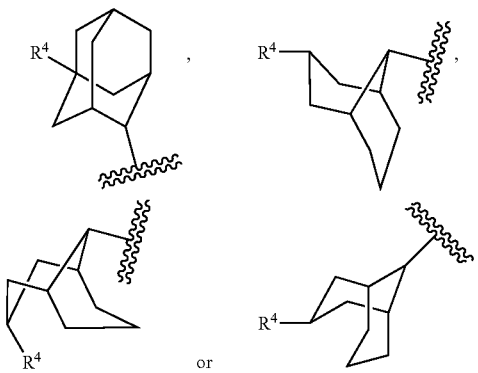

Ring B is optionally substituted heteroaryl, provided that optionally substituted isoxazole is excluded, or optionally substituted heterocycle, $R^1$ is hydrogen or optionally substituted alkyl, $R^2$ is —$OR^5$ or —$SR^5$, $R^3$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: —CH=CH—C($R^aR^b$)—$R^c$—$R^d$ or a group represented by the formula: —(C$R^eR^f$)$_m$—C($R^aR^b$)—$R_c$—$R^d$, wherein $R^a$ and $R^b$ are each independently hydrogen, optionally substituted alkyl or halogen, or $R^a$ and $R^b$ taken together with the adjacent carbon atom to which they are attached may form an optionally substituted ring, $R^c$ is —(CH$_2$)$_n$—, n is an integer of 0 to 3, $R^d$ is hydrogen, halogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl or optionally substituted heterocycle, a group represented by the formula: —C(=O)—NR$^g$R$^h$ or a group represented by the formula: —NR$^i$R$^j$, $R^e$ and $R^f$ are each independently hydrogen, halogen or optionally substituted alkyl, $R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocycle sulfonyl, optionally substituted alkyloxy, optionally substituted carbamoyl or $R^g$ and $R^h$ taken together with the adjacent nitrogen atom to which they are attached may form an optionally substituted ring, $R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, optionally substituted sulfamoyl or $R^i$ and $R^j$ taken together with the adjacent nitrogen atom to which they are attached may form an optionally substituted ring, $R^4$ is optionally substituted alkyl, optionally substituted alkenyl, —$OR^6$, —$CONR^7R^8$, —$NR^9CONR^7R^8$, —$NR^9SO_2NR^7R^8$, —$(CR^{10}R^{11})pOH$, —$(CR^{10}R^{11})pOCONR^7R^8$, —$NR^9COR^{12}$, $NR^9C(=O)OR^{12}$, —$(CR^{10}R^{11})pNR^9COR^{12}$, —$C(=O)NR^9OR^{12}$, —$CONR^9CONR^7R^8$, —CN, —COOH, halogen or —$NR^7R^8$, $R^5$ is optionally substituted alkyl, optionally substituted alkenyl, optionally substituted cycloalkyl, optionally substituted aryl, optionally substituted heteroaryl or optionally substituted heterocycle, $R^6$ is hydrogen, optionally substituted alkyl, optionally substituted alkenyl, optionally substituted cycloalkyl, optionally substituted aryl, optionally substituted heteroaryl, optionally substituted heterocycle, —$SO_2R^5$, —$SO_2NR^7R^8$ or —$CONR^7R^8$, $R^7$ and $R^8$ are each independently hydrogen, optionally substituted alkyl, optionally substituted cycloalkyl, optionally substituted aryl, optionally substituted heteroaryl, optionally substituted heterocycle or —$SO_2R^5$, $R^9$ is hydrogen or optionally substituted alkyl, $R^{10}$ and $R^{11}$ are each independently hydrogen, halogen or optionally substituted alkyl, $R^{12}$ is optionally substituted alkyl, optionally substituted cycloalkyl, optionally substituted aryl, optionally substituted heteroaryl or optionally substituted heterocycle, m and p are each independently integer of 1 to 3, provided that, the compounds shown as follows are excluded,

[Formula 18]

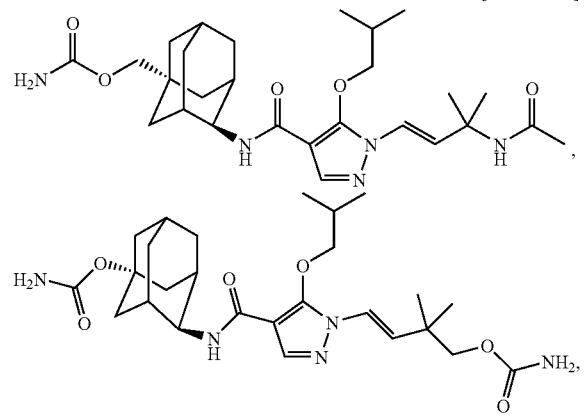

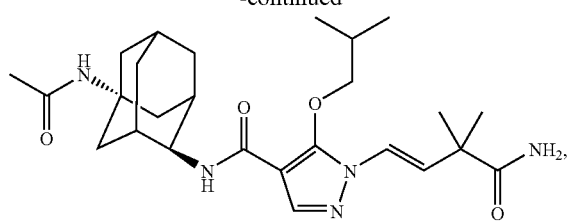
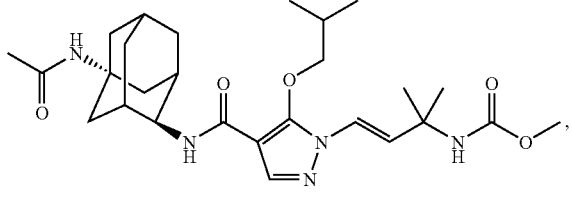
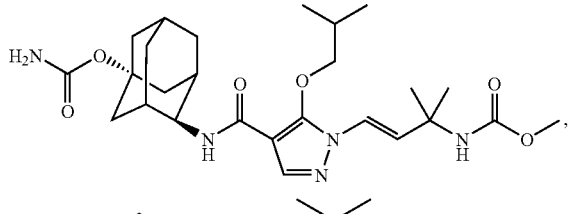
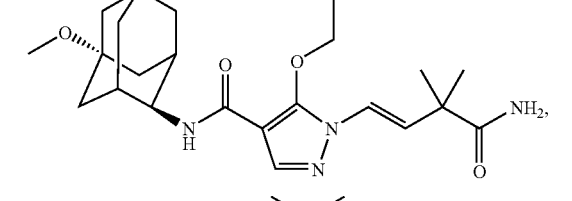
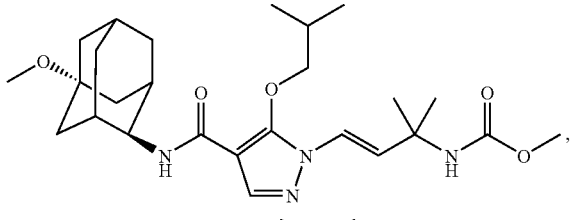
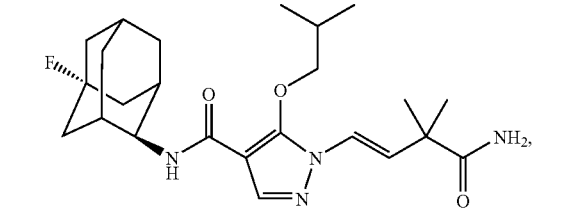
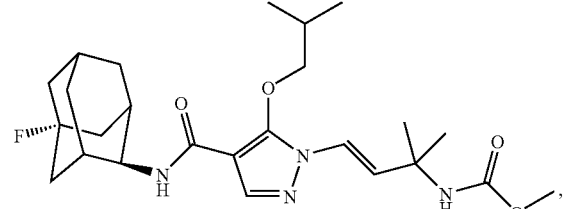
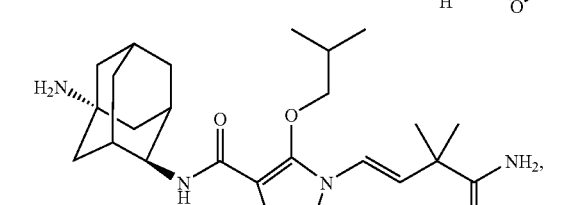
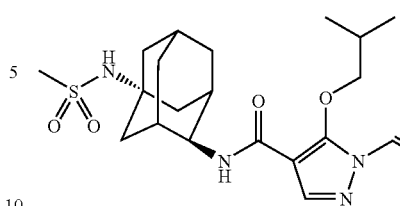
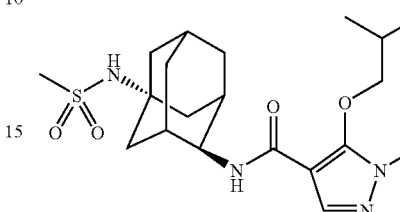
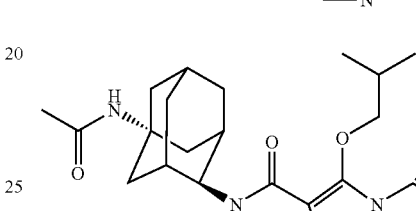
[Formula 19]
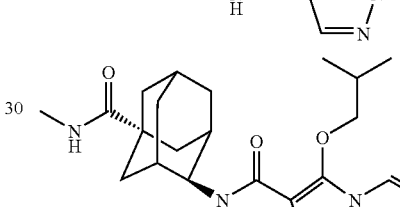
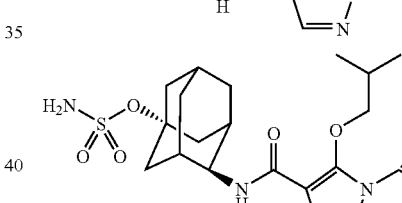
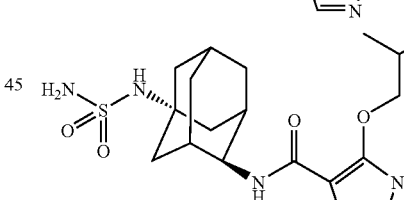
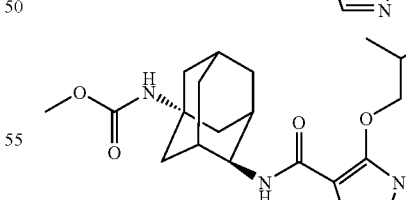
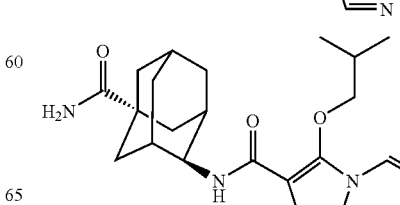

31
-continued
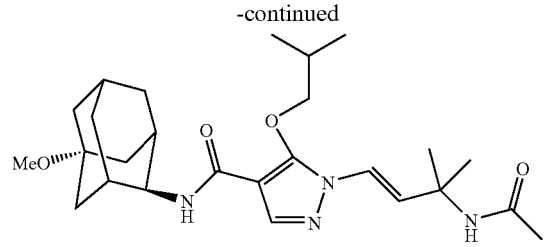
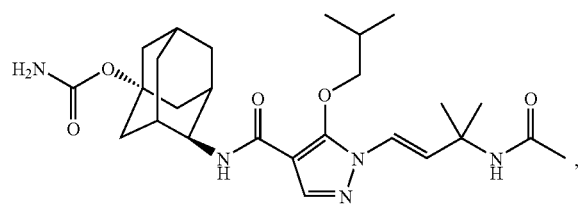
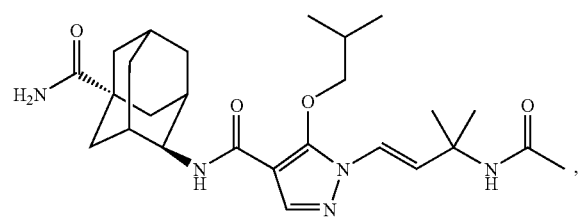
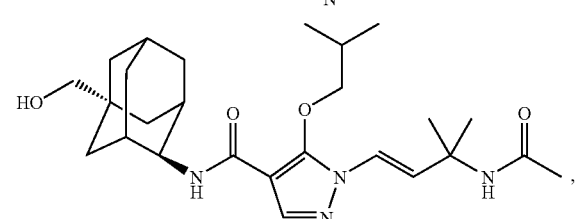
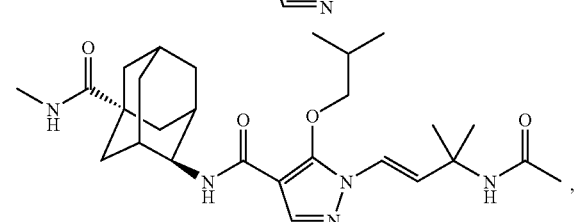
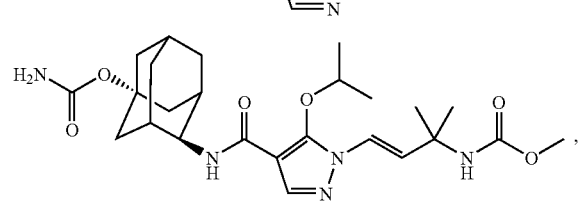
[Formula 20]
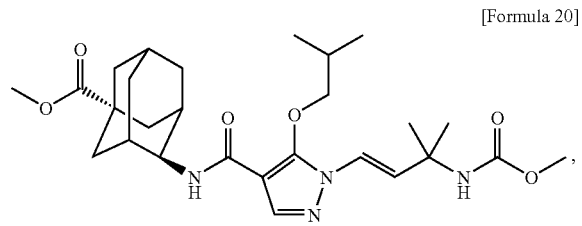
32
-continued
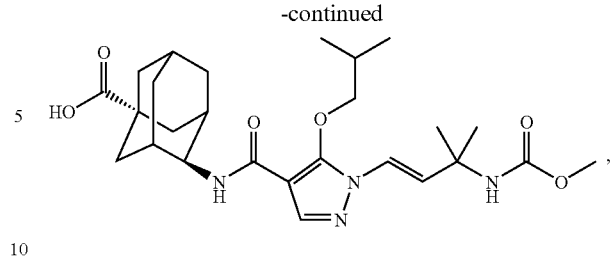
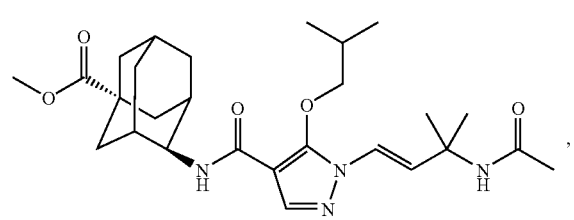
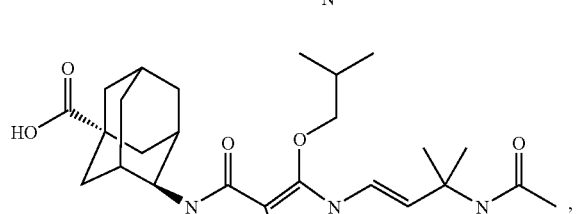
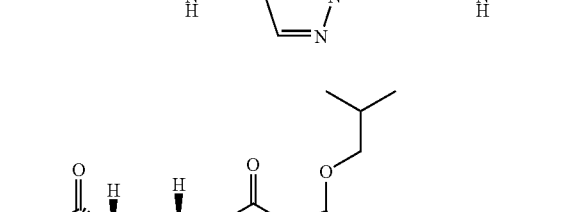
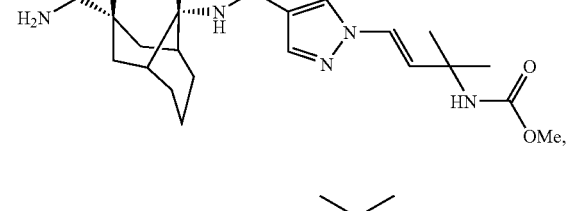
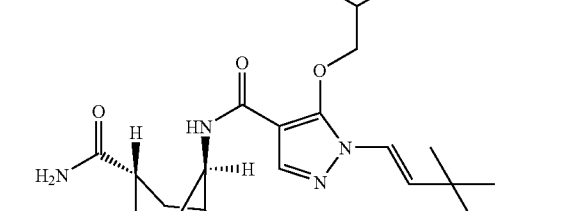
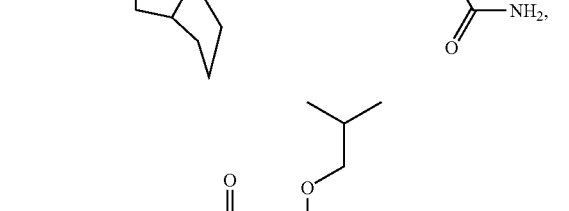

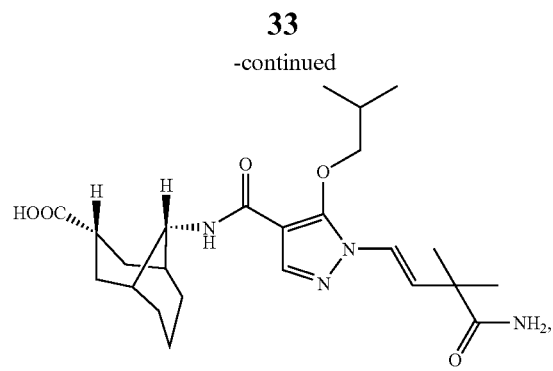

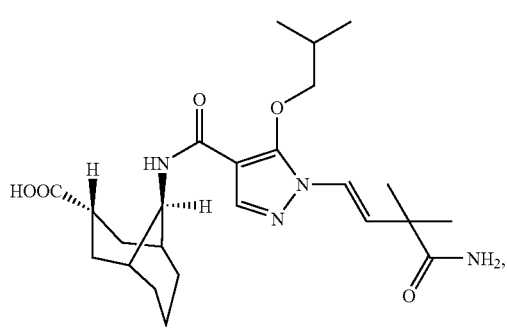

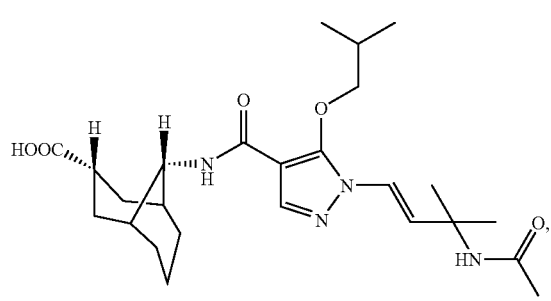

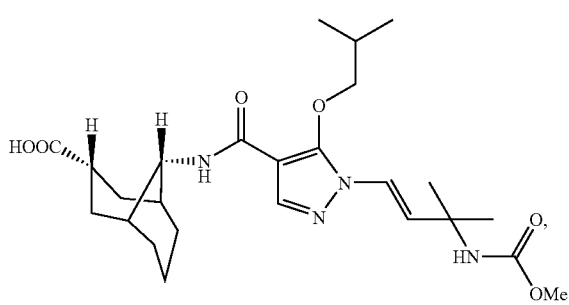

[Formula 21]

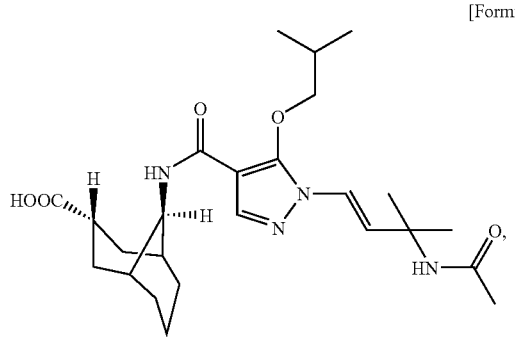

(A2)
The compound according to the above (A1), its pharmaceutically acceptable salt, or a solvate thereof, wherein $R^6$ is optionally substituted alkyl, optionally substituted alkenyl, optionally substituted cycloalkyl, optionally substituted aryl, optionally substituted heteroaryl, optionally substituted heterocycle or —CONR$^7$R$^8$, wherein $R^7$ and $R^8$ are as defined in the above (A1).

(A3)
The compound according to the above (A1) or (A2), its pharmaceutically acceptable salt, or a solvate thereof, wherein Ring A is a group represented by the formula:

[Formula 22]

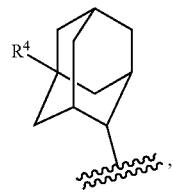

wherein $R^4$ is as defined in the above (A1), $R^6$ is optionally substituted alkyl, optionally substituted alkenyl, optionally substituted cycloalkyl, optionally substituted aryl, optionally substituted heteroaryl, optionally substituted heterocycle or —CONR$^7$R$^8$, wherein $R^7$ and $R^8$ are as defined in the above (A1).

(A4)
The compound according to any one of the above (A1) to (A3), its pharmaceutically acceptable salt, or a solvate thereof, wherein Ring B is optionally substituted heteroaryl, provided that optionally substituted isoxazole is excluded.

(A5)
The compound according to any one of the above (A1) to (A4), its pharmaceutically acceptable salt, or a solvate thereof, wherein $R^1$ is hydrogen.

(A6)
The compound according to any one of the above (A1) to (A5), its pharmaceutically acceptable salt, or a solvate thereof, wherein $R^2$ is —$OR^5$, wherein $R^5$ is as defined in the above (A1).

(A7)
The compound according to any one of the above (A1) to (A6), its pharmaceutically acceptable salt, or a solvate thereof, wherein $R^5$ is optionally substituted alkyl.

(A8)
The compound according to any one of the above (A1) to (A7), its pharmaceutically acceptable salt, or a solvate thereof, wherein $R^3$ is optionally substituted alkyl or optionally substituted alkenyl.

(A9)
The compound according to the above (A8), its pharmaceutically acceptable salt, or a solvate thereof, wherein $R^3$ is a group represented by the formula: —CH=CH—C($R^aR^b$)—$R^c$—$R^d$ or a group represented by the formula: —($CR^eR^f$)$_m$—C($R^aR^b$)—$R^c$—$R^d$, wherein $R^a$ to $R^f$ are as defined in the above (A1).

(A10)
The compound according to the above (A9), its pharmaceutically acceptable salt, or a solvate thereof, wherein $R^a$ and $R^b$ are each independently optionally substituted alkyl.

(A11)
The compound according to the above (A9) or (A10), its pharmaceutically acceptable salt, or a solvate thereof, wherein $R^c$ is —(CH$_2$)n-, wherein n is an integer of 0 or 1.

(A12)
The compound according to any one of the above (A9) to (A11), its pharmaceutically acceptable salt, or a solvate thereof, wherein $R^d$ is halogen, hydroxy, cyano, optionally substituted heteroaryl or optionally substituted heterocycle.

(A13)
The compound according to any one of the above (A9) to (A11), its pharmaceutically acceptable salt, or a solvate thereof, wherein $R^d$ is a group represented by the formula: —C(=O)—$NR^gR^h$, where in $R^g$ and $R^j$ are each independently hydrogen, optionally substituted alkyl, optionally substituted alkyloxy or optionally substituted carbamoyl.

(A14)
The compound according to any one of the above (A9) to (A11), its pharmaceutically acceptable salt, or a solvate thereof, wherein $R^d$ is a group represented by the formula: —$NR^iR^j$, wherein $R^i$ and $R^j$ are each independently hydrogen, optionally substituted alkylsulfonyl, optionally substituted alkyloxycarbonyl, optionally substituted alkylcarbonyl or optionally substituted heterocyclecarbonyl.

(A15)
The compound according to any one of the above (A1) to (A14), its pharmaceutically acceptable salt, or a solvate thereof, wherein $R^4$ is —$OR^6$, —$CONR^7R^8$, —$NR^9CONR^7R^8$, —$(CR^{10}R^{11})_n$OH, —$(CR^{10}R^{11})_n$OCONR$^7R^8$, —$NR^9COR^{12}$, —$NR^9C(=O)OR^{12}$, —$(CR^{10}R^{11})_nNR^9COR^{12}$, —C(=O)$NOR^{12}$, CONR$^9$CONR$^7R^8$ or —CN, wherein $R^6$ to $R^{12}$ are as defined in the above (A1).

(A16)
The compound according to the above (A15), its pharmaceutically acceptable salt, or a solvate thereof, wherein $R^7$ and $R^8$ are each independently hydrogen or optionally substituted alkyl.

(A17)
The compound according to the above (A15) or (A16), its pharmaceutically acceptable salt, or a solvate thereof, wherein $R^9$ is hydrogen.

(A18)
The compound according to any one of the above (A15) to (A17), its pharmaceutically acceptable salt, or a solvate thereof, wherein $R^{10}$ and $R^{11}$ are each independently hydrogen.

(A19)
The compound according to any one of the above (A15) to (A18), its pharmaceutically acceptable salt, or a solvate thereof, wherein $R^{12}$ is optionally substituted alkyl.

(A20)
A compound defined below, its pharmaceutically acceptable salt, or a solvate thereof,

[Formula 23]

37
-continued
38
-continued
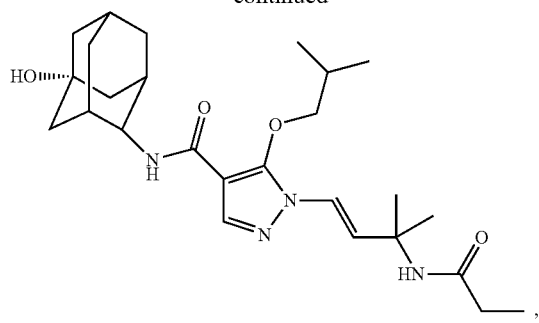
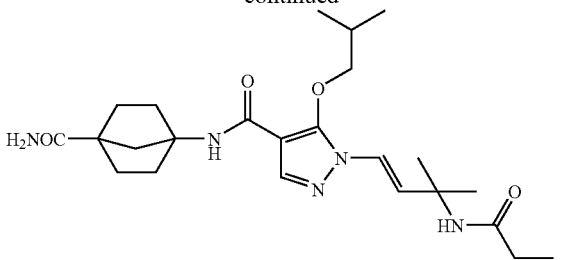
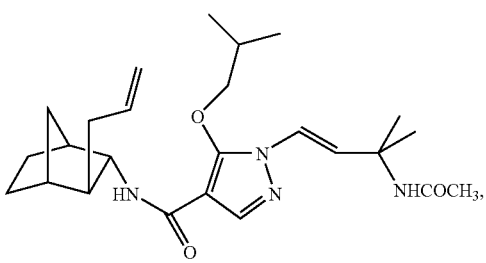
[Formula 24]
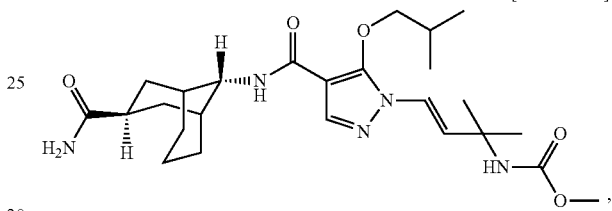
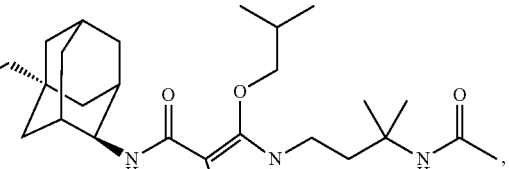
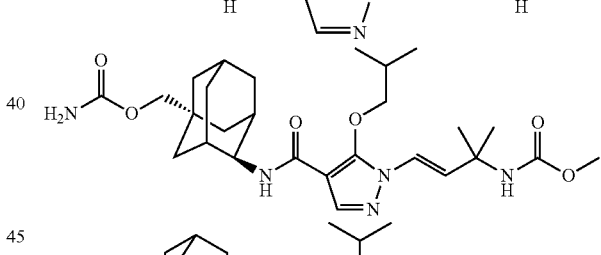
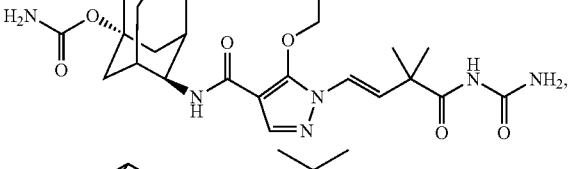
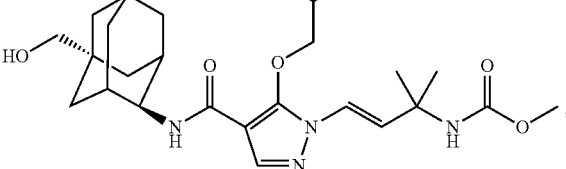
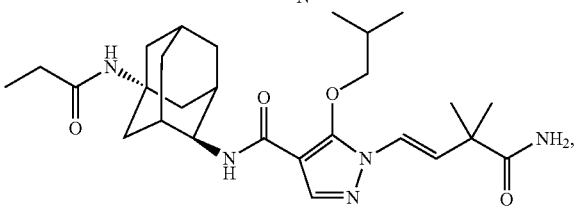

-continued
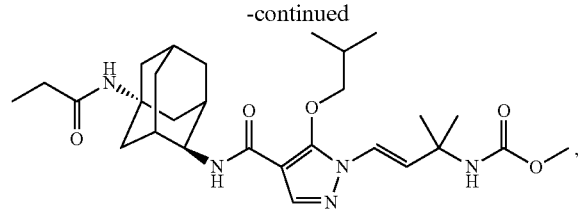
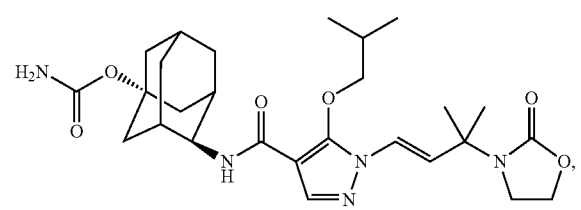
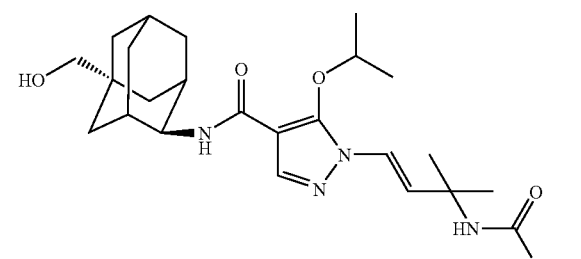
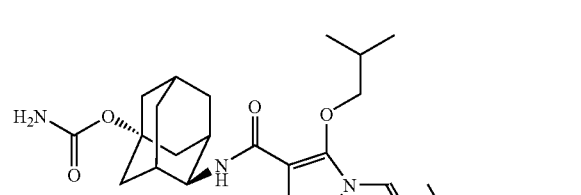
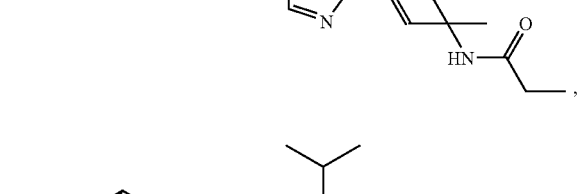
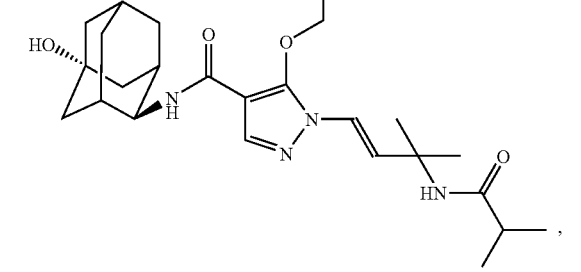
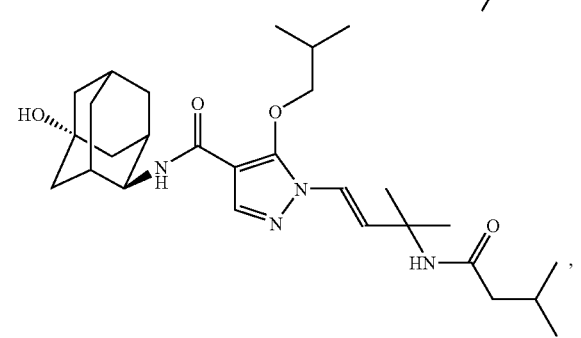
-continued
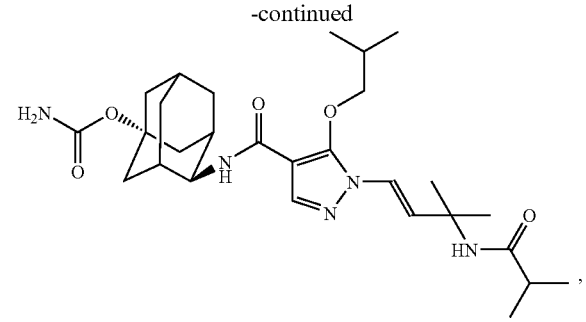
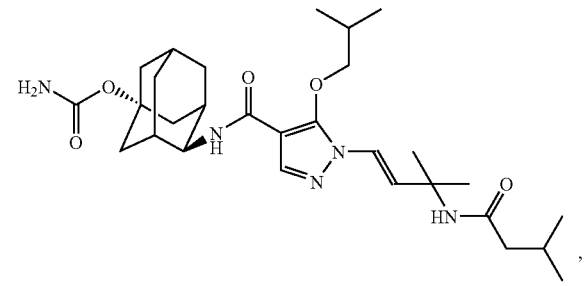
[Formula 25]
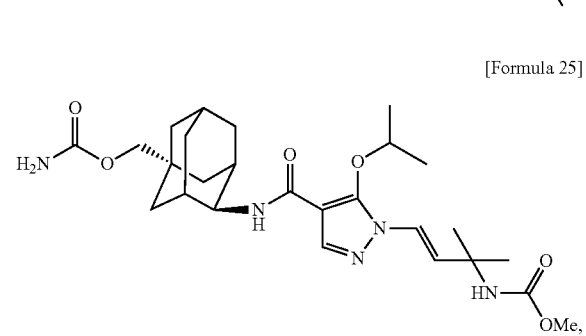
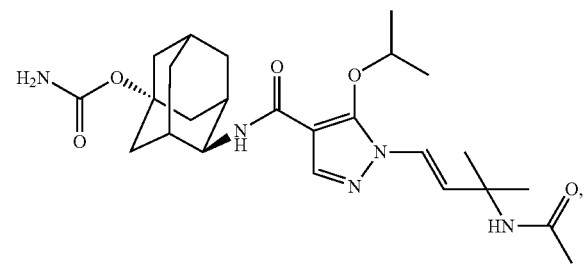
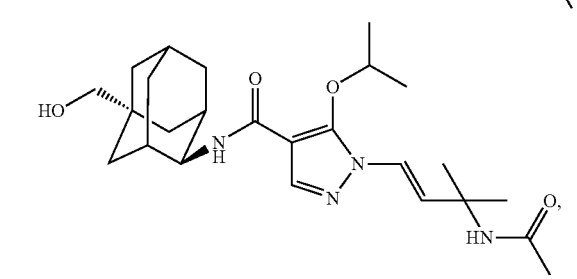
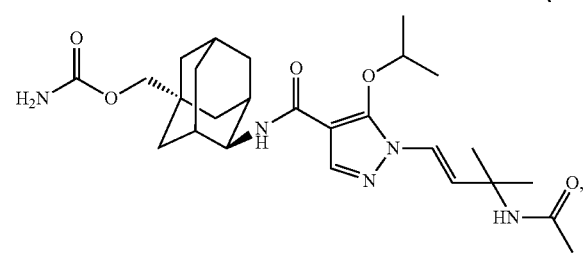

41
-continued
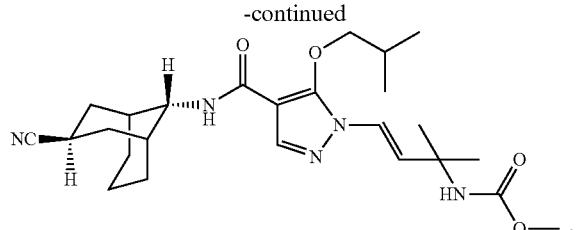
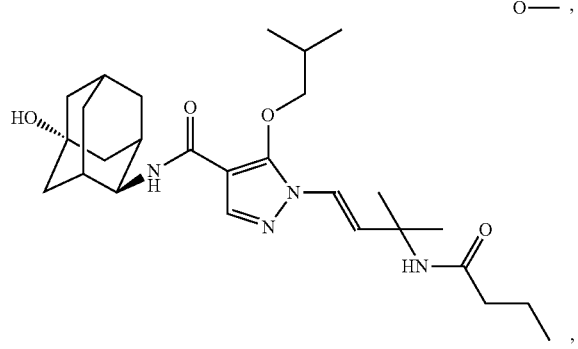
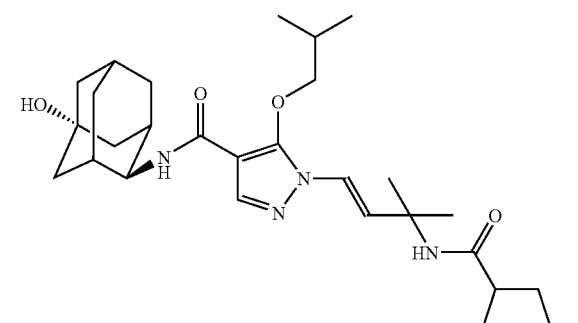
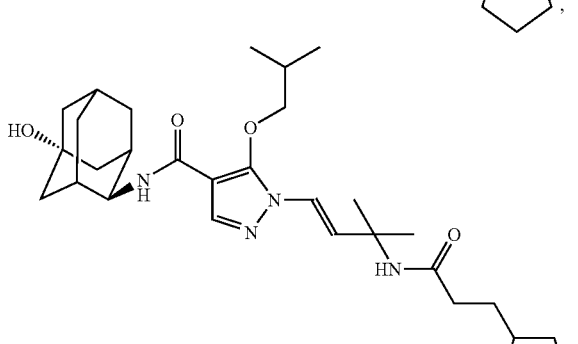
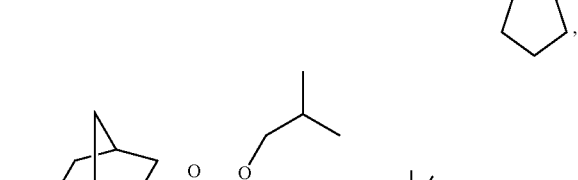
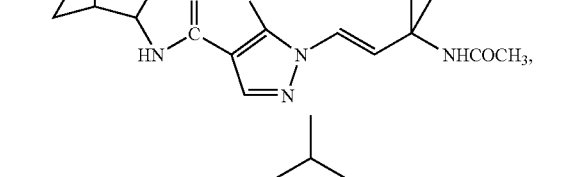
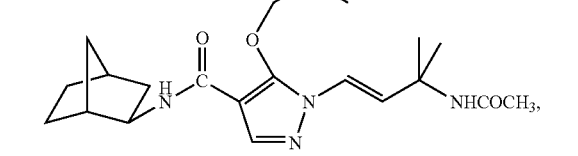
42
-continued
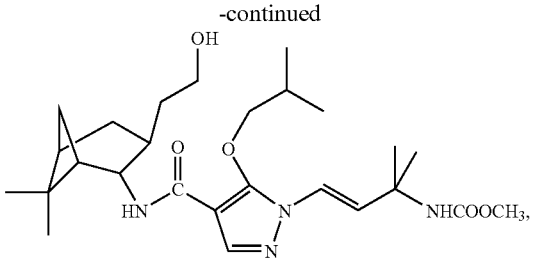
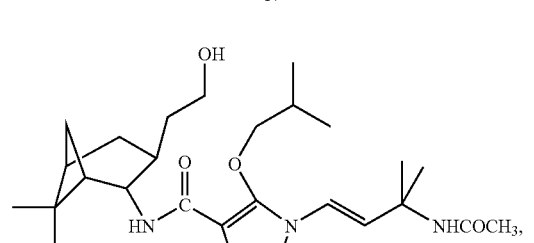
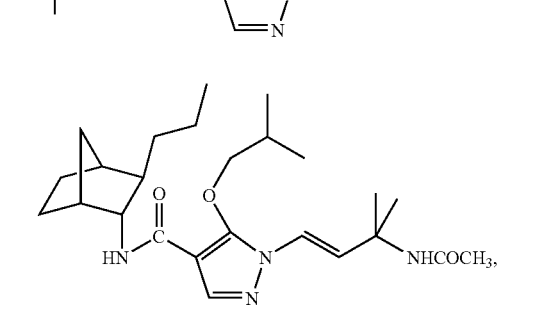
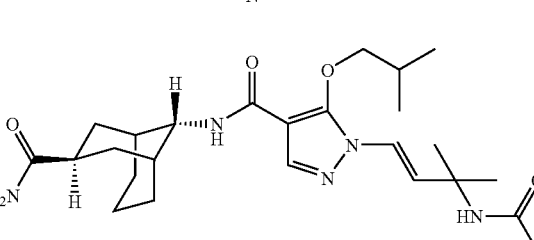
[Formula 26]
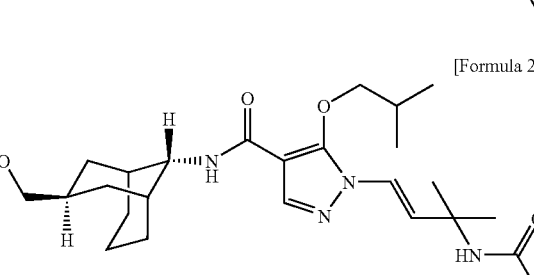
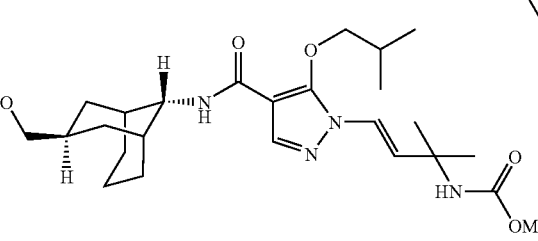
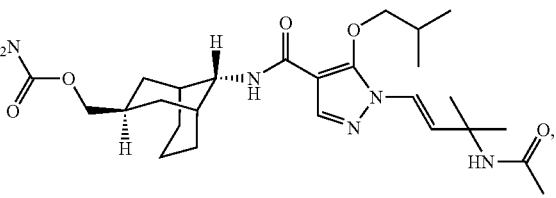

-continued
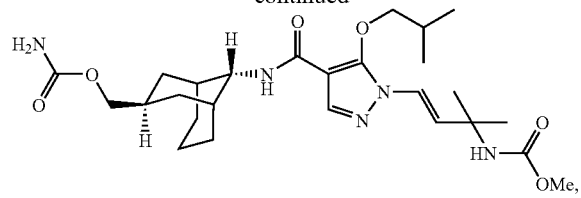
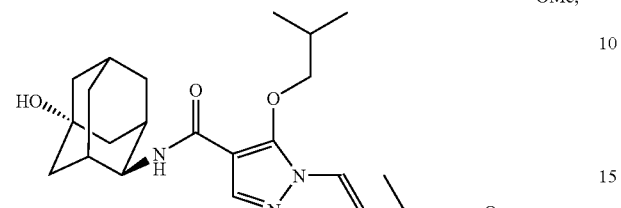
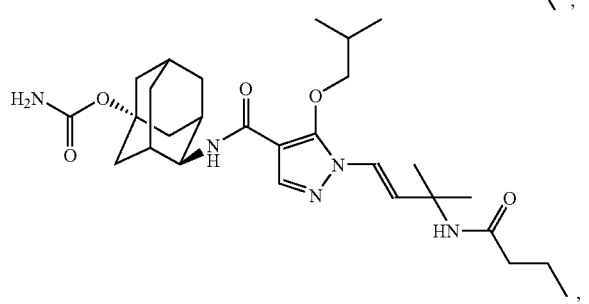
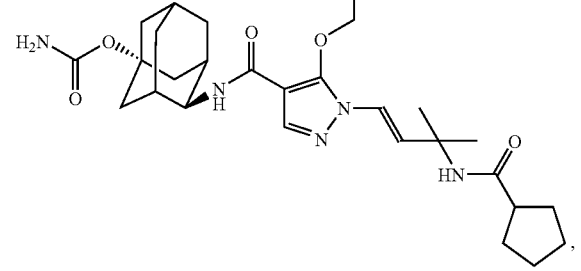
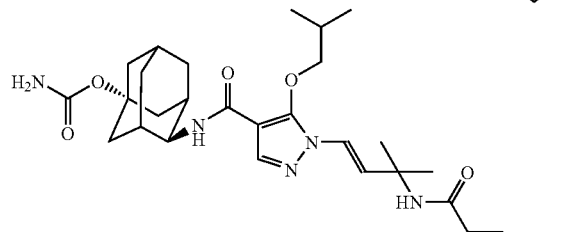
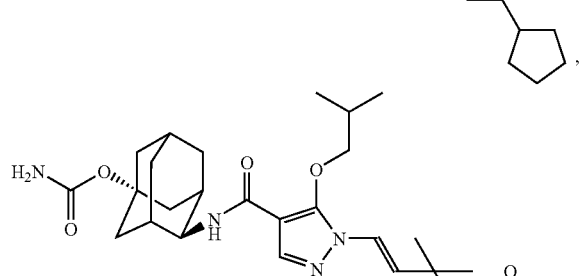
-continued
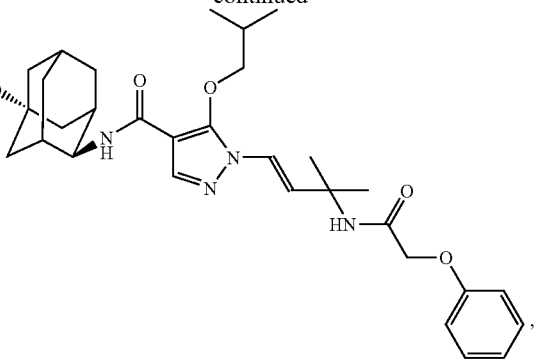
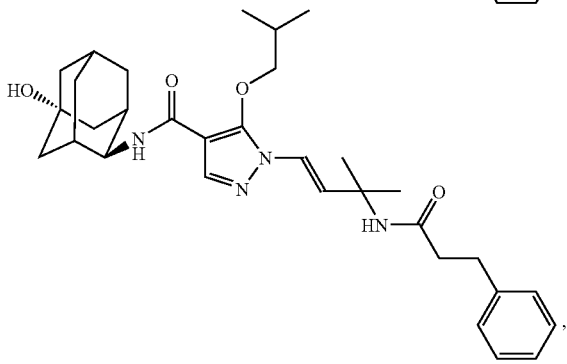
[Formula 27]
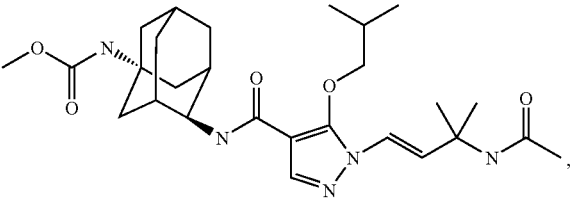 [SMILES: COC(=O)N[C@]12CC3CC(C1)[C@@H](NC(=O)c1cnn(/C=C/C(C)(C)NC(C)=O)c1OCC(C)C)C(C3)C2]
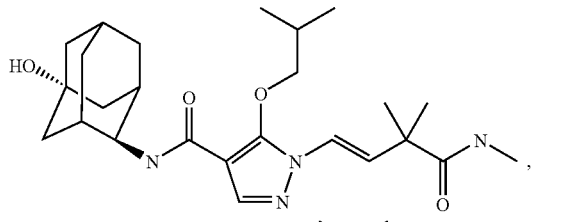
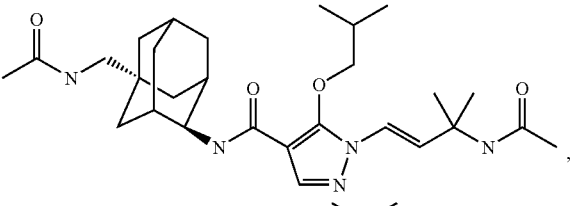
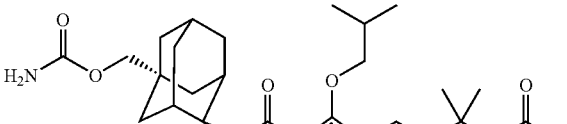
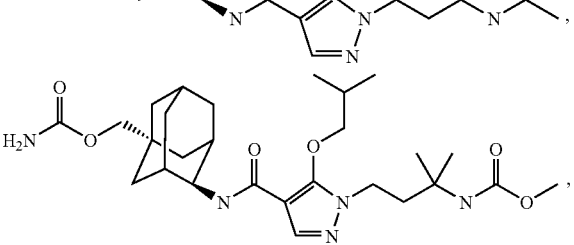

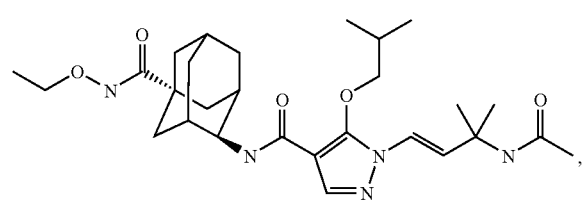
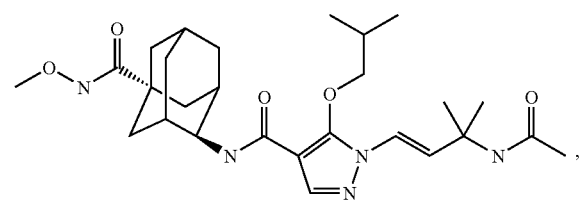
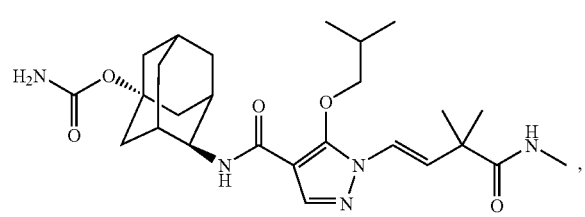
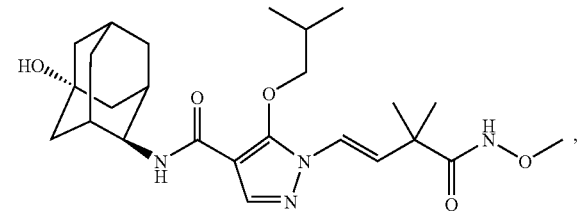
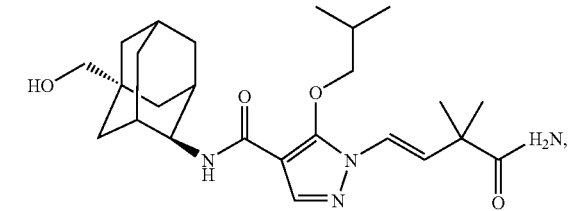
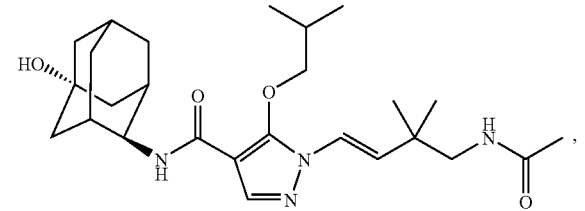
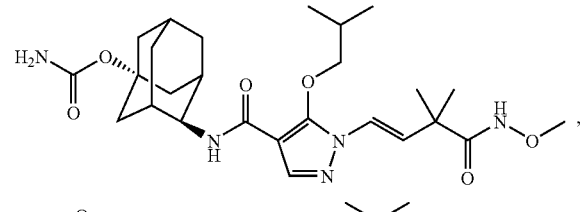
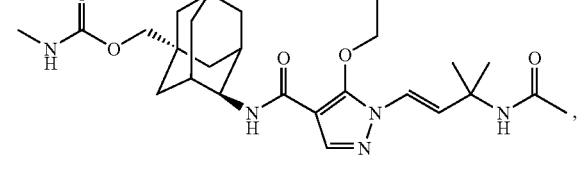
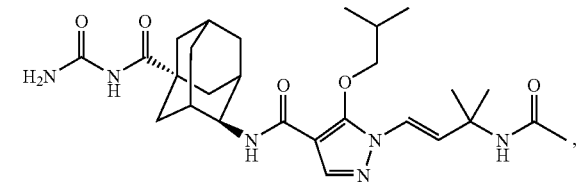
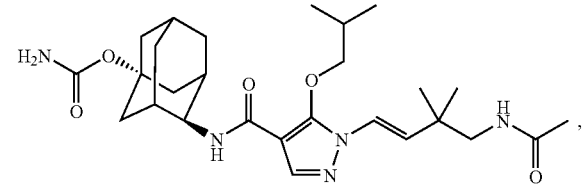
[Formula 28]
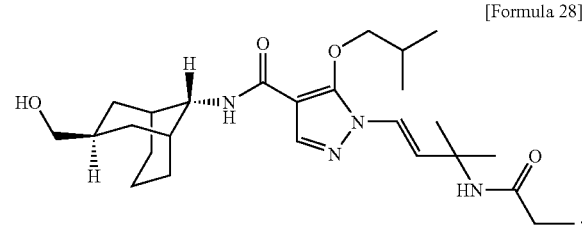
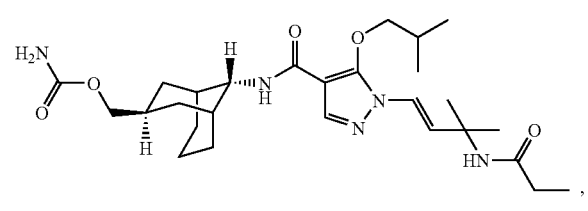
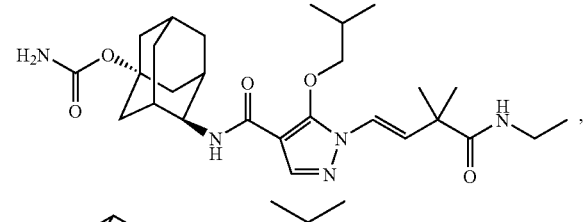
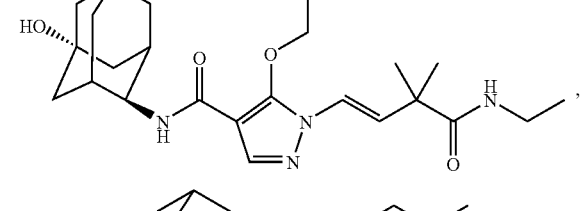
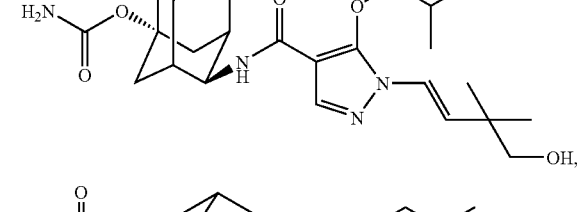
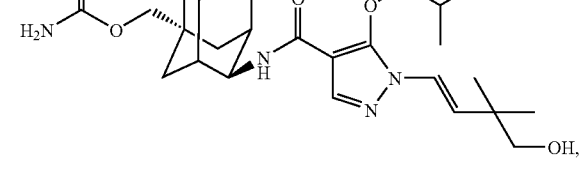

-continued

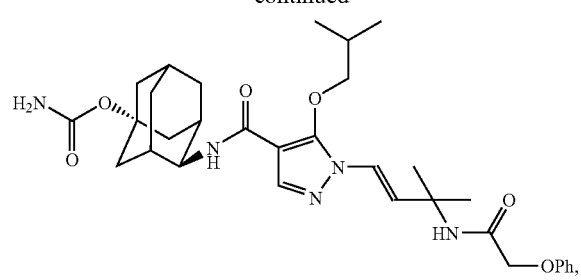

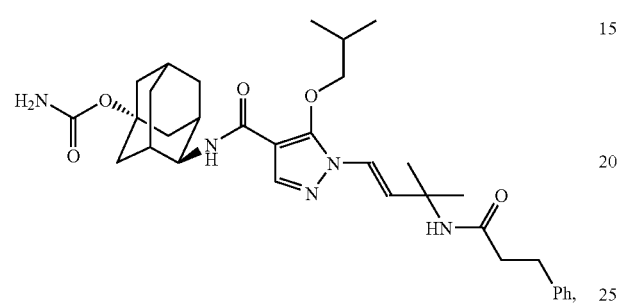

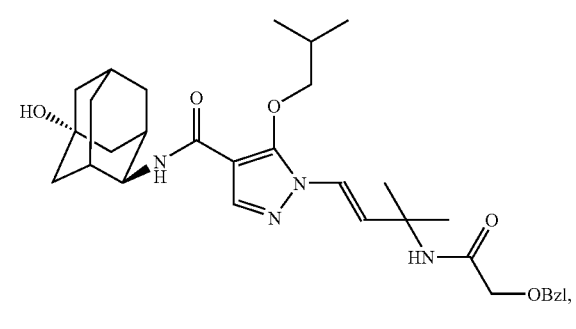

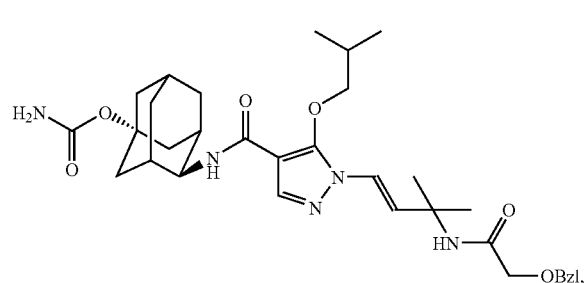

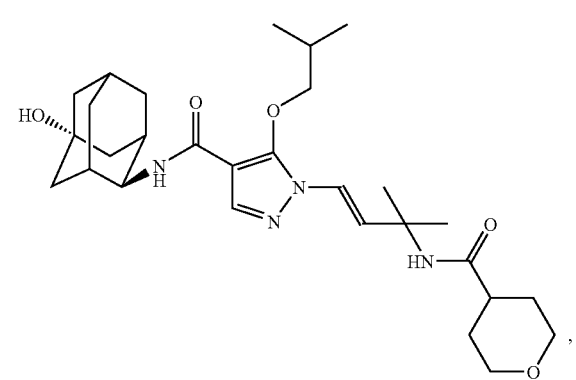

-continued

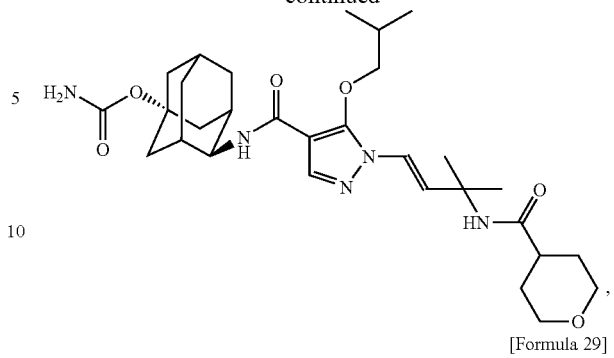

[Formula 29]

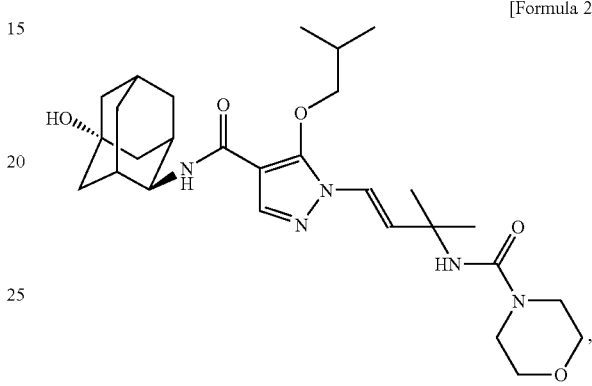

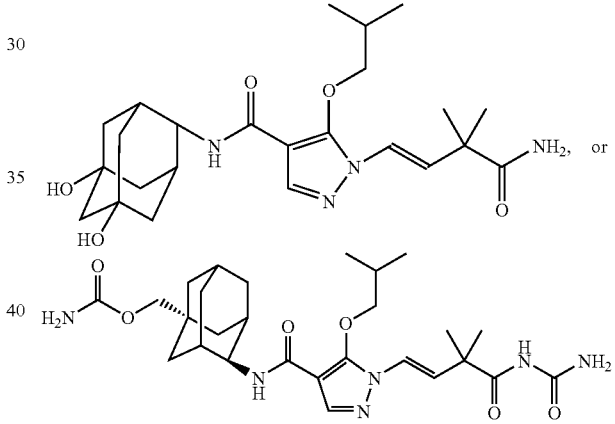

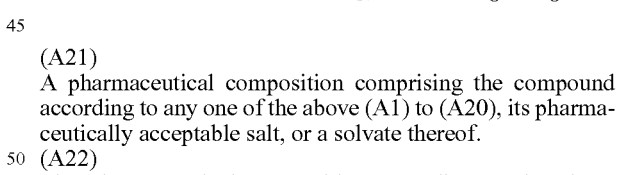

(A21)
A pharmaceutical composition comprising the compound according to any one of the above (A1) to (A20), its pharmaceutically acceptable salt, or a solvate thereof.
(A22)
The pharmaceutical composition according to the above (A21), which is an 11β-hydroxysteroid dehydrogenase type 1 inhibitor.
(A23)
A method for preventing or treating diabetes, comprising administering the compound according to any one of the above (A1) to (A20), its pharmaceutically acceptable salt, or a solvate thereof.
(A24)
A use of the compound according to any one of the above (A1) to (A20), its pharmaceutically acceptable salt, or a solvate thereof for manufacturing a medicament of treatment and/or prevention of diabetes.

Effect of the Invention

Since the present compound has inhibitory activity to 11β-hydroxysteroid dehydrogenase type 1, pharmaceutical compositions comprising the present compound are very useful as medicaments, especially, as medicaments for treatment and/or prevention of hyperlipidemia, diabetes, obesity, arteriosclerosis, atherosclerosis, hyperglycemia, and/or syndrome X. Moreover, the present compound selectively inhibits 11β-hydroxysteroid dehydrogenase type 1, and is a compound having other utility as a medicament. Here, the utility as a medicament includes high metabolic stability, a weak drug-metabolizing enzyme induction, a weak inhibition of drug metabolizing enzyme that metabolizes other drug, a high oral absorption, a low clearance, a long half-life period enough to exhibit drug efficacy and so on.

BEST MODE FOR CARRYING OUT THE INVENTION

In the following, meanings of terms used in the present specification will be explained. Each term has the same meaning when used alone or in combination with other term in this description.

"Halogen" includes fluorine, chlorine, bromine or iodine. Particularly, fluorine, chlorine and bromine are preferable.

"Alkyl" means a C1 to C10 straight or branched alkyl group, and example includes methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl or the like. Preferable is C1 to C6 or C1 to C4 alkyl, and example includes methyl, ethyl, n-propyl, isopropyl, n-butyl, isobutyl, sec-butyl, tert-butyl, n-pentyl, isopentyl, neopentyl, n-hexyl or isohexyl.

"Alkenyl" means C2 to C8 straight or branched alkenyl having one or more double bond(s) in the above "alkyl", and example includes vinyl, 1-propenyl, 2-propenyl, 1-butenyl, 2-butenyl, 3-butenyl, 1,3-butadienyl, 3-methyl-2-butenyl or the like.

"Alkynyl" means C2 to C8 straight or branched alkynyl having one or more triple bond(s) in the above "alkyl", and example includes ethynyl, propinyl, butynyl or the like.

"Cycloalkyl" means a C3 to C15 cyclic saturated hydrocarbon group, and example includes cyclopropyl, cyclobutyl, cyclopentyl, cyclohexyl, cycloheptyl, cyclooctyl, bridged cyclic hydrocarbon group, spiro hydrocarbon group or the like. Preferable is cyclopropyl, cyclobutyl, cyclopentyl, cyclohexyl or bridged cyclic hydrocarbon group.

"Spiro hydrocarbon group" includes a group which is derived by excluding one hydrogen from a cycle which consists of two hydrocarbon rings that share one carbon atom. Example includes spiro[3.4]octyl or the like.

"Bridged cyclic hydrocarbon group" includes a group which is derived by excluding one hydrogen from a C5 to C8 aliphatic cycle which consists of two or more rings that share two or more atoms. Example includes bicyclo[2.1.0]pentyl, bicyclo[2.2.1]heptyl, bicyclo[2.2.2]octyl, bicyclo[3.2.1]octyl, tricyclo[2.2.1.0]heptyl, the following groups or the like:

[Formula 30]

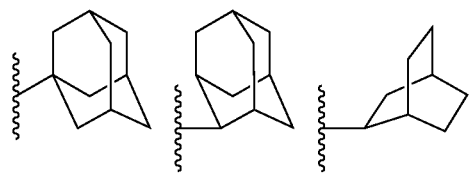

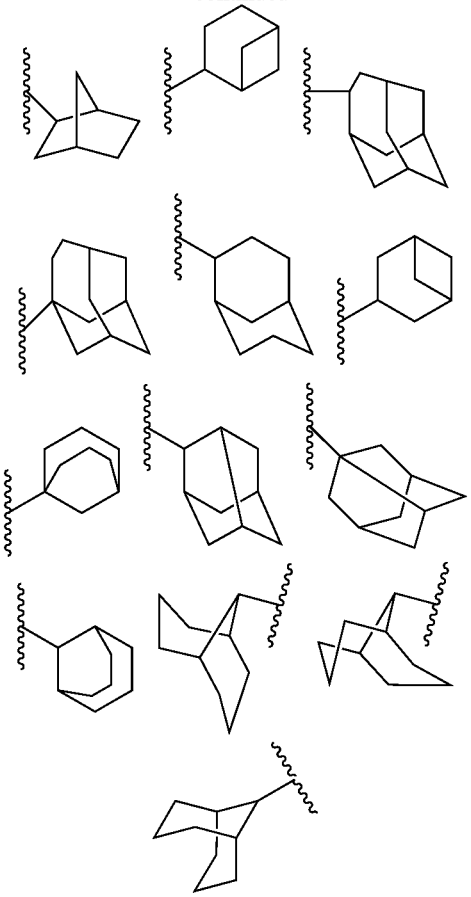

"Cycloalkenyl" means C3 to C15 cyclic unsaturated aliphatic hydrocarbon group, and example includes cyclopropenyl, cyclobutenyl, cyclopentenyl, cyclohexenyl, cycloheptenyl or the like. Preferable is cyclopropenyl, cyclobutenyl, cyclopentenyl or cyclohexenyl. Cycloalkenyl also includes bridged cyclic hydrocarbon group which have an unsaturated bond in the ring. Example includes a group having one or two double bond(s) in the ring of the bridged cyclic hydrocarbon group which is exemplified in the above "cycloalkyl".

"Aryl" means a monocyclic aromatic hydrocarbon group (e.g.: phenyl) and a polycyclic aromatic hydrocarbon group (e.g.: 1-naphthyl, 2-naphthyl, 1-anthryl, 2-anthryl, 9-anthryl, 1-phenanthryl, 2-phenanthryl, 3-phenanthryl, 4-phenanthryl or 9-phenanthryl). Preferable is phenyl or naphthyl (1-naphthyl or 2-naphthyl).

"Heteroaryl" means a monocyclic aromatic heterocyclic group or a fused aromatic heterocyclic group. The monocyclic aromatic heterocyclic group means a group derived from a 5- to 8-membered aromatic ring which may contain 1 to 4 oxygen, sulfur and/or nitrogen atom(s) in the ring, and may have a bond at a substitutable arbitrary position.

The fused aromatic heterocyclic group means a group in which a 5- to 8-membered aromatic ring optionally containing 1 to 4 oxygen, sulfur and/or nitrogen atom(s) in the ring is fused with 1 to 4 of 5- to 8-membered aromatic carbocycle(s) or other 5- to 8-membered aromatic heterocycle(s), and which may have a bond at a substitutable arbitrary position.

Example of the "heteroaryl" includes furyl (e.g.: 2-furyl or 3-furyl), thienyl (e.g.: 2-thienyl or 3-thienyl), pyrrolyl (e.g.: 1-pyrrolyl, 2-pyrrolyl or 3-pyrrolyl), imidazolyl (e.g.: 1-imidazolyl, 2-imidazolyl or 4-imidazolyl), pyrazolyl (e.g.: 1-pyrazolyl, 3-pyrazolyl or 4-pyrazolyl), triazolyl (e.g.: 1,2,4-triazole-1-yl, 1,2,4-triazole-3-yl or 1,2,4-triazole-4-yl), tetrazolyl (e.g.: 1-tetrazolyl, 2-tetrazolyl or 5-tetrazolyl), oxazolyl (e.g.: 2-oxazolyl, 4-oxazolyl or 5-oxazolyl), isoxazolyl (e.g.: 3-isoxazolyl, 4-isoxazolyl or 5-isoxazolyl), thiazolyl (e.g.: 2-thiazolyl, 4-thiazolyl or 5-thiazolyl), thiadiazolyl, isothiazolyl (e.g.: 3-isothiazolyl, 4-isothiazolyl or 5-isothiazolyl), pyridyl (e.g.: 2-pyridyl, 3-pyridyl or 4-pyridyl), pyridazinyl (e.g.: 3-pyridazinyl or 4-pyridazinyl), pyrimidinyl (e.g.: 2-pyrimidinyl, 4-pyrimidinyl or 5-pyrimidinyl), furazanyl (e.g.: 3-furazanyl), pyrazinyl (e.g.: 2-pyrazinyl), oxadiazolyl (e.g.: 1,3,4-oxadiazole-2-yl), benzofuryl (e.g.: 2-benzo[b]furyl, 3-benzo[b]furyl, 4-benzo[b]furyl, 5-benzo[b]furyl, 6-benzo[b]furyl or 7-benzo[b]furyl), benzothienyl (e.g.: 2-benzo[b]thienyl, 3-benzo[b]thienyl, 4-benzo[b]thienyl, 5-benzo[b]thienyl, 6-benzo[b]thienyl or 7-benzo[b]thienyl), benzimidazolyl (e.g.: 1-benzimidazolyl, 2-benzimidazolyl, 4-benzimidazolyl or 5-benzimidazolyl), benzothiazolyl, dibenzofuryl, benzoxazolyl, quinoxalinyl (e.g.: 2-quinoxalinyl, 5-quinoxalinyl or 6-quinoxalinyl), cinnolinyl (e.g.: 3-cinnolinyl, 4-cinnolinyl, 5-cinnolinyl, 6-cinnolinyl, 7-cinnolinyl or 8-cinnolinyl), quinazolinyl (e.g.: 2-quinazolinyl, 4-quinazolinyl, 5-quinazolinyl, 6-quinazolinyl, 7-quinazolinyl or 8-quinazolinyl), quinolyl (e.g.: 2-quinolyl, 3-quinolyl, 4-quinolyl, 5-quinolyl, 6-quinolyl, 7-quinolyl or 8-quinolyl), phthalazinyl (e.g.: 1-phthalazinyl, 5-phthalazinyl or 6-phthalazinyl), isoquinolyl (e.g.: 1-isoquinolyl, 3-isoquinolyl, 4-isoquinolyl, 5-isoquinolyl, 6-isoquinolyl, 7-isoquinolyl or 8-isoquinolyl), puryl, pteridinyl (e.g.: 2-pteridinyl, 4-pteridinyl, 6-pteridinyl or 7-pteridinyl), carbazolyl, phenanthridinyl, acridinyl (e.g.: 1-acridinyl, 2-acridinyl, 3-acridinyl, 4-acridinyl or 9-acridinyl), indolyl (e.g.: 1-indolyl, 2-indolyl, 3-indolyl, 4-indolyl, 5-indolyl, 6-indolyl or 7-indolyl), isoindolyl, phenadinyl (e.g.: 1-phenadinyl or 2-phenadinyl), phenothiadinyl (e.g.: 1-phenothiadinyl, 2-phenothiadinyl, 3-phenothiadinyl or 4-phenothiadinyl) or the like.

"Heterocycle" means a nonaromatic heterocyclic group which may contain 1 to 4 oxygen, sulfur and/or nitrogen atom(s) in the ring, and may have a bond at a substitutable arbitrary position. Moreover, the nonaromatic heterocyclic group can be bridged with a C1 to C4 alkyl chain, or can be fused with cycloalkane (5- to 6-membered ring is preferable) or benzene ring. Heterocycle can be saturated or unsaturated as long as it is non-aromatic. Preferable is a 5- to 8-membered ring. Example includes 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperadinyl, 2-piperadinyl, 2-morpholinyl, 3-morpholinyl, morpholino, tetrahydropyranyl, the following groups or the like:

[Formula 31]

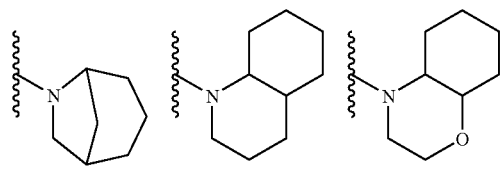

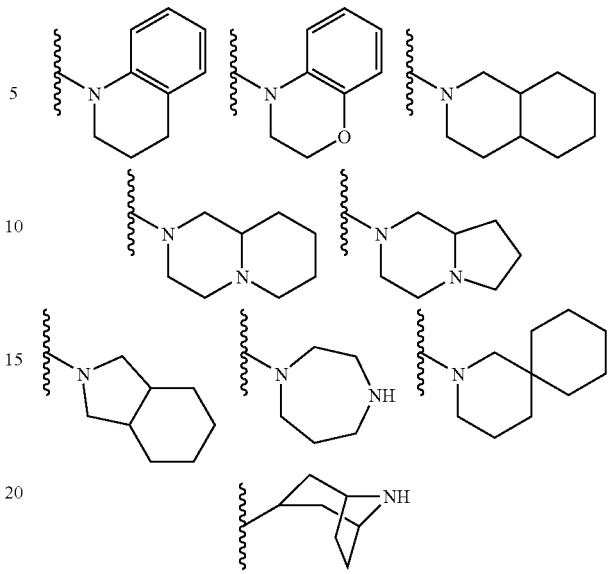

The alkyl part of "alkyloxy", "alkylsulfonyl", "alkyloxycarbonyl", "alkylcarbonyl" and "alkoxy" means the above "alkyl".

The cycloalkyl part of "cyclo alkylsulfonyl", "cycloalkyloxycarbonyl" and "cycloalkylcarbonyl" means the above "cycloalkyl".

The aryl part of "arylsulfonyl", "aryloxycarbonyl" and "arylcarbonyl" means the above "aryl".

The heteroaryl part of "heteroarylsulfonyl", "heteroaryloxycarbonyl" and "heteroarylcarbonyl" means the above "heteroaryl".

The heterocycle part of "heterocyclesulfonyl", "heterocycleoxycarbonyl" and "heterocyclecarbonyl" means the above "heterocycle."

"A ring formed by taking together $R^a$ and $R^b$ with the adjacent carbon atom to which they are attached" means a 3- to 15-membered saturated or unsaturated hydrocarbon ring or a 3- to 15-membered saturated or unsaturated hetero ring containing 1 to 4 oxygen, sulfur, and/or nitrogen atom(s) in said hydrocarbon ring. Preferable is nonaromatic ring, example includes cyclopropane, cyclobutane, cyclopentane, cyclohexane, cycloheptane, cyclooctane, cyclopropene, cyclobutene, cyclopentene, cyclohexene, cycloheptene, a saturated or unsaturated hetero ring containing 1 to 4 oxygen, sulfur, and/or nitrogen atom(s) in the above hydrocarbon ring.

For example, as a group of the formula: —C($R^a R^b$)—, wherein $R^a$ and $R^b$ taken together with the adjacent carbon atom to which they are attached may form an optionally substituted ring, the following groups are exemplified.

[Formula 32]

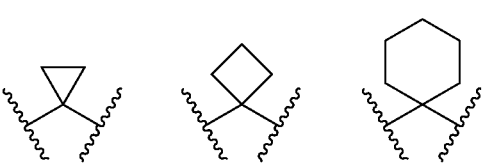

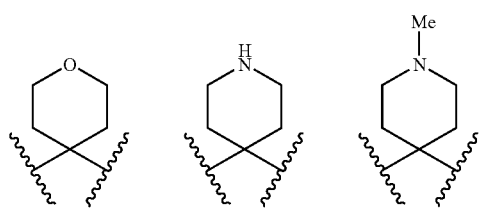

"A ring formed by taking together $R^g$ and $R^h$ with the adjacent nitrogen atom to which they are attached" and "a ring formed by taking together $R^i$ and $R^j$ with the adjacent nitrogen atom to which they are attached" mean 3- to 15-membered nonaromatic hetero ring which may contain 1 to 4 oxygen, sulfur, and/or nitrogen atom(s) besides the above nitrogen atom in the ring. Moreover, the nonaromatic hetero ring can be bridged with a C1 to C4 alkyl chain, or can be fused with cycloalkane (5- to 6-membered ring is preferable) or benzene ring. The ring can be saturated or unsaturated as long as it is nonaromatic. Preferable is a 5- to 8-membered ring. For example, as a group of the formula: —C(=O)—NR$^g$R$^h$, wherein R$^g$ and R$^h$ taken together with the adjacent nitrogen atom to which they are attached may form an optionally substituted ring and a group of the formula: —NR$^i$R$^j$, wherein R$^i$ and R$^j$ taken together with the adjacent nitrogen atom to which they are attached may form an optionally substituted ring, 1-pyrrolinyl, 1-pyrrolidinyl, 1-imidazolinyl, 1-imidazolidinyl, 1-pyrazolinyl, 1-pyrazolidinyl, piperidino, morpholino and the following groups are exemplified.

[Formula 33]

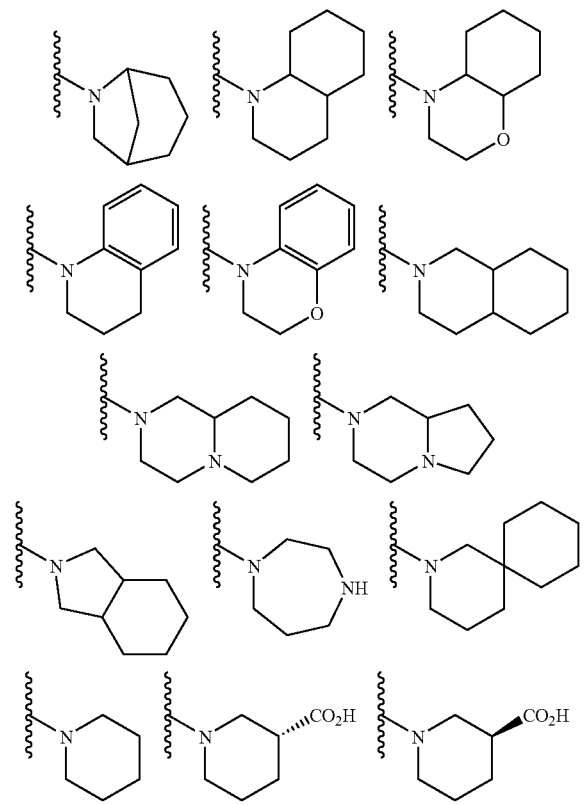

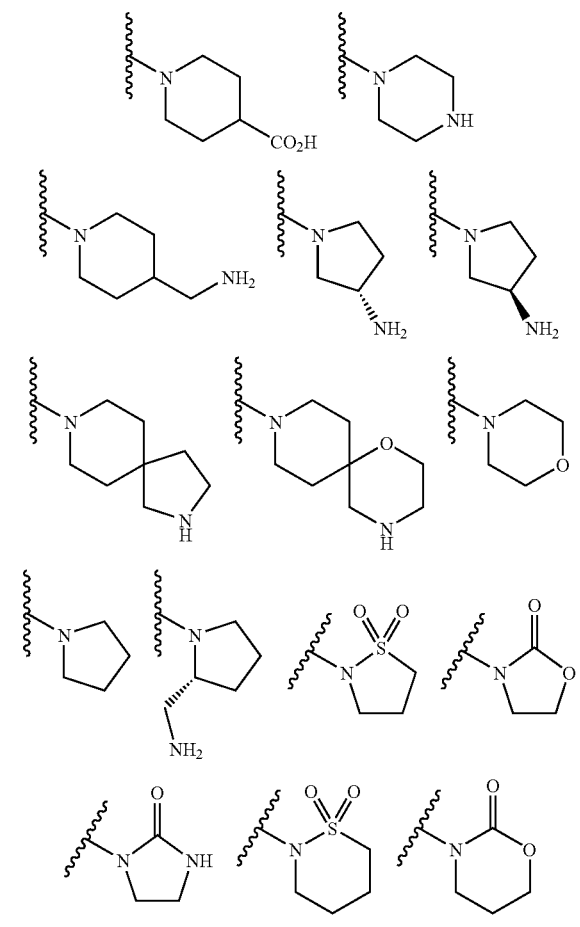

"A ring formed by taking together $R^{5A}$ and $R^{6A}$ with the adjacent nitrogen atom to which they are attached" and "a ring formed by taking together $R^7$ and $R^8$ with the adjacent nitrogen atom to which they are attached" mean 3- to 15-membered aromatic hetero ring or nonaromatic hetero ring which may contain 1 to 4 oxygen, sulfur, and/or nitrogen atom(s) besides the above nitrogen atom in the ring. The ring includes monocycle or fused ring, for example can be fused with cycloalkane (5- to 6-membered ring is preferable) or benzene ring. Moreover, the nonaromatic hetero ring can be bridged with a C1 to C4 alkyl chain. 5- to 8-membered ring is preferable. For example, the following examples are included:

[Formula 34]

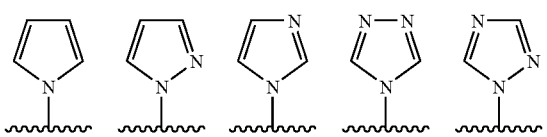

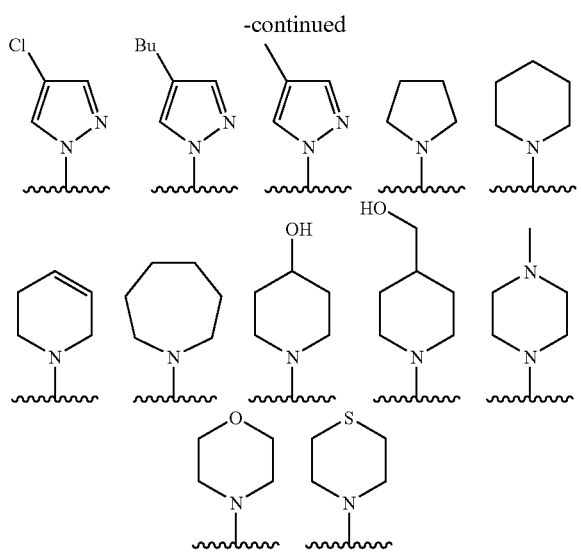

"optionally substituted alkyl", "optionally substituted alkenyl", "optionally substituted alkynyl", "optionally substituted cycloalkyl", "optionally substituted cycloalkenyl", "optionally substituted aryl", "optionally substituted heteroaryl", "optionally substituted heterocycle", optionally substituted alkylsulfonyl, optionally substituted cycloalkylsulfonyl, optionally substituted arylsulfonyl, optionally substituted heteroarylsulfonyl, optionally substituted heterocycle sulfonyl, optionally substituted alkyloxy, optionally substituted acyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, "a ring formed by taking together $R^a$ and $R^b$ with the adjacent carbon atom to which they are attached", "a ring formed by taking together $R^g$ and $R^h$ with the adjacent nitrogen atom to which they are attached", "a ring formed by taking together $R^i$ and $R^j$ with the adjacent nitrogen atom to which they are attached", "a ring formed by taking together $R^{5A}$ and $R^{6A}$ with the adjacent nitrogen atom to which they are attached" and "a ring formed by taking together $R^7$ and $R^8$ with the adjacent nitrogen atom to which they are attached" may be substituted with 1 to 4 substituent(s) selected from a group consisting of, for example, hydroxy, carboxy, halogen, halogenated alkyl (e.g.: —$CF_3$, —$CH_2CF_3$ or —$CH_2CCl_3$), nitro, nitroso, cyano,
alkyl (e.g.: methyl, ethyl, isopropyl or tert-butyl),
alkenyl (e.g.: vinyl), alkynyl (e.g.: ethynyl),
cycloalkyl (e.g.: cyclopropyl or adamantyl), hydroxyalkyl (e.g.: hydroxymethyl),
cycloalkylalkyl (e.g.: cyclohexylmethyl or adamantylmethyl),
cycloalkenyl (e.g.: cyclopropenyl), aryl (e.g.: phenyl or naphthyl),
arylalkyl (e.g.: benzyl or phenethyl), heteroaryl (e.g.: pyridyl or furyl),
heteroarylalkyl (e.g.: pyridylmethyl), heterocycle (e.g.: piperidyl), heterocyclealkyl (e.g.: morpholylmethyl), alkyloxy (e.g.: methoxy, ethoxy, propoxy or butoxy),
halogenated alkyloxy (e.g.: $OCF_3$), alkenyloxy (e.g.: vinyloxy or allyloxy), aryloxy (e.g.: phenyloxy), alkyloxycarbonyl (e.g.: methoxycarbonyl, ethoxycarbonyl or tert-butoxycarbonyl), arylalkyloxy (e.g.: benzyloxy), amino (e.g.: alkylamino (e.g.: methylamino, ethylamino or dimethylamino), acylamino (e.g.: acetylamino or benzoylamino), arylalkylamino (e.g.: benzylamino or tritylamino), hydroxyamino, alkylaminoalkyl (e.g.: diethylaminomethyl), sulfamoyl and the like.

The alkyl part of "hydroxyalkyl" means the above "alkyl".

The alkenyl part of "alkenyloxy" means the above "alkenyl".

The arylalkyl part of "arylalkyloxy" means the above "arylalkyl".

The aryl part of "aryloxy" means the above "aryl".

The alkyl part and the halogen part of "halogenated alkyl", "halogenated alkyloxy" and "halogenated alkoxy" are the same as the above.

Example of a substituent of "optionally substituted amino", "optionally substituted carbamoyl", "optionally substituted thiocarbamoyl, and "optionally substituted sulfamoyl" includes alkyl, alkenyl, aryl, heteroaryl, alkylcarbonyl, arylcarbonyl, heteroarylcarbonyl, heterocyclecarbonyl, alkyloxycarbonyl, aryloxycarbonyl, heteroaryloxycarbonyl, heterocycleoxycarbonyl, sulfamoyl, alkylsulfonyl, carbamoyl, cycloalkylsulfonyl, arylsulfonyl, heteroarylsulfonyl, heterocyclesulfonyl, acyl, hydroxy, sulfonyl, sulfinyl, amino or the like.

Among the present compound, the following embodiments are preferable.

Ring A is a group represented by the formula:

[Formula 35]

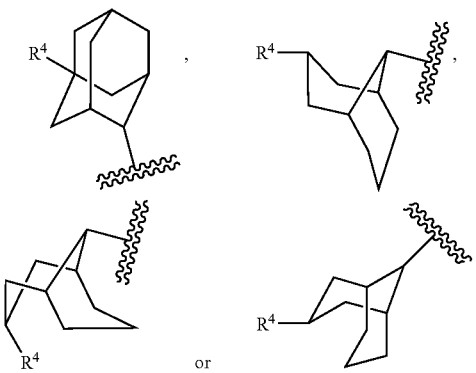

Ring A is preferably a group represented by the formula:

[Formula 36]

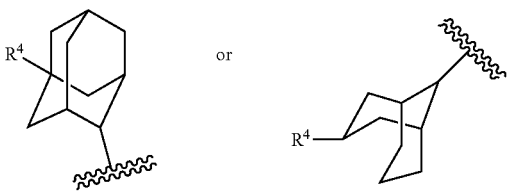

Especially Ring A is preferably a group represented by the formula:

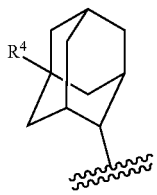

[Formula 37]

Ring A includes each isomer of syn and anti.

Ring B is optionally substituted heteroaryl, provided that optionally substituted isoxazolyl is excluded, or optionally substituted heterocycle.

Preferable is furyl, thienyl, pyrrolyl, pyrazolyl, triazolyl, oxazolyl, thiazolyl, isothiazolyl, pyridyl, morpholino, morpholinyl, piperidyl, piperidino, piperadinyl, pyrrolidinyl or tetrahydrothienyl.

Especially, Ring B is preferably pyrazolyl.

Moreover, Ring B may have substituents other than $R^2$ and $R^3$.

$R^1$ is hydrogen or optionally substituted alkyl. Preferable is hydrogen, methyl, ethyl, n-propyl or isopropyl. Especially, hydrogen is preferred.

$R^2$ is $-OR^5$, $-SR^5$, halogen, halogenated alkyl, halogenated alkoxy, hydroxy, cyano, nitro, carboxy, optionally substituted alkyl, optionally substituted alkenyl, optionally substituted alkynyl, optionally substituted aryl, optionally substituted cycloalkyl, optionally substituted cycloalkenyl, optionally substituted heteroaryl, optionally substituted heterocycle, a group represented by the formula: $-NR^{5A}R^{6A}$, wherein $R^{5A}$ and $R^{6A}$ are each independently hydrogen, hydroxy, alkoxy, optionally substituted alkyl, optionally substituted alkenyl, optionally substituted carbamoyl, optionally substituted aryl, optionally substituted cycloalkyl, optionally substituted cycloalkenyl, optionally substituted heteroaryl or optionally substituted heterocycle, or $R^{5A}$ and $R^{6A}$ taken together with the adjacent nitrogen atom to which they are attached may form an optionally substituted ring, a group represented by the formula: $-S(=O)x-R^{7A}$, wherein x is an integer of 1 or 2, $R^{7A}$ is optionally substituted alkyl, optionally substituted alkenyl, optionally substituted aryl, optionally substituted cycloalkyl, optionally substituted cycloalkenyl, optionally substituted heteroaryl or optionally substituted heterocycle, a group represented by the formula: $-C(=O)NR^{5A}R^{6A}$, wherein $R^{5A}$ and $R^{5A}$ are as defined in the above, or a group represented by the formula: $-(CR^{8A}R^{9A})y-O-(CR^{10A}R^{11A})z-CR^{12A}R^{13A}R^{14A}$, wherein y and z are each independently integer of 0 to 5, $R^{8A}$, $R^{9A}$, $R^{10A}$, $R^{11A}$, $R^{12A}$, $R^{13A}$ and $R^{14A}$ are each independently hydrogen, hydroxy, halogen, halogenated alkyl, halogenated alkoxy, alkoxy, cyano, carboxy, optionally substituted alkyl, optionally substituted alkenyl, optionally substituted aryl, optionally substituted cycloalkyl, optionally substituted cycloalkenyl, optionally substituted heteroaryl or optionally substituted heterocycle.

$R^2$ is preferably $-OR^5$, $-SR^5$, halogenated alkyl, cyano, optionally substituted alkyl, optionally substituted aryl, optionally substituted heteroaryl, a group represented by the formula: $-NR^{5A}R^{6A}$, or a group represented by the formula: $-(CR^{8A}R^{9A})y-O-(CR^{10A}R^{11A})z-CR^{12A}R^{13A}R^{14A}$, More preferable is $-OR^5$ or $-SR^5$.

Especially, preferable is $-OR^5$.

$R^{5A}$ and $R^{6A}$ are each independently hydrogen, hydroxy, alkoxy, optionally substituted alkyl, optionally substituted alkenyl, optionally substituted carbamoyl, optionally substituted aryl, optionally substituted cycloalkyl, optionally substituted cycloalkenyl, optionally substituted heteroaryl or optionally substituted heterocycle, or $R^{5A}$ and $R^{6A}$ taken together with the adjacent nitrogen atom to which they are attached may form an optionally substituted ring.

Preferable is hydrogen, optionally substituted alkyl or optionally substituted carbamoyl, or an optionally substituted ring formed by taking $R^{5A}$ and $R^{6A}$ together with the adjacent nitrogen atom to which they are attached.

x is an integer of 1 or 2.

$R^{7A}$ is optionally substituted alkyl, optionally substituted alkenyl, optionally substituted aryl, optionally substituted cycloalkyl, optionally substituted cycloalkenyl, optionally substituted heteroaryl or optionally substituted heterocycle.

$R^{8A}$, $R^{9A}$, $R^{10A}$, $R^{11A}$, $R^{12A}$, $R^{13A}$ and $R^{14A}$ are each independently hydrogen, hydroxy, halogen, halogenated alkyl, halogenated alkoxy, alkoxy, cyano, carboxy, optionally substituted alkyl, optionally substituted alkenyl, optionally substituted aryl, optionally substituted cycloalkyl, optionally substituted cycloalkenyl, optionally substituted heteroaryl or optionally substituted heterocycle.

Preferable is hydrogen, hydroxy, halogen, optionally substituted alkyl.

More preferable is hydrogen.

y is an integer of 0 to 5.

Preferable is an integer of 0 to 3. More preferable is 1.

z is an integer of 0 to 5.

Preferable is an integer of 0 to 3. More preferable is 0.

$R^3$ is optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: $-CH=CH-C(R^aR^b)-R^c-R^d$ or a group represented by the formula: $-(CR^eR^f)_m-C(R^aR^b)-R^c-R^d$, wherein $R^a$ and $R^b$ are each independently hydrogen, optionally substituted alkyl or halogen, or $R^a$ and $R^b$ taken together with the adjacent carbon atom to which they are attached may form an optionally substituted ring, $R^c$ is $-(CH_2)n-$, wherein n is an integer of 0 to 3, $R^d$ is hydrogen, halogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: $-C(=O)-NR^gR^h$ or a group represented by the formula: $-NR^iR^j$, $R^e$ and $R^f$ are each independently hydrogen, halogen or optionally substituted alkyl, $R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxy, optionally substituted carbamoyl or $R^g$ and $R^h$ taken together with the adjacent nitrogen atom to which they are attached may form an optionally substituted ring, $R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocycle sulfonyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, optionally substituted sulfamoyl or $R^i$ and $R^j$ taken together with the adjacent nitrogen atom to which they are attached may form an optionally substituted ring.

$R^3$ is preferably a group represented by the formula: —CH=CH—C($R^aR^b$)—$R^c$—$R^d$ or a group represented by the formula: —(C$R^eR^f$)$_m$—C($R^aR^b$)—$R^c$—$R^d$.

More preferably $R^3$ is a group represented by the formula: —CH=CH—C($R^aR^b$)—$R^c$—$R^d$.

$R^a$ and $R^b$ are each independently hydrogen, optionally substituted alkyl or halogen, or $R^a$ and $R^b$ taken together with the adjacent carbon atom to which they are attached may form an optionally substituted ring.

Preferable is hydrogen, optionally substituted alkyl or halogen.

Especially, $R^a$ and $R^b$ are preferably optionally substituted alkyl.

$R^c$ is —(CH$_2$)n-, wherein n is an integer of 0 to 3.

n is preferably 0 or 1.

$R^d$ is hydrogen, halogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, a group represented by the formula: —C(=O)—NR$^g$R$^h$ or a group represented by the formula: —NR$^i$R$^j$, wherein $R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocycle sulfonyl, optionally substituted alkyloxy, optionally substituted carbamoyl or $R^g$ and $R^h$ taken together with the adjacent nitrogen atom to which they are attached may form an optionally substituted ring, $R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocycle sulfonyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, optionally substituted sulfamoyl or $R^i$ and $R^j$ taken together with the adjacent nitrogen atom to which they are attached may form an optionally substituted ring.

$R^d$ is preferably halogen, hydroxy, cyano, optionally substituted heteroaryl, a group represented by the formula: —C(=O)—NR$^g$R$^h$ or a group represented by the formula: —NR$^i$R$^j$.

Especially, preferable is a group represented by the formula: —C(=O)—NR$^g$R$^h$ or a group represented by the formula: —NR$^i$R$^j$.

$R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxy, optionally substituted carbamoyl or $R^g$ and $R^h$ taken together with the adjacent nitrogen atom to which they are attached may form an optionally substituted ring.

Preferable is hydrogen, optionally substituted carbamoyl, optionally substituted alkyl or optionally substituted alkyloxy.

$R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, optionally substituted sulfamoyl or $R^i$ and $R^j$ taken together with the adjacent nitrogen atom to which they are attached may form an optionally substituted ring.

Preferable is hydrogen, optionally substituted alkyloxycarbonyl, optionally substituted alkylcarbonyl, optionally substituted alkylsulfonyl, optionally substituted cycloalkylcarbonyl, optionally substituted alkyl, optionally substituted heterocyclecarbonyl.

$R^e$ and $R^f$ are each independently hydrogen, halogen or optionally substituted alkyl.

Preferable is hydrogen or halogen. Especially, preferable is hydrogen.

$R^4$ is optionally substituted alkyl, optionally substituted alkenyl, —$OR^6$, —$CONR^7R^8$, —$NR^9CONR^7R^8$, —$NR^9SO_2NR^7R^8$, —$(CR^{10}R^{11})_pOH$, —$(CR^{10}R^{11})_pOCONR^7R^8$, —$NR^9COR^{12}$, —$NR^9C(=O)OR^{12}$, —$(CR^{10}R^{11})_pNR^9COR^{12}$, —$C(=O)NR^9OR^{12}$, —$CONR^9CONR^7R^8$, —CN, —COOH, halogen or —$NR^7R^8$.

Preferable is —$OR^6$, —$CONR^7R^8$, —$NR^9CONR^7R^8$, —$(CR^{10}R^{11})_pOH$, —$(CR^{10}R^{11})_pOCONR^7R^8$, —$NR^9COR^{12}$, —CN, —$NR^9C(=O)OR^{12}$, —$(CR^{10}R^{11})_pNR^9COR^{12}$, —$C(=O)NR^9OR^{12}$, —$CONR^9CONR^7R^8$.

Especially, preferable is —$OR^6$ or —$(CR^{10}R^{11})_pOCONR^7R^8$.

$R^5$ is optionally substituted alkyl, optionally substituted alkenyl, optionally substituted cycloalkyl, optionally substituted aryl, optionally substituted heteroaryl or optionally substituted heterocycle.

Preferable is optionally substituted alkyl, optionally substituted aryl, optionally substituted heteroaryl or optionally substituted heterocycle.

Especially, preferable is optionally substituted alkyl.

$R^6$ is hydrogen, optionally substituted alkyl, optionally substituted alkenyl, optionally substituted cycloalkyl, optionally substituted aryl, optionally substituted heteroaryl, optionally substituted heterocycle, —$SO_2R^5$, —$SO_2NR^7R^8$ or —$CONR^7R^8$.

Preferable is hydrogen or —$CONR^7R^8$.

$R^7$ and $R^8$ are each independently hydrogen, optionally substituted alkyl, optionally substituted cycloalkyl, optionally substituted aryl, optionally substituted heteroaryl, optionally substituted heterocycle or —$SO_2R^5$, or $R^7$ and $R^8$ taken together with the adjacent nitrogen atom to which they are attached may form an optionally substituted ring.

Preferable is hydrogen or optionally substituted alkyl.

Especially, preferable is hydrogen.

$R^9$ is hydrogen or optionally substituted alkyl. Preferable is hydrogen.

$R^{10}$ and $R^{11}$ are each independently hydrogen, halogen or optionally substituted alkyl.

Preferable is hydrogen.

$R^{12}$ is optionally substituted alkyl, optionally substituted cycloalkyl, optionally substituted aryl, optionally substituted heteroaryl or optionally substituted heterocycle.

Preferable is optionally substituted alkyl.

m and p are each independently integer of 1 to 3. m is preferably 1 or 2. p is preferably 1.

As a pharmaceutically acceptable salt of the present compound, the following salts can be included.

As a basic salt, example includes alkali metal salt such as sodium salt or potassium salt; alkaline earth metal salt such as calcium salt or magnesium salt; ammonium salt; aliphatic amine salt such as trimethylamine salt, triethylamine salt, dicyclohexylamine salt, ethanolamine salt, diethanolamine salt, triethanolamine salt, procaine salt, meglumine salt, diethanolamine salt or ethylenediamine salt; aralkylamine salt such as N,N-dibenzylethylenediamine salt or benethamine salt; heterocyclic aromatic amine salt such as pyridine salt, picoline salt, quinoline salt, or isoquinoline salt; quaternary ammonium salt such as tetramethylammonium salt, tetraethylammonium salt, benzyltrimethylammonium salt, benzyltriethylammonium salt, benzyltributylammonium salt, methyltrioctylammonium salt, or tetrabutylammonium salt; basic amino acid salt such as arginine salt or lysine salt or the like.

As an acidic salt, example includes inorganic acid salt such as hydrochloride, sulfate, nitrate, phosphate, carbonate, hydrogencarbonate, or perchlorate; organic acid salt such as acetate, propionate, lactate, maleate, fumarate, tartrate, malate, citrate or ascorbate; sulfonate such as methanesulfonate, isethionate, benzenesulfonate or p-toluenesulfonate; acidic amino acid salt such as aspartate or glutamate or the like.

The term "solvate" means a solvate of a compound of the present invention or a pharmaceutically acceptable salt thereof, and example includes alcohol (e.g.: ethanol) solvate, hydrate or the like. Example of hydrate includes monohydrate, dihydrate or the like.

A general method for producing the present compound is exemplified below. Also extraction, purification and the like may be conducted in a procedure executed in usual organic chemical experiment.

(Compounds wherein $R^2$=—$OR^5$)

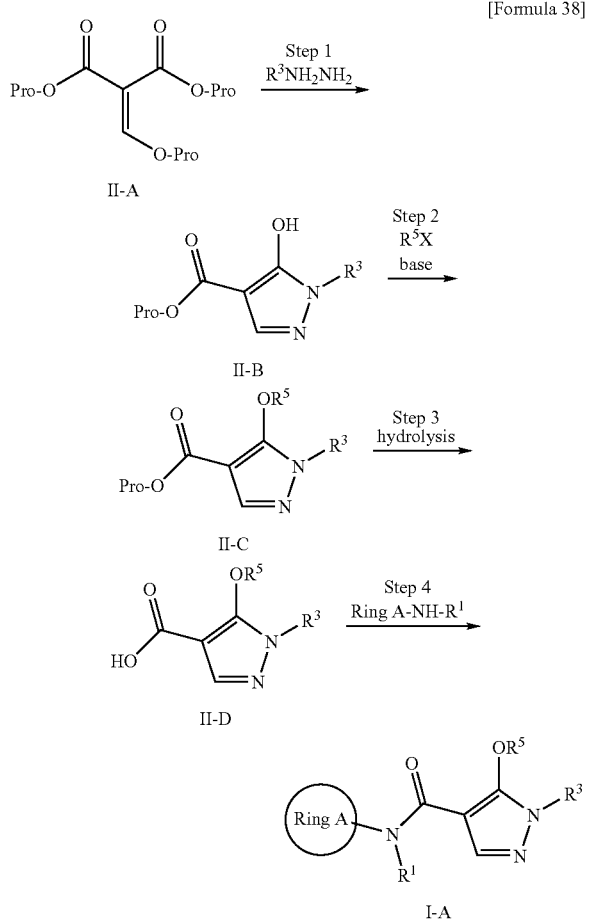

[Formula 38]

wherein each symbol in the above scheme has the same meaning as the above, and as to compound (II-A), a known compound can be used, or a compound derived from a known compound by a usual method can be used. Pro is a protecting group. As a protecting group, example includes an alkyl group or the like.

Step 1

Step 1 is a process for preparing the compound represented by the Formula (II-B) which comprises reacting the compound represented by the Formula (II-A) with hydrazine.

As a solvent, example includes N-dimethylformamide, dimethylsulfoxide, aromatic hydrocarbons (e.g., toluene, benzene, xylene or the like), saturated hydrocarbons (e.g., cyclohexane, hexane or the like), halogenated hydrocarbons (e.g., dichloromethane, chloroform, 1,2-dichloroethane or the like), ethers (e.g., tetrahydrofuran, diethylether, dioxane, 1,2-dimethoxyethane or the like), esters (e.g., methyl acetate, ethyl acetate or the like), ketones (e.g., acetone, methylethylketone or the like), nitriles (e.g., acetonitrile or the like), alcohols (e.g., methanol, ethanol, t-butanol or the like), water, a mixed solvent thereof or the like. Preferably, alcohols (e.g., methanol, ethanol, t-butanol or the like) can be used. More preferably, Pro-OH can be used. The reaction can be performed at a temperature ranging from room temperature to the temperature at which a solvent being used is refluxed, for 0.5 to 48 hours.

Step 2

Step 2 is a process for preparing the compound represented by the Formula (II-C) which comprises reacting the compound represented by the Formula (II-B) with the compound represented by the Formula $R^5X$ in the presence of a base. As a solvent, a solvent described in Step 1 can be used. Preferably, ketones (e.g., acetone, methylethylketone or the like) or N-dimethylformamide can be used.

As a base, example includes metal hydrides (e.g., sodium hydride or the like), metal hydroxides (e.g., sodium hydroxide, potassium hydroxide, lithium hydroxide, barium hydroxide or the like), metal carbonates (e.g., sodium carbonate, calcium carbonate, potassium carbonate, cesium carbonate or the like), metal alkoxides (e.g., sodium methoxide, sodium ethoxide, potassium t-butoxide or the like), sodium hydrogen carbonate, metal sodium, organic amines (e.g., triethylamine, diisopropylethylamine, DBU, 2,6-lutidine or the like), pyridine, alkyl lithiums (n-BuLi, sec-BuLi, tert-BuLi or the like) or the like. Preferably, metal carbonates (e.g., sodium carbonate, calcium carbonate, potassium carbonate, cesium carbonate or the like) can be used. The reaction can be performed at a temperature ranging from room temperature to the temperature at which a solvent being used is refluxed, for 0.5 to 48 hours.

Step 3

Step 3 is a process for preparing the compound represented by the Formula (II-D) which comprises hydrolyzing the compound represented by the Formula (II-C).

As a solvent, a solvent described in Step 1 can be used. Preferably, ethers (e.g., tetrahydrofuran, diethylether, dioxane, 1,2-dimethoxyethane or the like), alcohols (e.g., methanol, ethanol, t-butanol or the like), water, a mixed solvent thereof or the like can be used. As a base, a base described in Step 2 can be used. Preferably, metal hydroxides (e.g., sodium hydroxide, potassium hydroxide, lithium hydroxide, barium hydroxide or the like) can be used. The reaction can be performed at –20 to 40° C. for 0.5 to 24 hours.

Step 4

Step 4 is a process for preparing the compound represented by the Formula (I-A) which comprises reacting the compound represented by the Formula (II-D) with the compound represented by the Formula (Ring A-NH—$R^1$).

As a solvent, a solvent described in Step 1 can be used. Preferably, ethers (e.g., tetrahydrofuran, diethylether, dioxane, 1,2-dimethoxyethane or the like) or N-dimethylformamide can be used. As a base, a base described in Step 2 can be used. Preferably, organic amines (e.g., triethylamine, diisopropylethylamine, DBU, 2,6-lutidine or the like) can be used. 1-ethyl-3-(3'-dimethylaminopropyl)carbodiimide(WSCI) or 1,3-dicyclohexylcarbodiimide (DCCD) can be used as a condensing agent. N-hydroxybenzotriazole (HOBt) or N-hydroxysuccinimide (HOSu) can be used as an additive. The reaction can be performed at a temperature ranging from –20° C. to the temperature at which a solvent being used is refluxed, for 0.5 to 24 hours.

(Compounds wherein $R^2$=—$SR^5$)

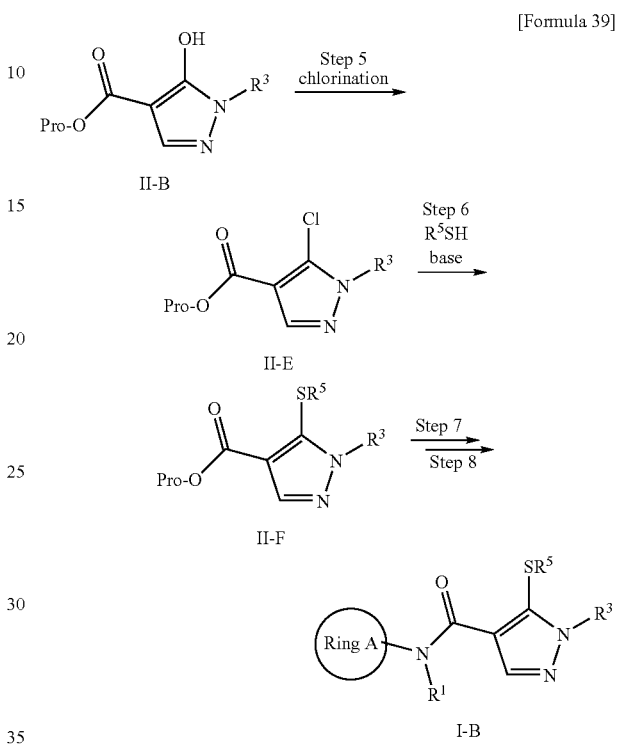

[Formula 39]

Step 5

Step 5 is a process for preparing the compound represented by the Formula (II-E) which comprises converting a hydroxy group in the compound represented by the Formula (II-B) into chlorine.

As a solvent, phosphoryl chloride (POCl$_3$) can be used. The reaction can be performed at a temperature ranging from –20° C. to the temperature at which phosphoryl chloride is refluxed, for 0.5 to 24 hours.

Step 6

Step 6 is a process for preparing the compound represented by the Formula (II-F) which comprises reacting the compound represented by the Formula (II-E) with the compound represented by the Formula $R^5SH$ in the presence of a base.

As a solvent, a solvent described in Step 1 can be used. Preferably, ketones (e.g., acetone, methylethylketone or the like) or N-dimethylformamide can be used. As a base, a base described in Step 2 can be used. Preferably, metal hydrides (e.g., sodium hydride or the like), metal carbonates (e.g., sodium carbonate, calcium carbonate, potassium carbonate, cesium carbonate or the like) or the like can be used. The reaction can be performed at a temperature ranging from room temperature to the temperature at which a solvent being used is refluxed, for 0.5 to 48 hours.

Step 7

Step 7 is a process for preparing the compound represented by the Formula (II-F) which comprises hydrolyzing the compound represented by the Formula (II-E)

The reaction can be performed under the same conditions as the above Step 3.

Step 8

Step 8 is a process for preparing the compound represented by the Formula (I-B) which comprises reacting the compound represented by the Formula (II-F) with the compound represented by the Formula (Ring A-NH—R$^1$).

The reaction can be performed under the same conditions as the above Step 4.

[Formula 40]

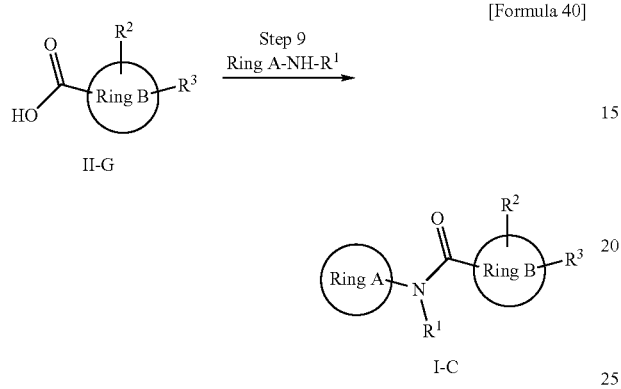

wherein each symbol in the above scheme has the same meaning as the above, and as to compound (II-G), a known compound can be used, or a compound derived from a known compound by a usual method can be used.

Step 9

Step 9 is a process for preparing the compound represented by the Formula (I-C) which comprises reacting the compound represented by the Formula (II-G) with the compound represented by the Formula (Ring A-NH—R$^1$).

The reaction can be performed under the same conditions as the above Step 4.

[Formula 41]

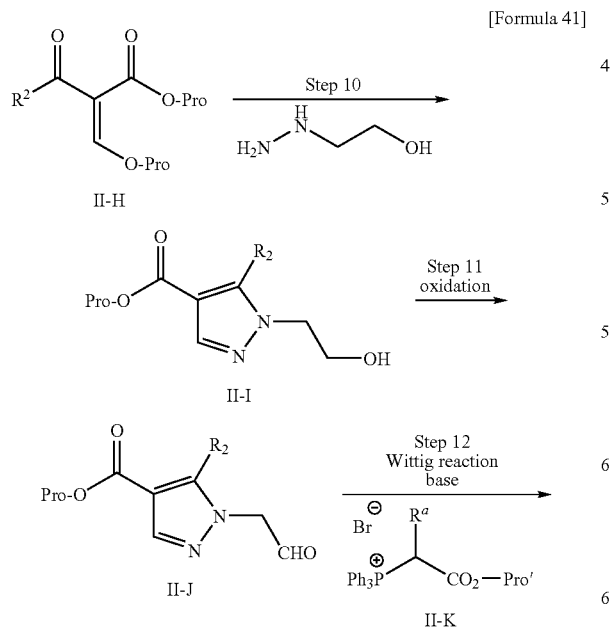

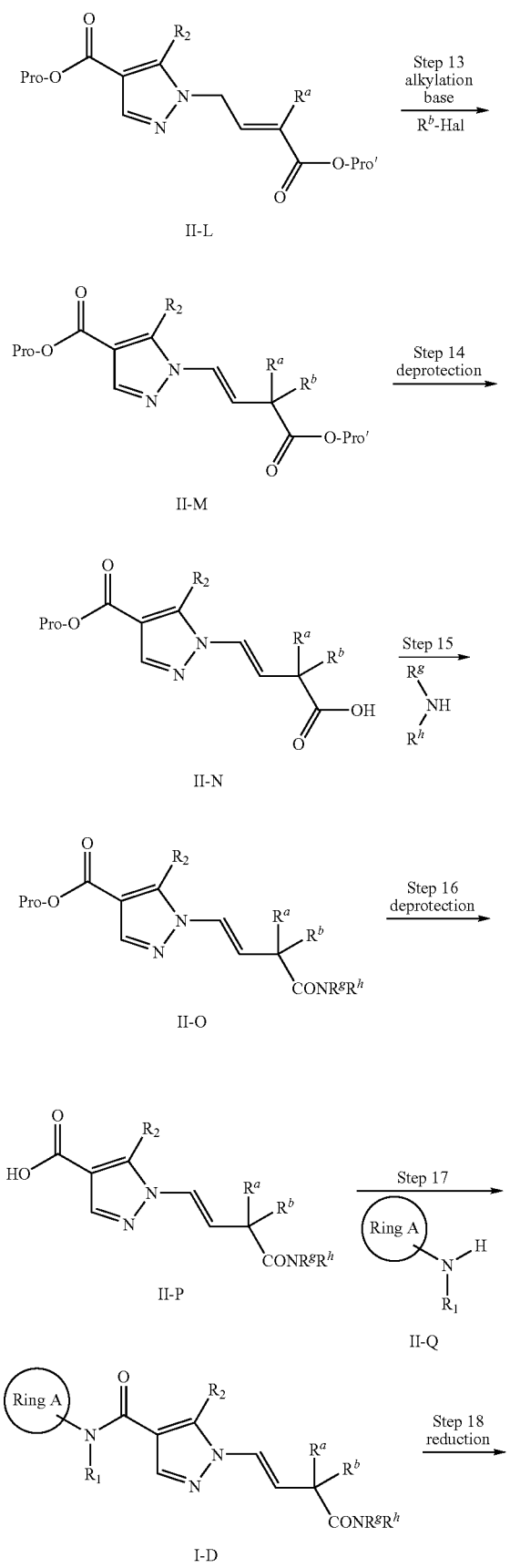

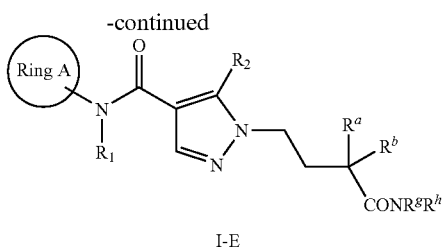

wherein each symbol in the above scheme has the same meaning as the above, and as to compound (II-H), a known compound can be used, or a compound derived from a known compound by a usual method can be used. Pro and Pro' are a protecting group. As Pro and Pro', example includes a methyl group, an ethyl group, a benzyl group, a benzoyl group, a t-butyl group or the like. Hal is halogen.

Step 10

Step 10 is a process for preparing the compound represented by the Formula (II-I) which comprises reacting the compound represented by the Formula (II-H) with hydrazine.

The reaction can be performed under the same conditions as the above Step 1.

Step 11

Step 11 is a process for preparing the compound represented by the Formula (II-J) which comprises oxidizing the compound represented by the Formula (II-I).

As a oxidant, IBX(2-iodoxybenzoic acid), metal salt or metal oxide of chrome, manganese, silver or the like, or organic oxidant can be used.

As a solvent, a solvent described in Step 1 can be used. Preferably, acetonitrile or esters (e.g., methyl acetate, ethyl acetate or the like) can be used.

The reaction can be performed at a temperature ranging from room temperature to the temperature at which a solvent being used is refluxed, for 0.5 to 24 hours.

The oxidation reaction can be performed under the conditions of Swern oxidation, TEMPO oxidation or the like.

Step 12

Step 12 is a process for preparing the compound represented by the Formula (II-L) which comprises subjecting the compound represented by the Formula (II-J) and the compound represented by the Formula (II-K) to Wittig reaction.

As a solvent, a solvent described in Step 1 can be used. Preferably, esters (e.g., methyl acetate, ethyl acetate or the like) or ethers (e.g., tetrahydrofuran, diethylether, dioxane, 1,2-dimethoxyethane or the like) can be used.

As a base, a base described in Step 2 can be used. Preferably, organic amines (e.g., triethylamine, diisopropylethylamine, DBU, 2,6-lutidine or the like) can be used. The reaction can be performed at −20 to 40° C. for 0.5 to 48 hours.

Step 13

Step 13 is a process for preparing the compound represented by the Formula (II-M) which comprises reacting the compound represented by the Formula (II-L) with the compound represented by the Formula $R^b$-Hal in the presence of a base.

As a solvent, a solvent described in Step 1 can be used. Preferably, ethers (e.g., tetrahydrofuran, diethylether, dioxane, 1,2-dimethoxyethane or the like) can be used.

As a base, a base described in Step 2 can be used. Preferably, metal alkoxides (e.g., sodium methoxide, sodium ethoxide, potassium t-butoxide or the like) or LDA can be used. The reaction can be performed at −78 to 40° C. for 0.5 to 24 hours.

Step 14

Step 14 is a process for preparing the compound represented by the Formula (II-N) which comprises deprotecting the compound represented by the Formula (II-M) under a strong acid condition.

For example, trifluoroacetic acid or surfuric acid can be used as a strong acid.

As a solvent, a solvent described in Step 1 can be used. Preferably, halogenated hydrocarbons (e.g., dichloromethane, chloroform, 1,2-dichloroethane or the like) can be used. The reaction can be performed at −78 to 40° C. for 0.5 to 24 hours.

Step 15

Step 15 is a process for preparing the compound represented by the Formula (II-O) which comprises reacting the compound represented by the Formula (II-N) with amine.

The reaction can be performed under the same conditions as the above Step 4.

Step 16

Step 16 is a process for preparing the compound represented by the Formula (II-P) which comprises deprotecting the compound represented by the Formula (II-O).

The reaction can be performed under the same conditions as the above Step 3.

Step 17

Step 17 is a process for preparing the compound represented by the Formula (I-D) which comprises reacting the compound represented by the Formula (II-P) with the compound represented by the Formula (II-Q).

The reaction can be performed under the same conditions as the above Step 4.

Step 18

Step 18 is a process for preparing the compound represented by the Formula (I-E) which comprises reducing the compound represented by the Formula (I-D).

The reaction can be performed by catalytic hydrogenation reaction using transition metal catalyst.

As a transition metal catalyst, platinum, palladium, rhodium, ruthenium, nickel or the like can be used.

As a solvent, a solvent described in Step 1 can be used. Preferably, alcohols (e.g., methanol, ethanol, t-butanol or the like), ethers (e.g., tetrahydrofuran, diethylether, dioxane, 1,2-dimethoxyethane or the like), water, a mixed solvent thereof or the like can be used. The reaction can be performed in the presence of hydrogen and a transition metal catalyst at 20 to 50° C. for 0.5 to 48 hours.

[Formula 42]

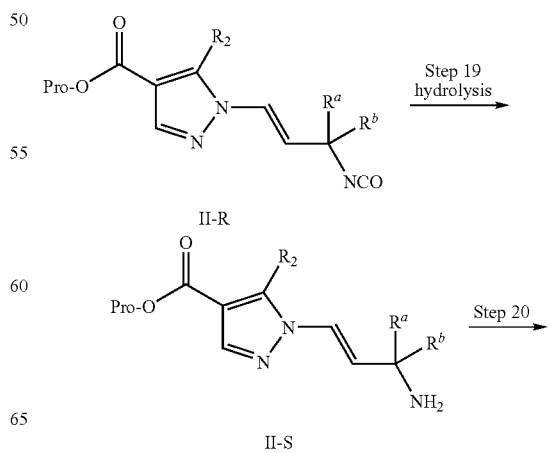

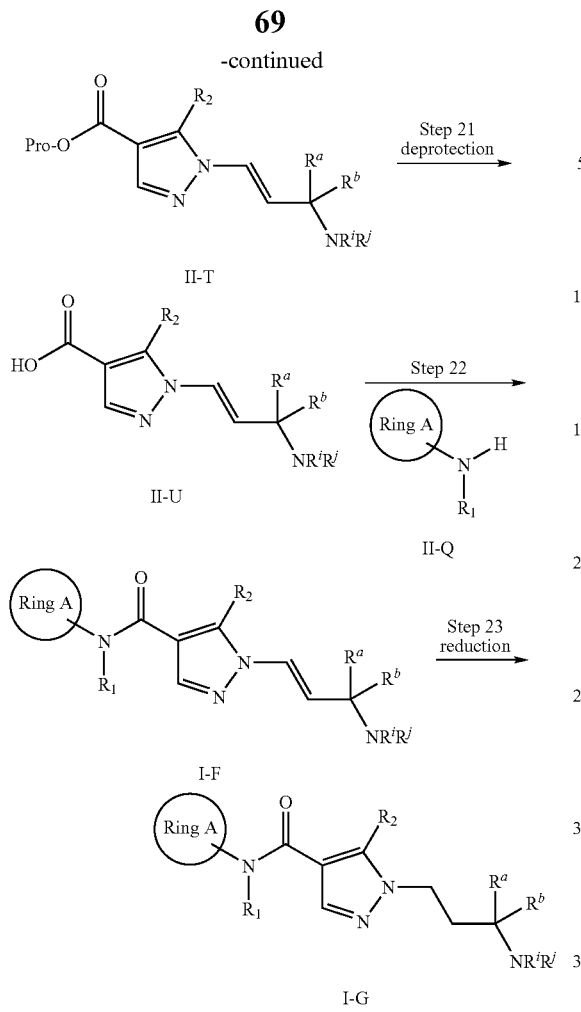

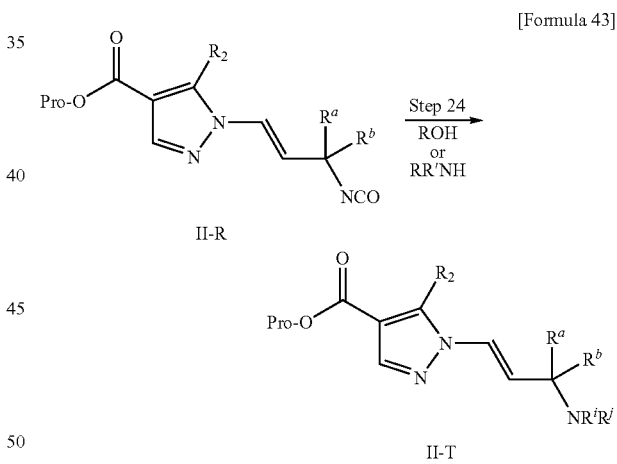

wherein each symbol in the above scheme has the same meaning as the above, and as to compound (II-R), a known compound can be used, or a compound derived from a known compound by a usual method can be used. Pro is a protecting group. As a protecting group, example includes a methyl group, an ethyl group, a benzyl group, a benzoyl group, a t-butyl group or the like.

Step 19

Step 19 is a process for preparing the compound represented by the Formula (II-S) which comprises subjecting the compound represented by the Formula (II-R) to acid hydrolysis.

As a solvent, a solvent described in Step 1 can be used. Preferably, water can be used. As an acid, strong acid such as sulfuric acid, nitric acid, hydrochloric acid or the like can be used. The reaction can be performed at −20 to 100° C. for 0.5 to 48 hours.

Step 20

Step 20 is a process for converting the compound represented by the Formula (II-S) into the compound represented by the Formula (II-T).

This process is a reaction process when one of $R^i$ and $R^j$ is hydrogen and the other of $R^i$ and $R^j$ is optionally substituted alkylsulfonyl, optionally substituted cycloalkylsulfonyl, optionally substituted arylsulfonyl, optionally substituted heteroarylsulfonyl, optionally substituted heterocycle sulfonyl, optionally substituted alkylcarbonyl, optionally substituted cycloalkylcarbonyl, optionally substituted arylcarbonyl, optionally substituted heteroarylcarbonyl or optionally substituted heterocyclecarbonyl. The reaction can be performed by reacting the compound represented by the Formula (II-S) with corresponding acid chloride, acid anhydride or sulfonyl chloride.

As a solvent, a solvent described in Step 1 can be used. Preferably, ethers (e.g., tetrahydrofuran, diethylether, dioxane, 1,2-dimethoxyethane or the like), N-dimethylformamide or halogenated hydrocarbons (e.g., dichloromethane, chloroform, 1,2-dichloroethane or the like) can be used.

As a base, a base described in Step 2 can be used. Preferably, organic amines (e.g., triethylamine, diisopropylethylamine, DBU, 2,6-lutidine or the like) or pyridine can be used.

The reaction can be performed at a temperature ranging from −20° C. to the temperature at which a solvent being used is refluxed, for 0.5 to 24 hours.

It is a process for preparing the compound represented by the Formula (II-U) which comprises deprotecting the compound represented by the Formula (II-T).

The reaction can be performed under the same conditions as the above Step 3.

It is a process for preparing the compound represented by the Formula (I-F) which comprises reacting the compound represented by the Formula (II-U) with the compound represented by the Formula (II-Q).

The reaction can be performed under the same conditions as the above Step 4.

It is a process for preparing the compound represented by the Formula (I-G) which comprises reducing the compound represented by the Formula (I-F).

The reaction can be performed under the same conditions as the above Step 18.

[Formula 43]

wherein each symbol in the above scheme has the same meaning as the above, and as to compound (II-R), a known compound can be used, or a compound derived from a known compound by a usual method can be used. Pro is a protecting group. As a protecting group, example includes a methyl group, an ethyl group, a benzyl group, a benzoyl group, a t-butyl group or the like.

Step 24

Step 24 is a process for converting the compound represented by the Formula (II-R) into the compound represented by the Formula (II-T).

This process is a reaction process when one of $R^i$ and $R^j$ is hydrogen and the other of $R^i$ and $R^j$ is optionally substituted carbamoyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl. The reaction can be performed by reacting the compound represented by the Formula (II-R) with corresponding alcohol or amine.

As a solvent, a solvent described in Step 1 can be used. Preferably, aromatic hydrocarbons (e.g., toluene, benzene, xylene or the like) or ethers (e.g., tetrahydrofuran, diethylether, dioxane, 1,2-dimethoxyethane or the like) can be used.

The reaction can be performed at a temperature ranging from −20° C. to the temperature at which a solvent being used is refluxed, for 0.5 to 24 hours.

compound represented by the Formula (II-N). The reaction can be performed by reacting the compound represented by the Formula (II-N) with ethyl chlorocarbonate to produce active ester, then reacting with reducing agent.

As a solvent, a solvent described in Step 1 can be used. Preferably, ethers (e.g., tetrahydrofuran, diethylether, dioxane, 1,2-dimethoxyethane or the like) can be used.

As a reducing agent, sodium triacetoxyhydroborate, sodium borohydride, lithium tetrahydroborate, pyridine borane complex, tetrahydrofuran borane complex, dimethyl sulfide-borane complex or 2-picoline borane complex can be used. Preferably, sodium borohydride can be used.

[Formula 44]

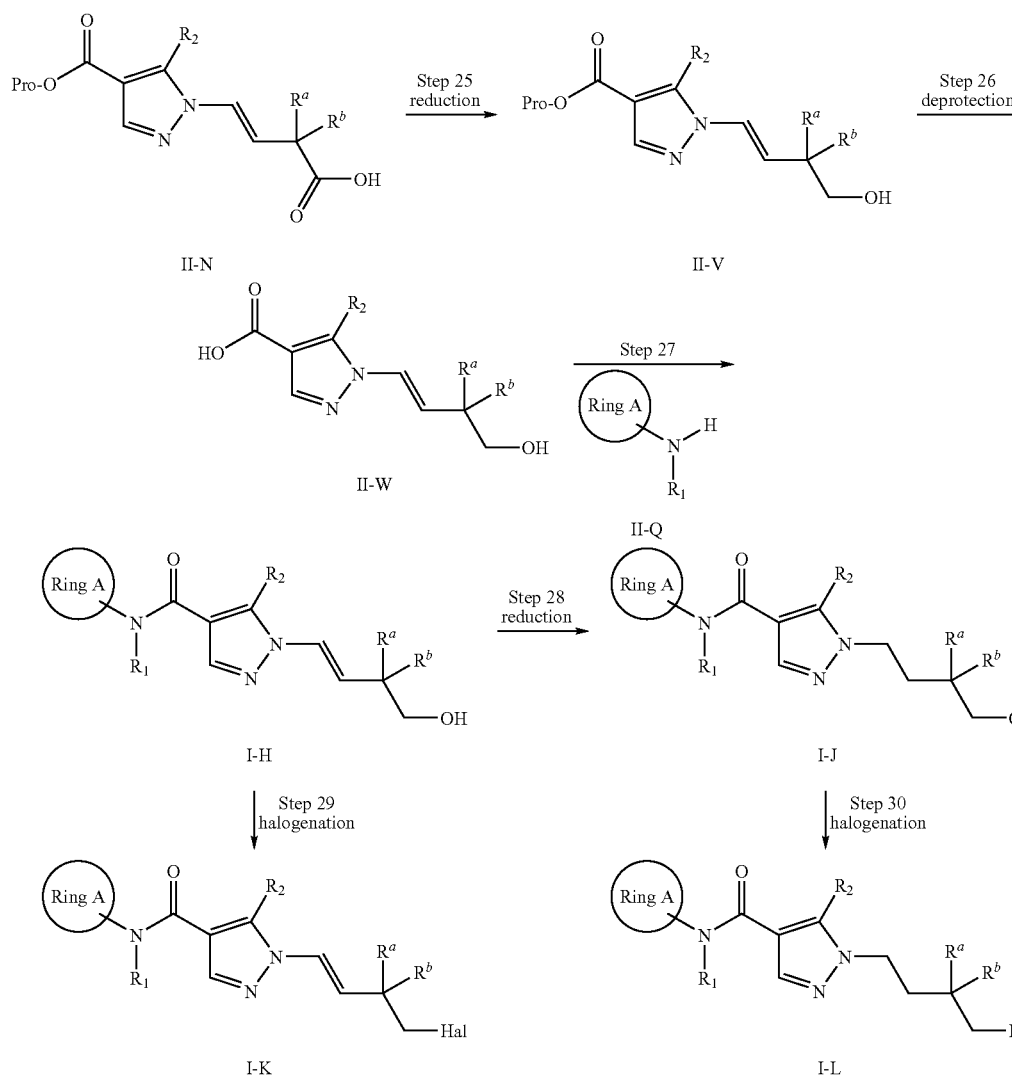

wherein each symbol in the above scheme has the same meaning as the above, and as to compound (II-N), a known compound can be used, or a compound derived from a known compound by a usual method can be used. Pro is a protecting group. As a protecting group, example includes a methyl group, an ethyl group, a benzyl group, a benzoyl group, a t-butyl group or the like. Hal is halogen.

Step 25

Step 25 is a process for preparing the compound represented by the Formula (II-V) which comprises reducing the The reaction can be performed at −20 to 50° C. for 0.5 to 24 hours.

Step 26

Step 26 is a process for preparing the compound represented by the Formula (II-W) which comprises deprotecting the compound represented by the Formula (II-V).

The reaction can be performed under the same conditions as the above Step 3.

Step 27

Step 27 is a process for preparing the compound represented by the Formula (I-H) which comprises reacting the compound represented by the Formula (II-W) with the compound represented by the Formula (II-Q).

The reaction can be performed under the same conditions as the above Step 4.

Step 28

Step 28 is a process for preparing the compound represented by the Formula (I-J) which comprises reducing the compound represented by the Formula (I-H).

The reaction can be performed under the same conditions as the above Step 18.

Step 29

Step 29 is a process for preparing the compound represented by the Formula (I-K) which comprises halogenating the compound represented by the Formula (I-H).

As a solvent, a solvent described in Step 1 can be used. Preferably, halogenated hydrocarbons (e.g., dichloromethane, chloroform, 1,2-dichloroethane or the like) can be used.

As a halogenating agent, DAST((diethylamino)sulfur trifluoride), NCS(N-chlorosuccinimide), NBS(N-bromosuccinimide), $CBr_4$, $PBr_3$ or $PBr_5$ can be used.

The reaction can be performed at a temperature ranging from −78° C. to the temperature at which a solvent being used is refluxed, for 0.5 to 24 hours.

Step 30

Step 30 is a process for preparing the compound represented by the Formula (I-L) which comprises halogenating the compound represented by the Formula (I-J).

The reaction can be performed under the same conditions as the above Step 29.

[Formula 45]

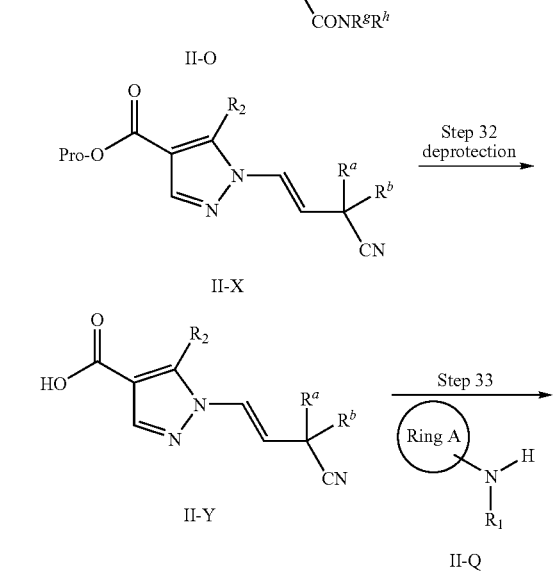

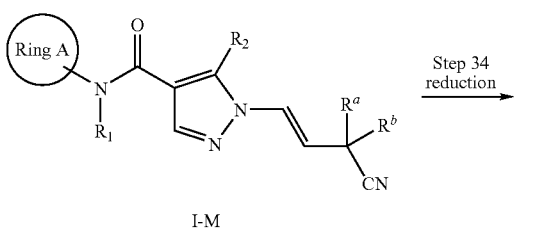

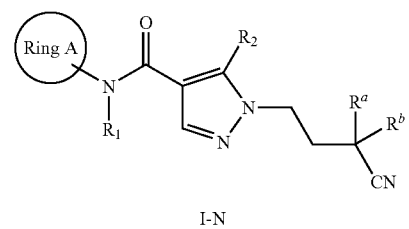

(compounds wherein $R^d =$ —CN)

wherein $R^g$ and $R^h$ are hydrogen, other each symbol in the above scheme has the same meaning as the above, and as to compound (II-O), a known compound can be used, or a compound derived from a known compound by a usual method can be used. Pro is a protecting group. As a protecting group, example includes a methyl group, an ethyl group, a benzyl group, a benzoyl group, a t-butyl group or the like.

Step 31

Step 31 is a process for preparing the compound represented by the Formula (II-X) which comprises dehydrating the compound represented by the Formula (II-O).

The reaction can be performed by reacting the compound represented by the Formula (II-O) with anhydrous trifluoroacetic acid and pyridine in halogenated hydrocarbons (e.g., dichloromethane, chloroform, 1,2-dichloroethane or the like) at −20 to 40° C. for 0.5 to 10 hours.

Step 32

Step 32 is a process for preparing the compound represented by the Formula (II-Y) which comprises deprotecting the compound represented by the Formula (II-X).

The reaction can be performed under the same conditions as the above Step 18.

Step 33

Step 33 is a process for preparing the compound represented by the Formula (I-M) which comprises reacting the compound represented by the Formula (II-Y) with the compound represented by the Formula (II-Q).

The reaction can be performed under the same conditions as the above Step 4.

Step 34

Step 34 is a process for preparing the compound represented by the Formula (I-N) which comprises reducing the compound represented by the Formula (I-M).

The reaction can be performed under the same conditions as the above Step 18.

[Formula 46]

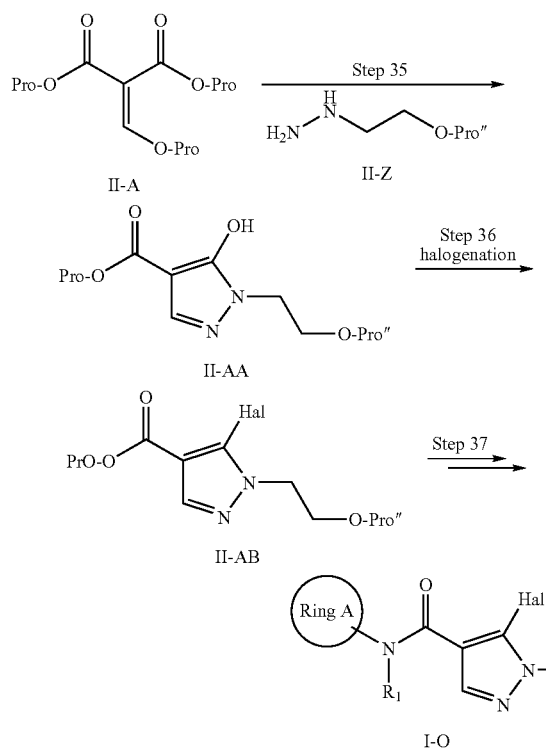

The reaction can be performed according to a general method described in the present specification.

[Formula 47]

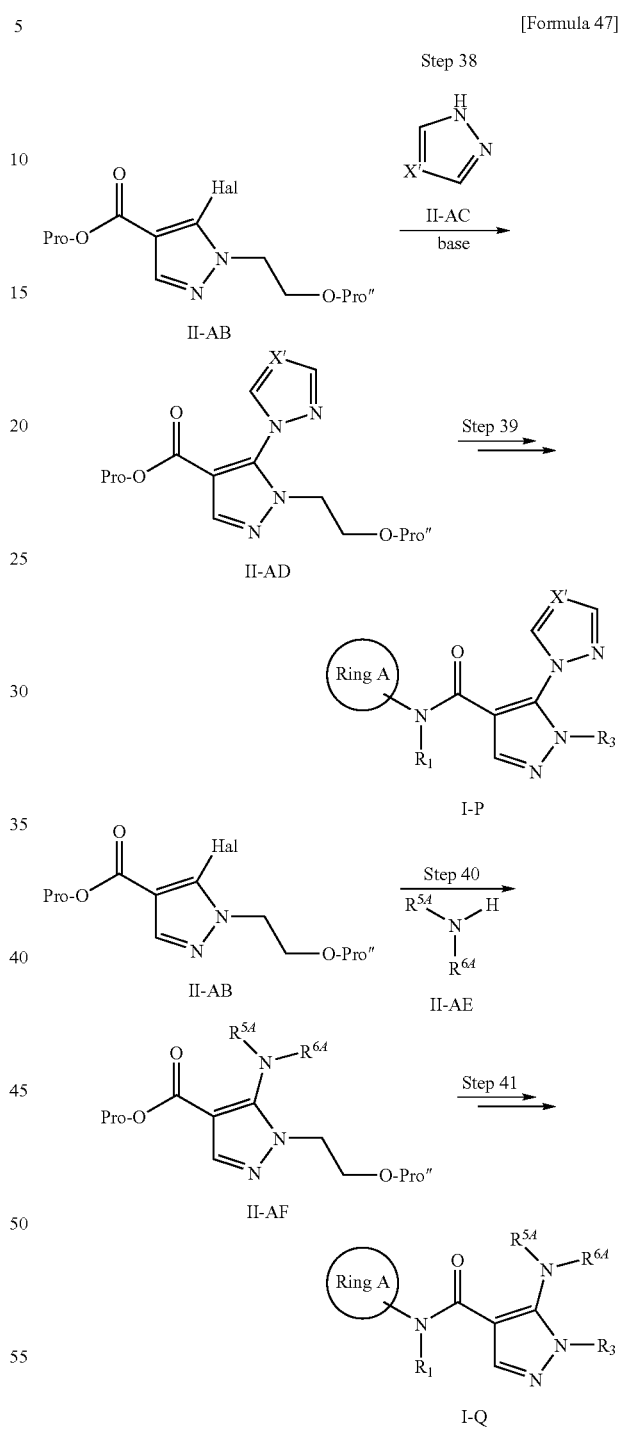

wherein each symbol in the above scheme has the same meaning as the above, and as to compound (II-A), a known compound can be used, or a compound derived from a known compound by a usual method can be used. Pro is a protecting group. As a protecting group, example includes a methyl group, an ethyl group, a benzyl group, a benzoyl group, a t-butyl group or the like. Pro" is a protecting group. As a protecting group, example includes a t-butyl group, a trityl group, a benzyl group, a p-methoxybenzyl group, a silyl group, a methanesulfonyl group, an acyl group or the like.

Step 35

Step 35 is a process for preparing the compound represented by the Formula (II-AA) which comprises reacting the compound represented by the Formula (II-A) with the compound represented by the Formula (II-Z).

The reaction can be performed under the same conditions as the above Step 1.

Step 36

Step 36 is a process for preparing the compound represented by the Formula (II-AB) which comprises halogenating the compound represented by the Formula (II-AA).

For example, halogenation can be performed by referring to example 3 in WO2007/058346.

The chlorination can be performed with phosphoryl chloride at a temperature ranging from −20° C. to the temperature at which phosphoryl chloride is refluxed, for 0.5 to 24 hours. This reaction can be performed in a solvent described in Step 1 or without any solvent.

The bromination can be performed with $PBr_3$ under the same conditions as the above. Fluorine derivative can be obtained by reacting corresponding chlorine derivative with potassium fluoride.

Step 37

Step 37 is a process for preparing the compound represented by the Formula (I-O) from the compound represented by the Formula (II-AB).

wherein each symbol in the above scheme has the same meaning as the above, and as to compound (II-AB), a known compound can be used, or a compound derived from a known compound by a usual method can be used. Pro is a protecting group. As a protecting group, example includes a methyl group, an ethyl group, a benzyl group, a benzoyl group, a t-butyl group or the like. Pro" is a protecting group. As a protecting group, example includes a t-butyl group, a trityl group, a benzyl group, a p-methoxybenzyl group, a silyl group, a methanesulfonyl group, an acyl group or the like. Hal is halogen. As X', example includes =N— or =CR$^Y$—, wherein R$^Y$ is hydrogen, C1 to C6 alkyl or halogen.

Step 38

Step 38 is a process for preparing the compound represented by the Formula (II-AD) which comprises reacting the compound represented by the Formula (II-AB) with the compound represented by the Formula (II-AC) in the presence of a base.

As a base, a base described in Step 2 can be used. Preferably, metal hydrides (e.g., sodium hydride or the like) or LDA can be used.

As a solvent, a solvent described in Step 1 can be used. Preferably, ethers (e.g., tetrahydrofuran, diethylether, dioxane, 1,2-dimethoxyethane or the like) can be used.

The reaction can be performed at −78 to 50° C. for 0.5 to 24 hours.

Step 39

Step 39 is a process for preparing the compound represented by the Formula (I-P) from the compound represented by the Formula (II-AD).

The reaction can be performed according to a general method described in the present specification.

Step 40

Step 40 is a process for preparing the compound represented by the Formula (II-AF) which comprises reacting the compound represented by the Formula (II-AB) with the compound represented by the Formula (II-AE).

As a solvent, a solvent described in Step 1 can be used. The reaction also can be performed without a solvent.

The reaction can be performed at 80 to 150° C. for 0.5 to 48 hours.

Also, microwave can be used for this reaction.

Step 41

Step 41 is a process for preparing the compound represented by the Formula (I-Q) from the compound represented by the Formula (II-AF).

The reaction can be performed according to a general method described in the present specification.

[Formula 48]

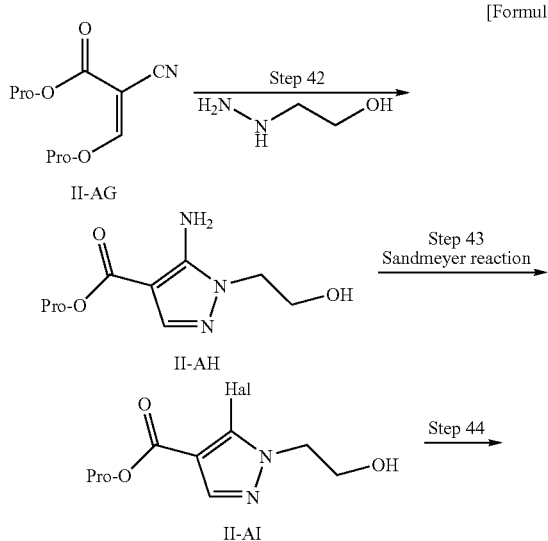

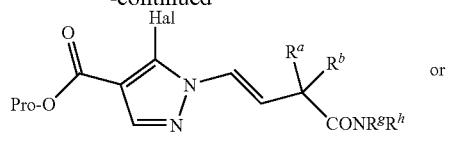

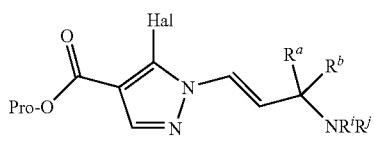

wherein each symbol in the above scheme has the same meaning as the above, and as to compound (II-AG), a known compound can be used, or a compound derived from a known compound by a usual method can be used.

Step 42

Step 42 is a process for preparing the compound represented by the Formula (II-AH) which comprises reacting the compound represented by the Formula (II-AG) with hydrazine.

The reaction can be performed under the same conditions as the above Step 1.

Step 43

Step 43 is a process for preparing the compound represented by the Formula (II-AI) which comprises halogenating the compound represented by the Formula (II-AH).

For example, halogenation can be performed by Sandmeye reaction. The bromination can be performed with CuBr at a temperature ranging from −20° C. to the temperature at which a solvent being used is refluxed, for 0.5 to 24 hours.

The chlorination can be performed with CuCl under the same conditions as the above. Also, under the same conditions as the above, the iodination can be performed with sodium iodide and fluorination can be performed with silver tetrafluoroborate.

Step 44

Step 44 is a process for preparing the compound represented by the Formula (II-AJ) or (II-AK) from the compound represented by the Formula (II-AI).

The reaction can be performed according to a general method described in the present specification.

The compound in which halogen group of the compound represented by the above Formula (II-AJ) or (II-AK) is substituted with various substituents can be prepared by reacting the compound represented by the above Formula (II-AJ) or (II-AK) under the same conditions as the above Step 6, Step 38 or Step 40.

Various substituents in the present compound can be introduced by referring to (1) Alan R. Katriszly et al., Comprehensive Heterocyclic Chemistry (2) Alan R. Katriszly et al., Comprehensive Heterocyclic Chemistry II (3) RODD'S CHEMISTRY OF CARBON COMPOUNDS VOLUME IV HETEROCYCLIC COMPOUNDS or the like.

The present compound has excellent inhibitory activity to 11β-hydroxysteroid dehydrogenase type 1. Therefore, it can be used for treatment or prevention of a disease concerning 11β-hydroxysteroid dehydrogenase type 1, especially, disease such as hyperlipidemia, diabetes, obesity, arteriosclerosis, atherosclerosis, hyperglycemia and/or syndrome X. It is particularly useful in treatment or prevention of diabetes.

The compound used in the present invention can be administered orally or parenterally. In the case of oral administration, the compound used in the present invention can be used in any dose form including normal formulations, for example, solid formulations such as a tablet, powder, granule, capsule or the like; aqueous formulations; oleaginous suspensions; or liquid formulations such as syrup or elixir. In the case of parenteral administration, the compound used in the present invention can be used as an aqueous or oleaginous suspension for injection or nasal solution. In preparation of such formulations, a conventional excipient, binder, lubricant, aqueous solvent, oleaginous solvent, emulsifying agent, suspending agent, preservative, stabilizer and the like can be optionally used. Especially, using in a form of an oral formulation is preferred.

A formulation of the compound used in the present invention can be produced by combining (e.g., mixing) a therapeutically effective amount of the compound used in the present invention with a pharmaceutically acceptable carrier or diluent. Formulation of the compound used in the present invention can be produced by a known method using a well-known easily available ingredient.

A dosage of the compound used in the present invention differs depending on the administration route, age, body weight, condition and kind of disease of the patient, and is typically, about 0.05 mg to 3000 mg and preferably about 0.1 mg to 1000 mg per a day for adult person, in the case of oral administration, and can be administered in divided doses as necessary. In the case of parenteral administration, about 0.01 mg to 1000 mg and preferably about 0.05 mg to 500 mg per a day for adult person can be administered. In administration, it can be used together with other therapeutic agents.

In the following, the present invention will be described in more detail by way of examples which are not intended to limit the scope of the present invention.

In addition, a group represented by the Formula (III');

[Formula 49]

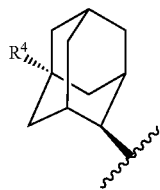

is equal to the following groups:

[Formula 50]

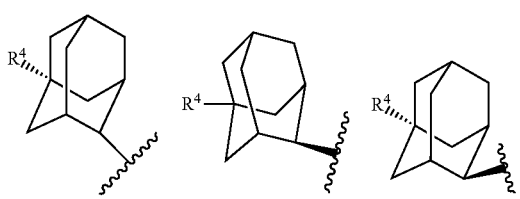

-continued

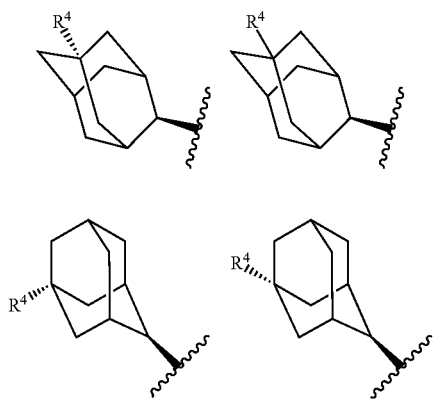

Example 1

[Formula 51]

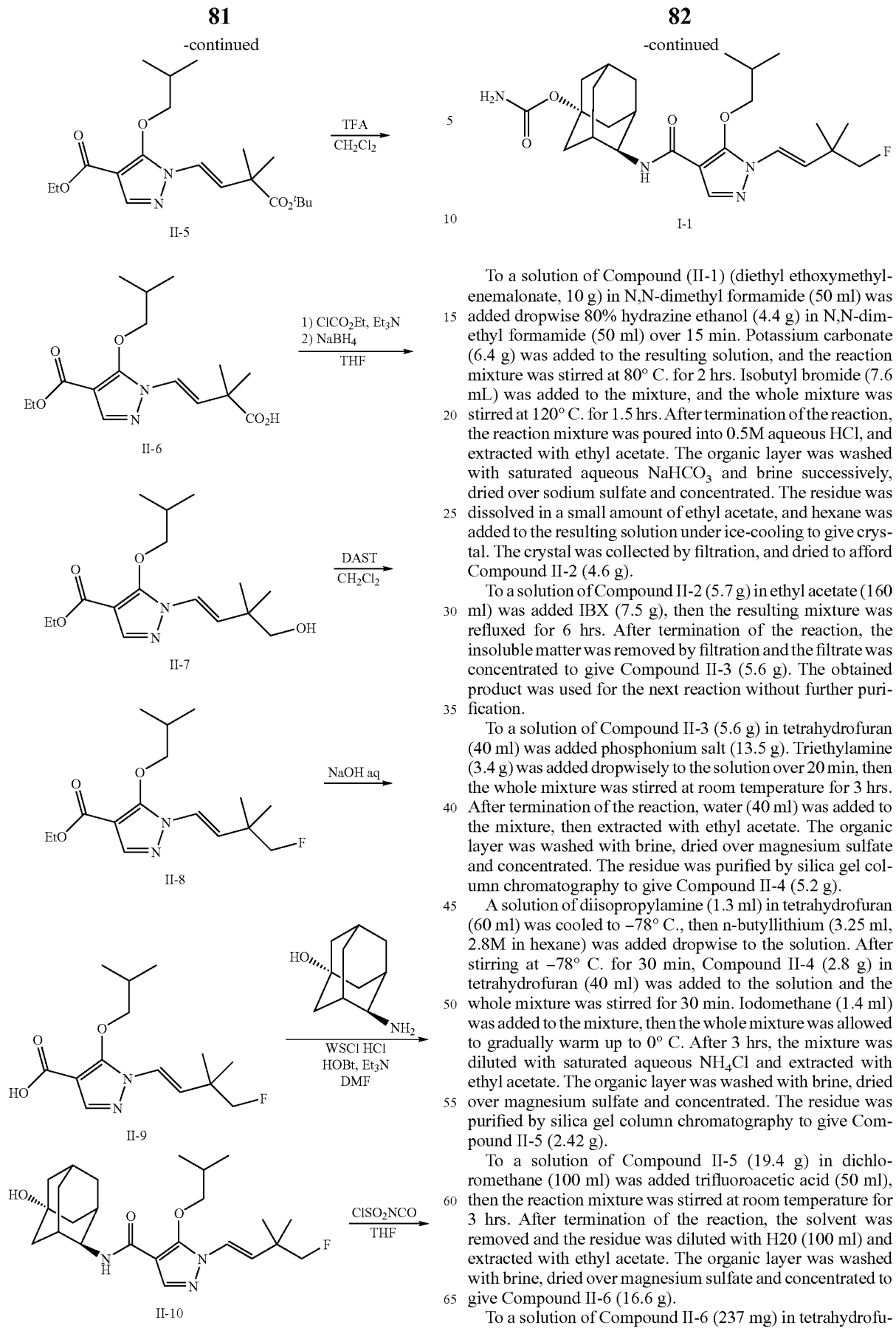

To a solution of Compound (II-1) (diethyl ethoxymethylenemalonate, 10 g) in N,N-dimethyl formamide (50 ml) was added dropwise 80% hydrazine ethanol (4.4 g) in N,N-dimethyl formamide (50 ml) over 15 min. Potassium carbonate (6.4 g) was added to the resulting solution, and the reaction mixture was stirred at 80° C. for 2 hrs. Isobutyl bromide (7.6 mL) was added to the mixture, and the whole mixture was stirred at 120° C. for 1.5 hrs. After termination of the reaction, the reaction mixture was poured into 0.5M aqueous HCl, and extracted with ethyl acetate. The organic layer was washed with saturated aqueous NaHCO₃ and brine successively, dried over sodium sulfate and concentrated. The residue was dissolved in a small amount of ethyl acetate, and hexane was added to the resulting solution under ice-cooling to give crystal. The crystal was collected by filtration, and dried to afford Compound II-2 (4.6 g).

To a solution of Compound II-2 (5.7 g) in ethyl acetate (160 ml) was added IBX (7.5 g), then the resulting mixture was refluxed for 6 hrs. After termination of the reaction, the insoluble matter was removed by filtration and the filtrate was concentrated to give Compound II-3 (5.6 g). The obtained product was used for the next reaction without further purification.

To a solution of Compound II-3 (5.6 g) in tetrahydrofuran (40 ml) was added phosphonium salt (13.5 g). Triethylamine (3.4 g) was added dropwisely to the solution over 20 min, then the whole mixture was stirred at room temperature for 3 hrs. After termination of the reaction, water (40 ml) was added to the mixture, then extracted with ethyl acetate. The organic layer was washed with brine, dried over magnesium sulfate and concentrated. The residue was purified by silica gel column chromatography to give Compound II-4 (5.2 g).

A solution of diisopropylamine (1.3 ml) in tetrahydrofuran (60 ml) was cooled to −78° C., then n-butyllithium (3.25 ml, 2.8M in hexane) was added dropwise to the solution. After stirring at −78° C. for 30 min, Compound II-4 (2.8 g) in tetrahydrofuran (40 ml) was added to the solution and the whole mixture was stirred for 30 min. Iodomethane (1.4 ml) was added to the mixture, then the whole mixture was allowed to gradually warm up to 0° C. After 3 hrs, the mixture was diluted with saturated aqueous NH₄Cl and extracted with ethyl acetate. The organic layer was washed with brine, dried over magnesium sulfate and concentrated. The residue was purified by silica gel column chromatography to give Compound II-5 (2.42 g).

To a solution of Compound II-5 (19.4 g) in dichloromethane (100 ml) was added trifluoroacetic acid (50 ml), then the reaction mixture was stirred at room temperature for 3 hrs. After termination of the reaction, the solvent was removed and the residue was diluted with H20 (100 ml) and extracted with ethyl acetate. The organic layer was washed with brine, dried over magnesium sulfate and concentrated to give Compound II-6 (16.6 g).

To a solution of Compound II-6 (237 mg) in tetrahydrofuran (3 ml) were added triethylamine (15 μl) and ethyl chlorocarbonate (84 µl) at 0° C., then the reaction mixture was stirred at room temperature for one hour. Sodium borohydride (69 mg) and water (1 ml) were added to the mixture at 0° C. and the whole mixture was stirred for 20 min. After termination of the reaction, aqueous HCl was added to the mixture. The extraction was carried out with ethyl acetate. The organic layer was washed with brine, dried over sodium sulfate and concentrated. The residue was purified by silica gel column chromatography to afford II-7 (185 mg).

To a solution of Compound II-7 (185 mg) in dichloromethane (5 ml) was added DAST (102 µl) at −78° C., then the reaction mixture was stirred at the same temperature for 30 min. After termination of the reaction, saturated aqueous $NH_4Cl$ was added to the mixture. The extraction was carried out with ethyl acetate. The organic layer was dried over sodium sulfate and concentrated. The residue was purified by silica gel column chromatography to afford Compound II-8 (62 mg).

To a solution of Compound II-8 (61.6 mg) in tetrahydrofuran (1 ml)-methanol (1 ml) was added 2N aqueous NaOH (1 ml), and then the reaction mixture was stirred at room temperature for 14 hrs. After termination of the reaction, the mixture was acidified with 2N aqueous HCl and extracted with ethyl acetate. The organic layer was washed with brine, dried over sodium sulfate and concentrated to give Compound II-9 (60.1 mg). The obtained product was used for the next reaction without further purification.

To a solution of Compound II-9 (60.1 mg) in dimethyl formamide (3 ml) were added hydroxy adamantanamine (38.8 mg), 1-(3-dimethylaminopropyl)-3-ethylcarbodiimide hydrochloride (48.5 mg), 1-hydroxybenzotriazole (8.5 mg) and triethylamine (50 µl), and then the reaction mixture was stirred at room temperature for 18 hrs. After termination of the reaction, the mixture was acidified with 2N aqueous HCl and extracted with ethyl acetate. The organic layer was washed with saturated aqueous $NaHCO_3$ and brine successively, and dried over sodium sulfate. The residue was purified by silica gel column chromatography to give Compound II-10 (62 mg).

To a solution of Compound II-10 (54 mg) in tetrahydrofuran (1.2 ml) was added chlorosulfonyl isocyanate (22 µl) at −45° C., and then the reaction mixture was stirred at −30° C. for 2 hrs. Solid $NaHCO_3$ (74 mg) and water (24 µl) were added to the solution and the whole mixture was stirred at room temperature for 2 hrs. After termination of the reaction, water was added to the mixture, then extracted with ethyl acetate. The organic layer was washed with brine and dried over sodium sulfate. The residue was purified by silica gel column chromatography to give Compound I-1 (51 mg). (Compound I-1)NMR (DMSO-d6); δ(ppm) 0.95 (d, J=6.6 Hz, 6H), 1.30 (s, 3H), 1.36 (s, 3H), 1.41 (d, J=12.4 Hz, 2H), 1.94-2.10 (m, 12H), 2.46-2.53 (m, 2H), 3.94 (s, 1H), 4.10 (d, J=6.3 Hz, 2H), 6.08-6.16 (m, 1H), 6.20 (br, 2H), 6.92 (d, J=14.2 Hz, 1H), 7.50 (d, J=6.6 Hz, 1H), 7.94 (s, 1H)

The compounds shown below were synthesized in a similar manner.

As to each compound, the measurement results of NMR or log k' were disclosed.

log k' is a value which means degree of the lipophilic character, and is calculated by the following formula.

$$\log k' = \log(t_R - t_0)/t_0$$

$t_R$: retention time of compound under gradient condition
$t_0$: retention time of standard material not retained in column
XTerra MS C18 5 µm, 2.1×100 mm column (made by Waters) was used for measurement. The elution was a straight line inclination of acetonitrile/pH6.8 buffer (5:95~95:5/20 min) at flow velocity 0.25 mL/min.

Example 2

[Formula 52]

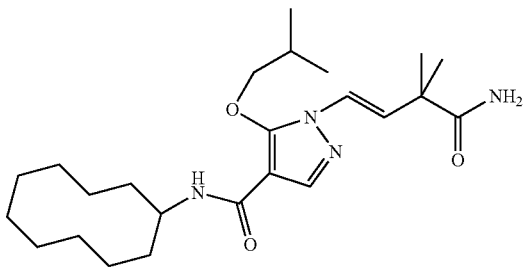

(Compound I-2) log k'=1.014

Example 3

[Formula 53]

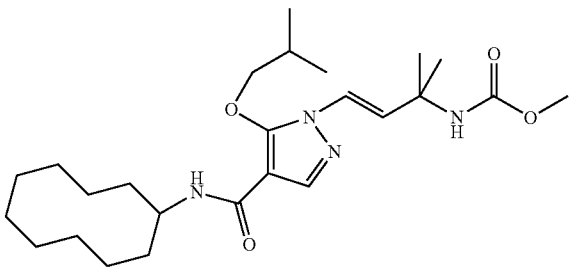

(Compound I-3) log k'=1.066

Example 4

[Formula 54]

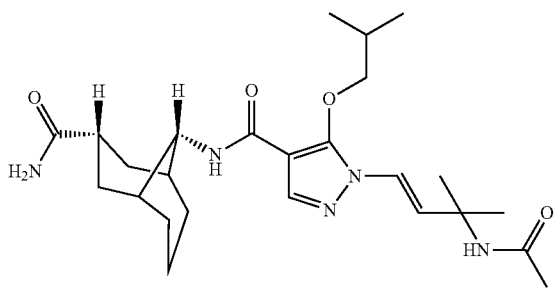

(Compound I-4) NMR(CDCl3); δ(ppm) 1.10 (d, J=6.7 Hz, 6H), 1.36-1.84 (m, 8H), 1.54 (s, 6H), 1.95 (s, 3H), 2.10-2.35 (m, 5H), 2.64-2.76 (m, 1H), 3.98 (d, J=6.8 Hz, 2H), 4.23-4.28

(m, 1H), 5.32 (br, 1H), 5.47 (s, 1H), 5.50 (br, 1H), 6.38 (d, J=14.1 Hz, 1H), 6.46 (d, J=8.0 Hz, 1H), 6.86 (d, J=14.1 Hz, 1H), 7.83 (s, 1H)

Example 5

[Formula 55]

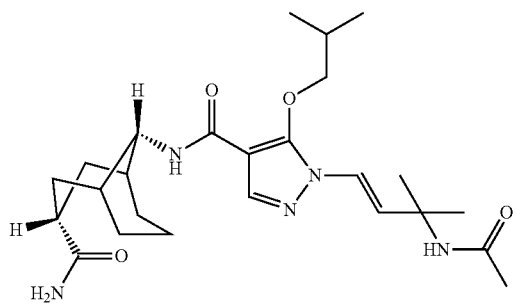

(Compound I-5) log k'=0.795

Example 6

[Formula 56]

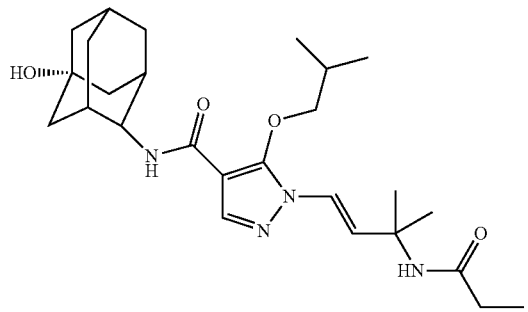

(Compound I-6) NMR (DMSO-d6); δ(ppm) 0.96 (t, J=7.5 Hz, 3H), 0.97 (d, J=6.6 Hz, 6H), 1.32-1.36 (m, 2H), 1.40 (s, 6H), 1.58-1.75 (m, 6H), 1.89-2.11 (m, 8H), 3.86-3.91 (m, 1H), 4.07 (d, J=6.3 Hz, 2H), 4.42 (s, 1H), 6.35 (d, J=14.1 Hz, 1H), 6.76 (d, J=14.1 Hz, 1H), 7.38 (d, J=6.9 Hz, 1H), 7.67 (s, 1H), 7.95 (s, 1H)

Example 7

[Formula 57]

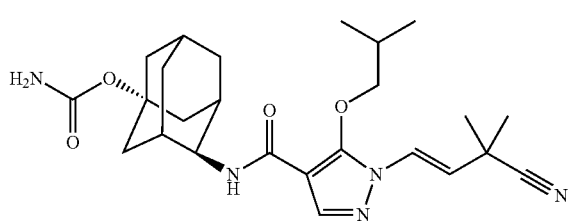

(Compound I-7) NMR (DMSO-d6); δ(ppm) 0.98 (d, J=6.8 Hz, 6H), 1.42 (d, J=13.1 Hz, 2H), 1.52 (s, 6H), 1.95-2.11 (m, 12H), 3.96 (s, 1H), 4.15 (d, J=6.3 Hz, 2H), 6.20 (br, 2H), 6.24 (d, J=14.2 Hz, 1H), 7.10 (d, J=14.2 Hz, 1H), 7.55 (d, J=6.1 Hz, 1H), 8.04 (s, 1H)

Example 8

[Formula 58]

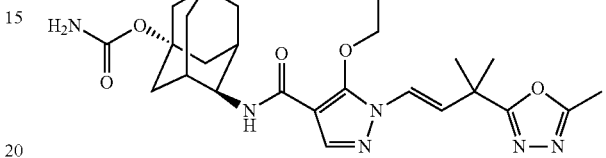

(Compound I-8) log k'=0.883

Example 9

[Formula 59]

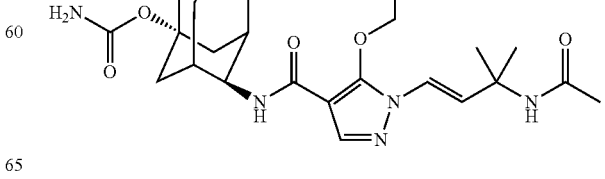

(Compound I-9) NMR (DMSO-d6); δ(ppm) 0.97 (d, J=6.6 Hz, 6H), 1.40-1.44 (m, 8H), 1.94-2.10 (m, 12H), 2.90 (s, 3H), 3.94-3.96 (m, 1H), 4.11 (d, J=6.3 Hz, 2H), 6.20 (br, 2H), 6.33 (d, J=14.4 Hz, 1H), 6.92 (d, J=14.4 Hz, 1H), 7.24 (s, 1H), 7.50 (d, J=6.8 Hz, 1H), 7.98 (s, 1H)

Example 10

[Formula 60]

(Compound I-10) log k'=0.798

Example 11
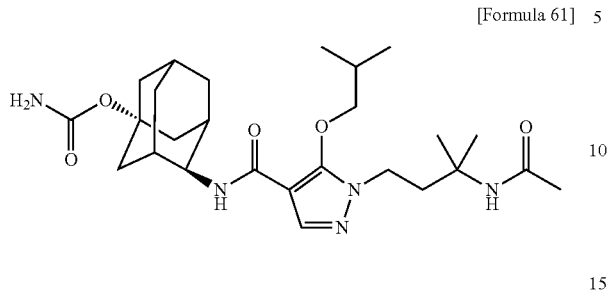
(Compound I-11) log k'=0.831
Example 12
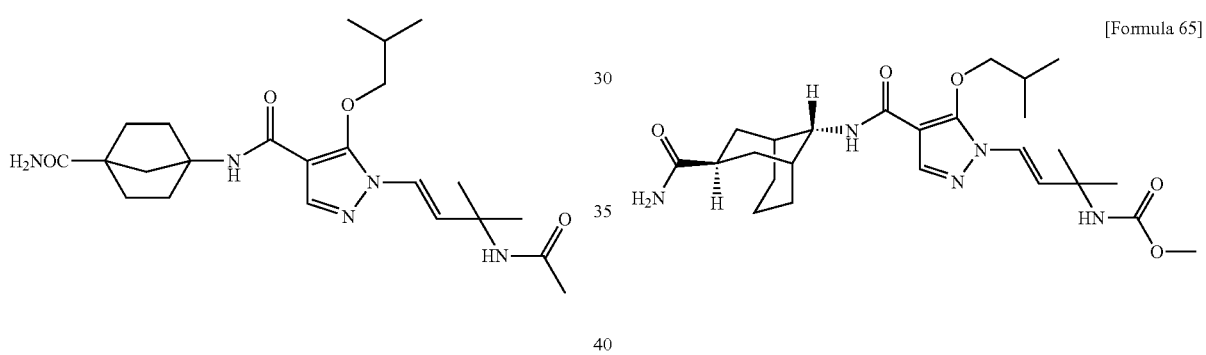
(Compound I-12) log k'=0.763
Example 13
(Compound I-13) log k'=0.822
Example 14
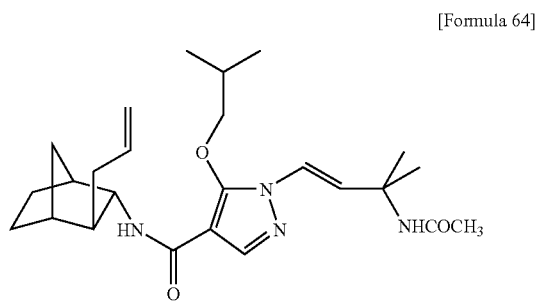
(Compound I-14) log k'=0.981
Example 15
(Compound I-15) NMR(CDCl3); δ(ppm) 1.08 (d, J=6.8 Hz, 6H), 1.51 (s, 6H), 1.58-1.85 (m, 6H), 2.02-2.11 (m, 6H), 2.12 (m, 1H), 2.92-3.04 (m, 1H), 3.62 (s, 3H), 3.97 (d, J=7.0 Hz, 2H), 4.07-4.10 (m, 1H), 4.83 (s, 1H), 5.35 (br, 1H), 5.51 (br, 1H), 6.37 (d, J=14.1 Hz, 1H), 6.46 (d, J=7.6 Hz, 1H), 6.87 (d, J=14.1 Hz, 1H), 7.83 (s, 1H)
Example 16
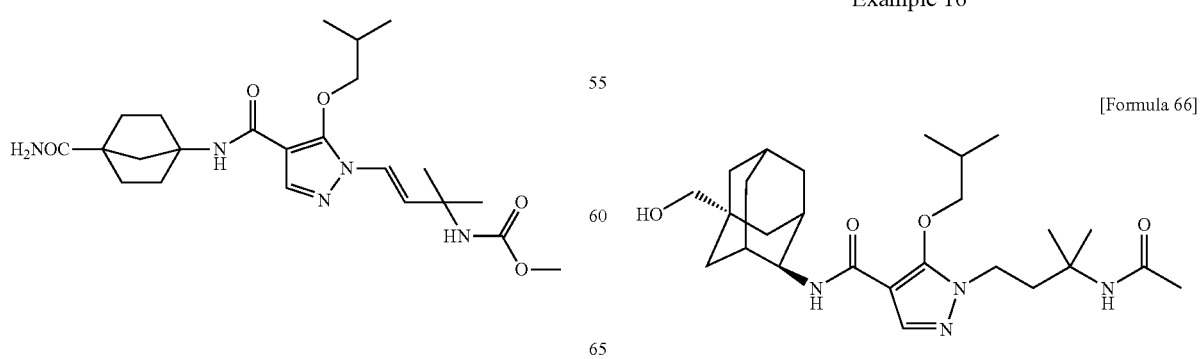
(Compound I-16) log k'=0.842

Example 17
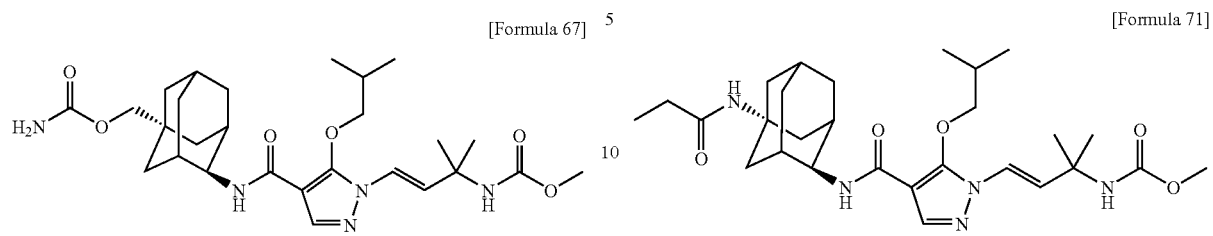
[Formula 67]
(Compound I-17) log k'=0.916
Example 18
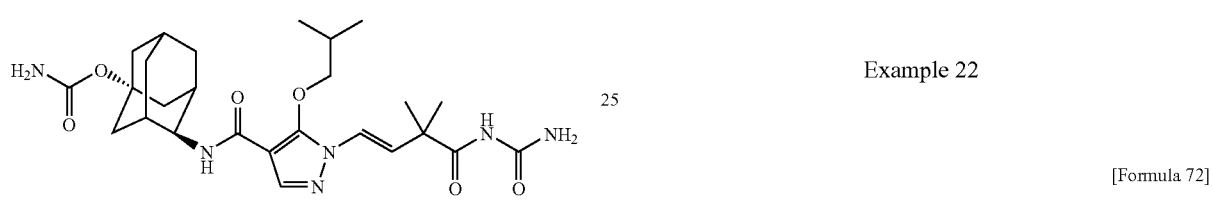
[Formula 68]
(Compound I-18) log k'=0.866
Example 19
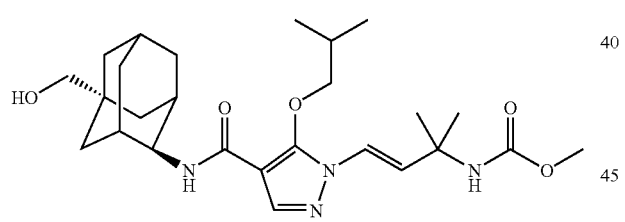
[Formula 69]
(Compound I-19) log k'=0.907
Example 20
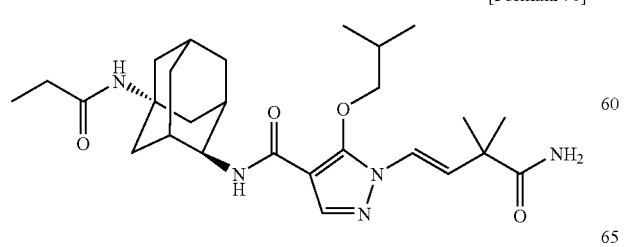
[Formula 70]
(Compound I-20) log k'=0.845
Example 21
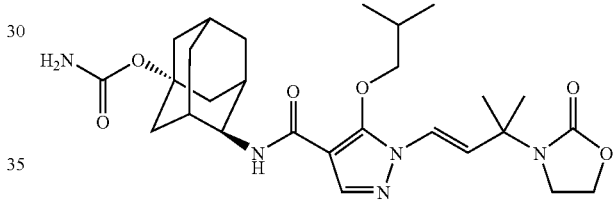
[Formula 71]
(Compound I-21) log k'=0.909
Example 22
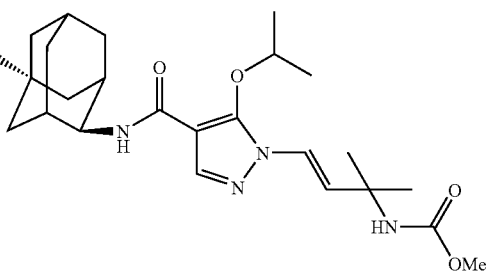
[Formula 72]
(Compound I-22) log k'=0.879
Example 23
[Formula 73]
(Compound I-23) log k'=0.864

91
Example 24
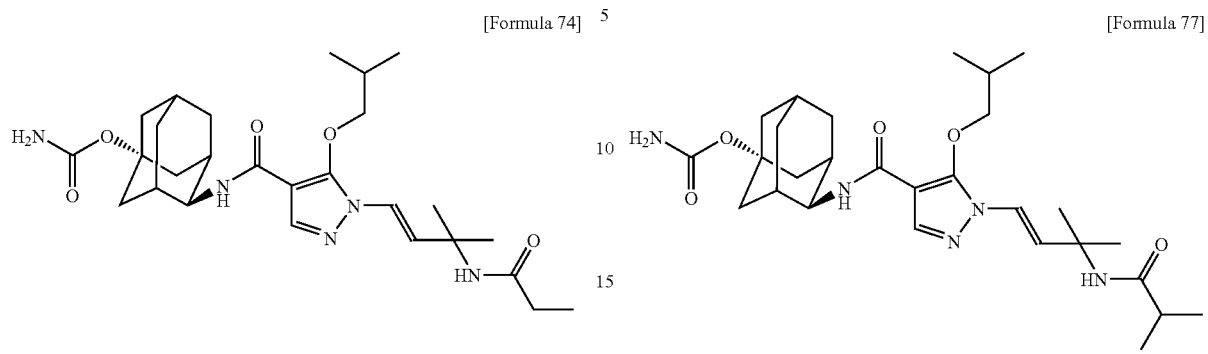
(Compound I-24) log k'=0.876
Example 25
(Compound I-25) log k'=0.87
Example 26
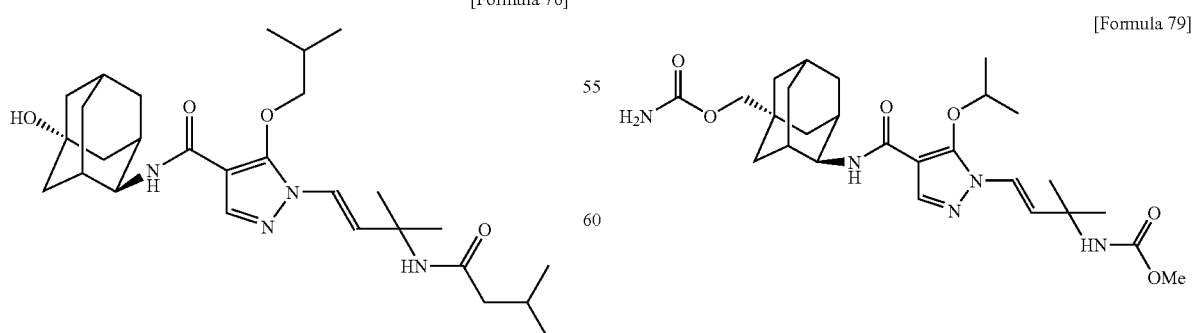
(Compound I-26) log k'=0.895
92
Example 27
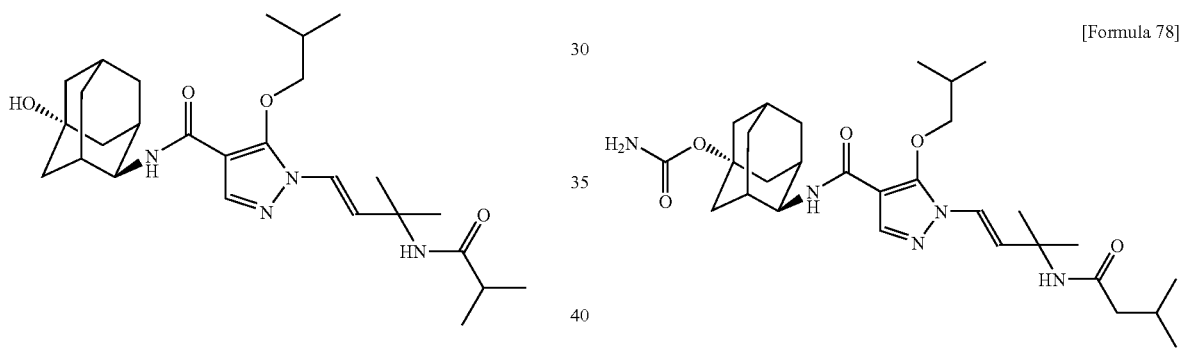
(Compound I-27) log k'=0.903
Example 28
(Compound I-28) log k'=0.927
Example 29
(Compound I-29) NMR(CDCl3); δ(ppm) 1.39 (d, J=6.3 Hz, 6H), 1.51 (s, 6H), 1.55-2.11 (m, 13H), 3.62 (s, 3H), 3.73 (s, 2H), 4.14-4.16 (m, 1H), 4.61 (br, 2H), 4.67-4.75 (m, 1H), 4.83 (m, 1H), 6.36 (d, J=14.2 Hz, 1H), 6.53 (d, J=7.3 Hz, 1H), 6.83 (d, J=14.2 Hz, 1H), 7.86 (s, 1H)
5.48 (s, 1H), 6.36 (d, J=14.2 Hz, 1H), 6.56 (d, J=7.8 Hz, 1H), 6.82 (d, J=14.2 Hz, 1H), 7.86 (s, 1H)
Example 30
[Formula 80]
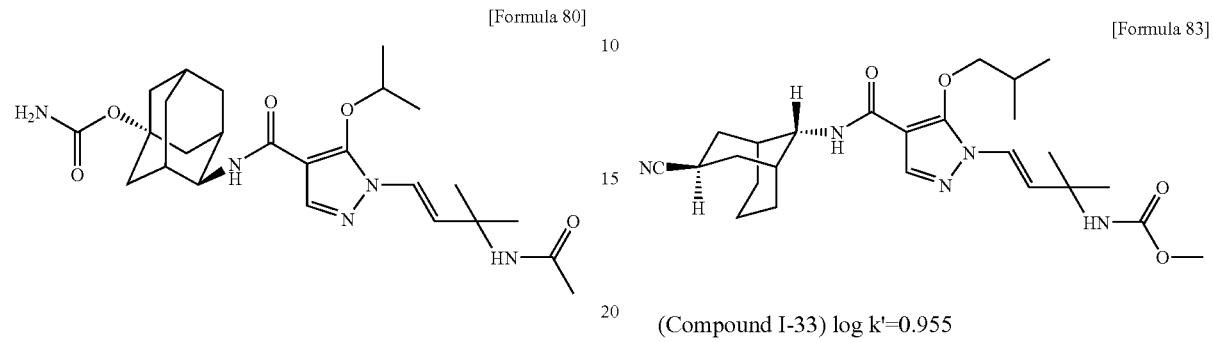
(Compound I-30) NMR(CDCl3); δ(ppm) 1.39 (d, J=6.3 Hz, 6H), 1.54 (s, 6H), 1.59-1.78 (m, 4H), 1.96 (s, 3H), 2.13-2.29 (m, 9H), 4.20-4.23 (m, 1H), 4.43 (br, 2H), 4.67-4.75 (m, 1H), 5.46 (s, 1H), 6.36 (d, J=14.2 Hz, 1H), 6.47 (d, J=7.6 Hz, 1H), 6.81 (d, J=14.2 Hz, 1H), 7.85 (s, 1H)
Example 31
[Formula 81]
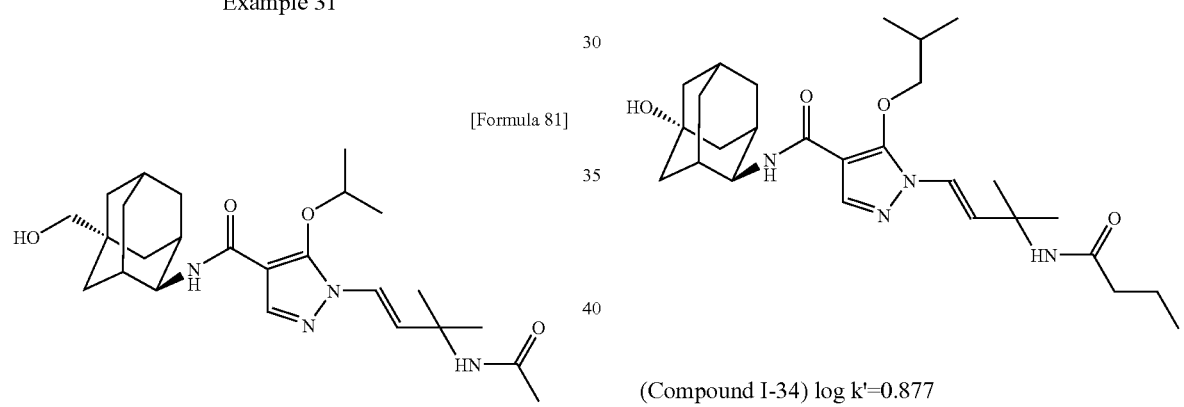
(Compound I-31) log k'=0.819
Example 32
[Formula 82]
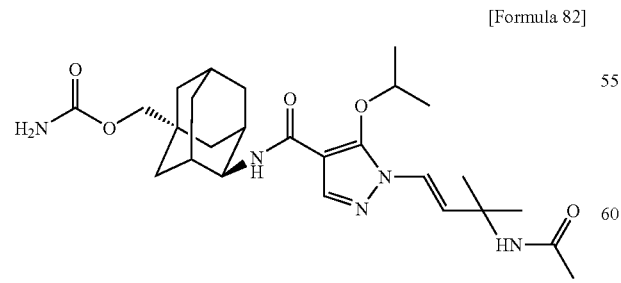
(Compound I-32) NMR(CDCl3); δ(ppm) 1.39 (d, J=6.3 Hz, 6H), 1.54 (s, 6H), 1.56-2.10 (m, 13H), 1.96 (s, 3H), 3.73 (s, 2H), 4.14-4.16 (m, 1H), 4.63 (br, 2H), 4.67-4.75 (m, 1H),
Example 33
[Formula 83]
(Compound I-33) log k'=0.955
Example 34
[Formula 84]
(Compound I-34) log k'=0.877
Example 35
[Formula 85]
(Compound I-35) log k'=0.921

Example 36
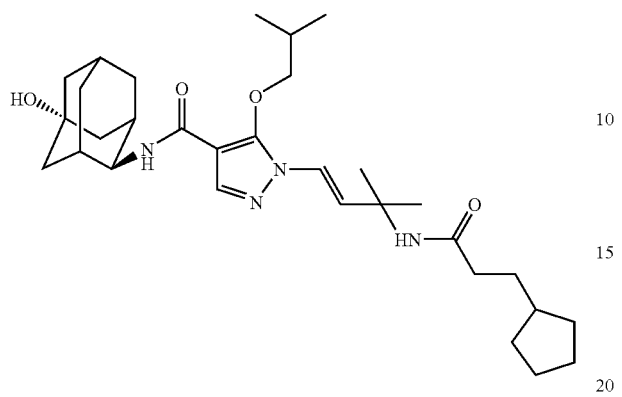
(Compound I-36) NMR (DMSO-d6): δ(ppm) 1.08 (d, J=6.6 Hz, 6H), 1.47-1.74 (m, 19H), 1.54 (s, 3H), 1.64 (s, 3H), 1.89-1.98 (m, 2H), 2.10-2.24 (m, 6H), 3.98 (d, J=6.9 Hz, 2H), 4.14-4.20 (m, 1H), 5.42 (s, 1H), 6.38 (d, J=14.4 Hz, 1H), 6.38 (s, 1H), 6.86 (d, J=14.4 Hz, 1H), 7.80 (s, 1H).
Example 37
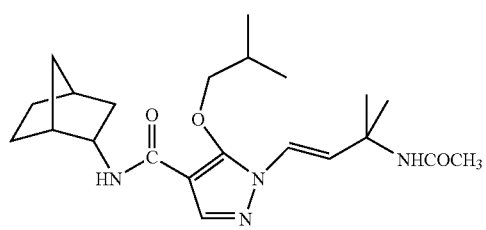
(Compound I-37)
Example 38
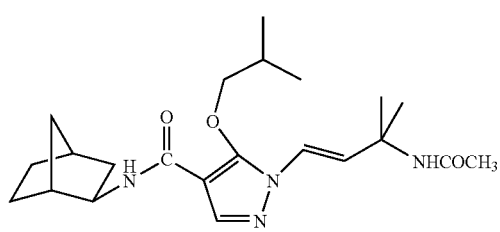
(Compound I-38)
Example 39
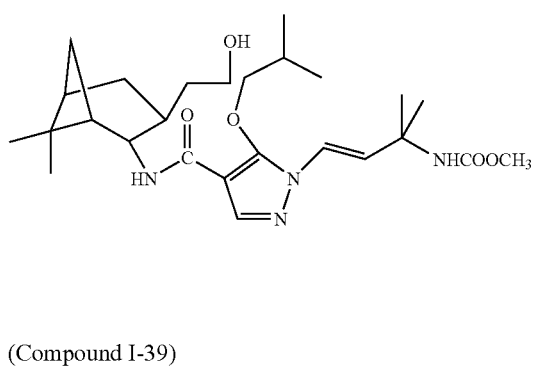
(Compound I-39)
Example 40
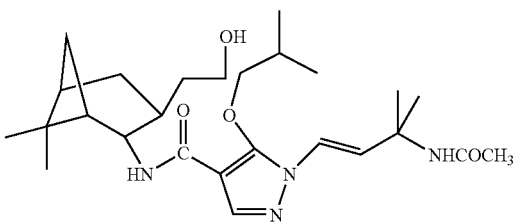
(Compound I-40)
Example 41
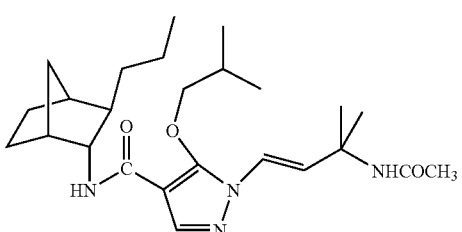
(Compound I-41)

Example 42
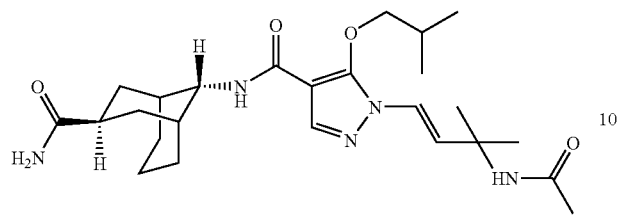
(Compound I-42) log k'=0.805
Example 43
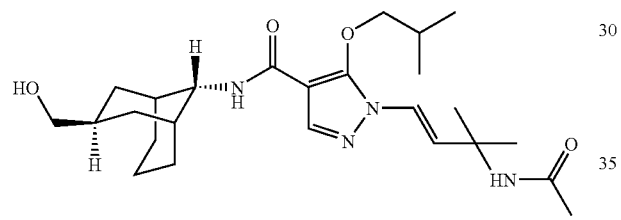
(Compound I-43) log k'=0.851
Example 44
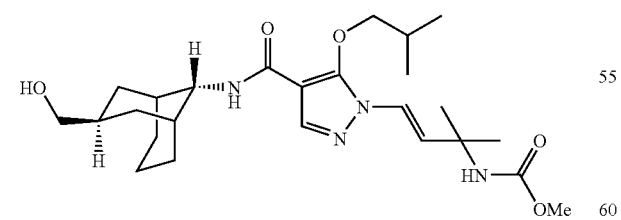
(Compound I-44) NMR(CDCl3); δ(ppm) 1.08 (d, J=6.7 Hz, 6H), 1.51 (s, 6H), 1.58-2.06 (m, 13H), 2.07-2.20 (m, 1H), 2.24-2.36 (m, 1H), 3.41 (d, J=6.2 Hz, 2H), 3.62 (s, 3H), 3.98 (d, J=6.7 Hz, 2H), 3.99-4.02 (m, 1H), 4.82 (s, 1H), 6.37 (d, J=14.2 Hz, 1H), 6.49 (d, J=7.6 Hz, 1H), 6.87 (d, J=14.2 Hz, 1H), 7.82 (s, 1H)
Example 45
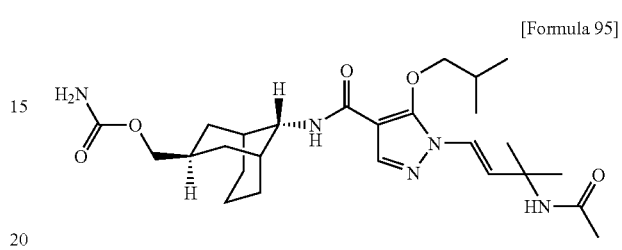
(Compound I-45) log k'=0.865
Example 46
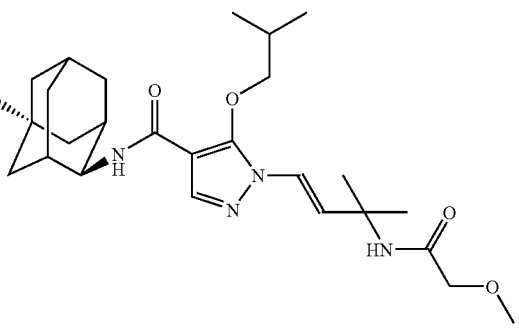
(Compound I-46) log k'=0.913
Example 47
(Compound I-47) NMR(CDCl3): δ(ppm) 1.08 (d, J=6.6 Hz, 6H), 1.51-1.84 (m, 8H), 1.58 (s, 3H), 1.66 (s, 3H), 1.88-1.98 (m, 2H), 2.06-2.24 (m, 4H), 3.41 (s, 3H), 3.80 (s, 2H), 3.98 (d, J=6.6 Hz, 2H), 4.14-4.20 (m, 1H), 6.35 (d, J=8.1 Hz, 1H), 6.41 (d, J=14.1 Hz, 1H), 6.52 (s, 1H), 6.87 (d, J=14.1 Hz, 1H), 7.81 (s, 1H).
Example 48
[Formula 98]
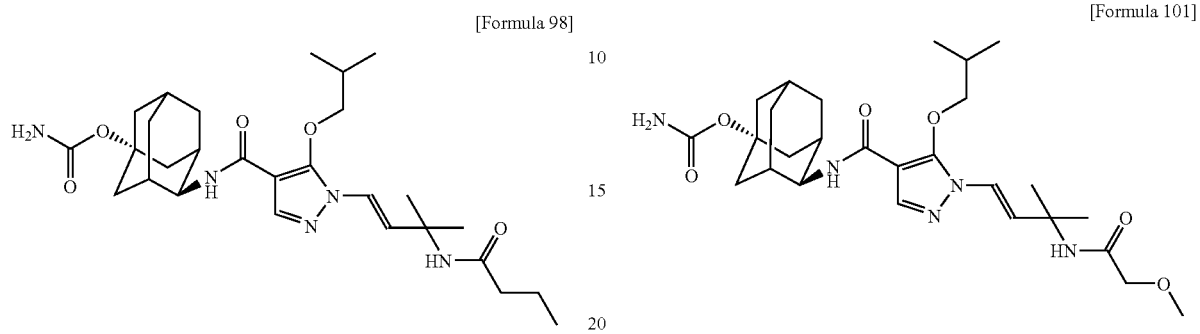
(Compound I-48) NMR (DMSO-d6): δ(ppm) 0.85 (t, J=7.2 Hz, 3H), 0.96 (d, J=6.6 Hz, 6H), 1.35-1.56 (m, 4H), 1.40 (s, 6H), 1.90-2.16 (m, 14H), 3.91-3.98 (m, 1H), 4.07 (d, J=6.3 Hz, 2H), 6.21 (br, 2H), 6.35 (d, J=14.4 Hz, 1H), 6.76 (d, J=14.4 Hz, 1H), 7.47 (d, J=6.3 Hz, 1H), 7.72 (s, 1H).
Example 49
[Formula 99]
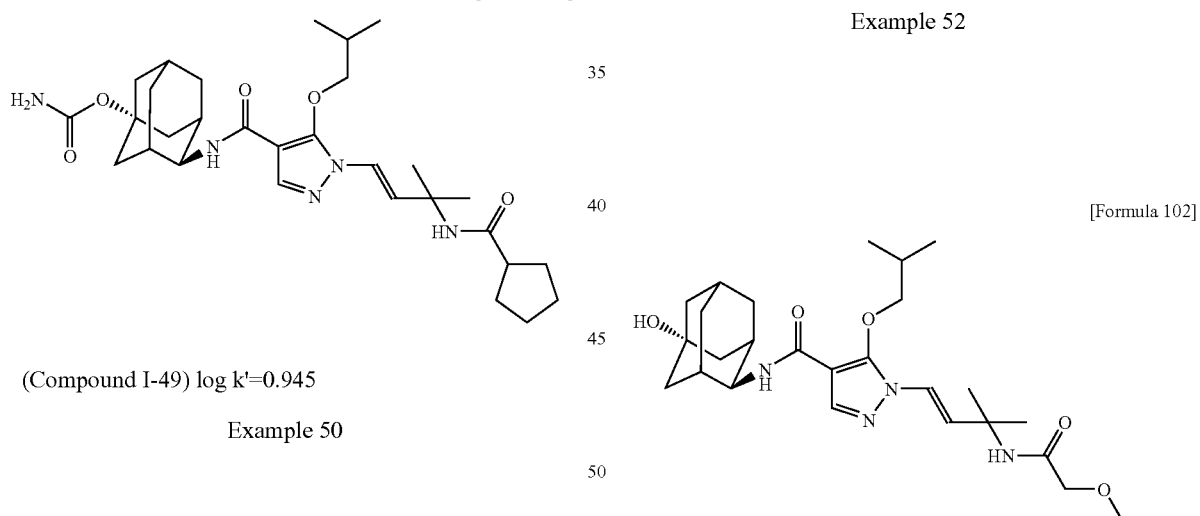
(Compound I-49) log k'=0.945
Example 50
[Formula 100]
(Compound I-50) log k'=0.989
Example 51
[Formula 101]
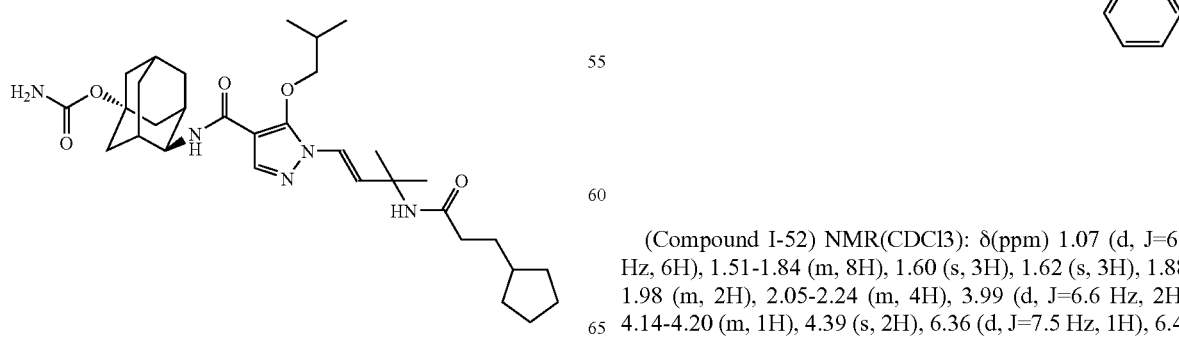
(Compound I-51) log k'=0.882
Example 52
[Formula 102]
(Compound I-52) NMR(CDCl3): δ(ppm) 1.07 (d, J=6.6 Hz, 6H), 1.51-1.84 (m, 8H), 1.60 (s, 3H), 1.62 (s, 3H), 1.88-1.98 (m, 2H), 2.05-2.24 (m, 4H), 3.99 (d, J=6.6 Hz, 2H), 4.14-4.20 (m, 1H), 4.39 (s, 2H), 6.36 (d, J=7.5 Hz, 1H), 6.44 (d, J=14.4 Hz, 1H), 6.58 (s, 1H), 6.86-6.96 (m, 3H), 7.00-7.06 (m, 1H), 7.28-7.36 (m, 2H), 7.81 (s, 1H).

Example 53

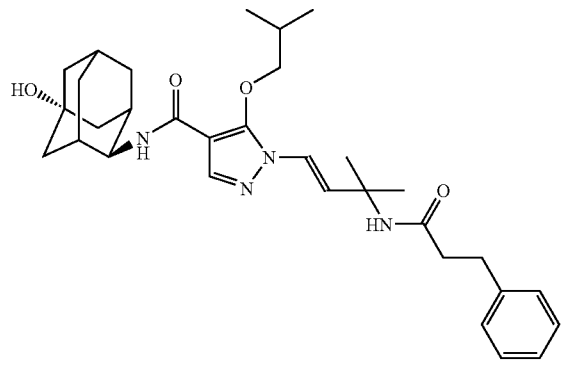

[Formula 103]

(Compound I-53) NMR(CDCl3): δ(ppm) 1.09 (d, J=6.9 Hz, 6H), 1.38-1.84 (m, 8H), 1.47 (s, 3H), 1.63 (s, 3H), 1.88-2.00 (m, 2H), 2.08-2.26 (m, 4H), 2.42 (t, J=7.5 Hz, 2H), 2.93 (t, J=7.5 Hz, 2H), 3.99 (d, J=6.9 Hz, 2H), 4.12-4.20 (m, 1H), 5.29 (s, 1H), 6.33 (d, J=14.1 Hz, 1H), 6.39 (s, 1H), 6.84 (d, J=14.1 Hz, 1H), 7.14-7.32 (m, 5H), 7.82 (s, 1H).

Example 54

[Formula 104]

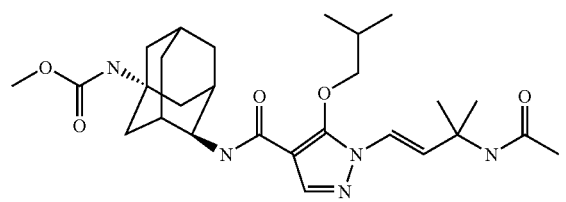

(Compound I-54) log k'=0.886

Example 55

[Formula 105]

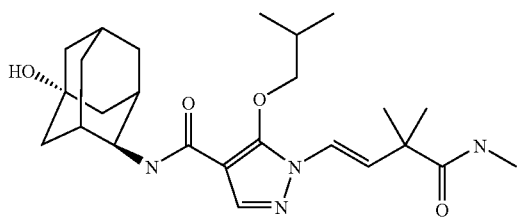

(Compound I-55) NMR (DMSO-d6); δ(ppm) 0.97 (d, J=6.6 Hz, 6H), 1.27 (s, 6H), 1.35 (d, J=12.1 Hz, 2H), 1.61-1.72 (m, 6H), 1.89-2.04 (m, 6H), 2.57 (d, J=4.3 Hz, 3H), 3.87-3.91 (m, 1H), 4.10 (d, J=6.3 Hz, 2H), 4.44 (s, 1H), 6.33 (d, J=14.2 Hz, 1H), 6.78 (d, J=14.7 Hz, 1H), 7.39 (d, J=6.1 Hz, 1H), 7.52-7.56 (m, 1H), 7.98 (s, 1H)

Example 56

[Formula 106]

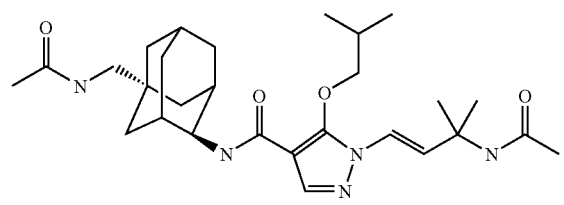

(Compound I-56) log k'=0.838

Example 57

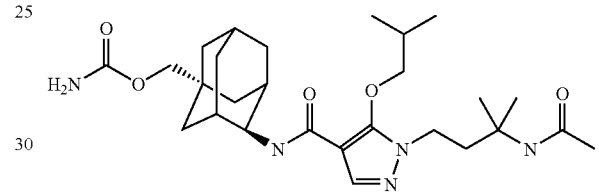

(Compound I-57) log k'=0.852

Example 58

[Formula 108]

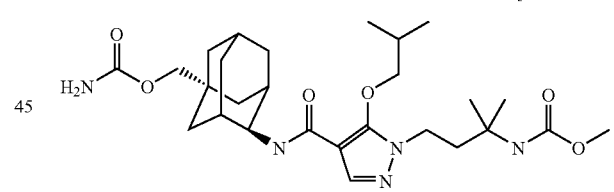

(Compound I-58) log k'=0.899

Example 59

[Formula 109]

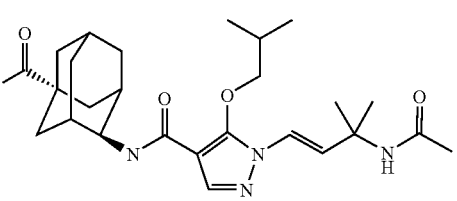

(Compound I-59) log k'=0.833

Example 60
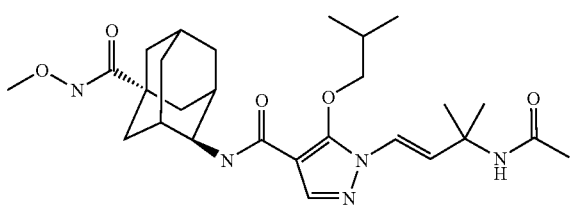
(Compound I-60) log k'=0.813
Example 61
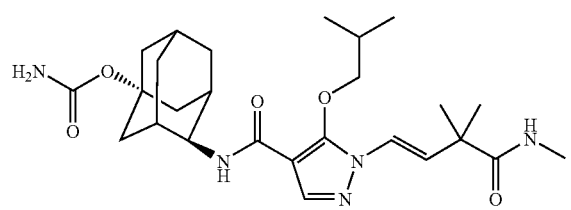
(Compound I-61) log k'=0.841
Example 62
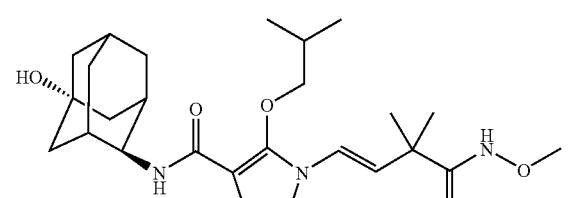
(Compound I-62) log k'=0.794
Example 63
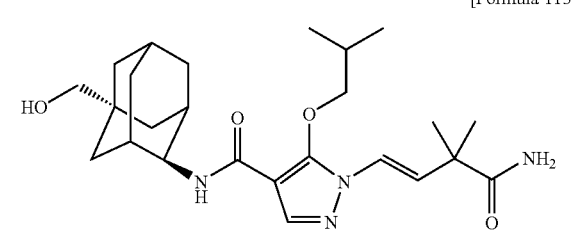
(Compound I-63) NMR (DMSO-d6); δ(ppm) 0.98 (d, J=6.8 Hz, 6H), 1.27 (s, 6H), 1.39-1.51 (m, 8H), 1.87-2.03 (m, 6H), 3.00 (d, J=5.6 Hz, 2H), 3.88 (s, 1H), 4.10 (d, J=6.3 Hz, 2H), 4.37 (t, J=5.6 Hz, 1H), 6.37 (d, J=14.4 Hz, 1H), 6.81 (d, J=14.4 Hz, 1H), 6.95 (s, 1H), 7.15 (s, 1H), 7.41 (d, J=7.1 Hz, 1H), 7.98 (s, 1H)
Example 64
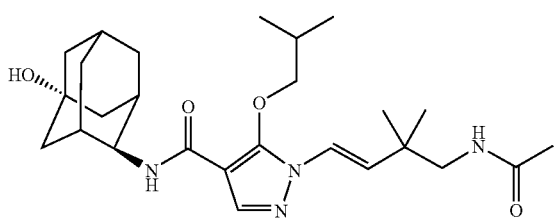
(Compound I-64) log k'=0.814
Example 65
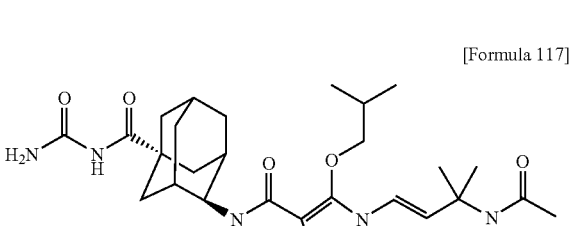
(Compound I-65) log k'=0.838
Example 66
(Compound I-66) log k'=0.886
Example 67
(Compound I-67) log k'=0.82

Example 68
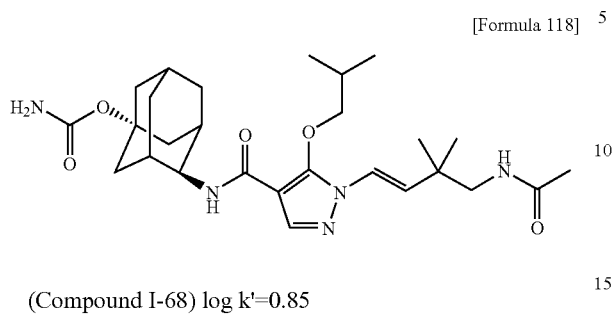
[Formula 118]
(Compound I-68) log k'=0.85
Example 69
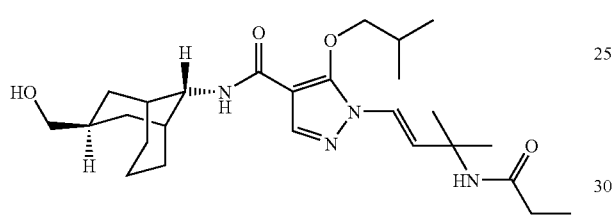
[Formula 119]
(Compound I-69) log k'=0.866
Example 70
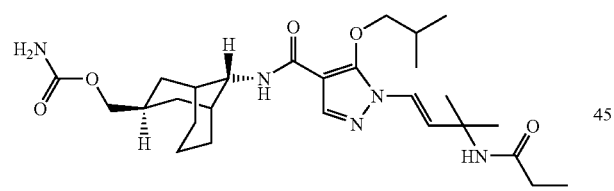
[Formula 120]
(Compound I-70) log k'=0.882
Example 71
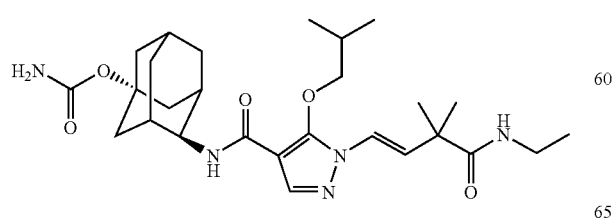
[Formula 121]
(Compound I-71) log k'=0.868
Example 72
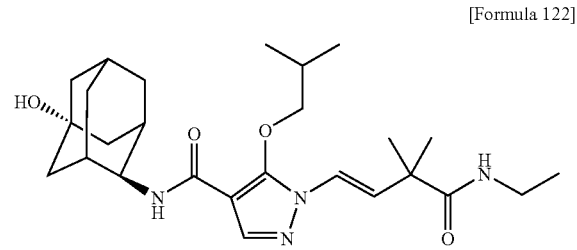 [SMILES: CCNC(=O)C(C)(C)/C=C/n1ncc(C(=O)N[C@H]2C3CC4CC2C[C@](O)(C4)C3)c1OCC(C)C]
[Formula 122]
(Compound I-72) NMR (DMSO-d6); δ(ppm) 0.96-1.01 (m, 9H), 1.27 (s, 6H), 1.34 (d, J=12.1 Hz, 2H), 1.61-1.72 (m, 6H), 1.89-2.04 (m, 6H), 3.03-3.08 (m, 2H), 3.89 (s, 1H), 4.10 (d, J=6.6 Hz, 2H), 4.44 (s, 1H), 6.34 (d, J=14.4 Hz, 1H), 6.78 (d, J=14.4 Hz, 1H), 7.39 (d, J=6.6 Hz, 1H), 7.57 (t, J=5.4 Hz, 1H), 7.98 (s, 1H)
Example 73
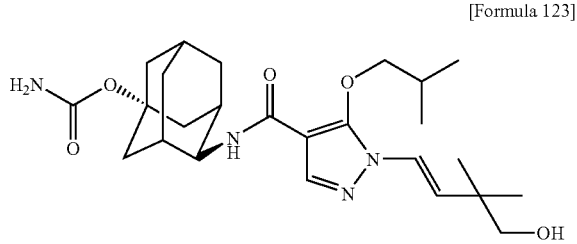
[Formula 123]
(Compound I-73) log k'=0.876
Example 74
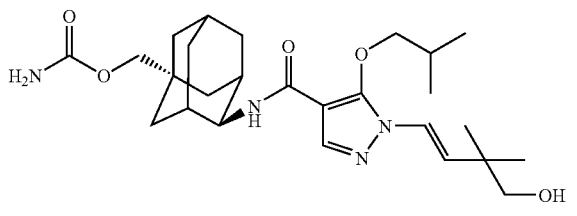
[Formula 124]
(Compound I-74) log k'=0.896

107
Example 75
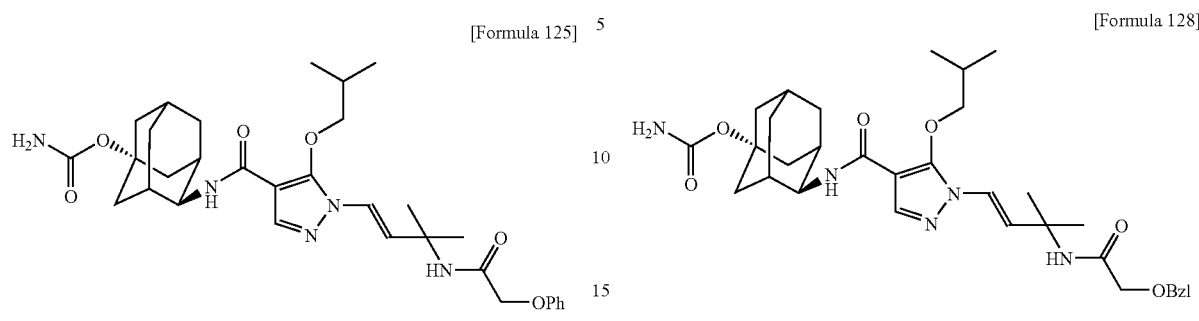
(Compound I-75) log k'=0.95
Example 76
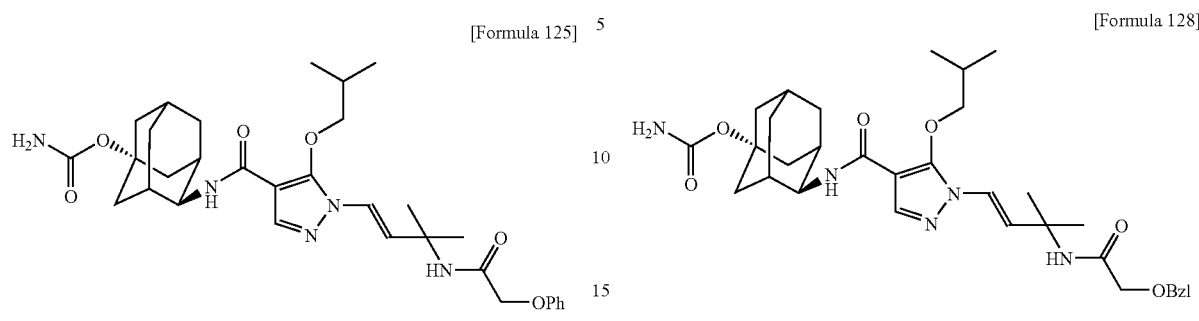
(Compound I-76) log k'=0.946
Example 77
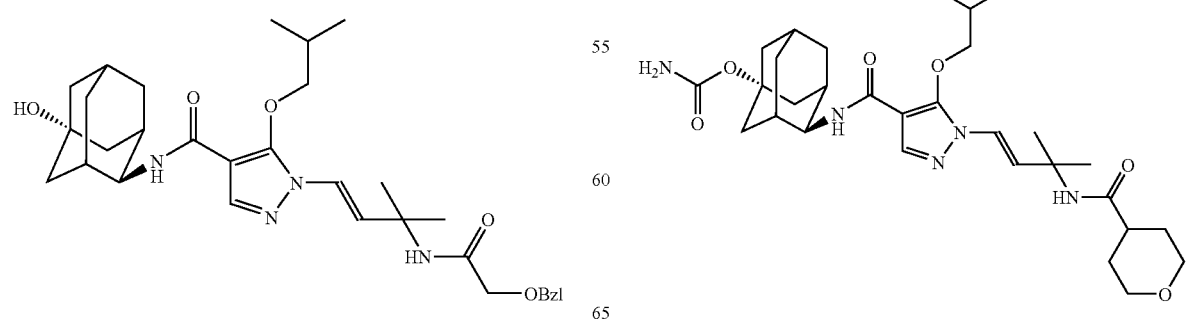
(Compound I-77) log k'=0.926
108
Example 78
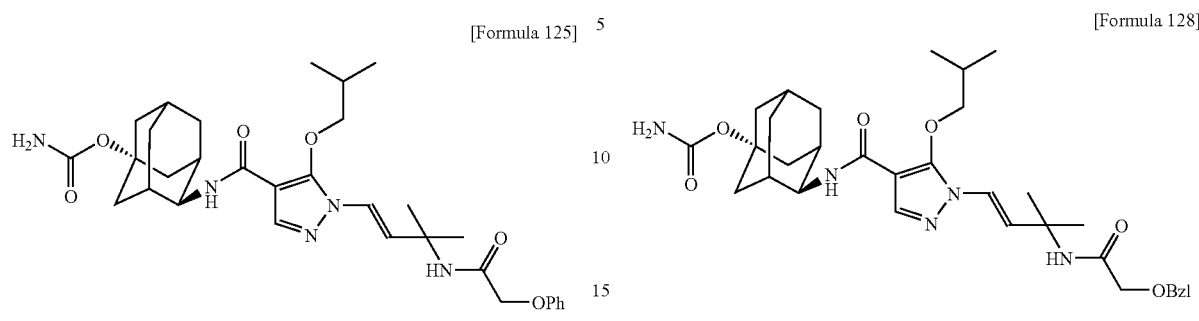
(Compound I-78) log k'=0.955
Example 79
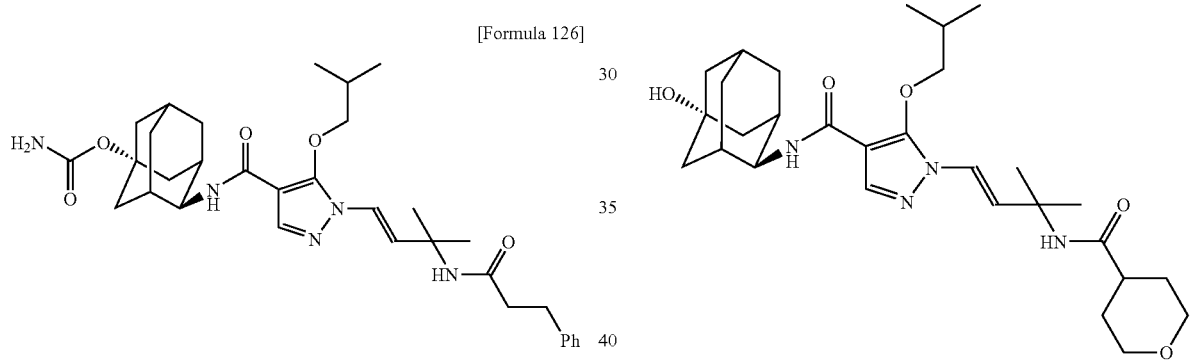
(Compound I-79) log k'=0.818
Example 80
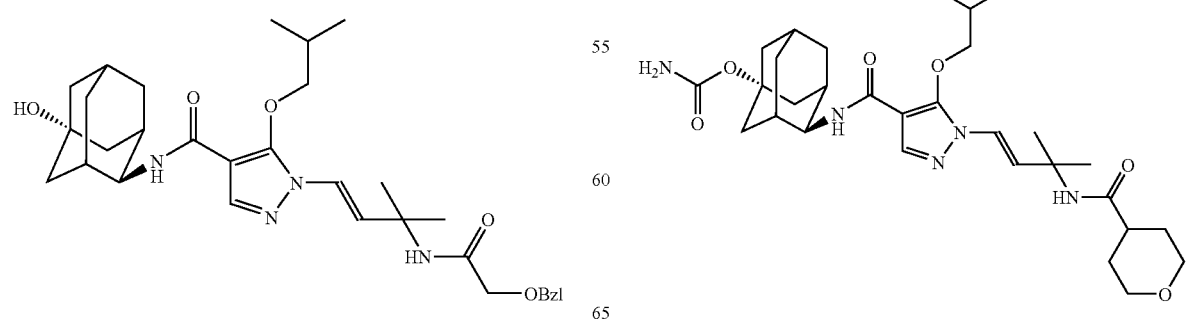
(Compound I-80) log k'=0.852

109
Example 81
110
Example 82
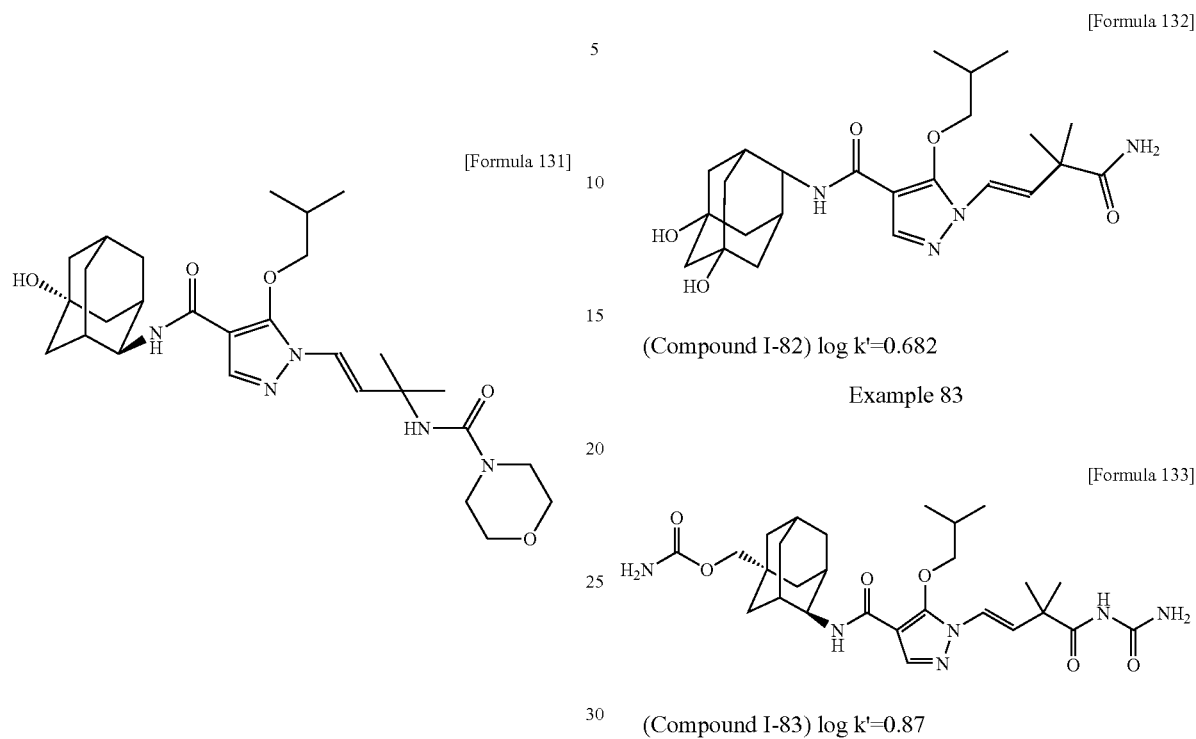
(Compound I-81) log k'=0.813
(Compound I-82) log k'=0.682
Example 83
(Compound I-83) log k'=0.87
Example 84
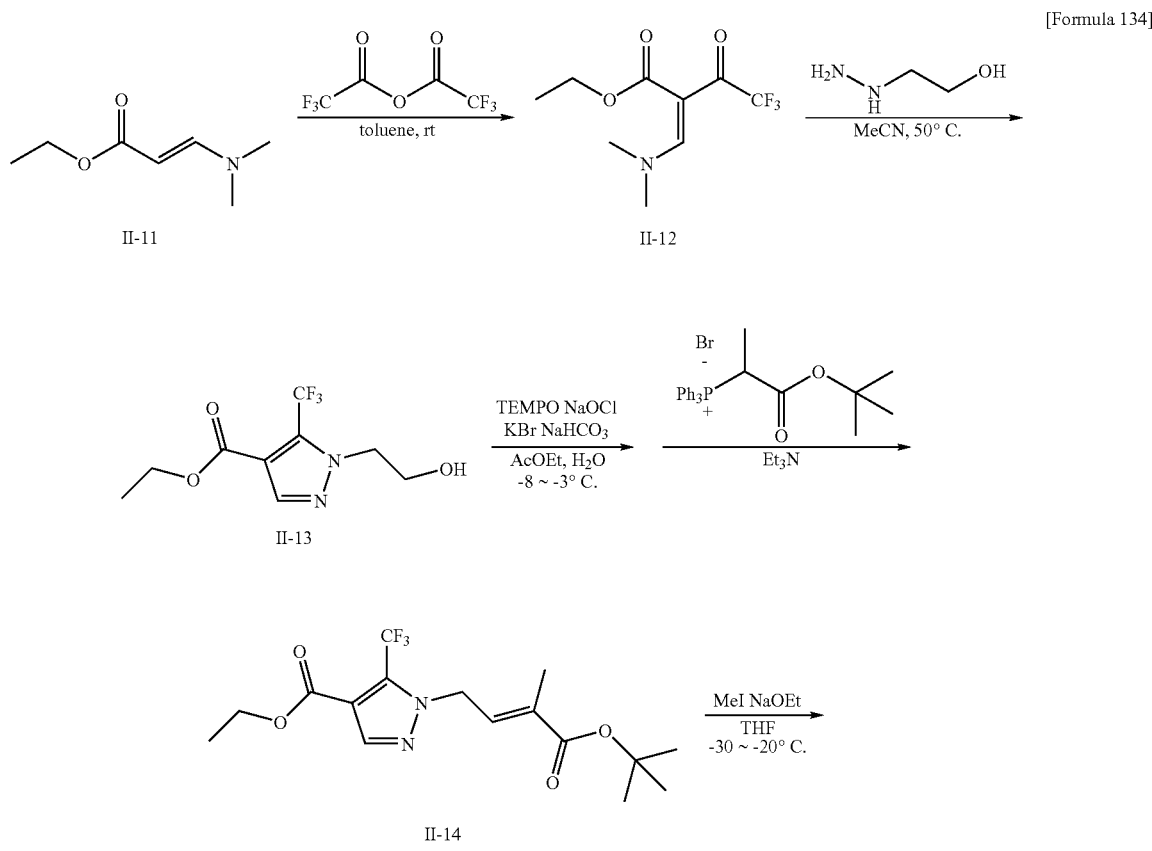

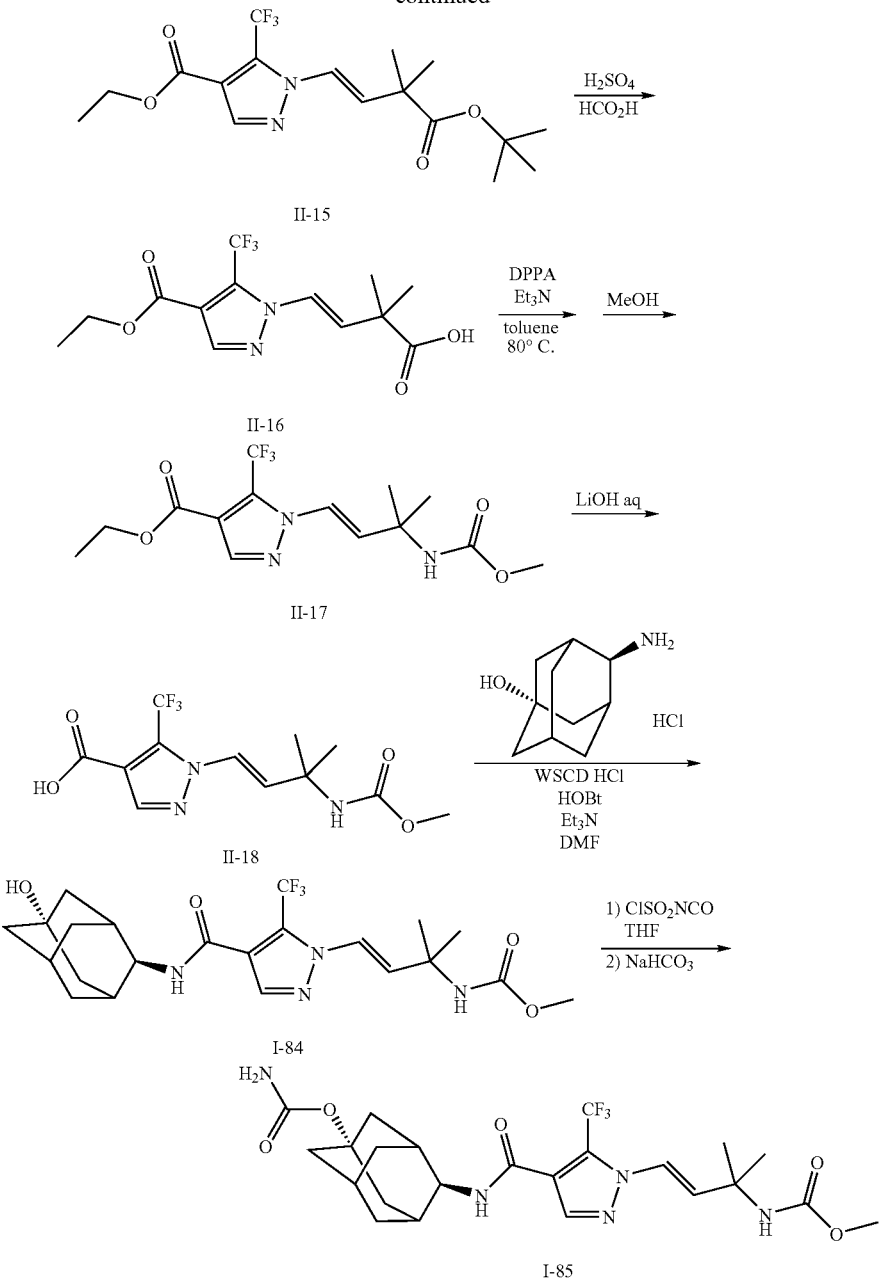

To a solution of Compound II-11 (ethyl 3-(dimethylamino) acrylate, 6.9 g) in toluene (100 ml) was added dropwise anhydrous trifluoroacetic acid (6.7 ml) over 20 min at −11° C., then the reaction mixture was stirred at room temperature for 4 hrs. After termination of the reaction, dichloromethane and H₂O were added to the mixture and the whole mixture was stirred for 20 min, then separated. The aqueous layer was extracted with dichloromethane. The organic layer was combined, dried over magnesium sulfate and concentrated. The residue was purified by silica gel column chromatography to give Compound II-12 (10.1 g).

To a solution of Compound II-12 (10.1 g) in acetonitrile (100 ml) was added dropwise 80% hydrazine ethanol (3.72 ml), and the reaction mixture was stirred at 50° C. for one hour. After termination of the reaction, the solvent was removed and H₂O was added to the residue and extracted with dichloromethane. The organic layer was dried over magnesium sulfate and concentrated. The residue was purified by silica gel column chromatography to give Compound II-13 (8.36 g).

To a solution of Compound II-13 (7.82 g) in ethyl acetate (156 ml) were added TEMPO (242 mg), potassium bromide (738 mg), solid NaHCO₃ (6.51 g) and H₂O (15.6 ml). 5% aqueous NaClO (48.5 ml) was added dropwise to the resulting mixture at −7° C. over 8 min, then the reaction mixture was stirred at the same temperature for one hour. After confirming the generation of the aldehyde, phosphonium salt (14.62 g) and triethylamine (5.2 ml) were added to the mixture, then the whole mixture was stirred at room temperature for 30 min. After termination of the reaction, H₂O was added to the reaction mixture, then extracted with ethyl acetate. The organic layer was washed with brine and dried over magnesium sulfate and concentrated. The residue was purified by silica gel column chromatography to give Compound II-14 (9.2 g).

To a solution of Compound II-14 (9.2 g) in tetrahydrofuran (92 ml) was added iodomethane (1.9 ml) and the resulting solution was cooled to −30° C. Sodium ethoxide (1.9 g) was added to the solution, then the reaction mixture was stirred at −25° C. for 2 hrs. After termination of the reaction, the reaction mixture was acidified with 1N aqueous HCl and extracted with ethyl acetate. The organic layer was washed with 10% aqueous $Na_2S_2O_3$ and brine successively, and dried over magnesium sulfate. The solvent was removed to give Compound II-15 (9.4 g). The obtained product was used for the next reaction without further purification.

To a solution of Compound II-15 (9.4 g) in formic acid (14.1 ml) was added $H_2SO_4$ (1.41 ml) at 0° C. After stirring at 0° C. for one hour, the reaction mixture was stirred at room temperature for one hour. After termination of the reaction, the reaction mixture was poured into ice-cold water and extracted with ethyl acetate. The organic layer was washed with brine and the solvent was removed. Aqueous $NaHCO_3$ was added to the residue and the mixture was washed with diisopropylether.

The organic layer was extracted with aqueous $NaHCO_3$ and combined with the aqueous layer. The whole mixture was acidified with aqueous HCl and extracted with ethyl acetate. The organic layer was washed with brine, and dried over magnesium sulfate and concentrated. The residue was purified by silica gel column chromatography to give Compound II-16 (7.04 g).

To a solution of Compound II-16 (1.5 g) in toluene (7.5 ml) were added triethylamine (718 μl) and diphenylphosphoryl azide (1.06 ml), then the reaction mixture was stirred at 80° C. for 3 hrs. After confirming the disappearance of the starting material, methanol (285 μl) was added to the mixture at 0° C., the whole mixture was stirred at 80° C. for one hour. After termination of the reaction, 2N aqueous NaOH was added to the mixture and extracted with ethyl acetate. The organic layer was washed with brine, and dried over magnesium sulfate and concentrated. The residue was purified by silica gel column chromatography to give Compound II-17 (1.13 g).

To a solution of Compound II-17 (1.13 g) in methanol (4.5 ml)-$H_2O$ (2.3 ml) was added 4N aqueous LiOH (1.62 ml), then the reaction mixture was stirred at room temperature for 1.5 hrs. After termination of the reaction, the mixture was acidified with 2N aqueous HCl and extracted with ethyl acetate. The organic layer was washed with brine and dried over magnesium sulfate and concentrated. The crystallization was carried with ethyl acetate-hexane to give Compound II-18 (677 mg).

To a solution of Compound II-18 (100 mg) in dimethylformamide (1.5 ml) were added hydroxy adamantanamine hydrochloride (76 mg), 1-(3-dimethylaminopropyl)-3-ethylcarbodiimide hydrochloride (78 mg), 1-hydroxybenzotriazole (12.6 mg) and triethylamine (108 μl), then the reaction mixture was stirred at room temperature for 6 hrs. After termination of the reaction, the mixture was acidified with 2N aqueous HCl and extracted with ethyl acetate. The organic layer was washed with saturated aqueous $NaHCO_3$ and brine successively, and dried over sodium sulfate. The residue was purified by silica gel column chromatography to afford Compound I-84 (139 mg). (Compound I-84) NMR (d6-DMSO); δ(ppm) 1.28-1.35 (m, 2H), 1.40 (s, 6H), 1.58-2.03 (m, 11H), 3.50 (s, 3H), 3.87-3.92 (m, 1H), 4.43 (s, 1H), 6.57 (d, J=13.6 Hz, 1H), 6.88 (d, J=13.6 Hz, 1H), 7.35 (s, 1H), 7.95 (s, 1H), 8.28 (d, J=6.8 Hz, 1H)

To a solution of Compound I-84 (117 mg) in tetrahydrofuran (4.7 ml) was added chlorosulfonyl isocyanate (33 μl) at −30° C., then the resulting solution was stirred at −30° C. for 2 hrs. Solid $NaHCO_3$ (104 mg) and $H_2O$ (157 μl) were added to the solution and the whole mixture was stirred at room temperature for 2 hrs. After termination of the reaction, $H_2O$ was added to the mixture and extracted with ethyl acetate. The organic layer was washed with brine and dried over sodium sulfate and concentrated.

The residue was purified by silica gel column chromatography to give Compound I-85 (116 mg).

(Compound I-85) NMR (d6-DMSO); δ(ppm) 1.40 (s, 8H), 1.88-2.13 (m, 11H), 3.50 (s, 3H), 3.94-3.99 (m, 1H), 6.05-6.35 (s, 2H), 6.58 (d, J=13.6 Hz, 1H), 6.88 (d, J=13.6 Hz, 1H), 7.35 (s, 1H), 7.96 (s, 1H), 8.33 (d, J=6.8 Hz, 1H)

The compounds shown below were synthesized in a similar manner.

Example 85

[Formula 135]

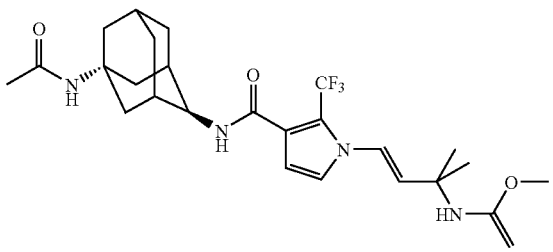

(Compound I-86) NMR (d6-DMSO); δ(ppm) 1.40 (s, 8H), 1.72-2.03 (m, 14H), 3.50 (s, 3H), 3.91-3.97 (m, 1H), 6.58 (d, J=13.6 Hz, 1H), 6.88 (d, J=13.6 Hz, 1H), 7.31-7.39 (m, 2H), 7.95 (s, 1H), 8.33 (d, J=7.2 Hz, 1H)

Example 86

[Formula 136]

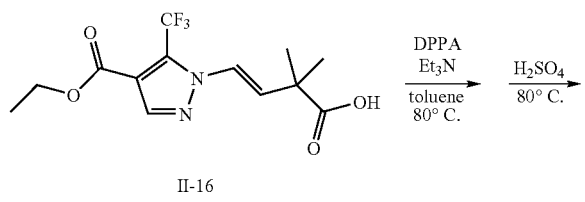

II-16

115

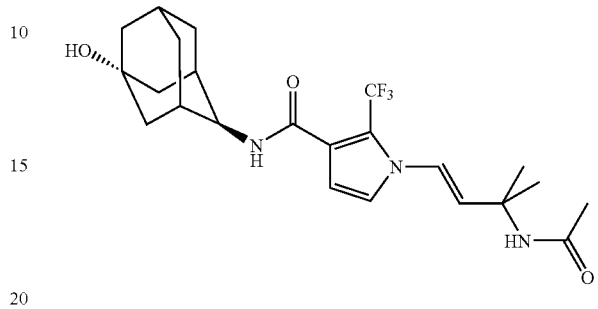

To a solution of Compound II-16 (1.5 g) in toluene (7.5 ml) were added triethylamine (718 μl), diphenylphosphoryl azide (1.06 ml), then the reaction mixture was stirred at 80° C. for 30 min. After confirming the disappearance of the starting material, sulfuric acid (374 μl) was added to the mixture at 0° C., then the whole mixture was stirred at 80° C. for one hour. After termination of the reaction, the mixture was alkalified with 2N aqueous NaOH and extracted with ethyl acetate. The organic layer was washed with brine, and dried over magnesium sulfate and concentrated. The obtained product was used for the next reaction without further purification.

According to the above procedure, the obtained residue was dissolved in dichloromethane (14 ml), and triethylamine (1.74 ml) and acetic anhydride (0.59 ml) were added to the resulting solution. The reaction mixture was stirred at room temperature for 3 hrs. After termination of the reaction, 1N aqueous HCl was added to the mixture and extracted with ethyl acetate. The organic layer was washed with saturated aqueous NaHCO$_3$ and brine successively, and dried over magnesium sulfate and concentrated. The obtained product was used for the next reaction without further purification.

According to the above procedure, the obtained residue was dissolved in methanol (5.5 ml)-H$_2$O (2.8 ml), and 4N aqueous LiOH (2.08 ml) was added to the resulting solution. The reaction mixture was stirred at room temperature for 1.5 hrs.

After termination of the reaction, the whole mixture was acidified with 2N aqueous HCl and extracted with ethyl acetate. The organic layer was washed with brine and dried over magnesium sulfate and concentrated. The crystallization was carried with chloroform to give Compound II-21 (1.09 g).

116

The compounds shown below were synthesized from Compound II-21 in accordance with the above Example.

Example 87

[Formula 137]

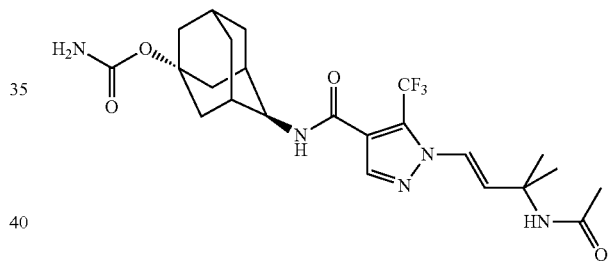

(Compound I-87) NMR (d6-DMSO); δ(ppm) 1.28-1.35 (m, 2H), 1.42 (s, 6H), 1.58-2.03 (m, 14H), 3.87-3.91 (m, 1H), 4.43 (s, 1H), 6.64 (d, J=13.6 Hz, 1H), 6.86 (d, J=13.6 Hz, 1H), 7.85 (s, 1H), 7.94 (s, 1H), 8.27 (d, J=7.2 Hz, 1H)

Example 88

[Formula 138]

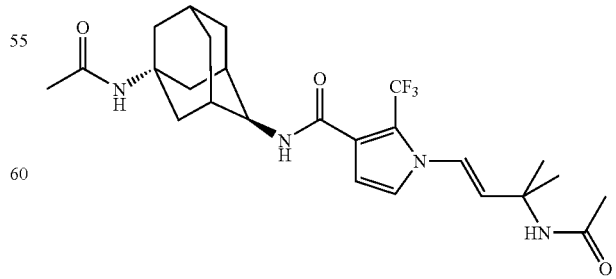

(Compound I-88) NMR (d6-DMSO); δ(ppm) 1.37-1.43 (m, 8H), 1.78-2.11 (m, 14H), 3.93-3.98 (m, 1H), 6.05-6.35 (s, 2H), 6.64 (d, J=13.6 Hz, 1H), 6.86 (d, J=13.6 Hz, 1H), 7.85 (s, 1H), 7.95 (s, 1H), 8.32 (d, J=6.0 Hz, 1H)

Example 89

[Formula 139]

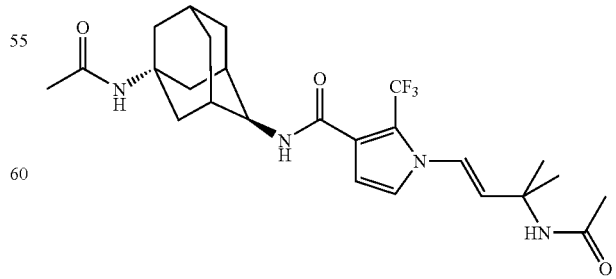

(Compound I-89) NMR (d6-DMSO); δ(ppm) 1.34-1.45 (m, 8H), 1.72-2.02 (m, 17H), 3.90-3.97 (m, 1H), 6.64 (d, J=13.6 Hz, 1H), 6.86 (d, J=13.6 Hz, 1H), 7.37 (s, 1H), 7.85 (s, 1H), 7.95 (s, 1H), 8.31 (d, J=7.2 Hz, 1H)

Example 90

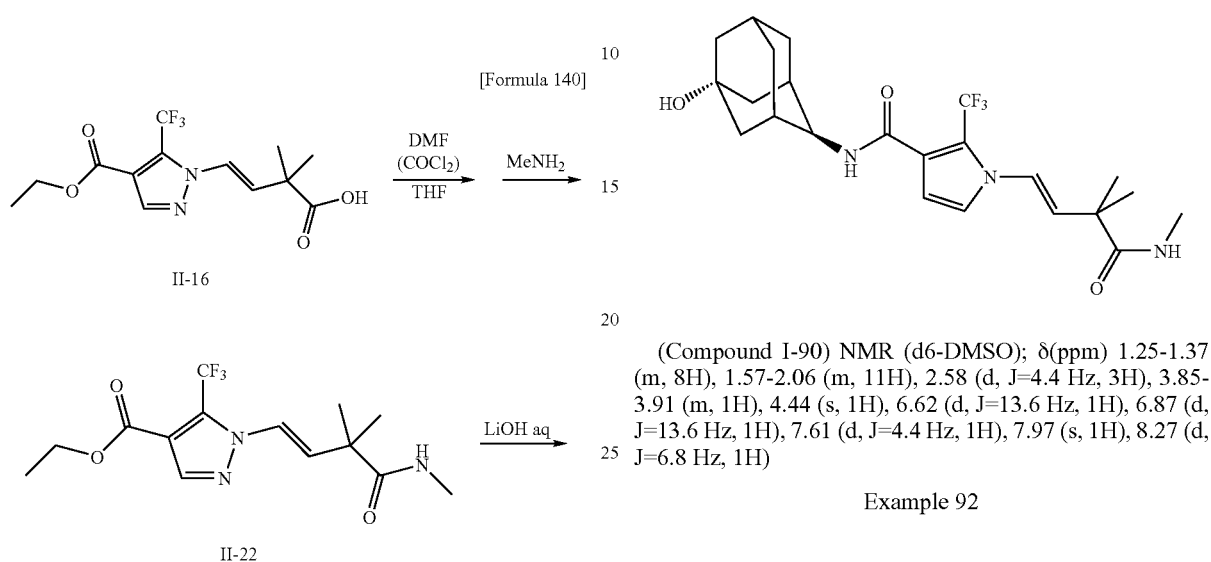

To a solution of Compound II-16 (1 g) in tetrahydrofuran (10 ml) were added dimethylformamide (24 µl) and oxalyl chloride (396 µl) under ice-cooling, then the resulting mixture was stirred at room temperature for one hour. The obtained acid chloride was added dropwisely to 40% aqueous methylamine (2.42 g) under ice-cooling, then the reaction mixture was stirred at room temperature for 3 hrs. After termination of the reaction, H₂O was added to the mixture and extracted with ethyl acetate. The organic layer was washed with brine, and dried over magnesium sulfate and concentrated. The obtained product was used for the next reaction without further purification.

According to the above procedure, the obtained residue was dissolved in methanol (4.1 ml)-H₂O (2 ml), and 4N aqueous LiOH (1.54 ml) was added to the resulting solution. The reaction mixture was stirred at room temperature for 30 min. After termination of the reaction, the whole mixture was diluted with water and washed with ethyl acetate. The aqueous layer was acidified with aqueous HCl, extracted with ethyl acetate, and dried over magnesium sulfate. The solvent was removed to give Compound II-23 (929 mg).

The compounds shown below were synthesized from Compound II-23 in accordance with the above Example.

Example 91

[Formula 141]

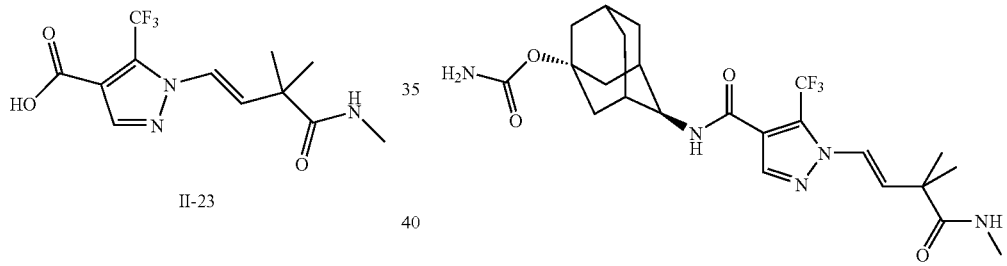

(Compound I-90) NMR (d6-DMSO); δ(ppm) 1.25-1.37 (m, 8H), 1.57-2.06 (m, 11H), 2.58 (d, J=4.4 Hz, 3H), 3.85-3.91 (m, 1H), 4.44 (s, 1H), 6.62 (d, J=13.6 Hz, 1H), 6.87 (d, J=13.6 Hz, 1H), 7.61 (d, J=4.4 Hz, 1H), 7.97 (s, 1H), 8.27 (d, J=6.8 Hz, 1H)

Example 92

[Formula 142]

(Compound I-91) NMR (d6-DMSO); δ(ppm) 1.30 (s, 6H), 1.35-1.46 (m, 2H), 1.87-2.13 (m, 11H), 2.55-2.61 (m, 3H), 3.92-3.98 (m, 1H), 6.00-6.35 (s, 2H), 6.62 (d, J=14.0 Hz, 1H), 6.88 (d, J=14.0 Hz, 1H), 7.61 (s, 1H), 7.98 (s, 1H), 8.32 (d, J=6.4 Hz, 1H)

Example 93

[Formula 143]

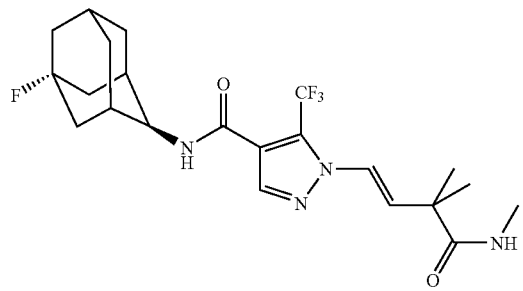

(Compound I-92) NMR (d6-DMSO); δ(ppm) 1.30 (s, 6H), 1.34-1.43 (m, 2H), 1.80-2.21 (m, 11H), 2.58 (d, J=4.4 Hz, 3H), 3.91-3.98 (m, 1H), 6.62 (d, J=13.6 Hz, 1H), 6.88 (d, J=13.6 Hz, 1H), 7.58-7.66 (m, 1H), 7.99 (s, 1H), 8.33 (d, J=6.4 Hz, 1H)

3.12 (m, 2H), 3.87-4.02 (m, 1H), 4.44 (s, 1H), 6.62 (d, J=13.6 Hz, 1H), 6.87 (d, J=13.6 Hz, 1H), 7.62-7.69 (m, 1H), 7.97 (s, 1H), 8.28 (d, J=7.2 Hz, 1H)

Example 96

Example 94

[Formula 146]

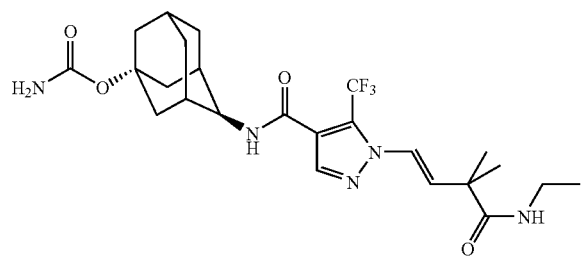

[Formula 144]

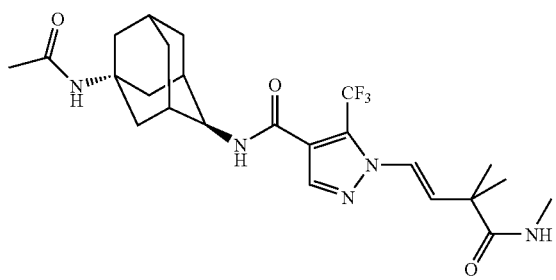

(Compound I-95) NMR (d6-DMSO); δ(ppm) 1.00 (t, J=6.8 Hz, 3H), 1.30 (s, 6H), 1.36-1.44 (m, 2H), 1.87-2.13 (m, 11H), 3.04-3.12 (m, 2H), 3.93-3.99 (m, 1H), 6.00-6.40 (s, 2H), 6.63 (d, J=13.6 Hz, 1H), 6.87 (d, J=13.6 Hz, 1H), 7.62-7.69 (m, 1H), 7.98 (s, 1H), 8.33 (d, J=6.8 Hz, 1H)

Example 97

(Compound I-93) NMR (d6-DMSO); δ(ppm) 1.30 (s, 6H), 1.35-1.43 (m, 2H), 1.72-2.03 (m, 14H), 2.58 (d, J=4.4 Hz, 3H), 3.91-3.97 (m, 1H), 6.62 (d, J=13.6 Hz, 1H), 6.88 (d, J=13.6 Hz, 1H), 7.37 (s, 1H), 7.61 (d, J=4.0 Hz, 1H), 7.97 (s, 1H), 8.31 (d, J=7.2 Hz, 1H)

[Formula 147]

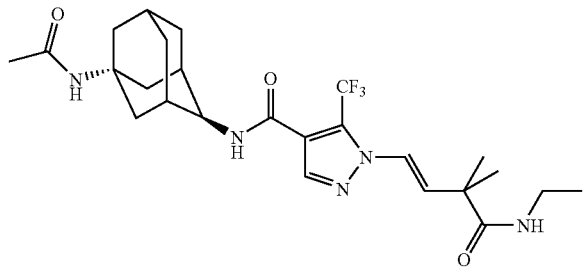

Example 95

(Compound I-96) NMR (d6-DMSO); δ(ppm) 1.00 (t, J=7.2 Hz, 3H), 1.30 (s, 6H), 1.35-1.43 (m, 2H), 1.72-2.03 (m, 14H), 3.03-3.13 (m, 2H), 3.90-3.96 (m, 1H), 6.62 (d, J=13.6 Hz, 1H), 6.87 (d, J=13.6 Hz, 1H), 7.37 (s, 1H), 7.62-7.69 (m, 1H), 7.97 (s, 1H), 8.32 (d, J=6.8 Hz, 1H)

[Formula 145]

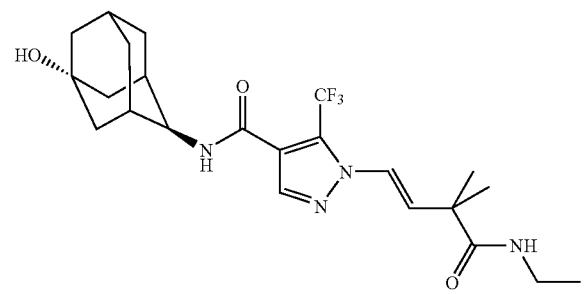

Example 98

[Formula 148]

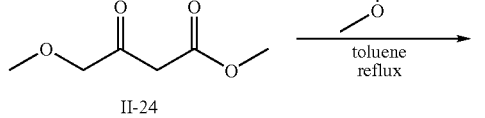

II-24

(Compound I-94) NMR (d6-DMSO); δ(ppm) 1.00 (t, J=7.2 Hz, 3H), 1.23-1.35 (m, 8H), 1.55-2.05 (m, 11H), 3.04-

3.86-3.92 (m, 1H), 4.41 (s, 1H), 4.82 (s, 2H), 6.48 (d, J=14.0 Hz, 1H), 6.99 (d, J=14.0 Hz, 1H), 7.24 (s, 1H), 7.59 (d, J=6.4 Hz, 1H), 8.14 (s, 1H)

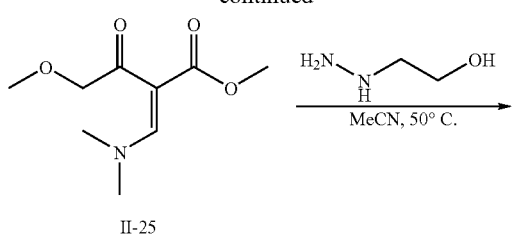

To a solution of Compound II-24 (4-methoxy-3-oxobutanoic acid methyl ester, 9.87 g) in toluene (99 ml) was added dropwise 1,1-dimethoxy-N,N-dimethylmethanamine (26.9 ml) over 10 min, then the reaction mixture was refluxed for 2 hrs. After termination of the reaction, the mixture was concentrated. The obtained product was used for the next reaction.

According to the above procedure, the obtained residue was dissolved in acetonitrile soln. (136 ml), and 80% hydrazine ethanol (6.58 g) was added to the resulting solution. The reaction mixture was stirred at 50° C. for one hour. After termination of the reaction, the mixture was concentrated. 1N aqueous HCl was added to the residue and extracted with ethyl acetate. The organic layer was washed with saturated aqueous NaHCO₃ and brine successively, and dried over magnesium sulfate and concentrated. The residue was purified by silica gel column chromatography to give Compound II-26 (9.74 g).

The compounds shown below were synthesized from Compound II-26 in accordance with the above Example.

Example 99

[Formula 149]

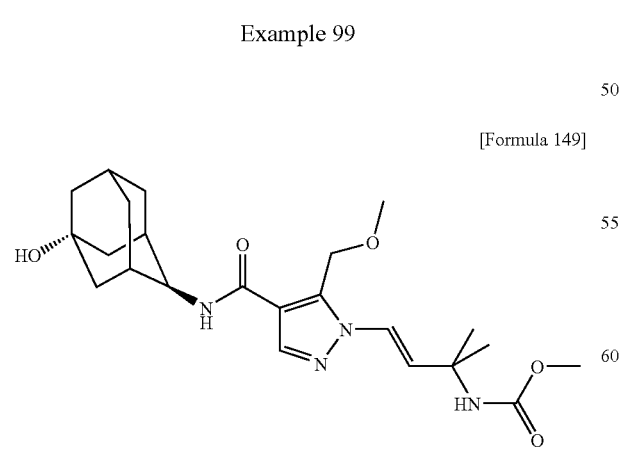

(Compound I-97) NMR (d6-DMSO); δ(ppm) 1.28-1.43 (m, 8H), 1.58-2.09 (m, 11H), 3.26 (s, 3H), 3.50 (s, 3H), Example 100

[Formula 150]

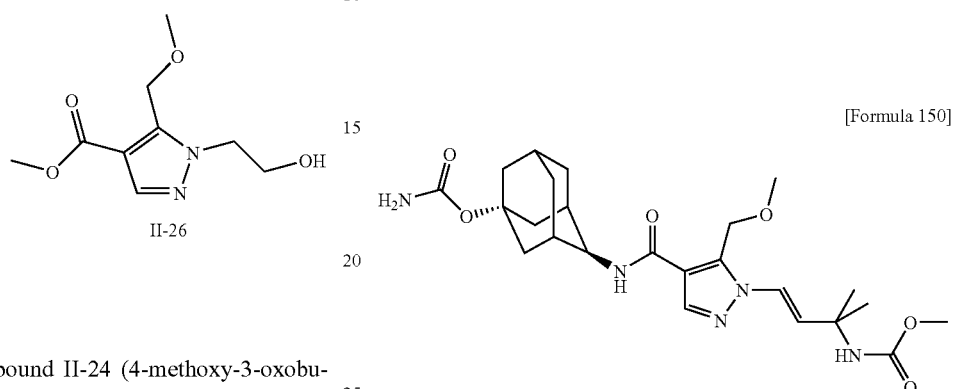

(Compound I-98) NMR (d6-DMSO); δ(ppm) 1.35-1.48 (m, 8H), 1.90-2.18 (m, 11H), 3.26 (s, 3H), 3.50 (s, 3H), 3.95-4.01 (m, 1H), 4.83 (s, 2H), 6.00-6.35 (s, 2H), 6.49 (d, J=14.0 Hz, 1H), 7.00 (d, J=14.0 Hz, 1H), 7.26 (s, 1H), 7.65 (d, J=6.8 Hz, 1H), 8.15 (s, 1H)

Example 101

[Formula 151]

(Compound I-99) NMR (d6-DMSO); δ(ppm) 1.30-1.47 (m, 8H), 1.56-2.09 (m, 14H), 3.26 (s, 3H), 3.88-3.95 (m, 1H), 4.41 (s, 1H), 4.82 (s, 2H), 6.55 (d, J=14.0 Hz, 1H), 6.98 (d, J=14.0 Hz, 1H), 7.59 (d, J=6.4 Hz, 1H), 7.77 (s, 1H), 8.13 (s, 1H)

Example 102

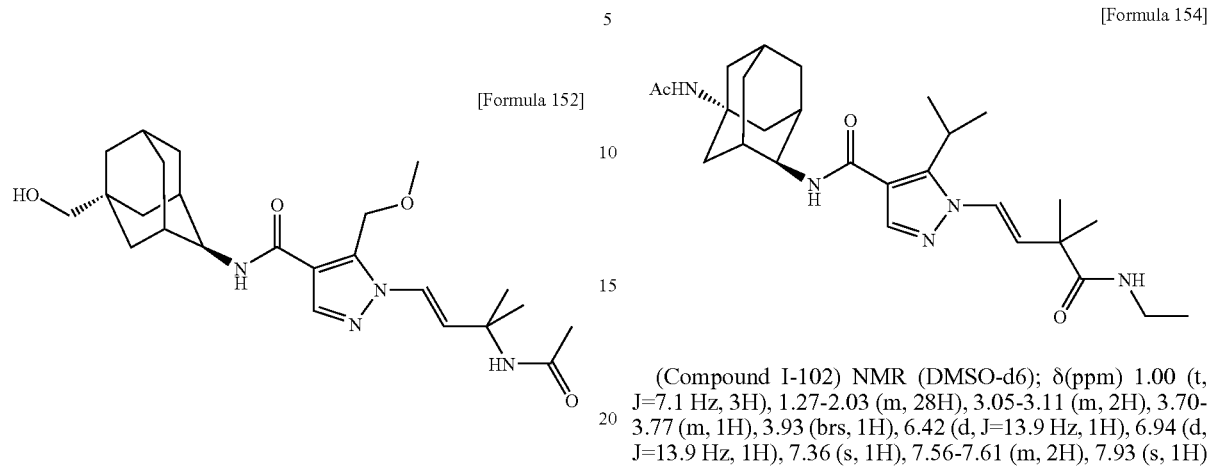

[Formula 152]

(Compound I-100) NMR (d6-DMSO); δ(ppm) 1.35-1.56 (m, 8H), 1.77-2.05 (m, 14H), 3.01 (d, J=5.6 Hz, 2H), 3.27 (s, 3H), 3.88-3.95 (m, 1H), 4.36 (t, J=5.6 Hz, 1H), 4.83 (s, 2H), 6.55 (d, J=14.0 Hz, 1H), 6.98 (d, J=14.0 Hz, 1H), 7.63 (d, J=6.8 Hz, 1H), 7.78 (s, 1H), 8.14 (s, 1H)

Example 103

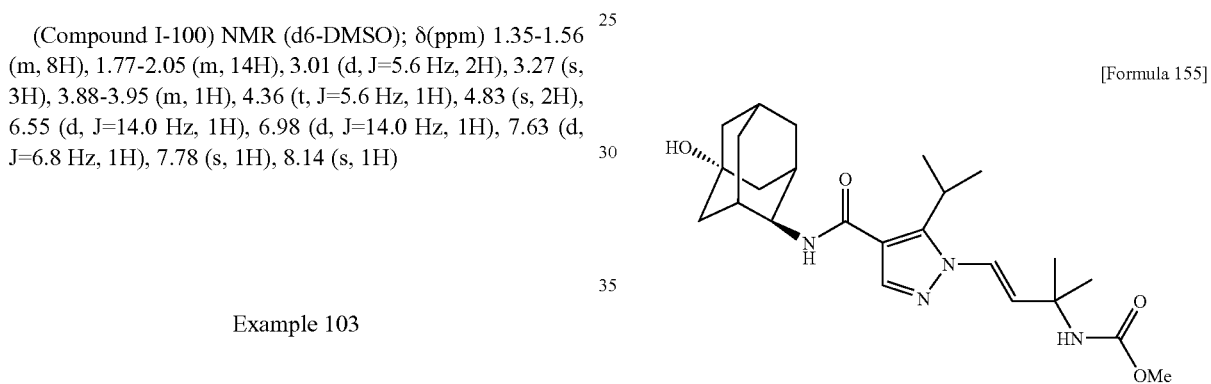

[Formula 153]

(Compound I-101) NMR (d6-DMSO); δ(ppm) 1.35-1.56 (m, 8H), 1.77-2.05 (m, 14H), 3.01 (d, J=5.6 Hz, 2H), 3.27 (s, 3H), 3.88-3.95 (m, 1H), 4.36 (t, J=5.6 Hz, 1H), 4.83 (s, 2H), 6.55 (d, J=14.0 Hz, 1H), 6.98 (d, J=14.0 Hz, 1H), 7.63 (d, J=6.8 Hz, 1H), 7.78 (s, 1H), 8.14 (s, 1H)

The compounds shown below were synthesized in a similar manner.

Example 104

[Formula 154]

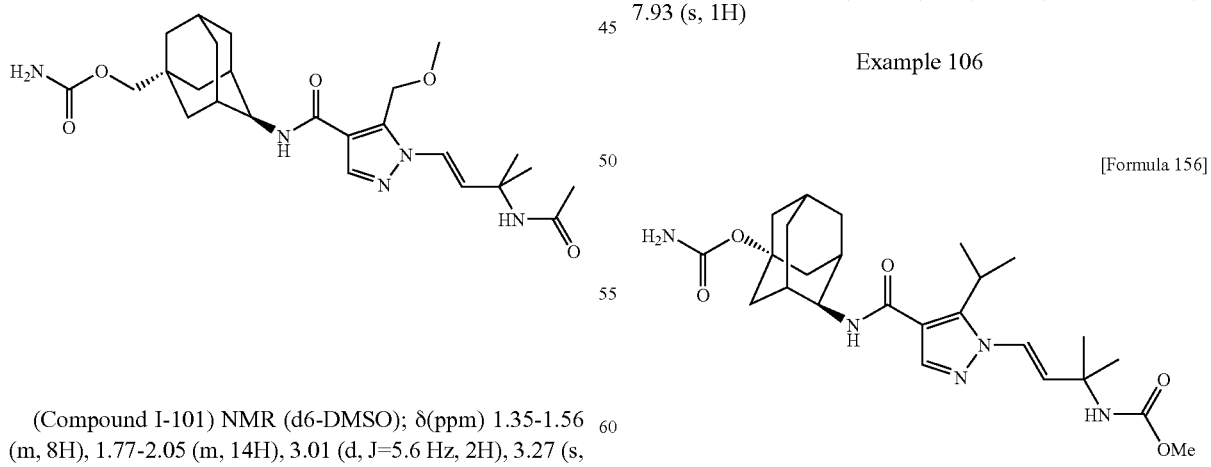

(Compound I-102) NMR (DMSO-d6); δ(ppm) 1.00 (t, J=7.1 Hz, 3H), 1.27-2.03 (m, 28H), 3.05-3.11 (m, 2H), 3.70-3.77 (m, 1H), 3.93 (brs, 1H), 6.42 (d, J=13.9 Hz, 1H), 6.94 (d, J=13.9 Hz, 1H), 7.36 (s, 1H), 7.56-7.61 (m, 2H), 7.93 (s, 1H)

Example 105

[Formula 155]

(Compound I-103) NMR (DMSO-d6); δ(ppm) 1.27 (d, J=7.3 Hz, 6H), 1.32-2.05 (m, 19H), 3.50 (s, 3H), 3.76-3.83 (m, 1H), 3.88 (brs, 1H), 4.41 (s, 1H), 6.38 (d, J=13.9 Hz, 1H), 6.96 (d, J=13.9 Hz, 1H), 7.27 (s, 1H), 7.56 (d, J=6.3 Hz, 1H), 7.93 (s, 1H)

Example 106

[Formula 156]

(Compound I-104) NMR (DMSO-d6); δ(ppm) 1.27 (d, J=7.1 Hz, 6H), 1.38-2.13 (m, 19H), 3.50 (s, 3H), 3.76-3.83 (m, 1H), 3.95 (brs, 1H), 6.18 (brs, 2H), 6.38 (d, J=13.9 Hz, 1H), 6.96 (d, J=13.9 Hz, 1H), 7.26 (s, 1H), 7.62 (d, J=6.1 Hz, 1H), 7.94 (s, 1H)

Example 107

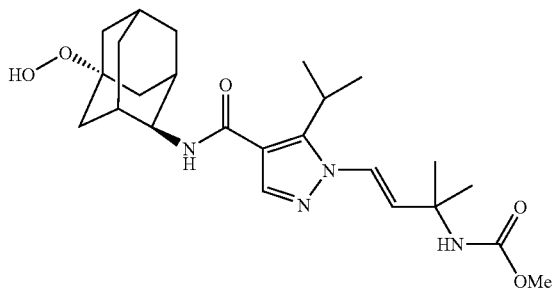

[Formula 157]

(Compound I-105) NMR (DMSO-d6); δ(ppm) 1.28 (d, J=71 Hz, 6H), 1.36-2.05 (m, 19H), 3.01 (d, J=5.6 Hz, 2H), 3.50 (s, 3H), 3.77-3.84 (m, 1H), 3.88 (brs, 1H), 4.35 (t, J=5.6 Hz, 1H), 6.38 (d, J=13.6 Hz, 1H), 6.96 (d, J=13.6 Hz, 1H), 7.25 (s, 1H), 7.57 (d, J=6.6 Hz, 2H), 7.94 (s, 1H)

Example 108

[Formula 158]

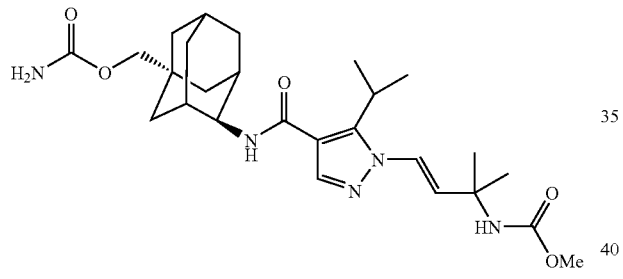

(Compound I-106) NMR (DMSO-d6); δ(ppm) 1.28 (d, J=7.1 Hz, 6H), 1.38-2.06 (m, 19H), 3.50 (s, 3H), 3.56 (s, 2H), 3.77-3.84 (m, 1H), 3.90 (brs, 1H), 6.38 (d, J=13.6 Hz, 1H), 6.40 (brs, 2H), 6.96 (d, J=13.6 Hz, 1H), 7.25 (s, 1H), 7.61 (d, J=6.3 Hz, 1H), 7.94 (s, 1H)

Example 109

[Formula 159]

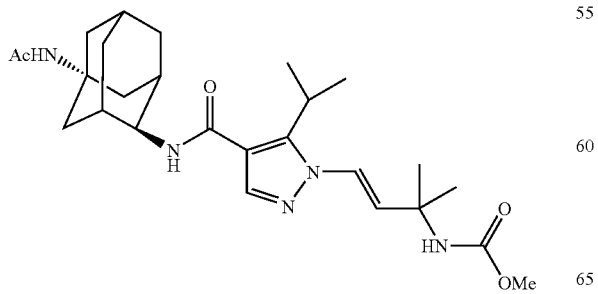

(Compound I-107) NMR (DMSO-d6); δ(ppm) 1.27 (d, J=7.1 Hz, 6H), 1.38-2.03 (m, 22H), 3.49 (s, 3H), 3.76-3.84 (m, 1H), 3.92 (brs, 1H), 6.38 (d, J=13.9 Hz, 1H), 6.96 (d, J=13.9 Hz, 1H), 7.27 (s, 1H), 7.36 (s, 1H), 7.60 (d, J=6.6 Hz, 1H), 7.94 (s, 1H)

Example 110

[Formula 160]

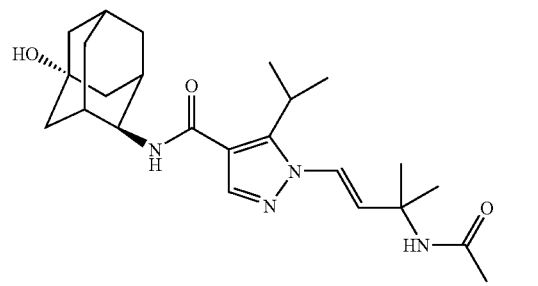

(Compound I-108) NMR (DMSO-d6); δ(ppm) 1.26-2.08 (m, 28H), 3.74-3.81 (m, 1H), 3.88 (brs, 1H), 4.41 (s, 1H), 6.44 (d, J=13.6 Hz, 1H), 6.94 (d, J=13.6 Hz, 1H), 7.56 (d, J=6.3 Hz, 1H), 7.77 (s, 1H), 7.93 (s, 1H)

Example 111

[Formula 161]

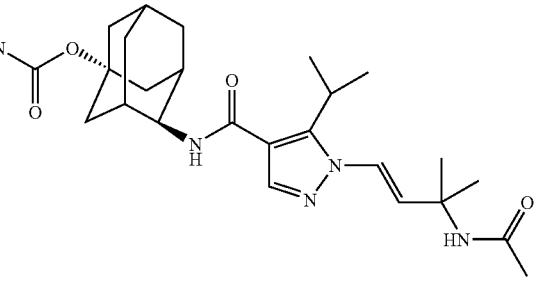

(Compound I-109) NMR (DMSO-d6); δ(ppm) 1.27 (d, J=7.1 Hz, 6H), 1.38-2.12 (m, 22H), 3.74-3.81 (m, 1H), 3.94 (brs, 1H), 6.19 (brs, 2H), 6.44 (d, J=13.9 Hz, 1H), 6.94 (d, J=13.9 Hz, 1H), 7.61 (d, J=5.8 Hz, 1H), 7.77 (s, 1H), 7.93 (s, 1H)

Example 112

[Formula 162]

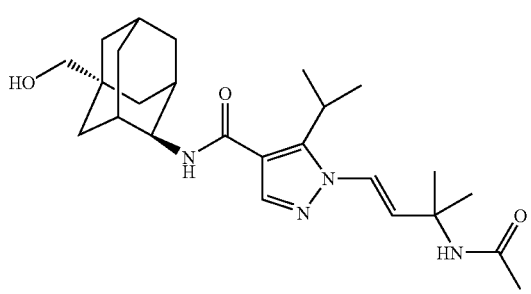

(Compound I-110) NMR (DMSO-d6); δ(ppm) 1.27 (d, J=7.1 Hz, 6H), 1.35-2.05 (m, 22H), 3.00 (d, J=5.3 Hz, 2H), 3.75-3.82 (m, 1H), 3.87 (brs, 1H), 4.36 (t, J=5.3 Hz, 1H), 6.44 (d, J=13.9 Hz, 1H), 6.94 (d, J=13.9 Hz, 1H), 7.58 (d, J=6.3 Hz, 1H), 7.78 (s, 1H), 7.93 (s, 1H)

(brs, 1H), 6.44 (d, J=13.6 Hz, 1H), 6.95 (d, J=13.6 Hz, 1H), 7.36 (s, 1H), 7.60 (d, J=6.3 Hz, 1H), 7.78 (s, 1H), 7.93 (s, 1H)

Example 113

[Formula 163]

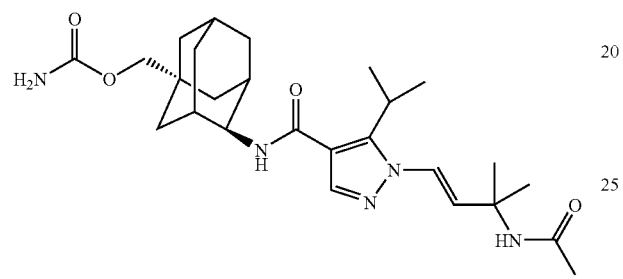

(Compound I-111) NMR (DMSO-d6); δ(ppm) 1.27 (d, J=7.1 Hz, 6H), 1.37-2.08 (m, 22H), 3.56 (s, 2H), 3.75-3.83 (m, 1H), 3.89 (brs, 1H), 6.42 (brs, 2H), 6.44 (d, J=13.9 Hz, 1H), 6.94 (d, J=13.9 Hz, 1H), 7.61 (d, J=7.1 Hz, 1H), 7.78 (s, 1H), 7.94 (s, 1H)

Example 114

[Formula 164]

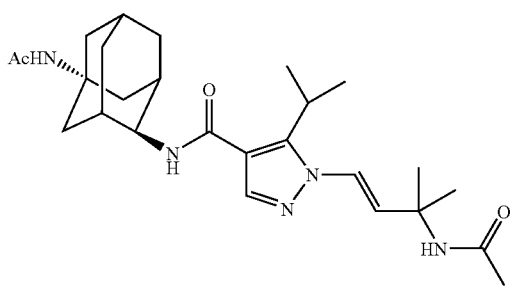

(Compound I-112) NMR (DMSO-d6); δ(ppm) 1.27 (d, J=7.1 Hz, 6H), 1.38-2.02 (m, 25H), 3.75-3.82 (m, 1H), 3.93

Example 115

[Formula 165]

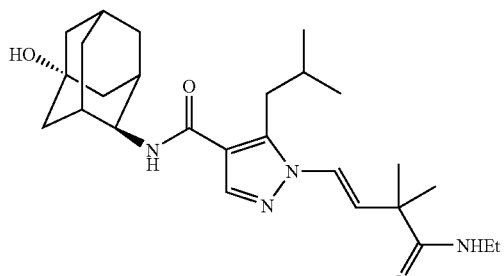

(Compound I-113) NMR (DMSO-d6); δ(ppm) 0.84 (d, J=6.6 Hz, 6H), 1.00 (t, J=7.1 Hz, 3H), 1.29-2.04 (m, 20H), 2.95 (d, J=7.1 Hz, 2H), 3.05-3.11 (m, 2H), 3.90 (brs, 1H), 4.40 (s, 1H), 6.46 (d, J=14.2 Hz, 1H), 6.88 (d, J=13.9 Hz, 1H), 7.41 (d, J=6.6 Hz, 1H), 7.54 (brs, 1H), 8.15 (s, 1H)

Example 116

[Formula 166]

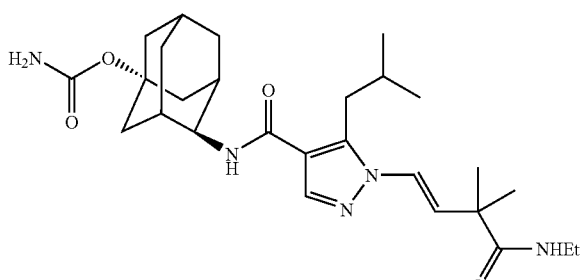

(Compound I-114) NMR (DMSO-d6); δ(ppm) 0.85 (d, J=6.6 Hz, 6H), 1.00 (t, J=7.2 Hz, 3H), 1.30 (s, 6H), 1.38-2.10 (m, 14H), 2.95 (d, J=7.1 Hz, 2H), 3.04-3.11 (m, 2H), 3.97 (brs, 1H), 6.17 (brs, 2H), 6.47 (d, J=13.9 Hz, 1H), 6.88 (d, J=13.9 Hz, 1H), 7.46 (d, J=6.6 Hz, 1H), 7.54 (brs, 1H), 8.15 (s, 1H)

Example 117

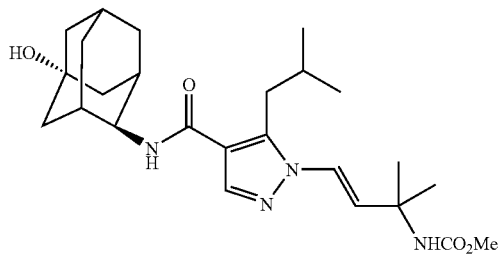

[Formula 167]

(Compound I-115) NMR (DMSO-d6); δ(ppm) 0.84 (d, J=6.6 Hz, 6H), 1.32-2.04 (m, 20H), 2.92 (d, J=7.3 Hz, 2H), 3.50 (s, 3H), 3.90 (brs, 1H), 4.41 (s, 1H), 6.43 (d, J=13.9 Hz, 1H), 6.88 (d, J=13.9 Hz, 1H), 7.24 (s, 1H), 7.42 (d, J=6.3 Hz, 1H), 8.14 (s, 1H)

Example 118

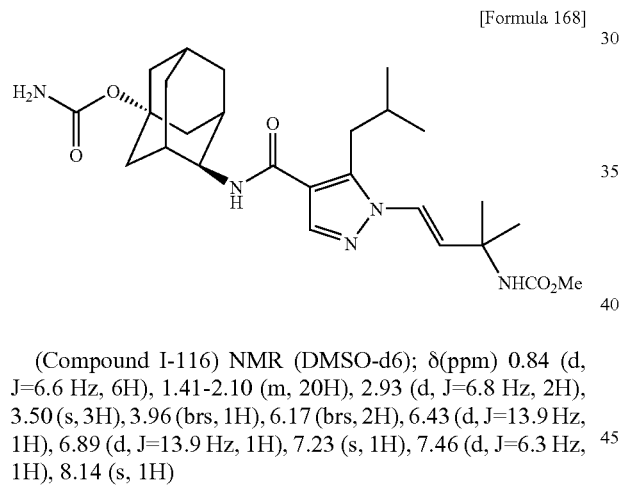

[Formula 168]

(Compound I-116) NMR (DMSO-d6); δ(ppm) 0.84 (d, J=6.6 Hz, 6H), 1.41-2.10 (m, 20H), 2.93 (d, J=6.8 Hz, 2H), 3.50 (s, 3H), 3.96 (brs, 1H), 6.17 (brs, 2H), 6.43 (d, J=13.9 Hz, 1H), 6.89 (d, J=13.9 Hz, 1H), 7.23 (s, 1H), 7.46 (d, J=6.3 Hz, 1H), 8.14 (s, 1H)

Example 119

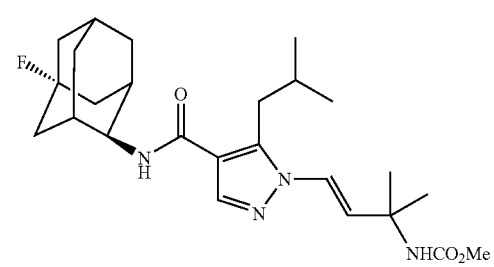

[Formula 169]

(Compound I-117) NMR (DMSO-d6); δ(ppm) 0.84 (d, J=6.6 Hz, 6H), 1.37-2.20 (m, 20H), 2.93 (d, J=6.8 Hz, 2H), 3.50 (s, 3H), 3.96 (brs, 1H), 6.44 (d, J=14.4 Hz, 1H), 6.89 (d, J=14.4 Hz, 1H), 7.23 (s, 1H), 7.48 (d, J=6.3 Hz, 1H), 8.14 (s, 1H)

Example 120

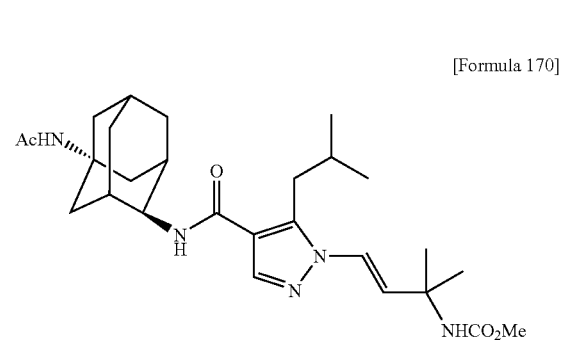

[Formula 170]

(Compound I-118) NMR (DMSO-d6); δ(ppm) 0.84 (d, J=6.6 Hz, 6H), 1.41-2.01 (m, 23H), 2.93 (d, J=7.1 Hz, 2H), 3.50 (s, 3H), 3.94 (brs, 1H), 6.43 (d, J=13.9 Hz, 1H), 6.89 (d, J=13.9 Hz, 1H), 7.24 (s, 1H), 7.36 (s, 1H), 7.45 (d, J=6.8 Hz, 1H), 8.14 (s, 1H)

Example 121

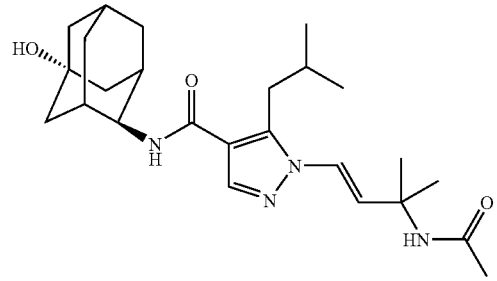

[Formula 171]

(Compound I-119) NMR(CDCl3); δ(ppm) 0.95 (d, J=6.6 Hz, 6H), 1.55-2.21 (m, 23H), 2.94 (d, J=7.1 Hz, 2H), 4.15 (brs, 1H), 5.47 (s, 1H), 5.89 (d, J=7.8 Hz, 1H), 6.50 (d, J=13.9 Hz, 1H), 6.88 (d, J=13.9 Hz, 1H), 7.67 (s, 1H)

Example 122

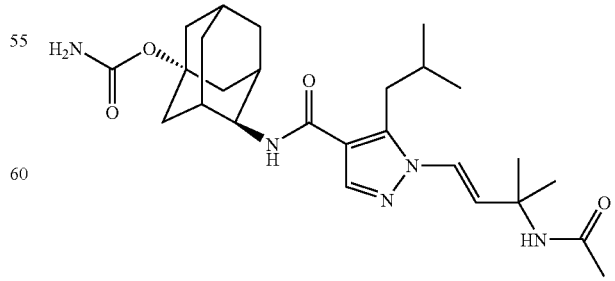

[Formula 172]

(Compound I-120) NMR (DMSO-d6); δ(ppm) 0.84 (d, J=6.6 Hz, 6H), 1.38-2.10 (m, 23H), 2.93 (d, J=6.8 Hz, 2H), 3.96 (brs, 1H), 6.19 (brs, 2H), 6.50 (d, J=13.6 Hz, 1H), 6.87 (d, J=13.6 Hz, 1H), 7.46 (d, J=6.3 Hz, 1H), 7.76 (s, 1H), 8.14 (s, 1H)

Example 123

[Formula 173]

(Compound I-121) NMR (DMSO-d6); δ(ppm) 0.84 (d, J=6.6 Hz, 6H), 1.36-2.05 (m, 23H), 2.93 (d, J=7.3 Hz, 2H), 3.01 (d, J=5.1 Hz, 2H), 3.89 (brs, 1H), 4.35 (t, J=5.1 Hz, 1H), 6.49 (d, J=13.9 Hz, 1H), 6.87 (d, J=13.9 Hz, 1H), 7.43 (d, J=6.8 Hz, 1H), 7.75 (s, 1H), 8.14 (s, 1H)

Example 124

[Formula 174]

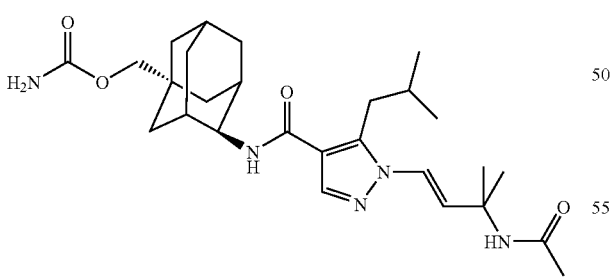

(Compound I-122) NMR (DMSO-d6); δ(ppm) 0.84 (d, J=6.6 Hz, 6H), 1.37-2.07 (m, 23H), 2.93 (d, J=7.1 Hz, 2H), 3.56 (s, 2H), 3.91 (brs, 1H), 6.42 (brs, 2H), 6.49 (d, J=14.2 Hz, 1H), 6.87 (d, J=14.2 Hz, 1H), 7.47 (d, J=6.8 Hz, 1H), 7.76 (s, 1H), 8.14 (s, 1H)

Example 125

[Formula 175]

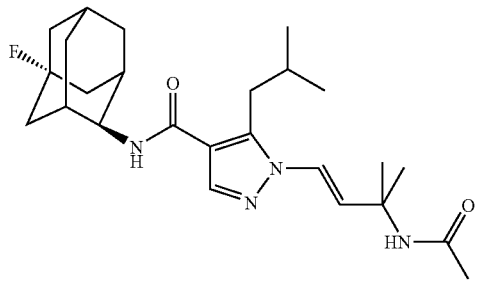

(Compound I-123) NMR(CDCl3); δ(ppm) 0.95 (d, J=6.6 Hz, 6H), 1.55-2.29 (m, 23H), 2.93 (d, J=7.1 Hz, 2H), 4.18 (brs, 1H), 5.61 (s, 1H), 5.91 (d, J=7.3 Hz, 1H), 6.51 (d, J=13.9 Hz, 1H), 6.88 (d, J=13.9 Hz, 1H), 7.68 (s, 1H)

Example 126

[Formula 176]

(Compound I-124) NMR (DMSO-d6); δ(ppm) 0.84 (d, J=6.6 Hz, 6H), 1.32-2.04 (m, 20H), 2.93 (d, J=7.1 Hz, 2H), 3.31 (s, 3H), 3.76 (s, 2H), 3.90 (brs, 1H), 4.40 (s, 1H), 6.51 (d, J=14.2 Hz, 1H), 6.91 (d, J=14.2 Hz, 1H), 7.36 (s, 1H), 7.41 (d, J=6.3 Hz, 1H), 8.14 (s, 1H)

Example 127

[Formula 177]

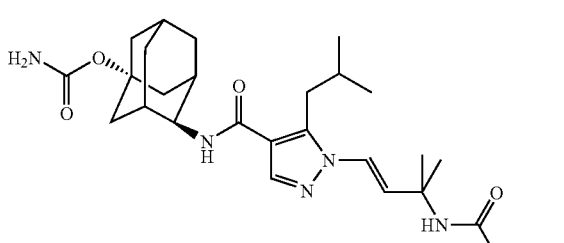

(Compound I-125) NMR (DMSO-d6); δ(ppm) 0.84 (d, J=6.6 Hz, 6H), 1.38-2.10 (m, 20H), 2.93 (d, J=6.6 Hz, 2H), 3.32 (s, 3H), 3.76 (s, 2H), 3.96 (s, 1H), 6.19 (brs, 2H), 6.51 (d, J=14.4 Hz, 1H), 6.91 (d, J=14.4 Hz, 1H), 7.36 (s, 1H), 7.46 (d, J=6.1 Hz, 1H), 8.14 (s, 1H)

Example 128

[Formula 178]

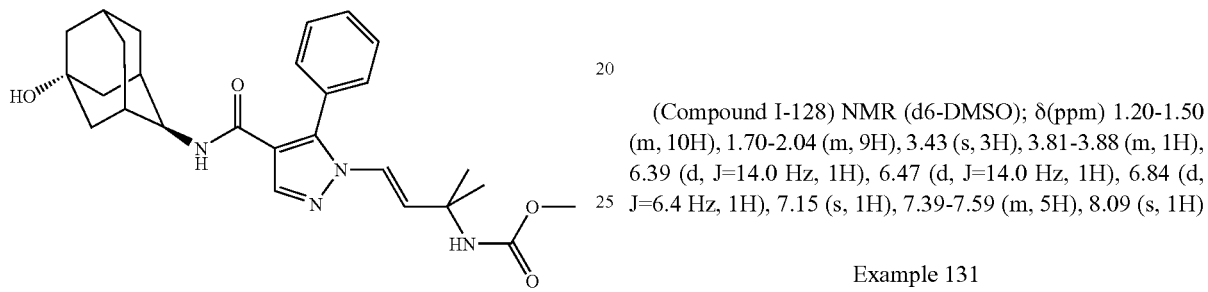

(Compound I-126) NMR (d6-DMSO); δ(ppm) 1.14-1.89 (m, 19H), 3.43 (s, 3H), 3.76-3.81 (m, 1H), 4.37 (s, 1H), 6.39 (d, J=14.0 Hz, 1H), 6.46 (d, J=14.0 Hz, 1H), 6.69 (d, J=6.4 Hz, 1H), 7.15 (s, 1H), 7.40-7.60 (m, 5H), 8.08 (s, 1H)

Example 129

[Formula 179]

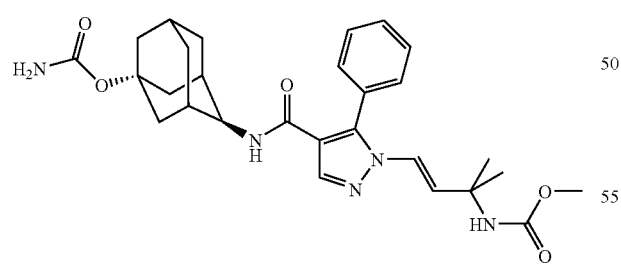

(Compound I-127) NMR (d6-DMSO); δ(ppm) 1.20-1.49 (m, 10H), 1.85-2.08 (s, 9H), 3.44 (s, 3H), 3.82-3.89 (m, 1H), 6.00-6.30 (s, 2H), 6.39 (d, J=14.0 Hz, 1H), 6.47 (d, J=14.0 Hz, 1H), 6.79 (d, J=6.8 Hz, 1H), 7.15 (s, 1H), 7.39-7.59 (m, 5H), 8.10 (s, 1H)

Example 130

[Formula 180]

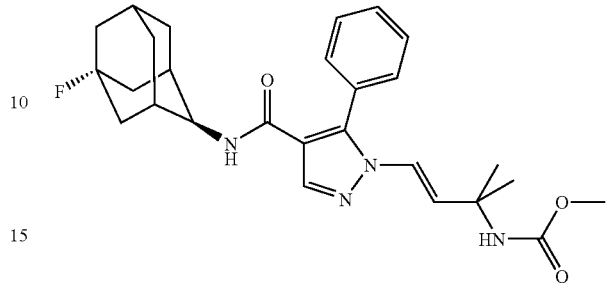

(Compound I-128) NMR (d6-DMSO); δ(ppm) 1.20-1.50 (m, 10H), 1.70-2.04 (m, 9H), 3.43 (s, 3H), 3.81-3.88 (m, 1H), 6.39 (d, J=14.0 Hz, 1H), 6.47 (d, J=14.0 Hz, 1H), 6.84 (d, J=6.4 Hz, 1H), 7.15 (s, 1H), 7.39-7.59 (m, 5H), 8.09 (s, 1H)

Example 131

[Formula 181]

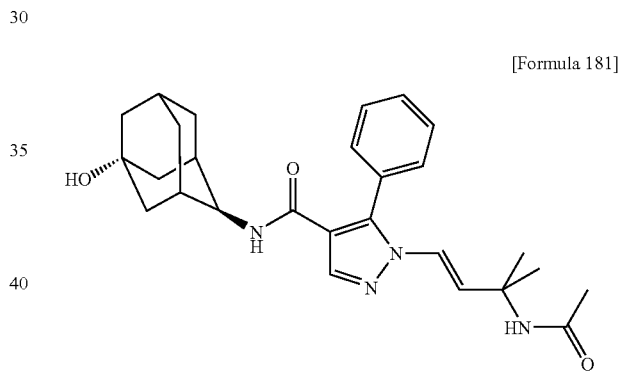

(Compound I-129) NMR (d6-DMSO); δ(ppm) 1.15-1.89 (m, 22H), 3.76-3.81 (m, 1H), 4.37 (s, 1H), 6.44 (s, 2H), 6.71 (d, J=6.4 Hz, 1H), 7.40-7.69 (m, 6H), 8.08 (s, 1H)

Example 132

[Formula 182]

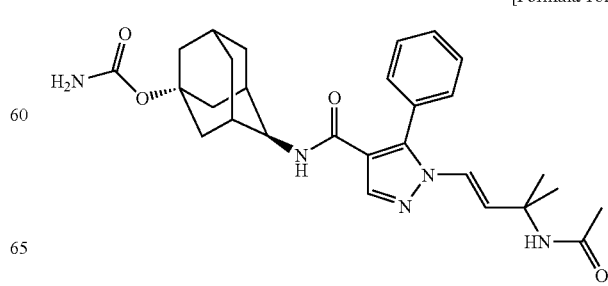

(Compound I-130) NMR (d6-DMSO); δ(ppm) 1.20-1.50 (m, 10H), 1.70 (s, 3H), 1.85-2.07 (m, 9H), 3.81-3.89 (m, 1H), 6.00-6.30 (s, 2H), 6.45 (s, 2H), 6.82 (d, J=6.8 Hz, 1H), 7.40-7.70 (m, 6H), 8.10 (s, 1H)

Example 133

[Formula 183]

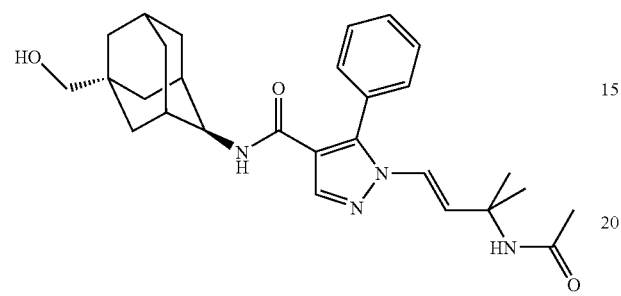

(Compound I-131) NMR (d6-DMSO); δ(ppm) 1.19-1.80 (m, 22H), 2.95 (d, J=4.8 Hz, 2H), 3.75-3.80 (m, 1H), 4.34 (t, J=5.2 Hz, 1H), 6.44 (s, 2H), 6.70 (d, J=6.4 Hz, 1H), 7.42-7.71 (m, 6H), 8.09 (s, 1H)

Example 134

[Formula 184]

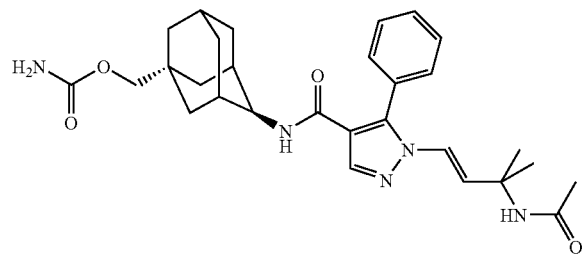

(Compound I-132) NMR (d6-DMSO); δ(ppm) 1.21-1.82 (m, 22H), 3.51 (s, 2H), 3.77-3.82 (m, 1H), 6.20-6.50 (m, 4H), 6.76 (d, J=6.8 Hz, 1H), 7.42-7.69 (m, 6H), 8.09 (s, 1H)

Example 135

[Formula 185]

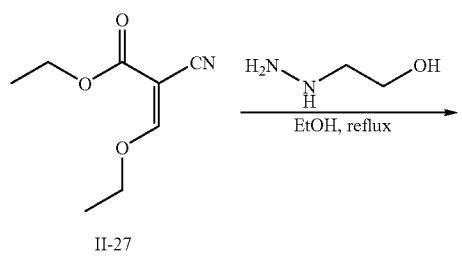

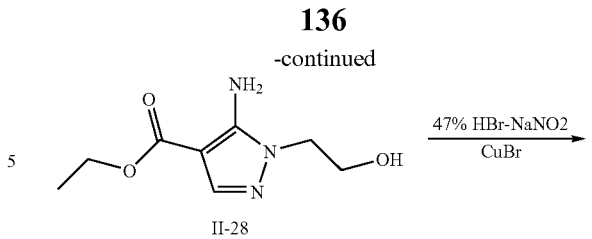

II-28

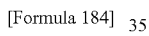

II-29

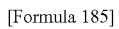

II-30

To a solution of Compound II-27 (ethoxymethylene cyano acetic acid ethyl ester, 50.75 g) in ethanol (100 ml) was added dropwise 80% hydrazine ethanol (28.54 g), then the reaction mixture was stirred at 125° C. for 3.5 hrs. After termination of the reaction, the mixture was concentrated. The residue was purified by silica gel column chromatography to give Compound II-28 (54.73 g).

To Compound II-28 (32.42 g) was added 48% aqueous hydrobromic acid (130 ml), then sodium nitrite (16.91 g)—H₂O (33.8 ml) was added dropwise to the resulting mixture at −11° C. over 5 min. The mixture was stirred at −3° C. for 2 hrs to afford diazonium salt. According to the above procedure, the obtained diazonium salt was added dropwise to CuBr—HBr soln. at room temperature, then the mixture was stirred at 50° C. for 1 hour and 40 minutes. After termination of the reaction, H₂O was added to the mixture and extracted with chloroform. The organic layer was washed with brine and dried over sodium sulfate. The solvent was removed to give Compound II-29 (33.54 g).

*Preparation of CuBr—HBr soln.; To H₂O (270 ml) were added copper sulfate pentahydrate (52.67 g) and sodium bromide (51.45 g). Sodium sulfite (21.43 g) in H₂O (33 ml) was added dropwise to the resulting mixture at 60° C. over 5 min, then the mixture was stirred at the same temperature for 10 min. The mixture was cooled to room temperature, supernatant was removed one hour later to give white precipitate of CuBr. Obtained white precipitate was washed with H₂O (100 ml) twice. 48% aqueous hydrobromic acid (130 ml) was added to the white precipitate, then the obtained mixture was used for the reaction.

Compound II-30 was synthesized from Compound II-29 as well as the above Example. The following compounds were synthesized by using Compound II-30 as a common intermediate.

Example 136

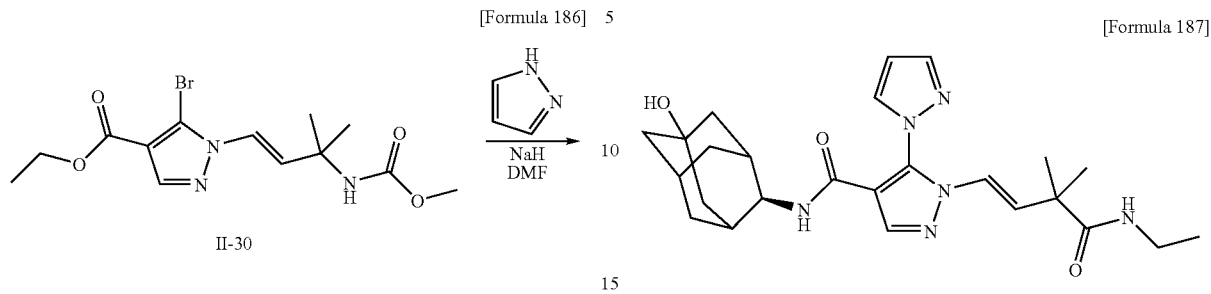

To a solution of pyrazole (378 mg) in dimethyl formamide (2 ml) was added 60% sodium hydride (211 mg) under ice-cooling, then the resulting mixture was stirred at 40° C. for one hour. A solution of Compound II-30 (1 g) in dimethyl formamide (6 ml) was added dropwise to the mixture, then the whole mixture was stirred at 80° C. for 35 min. After termination of the reaction, the reaction mixture was poured into 2N aqueous HCl, and extracted with ethyl acetate. The organic layer was washed with brine, and dried over sodium sulfate and concentrated. The residue was purified by silica gel column chromatography to give Compound II-31 (416 mg).

Compound I-133 was synthesized from Compound II-31 as well as the above Example.

(Compound I-133) NMR (d6-DMSO); δ(ppm) 1.29 (s, 6H), 1.30-2.00 (m, 13H), 3.45 (s, 3H), 3.80-3.87 (m, 1H), 4.43 (s, 1H), 6.36 (s, 2H), 6.66 (t, J=2.1 Hz, 1H), 7.23 (s, 1H), 7.37 (d, J=7.2 Hz, 1H), 7.98 (d, J=2.1 Hz, 1H), 8.19 (s, 1H), 8.23 (d, J=2.1 Hz, 1H)

The compounds shown below were synthesized in a similar manner.

Example 137

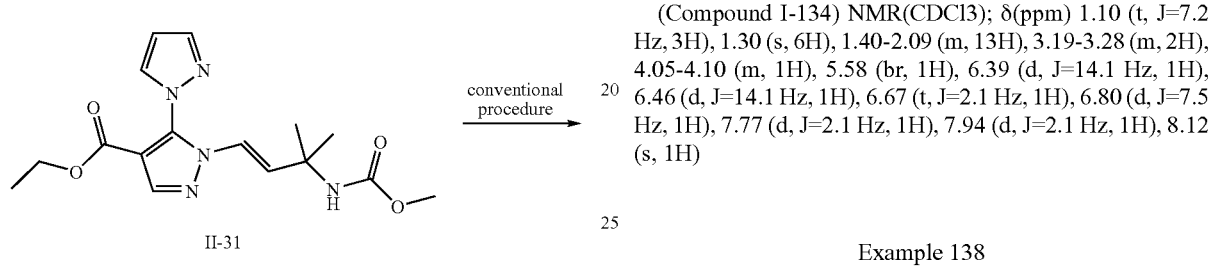

(Compound I-134) NMR(CDCl3); δ(ppm) 1.10 (t, J=7.2 Hz, 3H), 1.30 (s, 6H), 1.40-2.09 (m, 13H), 3.19-3.28 (m, 2H), 4.05-4.10 (m, 1H), 5.58 (br, 1H), 6.39 (d, J=14.1 Hz, 1H), 6.46 (d, J=14.1 Hz, 1H), 6.67 (t, J=2.1 Hz, 1H), 6.80 (d, J=7.5 Hz, 1H), 7.77 (d, J=2.1 Hz, 1H), 7.94 (d, J=2.1 Hz, 1H), 8.12 (s, 1H)

Example 138

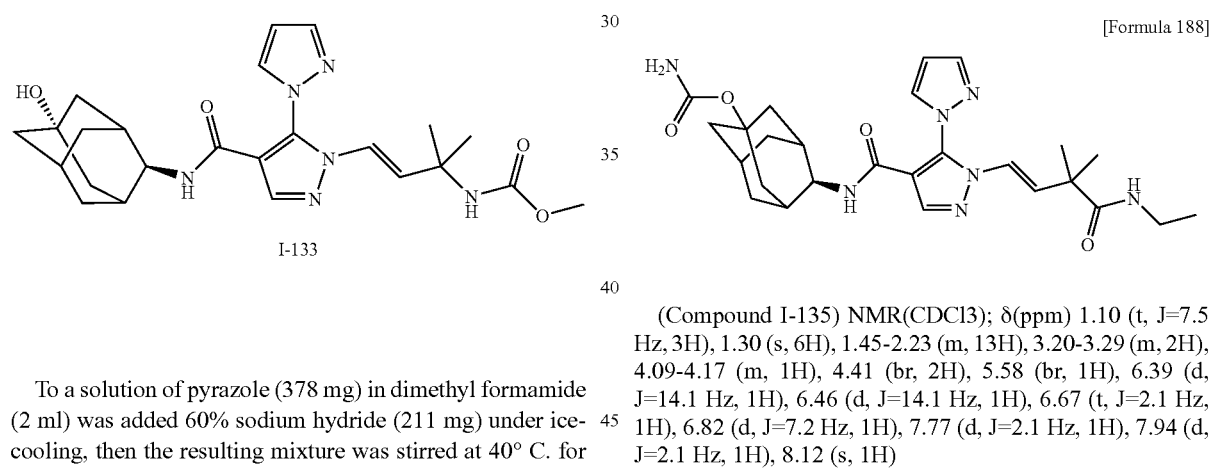

(Compound I-135) NMR(CDCl3); δ(ppm) 1.10 (t, J=7.5 Hz, 3H), 1.30 (s, 6H), 1.45-2.23 (m, 13H), 3.20-3.29 (m, 2H), 4.09-4.17 (m, 1H), 4.41 (br, 2H), 5.58 (br, 1H), 6.39 (d, J=14.1 Hz, 1H), 6.46 (d, J=14.1 Hz, 1H), 6.67 (t, J=2.1 Hz, 1H), 6.82 (d, J=7.2 Hz, 1H), 7.77 (d, J=2.1 Hz, 1H), 7.94 (d, J=2.1 Hz, 1H), 8.12 (s, 1H)

Example 139

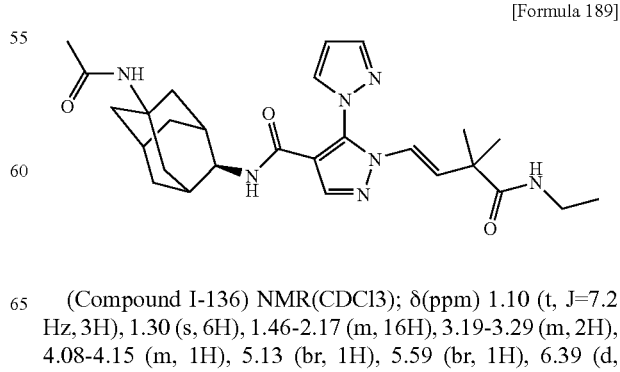

(Compound I-136) NMR(CDCl3); δ(ppm) 1.10 (t, J=7.2 Hz, 3H), 1.30 (s, 6H), 1.46-2.17 (m, 16H), 3.19-3.29 (m, 2H), 4.08-4.15 (m, 1H), 5.13 (br, 1H), 5.59 (br, 1H), 6.39 (d, J=14.1 Hz, 1H), 6.45 (d, J=14.1 Hz, 1H), 6.67 (t, J=2.1 Hz, 1H), 6.83 (d, J=7.2 Hz, 1H), 7.77 (d, J=2.1 Hz, 1H), 7.94 (d, J=2.1 Hz, 1H), 8.12 (s, 1H)

Example 140

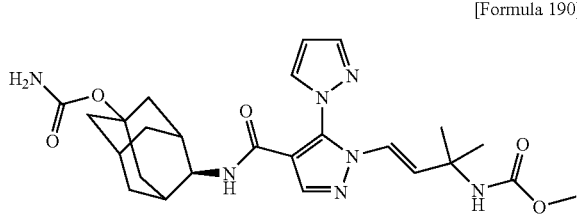

[Formula 190]

(Compound I-137) NMR(CDCl3); δ(ppm) 1.42 (s, 6H), 1.48-2.23 (m, 13H), 3.61 (s, 3H), 4.11-4.17 (m, 1H), 4.41 (br, 2H), 4.77 (s, 1H), 6.31 (d, J=14.1 Hz, 1H), 6.44 (d, J=14.1 Hz, 1H), 6.63 (t, J=2.1 Hz, 1H), 7.36 (br, 1H), 7.85 (d, J=2.1 Hz, 1H), 7.91 (d, J=2.1 Hz, 1H), 8.12 (s, 1H)

Example 141

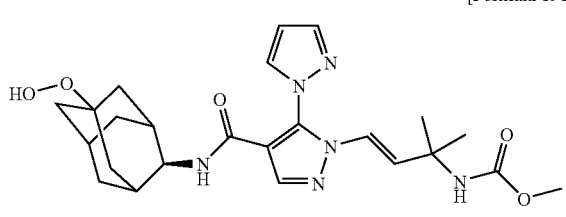

[Formula 191]

(Compound I-138) NMR(CDCl3); δ(ppm) 1.42 (s, 6H), 1.46-1.96 (m, 13H), 3.22 (d, J=3.6 Hz, 2H), 3.61 (s, 3H), 4.05-4.08 (m, 1H), 4.77 (s, 1H), 6.31 (d, J=14.1 Hz, 1H), 6.44 (d, J=14.1 Hz, 1H), 6.63 (t, J=2.1 Hz, 1H), 7.36 (br, 1H), 7.85 (d, J=2.1 Hz, 1H), 7.91 (d, J=2.1 Hz, 1H), 8.13 (s, 1H)

Example 142

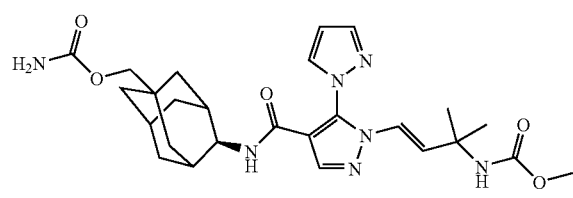

[Formula 192]

(Compound I-139) NMR(CDCl3); δ(ppm) 1.42 (s, 6H), 1.45-1.96 (m, 13H), 3.61 (s, 3H), 3.69 (s, 2H), 4.03-4.10 (m, 1H), 4.58 (br, 2H), 4.76 (s, 1H), 6.31 (d, J=14.1 Hz, 1H), 6.44 (d, J=14.1 Hz, 1H), 6.63 (t, J=2.1 Hz, 1H), 7.37 (br, 1H), 7.85 (d, J=2.1 Hz, 1H), 7.91 (d, J=2.1 Hz, 1H), 8.12 (s, 1H)

Example 143

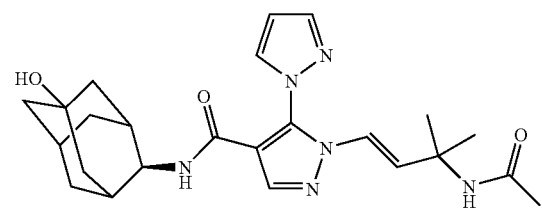

[Formula 193]

(Compound I-140) NMR (d6-DMSO); δ(ppm) 1.31 (s, 6H), 1.54-1.98 (m, 16H), 3.80-3.87 (m, 1H), 4.43 (s, 1H), 6.35 (d, J=14.1 Hz, 1H), 6.43 (d, J=14.1 Hz, 1H), 6.67 (t, J=2.4 Hz, 1H), 7.38 (d, J=6.9 Hz, 1H), 7.75 (s, 1H), 7.98 (d, J=2.4 Hz, 1H), 8.19 (s, 1H), 8.23 (d, J=2.4 Hz, 1H)

Example 144

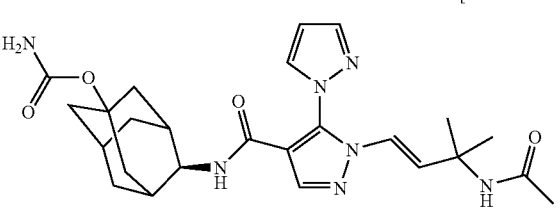

[Formula 194]

(Compound I-141) NMR(CDCl3); δ(ppm) 1.45 (s, 6H), 1.48-2.23 (m, 16H), 4.10-4.17 (m, 1H), 4.41 (br, 2H), 5.42 (s, 1H), 6.31 (d, J=14.1 Hz), 6.42 (d, J=14.1 Hz, 1H), 6.64 (t, J=2.4 Hz, 1H), 7.45 (d, J=7.8 Hz,), 7.90 (d, J=2.4 Hz, 2H), 8.12 (s, 1H)

Example 145

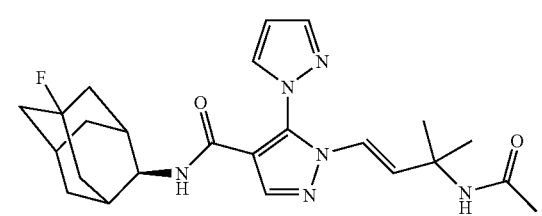

[Formula 195]

(Compound I-142) NMR(CDCl3); δ(ppm) 1.45 (s, 6H), 1.51-2.20 (m, 16H), 4.08-4.14 (m, 1H), 5.41 (br, 1H), 6.32 (d, J=13.8 Hz, 1H), 6.43 (d, J=13.8 Hz, 1H), 6.65 (t, J=2.1 Hz, 1H), 7.48 (d, J=7.2 Hz, 1H), 7.90 (d, J=2.1 Hz, 1H), 7.91 (d, J=2.1 Hz, 1H), 8.13 (s, 1H)

Example 146

[Formula 196]

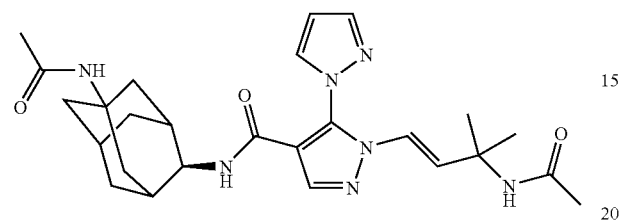

(Compound I-143) NMR(CDCl3); δ(ppm) 1.45 (s, 6H), 1.51-2.16 (m, 19H), 4.10-4.16 (m, 1H), 5.17 (s, 1H), 5.46 (s, 1H), 6.31 (d, J=14.1 Hz, 1H), 6.43 (d, J=14.1 Hz, 1H), 6.64 (t, J=2.1 Hz, 1H), 7.48 (d, J=7.8 Hz, 1H), 7.90 (d, J=2.1 Hz, 2H), 8.12 (s, 1H)

Example 147

[Formula 197]

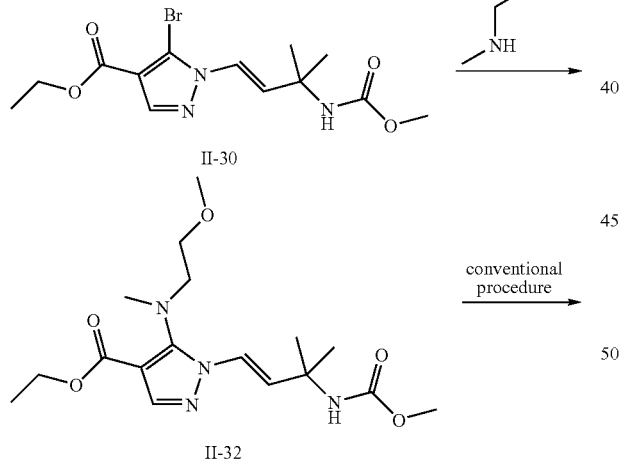

To Compound II-30 (300 mg) was added methoxyethylmethylamine (2 ml), then the reaction mixture was stirred at 80° C. for 16 hrs. After termination of the reaction, 2N aqueous HCl was added to the reaction mixture, and extracted with ethyl acetate. The organic layer was washed with brine, and concentrated. The residue was purified by silica gel column chromatography to give Compound II-32 (257 mg).

Compound I-144 was synthesized from Compound II-32 as well as the above Example.

(Compound I-144) NMR(CDCl3); δ(ppm) 1.52 (s, 6H), 1.54-2.25 (m, 13H), 2.94 (s, 3H), 3.25 (s, 3H), 3.32 (t, J=4.8 Hz, 2H), 3.41 (t, J=4.8 Hz, 2H), 3.62 (s, 3H), 4.12-4.19 (m, 1H), 4.84 (s, 1H), 6.38 (d, J=14.1 Hz, 1H), 6.93 (d, J=14.1 Hz, 1H), 7.43 (d, J=7.2 Hz, 1H), 7.89 (s, 1H)

The compounds shown below were synthesized in a similar manner.

Example 148

[Formula 198]

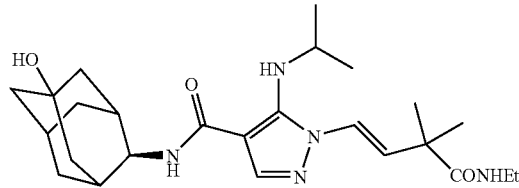

(Compound I-145) NMR(CDCl3); δ(ppm) 1.11 (t, J=7.2 Hz, 3H), 1.21 (d, J=6.3 Hz, 6H), 1.40 (s, 6H), 1.45-2.3 (m, 13H), 3.26 (m, 2H), 3.50 (m, 1H), 4.14 (brd, J=7.5 Hz, 1H), 5.74 (brs, 1H), 5.83 (d, J=7.5 Hz, 1H), 5.95 (d, J=9.9 Hz, 1H), 6.38 (d, J=14.1 Hz, 1H), 6.84 (d, J=14.1 Hz, 1H), 7.58 (s, 1H)

Example 149

[Formula 199]

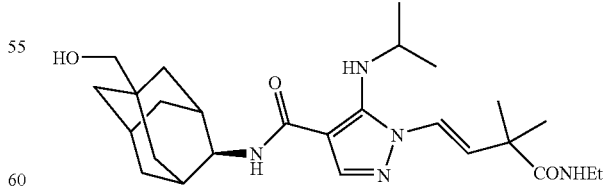

(Compound I-146) NMR(CDCl3); δ(ppm) 1.22 (t, J=7.2 Hz, 3H), 1.41 (s, 6H), 1.57 (s, 6H), 1.6-2.14 (m, 13H), 3.27 (m, 2H), 3.67 (s, 3H), 4.19 (m, 1H), 5.65 (m, 1H), 5.97 (d, J=7.5 Hz, 1H), 6.37 (d, J=14.7 Hz, 1H), 6.93 (d, J=14.1 Hz, 1H), 7.82 (s, 1H), 8.02 (s, 1H)

Example 150

[Formula 200]

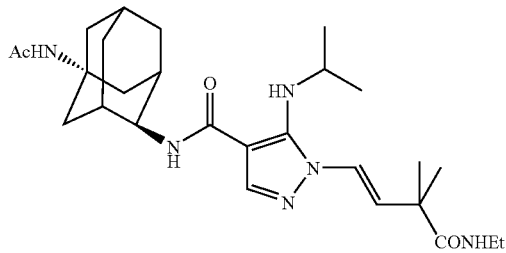

(Compound I-147) NMR(CDCl3); δ(ppm) 1.11 (t, J=7.2 Hz, 3H), 1.40 (s, 6H), 1.81 (d, J=6.6 Hz, 6H), 1.93 (s, 6H), 1.61-2.3 (m, 13H), 3.26 (m, 2H), 3.49 (m, 1H), 4.17 (brd, J=7.2 Hz, 1H), 5.16 (s, 1H), 5.71 (s, 1H), 5.86 (d, J=7.5 Hz, 1H), 5.94 (d, J=10.2 Hz, 1H), 6.38 (d, J=14.1 Hz, 1H), 6.84 (d, J=13.8 Hz, 1H), 7.57 (s, 1H)

Example 151

[Formula 201]

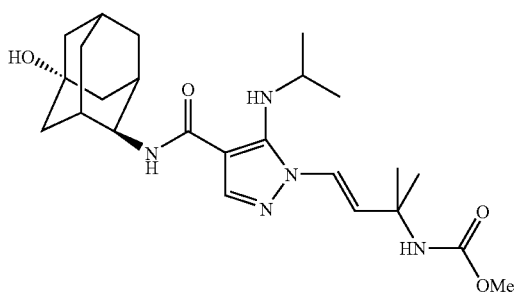

(Compound I-148) NMR (DMSO-d6); δ(ppm) 1.08 (d, J=6.3 Hz, 6H), 1.32-2.03 (m, 19H), 3.42-3.49 (m, 4H), 3.91 (brs, 1H), 4.42 (s, 1H), 6.04 (d, J=9.1 Hz, 1H), 6.25 (d, J=13.9 Hz, 1H), 6.75 (d, J=13.9 Hz, 1H), 7.25 (s, 1H), 7.40 (d, J=6.6 Hz, 1H), 8.09 (s, 1H)

Example 152

[Formula 202]

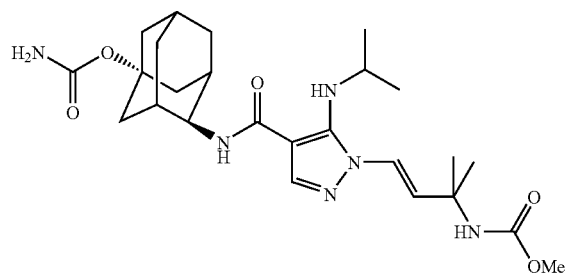

(Compound I-149) NMR (DMSO-d6); δ(ppm) 1.09 (d, J=6.3 Hz, 6H), 1.38-2.10 (m, 19H), 3.46-3.49 (m, 4H), 3.97 (brs, 1H), 6.04 (d, J=6.4 Hz, 1H), 6.19 (brs, 2H), 6.25 (d, J=14.4 Hz, 1H), 6.75 (d, J=14.4 Hz, 1H), 7.25 (s, 1H), 7.44 (d, J=6.1 Hz, 1H), 8.10 (s, 1H)

Example 153

[Formula 203]

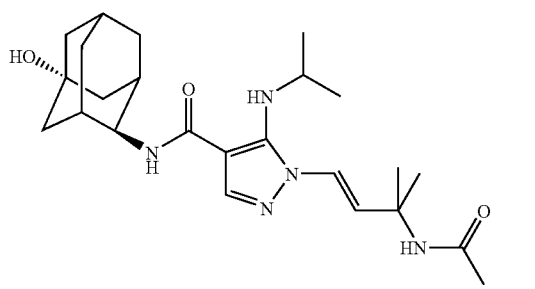

(Compound I-150) NMR(CDCl3); δ(ppm) 1.21-1.89 (d, J=6.6 Hz, 6H), 1.38-2.19 (m, 13H), 1.55 (s, 3H), 1.57 (s, 3H), 3.56 (m, 1H), 4.13 (m, 1H), 5.44 (s, 1H), 5.82 (m, 1H), 5.85 (s, 1H), 6.32 (d, J=14.1 Hz, 1H), 6.81 (d, J=14.1 Hz, 1H), 7.55 (s, 1H)

Example 154

[Formula 204]

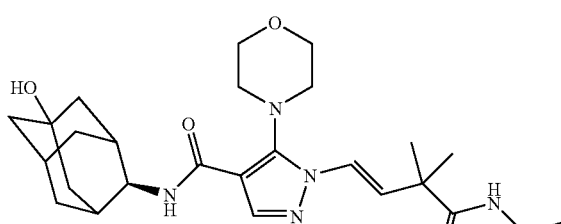

(Compound I-151) NMR(CDCl3); δ(ppm) 1.13 (t, J=7.2 Hz, 3H), 1.42 (s, 6H), 1.48-2.29 (m, 13H), 3.20 (t, J=4.5 Hz, 4H), 3.24-3.33 (m, 2H), 3.84 (t, J=4.5 Hz, 4H), 4.15-4.21 (m, 1H), 5.70 (br, 1H), 6.48 (d, J=7.5 Hz, 1H), 6.49 (d, J=14.4 Hz, 1H), 7.12 (d, J=14.4 Hz, 1H), 7.76 (s, 1H)

Example 155

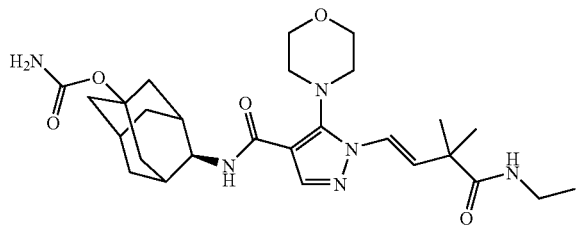

(Compound I-152) NMR(CDCl3); δ(ppm) 1.13 (t, J=7.2 Hz, 3H), 1.42 (s, 6H), 1.62-2.31 (m, 13H), 3.20 (t, J=4.5 Hz, 4H), 3.24-3.33 (m, 2H), 3.83 (t, J=4.5 Hz, 4H), 4.20-4.27 (m, 1H), 4.46 (br, 2H), 5.70 (br, 1H), 6.49 (d, J=14.1 Hz, 1H), 6.50 (d, J=7.8 Hz, 1H), 7.12 (d, J=14.1 Hz, 1H), 7.76 (s, 1H)

Example 156

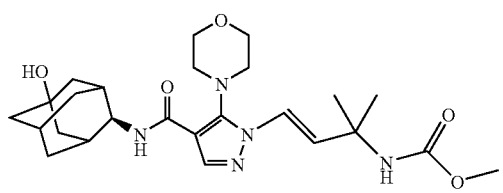

(Compound I-153) NMR(CDCl3); δ(ppm) 1.53 (s, 6H), 1.56-2.27 (m, 13H), 3.20 (t, J=4.5 Hz, 4H), 3.64 (s, 3H), 3.83 (t, J=4.5 Hz, 4H), 4.14-4.21 (m, 1H), 4.84 (s, 1H), 6.38 (d, J=14.1 Hz, 1H), 6.58 (d, J=7.5 Hz, 1H), 7.08 (d, J=14.1 Hz, 1H), 7.75 (s, 1H)

Example 157

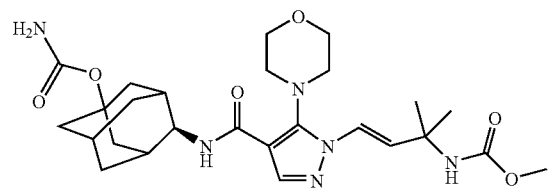

(Compound I-154) NMR(CDCl3); δ(ppm) 1.53 (s, 6H), 1.60-2.31 (m, 13H), 3.20 (t, J=4.5 Hz, 4H), 3.64 (s, 3H), 3.83 (t, J=4.5 Hz, 4H), 4.19-4.25 (m, 1H), 4.44 (br. s, 2H), 4.85 (s, 1H), 6.38 (d, J=14.1 Hz, 1H), 6.60 (d, J=7.8 Hz, 1H), 7.07 (d, J=14.1 Hz, 1H), 7.75 (s, 1H)

Example 158

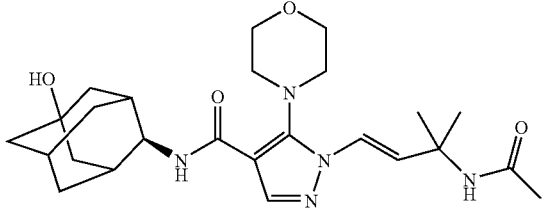

(Compound I-155) NMR(CDCl3); δ(ppm) 1.56 (s, 6H), 1.55-2.4 (m, 13H), 1.98 (s, 3H), 3.21 (m, 4H), 3.84 (m, 4H), 4.17 (brd, J=7.2 Hz, 1H), 5.53 (s, 1H), 6.39 (d, J=14.1 Hz, 1H), 6.63 (d, J=7.2 Hz, 1H), 7.07 (d, J=14.1 Hz, 1H), 7.75 (s, 1H)

Example 159

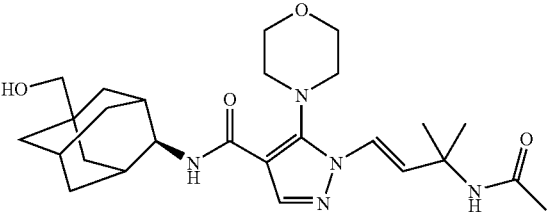

(Compound I-156) NMR(CDCl3); δ(ppm) 1.55 (s, 6H), 1.55-2.15 (m, 13H), 1.97 (s, 3H), 3.21 (brs, 4H), 3.25 (s, 2H), 3.83 (brs, 4H), 4.13 (m, 1H), 5.66 (s, 1H), 6.38 (d, J=14.1 Hz, 1H), 6.77 (brd, J=7.2 Hz, 1H), 7.06 (d, J=14.1 Hz, 1H), 7.76 (s, 1H)

Example 160

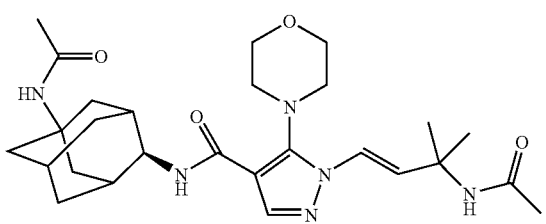

(Compound I-157) NMR(CDCl3); δ(ppm) 1.55 (s, 6H), 16-1.85 (m, 8H), 1.92 (s, 3H), 1.9-2.25 (m, 6H), 1.97 (s, 3H), 3.19 (m, 4H), 3.49 (s, 1H), 3.83 (m, 4H), 4.20 (brd, J=6.6 Hz, 1H), 5.21 (brs, 1H), 5.52 (brs, 1H), 6.38 (d, J=14.1 Hz, 1H), 6.67 (d, J=7.5 Hz, 1H), 7.06 (d, J=14.1 Hz, 1H), 7.75 (s, 1H)

Example 161

[Formula 211]

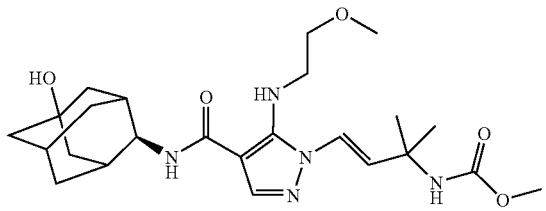

(Compound I-158) NMR(CDCl3); δ(ppm) 1.51 (s, 6H), 1.58-2.23 (m, 13H), 3.34-3.44 (m, 2H), 3.39 (s, 3H), 3.52 (t, J=4.8 Hz, 2H), 3.61 (s, 3H), 4.12-4.18 (m, 1H), 4.85 (s, 1H), 5.96 (d, J=7.5 Hz, 1H), 6.19 (t, J=6.6 Hz, 1H), 6.30 (d, J=14.1 Hz, 1H), 6.98 (d, J=14.1 Hz, 1H), 7.57 (s, 1H)

Example 162

[Formula 212]

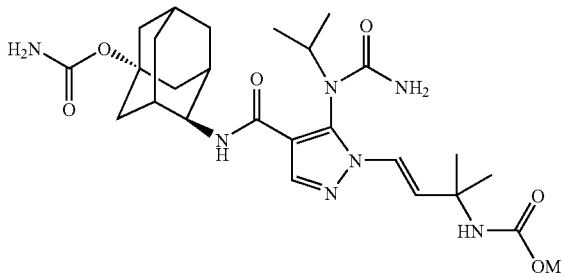

(Compound I-159) NMR (DMSO-d6); δ(ppm) 0.90-0.96 (m, 6H), 1.36-2.10 (m, 19H), 3.48 (s, 3H), 3.97 (brs, 1H), 4.33-4.40 (m, 1H), 6.21 (brs, 2H), 6.40-6.42 (m, 3H), 6.66 (d, J=13.6 Hz, 1H), 7.24 (d, J=8.1 Hz, 1H), 7.31 (s, 1H), 7.96 (s, 1H)

Example 163

[Formula 213]

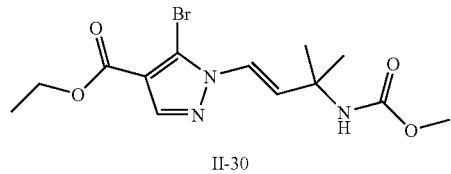

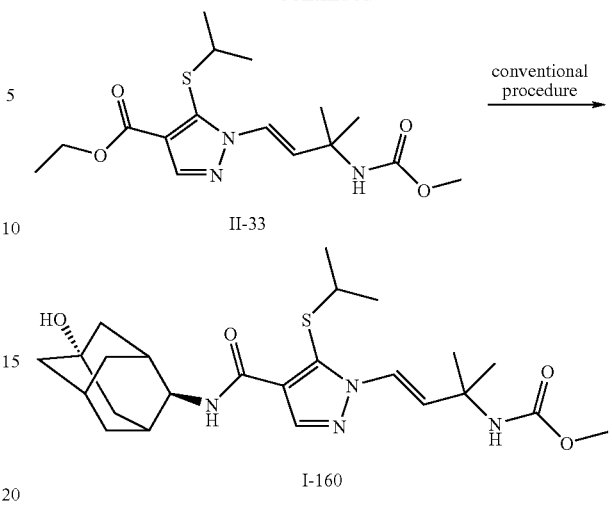

To a solution of propane-2-thiol (413 µl) in dimethyl formamide (8 ml) was added 60% sodium hydride (169 mg) under ice-cooling, then the resulting mixture was stirred at room temperature for one hour. A solution of Compound II-30 (800 mg) in dimethyl formamide (8 ml) was added dropwise to the mixture, then the whole mixture was stirred for 2 hrs. After termination of the reaction, the reaction mixture was poured into 1N aqueous HCl, and extracted with ethyl acetate. The organic layer was washed with saturated aqueous NaHCO₃ and brine successively, and dried over sodium sulfate and concentrated. The residue was purified by silica gel column chromatography to give Compound II-33 (738 mg).

Compound I-160 was synthesized from Compound II-33 as well as the above Example.

(Compound I-160) NMR(CDCl3); δ(ppm) 1.28 (d, J=6.8 Hz, 6H), 1.53-2.20 (m, 19H), 3.30-3.37 (m, 1H), 3.63 (s, 3H), 4.25 (d, J=7.3 Hz, 1H), 4.91 (s, 1H), 6.56 (d, J=14.2 Hz, 1H), 7.40 (d, J=14.2 Hz, 1H), 7.96 (d, J=7.6 Hz, 1H), 8.20 (s, 1H)

The compounds shown below were synthesized in a similar manner.

Example 164

[Formula 214]

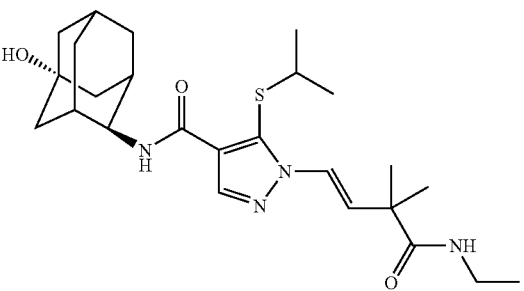

(Compound I-161) NMR(CDCl3); δ(ppm) 1.12 (t, J=7.2 Hz, 3H), 1.29 (d, J=6.8 Hz, 6H), 1.43 (s, 6H), 1.58-2.22 (m, 13H), 3.24-3.34 (m, 3H), 4.26 (brs, 1H), 5.76 (brs, 1H), 6.64 (d, J=14.2 Hz, 1H), 7.42 (d, J=14.2 Hz, 1H), 7.92 (d, J=7.8 Hz, 1H), 8.22 (s, 1H)

Example 165

[Formula 215]

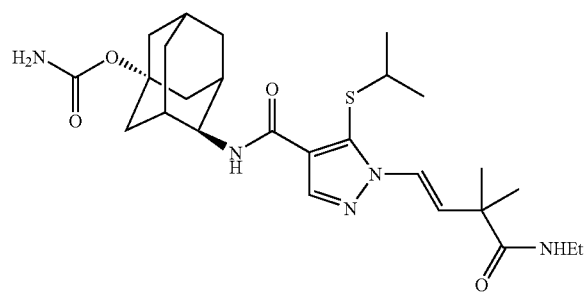

(Compound I-162) NMR(CDCl3); δ(ppm) 1.12 (t, J=7.2 Hz, 3H), 1.29 (d, J=6.6 Hz, 6H), 1.43 (s, 6H), 1.64-2.28 (m, 13H), 3.24-3.34 (m, 3H), 4.30 (brs, 1H), 4.55 (s, 2H), 5.74 (s, 1H), 6.64 (d, J=13.9 Hz, 1H), 7.42 (d, J=13.9 Hz, 1H), 7.92 (d, J=7.6 Hz, 1H), 8.22 (s, 1H)

Example 166

[Formula 216]

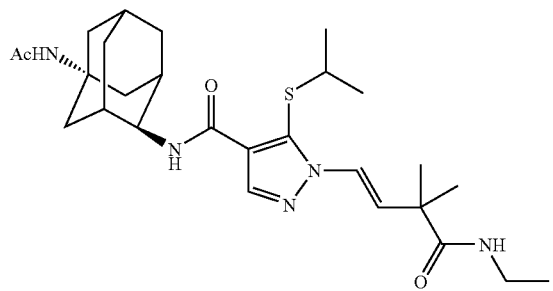

(Compound I-163) NMR(CDCl3); δ(ppm) 1.12 (t, J=7.2 Hz, 3H), 1.29 (d, J=6.6 Hz, 6H), 1.43 (s, 6H), 1.66-2.22 (m, 16H), 3.24-3.32 (m, 3H), 4.29 (brs, 1H), 5.26 (s, 1H), 5.70 (brs, 1H), 6.64 (d, J=14.4 Hz, 1H), 7.42 (d, J=14.4 Hz, 1H), 7.95 (d, J=8.3 Hz, 1H), 8.21 (s, 1H)

Example 167

[Formula 217]

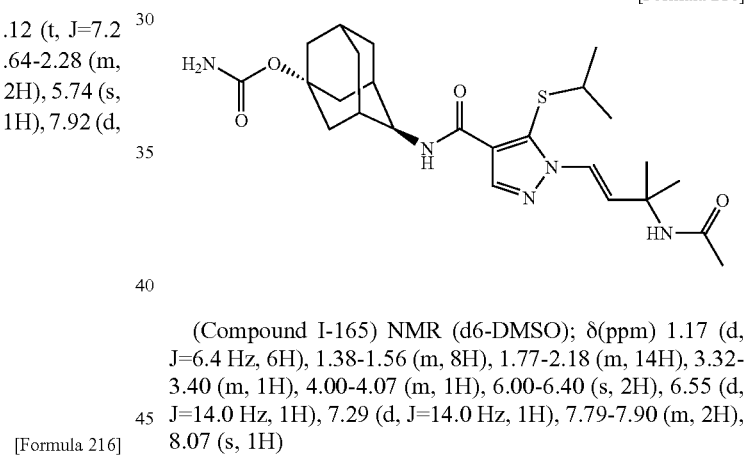

(Compound I-164) NMR(CDCl3); δ(ppm) 1.28 (d, J=6.6 Hz, 6H), 1.54 (s, 6H), 1.64-2.28 (m, 13H), 3.30-3.37 (m, 1H), 3.63 (s, 3H), 4.30 (d, J=7.1 Hz, 1H), 4.57 (s, 2H), 4.96 (s, 1H), 6.56 (d, J=13.9 Hz, 1H), 7.39 (d, J=13.9 Hz, 1H), 7.95 (d, J=7.8 Hz, 1H), 8.20 (s, 1H)

Example 168

[Formula 218]

(Compound I-165) NMR (d6-DMSO); δ(ppm) 1.17 (d, J=6.4 Hz, 6H), 1.38-1.56 (m, 8H), 1.77-2.18 (m, 14H), 3.32-3.40 (m, 1H), 4.00-4.07 (m, 1H), 6.00-6.40 (s, 2H), 6.55 (d, J=14.0 Hz, 1H), 7.29 (d, J=14.0 Hz, 1H), 7.79-7.90 (m, 2H), 8.07 (s, 1H)

Example 169

[Formula 219]

(Compound I-166) NMR (d6-DMSO); δ(ppm) 1.18 (d, J=6.8 Hz, 6H), 1.38-1.58 (m, 8H), 1.77-2.18 (m, 14H), 3.02

(d, J=5.6 Hz, 2H), 3.32-3.40 (m, 1H), 3.93-4.00 (m, 1H), 4.39 (t, J=5.6 Hz, 1H), 6.55 (d, J=14.0 Hz, 1H), 7.29 (d, J=14.0 Hz, 1H), 7.84 (s, 1H), 7.91 (d, J=7.2 Hz, 1H), 8.07 (s, 1H)

Example 170

[Formula 220]

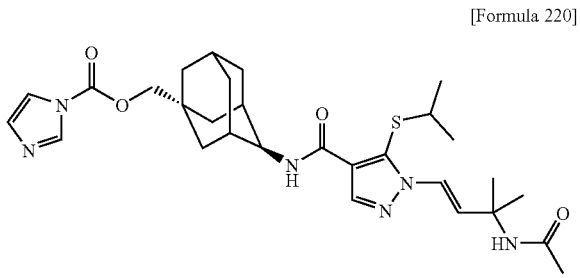 [SMILES: CC(=O)NC(C)(C)/C=C/n1ncc(C(=O)N[C@H]2C3CC4CC2C[C@](COC(=O)n2ccnc2)(C4)C3)c1SC(C)C]

(Compound I-167) NMR (d6-DMSO); δ(ppm) 1.18 (d, J=5.6 Hz, 6H), 1.44 (s, 6H), 1.50-2.07 (m, 16H), 3.32-3.40 (m, 1H), 3.98-4.10 (m, 3H), 6.55 (d, J=14.0 Hz, 1H), 7.09 (s, 1H), 7.29 (d, J=14.0 Hz, 1H), 7.66 (s, 1H), 7.85 (s, 1H), 7.92 (d, J=6.0 Hz, 1H), 8.08 (s, 1H), 8.33 (s, 1H)

Example 171

[Formula 221]

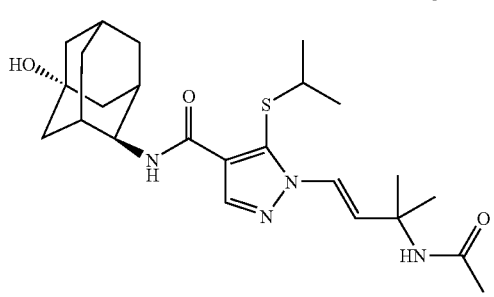

(Compound I-168) NMR(CDCl3); δ(ppm) 1.29 (d, J=6.6 Hz, 6H), 1.57-2.20 (m, 22H), 3.31-3.38 (m, 1H), 4.25 (d, J=6.6 Hz, 1H), 5.59 (s, 1H), 6.55 (d, J=14.2 Hz, 1H), 7.39 (d, J=14.2 Hz, 1H), 7.96 (d, J=7.8 Hz, 1H), 8.19 (s, 1H)

The compounds shown below were synthesized in accordance with the above Example.

Example 172

[Formula 222]

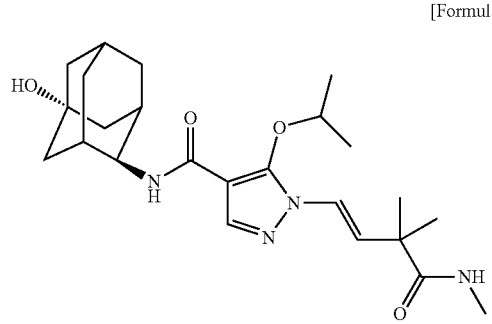

(Compound I-169) NMR (DMSO-d6); δ(ppm) 1.25-2.03 (m, 25H), 2.58 (d, J=4.3 Hz, 3H), 3.90 (brs, 1H), 4.42 (s, 1H), 4.88-4.94 (m, 1H), 6.35 (d, J=14.2 Hz, 1H), 6.77 (d, J=14.2 Hz, 1H), 7.30 (d, J=6.8 Hz, 1H), 7.52 (brs, 1H), 8.03 (s, 1H)

Example 173

[Formula 223]

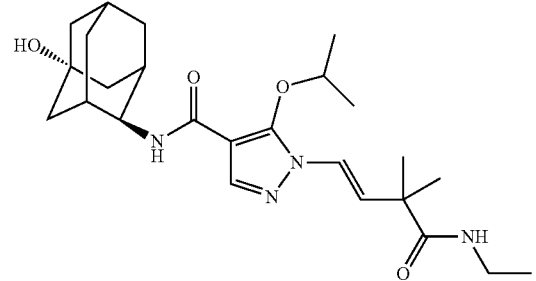

(Compound I-170) NMR (DMSO-d6); δ(ppm) 1.00 (t, J=7.1 Hz, 3H), 1.25-2.03 (m, 25H), 3.04-3.10 (m, 2H), 3.89 (brs, 1H), 4.42 (s, 1H), 4.89-4.94 (m, 1H), 6.35 (d, J=14.4 Hz, 1H), 6.77 (d, J=14.4 Hz, 1H), 7.31 (d, J=6.8 Hz, 1H), 7.57 (t, J=5.2 Hz, 1H), 8.02 (s, 1H)

Example 174

[Formula 224]

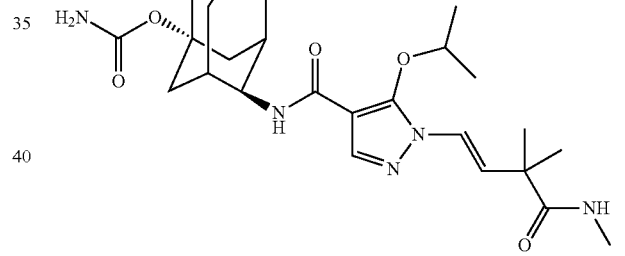

(Compound I-171) NMR (DMSO-d6); δ(ppm) 1.26-2.10 (m, 25H), 2.58 (d, J=4.6 Hz, 3H), 3.97 (brs, 1H), 4.89-4.96 (m, 1H), 6.19 (brs, 2H), 6.35 (d, J=14.4 Hz, 1H), 6.77 (d, J=14.4 Hz, 1H), 7.38 (d, J=6.3 Hz, 1H), 7.53 (brs, 1H), 8.04 (s, 1H)

Example 175

[Formula 225]

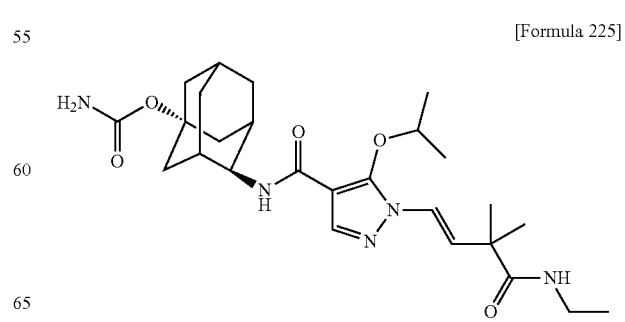

(Compound I-172) NMR (DMSO-d6); δ(ppm) 1.00 (t, J=7.2 Hz, 3H), 1.25-2.10 (m, 25H), 3.04-3.11 (m, 2H), 3.96 (brs, 1H), 4.90-4.97 (m, 1H), 6.20 (brs, 2H), 6.35 (d, J=14.4 Hz, 1H), 6.77 (d, J=14.4 Hz, 1H), 7.38 (d, J=7.1 Hz, 1H), 7.57 (t, J=5.4 Hz, 1H), 8.04 (s, 1H)

Example 176

[Formula 226]

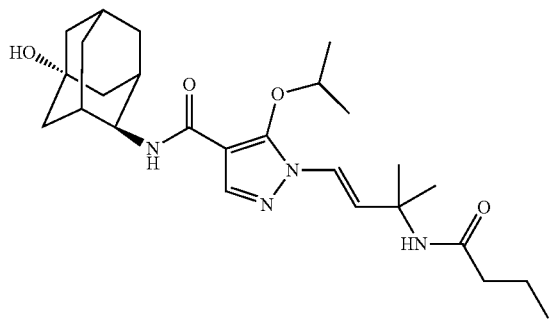

(Compound I-173) NMR (DMSO-d6); δ(ppm) 0.87 (t, J=7.3 Hz, 3H), 1.24 (d, J=6.1 Hz, 6H), 1.33-2.07 (m, 23H), 3.88 (brs, 1H), 4.42 (s, 1H), 4.87-4.93 (m, 1H), 6.35 (d, J=14.4 Hz, 1H), 6.75 (d, J=14.4 Hz, 1H), 7.31 (d, J=7.3 Hz, 1H), 7.69 (s, 1H), 8.00 (s, 1H)

Example 177

[Formula 227]

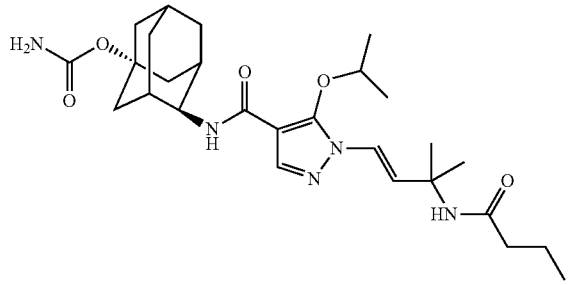

(Compound I-174) NMR (DMSO-d6); δ(ppm) 0.87 (t, J=7.3 Hz, 3H), 1.24 (d, J=6.1 Hz, 6H), 1.40-2.10 (m, 23H), 3.96 (brs, 1H), 4.89-4.95 (m, 1H), 6.20 (brs, 2H), 6.36 (d, J=14.4 Hz, 1H), 6.75 (d, J=14.4 Hz, 1H), 7.38 (d, J=6.6 Hz, 1H), 7.69 (s, 1H), 8.01 (s, 1H)

Example 178

[Formula 228]

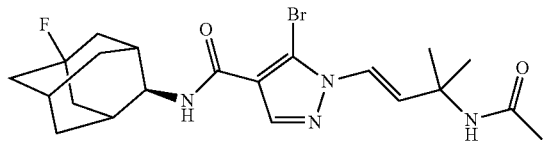

(Compound I-175) NMR (d6-DMSO); δ(ppm) 1.43 (s, 6H), 1.81 (s, 6H), 1.86-2.21 (m, 13H), 2.17 (m, 1H), 3.96 (brs, 1H), 6.59 (d, J=10.8 Hz, 1H), 7.00 (d, J=10.5 Hz, 1H), 7.64 (brd, J=4.5 Hz, 1H), 7.83 (s, 1H), 8.21 (s, 1H), 8.31 (brs, 1H)

Example 179

[Formula 229]

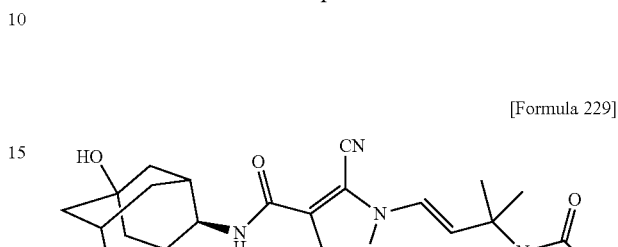

(Compound I-176) NMR (d6-DMSO); δ(ppm) 1.34-2.10 (m, 13H), 1.43 (s, 3H), 1.44 (s, 3H), 1.81 (s, 3H), 3.92 (m, 1H), 4.44 (m, 1H), 6.72 (d, J=10.5 Hz, 1H), 6.99 (d, J=10.5 Hz, 1H), 7.89 (s, 1H), 8.21 (s, 1H), 8.47 (s, 1H)

Example 180

[Formula 230]

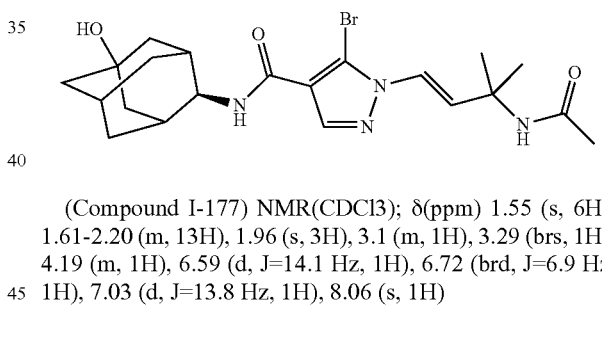

(Compound I-177) NMR(CDCl3); δ(ppm) 1.55 (s, 6H), 1.61-2.20 (m, 13H), 1.96 (s, 3H), 3.1 (m, 1H), 3.29 (brs, 1H), 4.19 (m, 1H), 6.59 (d, J=14.1 Hz, 1H), 6.72 (brd, J=6.9 Hz, 1H), 7.03 (d, J=13.8 Hz, 1H), 8.06 (s, 1H)

Example 181

[Formula 231]

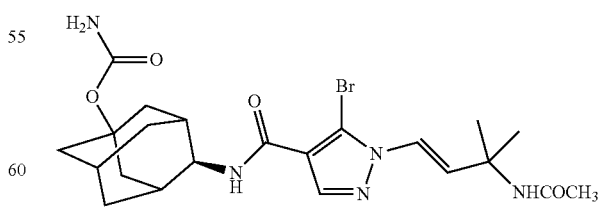

(Compound I-178) NMR(CDCl3); δ(ppm) 1.5-2.3 (m, 13H), 1.97 (s, 3H), 4.27 (brd, J=7.8 Hz, 1H), 4.41 (brs, 2H), 5.46 (s, 1H), 6.50 (d, J=7.2 Hz, 1H), 6.60 (d, J=13.2 Hz, 1H), 7.04 (d, J=13.8 Hz, 1H), 8.07 (s, 1H)

Example 182
[Formula 232]
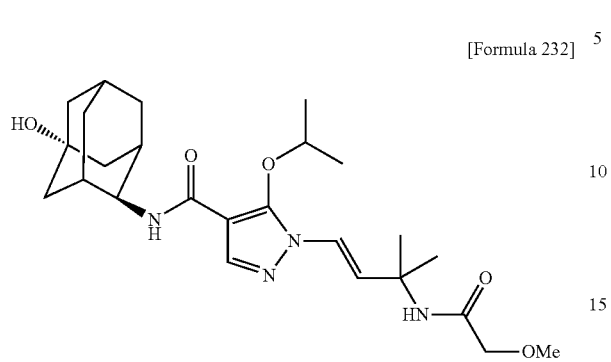
(Compound I-179) NMR (DMSO-d6); δ(ppm) 1.25 (d, J=6.1 Hz, 6H), 1.35-2.03 (m, 19H), 3.31 (s, 3H), 3.76 (s, 2H), 3.89 (brs, 1H), 4.43 (s, 1H), 4.86-4.93 (m, 1H), 6.39 (d, J=14.4 Hz, 1H), 6.79 (d, J=14.4 Hz, 1H), 7.31 (d, J=7.1 Hz, 1H), 7.40 (s, 1H), 8.01 (s, 1H)
Example 183
[Formula 233]
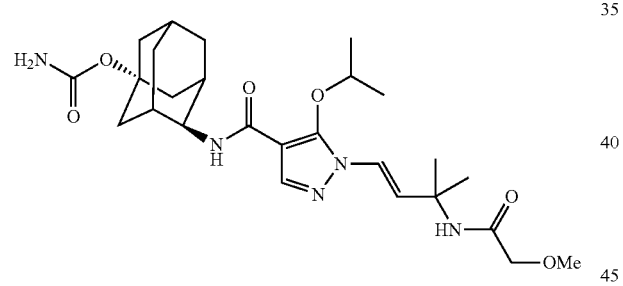
(Compound I-180) NMR (DMSO-d6); δ(ppm) 1.25 (d, J=6.1 Hz, 6H), 1.41-2.10 (m, 19H), 3.31 (s, 3H), 3.76 (s, 2H), 3.95 (brs, 1H), 4.87-4.94 (m, 1H), 6.19 (brs, 2H), 6.39 (d, J=14.4 Hz, 1H), 6.79 (d, J=14.4 Hz, 1H), 7.36-7.40 (m, 2H), 8.02 (s, 1H)
The following compounds as the present compound can be synthesized as well as the above Example.
[Formula 234]
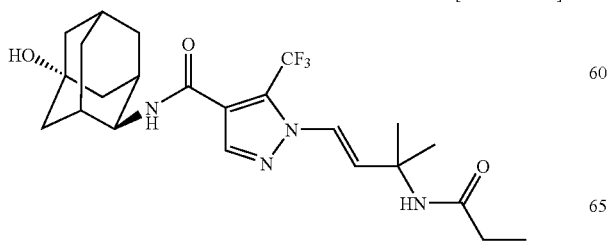
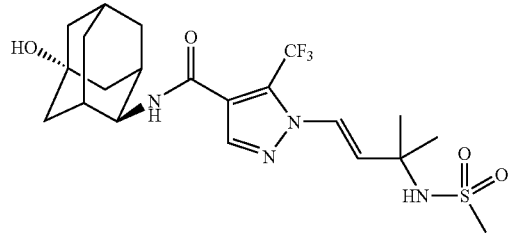
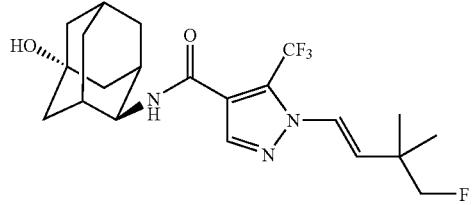
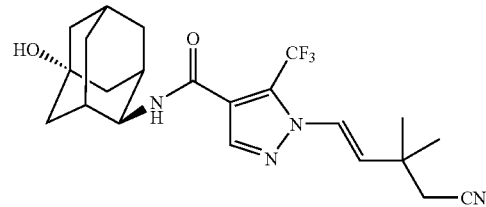
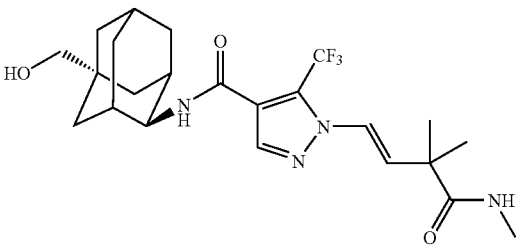
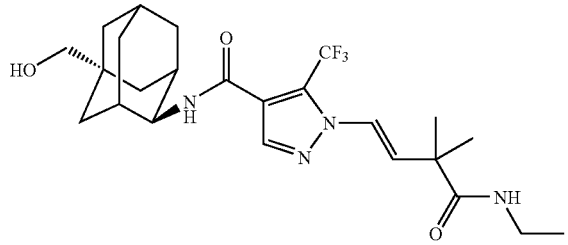
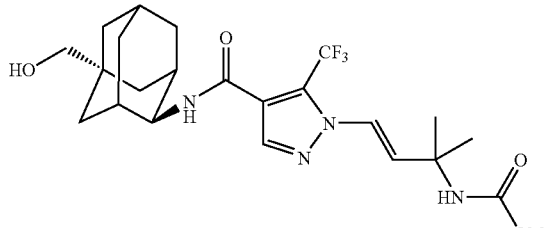
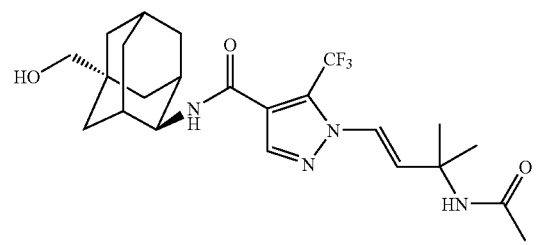

157
-continued
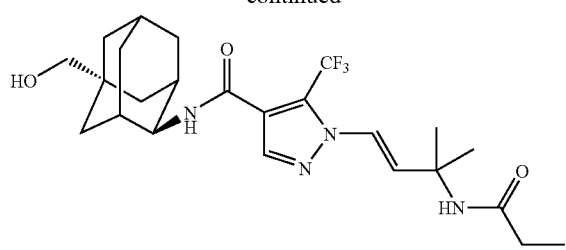
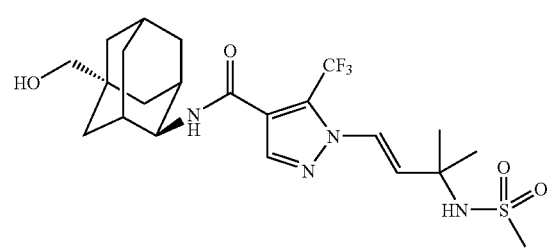
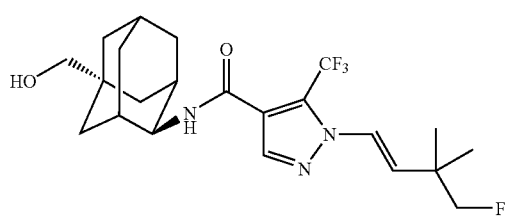
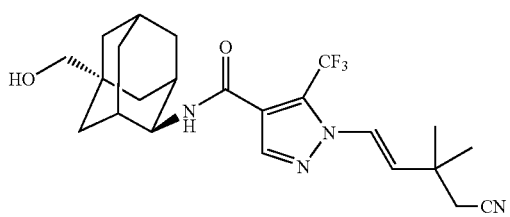
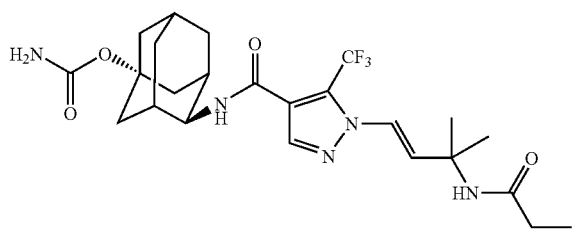
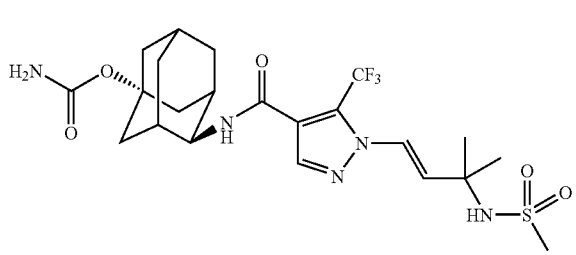
[Formula 235]
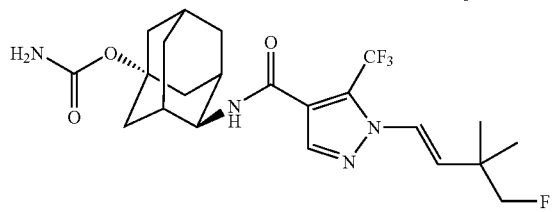
158
-continued
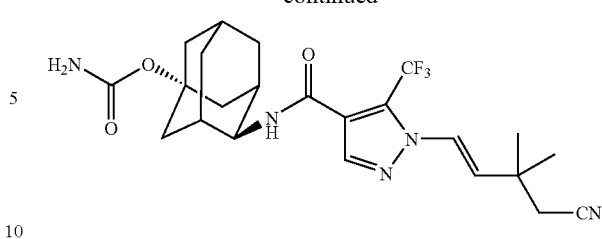
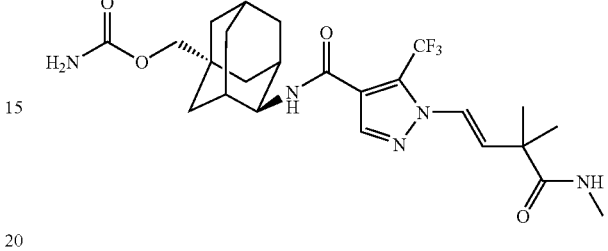
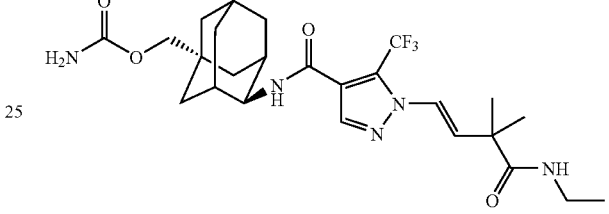
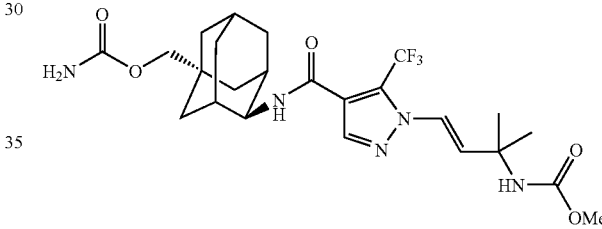
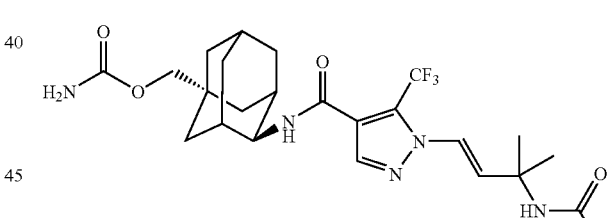
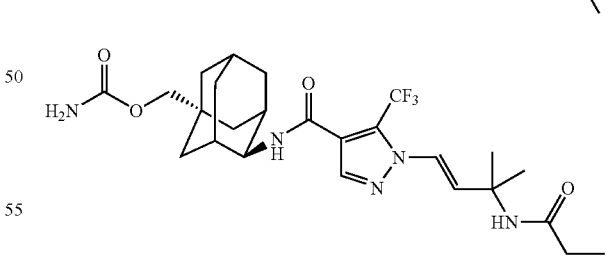
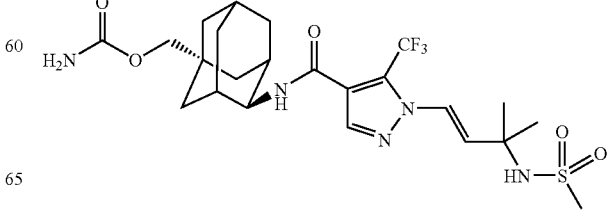

159
-continued
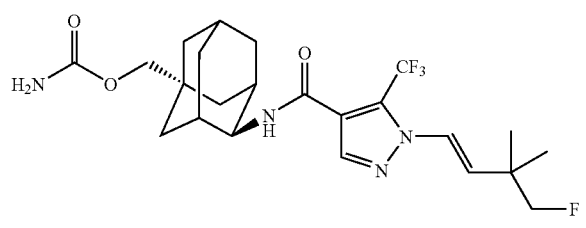
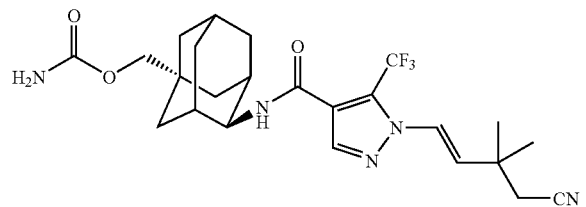
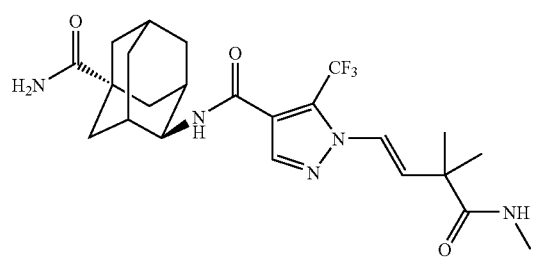
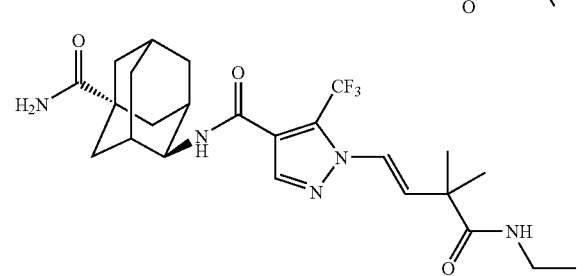
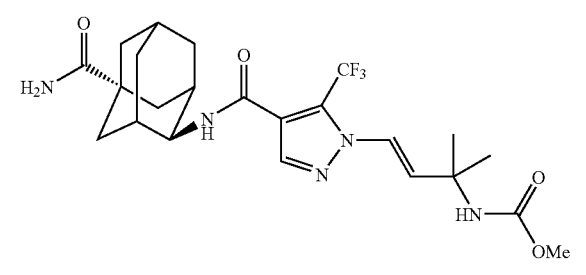
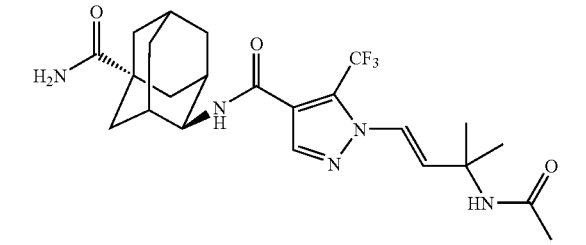
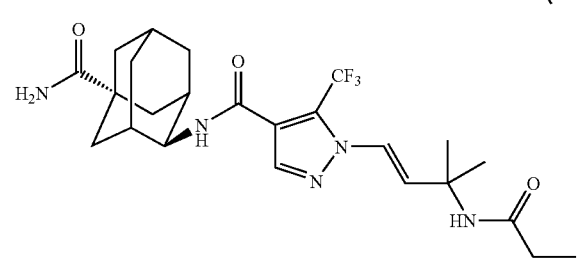
160
-continued
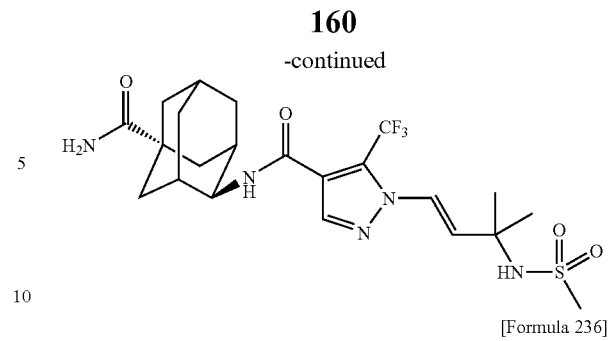
[Formula 236]
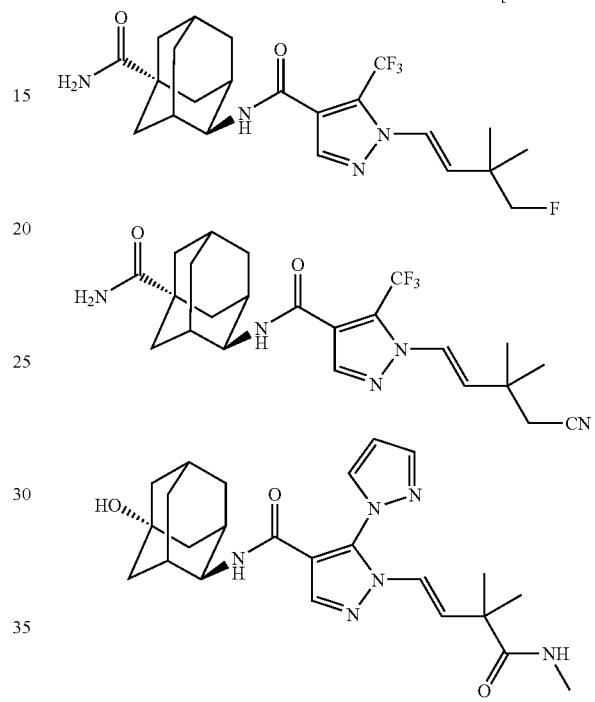

161
-continued
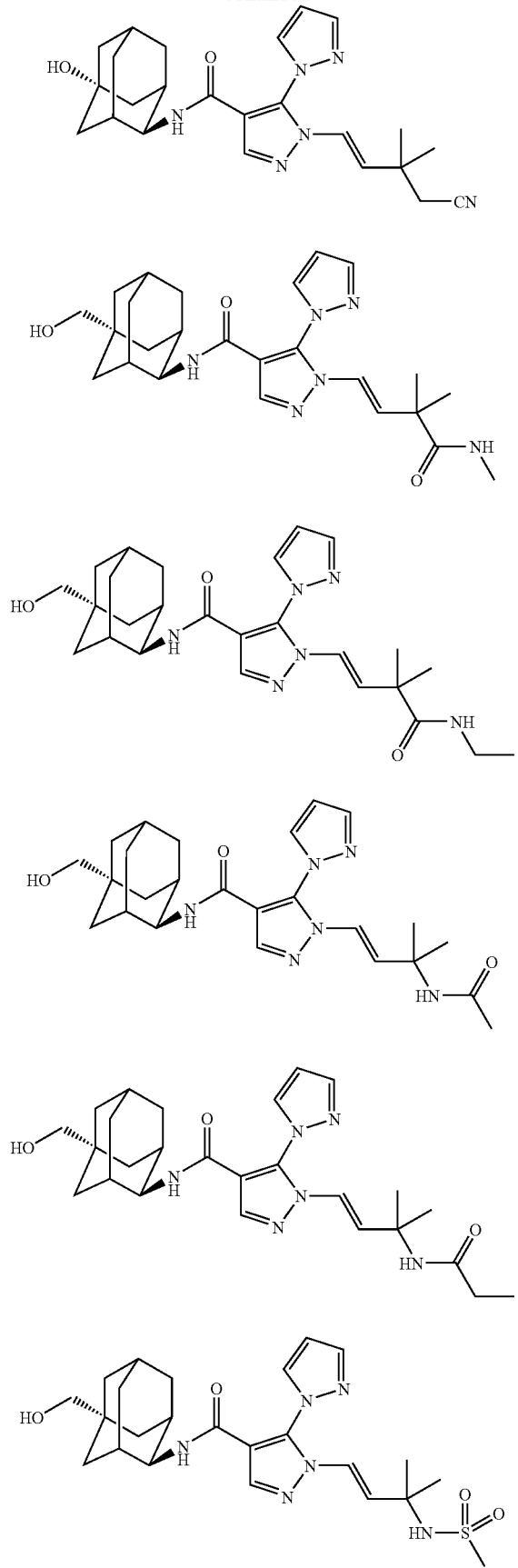
162
-continued
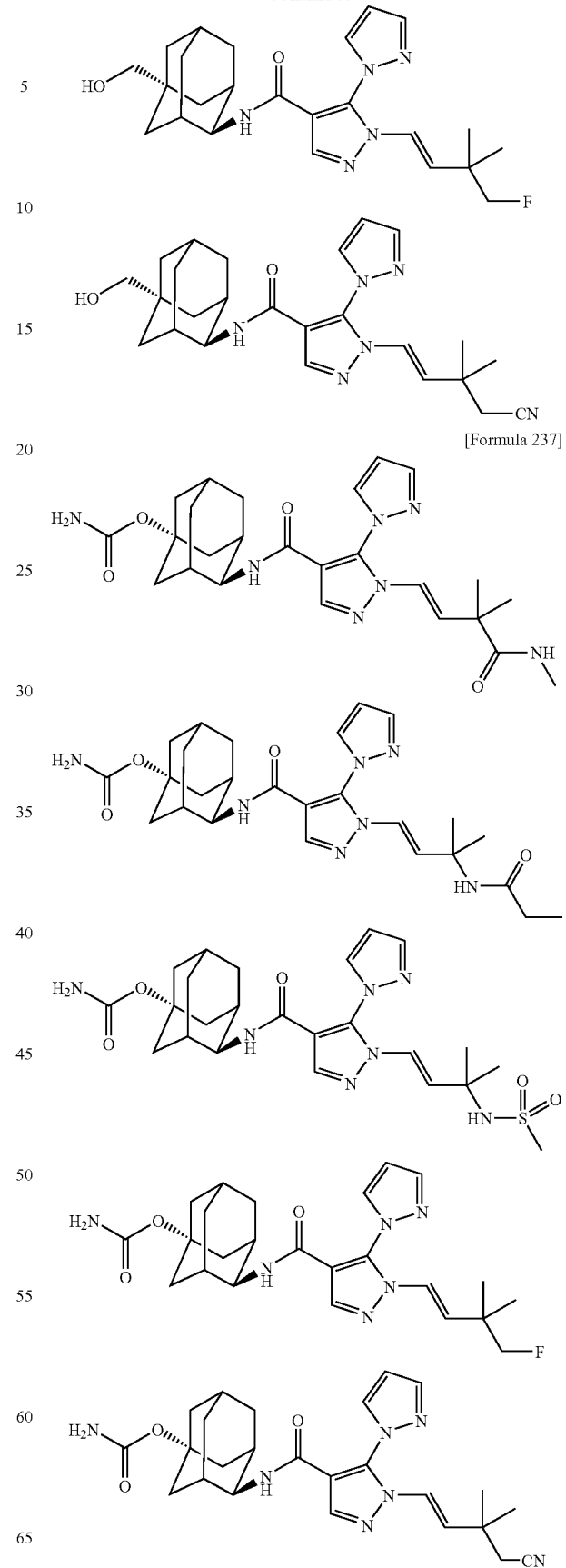
[Formula 237]

163
-continued
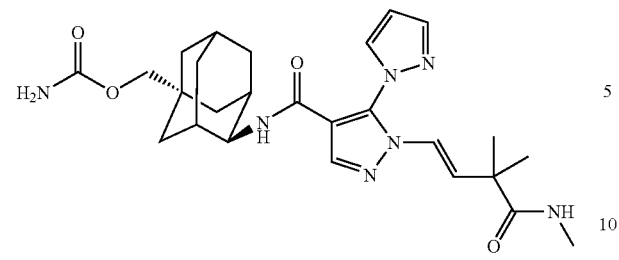
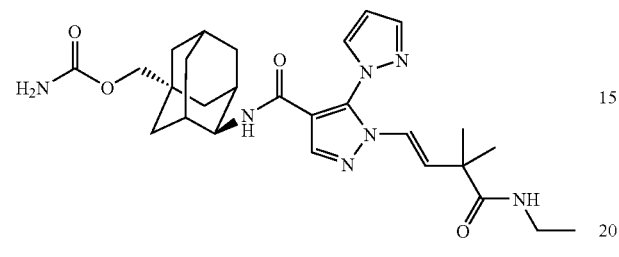
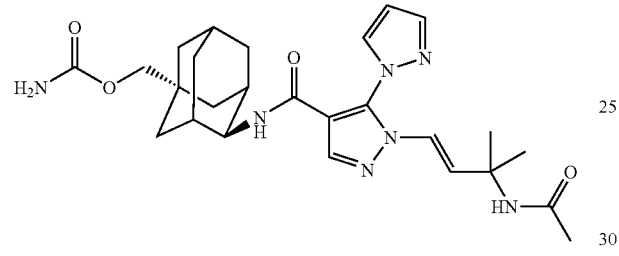
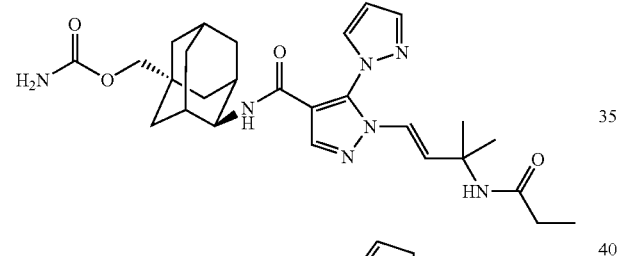
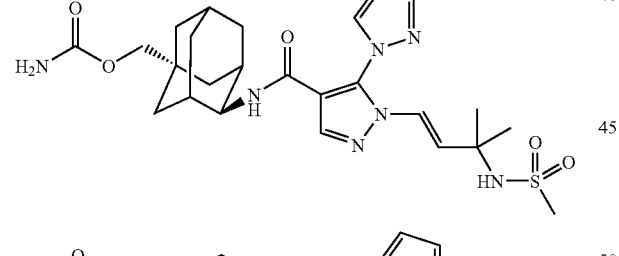
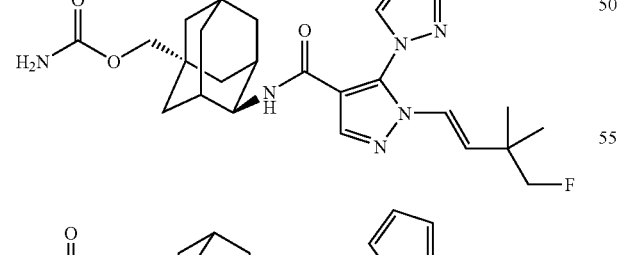
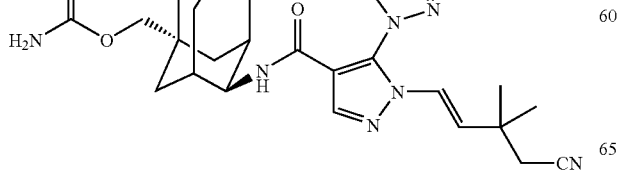
164
-continued
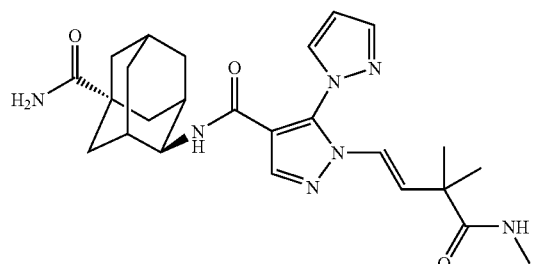
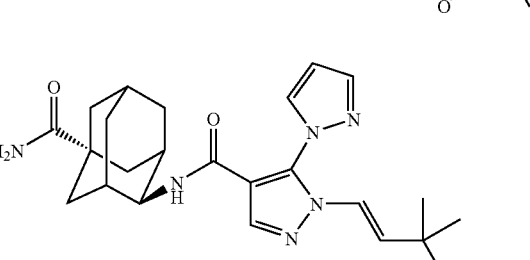
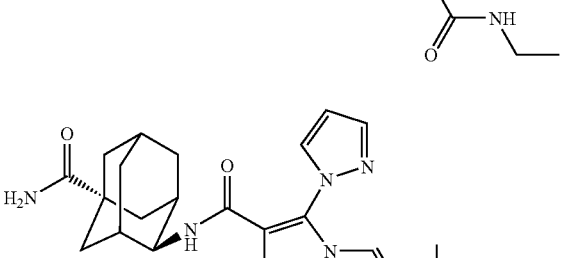
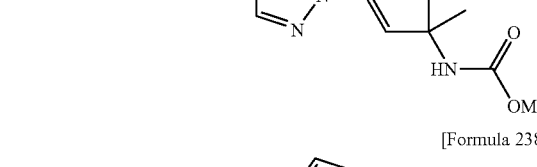
[Formula 238]
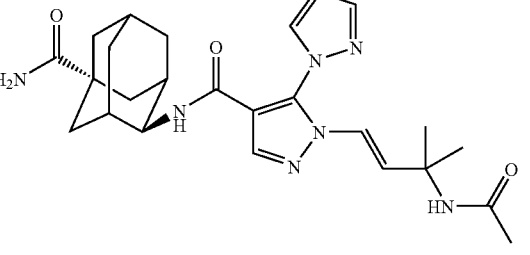
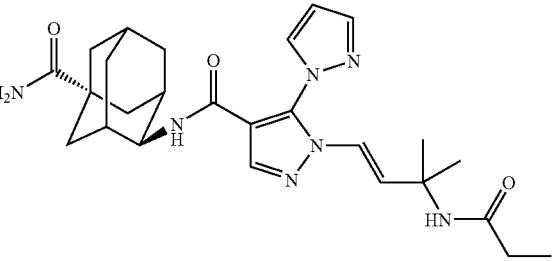
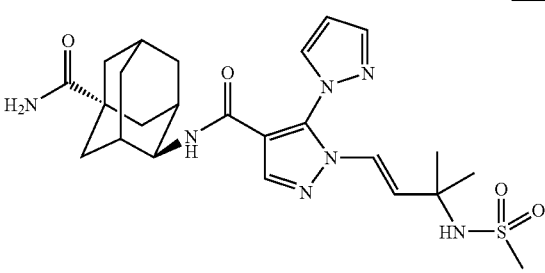

165
-continued
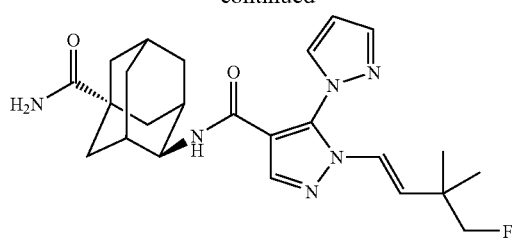
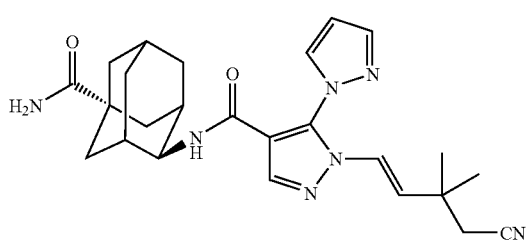
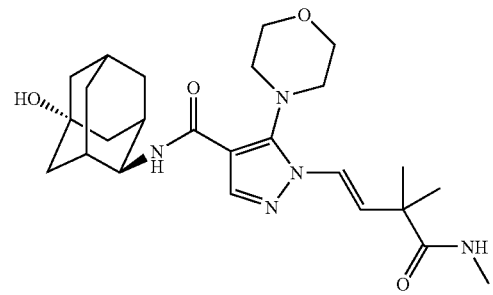
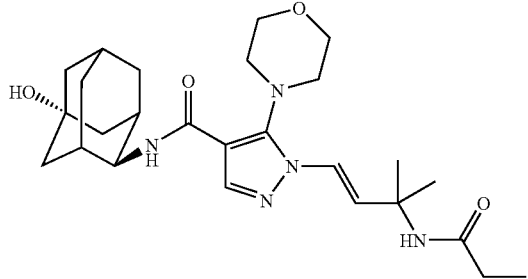
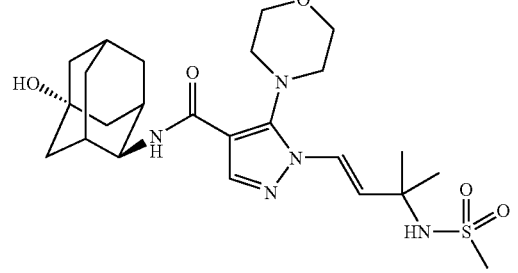
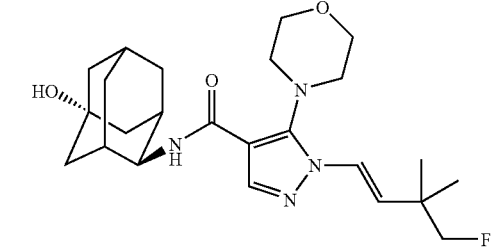
166
-continued
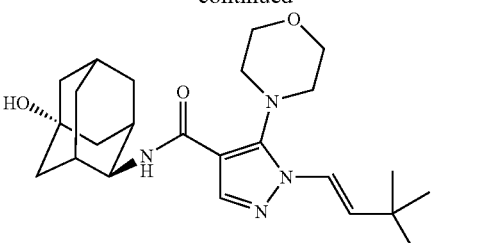
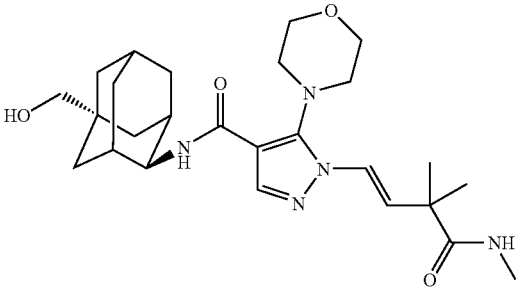
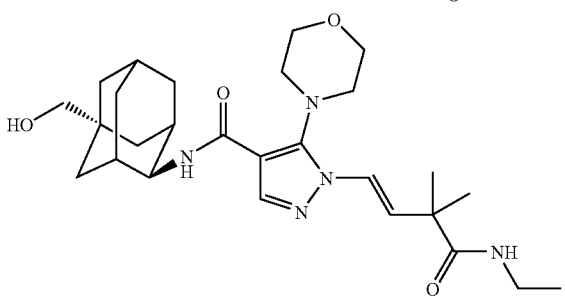
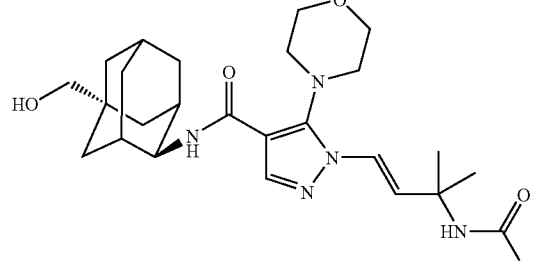
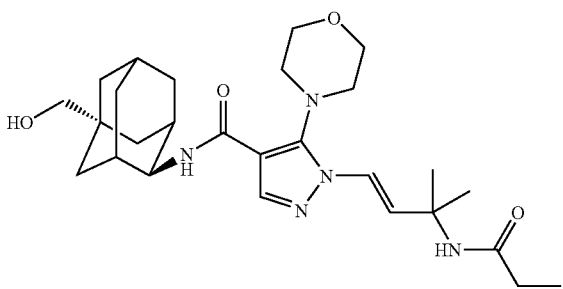
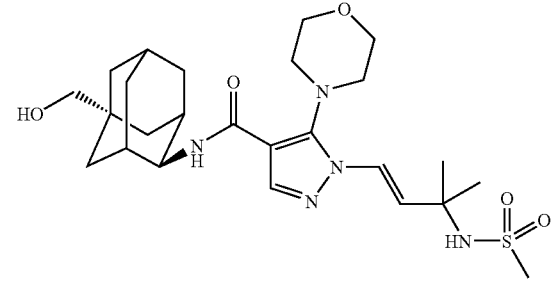

167
-continued
[Formula 239]
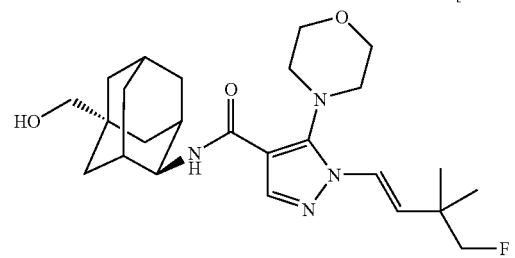
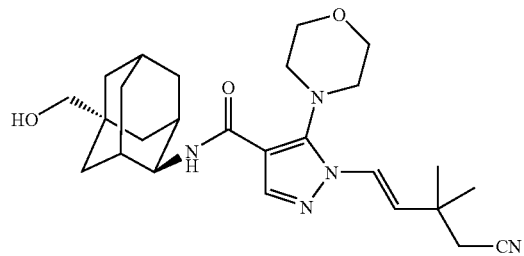
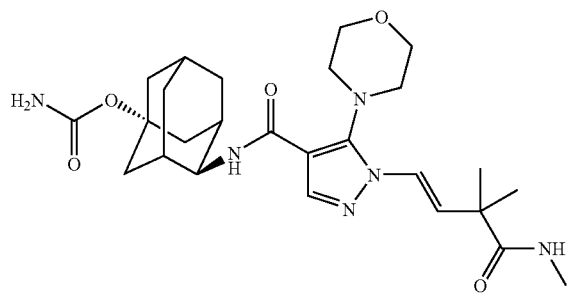
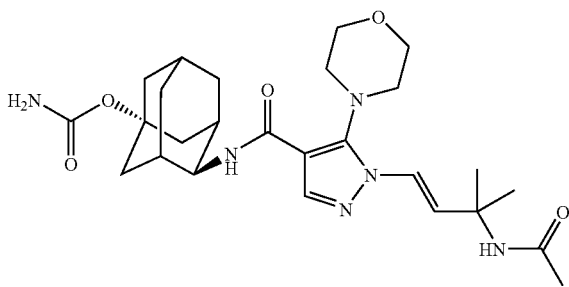
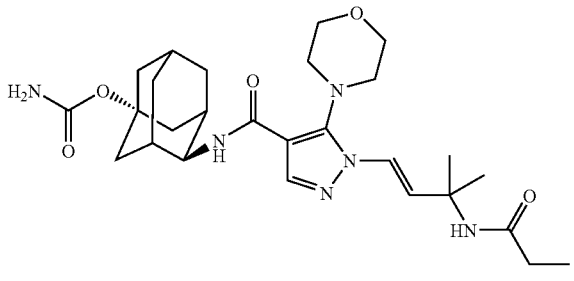
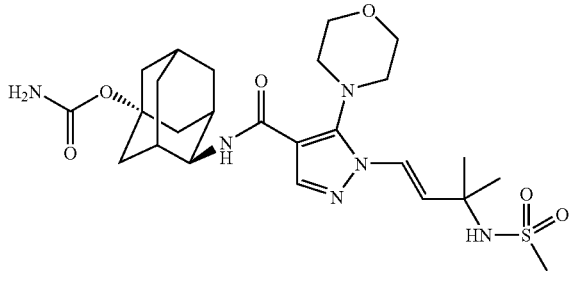
168
-continued
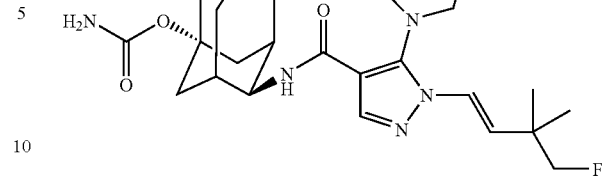
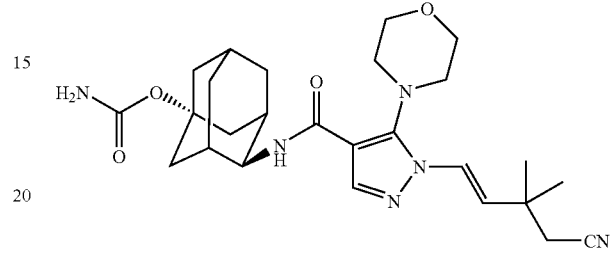
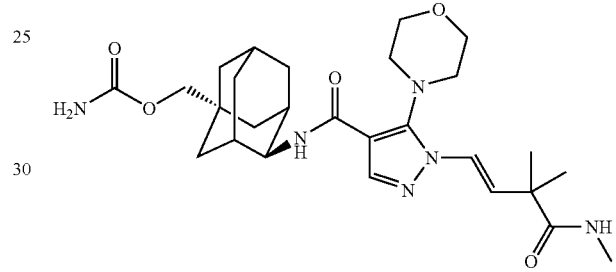
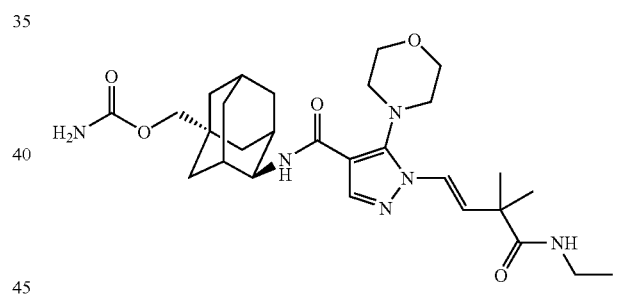
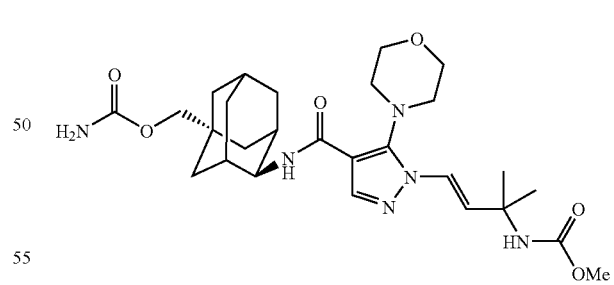
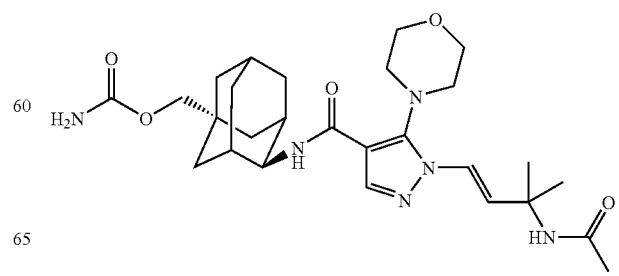

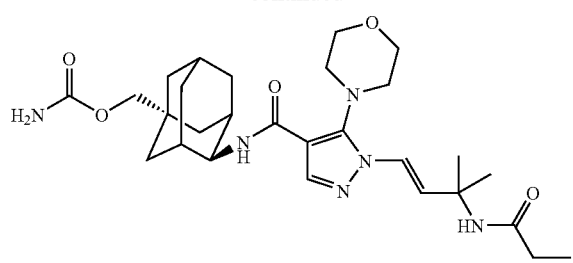
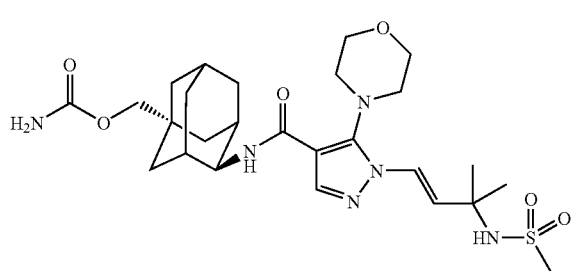
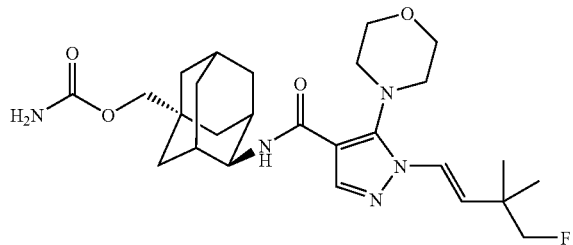
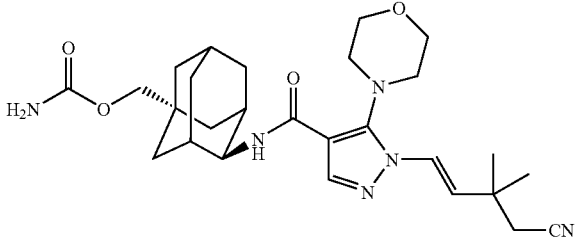
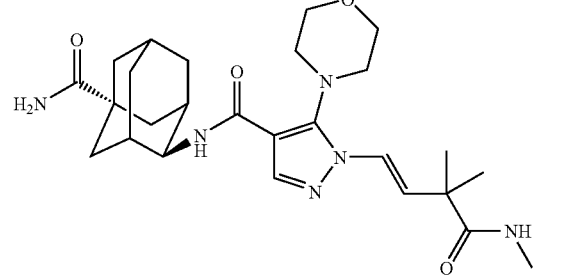
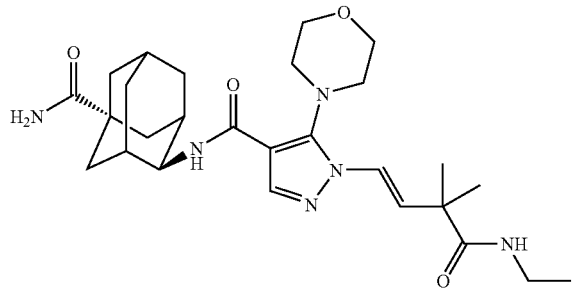
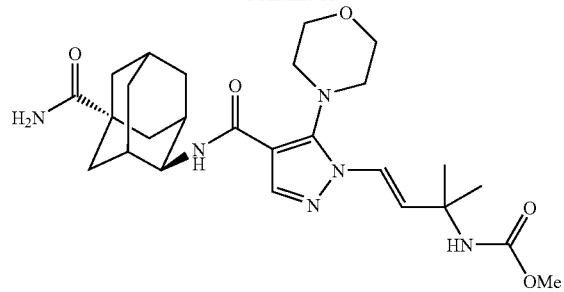
[Formula 240]
Moreover, the following compounds as the present compound can be synthesized.

Concretely, the compounds defined by the Formula (IV) are shown.
[Formula 241]
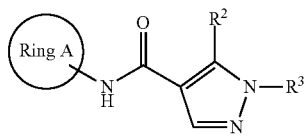
The abbreviations used for Ring A in the Formula (IV) are as follows.
[Formula 242]
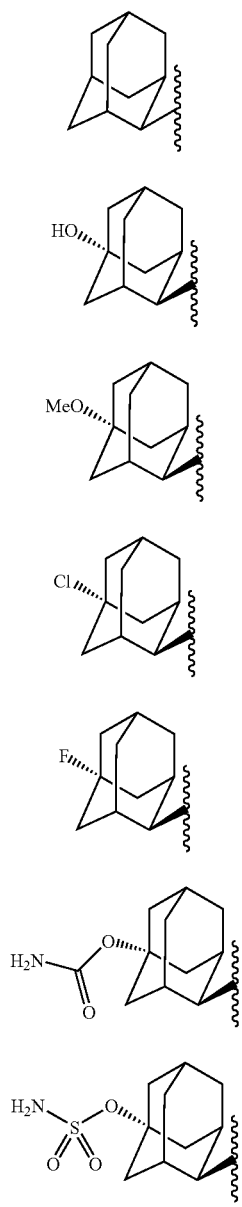
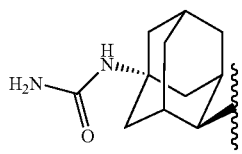
A-8
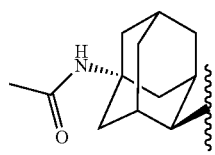
A-9
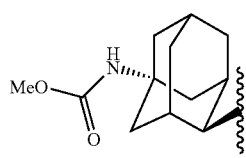
A-10
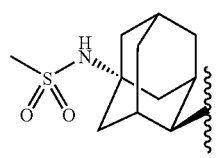
A-11
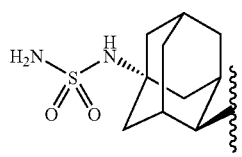
A-12
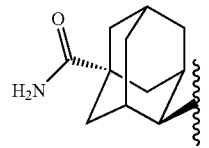
A-13
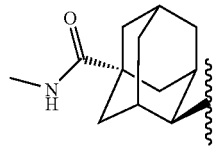
A-14
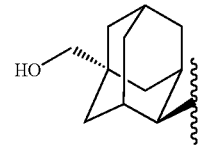
A-15
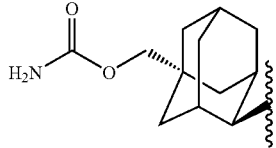
A-16
The abbreviations used for $R^3$ in the Formula (IV) are as follows.

[Formula 243]
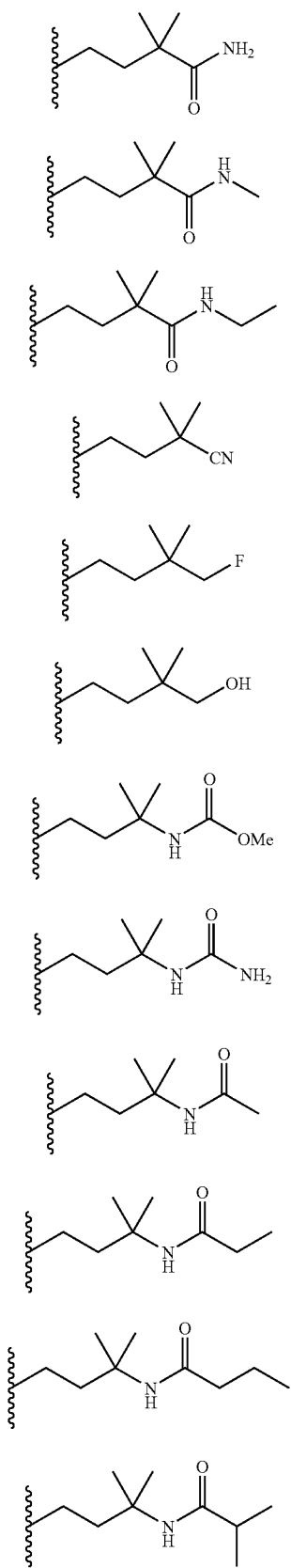
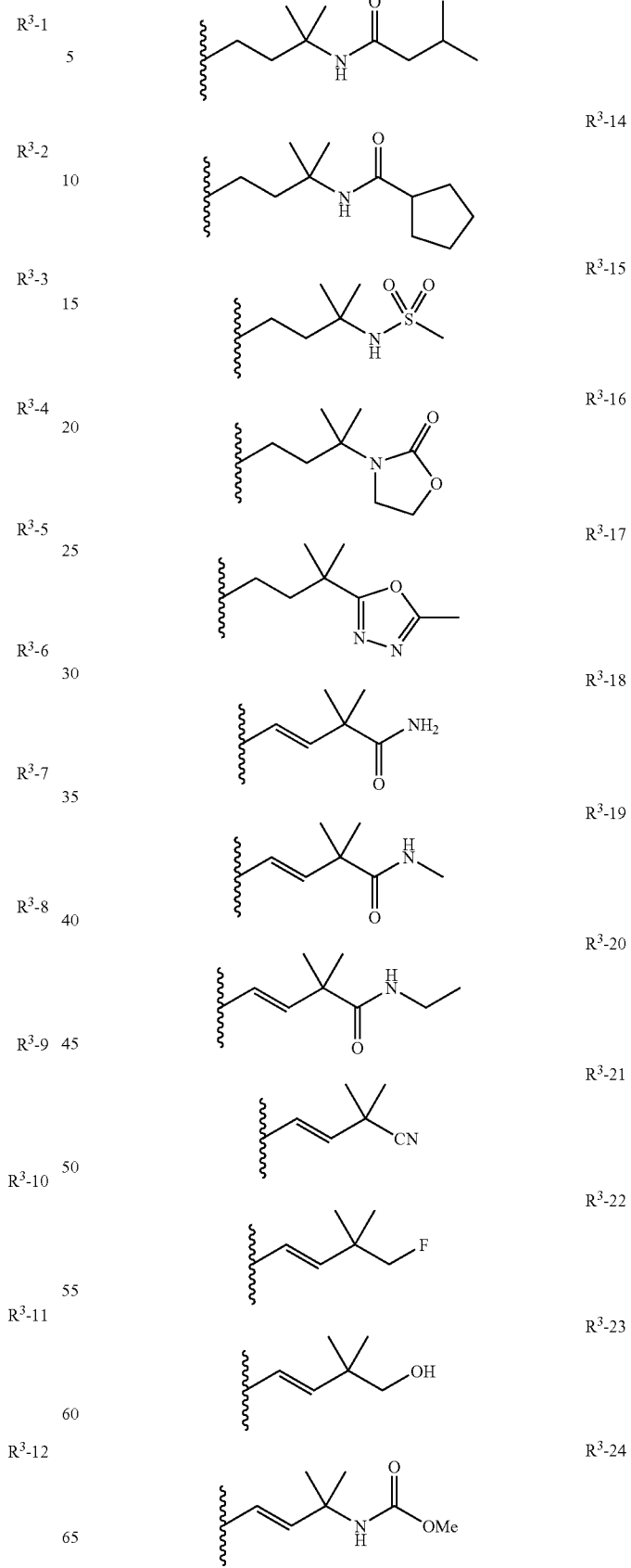

-continued
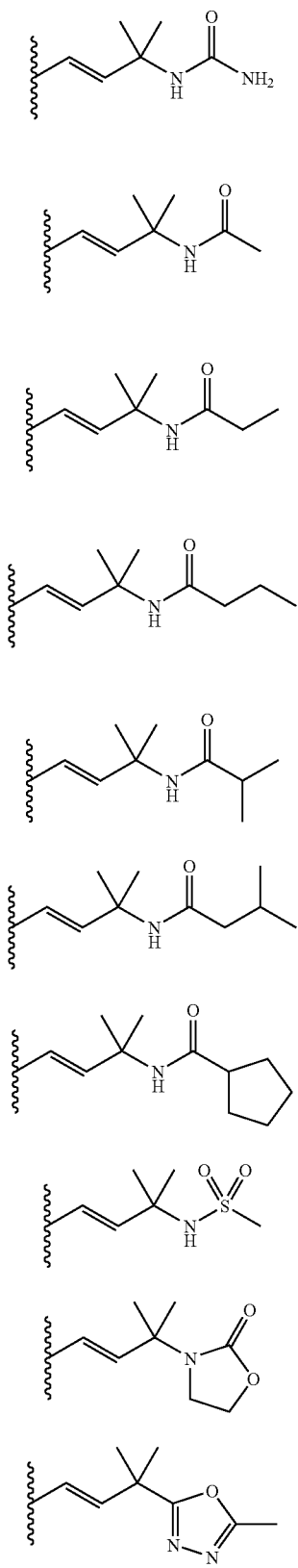
R³-25
R³-26
R³-27
R³-28
R³-29
R³-30
R³-31
R³-32
R³-33
R³-34
The abbreviations used for R² in the Formula (IV) are as follows.
[Formula 244]
 R²-1
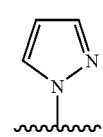 R²-2
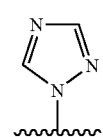 R²-3
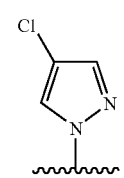 R²-4
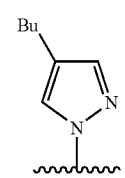 R²-5
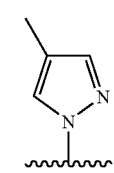 R²-6
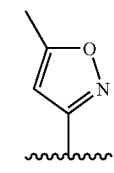 R²-7
 R²-8
 R²-9
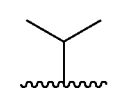 R²-10
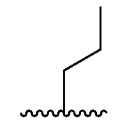 R²-11

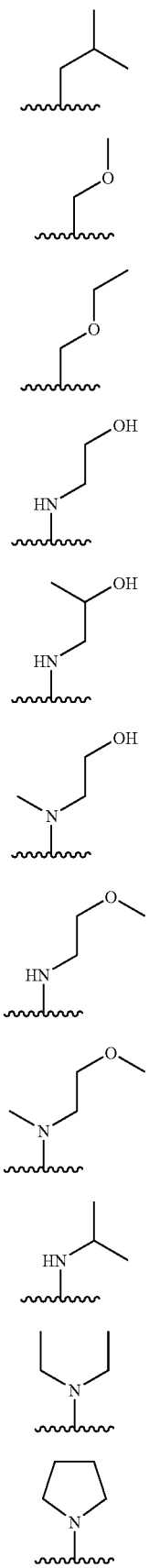
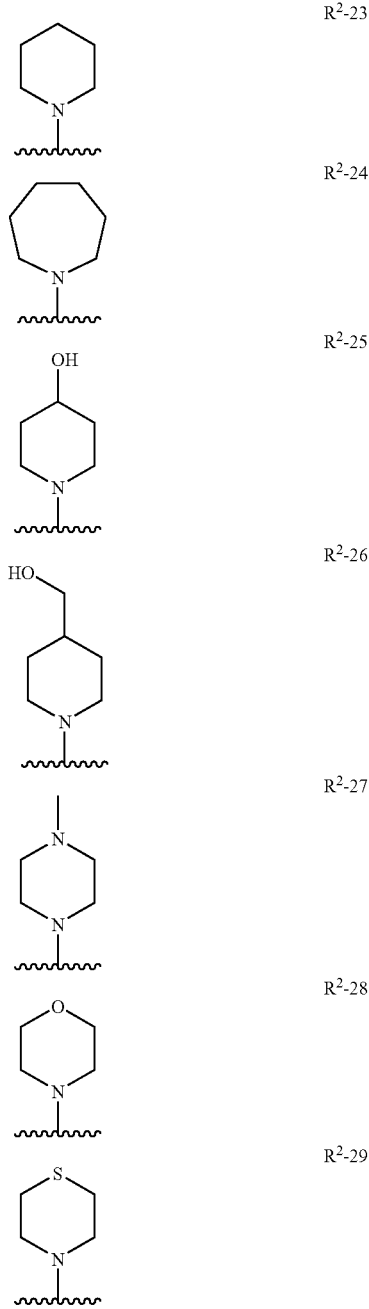
(Compound No, Ring A, R², R³)=(I-P1,A-1,R²-1,R³-1), (I-P2,A-1,R²-1,R³-2), (I-P3,A-1,R²-1,R³-3), (I-P4,A-1,R²-1, R³-4), (I-P5,A-1,R²-1,R³-5), (I-P6,A-1,R²-1,R³-6), (I-P7,A-1,R²-1,R³-7), (I-P8,A-1,R²-1,R³-8), (I-P9,A-1,R²-1,R³-9), (I-P10,A-1,R²-1,R³-10), (I-P11,A-1,R²-1,R³-11), (I-P12,A-1,R²-1,R³-12), (I-P13,A-1,R²-1,R³-13), (I-P14,A-1,R²-1, R³-14), (I-P15,A-1,R²-1,R³-15), (I-P16,A-1,R²-1,R³-16), (I-P17,A-1,R²-1,R³-17), (I-P18,A-1,R²-1,R³-18), (I-P19,A-1,R²-1,R³-19), (I-P20,A-1,R²-1,R³-20), (I-P21,A-1,R²-1, R³-21), (I-P22,A-1,R²-1,R³-22), (I-P23,A-1,R²-1,R³-23), (I-P24,A-1,R²-1,R³-24), (I-P25,A-1,R²-1,R³-25), (I-P26,A-1,R²-1,R³-26), (I-P27,A-1,R²-1,R³-27), (I-P28,A-1,R²-1, R³-28), (I-P29,A-1,R²-1,R³-29), (I-P30,A-1,R²-1,R³-30), (I-P31,A-1,R²-1,R³-31), (I-P32,A-1,R²-1,R³-32), (I-P33,A-1,R²-1,R³-33), (I-P34,A-1,R²-1,R³-34), (I-P35,A-1,R²-2, R³-1), (I-P36,A-1,R²-2,R³-2), (I-P37,A-1,R²-2,R³-3), (I-P38,A-1,R²-2,R³-4), (I-P39,A-1,R²-2,R³-5), (I-P40,A-1,R²-2,R³-6), (I-P41,A-1,R²-2,R³-7), (I-P42,A-1,R²-2,R³-8), (I-P43,A-1,R²-2,R³-9), (I-P44,A-1,R²-2,R³-10), (I-P45,A-1,R²-2,R³-11), (I-P46,A-1,R²-2,R³-12), (I-P47,A-1,R²-2,R³-13), (I-P48,A-1,R²-2,R³-14), (I-P49,A-1,R²-2,R³-15), (I-P50,A-1,R²-2,R³-16), (I-P51,A-1,R²-2,R³-17), (I-P52,A-1,R²-2,R³-18), (I-P53,A-1,R²-2,R³-19), 1,R²-2,R³-20), (I-P55,A-1,R²-2,R³-21), (I-P56,A-1,R²-2,R³-22), (I-P57,A-1,R²-2,R³-23), (I-P58,A-1,R²-2,R³-24), (I-P59,A-1,R²-2,R³-25), (I-P60,A-1,R²-2,R³-26), (I-P61,A-1,R²-2,R³-27), (I-P62,A-1,R²-2,R³-28), (I-P63,A-1,R²-2,R³-29), (I-P64,A-1,R²-2,R³-30), (I-P65,A-1,R²-2,R³-31), (I-P66,A-1,R²-2,R³-32), (I-P67,A-1,R²-2,R³-33), (I-P68,A-1,R²-2,R³-34), (I-P69,A-1,R²-3,R³-1), (I-P70,A-1,R²-3,R³-2), (I-P71,A-1,R²-3,R³-3), (I-P72,A-1,R²-3,R³-4), (I-P73,A-1,R²-3,R³-5), (I-P74,A-1,R²-3,R³-6), (I-P75,A-1,R²-3,R³-7), (I-P76,A-1,R²-3,R³-8), (I-P77,A-1,R²-3,R³-9), (I-P78,A-1,R²-3,R³-10), (I-P79,A-1,R²-3,R³-11), (I-P80,A-1,R²-3,R³-12), (I-P81,A-1,R²-3,R³-13), (I-P82,A-1,R²-3,R³-14), (I-P83,A-1,R²-3,R³-15), (I-P84,A-1,R²-3,R³-16), (I-P85,A-1,R²-3,R³-17), (I-P86,A-1,R²-3,R³-18), (I-P87,A-1,R²-3,R³-19), (I-P88,A-1,R²-3,R³-20), (I-P89,A-1,R²-3,R³-21), (I-P90,A-1,R²-3,R³-22), (I-P91,A-1,R²-3,R³-23), (I-P92,A-1,R²-3,R³-24), (I-P93,A-1,R²-3,R³-25), (I-P94,A-1,R²-3,R³-26), (I-P95,A-1,R²-3,R³-27), (I-P96,A-1,R²-3,R³-28), (I-P97,A-1,R²-3,R³-29), (I-P98,A-1,R²-3,R³-30), (I-P99,A-1,R²-3,R³-31), (I-P100,A-1,R²-3,R³-32), (I-P101,A-1,R²-3,R³-33), (I-P102,A-1,R²-3,R³-34), (I-P103,A-1,R²-4,R³-1), (I-P104,A-1,R²-4,R³-2), (I-P105,A-1,R²-4,R³-3), (I-P106,A-1,R²-4,R³-4), (I-P107,A-1,R²-4,R³-5), (I-P108,A-1,R²-4,R³-6), (I-P109,A-1,R²-4,R³-7), (I-P110,A-1,R²-4,R³-8), (I-P111,A-1,R²-4,R³-9), (I-P112,A-1,R²-4,R³-10), (I-P113,A-1,R²-4,R³-11), (I-P114,A-1,R²-4,R³-12), (I-P115,A-1,R²-4,R³-13), (I-P116,A-1,R²-4,R³-14), (I-P117,A-1,R²-4,R³-15), (I-P118,A-1,R²-4,R³-16), (I-P119,A-1,R²-4,R³-17), (I-P120,A-1,R²-4,R³-18), (I-P121,A-1,R²-4,R³-19), (I-P122,A-1,R²-4,R³-20), (I-P123,A-1,R²-4,R³-21), (I-P124,A-1,R²-4,R³-22), (I-P125,A-1,R²-4,R³-23), (I-P126,A-1,R²-4,R³-24), (I-P127,A-1,R²-4,R³-25), (I-P128,A-1,R²-4,R³-26), (I-P129,A-1,R²-4,R³-27), (I-P130,A-1,R²-4,R³-28), (I-P131,A-1,R²-4,R³-29), (I-P132,A-1,R²-4,R³-30), (I-P133,A-1,R²-4,R³-31), (I-P134,A-1,R²-4,R³-32), (I-P135,A-1,R²-4,R³-33), (I-P136,A-1,R²-4,R³-34), (I-P137,A-1,R²-5,R³-1), (I-P138,A-1,R²-5,R³-2), (I-P139,A-1,R²-5,R³-3), (I-P140,A-1,R²-5,R³-4), (I-P141,A-1,R²-5,R³-5), (I-P142,A-1,R²-5,R³-6), (I-P143,A-1,R²-5,R³-7), (I-P144,A-1,R²-5,R³-8), (I-P145,A-1,R²-5,R³-9), (I-P146,A-1,R²-5,R³-10), (I-P147,A-1,R²-5,R³-11), (I-P148,A-1,R²-5,R³-12), (I-P149,A-1,R²-5,R³-13), (I-P150,A-1,R²-5,R³-14), (I-P151,A-1,R²-5,R³-15), (I-P152,A-1,R²-5,R³-16), (I-P153,A-1,R²-5,R³-17), (I-P154,A-1,R²-5,R³-18), (I-P155,A-1,R²-5,R³-19), (I-P156,A-1,R²-5,R³-20), (I-P157,A-1,R²-5,R³-21), (I-P158,A-1,R²-5,R³-22), (I-P159,A-1,R²-5,R³-23), (I-P160,A-1,R²-5,R³-24), (I-P161,A-1,R²-5,R³-25), (I-P162,A-1,R²-5,R³-26), (I-P163,A-1,R²-5,R³-27), (I-P164,A-1,R²-5,R³-28), (I-P165,A-1,R²-5,R³-29), (I-P166,A-1,R²-5,R³-30), (I-P167,A-1,R²-5,R³-31), (I-P168,A-1,R²-5,R³-32), (I-P169,A-1,R²-5,R³-33), (I-P170,A-1,R²-5,R³-34), (I-P171,A-1,R²-6,R³-1), (I-P172,A-1,R²-6,R³-2), (I-P173,A-1,R²-6,R³-3), (I-P174,A-1,R²-6,R³-4), (I-P175,A-1,R²-6,R³-5), (I-P176,A-1,R²-6,R³-6), (I-P177,A-1,R²-6,R³-7), (I-P178,A-1,R²-6,R³-8), (I-P179,A-1,R²-6,R³-9), (I-P180,A-1,R²-6,R³-10), (I-P181,A-1,R²-6,R³-11), (I-P182,A-1,R²-6,R³-12), (I-P183,A-1,R²-6,R³-13), (I-P184,A-1,R²-6,R³-14), (I-P185,A-1,R²-6,R³-15), (I-P186,A-1,R²-6,R³-16), (I-P187,A-1,R²-6,R³-17), (I-P188,A-1,R²-6,R³-18), (I-P189,A-1,R²-6,R³-19), (I-P190,A-1,R²-6,R³-20), (I-P191,A-1,R²-6,R³-21), (I-P192,A-1,R²-6,R³-22), (I-P193,A-1,R²-6,R³-23), (I-P194,A-1,R²-6,R³-24), (I-P195,A-1,R²-6,R³-25), (I-P196,A-1,R²-6,R³-26), (I-P197,A-1,R²-6,R³-27), (I-P198,A-1,R²-6,R³-28), (I-P199,A-1,R²-6,R³-29), (I-P200,A-1,R²-6,R³-30), (I-P201,A-1,R²-6,R³-31), (I-P202,A-1,R²-6,R³-32), (I-P203,A-1,R²-6,R³-33), (I-P204,A-1,R²-6,R³-34), (I-P205,A-1,R²-7,R³-1), (I-P206,A-1,R²-7,R³-2), (I-P207,A-1,R²-7,R³-3), (I-P208,A-1,R²-7,R³-4), (I-P209,A-1,R²-7,R³-5), (I-P210,A-1,R²-7,R³-6), (I-P211,A-1,R²-7,R³-7), (I-P212,A-1,R²-7,R³-8), (I-P213,A-1,R²-7,R³-9), (I-P214,A-1,R²-7,R³-10), (I-P215,A-1,R²-7,R³-11), (I-P216,A-1,R²-7,R³-12), (I-P217,A-1,R²-7,R³-13), (I-P218,A-1,R²-7,R³-14), (I-P219,A-1,R²-7,R³-15), (I-P220,A-1,R²-7,R³-16), (I-P221,A-1,R²-7,R³-17), (I-P222,A-1,R²-7,R³-18), (I-P223,A-1,R²-7,R³-19), (I-P224,A-1,R²-7,R³-20), (I-P225,A-1,R²-7,R³-21), (I-P226,A-1,R²-7,R³-22), (I-P227,A-1,R²-7,R³-23), (I-P228,A-1,R²-7,R³-24), (I-P229,A-1,R²-7,R³-25), (I-P230,A-1,R²-7,R³-26), (I-P231,A-1,R²-7,R³-27), (I-P232,A-1,R²-7,R³-28), (I-P233,A-1,R²-7,R³-29), (I-P234,A-1,R²-7,R³-30), (I-P235,A-1,R²-7,R³-31), (I-P236,A-1,R²-7,R³-32), (I-P237,A-1,R²-7,R³-33), (I-P238,A-1,R²-7,R³-34), (I-P239,A-1,R²-8,R³-1), (I-P240,A-1,R²-8,R³-2), (I-P241,A-1,R²-8,R³-3), (I-P242,A-1,R²-8,R³-4), (I-P243,A-1,R²-8,R³-5), (I-P244,A-1,R²-8,R³-6), (I-P245,A-1,R²-8,R³-7), (I-P246,A-1,R²-8,R³-8), (I-P247,A-1,R²-8,R³-9), (I-P248,A-1,R²-8,R³-10), (I-P249,A-1,R²-8,R³-11), (I-P250,A-1,R²-8,R³-12), (I-P251,A-1,R²-8,R³-13), (I-P252,A-1,R²-8,R³-14), (I-P253,A-1,R²-8,R³-15), (I-P254,A-1,R²-8,R³-16), (I-P255,A-1,R²-8,R³-17), (I-P256,A-1,R²-8,R³-18), (I-P257,A-1,R²-8,R³-19), (I-P258,A-1,R²-8,R³-20), (I-P259,A-1,R²-8,R³-21), (I-P260,A-1,R²-8,R³-22), (I-P261,A-1,R²-8,R³-23), (I-P262,A-1,R²-8,R³-24), (I-P263,A-1,R²-8,R³-25), (I-P264,A-1,R²-8,R³-26), (I-P265,A-1,R²-8,R³-27), (I-P266,A-1,R²-8,R³-28), (I-P267,A-1,R²-8,R³-29), (I-P268,A-1,R²-8,R³-30), (I-P269,A-1,R²-8,R³-31), (I-P270,A-1,R²-8,R³-32), (I-P271,A-1,R²-8,R³-33), (I-P272,A-1,R²-8,R³-34), (I-P273,A-1,R²-9,R³-1), (I-P274,A-1,R²-9,R³-2), (I-P275,A-1,R²-9,R³-3), (I-P276,A-1,R²-9,R³-4), (I-P277,A-1,R²-9,R³-5), (I-P278,A-1,R²-9,R³-6), (I-P279,A-1,R²-9,R³-7), (I-P280,A-1,R²-9,R³-8), (I-P281,A-1,R²-9,R³-9), (I-P282,A-1,R²-9,R³-10), (I-P283,A-1,R²-9,R³-11), (I-P284,A-1,R²-9,R³-12), (I-P285,A-1,R²-9,R³-13), (I-P286,A-1,R²-9,R³-14), (I-P287,A-1,R²-9,R³-15), (I-P288,A-1,R²-9,R³-16), (I-P289,A-1,R²-9,R³-17), (I-P290,A-1,R²-9,R³-18), (I-P291,A-1,R²-9,R³-19), (I-P292,A-1,R²-9,R³-20), (I-P293,A-1,R²-9,R³-21), (I-P294,A-1,R²-9,R³-22), (I-P295,A-1,R²-9,R³-23), (I-P296,A-1,R²-9,R³-24), (I-P297,A-1,R²-9,R³-25), (I-P298,A-1,R²-9,R³-26), (I-P299,A-1,R²-9,R³-27), (I-P300,A-1,R²-9,R³-28), (I-P301,A-1,R²-9,R³-29), (I-P302,A-1,R²-9,R³-30), (I-P303,A-1,R²-9,R³-31), (I-P304,A-1,R²-9,R³-32), (I-P305,A-1,R²-9,R³-33), (I-P306,A-1,R²-9,R³-34), (I-P307,A-1,R²-10,R³-1), (I-P308,A-1,R²-10,R³-2), (I-P309,A-1,R²-10,R³-3), (I-P310,A-1,R²-10,R³-4), (I-P311,A-1,R²-10,R³-5), (I-P312,A-1,R²-10,R³-6), (I-P313,A-1,R²-10,R³-7), (I-P314,A-1,R²-10,R³-8), (I-P315,A-1,R²-10,R³-9), (I-P316,A-1,R²-10,R³-10), (I-P317,A-1,R²-10,R³-11), (I-P318,A-1,R²-10,R³-12), (I-P319,A-1,R²-10,R³-13), (I-P320,A-1,R²-10,R³-14), (I-P321,A-1,R²-10,R³-15), (I-P322,A-1,R²-10,R³-16), (I-P323,A-1,R²-10,R³-17), (I-P324,A-1,R²-10,R³-18), (I-P325,A-1,R²-10,R³-19), (I-P326,A-1,R²-10,R³-20), (I-P327,A-1,R²-10,R³-21),
(I-P328,A-1,R²-10,R³-22), (I-P329,A-1,R²-10,R³-23),
(I-P330,A-1,R²-10,R³-24), (I-P331,A-1,R²-10,R³-25),
(I-P332,A-1,R²-10,R³-26), (I-P333,A-1,R²-10,R³-27),
(I-P334,A-1,R²-10,R³-28), (I-P335,A-1,R²-10,R³-29),
(I-P336,A-1,R²-10,R³-30), (I-P337,A-1,R²-10,R³-31),
(I-P338,A-1,R²-10,R³-32), (I-P339,A-1,R²-10,R³-33),
(I-P340,A-1,R²-10,R³-34), (I-P341,A-1,R²-11,R³-1),
(I-P342,A-1,R²-11,R³-2), (I-P343,A-1,R²-11,R³-3),
(I-P344,A-1,R²-11,R³-4), (I-P345,A-1,R²-11,R³-5),
(I-P346,A-1,R²-11,R³-6), (I-P347,A-1,R²-11,R³-7),
(I-P348,A-1,R²-11,R³-8), (I-P349,A-1,R²-11,R³-9),
(I-P350,A-1,R²-11,R³-10), (I-P351,A-1,R²-11,R³-11),
(I-P352,A-1,R²-11,R³-12), (I-P353,A-1,R²-11,R³-13),
(I-P354,A-1,R²-11,R³-14), (I-P355,A-1,R²-11,R³-15),
(I-P356,A-1,R²-11,R³-16), (I-P357,A-1,R²-11,R³-17),
(I-P358,A-1,R²-11,R³-18), (I-P359,A-1,R²-11,R³-19),
(I-P360,A-1,R²-11,R³-20), (I-P361,A-1,R²-11,R³-21),
(I-P362,A-1,R²-11,R³-22), (I-P363,A-1,R²-11,R³-23),
(I-P364,A-1,R²-11,R³-24), (I-P365,A-1,R²-11,R³-25),
(I-P366,A-1,R²-11,R³-26), (I-P367,A-1,R²-11,R³-27),
(I-P368,A-1,R²-11,R³-28), (I-P369,A-1,R²-11,R³-29),
(I-P370,A-1,R²-11,R³-30), (I-P371,A-1,R²-11,R³-31),
(I-P372,A-1,R²-11,R³-32), (I-P373,A-1,R²-11,R³-33),
(I-P374,A-1,R²-11,R³-34), (I-P375,A-1,R²-12,R³-1),
(I-P376,A-1,R²-12,R³-2), (I-P377,A-1,R²-12,R³-3),
(I-P378,A-1,R²-12,R³-4), (I-P379,A-1,R²-12,R³-5),
(I-P380,A-1,R²-12,R³-6), (I-P381,A-1,R²-12,R³-7),
(I-P382,A-1,R²-12,R³-8), (I-P383,A-1,R²-12,R³-9),
(I-P384,A-1,R²-12,R³-10), (I-P385,A-1,R²-12,R³-11),
(I-P386,A-1,R²-12,R³-12), (I-P387,A-1,R²-12,R³-13),
(I-P388,A-1,R²-12,R³-14), (I-P389,A-1,R²-12,R³-15),
(I-P390,A-1,R²-12,R³-16), (I-P391,A-1,R²-12,R³-17),
(I-P392,A-1,R²-12,R³-18), (I-P393,A-1,R²-12,R³-19),
(I-P394,A-1,R²-12,R³-20), (I-P395,A-1,R²-12,R³-21),
(I-P396,A-1,R²-12,R³-22), (I-P397,A-1,R²-12,R³-23),
(I-P398,A-1,R²-12,R³-24), (I-P399,A-1,R²-12,R³-25),
(I-P400,A-1,R²-12,R³-26), (I-P401,A-1,R²-12,R³-27),
(I-P402,A-1,R²-12,R³-28), (I-P403,A-1,R²-12,R³-29),
(I-P404,A-1,R²-12,R³-30), (I-P405,A-1,R²-12,R³-31),
(I-P406,A-1,R²-12,R³-32), (I-P407,A-1,R²-12,R³-33),
(I-P408,A-1,R²-12,R³-34), (I-P409,A-1,R²-13,R³-1),
(I-P410,A-1,R²-13,R³-2), (I-P411,A-1,R²-13,R³-3),
(I-P412,A-1,R²-13,R³-4), (I-P413,A-1,R²-13,R³-5),
(I-P414,A-1,R²-13,R³-6), (I-P415,A-1,R²-13,R³-7),
(I-P416,A-1,R²-13,R³-8), (I-P417,A-1,R²-13,R³-9),
(I-P418,A-1,R²-13,R³-10), (I-P419,A-1,R²-13,R³-11),
(I-P420,A-1,R²-13,R³-12), (I-P421,A-1,R²-13,R³-13),
(I-P422,A-1,R²-13,R³-14), (I-P423,A-1,R²-13,R³-15),
(I-P424,A-1,R²-13,R³-16), (I-P425,A-1,R²-13,R³-17),
(I-P426,A-1,R²-13,R³-18), (I-P427,A-1,R²-13,R³-19),
(I-P428,A-1,R²-13,R³-20), (I-P429,A-1,R²-13,R³-21),
(I-P430,A-1,R²-13,R³-22), (I-P431,A-1,R²-13,R³-23),
(I-P432,A-1,R²-13,R³-24), (I-P433,A-1,R²-13,R³-25),
(I-P434,A-1,R²-13,R³-26), (I-P435,A-1,R²-13,R³-27),
(I-P436,A-1,R²-13,R³-28), (I-P437,A-1,R²-13,R³-29),
(I-P438,A-1,R²-13,R³-30), (I-P439,A-1,R²-13,R³-31),
(I-P440,A-1,R²-13,R³-32), (I-P441,A-1,R²-13,R³-33),
(I-P442,A-1,R²-13,R³-34), (I-P443,A-1,R²-14,R³-1),
(I-P444,A-1,R²-14,R³-2), (I-P445,A-1,R²-14,R³-3),
(I-P446,A-1,R²-14,R³-4), (I-P447,A-1,R²-14,R³-5),
(I-P448,A-1,R²-14,R³-6), (I-P449,A-1,R²-14,R³-7),
(I-P450,A-1,R²-14,R³-8), (I-P451,A-1,R²-14,R³-9),
(I-P452,A-1,R²-14,R³-10), (I-P453,A-1,R²-14,R³-11),
(I-P454,A-1,R²-14,R³-12), (I-P455,A-1,R²-14,R³-13),
(I-P456,A-1,R²-14,R³-14), (I-P457,A-1,R²-14,R³-15),
(I-P458,A-1,R²-14,R³-16), (I-P459,A-1,R²-14,R³-17),
(I-P460,A-1,R²-14,R³-18), (I-P461,A-1,R²-14,R³-19),
(I-P462,A-1,R²-14,R³-20), (I-P463,A-1,R²-14,R³-21),
(I-P464,A-1,R²-14,R³-22), (I-P465,A-1,R²-14,R³-23),
(I-P466,A-1,R²-14,R³-24), (I-P467,A-1,R²-14,R³-25),
(I-P468,A-1,R²-14,R³-26), (I-P469,A-1,R²-14,R³-27),
(I-P470,A-1,R²-14,R³-28), (I-P471,A-1,R²-14,R³-29),
(I-P472,A-1,R²-14,R³-30), (I-P473,A-1,R²-14,R³-31),
(I-P474,A-1,R²-14,R³-32), (I-P475,A-1,R²-14,R³-33),
(I-P476,A-1,R²-14,R³-34), (I-P477,A-1,R²-15,R³-1),
(I-P478,A-1,R²-15,R³-2), (I-P479,A-1,R²-15,R³-3),
(I-P480,A-1,R²-15,R³-4), (I-P481,A-1,R²-15,R³-5),
(I-P482,A-1,R²-15,R³-6), (I-P483,A-1,R²-15,R³-7),
(I-P484,A-1,R²-15,R³-8), (I-P485,A-1,R²-15,R³-9),
(I-P486,A-1,R²-15,R³-10), (I-P487,A-1,R²-15,R³-11),
(I-P488,A-1,R²-15,R³-12), (I-P489,A-1,R²-15,R³-13),
(I-P490,A-1,R²-15,R³-14), (I-P491,A-1,R²-15,R³-15),
(I-P492,A-1,R²-15,R³-16), (I-P493,A-1,R²-15,R³-17),
(I-P494,A-1,R²-15,R³-18), (I-P495,A-1,R²-15,R³-19),
(I-P496,A-1,R²-15,R³-20), (I-P497,A-1,R²-15,R³-21),
(I-P498,A-1,R²-15,R³-22), (I-P499,A-1,R²-15,R³-23),
(I-P500,A-1,R²-15,R³-24), (I-P501,A-1,R²-15,R³-25),
(I-P502,A-1,R²-15,R³-26), (I-P503,A-1,R²-15,R³-27),
(I-P504,A-1,R²-15,R³-28), (I-P505,A-1,R²-15,R³-29),
(I-P506,A-1,R²-15,R³-30), (I-P507,A-1,R²-15,R³-31),
(I-P508,A-1,R²-15,R³-32), (I-P509,A-1,R²-15,R³-33),
(I-P510,A-1,R²-15,R³-34), (I-P511,A-1,R²-16,R³-1),
(I-P512,A-1,R²-16,R³-2), (I-P513,A-1,R²-16,R³-3),
(I-P514,A-1,R²-16,R³-4), (I-P515,A-1,R²-16,R³-5),
(I-P516,A-1,R²-16,R³-6), (I-P517,A-1,R²-16,R³-7),
(I-P518,A-1,R²-16,R³-8), (I-P519,A-1,R²-16,R³-9),
(I-P520,A-1,R²-16,R³-10), (I-P521,A-1,R²-16,R³-11),
(I-P522,A-1,R²-16,R³-12), (I-P523,A-1,R²-16,R³-13),
(I-P524,A-1,R²-16,R³-14), (I-P525,A-1,R²-16,R³-15),
(I-P526,A-1,R²-16,R³-16), (I-P527,A-1,R²-16,R³-17),
(I-P528,A-1,R²-16,R³-18), (I-P529,A-1,R²-16,R³-19),
(I-P530,A-1,R²-16,R³-20), (I-P531,A-1,R²-16,R³-21),
(I-P532,A-1,R²-16,R³-22), (I-P533,A-1,R²-16,R³-23),
(I-P534,A-1,R²-16,R³-24), (I-P535,A-1,R²-16,R³-25),
(I-P536,A-1,R²-16,R³-26), (I-P537,A-1,R²-16,R³-27),
(I-P538,A-1,R²-16,R³-28), (I-P539,A-1,R²-16,R³-29),
(I-P540,A-1,R²-16,R³-30), (I-P541,A-1,R²-16,R³-31),
(I-P542,A-1,R²-16,R³-32), (I-P543,A-1,R²-16,R³-33),
(I-P544,A-1,R²-16,R³-34), (I-P545,A-1,R²-17,R³-1),
(I-P546,A-1,R²-17,R³-2), (I-P547,A-1,R²-17,R³-3),
(I-P548,A-1,R²-17,R³-4), (I-P549,A-1,R²-17,R³-5),
(I-P550,A-1,R²-17,R³-6), (I-P551,A-1,R²-17,R³-7),
(I-P552,A-1,R²-17,R³-8), (I-P553,A-1,R²-17,R³-9),
(I-P554,A-1,R²-17,R³-10), (I-P555,A-1,R²-17,R³-11),
(I-P556,A-1,R²-17,R³-12), (I-P557,A-1,R²-17,R³-13),
(I-P558,A-1,R²-17,R³-14), (I-P559,A-1,R²-17,R³-15),
(I-P560,A-1,R²-17,R³-16), (I-P561,A-1,R²-17,R³-17),
(I-P562,A-1,R²-17,R³-18), (I-P563,A-1,R²-17,R³-19),
(I-P564,A-1,R²-17,R³-20), (I-P565,A-1,R²-17,R³-21),
(I-P566,A-1,R²-17,R³-22), (I-P567,A-1,R²-17,R³-23),
(I-P568,A-1,R²-17,R³-24), (I-P569,A-1,R²-17,R³-25),
(I-P570,A-1,R²-17,R³-26), (I-P571,A-1,R²-17,R³-27),
(I-P572,A-1,R²-17,R³-28), (I-P573,A-1,R²-17,R³-29),
(I-P574,A-1,R²-17,R³-30), (I-P575,A-1,R²-17,R³-31),
(I-P576,A-1,R²-17,R³-32), (I-P577,A-1,R²-17,R³-33),
(I-P578,A-1,R²-17,R³-34), (I-P579,A-1,R²-18,R³-1),
(I-P580,A-1,R²-18,R³-2), (I-P581,A-1,R²-18,R³-3),
(I-P582,A-1,R²-18,R³-4), (I-P583,A-1,R²-18,R³-5),
(I-P584,A-1,R²-18,R³-6), (I-P585,A-1,R²-18,R³-7),
(I-P586,A-1,R²-18,R³-8), (I-P587,A-1,R²-18,R³-9),
(I-P588,A-1,R²-18,R³-10), (I-P589,A-1,R²-18,R³-11),
(I-P590,A-1,R²-18,R³-12), (I-P591,A-1,R²-18,R³-13),
(I-P592,A-1,R²-18,R³-14), (I-P593,A-1,R²-18,R³-15), (I-P594,A-1,R²-18,R³-16), (I-P595,A-1,R²-18,R³-17), (I-P728,A-1,R²-22,R³-14), (I-P729,A-1,R²-22,R³-15),
(I-P596,A-1,R²-18,R³-18), (I-P597,A-1,R²-18,R³-19), (I-P730,A-1,R²-22,R³-16), (I-P731,A-1,R²-22,R³-17),
(I-P598,A-1,R²-18,R³-20), (I-P599,A-1,R²-18,R³-21), (I-P732,A-1,R²-22,R³-18), (I-P733,A-1,R²-22,R³-19),
(I-P600,A-1,R²-18,R³-22), (I-P601,A-1,R²-18,R³-23), (I-P734,A-1,R²-22,R³-20), (I-P735,A-1,R²-22,R³-21),
(I-P602,A-1,R²-18,R³-24), (I-P603,A-1,R²-18,R³-25), (I-P736,A-1,R²-22,R³-22), (I-P737,A-1,R²-22,R³-23),
(I-P604,A-1,R²-18,R³-26), (I-P605,A-1,R²-18,R³-27), (I-P738,A-1,R²-22,R³-24), (I-P739,A-1,R²-22,R³-25),
(I-P606,A-1,R²-18,R³-28), (I-P607,A-1,R²-18,R³-29), (I-P740,A-1,R²-22,R³-26), (I-P741,A-1,R²-22,R³-27),
(I-P608,A-1,R²-18,R³-30), (I-P609,A-1,R²-18,R³-31), (I-P742,A-1,R²-22,R³-28), (I-P743,A-1,R²-22,R³-29),
(I-P610,A-1,R²-18,R³-32), (I-P611,A-1,R²-18,R³-33), (I-P744,A-1,R²-22,R³-30), (I-P745,A-1,R²-22,R³-31),
(I-P612,A-1,R²-18,R³-34), (I-P613,A-1,R²-19,R³-1), (I-P746,A-1,R²-22,R³-32), (I-P747,A-1,R²-22,R³-33),
(I-P614,A-1,R²-19,R³-2), (I-P615,A-1,R²-19,R³-3), (I-P748,A-1,R²-22,R³-34), (I-P749,A-1,R²-23,R³-1),
(I-P616,A-1,R²-19, R³-4), (I-P617,A-1,R²-19,R³-5), (I-P750,A-1,R²-23,R³-2), (I-P751,A-1,R²-23,R³-3),
(I-P618,A-1,R²-19,R³-6), (I-P619,A-1,R²-19,R³-7), (I-P752,A-1,R²-23,R³-4), (I-P753,A-1,R²-23,R³-5),
(I-P620,A-1,R²-19,R³-8), (I-P621,A-1,R²-19,R³-9), (I-P754,A-1,R²-23,R³-6), (I-P755,A-1,R²-23,R³-7),
(I-P622,A-1,R²-19,R³-10), (I-P623,A-1,R²-19,R³-11), (I-P756,A-1,R²-23,R³-8), (I-P757,A-1,R²-23,R³-9),
(I-P624,A-1,R²-19,R³-12), (I-P625,A-1,R²-19,R³-13), (I-P758,A-1,R²-23,R³-10), (I-P759,A-1,R²-23,R³-11),
(I-P626,A-1,R²-19,R³-14), (I-P627,A-1,R²-19,R³-15), (I-P760,A-1,R²-23,R³-12), (I-P761,A-1,R²-23,R³-13),
(I-P628,A-1,R²-19,R³-16), (I-P629,A-1,R²-19,R³-17), (I-P762,A-1,R²-23,R³-14), (I-P763,A-1,R²-23,R³-15),
(I-P630,A-1,R²-19,R³-18), (I-P631,A-1,R²-19,R³-19), (I-P764,A-1,R²-23,R³-16), (I-P765,A-1,R²-23,R³-17),
(I-P632,A-1,R²-19,R³-20), (I-P633,A-1,R²-19,R³-21), (I-P766,A-1,R²-23,R³-18), (I-P767,A-1,R²-23,R³-19),
(I-P634,A-1,R²-19,R³-22), (I-P635,A-1,R²-19,R³-23), (I-P768,A-1,R²-23,R³-20), (I-P769,A-1,R²-23,R³-21),
(I-P636,A-1,R²-19,R³-24), (I-P637,A-1,R²-19,R³-25), (I-P770,A-1,R²-23,R³-22), (I-P771,A-1,R²-23,R³-23),
(I-P638,A-1,R²-19,R³-26), (I-P639,A-1,R²-19,R³-27), (I-P772,A-1,R²-23,R³-24), (I-P773,A-1,R²-23,R³-25),
(I-P640,A-1,R²-19,R³-28), (I-P641,A-1,R²-19,R³-29), (I-P774,A-1,R²-23,R³-26), (I-P775,A-1,R²-23,R³-27),
(I-P642,A-1,R²-19,R³-30), (I-P643,A-1,R²-19,R³-31), (I-P776,A-1,R²-23,R³-28), (I-P777,A-1,R²-23,R³-29),
(I-P644,A-1,R²-19,R³-32), (I-P645,A-1,R²-19,R³-33), (I-P778,A-1,R²-23,R³-30), (I-P779,A-1,R²-23,R³-31),
(I-P646,A-1,R²-19,R³-34), (I-P647,A-1,R²-20,R³-1), (I-P780,A-1,R²-23,R³-32), (I-P781,A-1,R²-23,R³-33),
(I-P648,A-1,R²-20,R³-2), (I-P649,A-1,R²-20,R³-3), (I-P782,A-1,R²-23,R³-34), (I-P783,A-1,R²-24,R³-1),
(I-P650,A-1,R²-20,R³-4), (I-P651,A-1,R²-20,R³-5), (I-P784,A-1,R²-24,R³-2), (I-P785,A-1,R²-24,R³-3),
(I-P652,A-1,R²-20,R³-6), (I-P653,A-1,R²-20,R³-7), (I-P786,A-1,R²-24,R³-4), (I-P787,A-1,R²-24,R³-5),
(I-P654,A-1,R²-20,R³-8), (I-P655,A-1,R²-20,R³-9), (I-P788,A-1,R²-24,R³-6), (I-P789,A-1,R²-24,R³-7),
(I-P656,A-1,R²-20,R³-10), (I-P657,A-1,R²-20,R³-11), (I-P790,A-1,R²-24,R³-8), (I-P791,A-1,R²-24,R³-9),
(I-P658,A-1,R²-20,R³-12), (I-P659,A-1,R²-20,R³-13), (I-P792,A-1,R²-24,R³-10), (I-P793,A-1,R²-24,R³-11),
(I-P660,A-1,R²-20,R³-14), (I-P661,A-1,R²-20,R³-15), (I-P794,A-1,R²-24,R³-12), (I-P795,A-1,R²-24,R³-13),
(I-P662,A-1,R²-20,R³-16), (I-P663,A-1,R²-20,R³-17), (I-P796,A-1,R²-24,R³-14), (I-P797,A-1,R²-24,R³-15),
(I-P664,A-1,R²-20,R³-18), (I-P665,A-1,R²-20,R³-19), (I-P798,A-1,R²-24,R³-16), (I-P799,A-1,R²-24,R³-17),
(I-P666,A-1,R²-20,R³-20), (I-P667,A-1,R²-20,R³-21), (I-P800,A-1,R²-24,R³-18), (I-P801,A-1,R²-24,R³-19),
(I-P668,A-1,R²-20,R³-22), (I-P669,A-1,R²-20,R³-23), (I-P802,A-1,R²-24,R³-20), (I-P803,A-1,R²-24,R³-21),
(I-P670,A-1,R²-20,R³-24), (I-P671,A-1,R²-20,R³-25), (I-P804,A-1,R²-24,R³-22), (I-P805,A-1,R²-24,R³-23),
(I-P672,A-1,R²-20,R³-26), (I-P673,A-1,R²-20,R³-27), (I-P806,A-1,R²-24,R³-24), (I-P807,A-1,R²-24,R³-25),
(I-P674,A-1,R²-20,R³-28), (I-P675,A-1,R²-20,R³-29), (I-P808,A-1,R²-24,R³-26), (I-P809,A-1,R²-24,R³-27),
(I-P676,A-1,R²-20,R³-30), (I-P677,A-1,R²-20,R³-31), (I-P810,A-1,R²-24,R³-28), (I-P811,A-1,R²-24,R³-29),
(I-P678,A-1,R²-20,R³-32), (I-P679,A-1,R²-20,R³-33), (I-P812,A-1,R²-24,R³-30), (I-P813,A-1,R²-24,R³-31),
(I-P680,A-1,R²-20,R³-34), (I-P681,A-1,R²-21,R³-1), (I-P814,A-1,R²-24,R³-32), (I-P815,A-1,R²-24,R³-33),
(I-P682,A-1,R²-21,R³-2), (I-P683,A-1,R²-21,R³-3), (I-P816,A-1,R²-24,R³-34), (I-P817,A-1,R²-25,R³-1),
(I-P684,A-1,R²-21,R³-4), (I-P685,A-1,R²-21,R³-5), (I-P818,A-1,R²-25,R³-2), (I-P819,A-1,R²-25,R³-3),
(I-P686,A-1,R²-21,R³-6), (I-P687,A-1,R²-21,R³-7), (I-P820,A-1,R²-25,R³-4), (I-P821,A-1,R²-25,R³-5),
(I-P688,A-1,R²-21,R³-8), (I-P689,A-1,R²-21,R³-9), (I-P822,A-1,R²-25,R³-6), (I-P823,A-1,R²-25,R³-7),
(I-P690,A-1,R²-21,R³-10), (I-P691,A-1,R²-21,R³-11), (I-P824,A-1,R²-25,R³-8), (I-P825,A-1,R²-25,R³-9),
(I-P692,A-1,R²-21,R³-12), (I-P693,A-1,R²-21,R³-13), (I-P826,A-1,R²-25,R³-10), (I-P827,A-1,R²-25,R³-11),
(I-P694,A-1,R²-21,R³-14), (I-P695,A-1,R²-21,R³-15), (I-P828,A-1,R²-25,R³-12), (I-P829,A-1,R²-25,R³-13),
(I-P696,A-1,R²-21,R³-16), (I-P697,A-1,R²-21,R³-17), (I-P830,A-1,R²-25,R³-14), (I-P831,A-1,R²-25,R³-15),
(I-P698,A-1,R²-21,R³-18), (I-P699,A-1,R²-21,R³-19), (I-P832,A-1,R²-25,R³-16), (I-P833,A-1,R²-25,R³-17),
(I-P700,A-1,R²-21,R³-20), (I-P701,A-1,R²-21,R³-21), (I-P834,A-1,R²-25,R³-18), (I-P835,A-1,R²-25,R³-19),
(I-P702,A-1,R²-21,R³-22), (I-P703,A-1,R²-21,R³-23), (I-P836,A-1,R²-25,R³-20), (I-P837,A-1,R²-25,R³-21),
(I-P704,A-1,R²-21,R³-24), (I-P705,A-1,R²-21,R³-25), (I-P838,A-1,R²-25,R³-22), (I-P839,A-1,R²-25,R³-23),
(I-P706,A-1,R²-21,R³-26), (I-P707,A-1,R²-21,R³-27), (I-P840,A-1,R²-25,R³-24), (I-P841,A-1,R²-25,R³-25),
(I-P708,A-1,R²-21,R³-28), (I-P709,A-1,R²-21,R³-29), (I-P842,A-1,R²-25,R³-26), (I-P843,A-1,R²-25,R³-27),
(I-P710,A-1,R²-21,R³-30), (I-P711,A-1,R²-21,R³-31), (I-P844,A-1,R²-25,R³-28), (I-P845,A-1,R²-25,R³-29),
(I-P712,A-1,R²-21,R³-32), (I-P713,A-1,R²-21,R³-33), (I-P846,A-1,R²-25,R³-30), (I-P847,A-1,R²-25,R³-31),
(I-P714,A-1,R²-21,R³-34), (I-P715,A-1,R²-22,R³-1), (I-P848,A-1,R²-25,R³-32), (I-P849,A-1,R²-25,R³-33),
(I-P716,A-1,R²-22,R³-2), (I-P717,A-1,R²-22,R³-3), (I-P850,A-1,R²-25,R³-34), (I-P851,A-1,R²-26,R³-1),
(I-P718,A-1,R²-22,R³-4), (I-P719,A-1,R²-22,R³-5), (I-P852,A-1,R²-26,R³-2), (I-P853,A-1,R²-26,R³-3),
(I-P720,A-1,R²-22,R³-6), (I-P721,A-1,R²-22,R³-7), (I-P854,A-1,R²-26,R³-4), (I-P855,A-1,R²-26,R³-5),
(I-P722,A-1,R²-22,R³-8), (I-P723,A-1,R²-22,R³-9), (I-P856,A-1,R²-26,R³-6), (I-P857,A-1,R²-26,R³-7),
(I-P724,A-1,R²-22,R³-10), (I-P725,A-1,R²-22,R³-11), (I-P858,A-1,R²-26,R³-8), (I-P859,A-1,R²-26,R³-9),
(I-P726,A-1,R²-22,R³-12), (I-P727,A-1,R²-22,R³-13), (I-P860,A-1,R²-26,R³-10), (I-P861,A-1,R²-26,R³-11), (I-P862,A-1,R²-26,R³-12), (I-P863,A-1,R²-26,R³-13),
(I-P864,A-1,R²-26,R³-14), (I-P865,A-1,R²-26,R³-15),
(I-P866,A-1,R²-26,R³-16), (I-P867,A-1,R²-26,R³-17),
(I-P868,A-1,R²-26,R³-18), (I-P869,A-1,R²-26,R³-19),
(I-P870,A-1,R²-26,R³-20), (I-P871,A-1,R²-26,R³-21),
(I-P872,A-1,R²-26,R³-22), (I-P873,A-1,R²-26,R³-23),
(I-P874,A-1,R²-26,R³-24), (I-P875,A-1,R²-26,R³-25),
(I-P876,A-1,R²-26,R³-26), (I-P877,A-1,R²-26,R³-27),
(I-P878,A-1,R²-26,R³-28), (I-P879,A-1,R²-26,R³-29),
(I-P880,A-1,R²-26,R³-30), (I-P881,A-1,R²-26,R³-31),
(I-P882,A-1,R²-26,R³-32), (I-P883,A-1,R²-26,R³-33),
(I-P884,A-1,R²-26,R³-34), (I-P885,A-1,R²-27,R³-1),
(I-P886,A-1,R²-27,R³-2), (I-P887,A-1,R²-27,R³-3),
(I-P888,A-1,R²-27,R³-4), (I-P889,A-1,R²-27,R³-5),
(I-P890,A-1,R²-27,R³-6), (I-P891,A-1,R²-27,R³-7),
(I-P892,A-1,R²-27,R³-8), (I-P893,A-1,R²-27,R³-9),
(I-P894,A-1,R²-27,R³-10), (I-P895,A-1,R²-27,R³-11),
(I-P896,A-1,R²-27,R³-12), (I-P897,A-1,R²-27,R³-13),
(I-P898,A-1,R²-27,R³-14), (I-P899,A-1,R²-27,R³-15),
(I-P900,A-1,R²-27,R³-16), (I-P901,A-1,R²-27,R³-17),
(I-P902,A-1,R²-27,R³-18), (I-P903,A-1,R²-27,R³-19),
(I-P904,A-1,R²-27,R³-20), (I-P905,A-1,R²-27,R³-21),
(I-P906,A-1,R²-27,R³-22), (I-P907,A-1,R²-27,R³-23),
(I-P908,A-1,R²-27,R³-24), (I-P909,A-1,R²-27,R³-25),
(I-P910,A-1,R²-27,R³-26), (I-P911,A-1,R²-27,R³-27),
(I-P912,A-1,R²-27,R³-28), (I-P913,A-1,R²-27,R³-29),
(I-P914,A-1,R²-27,R³-30), (I-P915,A-1,R²-27,R³-31),
(I-P916,A-1,R²-27,R³-32), (I-P917,A-1,R²-27,R³-33),
(I-P918,A-1,R²-27,R³-34), (I-P919,A-1,R²-28,R³-1),
(I-P920,A-1,R²-28,R³-2), (I-P921,A-1,R²-28,R³-3),
(I-P922,A-1,R²-28,R³-4), (I-P923,A-1,R²-28,R³-5),
(I-P924,A-1,R²-28,R³-6), (I-P925,A-1,R²-28,R³-7),
(I-P926,A-1,R²-28,R³-8), (I-P927,A-1,R²-28,R³-9),
(I-P928,A-1,R²-28,R³-10), (I-P929,A-1,R²-28,R³-11),
(I-P930,A-1,R²-28,R³-12), (I-P931,A-1,R²-28,R³-13),
(I-P932,A-1,R²-28,R³-14), (I-P933,A-1,R²-28,R³-15),
(I-P934,A-1,R²-28,R³-16), (I-P935,A-1,R²-28,R³-17),
(I-P936,A-1,R²-28,R³-18), (I-P937,A-1,R²-28,R³-19),
(I-P938,A-1,R²-28,R³-20), (I-P939,A-1,R²-28,R³-21),
(I-P940,A-1,R²-28,R³-22), (I-P941,A-1,R²-28,R³-23),
(I-P942,A-1,R²-28,R³-24), (I-P943,A-1,R²-28,R³-25),
(I-P944,A-1,R²-28,R³-26), (I-P945,A-1,R²-28,R³-27),
(I-P946,A-1,R²-28,R³-28), (I-P947,A-1,R²-28,R³-29),
(I-P948,A-1,R²-28,R³-30), (I-P949,A-1,R²-28,R³-31),
(I-P950,A-1,R²-28,R³-32), (I-P951,A-1,R²-28,R³-33),
(I-P952,A-1,R²-28,R³-34), (I-P953,A-1,R²-29,R³-1),
(I-P954,A-1,R²-29,R³-2), (I-P955,A-1,R²-29,R³-3),
(I-P956,A-1,R²-29,R³-4), (I-P957,A-1,R²-29,R³-5),
(I-P958,A-1,R²-29,R³-6), (I-P959,A-1,R²-29,R³-7),
(I-P960,A-1,R²-29,R³-8), (I-P961,A-1,R²-29,R³-9),
(I-P962,A-1,R²-29,R³-10), (I-P963,A-1,R²-29,R³-11),
(I-P964,A-1,R²-29,R³-12), (I-P965,A-1,R²-29,R³-13),
(I-P966,A-1,R²-29,R³-14), (I-P967,A-1,R²-29,R³-15),
(I-P968,A-1,R²-29,R³-16), (I-P969,A-1,R²-29,R³-17),
(I-P970,A-1,R²-29,R³-18), (I-P971,A-1,R²-29,R³-19),
(I-P972,A-1,R²-29,R³-20), (I-P973,A-1,R²-29,R³-21),
(I-P974,A-1,R²-29,R³-22), (I-P975,A-1,R²-29,R³-23),
(I-P976,A-1,R²-29,R³-24), (I-P977,A-1,R²-29,R³-25),
(I-P978,A-1,R²-29,R³-26), (I-P979,A-1,R²-29,R³-27),
(I-P980,A-1,R²-29,R³-28), (I-P981,A-1,R²-29,R³-29),
(I-P982,A-1,R²-29,R³-30), (I-P983,A-1,R²-29,R³-31),
(I-P984,A-1,R²-29,R³-32), (I-P985,A-1,R²-29,R³-33),
(I-P986,A-1,R²-29,R³-34), (I-P987,A-2,R²-1,R³-1),
(I-P988,A-2,R²-1,R³-2), (I-P989,A-2,R²-1,R³-3), (I-P990,A-2,R²-1,R³-4), (I-P991,A-2,R²-1,R³-5), (I-P992,A-2,R²-1,R³-6), (I-P993,A-2,R²-1,R³-7), (I-P994,A-2,R²-1,R³-8), (I-P995,A-2,R²-1,R³-9), (I-P996,A-2,R²-1,R³-10), (I-P997,A-2,R²-1,R³-11), (I-P998,A-2,R²-1,R³-12), (I-P999,A-2,R²-1,R³-13), (I-P1000,A-2,R²-1,R³-14), (I-P1001,A-2,R²-1,R³-15), (I-P1002,A-2,R²-1,R³-16), (I-P1003,A-2,R²-1,R³-17),
(I-P1004,A-2,R²-1,R³-18), (I-P1005,A-2,R²-1,R³-19),
(I-P1006,A-2,R²-1,R³-20), (I-P1007,A-2,R²-1,R³-21),
(I-P1008,A-2,R²-1,R³-22), (I-P1009,A-2,R²-1,R³-23),
(I-P1010,A-2,R²-1,R³-24), (I-P1011,A-2,R²-1,R³-25),
(I-P1012,A-2,R²-1,R³-26), (I-P1013,A-2,R²-1,R³-27),
(I-P1014,A-2,R²-1,R³-28), (I-P1015,A-2,R²-1,R³-29),
(I-P1016,A-2,R²-1,R³-30), (I-P1017,A-2,R²-1,R³-31),
(I-P1018,A-2,R²-1,R³-32), (I-P1019,A-2,R²-1,R³-33),
(I-P1020,A-2,R²-1,R³-34), (I-P1021,A-2,R²-2,R³-1),
(I-P1022,A-2,R²-2,R³-2), (I-P1023,A-2,R²-2,R³-3),
(I-P1024,A-2,R²-2,R³-4), (I-P1025,A-2,R²-2,R³-5),
(I-P1026,A-2,R²-2,R³-6), (I-P1027,A-2,R²-2,R³-7),
(I-P1028,A-2,R²-2,R³-8), (I-P1029,A-2,R²-2,R³-9),
(I-P1030,A-2,R²-2,R³-10), (I-P1031,A-2,R²-2,R³-11),
(I-P1032,A-2,R²-2,R³-12), (I-P1033,A-2,R²-2,R³-13),
(I-P1034,A-2,R²-2,R³-14), (I-P1035,A-2,R²-2,R³-15),
(I-P1036,A-2,R²-2,R³-16), (I-P1037,A-2,R²-2,R³-17),
(I-P1038,A-2,R²-2,R³-18), (I-P1039,A-2,R²-2,R³-19),
(I-P1040,A-2,R²-2,R³-20), (I-P1041,A-2,R²-2,R³-21),
(I-P1042,A-2,R²-2,R³-22), (I-P1043,A-2,R²-2,R³-23),
(I-P1044,A-2,R²-2,R³-24), (I-P1045,A-2,R²-2,R³-25),
(I-P1046,A-2,R²-2,R³-26), (I-P1047,A-2,R²-2,R³-27),
(I-P1048,A-2,R²-2,R³-28), (I-P1049,A-2,R²-2,R³-29),
(I-P1050,A-2,R²-2,R³-30), (I-P1051,A-2,R²-2,R³-31),
(I-P1052,A-2,R²-2,R³-32), (I-P1053,A-2,R²-2,R³-33),
(I-P1054,A-2,R²-2,R³-34), (I-P1055,A-2,R²-3,R³-1),
(I-P1056,A-2,R²-3,R³-2), (I-P1057,A-2,R²-3,R³-3),
(I-P1058,A-2,R²-3,R³-4), (I-P1059,A-2,R²-3,R³-5),
(I-P1060,A-2,R²-3,R³-6), (I-P1061,A-2,R²-3,R³-7),
(I-P1062,A-2,R²-3,R³-8), (I-P1063,A-2,R²-3,R³-9),
(I-P1064,A-2,R²-3,R³-10), (I-P1065,A-2,R²-3,R³-11),
(I-P1066,A-2,R²-3,R³-12), (I-P1067,A-2,R²-3,R³-13),
(I-P1068,A-2,R²-3,R³-14), (I-P1069,A-2,R²-3,R³-15),
(I-P1070,A-2,R²-3,R³-16), (I-P1071,A-2,R²-3,R³-17),
(I-P1072,A-2,R²-3,R³-18), (I-P1073,A-2,R²-3,R³-19),
(I-P1074,A-2,R²-3,R³-20), (I-P1075,A-2,R²-3,R³-21),
(I-P1076,A-2,R²-3,R³-22), (I-P1077,A-2,R²-3,R³-23),
(I-P1078,A-2,R²-3,R³-24), (I-P1079,A-2,R²-3,R³-25),
(I-P1080,A-2,R²-3,R³-26), (I-P1081,A-2,R²-3,R³-27),
(I-P1082,A-2,R²-3,R³-28), (I-P1083,A-2,R²-3,R³-29),
(I-P1084,A-2,R²-3,R³-30), (I-P1085,A-2,R²-3,R³-31),
(I-P1086,A-2,R²-3,R³-32), (I-P1087,A-2,R²-3,R³-33),
(I-P1088,A-2,R²-3,R³-34), (I-P1089,A-2,R²-4,R³-1),
(I-P1090,A-2,R²-4,R³-2), (I-P1091,A-2,R²-4,R³-3),
(I-P1092,A-2,R²-4,R³-4), (I-P1093,A-2,R²-4,R³-5),
(I-P1094,A-2,R²-4,R³-6), (I-P1095,A-2,R²-4,R³-7),
(I-P1096,A-2,R²-4,R³-8), (I-P1097,A-2,R²-4,R³-9),
(I-P1098,A-2,R²-4,R³-10), (I-P1099,A-2,R²-4,R³-11),
(I-P1100,A-2,R²-4,R³-12), (I-P1101,A-2,R²-4,R³-13),
(I-P1102,A-2,R²-4,R³-14), (I-P1103,A-2,R²-4,R³-15),
(I-P1104,A-2,R²-4,R³-16), (I-P1105,A-2,R²-4,R³-17),
(I-P1106,A-2,R²-4,R³-18), (I-P1107,A-2,R²-4,R³-19),
(I-P1108,A-2,R²-4,R³-20), (I-P1109,A-2,R²-4,R³-21),
(I-P1110,A-2,R²-4,R³-22), (I-P1111,A-2,R²-4,R³-23),
(I-P1112,A-2,R²-4,R³-24), (I-P1113,A-2,R²-4,R³-25),
(I-P1114,A-2,R²-4,R³-26), (I-P1115,A-2,R²-4,R³-27),
(I-P1116,A-2,R²-4,R³-28), (I-P1117,A-2,R²-4,R³-29),
(I-P1118,A-2,R²-4,R³-30), (I-P1119,A-2,R²-4,R³-31),
(I-P1120,A-2,R²-4,R³-32), (I-P1121,A-2,R²-4,R³-33),
(I-P1122,A-2,R²-4,R³-34), (I-P1123,A-2,R²-5,R³-1),
(I-P1124,A-2,R²-5,R³-2), (I-P1125,A-2,R²-5,R³-3),
(I-P1126,A-2,R²-5,R³-4), (I-P1127,A-2,R²-5,R³-5),
(I-P1128,A-2,R²-5,R³-6), (I-P1129,A-2,R²-5,R³-7),
(I-P1130,A-2,R²-5,R³-8), (I-P1131,A-2,R²-5,R³-9), (I-P1132,A-2,R²-5,R³-10), (I-P1133,A-2,R²-5,R³-11), (I-P1266,A-2,R²-9,R³-8), (I-P1267,A-2,R²-9,R³-9),
(I-P1134,A-2,R²-5,R³-12), (I-P1135,A-2,R²-5,R³-13), (I-P1268,A-2,R²-9,R³-10), (I-P1269,A-2,R²-9,R³-11),
(I-P1136,A-2,R²-5,R³-14), (I-P1137,A-2,R²-5,R³-15), (I-P1270,A-2,R²-9,R³-12), (I-P1271,A-2,R²-9,R³-13),
(I-P1138,A-2,R²-5,R³-16), (I-P1139,A-2,R²-5,R³-17), (I-P1272,A-2,R²-9,R³-14), (I-P1273,A-2,R²-9,R³-15),
(I-P1140,A-2,R²-5,R³-18), (I-P1141,A-2,R²-5,R³-19), (I-P1274,A-2,R²-9,R³-16), (I-P1275,A-2,R²-9,R³-17),
(I-P1142,A-2,R²-5,R³-20), (I-P1143,A-2,R²-5,R³-21), (I-P1276,A-2,R²-9,R³-18), (I-P1277,A-2,R²-9,R³-19),
(I-P1144,A-2,R²-5,R³-22), (I-P1145,A-2,R²-5,R³-23), (I-P1278,A-2,R²-9,R³-20), (I-P1279,A-2,R²-9,R³-21),
(I-P1146,A-2,R²-5,R³-24), (I-P1147,A-2,R²-5,R³-25), (I-P1280,A-2,R²-9,R³-22), (I-P1281,A-2,R²-9,R³-23),
(I-P1148,A-2,R²-5,R³-26), (I-P1149,A-2,R²-5,R³-27), (I-P1282,A-2,R²-9,R³-24), (I-P1283,A-2,R²-9,R³-25),
(I-P1150,A-2,R²-5,R³-28), (I-P1151,A-2,R²-5,R³-29), (I-P1284,A-2,R²-9,R³-26), (I-P1285,A-2,R²-9,R³-27),
(I-P1152,A-2,R²-5,R³-30), (I-P1153,A-2,R²-5,R³-31), (I-P1286,A-2,R²-9,R³-28), (I-P1287,A-2,R²-9,R³-29),
(I-P1154,A-2,R²-5,R³-32), (I-P1155,A-2,R²-5,R³-33), (I-P1288,A-2,R²-9,R³-30), (I-P1289,A-2,R²-9,R³-31),
(I-P1156,A-2,R²-5,R³-34), (I-P1157,A-2,R²-6,R³-1), (I-P1290,A-2,R²-9,R³-32), (I-P1291,A-2,R²-9,R³-33),
(I-P1158,A-2,R²-6,R³-2), (I-P1159,A-2,R²-6,R³-3), (I-P1292,A-2,R²-9,R³-34), (I-P1293,A-2,R²-10,R³-1),
(I-P1160,A-2,R²-6,R³-4), (I-P1161,A-2,R²-6,R³-5), (I-P1294,A-2,R²-10,R³-2), (I-P1295,A-2,R²-10,R³-3),
(I-P1162,A-2,R²-6,R³-6), (I-P1163,A-2,R²-6,R³-7), (I-P1296,A-2,R²-10,R³-4), (I-P1297,A-2,R²-10,R³-5),
(I-P1164,A-2,R²-6,R³-8), (I-P1165,A-2,R²-6,R³-9), (I-P1298,A-2,R²-10,R³-6), (I-P1299,A-2,R²-10,R³-7),
(I-P1166,A-2,R²-6,R³-10), (I-P1167,A-2,R²-6,R³-11), (I-P1300,A-2,R²-10,R³-8), (I-P1301,A-2,R²-10,R³-9),
(I-P1168,A-2,R²-6,R³-12), (I-P1169,A-2,R²-6,R³-13), (I-P1302,A-2,R²-10,R³-10), (I-P1303,A-2,R²-10,R³-11),
(I-P1170,A-2,R²-6,R³-14), (I-P1171,A-2,R²-6,R³-15), (I-P1304,A-2,R²-10,R³-12), (I-P1305,A-2,R²-10,R³-13),
(I-P1172,A-2,R²-6,R³-16), (I-P1173,A-2,R²-6,R³-17), (I-P1306,A-2,R²-10,R³-14), (I-P1307,A-2,R²-10,R³-15),
(I-P1174,A-2,R²-6,R³-18), (I-P1175,A-2,R²-6,R³-19), (I-P1308,A-2,R²-10,R³-16), (I-P1309,A-2,R²-10,R³-17),
(I-P1176,A-2,R²-6,R³-20), (I-P1177,A-2,R²-6,R³-21), (I-P1310,A-2,R²-10,R³-18), (I-P1311,A-2,R²-10,R³-19),
(I-P1178,A-2,R²-6,R³-22), (I-P1179,A-2,R²-6,R³-23), (I-P1312,A-2,R²-10,R³-20), (I-P1313,A-2,R²-10,R³-21),
(I-P1180,A-2,R²-6,R³-24), (I-P1181,A-2,R²-6,R³-25), (I-P1314,A-2,R²-10,R³-22), (I-P1315,A-2,R²-10,R³-23),
(I-P1182,A-2,R²-6,R³-26), (I-P1183,A-2,R²-6,R³-27), (I-P1316,A-2,R²-10,R³-24), (I-P1317,A-2,R²-10,R³-25),
(I-P1184,A-2,R²-6,R³-28), (I-P1185,A-2,R²-6,R³-29), (I-P1318,A-2,R²-10,R³-26), (I-P1319,A-2,R²-10,R³-27),
(I-P1186,A-2,R²-6,R³-30), (I-P1187,A-2,R²-6,R³-31), (I-P1320,A-2,R²-10,R³-28), (I-P1321,A-2,R²-10,R³-29),
(I-P1188,A-2,R²-6,R³-32), (I-P1189,A-2,R²-6,R³-33), (I-P1322,A-2,R²-10,R³-30), (I-P1323,A-2,R²-10,R³-31),
(I-P1190,A-2,R²-6,R³-34), (I-P1191,A-2,R²-7,R³-1), (I-P1324,A-2,R²-10,R³-32), (I-P1325,A-2,R²-10,R³-33),
(I-P1192,A-2,R²-7,R³-2), (I-P1193,A-2,R²-7,R³-3), (I-P1326,A-2,R²-10,R³-34), (I-P1327,A-2,R²-11,R³-1),
(I-P1194,A-2,R²-7,R³-4), (I-P1195,A-2,R²-7,R³-5), (I-P1328,A-2,R²-11,R³-2), (I-P1329,A-2,R²-11,R³-3),
(I-P1196,A-2,R²-7,R³-6), (I-P1197,A-2,R²-7,R³-7), (I-P1330,A-2,R²-11,R³-4), (I-P1331,A-2,R²-11,R³-5),
(I-P1198,A-2,R²-7,R³-8), (I-P1199,A-2,R²-7,R³-9), (I-P1332,A-2,R²-11,R³-6), (I-P1333,A-2,R²-11,R³-7),
(I-P1200,A-2,R²-7,R³-10), (I-P1201,A-2,R²-7,R³-11), (I-P1334,A-2,R²-11,R³-8), (I-P1335,A-2,R²-11,R³-9),
(I-P1202,A-2,R²-7,R³-12), (I-P1203,A-2,R²-7,R³-13), (I-P1336,A-2,R²-11,R³-10), (I-P1337,A-2,R²-11,R³-11),
(I-P1204,A-2,R²-7,R³-14), (I-P1205,A-2,R²-7,R³-15), (I-P1338,A-2,R²-11,R³-12), (I-P1339,A-2,R²-11,R³-13),
(I-P1206,A-2,R²-7,R³-16), (I-P1207,A-2,R²-7,R³-17), (I-P1340,A-2,R²-11,R³-14), (I-P1341,A-2,R²-11,R³-15),
(I-P1208,A-2,R²-7,R³-18), (I-P1209,A-2,R²-7,R³-19), (I-P1342,A-2,R²-11,R³-16), (I-P1343,A-2,R²-11,R³-17),
(I-P1210,A-2,R²-7,R³-20), (I-P1211,A-2,R²-7,R³-21), (I-P1344,A-2,R²-11,R³-18), (I-P1345,A-2,R²-11,R³-19),
(I-P1212,A-2,R²-7,R³-22), (I-P1213,A-2,R²-7,R³-23), (I-P1346,A-2,R²-11,R³-20), (I-P1347,A-2,R²-11,R³-21),
(I-P1214,A-2,R²-7,R³-24), (I-P1215,A-2,R²-7,R³-25), (I-P1348,A-2,R²-11,R³-22), (I-P1349,A-2,R²-11,R³-23),
(I-P1216,A-2,R²-7,R³-26), (I-P1217,A-2,R²-7,R³-27), (I-P1350,A-2,R²-11,R³-24), (I-P1351,A-2,R²-11,R³-25),
(I-P1218,A-2,R²-7,R³-28), (I-P1219,A-2,R²-7,R³-29), (I-P1352,A-2,R²-11,R³-26), (I-P1353,A-2,R²-11,R³-27),
(I-P1220,A-2,R²-7,R³-30), (I-P1221,A-2,R²-7,R³-31), (I-P1354,A-2,R²-11,R³-28), (I-P1355,A-2,R²-11,R³-29),
(I-P1222,A-2,R²-7,R³-32), (I-P1223,A-2,R²-7,R³-33), (I-P1356,A-2,R²-11,R³-30), (I-P1357,A-2,R²-11,R³-31),
(I-P1224,A-2,R²-7,R³-34), (I-P1225,A-2,R²-8,R³-1), (I-P1358,A-2,R²-11,R³-32), (I-P1359,A-2,R²-11,R³-33),
(I-P1226,A-2,R²-8,R³-2), (I-P1227,A-2,R²-8,R³-3), (I-P1360,A-2,R²-11,R³-34), (I-P1361,A-2,R²-12,R³-1),
(I-P1228,A-2,R²-8,R³-4), (I-P1229,A-2,R²-8,R³-5), (I-P1362,A-2,R²-12,R³-2), (I-P1363,A-2,R²-12,R³-3),
(I-P1230,A-2,R²-8,R³-6), (I-P1231,A-2,R²-8,R³-7), (I-P1364,A-2,R²-12,R³-4), (I-P1365,A-2,R²-12,R³-5),
(I-P1232,A-2,R²-8,R³-8), (I-P1233,A-2,R²-8,R³-9), (I-P1366,A-2,R²-12,R³-6), (I-P1367,A-2,R²-12,R³-7),
(I-P1234,A-2,R²-8,R³-10), (I-P1235,A-2,R²-8,R³-11), (I-P1368,A-2,R²-12,R³-8), (I-P1369,A-2,R²-12,R³-9),
(I-P1236,A-2,R²-8,R³-12), (I-P1237,A-2,R²-8,R³-13), (I-P1370,A-2,R²-12,R³-10), (I-P1371,A-2,R²-12,R³-11),
(I-P1238,A-2,R²-8,R³-14), (I-P1239,A-2,R²-8,R³-15), (I-P1372,A-2,R²-12,R³-12), (I-P1373,A-2,R²-12,R³-13),
(I-P1240,A-2,R²-8,R³-16), (I-P1241,A-2,R²-8,R³-17), (I-P1374,A-2,R²-12,R³-14), (I-P1375,A-2,R²-12,R³-15),
(I-P1242,A-2,R²-8,R³-18), (I-P1243,A-2,R²-8,R³-19), (I-P1376,A-2,R²-12,R³-16), (I-P1377,A-2,R²-12,R³-17),
(I-P1244,A-2,R²-8,R³-20), (I-P1245,A-2,R²-8,R³-21), (I-P1378,A-2,R²-12,R³-18), (I-P1379,A-2,R²-12,R³-19),
(I-P1246,A-2,R²-8,R³-22), (I-P1247,A-2,R²-8,R³-23), (I-P1380,A-2,R²-12,R³-20), (I-P1381,A-2,R²-12,R³-21),
(I-P1248,A-2,R²-8,R³-24), (I-P1249,A-2,R²-8,R³-25), (I-P1382,A-2,R²-12,R³-22), (I-P1383,A-2,R²-12,R³-23),
(I-P1250,A-2,R²-8,R³-26), (I-P1251,A-2,R²-8,R³-27), (I-P1384,A-2,R²-12,R³-24), (I-P1385,A-2,R²-12,R³-25),
(I-P1252,A-2,R²-8,R³-28), (I-P1253,A-2,R²-8,R³-29), (I-P1386,A-2,R²-12,R³-26), (I-P1387,A-2,R²-12,R³-27),
(I-P1254,A-2,R²-8,R³-30), (I-P1255,A-2,R²-8,R³-31), (I-P1388,A-2,R²-12,R³-28), (I-P1389,A-2,R²-12,R³-29),
(I-P1256,A-2,R²-8,R³-32), (I-P1257,A-2,R²-8,R³-33), (I-P1390,A-2,R²-12,R³-30), (I-P1391,A-2,R²-12,R³-31),
(I-P1258,A-2,R²-8,R³-34), (I-P1259,A-2,R²-9,R³-1), (I-P1392,A-2,R²-12,R³-32), (I-P1393,A-2,R²-12,R³-33),
(I-P1260,A-2,R²-9,R³-2), (I-P1261,A-2,R²-9,R³-3), (I-P1394,A-2,R²-12,R³-34), (I-P1395,A-2,R²-13,R³-1),
(I-P1262,A-2,R²-9,R³-4), (I-P1263,A-2,R²-9,R³-5), (I-P1396,A-2,R²-13,R³-2), (I-P1397,A-2,R²-13,R³-3),
(I-P1264,A-2,R²-9,R³-6), (I-P1265,A-2,R²-9,R³-7), (I-P1398,A-2,R²-13,R³-4), (I-P1399,A-2,R²-13,R³-5), (I-P1400,A-2,R²-13,R³-6), (I-P1401,A-2,R²-13,R³-7), (I-P1534,A-2,R²-17,R³-4), (I-P1535,A-2,R²-17,R³-5),
(I-P1402,A-2,R²-13,R³-8), (I-P1403,A-2,R²-13,R³-9), (I-P1536,A-2,R²-17,R³-6), (I-P1537,A-2,R²-17,R³-7),
(I-P1404,A-2,R²-13,R³-10), (I-P1405,A-2,R²-13,R³-11), (I-P1538,A-2,R²-17,R³-8), (I-P1539,A-2,R²-17,R³-9),
(I-P1406,A-2,R²-13,R³-12), (I-P1407,A-2,R²-13,R³-13), (I-P1540,A-2,R²-17,R³-10), (I-P1541,A-2,R²-17,R³-11),
(I-P1408,A-2,R²-13,R³-14), (I-P1409,A-2,R²-13,R³-15), (I-P1542,A-2,R²-17,R³-12), (I-P1543,A-2,R²-17,R³-13),
(I-P1410,A-2,R²-13,R³-16), (I-P1411,A-2,R²-13,R³-17), (I-P1544,A-2,R²-17,R³-14), (I-P1545,A-2,R²-17,R³-15),
(I-P1412,A-2,R²-13,R³-18), (I-P1413,A-2,R²-13,R³-19), (I-P1546,A-2,R²-17,R³-16), (I-P1547,A-2,R²-17,R³-17),
(I-P1414,A-2,R²-13,R³-20), (I-P1415,A-2,R²-13,R³-21), (I-P1548,A-2,R²-17,R³-18), (I-P1549,A-2,R²-17,R³-19),
(I-P1416,A-2,R²-13,R³-22), (I-P1417,A-2,R²-13,R³-23), (I-P1550,A-2,R²-17,R³-20), (I-P1551,A-2,R²-17,R³-21),
(I-P1418,A-2,R²-13,R³-24), (I-P1419,A-2,R²-13,R³-25), (I-P1552,A-2,R²-17,R³-22), (I-P1553,A-2,R²-17,R³-23),
(I-P1420,A-2,R²-13,R³-26), (I-P1421,A-2,R²-13,R³-27), (I-P1554,A-2,R²-17,R³-24), (I-P1555,A-2,R²-17,R³-25),
(I-P1422,A-2,R²-13,R³-28), (I-P1423,A-2,R²-13,R³-29), (I-P1556,A-2,R²-17,R³-26), (I-P1557,A-2,R²-17,R³-27),
(I-P1424,A-2,R²-13,R³-30), (I-P1425,A-2,R²-13,R³-31), (I-P1558,A-2,R²-17,R³-28), (I-P1559,A-2,R²-17,R³-29),
(I-P1426,A-2,R²-13,R³-32), (I-P1427,A-2,R²-13,R³-33), (I-P1560,A-2,R²-17,R³-30), (I-P1561,A-2,R²-17,R³-31),
(I-P1428,A-2,R²-13,R³-34), (I-P1429,A-2,R²-14,R³-1), (I-P1562,A-2,R²-17,R³-32), (I-P1563,A-2,R²-17,R³-33),
(I-P1430,A-2,R²-14,R³-2), (I-P1431,A-2,R²-14,R³-3), (I-P1564,A-2,R²-17,R³-34), (I-P1565,A-2,R²-18,R³-1),
(I-P1432,A-2,R²-14,R³-4), (I-P1433,A-2,R²-14,R³-5), (I-P1566,A-2,R²-18,R³-2), (I-P1567,A-2,R²-18,R³-3),
(I-P1434,A-2,R²-14,R³-6), (I-P1435,A-2,R²-14,R³-7), (I-P1568,A-2,R²-18,R³-4), (I-P1569,A-2,R²-18,R³-5),
(I-P1436,A-2,R²-14,R³-8), (I-P1437,A-2,R²-14,R³-9), (I-P1570,A-2,R²-18,R³-6), (I-P1571,A-2,R²-18,R³-7),
(I-P1438,A-2,R²-14,R³-10), (I-P1439,A-2,R²-14,R³-11), (I-P1572,A-2,R²-18,R³-8), (I-P1573,A-2,R²-18,R³-9),
(I-P1440,A-2,R²-14,R³-12), (I-P1441,A-2,R²-14,R³-13), (I-P1574,A-2,R²-18,R³-10), (I-P1575,A-2,R²-18,R³-11),
(I-P1442,A-2,R²-14,R³-14), (I-P1443,A-2,R²-14,R³-15), (I-P1576,A-2,R²-18,R³-12), (I-P1577,A-2,R²-18,R³-13),
(I-P1444,A-2,R²-14,R³-16), (I-P1445,A-2,R²-14,R³-17), (I-P1578,A-2,R²-18,R³-14), (I-P1579,A-2,R²-18,R³-15),
(I-P1446,A-2,R²-14,R³-18), (I-P1447,A-2,R²-14,R³-19), (I-P1580,A-2,R²-18,R³-16), (I-P1581,A-2,R²-18,R³-17),
(I-P1448,A-2,R²-14,R³-20), (I-P1449,A-2,R²-14,R³-21), (I-P1582,A-2,R²-18,R³-18), (I-P1583,A-2,R²-18,R³-19),
(I-P1450,A-2,R²-14,R³-22), (I-P1451,A-2,R²-14,R³-23), (I-P1584,A-2,R²-18,R³-20), (I-P1585,A-2,R²-18,R³-21),
(I-P1452,A-2,R²-14,R³-24), (I-P1453,A-2,R²-14,R³-25), (I-P1586,A-2,R²-18,R³-22), (I-P1587,A-2,R²-18,R³-23),
(I-P1454,A-2,R²-14,R³-26), (I-P1455,A-2,R²-14,R³-27), (I-P1588,A-2,R²-18,R³-24), (I-P1589,A-2,R²-18,R³-25),
(I-P1456,A-2,R²-14,R³-28), (I-P1457,A-2,R²-14,R³-29), (I-P1590,A-2,R²-18,R³-26), (I-P1591,A-2,R²-18,R³-27),
(I-P1458,A-2,R²-14,R³-30), (I-P1459,A-2,R²-14,R³-31), (I-P1592,A-2,R²-18,R³-28), (I-P1593,A-2,R²-18,R³-29),
(I-P1460,A-2,R²-14,R³-32), (I-P1461,A-2,R²-14,R³-33), (I-P1594,A-2,R²-18,R³-30), (I-P1595,A-2,R²-18,R³-31),
(I-P1462,A-2,R²-14,R³-34), (I-P1463,A-2,R²-15,R³-1), (I-P1596,A-2,R²-18,R³-32), (I-P1597,A-2,R²-18,R³-33),
(I-P1464,A-2,R²-15,R³-2), (I-P1465,A-2,R²-15,R³-3), (I-P1598,A-2,R²-18,R³-34), (I-P1599,A-2,R²-19,R³-1),
(I-P1466,A-2,R²-15,R³-4), (I-P1467,A-2,R²-15,R³-5), (I-P1600,A-2,R²-19,R³-2), (I-P1601,A-2,R²-19,R³-3),
(I-P1468,A-2,R²-15,R³-6), (I-P1469,A-2,R²-15,R³-7), (I-P1602,A-2,R²-19,R³-4), (I-P1603,A-2,R²-19,R³-5),
(I-P1470,A-2,R²-15,R³-8), (I-P1471,A-2,R²-15,R³-9), (I-P1604,A-2,R²-19,R³-6), (I-P1605,A-2,R²-19,R³-7),
(I-P1472,A-2,R²-15,R³-10), (I-P1473,A-2,R²-15,R³-11), (I-P1606,A-2,R²-19,R³-8), (I-P1607,A-2,R²-19,R³-9),
(I-P1474,A-2,R²-15,R³-12), (I-P1475,A-2,R²-15,R³-13), (I-P1608,A-2,R²-19,R³-10), (I-P1609,A-2,R²-19,R³-11),
(I-P1476,A-2,R²-15,R³-14), (I-P1477,A-2,R²-15,R³-15), (I-P1610,A-2,R²-19,R³-12), (I-P1611,A-2,R²-19,R³-13),
(I-P1478,A-2,R²-15,R³-16), (I-P1479,A-2,R²-15,R³-17), (I-P1612,A-2,R²-19,R³-14), (I-P1613,A-2,R²-19,R³-15),
(I-P1480,A-2,R²-15,R³-18), (I-P1481,A-2,R²-15,R³-19), (I-P1614,A-2,R²-19,R³-16), (I-P1615,A-2,R²-19,R³-17),
(I-P1482,A-2,R²-15,R³-20), (I-P1483,A-2,R²-15,R³-21), (I-P1616,A-2,R²-19,R³-18), (I-P1617,A-2,R²-19,R³-19),
(I-P1484,A-2,R²-15,R³-22), (I-P1485,A-2,R²-15,R³-23), (I-P1618,A-2,R²-19,R³-20), (I-P1619,A-2,R²-19,R³-21),
(I-P1486,A-2,R²-15,R³-24), (I-P1487,A-2,R²-15,R³-25), (I-P1620,A-2,R²-19,R³-22), (I-P1621,A-2,R²-19,R³-23),
(I-P1488,A-2,R²-15,R³-26), (I-P1489,A-2,R²-15,R³-27), (I-P1622,A-2,R²-19,R³-24), (I-P1623,A-2,R²-19,R³-25),
(I-P1490,A-2,R²-15,R³-28), (I-P1491,A-2,R²-15,R³-29), (I-P1624,A-2,R²-19,R³-26), (I-P1625,A-2,R²-19,R³-27),
(I-P1492,A-2,R²-15,R³-30), (I-P1493,A-2,R²-15,R³-31), (I-P1626,A-2,R²-19,R³-28), (I-P1627,A-2,R²-19,R³-29),
(I-P1494,A-2,R²-15,R³-32), (I-P1495,A-2,R²-15,R³-33), (I-P1628,A-2,R²-19,R³-30), (I-P1629,A-2,R²-19,R³-31),
(I-P1496,A-2,R²-15,R³-34), (I-P1497,A-2,R²-16,R³-1), (I-P1630,A-2,R²-19,R³-32), (I-P1631,A-2,R²-19,R³-33),
(I-P1498,A-2,R²-16,R³-2), (I-P1499,A-2,R²-16,R³-3), (I-P1632,A-2,R²-19,R³-34), (I-P1633,A-2,R²-20,R³-1),
(I-P1500,A-2,R²-16,R³-4), (I-P1501,A-2,R²-16,R³-5), (I-P1634,A-2,R²-20,R³-2), (I-P1635,A-2,R²-20,R³-3),
(I-P1502,A-2,R²-16,R³-6), (I-P1503,A-2,R²-16,R³-7), (I-P1636,A-2,R²-20,R³-4), (I-P1637,A-2,R²-20,R³-5),
(I-P1504,A-2,R²-16,R³-8), (I-P1505,A-2,R²-16,R³-9), (I-P1638,A-2,R²-20,R³-6), (I-P1639,A-2,R²-20,R³-7),
(I-P1506,A-2,R²-16,R³-10), (I-P1507,A-2,R²-16,R³-11), (I-P1640,A-2,R²-20,R³-8), (I-P1641,A-2,R²-20,R³-9),
(I-P1508,A-2,R²-16,R³-12), (I-P1509,A-2,R²-16,R³-13), (I-P1642,A-2,R²-20,R³-10), (I-P1643,A-2,R²-20,R³-11),
(I-P1510,A-2,R²-16,R³-14), (I-P1511,A-2,R²-16,R³-15), (I-P1644,A-2,R²-20,R³-12), (I-P1645,A-2,R²-20,R³-13),
(I-P1512,A-2,R²-16,R³-16), (I-P1513,A-2,R²-16,R³-17), (I-P1646,A-2,R²-20,R³-14), (I-P1647,A-2,R²-20,R³-15),
(I-P1514,A-2,R²-16,R³-18), (I-P1515,A-2,R²-16,R³-19), (I-P1648,A-2,R²-20,R³-16), (I-P1649,A-2,R²-20,R³-17),
(I-P1516,A-2,R²-16,R³-20), (I-P1517,A-2,R²-16,R³-21), (I-P1650,A-2,R²-20,R³-18), (I-P1651,A-2,R²-20,R³-19),
(I-P1518,A-2,R²-16,R³-22), (I-P1519,A-2,R²-16,R³-23), (I-P1652,A-2,R²-20,R³-20), (I-P1653,A-2,R²-20,R³-21),
(I-P1520,A-2,R²-16,R³-24), (I-P1521,A-2,R²-16,R³-25), (I-P1654,A-2,R²-20,R³-22), (I-P1655,A-2,R²-20,R³-23),
(I-P1522,A-2,R²-16,R³-26), (I-P1523,A-2,R²-16,R³-27), (I-P1656,A-2,R²-20,R³-24), (I-P1657,A-2,R²-20,R³-25),
(I-P1524,A-2,R²-16,R³-28), (I-P1525,A-2,R²-16,R³-29), (I-P1658,A-2,R²-20,R³-26), (I-P1659,A-2,R²-20,R³-27),
(I-P1526,A-2,R²-16,R³-30), (I-P1527,A-2,R²-16,R³-31), (I-P1660,A-2,R²-20,R³-28), (I-P1661,A-2,R²-20,R³-29),
(I-P1528,A-2,R²-16,R³-32), (I-P1529,A-2,R²-16,R³-33), (I-P1662,A-2,R²-20,R³-30), (I-P1663,A-2,R²-20,R³-31),
(I-P1530,A-2,R²-16,R³-34), (I-P1531,A-2,R²-17,R³-1), (I-P1664,A-2,R²-20,R³-32), (I-P1665,A-2,R²-20,R³-33),
(I-P1532,A-2,R²-17,R³-2), (I-P1533,A-2,R²-17,R³-3), (I-P1666,A-2,R²-20,R³-34), (I-P1667,A-2,R²-21,R³-1), (I-P1668,A-2,R²-21,R³-2), (I-P1669,A-2,R²-21,R³-3), (I-P1802,A-2,R²-24,R³-34), (I-P1803,A-2,R²-25,R³-1),
(I-P1670,A-2,R²-21,R³-4), (I-P1671,A-2,R²-21,R³-5), (I-P1804,A-2,R²-25,R³-2), (I-P1805,A-2,R²-25,R³-3),
(I-P1672,A-2,R²-21,R³-6), (I-P1673,A-2,R²-21,R³-7), (I-P1806,A-2,R²-25,R³-4), (I-P1807,A-2,R²-25,R³-5),
(I-P1674,A-2,R²-21,R³-8), (I-P1675,A-2,R²-21,R³-9), (I-P1808,A-2,R²-25,R³-6), (I-P1809,A-2,R²-25,R³-7),
(I-P1676,A-2,R²-21,R³-10), (I-P1677,A-2,R²-21,R³-11), (I-P1810,A-2,R²-25,R³-8), (I-P1811,A-2,R²-25,R³-9),
(I-P1678,A-2,R²-21,R³-12), (I-P1679,A-2,R²-21,R³-13), (I-P1812,A-2,R²-25,R³-10), (I-P1813,A-2,R²-25,R³-11),
(I-P1680,A-2,R²-21,R³-14), (I-P1681,A-2,R²-21,R³-15), (I-P1814,A-2,R²-25,R³-12), (I-P1815,A-2,R²-25,R³-13),
(I-P1682,A-2,R²-21,R³-16), (I-P1683,A-2,R²-21,R³-17), (I-P1816,A-2,R²-25,R³-14), (I-P1817,A-2,R²-25,R³-15),
(I-P1684,A-2,R²-21,R³-18), (I-P1685,A-2,R²-21,R³-19), (I-P1818,A-2,R²-25,R³-16), (I-P1819,A-2,R²-25,R³-17),
(I-P1686,A-2,R²-21,R³-20), (I-P1687,A-2,R²-21,R³-21), (I-P1820,A-2,R²-25,R³-18), (I-P1821,A-2,R²-25,R³-19),
(I-P1688,A-2,R²-21,R³-22), (I-P1689,A-2,R²-21,R³-23), (I-P1822,A-2,R²-25,R³-20), (I-P1823,A-2,R²-25,R³-21),
(I-P1690,A-2,R²-21,R³-24), (I-P1691,A-2,R²-21,R³-25), (I-P1824,A-2,R²-25,R³-22), (I-P1825,A-2,R²-25,R³-23),
(I-P1692,A-2,R²-21,R³-26), (I-P1693,A-2,R²-21,R³-27), (I-P1826,A-2,R²-25,R³-24), (I-P1827,A-2,R²-25,R³-25),
(I-P1694,A-2,R²-21,R³-28), (I-P1695,A-2,R²-21,R³-29), (I-P1828,A-2,R²-25,R³-26), (I-P1829,A-2,R²-25,R³-27),
(I-P1696,A-2,R²-21,R³-30), (I-P1697,A-2,R²-21,R³-31), (I-P1830,A-2,R²-25,R³-28), (I-P1831,A-2,R²-25,R³-29),
(I-P1698,A-2,R²-21,R³-32), (I-P1699,A-2,R²-21,R³-33), (I-P1832,A-2,R²-25,R³-30), (I-P1833,A-2,R²-25,R³-31),
(I-P1700,A-2,R²-21,R³-34), (I-P1701,A-2,R²-22,R³-1), (I-P1834,A-2,R²-25,R³-32), (I-P1835,A-2,R²-25,R³-33),
(I-P1702,A-2,R²-22,R³-2), (I-P1703,A-2,R²-22,R³-3), (I-P1836,A-2,R²-25,R³-34), (I-P1837,A-2,R²-26,R³-1),
(I-P1704,A-2,R²-22,R³-4), (I-P1705,A-2,R²-22,R³-5), (I-P1838,A-2,R²-26,R³-2), (I-P1839,A-2,R²-26,R³-3),
(I-P1706,A-2,R²-22,R³-6), (I-P1707,A-2,R²-22,R³-7), (I-P1840,A-2,R²-26,R³-4), (I-P1841,A-2,R²-26,R³-5),
(I-P1708,A-2,R²-22,R³-8), (I-P1709,A-2,R²-22,R³-9), (I-P1842,A-2,R²-26,R³-6), (I-P1843,A-2,R²-26,R³-7),
(I-P1710,A-2,R²-22,R³-10), (I-P1711,A-2,R²-22,R³-11), (I-P1844,A-2,R²-26,R³-8), (I-P1845,A-2,R²-26,R³-9),
(I-P1712,A-2,R²-22,R³-12), (I-P1713,A-2,R²-22,R³-13), (I-P1846,A-2,R²-26,R³-10), (I-P1847,A-2,R²-26,R³-11),
(I-P1714,A-2,R²-22,R³-14), (I-P1715,A-2,R²-22,R³-15), (I-P1848,A-2,R²-26,R³-12), (I-P1849,A-2,R²-26,R³-13),
(I-P1716,A-2,R²-22,R³-16), (I-P1717,A-2,R²-22,R³-17), (I-P1850,A-2,R²-26,R³-14), (I-P1851,A-2,R²-26,R³-15),
(I-P1718,A-2,R²-22,R³-18), (I-P1719,A-2,R²-22,R³-19), (I-P1852,A-2,R²-26,R³-16), (I-P1853,A-2,R²-26,R³-17),
(I-P1720,A-2,R²-22,R³-20), (I-P1721,A-2,R²-22,R³-21), (I-P1854,A-2,R²-26,R³-18), (I-P1855,A-2,R²-26,R³-19),
(I-P1722,A-2,R²-22,R³-22), (I-P1723,A-2,R²-22,R³-23), (I-P1856,A-2,R²-26,R³-20), (I-P1857,A-2,R²-26,R³-21),
(I-P1724,A-2,R²-22,R³-24), (I-P1725,A-2,R²-22,R³-25), (I-P1858,A-2,R²-26,R³-22), (I-P1859,A-2,R²-26,R³-23),
(I-P1726,A-2,R²-22,R³-26), (I-P1727,A-2,R²-22,R³-27), (I-P1860,A-2,R²-26,R³-24), (I-P1861,A-2,R²-26,R³-25),
(I-P1728,A-2,R²-22,R³-28), (I-P1729,A-2,R²-22,R³-29), (I-P1862,A-2,R²-26,R³-26), (I-P1863,A-2,R²-26,R³-27),
(I-P1730,A-2,R²-22,R³-30), (I-P1731,A-2,R²-22,R³-31), (I-P1864,A-2,R²-26,R³-28), (I-P1865,A-2,R²-26,R³-29),
(I-P1732,A-2,R²-22,R³-32), (I-P1733,A-2,R²-22,R³-33), (I-P1866,A-2,R²-26,R³-30), (I-P1867,A-2,R²-26,R³-31),
(I-P1734,A-2,R²-22,R³-34), (I-P1735,A-2,R²-23,R³-1), (I-P1868,A-2,R²-26,R³-32), (I-P1869,A-2,R²-26,R³-33),
(I-P1736,A-2,R²-23,R³-2), (I-P1737,A-2,R²-23,R³-3), (I-P1870,A-2,R²-26,R³-34), (I-P1871,A-2,R²-27,R³-1),
(I-P1738,A-2,R²-23,R³-4), (I-P1739,A-2,R²-23,R³-5), (I-P1872,A-2,R²-27,R³-27,R³-2), (I-P1873,A-2,R²-27,R³-3), (I-P1874,A-2,R²-27,R³-4), (I-P1875,A-2,R²-27,R³-5),
(I-P1740,A-2,R²-23,R³-6), (I-P1741,A-2,R²-23,R³-7), (I-P1876,A-2,R²-27,R³-6), (I-P1877,A-2,R²-27,R³-7),
(I-P1742,A-2,R²-23,R³-8), (I-P1743,A-2,R²-23,R³-9), (I-P1878,A-2,R²-27,R³-8), (I-P1879,A-2,R²-27,R³-9),
(I-P1744,A-2,R²-23,R³-10), (I-P1745,A-2,R²-23,R³-11), (I-P1880,A-2,R²-27,R³-10), (I-P1881,A-2,R²-27,R³-11),
(I-P1746,A-2,R²-23,R³-12), (I-P1747,A-2,R²-23,R³-13), (I-P1882,A-2,R²-27,R³-12), (I-P1883,A-2,R²-27,R³-13),
(I-P1748,A-2,R²-23,R³-14), (I-P1749,A-2,R²-23,R³-15), (I-P1884,A-2,R²-27,R³-14), (I-P1885,A-2,R²-27,R³-15),
(I-P1750,A-2,R²-23,R³-16), (I-P1751,A-2,R²-23,R³-17), (I-P1886,A-2,R²-27,R³-16), (I-P1887,A-2,R²-27,R³-17),
(I-P1752,A-2,R²-23,R³-18), (I-P1753,A-2,R²-23,R³-19), (I-P1888,A-2,R²-27,R³-18), (I-P1889,A-2,R²-27,R³-19),
(I-P1754,A-2,R²-23,R³-20), (I-P1755,A-2,R²-23,R³-21), (I-P1890,A-2,R²-27,R³-20), (I-P1891,A-2,R²-27,R³-21),
(I-P1756,A-2,R²-23,R³-22), (I-P1757,A-2,R²-23,R³-23), (I-P1892,A-2,R²-27,R³-22), (I-P1893,A-2,R²-27,R³-23),
(I-P1758,A-2,R²-23,R³-24), (I-P1759,A-2,R²-23,R³-25), (I-P1894,A-2,R²-27,R³-24), (I-P1895,A-2,R²-27,R³-25),
(I-P1760,A-2,R²-23,R³-26), (I-P1761,A-2,R²-23,R³-27), (I-P1896,A-2,R²-27,R³-26), (I-P1897,A-2,R²-27,R³-27),
(I-P1762,A-2,R²-23,R³-28), (I-P1763,A-2,R²-23,R³-29), (I-P1898,A-2,R²-27,R³-28), (I-P1899,A-2,R²-27,R³-29),
(I-P1764,A-2,R²-23,R³-30), (I-P1765,A-2,R²-23,R³-31), (I-P1900,A-2,R²-27,R³-30), (I-P1901,A-2,R²-27,R³-31),
(I-P1766,A-2,R²-23,R³-32), (I-P1767,A-2,R²-23,R³-33), (I-P1902,A-2,R²-27,R³-32), (I-P1903,A-2,R²-27,R³-33),
(I-P1768,A-2,R²-23,R³-34), (I-P1769,A-2,R²-24,R³-1), (I-P1904,A-2,R²-27,R³-34), (I-P1905,A-2,R²-28,R³-1),
(I-P1770,A-2,R²-24,R³-2), (I-P1771,A-2,R²-24,R³-3), (I-P1906,A-2,R²-28,R³-2), (I-P1907,A-2,R²-28,R³-3),
(I-P1772,A-2,R²-24,R³-4), (I-P1773,A-2,R²-24,R³-5), (I-P1908,A-2,R²-28,R³-4), (I-P1909,A-2,R²-28,R³-5),
(I-P1774,A-2,R²-24,R³-6), (I-P1775,A-2,R²-24,R³-7), (I-P1910,A-2,R²-28,R³-6), (I-P1911,A-2,R²-28,R³-7),
(I-P1776,A-2,R²-24,R³-8), (I-P1777,A-2,R²-24,R³-9), (I-P1912,A-2,R²-28,R³-8), (I-P1913,A-2,R²-28,R³-9),
(I-P1778,A-2,R²-24,R³-10), (I-P1779,A-2,R²-24,R³-11), (I-P1914,A-2,R²-28,R³-10), (I-P1915,A-2,R²-28,R³-11),
(I-P1780,A-2,R²-24,R³-12), (I-P1781,A-2,R²-24,R³-13), (I-P1916,A-2,R²-28,R³-12), (I-P1917,A-2,R²-28,R³-13),
(I-P1782,A-2,R²-24,R³-14), (I-P1783,A-2,R²-24,R³-15), (I-P1918,A-2,R²-28,R³-14), (I-P1919,A-2,R²-28,R³-15),
(I-P1784,A-2,R²-24,R³-16), (I-P1785,A-2,R²-24,R³-17), (I-P1920,A-2,R²-28,R³-16), (I-P1921,A-2,R²-28,R³-17),
(I-P1786,A-2,R²-24,R³-18), (I-P1787,A-2,R²-24,R³-19), (I-P1922,A-2,R²-28,R³-18), (I-P1923,A-2,R²-28,R³-19),
(I-P1788,A-2,R²-24,R³-20), (I-P1789,A-2,R²-24,R³-21), (I-P1924,A-2,R²-28,R³-20), (I-P1925,A-2,R²-28,R³-21),
(I-P1790,A-2,R²-24,R³-22), (I-P1791,A-2,R²-24,R³-23), (I-P1926,A-2,R²-28,R³-22), (I-P1927,A-2,R²-28,R³-23),
(I-P1792,A-2,R²-24,R³-24), (I-P1793,A-2,R²-24,R³-25), (I-P1928,A-2,R²-28,R³-24), (I-P1929,A-2,R²-28,R³-25),
(I-P1794,A-2,R²-24,R³-26), (I-P1795,A-2,R²-24,R³-27), (I-P1930,A-2,R²-28,R³-26), (I-P1931,A-2,R²-28,R³-27),
(I-P1796,A-2,R²-24,R³-28), (I-P1797,A-2,R²-24,R³-29), (I-P1932,A-2,R²-28,R³-28), (I-P1933,A-2,R²-28,R³-29),
(I-P1798,A-2,R²-24,R³-30), (I-P1799,A-2,R²-24,R³-31), (I-P1934,A-2,R²-28,R³-30), (I-P1935,A-2,R²-28,R³-31),
(I-P1800,A-2,R²-24,R³-32), (I-P1801,A-2,R²-24,R³-33), (I-P1936,A-2,R²-28,R³-32), (I-P1937,A-2,R²-28,R³-33), (I-P2070,A-3,R²-3,R³-30), (I-P2071,A-3,R²-3,R³-31),
(I-P1938,A-2,R²-28,R³-34), (I-P1939,A-2,R²-29,R³-1), (I-P2072,A-3,R²-3,R³-32), (I-P2073,A-3,R²-3,R³-33),
(I-P1940,A-2,R²-29,R³-2), (I-P1941,A-2,R²-29,R³-3), (I-P2074,A-3,R²-3,R³-34), (I-P2075,A-3,R²-4,R³-1),
(I-P1942,A-2,R²-29,R³-4), (I-P1943,A-2,R²-29,R³-5), (I-P2076,A-3,R²-4,R³-2), (I-P2077,A-3,R²-4,R³-3),
(I-P1944,A-2,R²-29,R³-6), (I-P1945,A-2,R²-29,R³-7), (I-P2078,A-3,R²-4,R³-4), (I-P2079,A-3,R²-4,R³-5),
(I-P1946,A-2,R²-29,R³-8), (I-P1947,A-2,R²-29,R³-9), (I-P2080,A-3,R²-4,R³-6), (I-P2081,A-3,R²-4,R³-7),
(I-P1948,A-2,R²-29,R³-10), (I-P1949,A-2,R²-29,R³-11), (I-P2082,A-3,R²-4,R³-8), (I-P2083,A-3,R²-4,R³-9),
(I-P1950,A-2,R²-29,R³-12), (I-P1951,A-2,R²-29,R³-13), (I-P2084,A-3,R²-4,R³-10), (I-P2085,A-3,R²-4,R³-11),
(I-P1952,A-2,R²-29,R³-14), (I-P1953,A-2,R²-29,R³-15), (I-P2086,A-3,R²-4,R³-12), (I-P2087,A-3,R²-4,R³-13),
(I-P1954,A-2,R²-29,R³-16), (I-P1955,A-2,R²-29,R³-17), (I-P2088,A-3,R²-4,R³-14), (I-P2089,A-3,R²-4,R³-15),
(I-P1956,A-2,R²-29,R³-18), (I-P1957,A-2,R²-29,R³-19), (I-P2090,A-3,R²-4,R³-16), (I-P2091,A-3,R²-4,R³-17),
(I-P1958,A-2,R²-29,R³-20), (I-P1959,A-2,R²-29,R³-21), (I-P2092,A-3,R²-4,R³-18), (I-P2093,A-3,R²-4,R³-19),
(I-P1960,A-2,R²-29,R³-22), (I-P1961,A-2,R²-29,R³-23), (I-P2094,A-3,R²-4,R³-20), (I-P2095,A-3,R²-4,R³-21),
(I-P1962,A-2,R²-29,R³-24), (I-P1963,A-2,R²-29,R³-25), (I-P2096,A-3,R²-4,R³-22), (I-P2097,A-3,R²-4,R³-23),
(I-P1964,A-2,R²-29,R³-26), (I-P1965,A-2,R²-29,R³-27), (I-P2098,A-3,R²-4,R³-24), (I-P2099,A-3,R²-4,R³-25),
(I-P1966,A-2,R²-29,R³-28), (I-P1967,A-2,R²-29,R³-29), (I-P2100,A-3,R²-4,R³-26), (I-P2101,A-3,R²-4,R³-27),
(I-P1968,A-2,R²-29,R³-30), (I-P1969,A-2,R²-29,R³-31), (I-P2102,A-3,R²-4,R³-28), (I-P2103,A-3,R²-4,R³-29),
(I-P1970,A-2,R²-29,R³-32), (I-P1971,A-2,R²-29,R³-33), (I-P2104,A-3,R²-4,R³-30), (I-P2105,A-3,R²-4,R³-31),
(I-P1972,A-2,R²-29,R³-34), (I-P1973,A-3,R²-1,R³-1), (I-P2106,A-3,R²-4,R³-32), (I-P2107,A-3,R²-4,R³-33),
(I-P1974,A-3,R²-1,R³-2), (I-P1975,A-3,R²-1,R³-3), (I-P2108,A-3,R²-4,R³-34), (I-P2109,A-3,R²-5,R³-1),
(I-P1976,A-3,R²-1,R³-4), (I-P1977,A-3,R²-1,R³-5), (I-P2110,A-3,R²-5,R³-2), (I-P2111,A-3,R²-5,R³-3),
(I-P1978,A-3,R²-1,R³-6), (I-P1979,A-3,R²-1,R³-7), (I-P2112,A-3,R²-5,R³-4), (I-P2113,A-3,R²-5,R³-5),
(I-P1980,A-3,R²-1,R³-8), (I-P1981,A-3,R²-1,R³-9), (I-P2114,A-3,R²-5,R³-6), (I-P2115,A-3,R²-5,R³-7),
(I-P1982,A-3,R²-1,R³-10), (I-P1983,A-3,R²-1,R³-11), (I-P2116,A-3,R²-5,R³-8), (I-P2117,A-3,R²-5,R³-9),
(I-P1984,A-3,R²-1,R³-12), (I-P1985,A-3,R²-1,R³-13), (I-P2118,A-3,R²-5,R³-10), (I-P2119,A-3,R²-5,R³-11),
(I-P1986,A-3,R²-1,R³-14), (I-P1987,A-3,R²-1,R³-15), (I-P2120,A-3,R²-5,R³-12), (I-P2121,A-3,R²-5,R³-13),
(I-P1988,A-3,R²-1,R³-16), (I-P1989,A-3,R²-1,R³-17), (I-P2122,A-3,R²-5,R³-14), (I-P2123,A-3,R²-5,R³-15),
(I-P1990,A-3,R²-1,R³-18), (I-P1991,A-3,R²-1,R³-19), (I-P2124,A-3,R²-5,R³-16), (I-P2125,A-3,R²-5,R³-17),
(I-P1992,A-3,R²-1,R³-20), (I-P1993,A-3,R²-1,R³-21), (I-P2126,A-3,R²-5,R³-18), (I-P2127,A-3,R²-5,R³-19),
(I-P1994,A-3,R²-1,R³-22), (I-P1995,A-3,R²-1,R³-23), (I-P2128,A-3,R²-5,R³-20), (I-P2129,A-3,R²-5,R³-21),
(I-P1996,A-3,R²-1,R³-24), (I-P1997,A-3,R²-1,R³-25), (I-P2130,A-3,R²-5,R³-22), (I-P2131,A-3,R²-5,R³-23),
(I-P1998,A-3,R²-1,R³-26), (I-P1999,A-3,R²-1,R³-27), (I-P2132,A-3,R²-5,R³-24), (I-P2133,A-3,R²-5,R³-25),
(I-P2000,A-3,R²-1,R³-28), (I-P2001,A-3,R²-1,R³-29), (I-P2134,A-3,R²-5,R³-26), (I-P2135,A-3,R²-5,R³-27),
(I-P2002,A-3,R²-1,R³-30), (I-P2003,A-3,R²-1,R³-31), (I-P2136,A-3,R²-5,R³-28), (I-P2137,A-3,R²-5,R³-29),
(I-P2004,A-3,R²-1,R³-32), (I-P2005,A-3,R²-1,R³-33), (I-P2138,A-3,R²-5,R³-30), (I-P2139,A-3,R²-5,R³-31),
(I-P2006,A-3,R²-1,R³-34), (I-P2007,A-3,R²-2,R³-1), (I-P2140,A-3,R²-5,R³-32), (I-P2141,A-3,R²-5,R³-33),
(I-P2008,A-3,R²-2,R³-2), (I-P2009,A-3,R²-2,R³-3), (I-P2142,A-3,R²-5,R³-34), (I-P2143,A-3,R²-6,R³-1),
(I-P2010,A-3,R²-2,R³-4), (I-P2011,A-3,R²-2,R³-5), (I-P2144,A-3,R²-6,R³-2), (I-P2145,A-3,R²-6,R³-3),
(I-P2012,A-3,R²-2,R³-6), (I-P2013,A-3,R²-2,R³-7), (I-P2146,A-3,R²-6,R³-4), (I-P2147,A-3,R²-6,R³-5),
(I-P2014,A-3,R²-2,R³-8), (I-P2015,A-3,R²-2,R³-9), (I-P2148,A-3,R²-6,R³-6), (I-P2149,A-3,R²-6,R³-7),
(I-P2016,A-3,R²-2,R³-10), (I-P2017,A-3,R²-2,R³-11), (I-P2150,A-3,R²-6,R³-8), (I-P2151,A-3,R²-6,R³-9),
(I-P2018,A-3,R²-2,R³-12), (I-P2019,A-3,R²-2,R³-13), (I-P2152,A-3,R²-6,R³-10), (I-P2153,A-3,R²-6,R³-11),
(I-P2020,A-3,R²-2,R³-14), (I-P2021,A-3,R²-2,R³-15), (I-P2154,A-3,R²-6,R³-12), (I-P2155,A-3,R²-6,R³-13),
(I-P2022,A-3,R²-2,R³-16), (I-P2023,A-3,R²-2,R³-17), (I-P2156,A-3,R²-6,R³-14), (I-P2157,A-3,R²-6,R³-15),
(I-P2024,A-3,R²-2,R³-18), (I-P2025,A-3,R²-2,R³-19), (I-P2158,A-3,R²-6,R³-16), (I-P2159,A-3,R²-6,R³-17),
(I-P2026,A-3,R²-2,R³-20), (I-P2027,A-3,R²-2,R³-21), (I-P2160,A-3,R²-6,R³-18), (I-P2161,A-3,R²-6,R³-19),
(I-P2028,A-3,R²-2,R³-22), (I-P2029,A-3,R²-2,R³-23), (I-P2162,A-3,R²-6,R³-20), (I-P2163,A-3,R²-6,R³-21),
(I-P2030,A-3,R²-2,R³-24), (I-P2031,A-3,R²-2,R³-25), (I-P2164,A-3,R²-6,R³-22), (I-P2165,A-3,R²-6,R³-23),
(I-P2032,A-3,R²-2,R³-26), (I-P2033,A-3,R²-2,R³-27), (I-P2166,A-3,R²-6,R³-24), (I-P2167,A-3,R²-6,R³-25),
(I-P2034,A-3,R²-2,R³-28), (I-P2035,A-3,R²-2,R³-29), (I-P2168,A-3,R²-6,R³-26), (I-P2169,A-3,R²-6,R³-27),
(I-P2036,A-3,R²-2,R³-30), (I-P2037,A-3,R²-2,R³-31), (I-P2170,A-3,R²-6,R³-28), (I-P2171,A-3,R²-6,R³-29),
(I-P2038,A-3,R²-2,R³-32), (I-P2039,A-3,R²-2,R³-33), (I-P2172,A-3,R²-6,R³-30), (I-P2173,A-3,R²-6,R³-31),
(I-P2040,A-3,R²-2,R³-34), (I-P2041,A-3,R²-3,R³-1), (I-P2174,A-3,R²-6,R³-32), (I-P2175,A-3,R²-6,R³-33),
(I-P2042,A-3,R²-3,R³-2), (I-P2043,A-3,R²-3,R³-3), (I-P2176,A-3,R²-6,R³-34), (I-P2177,A-3,R²-7,R³-1),
(I-P2044,A-3,R²-3,R³-4), (I-P2045,A-3,R²-3,R³-5), (I-P2178,A-3,R²-7,R³-2), (I-P2179,A-3,R²-7,R³-3),
(I-P2046,A-3,R²-3,R³-6), (I-P2047,A-3,R²-3,R³-7), (I-P2180,A-3,R²-7,R³-4), (I-P2181,A-3,R²-7,R³-5),
(I-P2048,A-3,R²-3,R³-8), (I-P2049,A-3,R²-3,R³-9), (I-P2182,A-3,R²-7,R³-6), (I-P2183,A-3,R²-7,R³-7),
(I-P2050,A-3,R²-3,R³-10), (I-P2051,A-3,R²-3,R³-11), (I-P2184,A-3,R²-7,R³-8), (I-P2185,A-3,R²-7,R³-9),
(I-P2052,A-3,R²-3,R³-12), (I-P2053,A-3,R²-3,R³-13), (I-P2186,A-3,R²-7,R³-10), (I-P2187,A-3,R²-7,R³-11),
(I-P2054,A-3,R²-3,R³-14), (I-P2055,A-3,R²-3,R³-15), (I-P2188,A-3,R²-7,R³-12), (I-P2189,A-3,R²-7,R³-13),
(I-P2056,A-3,R²-3,R³-16), (I-P2057,A-3,R²-3,R³-17), (I-P2190,A-3,R²-7,R³-14), (I-P2191,A-3,R²-7,R³-15),
(I-P2058,A-3,R²-3,R³-18), (I-P2059,A-3,R²-3,R³-19), (I-P2192,A-3,R²-7,R³-16), (I-P2193,A-3,R²-7,R³-17),
(I-P2060,A-3,R²-3,R³-20), (I-P2061,A-3,R²-3,R³-21), (I-P2194,A-3,R²-7,R³-18), (I-P2195,A-3,R²-7,R³-19),
(I-P2062,A-3,R²-3,R³-22), (I-P2063,A-3,R²-3,R³-23), (I-P2196,A-3,R²-7,R³-20), (I-P2197,A-3,R²-7,R³-21),
(I-P2064,A-3,R²-3,R³-24), (I-P2065,A-3,R²-3,R³-25), (I-P2198,A-3,R²-7,R³-22), (I-P2199,A-3,R²-7,R³-23),
(I-P2066,A-3,R²-3,R³-26), (I-P2067,A-3,R²-3,R³-27), (I-P2200,A-3,R²-7,R³-24), (I-P2201,A-3,R²-7,R³-25),
(I-P2068,A-3,R²-3,R³-28), (I-P2069,A-3,R²-3,R³-29), (I-P2202,A-3,R²-7,R³-26), (I-P2203,A-3,R²-7,R³-27), (I-P2204,A-3,$R^2$-7,$R^3$-28), (I-P2205,A-3,$R^2$-7,$R^3$-29), (I-P2338,A-3,$R^2$-11,$R^3$-26), (I-P2339,A-3,$R^2$-11,$R^3$-27),
(I-P2206,A-3,$R^2$-7,$R^3$-30), (I-P2207,A-3,$R^2$-7,$R^3$-31), (I-P2340,A-3,$R^2$-11,$R^3$-28), (I-P2341,A-3,$R^2$-11,$R^3$-29),
(I-P2208,A-3,$R^2$-7,$R^3$-32), (I-P2209,A-3,$R^2$-7,$R^3$-33), (I-P2342,A-3,$R^2$-11,$R^3$-30), (I-P2343,A-3,$R^2$-11,$R^3$-31),
(I-P2210,A-3,$R^2$-7,$R^3$-34), (I-P2211,A-3,$R^2$-8,$R^3$-1), (I-P2344,A-3,$R^2$-11,$R^3$-32), (I-P2345,A-3,$R^2$-11,$R^3$-33),
(I-P2212,A-3,$R^2$-8,$R^3$-2), (I-P2213,A-3,$R^2$-8,$R^3$-3), (I-P2346,A-3,$R^2$-11,$R^3$-34), (I-P2347,A-3,$R^2$-12,$R^3$-1),
(I-P2214,A-3,$R^2$-8,$R^3$-4), (I-P2215,A-3,$R^2$-8,$R^3$-5), (I-P2348,A-3,$R^2$-12,$R^3$-2), (I-P2349,A-3,$R^2$-12,$R^3$-3),
(I-P2216,A-3,$R^2$-8,$R^3$-6), (I-P2217,A-3,$R^2$-8,$R^3$-7), (I-P2350,A-3,$R^2$-12,$R^3$-4), (I-P2351,A-3,$R^2$-12,$R^3$-5),
(I-P2218,A-3,$R^2$-8,$R^3$-8), (I-P2219,A-3,$R^2$-8,$R^3$-9), (I-P2352,A-3,$R^2$-12,$R^3$-6), (I-P2353,A-3,$R^2$-12,$R^3$-7),
(I-P2220,A-3,$R^2$-8,$R^3$-10), (I-P2221,A-3,$R^2$-8,$R^3$-11), (I-P2354,A-3,$R^2$-12,$R^3$-8), (I-P2355,A-3,$R^2$-12,$R^3$-9),
(I-P2222,A-3,$R^2$-8,$R^3$-12), (I-P2223,A-3,$R^2$-8,$R^3$-13), (I-P2356,A-3,$R^2$-12,$R^3$-10), (I-P2357,A-3,$R^2$-12,$R^3$-11),
(I-P2224,A-3,$R^2$-8,$R^3$-14), (I-P2225,A-3,$R^2$-8,$R^3$-15), (I-P2358,A-3,$R^2$-12,$R^3$-12), (I-P2359,A-3,$R^2$-12,$R^3$-13),
(I-P2226,A-3,$R^2$-8,$R^3$-16), (I-P2227,A-3,$R^2$-8,$R^3$-17), (I-P2360,A-3,$R^2$-12,$R^3$-14), (I-P2361,A-3,$R^2$-12,$R^3$-15),
(I-P2228,A-3,$R^2$-8,$R^3$-18), (I-P2229,A-3,$R^2$-8,$R^3$-19), (I-P2362,A-3,$R^2$-12,$R^3$-16), (I-P2363,A-3,$R^2$-12,$R^3$-17),
(I-P2230,A-3,$R^2$-8,$R^3$-20), (I-P2231,A-3,$R^2$-8,$R^3$-21), (I-P2364,A-3,$R^2$-12,$R^3$-18), (I-P2365,A-3,$R^2$-12,$R^3$-19),
(I-P2232,A-3,$R^2$-8,$R^3$-22), (I-P2233,A-3,$R^2$-8,$R^3$-23), (I-P2366,A-3,$R^2$-12,$R^3$-20), (I-P2367,A-3,$R^2$-12,$R^3$-21),
(I-P2234,A-3,$R^2$-8,$R^3$-24), (I-P2235,A-3,$R^2$-8,$R^3$-25), (I-P2368,A-3,$R^2$-12,$R^3$-22), (I-P2369,A-3,$R^2$-12,$R^3$-23),
(I-P2236,A-3,$R^2$-8,$R^3$-26), (I-P2237,A-3,$R^2$-8,$R^3$-27), (I-P2370,A-3,$R^2$-12,$R^3$-24), (I-P2371,A-3,$R^2$-12,$R^3$-25),
(I-P2238,A-3,$R^2$-8,$R^3$-28), (I-P2239,A-3,$R^2$-8,$R^3$-29), (I-P2372,A-3,$R^2$-12,$R^3$-26), (I-P2373,A-3,$R^2$-12,$R^3$-27),
(I-P2240,A-3,$R^2$-8,$R^3$-30), (I-P2241,A-3,$R^2$-8,$R^3$-31), (I-P2374,A-3,$R^2$-12,$R^3$-28), (I-P2375,A-3,$R^2$-12,$R^3$-29),
(I-P2242,A-3,$R^2$-8,$R^3$-32), (I-P2243,A-3,$R^2$-8,$R^3$-33), (I-P2376,A-3,$R^2$-12,$R^3$-30), (I-P2377,A-3,$R^2$-12,$R^3$-31),
(I-P2244,A-3,$R^2$-8,$R^3$-34), (I-P2245,A-3,$R^2$-9,$R^3$-1), (I-P2378,A-3,$R^2$-12,$R^3$-32), (I-P2379,A-3,$R^2$-12,$R^3$-33),
(I-P2246,A-3,$R^2$-9,$R^3$-2), (I-P2247,A-3,$R^2$-9,$R^3$-3), (I-P2380,A-3,$R^2$-12,$R^3$-34), (I-P2381,A-3,$R^2$-13,$R^3$-1),
(I-P2248,A-3,$R^2$-9,$R^3$-4), (I-P2249,A-3,$R^2$-9,$R^3$-5), (I-P2382,A-3,$R^2$-13,$R^3$-2), (I-P2383,A-3,$R^2$-13,$R^3$-3),
(I-P2250,A-3,$R^2$-9,$R^3$-6), (I-P2251,A-3,$R^2$-9,$R^3$-7), (I-P2384,A-3,$R^2$-13,$R^3$-4), (I-P2385,A-3,$R^2$-13,$R^3$-5),
(I-P2252,A-3,$R^2$-9,$R^3$-8), (I-P2253,A-3,$R^2$-9,$R^3$-9), (I-P2386,A-3,$R^2$-13,$R^3$-6), (I-P2387,A-3,$R^2$-13,$R^3$-7),
(I-P2254,A-3,$R^2$-9,$R^3$-10), (I-P2255,A-3,$R^2$-9,$R^3$-11), (I-P2388,A-3,$R^2$-13,$R^3$-8), (I-P2389,A-3,$R^2$-13,$R^3$-9),
(I-P2256,A-3,$R^2$-9,$R^3$-12), (I-P2257,A-3,$R^2$-9,$R^3$-13), (I-P2390,A-3,$R^2$-13,$R^3$-10), (I-P2391,A-3,$R^2$-13,$R^3$-11),
(I-P2258,A-3,$R^2$-9,$R^3$-14), (I-P2259,A-3,$R^2$-9,$R^3$-15), (I-P2392,A-3,$R^2$-13,$R^3$-12), (I-P2393,A-3,$R^2$-13,$R^3$-13),
(I-P2260,A-3,$R^2$-9,$R^3$-16), (I-P2261,A-3,$R^2$-9,$R^3$-17), (I-P2394,A-3,$R^2$-13,$R^3$-14), (I-P2395,A-3,$R^2$-13,$R^3$-15),
(I-P2262,A-3,$R^2$-9,$R^3$-18), (I-P2263,A-3,$R^2$-9,$R^3$-19), (I-P2396,A-3,$R^2$-13,$R^3$-16), (I-P2397,A-3,$R^2$-13,$R^3$-17),
(I-P2264,A-3,$R^2$-9,$R^3$-20), (I-P2265,A-3,$R^2$-9,$R^3$-21), (I-P2398,A-3,$R^2$-13,$R^3$-18), (I-P2399,A-3,$R^2$-13,$R^3$-19),
(I-P2266,A-3,$R^2$-9,$R^3$-22), (I-P2267,A-3,$R^2$-9,$R^3$-23), (I-P2400,A-3,$R^2$-13,$R^3$-20), (I-P2401,A-3,$R^2$-13,$R^3$-21),
(I-P2268,A-3,$R^2$-9,$R^3$-24), (I-P2269,A-3,$R^2$-9,$R^3$-25), (I-P2402,A-3,$R^2$-13,$R^3$-22), (I-P2403,A-3,$R^2$-13,$R^3$-23),
(I-P2270,A-3,$R^2$-9,$R^3$-26), (I-P2271,A-3,$R^2$-9,$R^3$-27), (I-P2404,A-3,$R^2$-13,$R^3$-24), (I-P2405,A-3,$R^2$-13,$R^3$-25),
(I-P2272,A-3,$R^2$-9,$R^3$-28), (I-P2273,A-3,$R^2$-9,$R^3$-29), (I-P2406,A-3,$R^2$-13,$R^3$-26), (I-P2407,A-3,$R^2$-13,$R^3$-27),
(I-P2274,A-3,$R^2$-9,$R^3$-30), (I-P2275,A-3,$R^2$-9,$R^3$-31), (I-P2408,A-3,$R^2$-13,$R^3$-28), (I-P2409,A-3,$R^2$-13,$R^3$-29),
(I-P2276,A-3,$R^2$-9,$R^3$-32), (I-P2277,A-3,$R^2$-9,$R^3$-33), (I-P2410,A-3,$R^2$-13,$R^3$-30), (I-P2411,A-3,$R^2$-13,$R^3$-31),
(I-P2278,A-3,$R^2$-9,$R^3$-34), (I-P2279,A-3,$R^2$-10,$R^3$-1), (I-P2412,A-3,$R^2$-13,$R^3$-32), (I-P2413,A-3,$R^2$-13,$R^3$-33),
(I-P2280,A-3,$R^2$-10,$R^3$-2), (I-P2281,A-3,$R^2$-10,$R^3$-3), (I-P2414,A-3,$R^2$-13,$R^3$-34), (I-P2415,A-3,$R^2$-14,$R^3$-1),
(I-P2282,A-3,$R^2$-10,$R^3$-4), (I-P2283,A-3,$R^2$-10,$R^3$-5), (I-P2416,A-3,$R^2$-14,$R^3$-2), (I-P2417,A-3,$R^2$-14,$R^3$-3),
(I-P2284,A-3,$R^2$-10,$R^3$-6), (I-P2285,A-3,$R^2$-10,$R^3$-7), (I-P2418,A-3,$R^2$-14,$R^3$-4), (I-P2419,A-3,$R^2$-14,$R^3$-5),
(I-P2286,A-3,$R^2$-10,$R^3$-8), (I-P2287,A-3,$R^2$-10,$R^3$-9), (I-P2420,A-3,$R^2$-14,$R^3$-6), (I-P2421,A-3,$R^2$-14,$R^3$-7),
(I-P2288,A-3,$R^2$-10,$R^3$-10), (I-P2289,A-3,$R^2$-10,$R^3$-11), (I-P2422,A-3,$R^2$-14,$R^3$-8), (I-P2423,A-3,$R^2$-14,$R^3$-9),
(I-P2290,A-3,$R^2$-10,$R^3$-12), (I-P2291,A-3,$R^2$-10,$R^3$-13), (I-P2424,A-3,$R^2$-14,$R^3$-10), (I-P2425,A-3,$R^2$-14,$R^3$-11),
(I-P2292,A-3,$R^2$-10,$R^3$-14), (I-P2293,A-3,$R^2$-10,$R^3$-15), (I-P2426,A-3,$R^2$-14,$R^3$-12), (I-P2427,A-3,$R^2$-14,$R^3$-13),
(I-P2294,A-3,$R^2$-10,$R^3$-16), (I-P2295,A-3,$R^2$-10,$R^3$-17), (I-P2428,A-3,$R^2$-14,$R^3$-14), (I-P2429,A-3,$R^2$-14,$R^3$-15),
(I-P2296,A-3,$R^2$-10,$R^3$-18), (I-P2297,A-3,$R^2$-10,$R^3$-19), (I-P2430,A-3,$R^2$-14,$R^3$-16), (I-P2431,A-3,$R^2$-14,$R^3$-17),
(I-P2298,A-3,$R^2$-10,$R^3$-20), (I-P2299,A-3,$R^2$-10,$R^3$-21), (I-P2432,A-3,$R^2$-14,$R^3$-18), (I-P2433,A-3,$R^2$-14,$R^3$-19),
(I-P2300,A-3,$R^2$-10,$R^3$-22), (I-P2301,A-3,$R^2$-10,$R^3$-23), (I-P2434,A-3,$R^2$-14,$R^3$-20), (I-P2435,A-3,$R^2$-14,$R^3$-21),
(I-P2302,A-3,$R^2$-10,$R^3$-24), (I-P2303,A-3,$R^2$-10,$R^3$-25), (I-P2436,A-3,$R^2$-14,$R^3$-22), (I-P2437,A-3,$R^2$-14,$R^3$-23),
(I-P2304,A-3,$R^2$-10,$R^3$-26), (I-P2305,A-3,$R^2$-10,$R^3$-27), (I-P2438,A-3,$R^2$-14,$R^3$-24), (I-P2439,A-3,$R^2$-14,$R^3$-25),
(I-P2306,A-3,$R^2$-10,$R^3$-28), (I-P2307,A-3,$R^2$-10,$R^3$-29), (I-P2440,A-3,$R^2$-14,$R^3$-26), (I-P2441,A-3,$R^2$-14,$R^3$-27),
(I-P2308,A-3,$R^2$-10,$R^3$-30), (I-P2309,A-3,$R^2$-10,$R^3$-31), (I-P2442,A-3,$R^2$-14,$R^3$-28), (I-P2443,A-3,$R^2$-14,$R^3$-29),
(I-P2310,A-3,$R^2$-10,$R^3$-32), (I-P2311,A-3,$R^2$-10,$R^3$-33), (I-P2444,A-3,$R^2$-14,$R^3$-30), (I-P2445,A-3,$R^2$-14,$R^3$-31),
(I-P2312,A-3,$R^2$-10,$R^3$-34), (I-P2313,A-3,$R^2$-11,$R^3$-1), (I-P2446,A-3,$R^2$-14,$R^3$-32), (I-P2447,A-3,$R^2$-14,$R^3$-33),
(I-P2314,A-3,$R^2$-11,$R^3$-2), (I-P2315,A-3,$R^2$-11,$R^3$-3), (I-P2448,A-3,$R^2$-14,$R^3$-34), (I-P2449,A-3,$R^2$-15,$R^3$-1),
(I-P2316,A-3,$R^2$-11,$R^3$-4), (I-P2317,A-3,$R^2$-11,$R^3$-5), (I-P2450,A-3,$R^2$-15,$R^3$-2), (I-P2451,A-3,$R^2$-15,$R^3$-3),
(I-P2318,A-3,$R^2$-11,$R^3$-6), (I-P2319,A-3,$R^2$-11,$R^3$-7), (I-P2452,A-3,$R^2$-15,$R^3$-4), (I-P2453,A-3,$R^2$-15,$R^3$-5),
(I-P2320,A-3,$R^2$-11,$R^3$-8), (I-P2321,A-3,$R^2$-11,$R^3$-9), (I-P2454,A-3,$R^2$-15,$R^3$-6), (I-P2455,A-3,$R^2$-15,$R^3$-7),
(I-P2322,A-3,$R^2$-11,$R^3$-10), (I-P2323,A-3,$R^2$-11,$R^3$-11), (I-P2456,A-3,$R^2$-15,$R^3$-8), (I-P2457,A-3,$R^2$-15,$R^3$-9),
(I-P2324,A-3,$R^2$-11,$R^3$-12), (I-P2325,A-3,$R^2$-11,$R^3$-13), (I-P2458,A-3,$R^2$-15,$R^3$-10), (I-P2459,A-3,$R^2$-15,$R^3$-11),
(I-P2326,A-3,$R^2$-11,$R^3$-14), (I-P2327,A-3,$R^2$-11,$R^3$-15), (I-P2460,A-3,$R^2$-15,$R^3$-12), (I-P2461,A-3,$R^2$-15,$R^3$-13),
(I-P2328,A-3,$R^2$-11,$R^3$-16), (I-P2329,A-3,$R^2$-11,$R^3$-17), (I-P2462,A-3,$R^2$-15,$R^3$-14), (I-P2463,A-3,$R^2$-15,$R^3$-15),
(I-P2330,A-3,$R^2$-11,$R^3$-18), (I-P2331,A-3,$R^2$-11,$R^3$-19), (I-P2464,A-3,$R^2$-15,$R^3$-16), (I-P2465,A-3,$R^2$-15,$R^3$-17),
(I-P2332,A-3,$R^2$-11,$R^3$-20), (I-P2333,A-3,$R^2$-11,$R^3$-21), (I-P2466,A-3,$R^2$-15,$R^3$-18), (I-P2467,A-3,$R^2$-15,$R^3$-19),
(I-P2334,A-3,$R^2$-11,$R^3$-22), (I-P2335,A-3,$R^2$-11,$R^3$-23), (I-P2468,A-3,$R^2$-15,$R^3$-20), (I-P2469,A-3,$R^2$-15,$R^3$-21),
(I-P2336,A-3,$R^2$-11,$R^3$-24), (I-P2337,A-3,$R^2$-11,$R^3$-25), (I-P2470,A-3,$R^2$-15,$R^3$-22), (I-P2471,A-3,$R^2$-15,$R^3$-23), (I-P2472,A-3,$R^2$-15,$R^3$-24), (I-P2473,A-3,$R^2$-15,$R^3$-25), (I-P2606,A-3,$R^2$-19,$R^3$-22), (I-P2607,A-3,$R^2$-19,$R^3$-23),
(I-P2474,A-3,$R^2$-15,$R^3$-26), (I-P2475,A-3,$R^2$-15,$R^3$-27), (I-P2608,A-3,$R^2$-19,$R^3$-24), (I-P2609,A-3,$R^2$-19,$R^3$-25),
(I-P2476,A-3,$R^2$-15,$R^3$-28), (I-P2477,A-3,$R^2$-15,$R^3$-29), (I-P2610,A-3,$R^2$-19,$R^3$-26), (I-P2611,A-3,$R^2$-19,$R^3$-27),
(I-P2478,A-3,$R^2$-15,$R^3$-30), (I-P2479,A-3,$R^2$-15,$R^3$-31), (I-P2612,A-3,$R^2$-19,$R^3$-28), (I-P2613,A-3,$R^2$-19,$R^3$-29),
(I-P2480,A-3,$R^2$-15,$R^3$-32), (I-P2481,A-3,$R^2$-15,$R^3$-33), (I-P2614,A-3,$R^2$-19,$R^3$-30), (I-P2615,A-3,$R^2$-19,$R^3$-31),
(I-P2482,A-3,$R^2$-15,$R^3$-34), (I-P2483,A-3,$R^2$-16,$R^3$-1), (I-P2616,A-3,$R^2$-19,$R^3$-32), (I-P2617,A-3,$R^2$-19,$R^3$-33),
(I-P2484,A-3,$R^2$-16,$R^3$-2), (I-P2485,A-3,$R^2$-16,$R^3$-3), (I-P2618,A-3,$R^2$-19,$R^3$-34), (I-P2619,A-3,$R^2$-20,$R^3$-1),
(I-P2486,A-3,$R^2$-16,$R^3$-4), (I-P2487,A-3,$R^2$-16,$R^3$-5), (I-P2620,A-3,$R^2$-20,$R^3$-2), (I-P2621,A-3,$R^2$-20,$R^3$-3),
(I-P2488,A-3,$R^2$-16,$R^3$-6), (I-P2489,A-3,$R^2$-16,$R^3$-7), (I-P2622,A-3,$R^2$-20,$R^3$-4), (I-P2623,A-3,$R^2$-20,$R^3$-5),
(I-P2490,A-3,$R^2$-16,$R^3$-8), (I-P2491,A-3,$R^2$-16,$R^3$-9), (I-P2624,A-3,$R^2$-20,$R^3$-6), (I-P2625,A-3,$R^2$-20,$R^3$-7),
(I-P2492,A-3,$R^2$-16,$R^3$-10), (I-P2493,A-3,$R^2$-16,$R^3$-11), (I-P2626,A-3,$R^2$-20,$R^3$-8), (I-P2627,A-3,$R^2$-20,$R^3$-9),
(I-P2494,A-3,$R^2$-16,$R^3$-12), (I-P2495,A-3,$R^2$-16,$R^3$-13), (I-P2628,A-3,$R^2$-20,$R^3$-10), (I-P2629,A-3,$R^2$-20,$R^3$-11),
(I-P2496,A-3,$R^2$-16,$R^3$-14), (I-P2497,A-3,$R^2$-16,$R^3$-15), (I-P2630,A-3,$R^2$-20,$R^3$-12), (I-P2631,A-3,$R^2$-20,$R^3$-13),
(I-P2498,A-3,$R^2$-16,$R^3$-16), (I-P2499,A-3,$R^2$-16,$R^3$-17), (I-P2632,A-3,$R^2$-20,$R^3$-14), (I-P2633,A-3,$R^2$-20,$R^3$-15),
(I-P2500,A-3,$R^2$-16,$R^3$-18), (I-P2501,A-3,$R^2$-16,$R^3$-19), (I-P2634,A-3,$R^2$-20,$R^3$-16), (I-P2635,A-3,$R^2$-20,$R^3$-17),
(I-P2502,A-3,$R^2$-16,$R^3$-20), (I-P2503,A-3,$R^2$-16,$R^3$-21), (I-P2636,A-3,$R^2$-20,$R^3$-18), (I-P2637,A-3,$R^2$-20,$R^3$-19),
(I-P2504,A-3,$R^2$-16,$R^3$-22), (I-P2505,A-3,$R^2$-16,$R^3$-23), (I-P2638,A-3,$R^2$-20,$R^3$-20), (I-P2639,A-3,$R^2$-20,$R^3$-21),
(I-P2506,A-3,$R^2$-16,$R^3$-24), (I-P2507,A-3,$R^2$-16,$R^3$-25), (I-P2640,A-3,$R^2$-20,$R^3$-22), (I-P2641,A-3,$R^2$-20,$R^3$-23),
(I-P2508,A-3,$R^2$-16,$R^3$-26), (I-P2509,A-3,$R^2$-16,$R^3$-27), (I-P2642,A-3,$R^2$-20,$R^3$-24), (I-P2643,A-3,$R^2$-20,$R^3$-25),
(I-P2510,A-3,$R^2$-16,$R^3$-28), (I-P2511,A-3,$R^2$-16,$R^3$-29), (I-P2644,A-3,$R^2$-20,$R^3$-26), (I-P2645,A-3,$R^2$-20,$R^3$-27),
(I-P2512,A-3,$R^2$-16,$R^3$-30), (I-P2513,A-3,$R^2$-16,$R^3$-31), (I-P2646,A-3,$R^2$-20,$R^3$-28), (I-P2647,A-3,$R^2$-20,$R^3$-29),
(I-P2514,A-3,$R^2$-16,$R^3$-32), (I-P2515,A-3,$R^2$-16,$R^3$-33), (I-P2648,A-3,$R^2$-20,$R^3$-30), (I-P2649,A-3,$R^2$-20,$R^3$-31),
(I-P2516,A-3,$R^2$-16,$R^3$-34), (I-P2517,A-3,$R^2$-17,$R^3$-1), (I-P2650,A-3,$R^2$-20,$R^3$-32), (I-P2651,A-3,$R^2$-20,$R^3$-33),
(I-P2518,A-3,$R^2$-17,$R^3$-2), (I-P2519,A-3,$R^2$-17,$R^3$-3), (I-P2652,A-3,$R^2$-20,$R^3$-34), (I-P2653,A-3,$R^2$-21,$R^3$-1),
(I-P2520,A-3,$R^2$-17,$R^3$-4), (I-P2521,A-3,$R^2$-17,$R^3$-5), (I-P2654,A-3,$R^2$-21,$R^3$-2), (I-P2655,A-3,$R^2$-21,$R^3$-3),
(I-P2522,A-3,$R^2$-17,$R^3$-6), (I-P2523,A-3,$R^2$-17,$R^3$-7), (I-P2656,A-3,$R^2$-21,$R^3$-4), (I-P2657,A-3,$R^2$-21,$R^3$-5),
(I-P2524,A-3,$R^2$-17,$R^3$-8), (I-P2525,A-3,$R^2$-17,$R^3$-9), (I-P2658,A-3,$R^2$-21,$R^3$-6), (I-P2659,A-3,$R^2$-21,$R^3$-7),
(I-P2526,A-3,$R^2$-17,$R^3$-10), (I-P2527,A-3,$R^2$-17,$R^3$-11), (I-P2660,A-3,$R^2$-21,$R^3$-8), (I-P2661,A-3,$R^2$-21,$R^3$-9),
(I-P2528,A-3,$R^2$-17,$R^3$-12), (I-P2529,A-3,$R^2$-17,$R^3$-13), (I-P2662,A-3,$R^2$-21,$R^3$-10), (I-P2663,A-3,$R^2$-21,$R^3$-11),
(I-P2530,A-3,$R^2$-17,$R^3$-14), (I-P2531,A-3,$R^2$-17,$R^3$-15), (I-P2664,A-3,$R^2$-21,$R^3$-12), (I-P2665,A-3,$R^2$-21,$R^3$-13),
(I-P2532,A-3,$R^2$-17,$R^3$-16), (I-P2533,A-3,$R^2$-17,$R^3$-17), (I-P2666,A-3,$R^2$-21,$R^3$-14), (I-P2667,A-3,$R^2$-21,$R^3$-15),
(I-P2534,A-3,$R^2$-17,$R^3$-18), (I-P2535,A-3,$R^2$-17,$R^3$-19), (I-P2668,A-3,$R^2$-21,$R^3$-16), (I-P2669,A-3,$R^2$-21,$R^3$-17),
(I-P2536,A-3,$R^2$-17,$R^3$-20), (I-P2537,A-3,$R^2$-17,$R^3$-21), (I-P2670,A-3,$R^2$-21,$R^3$-18), (I-P2671,A-3,$R^2$-21,$R^3$-19),
(I-P2538,A-3,$R^2$-17,$R^3$-22), (I-P2539,A-3,$R^2$-17,$R^3$-23), (I-P2672,A-3,$R^2$-21,$R^3$-20), (I-P2673,A-3,$R^2$-21,$R^3$-21),
(I-P2540,A-3,$R^2$-17,$R^3$-24), (I-P2541,A-3,$R^2$-17,$R^3$-25), (I-P2674,A-3,$R^2$-21,$R^3$-22), (I-P2675,A-3,$R^2$-21,$R^3$-23),
(I-P2542,A-3,$R^2$-17,$R^3$-26), (I-P2543,A-3,$R^2$-17,$R^3$-27), (I-P2676,A-3,$R^2$-21,$R^3$-24), (I-P2677,A-3,$R^2$-21,$R^3$-25),
(I-P2544,A-3,$R^2$-17,$R^3$-28), (I-P2545,A-3,$R^2$-17,$R^3$-29), (I-P2678,A-3,$R^2$-21,$R^3$-26), (I-P2679,A-3,$R^2$-21,$R^3$-27),
(I-P2546,A-3,$R^2$-17,$R^3$-30), (I-P2547,A-3,$R^2$-17,$R^3$-31), (I-P2680,A-3,$R^2$-21,$R^3$-28), (I-P2681,A-3,$R^2$-21,$R^3$-29),
(I-P2548,A-3,$R^2$-17,$R^3$-32), (I-P2549,A-3,$R^2$-17,$R^3$-33), (I-P2682,A-3,$R^2$-21,$R^3$-30), (I-P2683,A-3,$R^2$-21,$R^3$-31),
(I-P2550,A-3,$R^2$-17,$R^3$-34), (I-P2551,A-3,$R^2$-18,$R^3$-1), (I-P2684,A-3,$R^2$-21,$R^3$-32), (I-P2685,A-3,$R^2$-21,$R^3$-33),
(I-P2552,A-3,$R^2$-18,$R^3$-2), (I-P2553,A-3,$R^2$-18,$R^3$-3), (I-P2686,A-3,$R^2$-21,$R^3$-34), (I-P2687,A-3,$R^2$-22,$R^3$-1),
(I-P2554,A-3,$R^2$-18,$R^3$-4), (I-P2555,A-3,$R^2$-18,$R^3$-5), (I-P2688,A-3,$R^2$-22,$R^3$-2), (I-P2689,A-3,$R^2$-22,$R^3$-3),
(I-P2556,A-3,$R^2$-18,$R^3$-6), (I-P2557,A-3,$R^2$-18,$R^3$-7), (I-P2690,A-3,$R^2$-22,$R^3$-4), (I-P2691,A-3,$R^2$-22,$R^3$-5),
(I-P2558,A-3,$R^2$-18,$R^3$-8), (I-P2559,A-3,$R^2$-18,$R^3$-9), (I-P2692,A-3,$R^2$-22,$R^3$-6), (I-P2693,A-3,$R^2$-22,$R^3$-7),
(I-P2560,A-3,$R^2$-18,$R^3$-10), (I-P2561,A-3,$R^2$-18,$R^3$-11), (I-P2694,A-3,$R^2$-22,$R^3$-8), (I-P2695,A-3,$R^2$-22,$R^3$-9),
(I-P2562,A-3,$R^2$-18,$R^3$-12), (I-P2563,A-3,$R^2$-18,$R^3$-13), (I-P2696,A-3,$R^2$-22,$R^3$-10), (I-P2697,A-3,$R^2$-22,$R^3$-11),
(I-P2564,A-3,$R^2$-18,$R^3$-14), (I-P2565,A-3,$R^2$-18,$R^3$-15), (I-P2698,A-3,$R^2$-22,$R^3$-12), (I-P2699,A-3,$R^2$-22,$R^3$-13),
(I-P2566,A-3,$R^2$-18,$R^3$-16), (I-P2567,A-3,$R^2$-18,$R^3$-17), (I-P2700,A-3,$R^2$-22,$R^3$-14), (I-P2701,A-3,$R^2$-22,$R^3$-15),
(I-P2568,A-3,$R^2$-18,$R^3$-18), (I-P2569,A-3,$R^2$-18,$R^3$-19), (I-P2702,A-3,$R^2$-22,$R^3$-16), (I-P2703,A-3,$R^2$-22,$R^3$-17),
(I-P2570,A-3,$R^2$-18,$R^3$-20), (I-P2571,A-3,$R^2$-18,$R^3$-21), (I-P2704,A-3,$R^2$-22,$R^3$-18), (I-P2705,A-3,$R^2$-22,$R^3$-19),
(I-P2572,A-3,$R^2$-18,$R^3$-22), (I-P2573,A-3,$R^2$-18,$R^3$-23), (I-P2706,A-3,$R^2$-22,$R^3$-20), (I-P2707,A-3,$R^2$-22,$R^3$-21),
(I-P2574,A-3,$R^2$-18,$R^3$-24), (I-P2575,A-3,$R^2$-18,$R^3$-25), (I-P2708,A-3,$R^2$-22,$R^3$-22), (I-P2709,A-3,$R^2$-22,$R^3$-23),
(I-P2576,A-3,$R^2$-18,$R^3$-26), (I-P2577,A-3,$R^2$-18,$R^3$-27), (I-P2710,A-3,$R^2$-22,$R^3$-24), (I-P2711,A-3,$R^2$-22,$R^3$-25),
(I-P2578,A-3,$R^2$-18,$R^3$-28), (I-P2579,A-3,$R^2$-18,$R^3$-29), (I-P2712,A-3,$R^2$-22,$R^3$-26), (I-P2713,A-3,$R^2$-22,$R^3$-27),
(I-P2580,A-3,$R^2$-18,$R^3$-30), (I-P2581,A-3,$R^2$-18,$R^3$-31), (I-P2714,A-3,$R^2$-22,$R^3$-28), (I-P2715,A-3,$R^2$-22,$R^3$-29),
(I-P2582,A-3,$R^2$-18,$R^3$-32), (I-P2583,A-3,$R^2$-18,$R^3$-33), (I-P2716,A-3,$R^2$-22,$R^3$-30), (I-P2717,A-3,$R^2$-22,$R^3$-31),
(I-P2584,A-3,$R^2$-18,$R^3$-34), (I-P2585,A-3,$R^2$-19,$R^3$-1), (I-P2718,A-3,$R^2$-22,$R^3$-32), (I-P2719,A-3,$R^2$-22,$R^3$-33),
(I-P2586,A-3,$R^2$-19,$R^3$-2), (I-P2587,A-3,$R^2$-19,$R^3$-3), (I-P2720,A-3,$R^2$-22,$R^3$-34), (I-P2721,A-3,$R^2$-23,$R^3$-1),
(I-P2588,A-3,$R^2$-19,$R^3$-4), (I-P2589,A-3,$R^2$-19,$R^3$-5), (I-P2722,A-3,$R^2$-23,$R^3$-2), (I-P2723,A-3,$R^2$-23,$R^3$-3),
(I-P2590,A-3,$R^2$-19,$R^3$-6), (I-P2591,A-3,$R^2$-19,$R^3$-7), (I-P2724,A-3,$R^2$-23,$R^3$-4), (I-P2725,A-3,$R^2$-23,$R^3$-5),
(I-P2592,A-3,$R^2$-19,$R^3$-8), (I-P2593,A-3,$R^2$-19,$R^3$-9), (I-P2726,A-3,$R^2$-23,$R^3$-6), (I-P2727,A-3,$R^2$-23,$R^3$-7),
(I-P2594,A-3,$R^2$-19,$R^3$-10), (I-P2595,A-3,$R^2$-19,$R^3$-11), (I-P2728,A-3,$R^2$-23,$R^3$-8), (I-P2729,A-3,$R^2$-23,$R^3$-9),
(I-P2596,A-3,$R^2$-19,$R^3$-12), (I-P2597,A-3,$R^2$-19,$R^3$-13), (I-P2730,A-3,$R^2$-23,$R^3$-10), (I-P2731,A-3,$R^2$-23,$R^3$-11),
(I-P2598,A-3,$R^2$-19,$R^3$-14), (I-P2599,A-3,$R^2$-19,$R^3$-15), (I-P2732,A-3,$R^2$-23,$R^3$-12), (I-P2733,A-3,$R^2$-23,$R^3$-13),
(I-P2600,A-3,$R^2$-19,$R^3$-16), (I-P2601,A-3,$R^2$-19,$R^3$-17), (I-P2734,A-3,$R^2$-23,$R^3$-14), (I-P2735,A-3,$R^2$-23,$R^3$-15),
(I-P2602,A-3,$R^2$-19,$R^3$-18), (I-P2603,A-3,$R^2$-19,$R^3$-19), (I-P2736,A-3,$R^2$-23,$R^3$-16), (I-P2737,A-3,$R^2$-23,$R^3$-17),
(I-P2604,A-3,$R^2$-19,$R^3$-20), (I-P2605,A-3,$R^2$-19,$R^3$-21), (I-P2738,A-3,$R^2$-23,$R^3$-18), (I-P2739,A-3,$R^2$-23,$R^3$-19), (I-P2740,A-3,$R^2$-23,$R^3$-20), (I-P2741,A-3,$R^2$-23,$R^3$-21), (I-P2874,A-3,$R^2$-27,$R^3$-18), (I-P2875,A-3,$R^2$-27,$R^3$-19),
(I-P2742,A-3,$R^2$-23,$R^3$-22), (I-P2743,A-3,$R^2$-23,$R^3$-23), (I-P2876,A-3,$R^2$-27,$R^3$-20), (I-P2877,A-3,$R^2$-27,$R^3$-21),
(I-P2744,A-3,$R^2$-23,$R^3$-24), (I-P2745,A-3,$R^2$-23,$R^3$-25), (I-P2878,A-3,$R^2$-27,$R^3$-22), (I-P2879,A-3,$R^2$-27,$R^3$-23),
(I-P2746,A-3,$R^2$-23,$R^3$-26), (I-P2747,A-3,$R^2$-23,$R^3$-27), (I-P2880,A-3,$R^2$-27,$R^3$-24), (I-P2881,A-3,$R^2$-27,$R^3$-25),
(I-P2748,A-3,$R^2$-23,$R^3$-28), (I-P2749,A-3,$R^2$-23,$R^3$-29), (I-P2882,A-3,$R^2$-27,$R^3$-26), (I-P2883,A-3,$R^2$-27,$R^3$-27),
(I-P2750,A-3,$R^2$-23,$R^3$-30), (I-P2751,A-3,$R^2$-23,$R^3$-31), (I-P2884,A-3,$R^2$-27,$R^3$-28), (I-P2885,A-3,$R^2$-27,$R^3$-29),
(I-P2752,A-3,$R^2$-23,$R^3$-32), (I-P2753,A-3,$R^2$-23,$R^3$-33), (I-P2886,A-3,$R^2$-27,$R^3$-30), (I-P2887,A-3,$R^2$-27,$R^3$-31),
(I-P2754,A-3,$R^2$-23,$R^3$-34), (I-P2755,A-3,$R^2$-24,$R^3$-1), (I-P2888,A-3,$R^2$-27,$R^3$-32), (I-P2889,A-3,$R^2$-27,$R^3$-33),
(I-P2756,A-3,$R^2$-24,$R^3$-2), (I-P2757,A-3,$R^2$-24,$R^3$-3), (I-P2890,A-3,$R^2$-27,$R^3$-34), (I-P2891,A-3,$R^2$-28,$R^3$-1),
(I-P2758,A-3,$R^2$-24,$R^3$-4), (I-P2759,A-3,$R^2$-24,$R^3$-5), (I-P2892,A-3,$R^2$-28,$R^3$-2), (I-P2893,A-3,$R^2$-28,$R^3$-3),
(I-P2760,A-3,$R^2$-24,$R^3$-6), (I-P2761,A-3,$R^2$-24,$R^3$-7), (I-P2894,A-3,$R^2$-28,$R^3$-4), (I-P2895,A-3,$R^2$-28,$R^3$-5),
(I-P2762,A-3,$R^2$-24,$R^3$-8), (I-P2763,A-3,$R^2$-24,$R^3$-9), (I-P2896,A-3,$R^2$-28,$R^3$-6), (I-P2897,A-3,$R^2$-28,$R^3$-7),
(I-P2764,A-3,$R^2$-24,$R^3$-10), (I-P2765,A-3,$R^2$-24,$R^3$-11), (I-P2898,A-3,$R^2$-28,$R^3$-8), (I-P2899,A-3,$R^2$-28,$R^3$-9),
(I-P2766,A-3,$R^2$-24,$R^3$-12), (I-P2767,A-3,$R^2$-24,$R^3$-13), (I-P2900,A-3,$R^2$-28,$R^3$-10), (I-P2901,A-3,$R^2$-28,$R^3$-11),
(I-P2768,A-3,$R^2$-24,$R^3$-14), (I-P2769,A-3,$R^2$-24,$R^3$-15), (I-P2902,A-3,$R^2$-28,$R^3$-12), (I-P2903,A-3,$R^2$-28,$R^3$-13),
(I-P2770,A-3,$R^2$-24,$R^3$-16), (I-P2771,A-3,$R^2$-24,$R^3$-17), (I-P2904,A-3,$R^2$-28,$R^3$-14), (I-P2905,A-3,$R^2$-28,$R^3$-15),
(I-P2772,A-3,$R^2$-24,$R^3$-18), (I-P2773,A-3,$R^2$-24,$R^3$-19), (I-P2906,A-3,$R^2$-28,$R^3$-16), (I-P2907,A-3,$R^2$-28,$R^3$-17),
(I-P2774,A-3,$R^2$-24,$R^3$-20), (I-P2775,A-3,$R^2$-24,$R^3$-21), (I-P2908,A-3,$R^2$-28,$R^3$-18), (I-P2909,A-3,$R^2$-28,$R^3$-19),
(I-P2776,A-3,$R^2$-24,$R^3$-22), (I-P2777,A-3,$R^2$-24,$R^3$-23), (I-P2910,A-3,$R^2$-28,$R^3$-20), (I-P2911,A-3,$R^2$-28,$R^3$-21),
(I-P2778,A-3,$R^2$-24,$R^3$-24), (I-P2779,A-3,$R^2$-24,$R^3$-25), (I-P2912,A-3,$R^2$-28,$R^3$-22), (I-P2913,A-3,$R^2$-28,$R^3$-23),
(I-P2780,A-3,$R^2$-24,$R^3$-26), (I-P2781,A-3,$R^2$-24,$R^3$-27), (I-P2914,A-3,$R^2$-28,$R^3$-24), (I-P2915,A-3,$R^2$-28,$R^3$-25),
(I-P2782,A-3,$R^2$-24,$R^3$-28), (I-P2783,A-3,$R^2$-24,$R^3$-29), (I-P2916,A-3,$R^2$-28,$R^3$-26), (I-P2917,A-3,$R^2$-28,$R^3$-27),
(I-P2784,A-3,$R^2$-24,$R^3$-30), (I-P2785,A-3,$R^2$-24,$R^3$-31), (I-P2918,A-3,$R^2$-28,$R^3$-28), (I-P2919,A-3,$R^2$-28,$R^3$-29),
(I-P2786,A-3,$R^2$-24,$R^3$-32), (I-P2787,A-3,$R^2$-24,$R^3$-33), (I-P2920,A-3,$R^2$-28,$R^3$-30), (I-P2921,A-3,$R^2$-28,$R^3$-31),
(I-P2788,A-3,$R^2$-24,$R^3$-34), (I-P2789,A-3,$R^2$-25,$R^3$-1), (I-P2922,A-3,$R^2$-28,$R^3$-32), (I-P2923,A-3,$R^2$-28,$R^3$-33),
(I-P2790,A-3,$R^2$-25,$R^3$-2), (I-P2791,A-3,$R^2$-25,$R^3$-3), (I-P2924,A-3,$R^2$-28,$R^3$-34), (I-P2925,A-3,$R^2$-29,$R^3$-1),
(I-P2792,A-3,$R^2$-25,$R^3$-4), (I-P2793,A-3,$R^2$-25,$R^3$-5), (I-P2926,A-3,$R^2$-29,$R^3$-2), (I-P2927,A-3,$R^2$-29,$R^3$-3),
(I-P2794,A-3,$R^2$-25,$R^3$-6), (I-P2795,A-3,$R^2$-25,$R^3$-7), (I-P2928,A-3,$R^2$-29,$R^3$-4), (I-P2929,A-3,$R^2$-29,$R^3$-5),
(I-P2796,A-3,$R^2$-25,$R^3$-8), (I-P2797,A-3,$R^2$-25,$R^3$-9), (I-P2930,A-3,$R^2$-29,$R^3$-6), (I-P2931,A-3,$R^2$-29,$R^3$-7),
(I-P2798,A-3,$R^2$-25,$R^3$-10), (I-P2799,A-3,$R^2$-25,$R^3$-11), (I-P2932,A-3,$R^2$-29,$R^3$-8), (I-P2933,A-3,$R^2$-29,$R^3$-9),
(I-P2800,A-3,$R^2$-25,$R^3$-12), (I-P2801,A-3,$R^2$-25,$R^3$-13), (I-P2934,A-3,$R^2$-29,$R^3$-10), (I-P2935,A-3,$R^2$-29,$R^3$-11),
(I-P2802,A-3,$R^2$-25,$R^3$-14), (I-P2803,A-3,$R^2$-25,$R^3$-15), (I-P2936,A-3,$R^2$-29,$R^3$-12), (I-P2937,A-3,$R^2$-29,$R^3$-13),
(I-P2804,A-3,$R^2$-25,$R^3$-16), (I-P2805,A-3,$R^2$-25,$R^3$-17), (I-P2938,A-3,$R^2$-29,$R^3$-14), (I-P2939,A-3,$R^2$-29,$R^3$-15),
(I-P2806,A-3,$R^2$-25,$R^3$-18), (I-P2807,A-3,$R^2$-25,$R^3$-19), (I-P2940,A-3,$R^2$-29,$R^3$-16), (I-P2941,A-3,$R^2$-29,$R^3$-17),
(I-P2808,A-3,$R^2$-25,$R^3$-20), (I-P2809,A-3,$R^2$-25,$R^3$-21), (I-P2942,A-3,$R^2$-29,$R^3$-18), (I-P2943,A-3,$R^2$-29,$R^3$-19),
(I-P2810,A-3,$R^2$-25,$R^3$-22), (I-P2811,A-3,$R^2$-25,$R^3$-23), (I-P2944,A-3,$R^2$-29,$R^3$-20), (I-P2945,A-3,$R^2$-29,$R^3$-21),
(I-P2812,A-3,$R^2$-25,$R^3$-24), (I-P2813,A-3,$R^2$-25,$R^3$-25), (I-P2946,A-3,$R^2$-29,$R^3$-22), (I-P2947,A-3,$R^2$-29,$R^3$-23),
(I-P2814,A-3,$R^2$-25,$R^3$-26), (I-P2815,A-3,$R^2$-25,$R^3$-27), (I-P2948,A-3,$R^2$-29,$R^3$-24), (I-P2949,A-3,$R^2$-29,$R^3$-25),
(I-P2816,A-3,$R^2$-25,$R^3$-28), (I-P2817,A-3,$R^2$-25,$R^3$-29), (I-P2950,A-3,$R^2$-29,$R^3$-26), (I-P2951,A-3,$R^2$-29,$R^3$-27),
(I-P2818,A-3,$R^2$-25,$R^3$-30), (I-P2819,A-3,$R^2$-25,$R^3$-31), (I-P2952,A-3,$R^2$-29,$R^3$-28), (I-P2953,A-3,$R^2$-29,$R^3$-29),
(I-P2820,A-3,$R^2$-25,$R^3$-32), (I-P2821,A-3,$R^2$-25,$R^3$-33), (I-P2954,A-3,$R^2$-29,$R^3$-30), (I-P2955,A-3,$R^2$-29,$R^3$-31),
(I-P2822,A-3,$R^2$-25,$R^3$-34), (I-P2823,A-3,$R^2$-26,$R^3$-1), (I-P2956,A-3,$R^2$-29,$R^3$-32), (I-P2957,A-3,$R^2$-29,$R^3$-33),
(I-P2824,A-3,$R^2$-26,$R^3$-2), (I-P2825,A-3,$R^2$-26,$R^3$-3), (I-P2958,A-3,$R^2$-29,$R^3$-34), (I-P2959,A-4,$R^2$-1,$R^3$-1),
(I-P2826,A-3,$R^2$-26,$R^3$-4), (I-P2827,A-3,$R^2$-26,$R^3$-5), (I-P2960,A-4,$R^2$-1,$R^3$-2), (I-P2961,A-4,$R^2$-1,$R^3$-3),
(I-P2828,A-3,$R^2$-26,$R^3$-6), (I-P2829,A-3,$R^2$-26,$R^3$-7), (I-P2962,A-4,$R^2$-1,$R^3$-4), (I-P2963,A-4,$R^2$-1,$R^3$-5),
(I-P2830,A-3,$R^2$-26,$R^3$-8), (I-P2831,A-3,$R^2$-26,$R^3$-9), (I-P2964,A-4,$R^2$-1,$R^3$-6), (I-P2965,A-4,$R^2$-1,$R^3$-7),
(I-P2832,A-3,$R^2$-26,$R^3$-10), (I-P2833,A-3,$R^2$-26,$R^3$-11), (I-P2966,A-4,$R^2$-1,$R^3$-8), (I-P2967,A-4,$R^2$-1,$R^3$-9),
(I-P2834,A-3,$R^2$-26,$R^3$-12), (I-P2835,A-3,$R^2$-26,$R^3$-13), (I-P2968,A-4,$R^2$-1,$R^3$-10), (I-P2969,A-4,$R^2$-1,$R^3$-11),
(I-P2836,A-3,$R^2$-26,$R^3$-14), (I-P2837,A-3,$R^2$-26,$R^3$-15), (I-P2970,A-4,$R^2$-1,$R^3$-12), (I-P2971,A-4,$R^2$-1,$R^3$-13),
(I-P2838,A-3,$R^2$-26,$R^3$-16), (I-P2839,A-3,$R^2$-26,$R^3$-17), (I-P2972,A-4,$R^2$-1,$R^3$-14), (I-P2973,A-4,$R^2$-1,$R^3$-15),
(I-P2840,A-3,$R^2$-26,$R^3$-18), (I-P2841,A-3,$R^2$-26,$R^3$-19), (I-P2974,A-4,$R^2$-1,$R^3$-16), (I-P2975,A-4,$R^2$-1,$R^3$-17),
(I-P2842,A-3,$R^2$-26,$R^3$-20), (I-P2843,A-3,$R^2$-26,$R^3$-21), (I-P2976,A-4,$R^2$-1,$R^3$-18), (I-P2977,A-4,$R^2$-1,$R^3$-19),
(I-P2844,A-3,$R^2$-26,$R^3$-22), (I-P2845,A-3,$R^2$-26,$R^3$-23), (I-P2978,A-4,$R^2$-1,$R^3$-20), (I-P2979,A-4,$R^2$-1,$R^3$-21),
(I-P2846,A-3,$R^2$-26,$R^3$-24), (I-P2847,A-3,$R^2$-26,$R^3$-25), (I-P2980,A-4,$R^2$-1,$R^3$-22), (I-P2981,A-4,$R^2$-1,$R^3$-23),
(I-P2848,A-3,$R^2$-26,$R^3$-26), (I-P2849,A-3,$R^2$-26,$R^3$-27), (I-P2982,A-4,$R^2$-1,$R^3$-24), (I-P2983,A-4,$R^2$-1,$R^3$-25),
(I-P2850,A-3,$R^2$-26,$R^3$-28), (I-P2851,A-3,$R^2$-26,$R^3$-29), (I-P2984,A-4,$R^2$-1,$R^3$-26), (I-P2985,A-4,$R^2$-1,$R^3$-27),
(I-P2852,A-3,$R^2$-26,$R^3$-30), (I-P2853,A-3,$R^2$-26,$R^3$-31), (I-P2986,A-4,$R^2$-1,$R^3$-28), (I-P2987,A-4,$R^2$-1,$R^3$-29),
(I-P2854,A-3,$R^2$-26,$R^3$-32), (I-P2855,A-3,$R^2$-26,$R^3$-33), (I-P2988,A-4,$R^2$-1,$R^3$-30), (I-P2989,A-4,$R^2$-1,$R^3$-31),
(I-P2856,A-3,$R^2$-26,$R^3$-34), (I-P2857,A-3,$R^2$-27,$R^3$-1), (I-P2990,A-4,$R^2$-1,$R^3$-32), (I-P2991,A-4,$R^2$-1,$R^3$-33),
(I-P2858,A-3,$R^2$-27,$R^3$-2), (I-P2859,A-3,$R^2$-27,$R^3$-3), (I-P2992,A-4,$R^2$-1,$R^3$-34), (I-P2993,A-4,$R^2$-2,$R^3$-1),
(I-P2860,A-3,$R^2$-27,$R^3$-4), (I-P2861,A-3,$R^2$-27,$R^3$-5), (I-P2994,A-4,$R^2$-2,$R^3$-2), (I-P2995,A-4,$R^2$-2,$R^3$-3),
(I-P2862,A-3,$R^2$-27,$R^3$-6), (I-P2863,A-3,$R^2$-27,$R^3$-7), (I-P2996,A-4,$R^2$-2,$R^3$-4), (I-P2997,A-4,$R^2$-2,$R^3$-5),
(I-P2864,A-3,$R^2$-27,$R^3$-8), (I-P2865,A-3,$R^2$-27,$R^3$-9), (I-P2998,A-4,$R^2$-2,$R^3$-6), (I-P2999,A-4,$R^2$-2,$R^3$-7),
(I-P2866,A-3,$R^2$-27,$R^3$-10), (I-P2867,A-3,$R^2$-27,$R^3$-11), (I-P3000,A-4,$R^2$-2,$R^3$-8), (I-P3001,A-4,$R^2$-2,$R^3$-9),
(I-P2868,A-3,$R^2$-27,$R^3$-12), (I-P2869,A-3,$R^2$-27,$R^3$-13), (I-P3002,A-4,$R^2$-2,$R^3$-10), (I-P3003,A-4,$R^2$-2,$R^3$-11),
(I-P2870,A-3,$R^2$-27,$R^3$-14), (I-P2871,A-3,$R^2$-27,$R^3$-15), (I-P3004,A-4,$R^2$-2,$R^3$-12), (I-P3005,A-4,$R^2$-2,$R^3$-13),
(I-P2872,A-3,$R^2$-27,$R^3$-16), (I-P2873,A-3,$R^2$-27,$R^3$-17), (I-P3006,A-4,$R^2$-2,$R^3$-14), (I-P3007,A-4,$R^2$-2,$R^3$-15), (I-P3008,A-4,R²-2,R³-16), (I-P3009,A-4,R²-2,R³-17), (I-P3142,A-4,R²-6,R³-14), (I-P3143,A-4,R²-6,R³-15),
(I-P3010,A-4,R²-2,R³-18), (I-P3011,A-4,R²-2,R³-19), (I-P3144,A-4,R²-6,R³-16), (I-P3145,A-4,R²-6,R³-17),
(I-P3012,A-4,R²-2,R³-20), (I-P3013,A-4,R²-2,R³-21), (I-P3146,A-4,R²-6,R³-18), (I-P3147,A-4,R²-6,R³-19),
(I-P3014,A-4,R²-2,R³-22), (I-P3015,A-4,R²-2,R³-23), (I-P3148,A-4,R²-6,R³-20), (I-P3149,A-4,R²-6,R³-21),
(I-P3016,A-4,R²-2,R³-24), (I-P3017,A-4,R²-2,R³-25), (I-P3150,A-4,R²-6,R³-22), (I-P3151,A-4,R²-6,R³-23),
(I-P3018,A-4,R²-2,R³-26), (I-P3019,A-4,R²-2,R³-27), (I-P3152,A-4,R²-6,R³-24), (I-P3153,A-4,R²-6,R³-25),
(I-P3020,A-4,R²-2,R³-28), (I-P3021,A-4,R²-2,R³-29), (I-P3154,A-4,R²-6,R³-26), (I-P3155,A-4,R²-6,R³-27),
(I-P3022,A-4,R²-2,R³-30), (I-P3023,A-4,R²-2,R³-31), (I-P3156,A-4,R²-6,R³-28), (I-P3157,A-4,R²-6,R³-29),
(I-P3024,A-4,R²-2,R³-32), (I-P3025,A-4,R²-2,R³-33), (I-P3158,A-4,R²-6,R³-30), (I-P3159,A-4,R²-6,R³-31),
(I-P3026,A-4,R²-2,R³-34), (I-P3027,A-4,R²-3,R³-1), (I-P3160,A-4,R²-6,R³-32), (I-P3161,A-4,R²-6,R³-33),
(I-P3028,A-4,R²-3,R³-2), (I-P3029,A-4,R²-3,R³-3), (I-P3162,A-4,R²-6,R³-34), (I-P3163,A-4,R²-7,R³-1),
(I-P3030,A-4,R²-3,R³-4), (I-P3031,A-4,R²-3,R³-5), (I-P3164,A-4,R²-7,R³-2), (I-P3165,A-4,R²-7,R³-3),
(I-P3032,A-4,R²-3,R³-6), (I-P3033,A-4,R²-3,R³-7), (I-P3166,A-4,R²-7,R³-4), (I-P3167,A-4,R²-7,R³-5),
(I-P3034,A-4,R²-3,R³-8), (I-P3035,A-4,R²-3,R³-9), (I-P3168,A-4,R²-7,R³-6), (I-P3169,A-4,R²-7,R³-7),
(I-P3036,A-4,R²-3,R³-10), (I-P3037,A-4,R²-3,R³-11), (I-P3170,A-4,R²-7,R³-8), (I-P3171,A-4,R²-7,R³-9),
(I-P3038,A-4,R²-3,R³-12), (I-P3039,A-4,R²-3,R³-13), (I-P3172,A-4,R²-7,R³-10), (I-P3173,A-4,R²-7,R³-11),
(I-P3040,A-4,R²-3,R³-14), (I-P3041,A-4,R²-3,R³-15), (I-P3174,A-4,R²-7,R³-12), (I-P3175,A-4,R²-7,R³-13),
(I-P3042,A-4,R²-3,R³-16), (I-P3043,A-4,R²-3,R³-17), (I-P3176,A-4,R²-7,R³-14), (I-P3177,A-4,R²-7,R³-15),
(I-P3044,A-4,R²-3,R³-18), (I-P3045,A-4,R²-3,R³-19), (I-P3178,A-4,R²-7,R³-16), (I-P3179,A-4,R²-7,R³-17),
(I-P3046,A-4,R²-3,R³-20), (I-P3047,A-4,R²-3,R³-21), (I-P3180,A-4,R²-7,R³-18), (I-P3181,A-4,R²-7,R³-19),
(I-P3048,A-4,R²-3,R³-22), (I-P3049,A-4,R²-3,R³-23), (I-P3182,A-4,R²-7,R³-20), (I-P3183,A-4,R²-7,R³-21),
(I-P3050,A-4,R²-3,R³-24), (I-P3051,A-4,R²-3,R³-25), (I-P3184,A-4,R²-7,R³-22), (I-P3185,A-4,R²-7,R³-23),
(I-P3052,A-4,R²-3,R³-26), (I-P3053,A-4,R²-3,R³-27), (I-P3186,A-4,R²-7,R³-24), (I-P3187,A-4,R²-7,R³-25),
(I-P3054,A-4,R²-3,R³-28), (I-P3055,A-4,R²-3,R³-29), (I-P3188,A-4,R²-7,R³-26), (I-P3189,A-4,R²-7,R³-27),
(I-P3056,A-4,R²-3,R³-30), (I-P3057,A-4,R²-3,R³-31), (I-P3190,A-4,R²-7,R³-28), (I-P3191,A-4,R²-7,R³-29),
(I-P3058,A-4,R²-3,R³-32), (I-P3059,A-4,R²-3,R³³), (I-P3192,A-4,R²-7,R³-30), (I-P3193,A-4,R²-7,R³-31),
(I-P3060,A-4,R²-3,R³-34), (I-P3061,A-4,R²-4,R³-1), (I-P3194,A-4,R²-7,R³-32), (I-P3195,A-4,R²-7,R³-33),
(I-P3062,A-4,R²-4,R³-2), (I-P3063,A-4,R²-4,R³-3), (I-P3196,A-4,R²-7,R³-34), (I-P3197,A-4,R²-8,R³-1),
(I-P3064,A-4,R²-4,R³-4), (I-P3065,A-4,R²-4,R³-5), (I-P3198,A-4,R²-8,R³-2), (I-P3199,A-4,R²-8,R³-3),
(I-P3066,A-4,R²-4,R³-6), (I-P3067,A-4,R²-4,R³-7), (I-P3200,A-4,R²-8,R³-4), (I-P3201,A-4,R²-8,R³-5),
(I-P3068,A-4,R²-4,R³-8), (I-P3069,A-4,R²-4,R³-9), (I-P3202,A-4,R²-8,R³-6), (I-P3203,A-4,R²-8,R³-7),
(I-P3070,A-4,R²-4,R³-10), (I-P3071,A-4,R²-4,R³-11), (I-P3204,A-4,R²-8,R³-8), (I-P3205,A-4,R²-8,R³-9),
(I-P3072,A-4,R²-4,R³-12), (I-P3073,A-4,R²-4,R³-13), (I-P3206,A-4,R²-8,R³-10), (I-P3207,A-4,R²-8,R³-11),
(I-P3074,A-4,R²-4,R³-14), (I-P3075,A-4,R²-4,R³-15), (I-P3208,A-4,R²-8,R³-12), (I-P3209,A-4,R²-8,R³-13),
(I-P3076,A-4,R²-4,R³-16), (I-P3077,A-4,R²-4,R³-17), (I-P3210,A-4,R²-8,R³-14), (I-P3211,A-4,R²-8,R³-15),
(I-P3078,A-4,R²-4,R³-18), (I-P3079,A-4,R²-4,R³-19), (I-P3212,A-4,R²-8,R³-16), (I-P3213,A-4,R²-8,R³-17),
(I-P3080,A-4,R²-4,R³-20), (I-P3081,A-4,R²-4,R³-21), (I-P3214,A-4,R²-8,R³-18), (I-P3215,A-4,R²-8,R³-19),
(I-P3082,A-4,R²-4,R³-22), (I-P3083,A-4,R²-4,R³-23), (I-P3216,A-4,R²-8,R³-20), (I-P3217,A-4,R²-8,R³-21),
(I-P3084,A-4,R²-4,R³-24), (I-P3085,A-4,R²-4,R³-25), (I-P3218,A-4,R²-8,R³-22), (I-P3219,A-4,R²-8,R³-23),
(I-P3086,A-4,R²-4,R³-26), (I-P3087,A-4,R²-4,R³-27), (I-P3220,A-4,R²-8,R³-24), (I-P3221,A-4,R²-8,R³-25),
(I-P3088,A-4,R²-4,R³-28), (I-P3089,A-4,R²-4,R³-29), (I-P3222,A-4,R²-8,R³-26), (I-P3223,A-4,R²-8,R³-27),
(I-P3090,A-4,R²-4,R³-30), (I-P3091,A-4,R²-4,R³-31), (I-P3224,A-4,R²-8,R³-28), (I-P3225,A-4,R²-8,R³-29),
(I-P3092,A-4,R²-4,R³-32), (I-P3093,A-4,R²-4,R³-33), (I-P3226,A-4,R²-8,R³-30), (I-P3227,A-4,R²-8,R³-31),
(I-P3094,A-4,R²-4,R³-34), (I-P3095,A-4,R²-5,R³-1), (I-P3228,A-4,R²-8,R³-32), (I-P3229,A-4,R²-8,R³-33),
(I-P3096,A-4,R²-5,R³-2), (I-P3097,A-4,R²-5,R³-3), (I-P3230,A-4,R²-8,R³-34), (I-P3231,A-4,R²-9,R³-1),
(I-P3098,A-4,R²-5,R³-4), (I-P3099,A-4,R²-5,R³-5), (I-P3232,A-4,R²-9,R³-2), (I-P3233,A-4,R²-9,R³-3),
(I-P3100,A-4,R²-5,R³-6), (I-P3101,A-4,R²-5,R³-7), (I-P3234,A-4,R²-9,R³-4), (I-P3235,A-4,R²-9,R³-5),
(I-P3102,A-4,R²-5,R³-8), (I-P3103,A-4,R²-5,R³-9), (I-P3236,A-4,R²-9,R³-6), (I-P3237,A-4,R²-9,R³-7),
(I-P3104,A-4,R²-5,R³-10), (I-P3105,A-4,R²-5,R³-11), (I-P3238,A-4,R²-9,R³-8), (I-P3239,A-4,R²-9,R³-9),
(I-P3106,A-4,R²-5,R³-12), (I-P3107,A-4,R²-5,R³-13), (I-P3240,A-4,R²-9,R³-10), (I-P3241,A-4,R²-9,R³-11),
(I-P3108,A-4,R²-5,R³-14), (I-P3109,A-4,R²-5,R³-15), (I-P3242,A-4,R²-9,R³-12), (I-P3243,A-4,R²-9,R³-13),
(I-P3110,A-4,R²-5,R³-16), (I-P3111,A-4,R²-5,R³-17), (I-P3244,A-4,R²-9,R³-14), (I-P3245,A-4,R²-9,R³-15),
(I-P3112,A-4,R²-5,R³-18), (I-P3113,A-4,R²-5,R³-19), (I-P3246,A-4,R²-9,R³-16), (I-P3247,A-4,R²-9,R³-17),
(I-P3114,A-4,R²-5,R³-20), (I-P3115,A-4,R²-5,R³-21), (I-P3248,A-4,R²-9,R³-18), (I-P3249,A-4,R²-9,R³-19),
(I-P3116,A-4,R²-5,R³-22), (I-P3117,A-4,R²-5,R³-23), (I-P3250,A-4,R²-9,R³-20), (I-P3251,A-4,R²-9,R³-21),
(I-P3118,A-4,R²-5,R³-24), (I-P3119,A-4,R²-5,R³-25), (I-P3252,A-4,R²-9,R³-22), (I-P3253,A-4,R²-9,R³-23),
(I-P3120,A-4,R²-5,R³-26), (I-P3121,A-4,R²-5,R³-27), (I-P3254,A-4,R²-9,R³-24), (I-P3255,A-4,R²-9,R³-25),
(I-P3122,A-4,R²-5,R³-28), (I-P3123,A-4,R²-5,R³-29), (I-P3256,A-4,R²-9,R³-26), (I-P3257,A-4,R²-9,R³-27),
(I-P3124,A-4,R²-5,R³-30), (I-P3125,A-4,R²-5,R³-31), (I-P3258,A-4,R²-9,R³-28), (I-P3259,A-4,R²-9,R³-29),
(I-P3126,A-4,R²-5,R³-32), (I-P3127,A-4,R²-5,R³-33), (I-P3260,A-4,R²-9,R³-30), (I-P3261,A-4,R²-9,R³-31),
(I-P3128,A-4,R²-5,R³-34), (I-P3129,A-4,R²-6,R³-1), (I-P3262,A-4,R²-9,R³-32), (I-P3263,A-4,R²-9,R³-33),
(I-P3130,A-4,R²-6,R³-2), (I-P3131,A-4,R²-6,R³-3), (I-P3264,A-4,R²-9,R³-34), (I-P3265,A-4,R²-10,R³-1),
(I-P3132,A-4,R²-6,R³-4), (I-P3133,A-4,R²-6,R³-5), (I-P3266,A-4,R²-10,R³-2), (I-P3267,A-4,R²-10,R³-3),
(I-P3134,A-4,R²-6,R³-6), (I-P3135,A-4,R²-6,R³-7), (I-P3268,A-4,R²-10,R³-4), (I-P3269,A-4,R²-10,R³-5),
(I-P3136,A-4,R²-6,R³-8), (I-P3137,A-4,R²-6,R³-9), (I-P3270,A-4,R²-10,R³-6), (I-P3271,A-4,R²-10,R³-7),
(I-P3138,A-4,R²-6,R³-10), (I-P3139,A-4,R²-6,R³-11), (I-P3272,A-4,R²-10,R³-8), (I-P3273,A-4,R²-10,R³-9),
(I-P3140,A-4,R²-6,R³-12), (I-P3141,A-4,R²-6,R³-13), (I-P3274,A-4,R²-10,R³-10), (I-P3275,A-4,R²-10,R³-11), (I-P3276,A-4,R²-10,R³-12), (I-P3277,A-4,R²-10,R³-13), (I-P3410,A-4,R²-14,R³-10), (I-P3411,A-4,R²-14,R³-11),
(I-P3278,A-4,R²-10,R³-14), (I-P3279,A-4,R²-10,R³-15), (I-P3412,A-4,R²-14,R³-12), (I-P3413,A-4,R²-14,R³-13),
(I-P3280,A-4,R²-10,R³-16), (I-P3281,A-4,R²-10,R³-17), (I-P3414,A-4,R²-14,R³-14), (I-P3415,A-4,R²-14,R³-15),
(I-P3282,A-4,R²-10,R³-18), (I-P3283,A-4,R²-10,R³-19), (I-P3416,A-4,R²-14,R³-16), (I-P3417,A-4,R²-14,R³-17),
(I-P3284,A-4,R²-10,R³-20), (I-P3285,A-4,R²-10,R³-21), (I-P3418,A-4,R²-14,R³-18), (I-P3419,A-4,R²-14,R³-19),
(I-P3286,A-4,R²-10,R³-22), (I-P3287,A-4,R²-10,R³-23), (I-P3420,A-4,R²-14,R³-20), (I-P3421,A-4,R²-14,R³-21),
(I-P3288,A-4,R²-10,R³-24), (I-P3289,A-4,R²-10,R³-25), (I-P3422,A-4,R²-14,R³-22), (I-P3423,A-4,R²-14,R³-23),
(I-P3290,A-4,R²-10,R³-26), (I-P3291,A-4,R²-10,R³-27), (I-P3424,A-4,R²-14,R³-24), (I-P3425,A-4,R²-14,R³-25),
(I-P3292,A-4,R²-10,R³-28), (I-P3293,A-4,R²-10,R³-29), (I-P3426,A-4,R²-14,R³-26), (I-P3427,A-4,R²-14,R³-27),
(I-P3294,A-4,R²-10,R³-30), (I-P3295,A-4,R²-10,R³-31), (I-P3428,A-4,R²-14,R³-28), (I-P3429,A-4,R²-14,R³-29),
(I-P3296,A-4,R²-10,R³-32), (I-P3297,A-4,R²-10,R³-33), (I-P3430,A-4,R²-14,R³-30), (I-P3431,A-4,R²-14,R³-31),
(I-P3298,A-4,R²-10,R³-34), (I-P3299,A-4,R²-11,R³-1), (I-P3432,A-4,R²-14,R³-32), (I-P3433,A-4,R²-14,R³-33),
(I-P3300,A-4,R²-11,R³-2), (I-P3301,A-4,R²-11,R³-3), (I-P3434,A-4,R²-14,R³-34), (I-P3435,A-4,R²-15,R³-1),
(I-P3302,A-4,R²-11,R³-4), (I-P3303,A-4,R²-11,R³-5), (I-P3436,A-4,R²-15,R³-2), (I-P3437,A-4,R²-15,R³-3),
(I-P3304,A-4,R²-11,R³-6), (I-P3305,A-4,R²-11,R³-7), (I-P3438,A-4,R²-15,R³-4), (I-P3439,A-4,R²-15,R³-5),
(I-P3306,A-4,R²-11,R³-8), (I-P3307,A-4,R²-11,R³-9), (I-P3440,A-4,R²-15,R³-6), (I-P3441,A-4,R²-15,R³-7),
(I-P3308,A-4,R²-11,R³-10), (I-P3309,A-4,R²-11,R³-11), (I-P3442,A-4,R²-15,R³-8), (I-P3443,A-4,R²-15,R³-9),
(I-P3310,A-4,R²-11,R³-12), (I-P3311,A-4,R²-11,R³-13), (I-P3444,A-4,R²-15,R³-10), (I-P3445,A-4,R²-15,R³-11),
(I-P3312,A-4,R²-11,R³-14), (I-P3313,A-4,R²-11,R³-15), (I-P3446,A-4,R²-15,R³-12), (I-P3447,A-4,R²-15,R³-13),
(I-P3314,A-4,R²-11,R³-16), (I-P3315,A-4,R²-11,R³-17), (I-P3448,A-4,R²-15,R³-14), (I-P3449,A-4,R²-15,R³-15),
(I-P3316,A-4,R²-11,R³-18), (I-P3317,A-4,R²-11,R³-19), (I-P3450,A-4,R²-15,R³-16), (I-P3451,A-4,R²-15,R³-17),
(I-P3318,A-4,R²-11,R³-20), (I-P3319,A-4,R²-11,R³-21), (I-P3452,A-4,R²-15,R³-18), (I-P3453,A-4,R²-15,R³-19),
(I-P3320,A-4,R²-11,R³-22), (I-P3321,A-4,R²-11,R³-23), (I-P3454,A-4,R²-15,R³-20), (I-P3455,A-4,R²-15,R³-21),
(I-P3322,A-4,R²-11,R³-24), (I-P3323,A-4,R²-11,R³-25), (I-P3456,A-4,R²-15,R³-22), (I-P3457,A-4,R²-15,R³-23),
(I-P3324,A-4,R²-11,R³-26), (I-P3325,A-4,R²-11,R³-27), (I-P3458,A-4,R²-15,R³-24), (I-P3459,A-4,R²-15,R³-25),
(I-P3326,A-4,R²-11,R³-28), (I-P3327,A-4,R²-11,R³-29), (I-P3460,A-4,R²-15,R³-26), (I-P3461,A-4,R²-15,R³-27),
(I-P3328,A-4,R²-11,R³-30), (I-P3329,A-4,R²-11,R³-31), (I-P3462,A-4,R²-15,R³-28), (I-P3463,A-4,R²-15,R³-29),
(I-P3330,A-4,R²-11,R³-32), (I-P3331,A-4,R²-11,R³-33), (I-P3464,A-4,R²-15,R³-30), (I-P3465,A-4,R²-15,R³-31),
(I-P3332,A-4,R²-11,R³-34), (I-P3333,A-4,R²-12,R³-1), (I-P3466,A-4,R²-15,R³-32), (I-P3467,A-4,R²-15,R³-33),
(I-P3334,A-4,R²-12,R³-2), (I-P3335,A-4,R²-12,R³-3), (I-P3468,A-4,R²-15,R³-34), (I-P3469,A-4,R²-16,R³-1),
(I-P3336,A-4,R²-12,R³-4), (I-P3337,A-4,R²-12,R³-5), (I-P3470,A-4,R²-16,R³-2), (I-P3471,A-4,R²-16,R³-3),
(I-P3338,A-4,R²-12,R³-6), (I-P3339,A-4,R²-12,R³-7), (I-P3472,A-4,R²-16,R³-4), (I-P3473,A-4,R²-16,R³-5),
(I-P3340,A-4,R²-12,R³-8), (I-P3341,A-4,R²-12,R³-9), (I-P3474,A-4,R²-16,R³-6), (I-P3475,A-4,R²-16,R³-7),
(I-P3342,A-4,R²-12,R³-10), (I-P3343,A-4,R²-12,R³-11), (I-P3476,A-4,R²-16,R³-8), (I-P3477,A-4,R²-16,R³-9),
(I-P3344,A-4,R²-12,R³-12), (I-P3345,A-4,R²-12,R³-13), (I-P3478,A-4,R²-16,R³-10), (I-P3479,A-4,R²-16,R³-11),
(I-P3346,A-4,R²-12,R³-14), (I-P3347,A-4,R²-12,R³-15), (I-P3480,A-4,R²-16,R³-12), (I-P3481,A-4,R²-16,R³-13),
(I-P3348,A-4,R²-12,R³-16), (I-P3349,A-4,R²-12,R³-17), (I-P3482,A-4,R²-16,R³-14), (I-P3483,A-4,R²-16,R³-15),
(I-P3350,A-4,R²-12,R³-18), (I-P3351,A-4,R²-12,R³-19), (I-P3484,A-4,R²-16,R³-16), (I-P3485,A-4,R²-16,R³-17),
(I-P3352,A-4,R²-12,R³-20), (I-P3353,A-4,R²-12,R³-21), (I-P3486,A-4,R²-16,R³-18), (I-P3487,A-4,R²-16,R³-19),
(I-P3354,A-4,R²-12,R³-22), (I-P3355,A-4,R²-12,R³-23), (I-P3488,A-4,R²-16,R³-20), (I-P3489,A-4,R²-16,R³-21),
(I-P3356,A-4,R²-12,R³-24), (I-P3357,A-4,R²-12,R³-25), (I-P3490,A-4,R²-16,R³-22), (I-P3491,A-4,R²-16,R³-23),
(I-P3358,A-4,R²-12,R³-26), (I-P3359,A-4,R²-12,R³-27), (I-P3492,A-4,R²-16,R³-24), (I-P3493,A-4,R²-16,R³-25),
(I-P3360,A-4,R²-12,R³-28), (I-P3361,A-4,R²-12,R³-29), (I-P3494,A-4,R²-16,R³-26), (I-P3495,A-4,R²-16,R³-27),
(I-P3362,A-4,R²-12,R³-30), (I-P3363,A-4,R²-12,R³-31), (I-P3496,A-4,R²-16,R³-28), (I-P3497,A-4,R²-16,R³-29),
(I-P3364,A-4,R²-12,R³-32), (I-P3365,A-4,R²-12,R³-33), (I-P3498,A-4,R²-16,R³-30), (I-P3499,A-4,R²-16,R³-31),
(I-P3366,A-4,R²-12,R³-34), (I-P3367,A-4,R²-13,R³-1), (I-P3500,A-4,R²-16,R³-32), (I-P3501,A-4,R²-16,R³-33),
(I-P3368,A-4,R²-13,R³-2), (I-P3369,A-4,R²-13,R³-3), (I-P3502,A-4,R²-16,R³-34), (I-P3503,A-4,R²-17,R³-1),
(I-P3370,A-4,R²-13,R³-4), (I-P3371,A-4,R²-13,R³-5), (I-P3504,A-4,R²-17,R³-2), (I-P3505,A-4,R²-17,R³-3),
(I-P3372,A-4,R²-13,R³-6), (I-P3373,A-4,R²-13,R³-7), (I-P3506,A-4,R²-17,R³-4), (I-P3507,A-4,R²-17,R³-5),
(I-P3374,A-4,R²-13,R³-8), (I-P3375,A-4,R²-13,R³-9), (I-P3508,A-4,R²-17,R³-6), (I-P3509,A-4,R²-17,R³-7),
(I-P3376,A-4,R²-13,R³-10), (I-P3377,A-4,R²-13,R³-11), (I-P3510,A-4,R²-17,R³-8), (I-P3511,A-4,R²-17,R³-9),
(I-P3378,A-4,R²-13,R³-12), (I-P3379,A-4,R²-13,R³-13), (I-P3512,A-4,R²-17,R³-10), (I-P3513,A-4,R²-17,R³-11),
(I-P3380,A-4,R²-13,R³-14), (I-P3381,A-4,R²-13,R³-15), (I-P3514,A-4,R²-17,R³-12), (I-P3515,A-4,R²-17,R³-13),
(I-P3382,A-4,R²-13,R³-16), (I-P3383,A-4,R²-13,R³-17), (I-P3516,A-4,R²-17,R³-14), (I-P3517,A-4,R²-17,R³-15),
(I-P3384,A-4,R²-13,R³-18), (I-P3385,A-4,R²-13,R³-19), (I-P3518,A-4,R²-17,R³-16), (I-P3519,A-4,R²-17,R³-17),
(I-P3386,A-4,R²-13,R³-20), (I-P3387,A-4,R²-13,R³-21), (I-P3520,A-4,R²-17,R³-18), (I-P3521,A-4,R²-17,R³-19),
(I-P3388,A-4,R²-13,R³-22), (I-P3389,A-4,R²-13,R³-23), (I-P3522,A-4,R²-17,R³-20), (I-P3523,A-4,R²-17,R³-21),
(I-P3390,A-4,R²-13,R³-24), (I-P3391,A-4,R²-13,R³-25), (I-P3524,A-4,R²-17,R³-22), (I-P3525,A-4,R²-17,R³-23),
(I-P3392,A-4,R²-13,R³-26), (I-P3393,A-4,R²-13,R³-27), (I-P3526,A-4,R²-17,R³-24), (I-P3527,A-4,R²-17,R³-25),
(I-P3394,A-4,R²-13,R³-28), (I-P3395,A-4,R²-13,R³-29), (I-P3528,A-4,R²-17,R³-26), (I-P3529,A-4,R²-17,R³-27),
(I-P3396,A-4,R²-13,R³-30), (I-P3397,A-4,R²-13,R³-31), (I-P3530,A-4,R²-17,R³-28), (I-P3531,A-4,R²-17,R³-29),
(I-P3398,A-4,R²-13,R³-32), (I-P3399,A-4,R²-13,R³-33), (I-P3532,A-4,R²-17,R³-30), (I-P3533,A-4,R²-17,R³-31),
(I-P3400,A-4,R²-13,R³-34), (I-P3401,A-4,R²-14,R³-1), (I-P3534,A-4,R²-17,R³-32), (I-P3535,A-4,R²-17,R³-33),
(I-P3402,A-4,R²-14,R³-2), (I-P3403,A-4,R²-14,R³-3), (I-P3536,A-4,R²-17,R³-34), (I-P3537,A-4,R²-18,R³-1),
(I-P3404,A-4,R²-14,R³-4), (I-P3405,A-4,R²-14,R³-5), (I-P3538,A-4,R²-18,R³-2), (I-P3539,A-4,R²-18,R³-3),
(I-P3406,A-4,R²-14,R³-6), (I-P3407,A-4,R²-14,R³-7), (I-P3540,A-4,R²-18,R³-4), (I-P3541,A-4,R²-18,R³-5),
(I-P3408,A-4,R²-14,R³-8), (I-P3409,A-4,R²-14,R³-9), (I-P3542,A-4,R²-18,R³-6), (I-P3543,A-4,R²-18,R³-7), (I-P3544,A-4,R²-18,R³-8), (I-P3545,A-4,R²-18,R³-9), (I-P3678,A-4,R²-22,R³-6), (I-P3679,A-4,R²-22,R³-7),
(I-P3546,A-4,R²-18,R³-10), (I-P3547,A-4,R²-18,R³-11), (I-P3680,A-4,R²-22,R³-8), (I-P3681,A-4,R²-22,R³-9),
(I-P3548,A-4,R²-18,R³-12), (I-P3549,A-4,R²-18,R³-13), (I-P3682,A-4,R²-22,R³-10), (I-P3683,A-4,R²-22,R³-11),
(I-P3550,A-4,R²-18,R³-14), (I-P3551,A-4,R²-18,R³-15), (I-P3684,A-4,R²-22,R³-12), (I-P3685,A-4,R²-22,R³-13),
(I-P3552,A-4,R²-18,R³-16), (I-P3553,A-4,R²-18,R³-17), (I-P3686,A-4,R²-22,R³-14), (I-P3687,A-4,R²-22,R³-15),
(I-P3554,A-4,R²-18,R³-18), (I-P3555,A-4,R²-18,R³-19), (I-P3688,A-4,R²-22,R³-16), (I-P3689,A-4,R²-22,R³-17),
(I-P3556,A-4,R²-18,R³-20), (I-P3557,A-4,R²-18,R³-21), (I-P3690,A-4,R²-22,R³-18), (I-P3691,A-4,R²-22,R³-19),
(I-P3558,A-4,R²-18,R³-22), (I-P3559,A-4,R²-18,R³-23), (I-P3692,A-4,R²-22,R³-20), (I-P3693,A-4,R²-22,R³-21),
(I-P3560,A-4,R²-18,R³-24), (I-P3561,A-4,R²-18,R³-25), (I-P3694,A-4,R²-22,R³-22), (I-P3695,A-4,R²-22,R³-23),
(I-P3562,A-4,R²-18,R³-26), (I-P3563,A-4,R²-18,R³-27), (I-P3696,A-4,R²-22,R³-24), (I-P3697,A-4,R²-22,R³-25),
(I-P3564,A-4,R²-18,R³-28), (I-P3565,A-4,R³-18,R³-29), (I-P3698,A-4,R²-22,R³-26), (I-P3699,A-4,R²-22,R³-27),
(I-P3566,A-4,R²-18,R³-30), (I-P3567,A-4,R²-18,R³-31), (I-P3700,A-4,R²-22,R³-28), (I-P3701,A-4,R²-22,R³-29),
(I-P3568,A-4,R²-18,R³-32), (I-P3569,A-4,R²-18,R³-33), (I-P3702,A-4,R²-22,R³-30), (I-P3703,A-4,R²-22,R³-31),
(I-P3570,A-4,R²-18,R³-34), (I-P3571,A-4,R²-19,R³-1), (I-P3704,A-4,R²-22,R³-32), (I-P3705,A-4,R²-22,R³-33),
(I-P3572,A-4,R²-19,R³-2), (I-P3573,A-4,R²-19,R³-3), (I-P3706,A-4,R²-22,R³-34), (I-P3707,A-4,R²-23,R³-1),
(I-P3574,A-4,R²-19,R³-4), (I-P3575,A-4,R²-19,R³-5), (I-P3708,A-4,R²-23,R³-2), (I-P3709,A-4,R²-23,R³-3),
(I-P3576,A-4,R²-19,R³-6), (I-P3577,A-4,R²-19,R³-7), (I-P3710,A-4,R²-23,R³-4), (I-P3711,A-4,R²-23,R³-5),
(I-P3578,A-4,R²-19,R³-8), (I-P3579,A-4,R²-19,R³-9), (I-P3712,A-4,R²-23,R³-6), (I-P3713,A-4,R²-23,R³-7),
(I-P3580,A-4,R²-19,R³-10), (I-P3581,A-4,R²-19,R³-11), (I-P3714,A-4,R²-23,R³-8), (I-P3715,A-4,R²-23,R³-9),
(I-P3582,A-4,R²-19,R³-12), (I-P3583,A-4,R²-19,R³-13), (I-P3716,A-4,R²-23,R³-10), (I-P3717,A-4,R²-23,R³-11),
(I-P3584,A-4,R²-19,R³-14), (I-P3585,A-4,R²-19,R³-15), (I-P3718,A-4,R²-23,R³-12), (I-P3719,A-4,R²-23,R³-13),
(I-P3586,A-4,R²-19,R³-16), (I-P3587,A-4,R²-19,R³-17), (I-P3720,A-4,R²-23,R³-14), (I-P3721,A-4,R²-23,R³-15),
(I-P3588,A-4,R²-19,R³-18), (I-P3589,A-4,R²-19,R³-19), (I-P3722,A-4,R²-23,R³-16), (I-P3723,A-4,R²-23,R³-17),
(I-P3590,A-4,R²-19,R³-20), (I-P3591,A-4,R²-19,R³-21), (I-P3724,A-4,R²-23,R³-18), (I-P3725,A-4,R²-23,R³-19),
(I-P3592,A-4,R²-19,R³-22), (I-P3593,A-4,R²-19,R³-23), (I-P3726,A-4,R²-23,R³-20), (I-P3727,A-4,R²-23,R²-21),
(I-P3594,A-4,R²-19,R³-24), (I-P3595,A-4,R²-19,R³-25), (I-P3728,A-4,R²-23,R³-22), (I-P3729,A-4,R²-23,R³-23),
(I-P3596,A-4,R²-19,R³-26), (I-P3597,A-4,R²-19,R³-27), (I-P3730,A-4,R²-23,R³-24), (I-P3731,A-4,R²-23,R³-25),
(I-P3598,A-4,R²-19,R³-28), (I-P3599,A-4,R²-19,R³-29), (I-P3732,A-4,R²-23,R³-26), (I-P3733,A-4,R²-23,R³-27),
(I-P3600,A-4,R²-19,R³-30), (I-P3601,A-4,R²-19,R³-31), (I-P3734,A-4,R²-23,R³-28), (I-P3735,A-4,R²-23,R³-29),
(I-P3602,A-4,R²-19,R³-32), (I-P3603,A-4,R²-19,R³-33), (I-P3736,A-4,R²-23,R³-30), (I-P3737,A-4,R²-23,R³-31),
(I-P3604,A-4,R²-19,R³-34), (I-P3605,A-4,R²-20,R³-1), (I-P3738,A-4,R²-23,R³-32), (I-P3739,A-4,R²-23,R³-33),
(I-P3606,A-4,R²-20,R³-2), (I-P3607,A-4,R²-20,R³-3), (I-P3740,A-4,R²-23,R³-34), (I-P3741,A-4,R²-24,R³-1),
(I-P3608,A-4,R²-20,R³-4), (I-P3609,A-4,R²-20,R³-5), (I-P3742,A-4,R²-24,R³-2), (I-P3743,A-4,R²-24,R³-3),
(I-P3610,A-4,R²-20,R³-6), (I-P3611,A-4,R²-20,R³-7), (I-P3744,A-4,R²-24,R³-4), (I-P3745,A-4,R²-24,R³-5),
(I-P3612,A-4,R²-20,R³-8), (I-P3613,A-4,R²-20,R³-9), (I-P3746,A-4,R²-24,R³-6), (I-P3747,A-4,R²-24,R³-7),
(I-P3614,A-4,R²-20,R³-10), (I-P3615,A-4,R²-20,R³-11), (I-P3748,A-4,R²-24,R³-8), (I-P3749,A-4,R²-24,R³-9),
(I-P3616,A-4,R²-20,R³-12), (I-P3617,A-4,R²-20,R³-13), (I-P3750,A-4,R²-24,R³-10), (I-P3751,A-4,R²-24,R³-11),
(I-P3618,A-4,R²-20,R³-14), (I-P3619,A-4,R²-20,R³-15), (I-P3752,A-4,R²-24,R³-12), (I-P3753,A-4,R²-24,R³-13),
(I-P3620,A-4,R²-20,R³-16), (I-P3621,A-4,R²-20,R³-17), (I-P3754,A-4,R²-24,R³-14), (I-P3755,A-4,R²-24,R³-15),
(I-P3622,A-4,R²-20,R³-18), (I-P2623,A-4,R²-20,R³-19), (I-P3756,A-4,R²-24,R³-16), (I-P3757,A-4,R²-24,R³-17),
(I-P3624,A-4,R²-20,R³-20), (I-P3625,A-4,R²-20,R³-21), (I-P3758,A-4,R²-24,R³-18), (I-P3759,A-4,R²-24,R³-19),
(I-P3626,A-4,R²-20,R³-22), (I-P3627,A-4,R²-20,R³-23), (I-P3760,A-4,R²-24,R³-20), (I-P3761,A-4,R²-24,R³-21),
(I-P3628,A-4,R²-20,R³-24), (I-P3629,A-4,R²-20,R³-25), (I-P3762,A-4,R²-24,R³-22), (I-P3763,A-4,R²-24,R³-23),
(I-P3630,A-4,R²-20,R³-26), (I-P3631,A-4,R²-20,R³-27), (I-P3764,A-4,R²-24,R³-24), (I-P3765,A-4,R²-24,R³-25),
(I-P3632,A-4,R²-20,R³-28), (I-P3633,A-4,R²-20,R³-29), (I-P3766,A-4,R²-24,R³-26), (I-P3767,A-4,R²-24,R³-27),
(I-P3634,A-4,R²-20,R³-30), (I-P3635,A-4,R²-20,R³-31), (I-P3768,A-4,R²-24,R³-28), (I-P3769,A-4,R²-24,R³-29),
(I-P3636,A-4,R²-20,R³-32), (I-P3637,A-4,R²-20,R³-33), (I-P3770,A-4,R²-24,R³-30), (I-P3771,A-4,R²-24,R³-31),
(I-P3638,A-4,R²-20,R³-34), (I-P3639,A-4,R²-21,R³-1), (I-P3772,A-4,R²-24,R³-32), (I-P3773,A-4,R²-24,R³-33),
(I-P3640,A-4,R²-21,R³-2), (I-P3641,A-4,R²-21,R³-3), (I-P3774,A-4,R²-24,R³-34), (I-P3775,A-4,R²-25,R³-1),
(I-P3642,A-4,R²-21,R³-4), (I-P3643,A-4,R²-21,R³-5), (I-P3776,A-4,R²-25,R³-2), (I-P3777,A-4,R²-25,R³-3),
(I-P3644,A-4,R²-21,R³-6), (I-P3645,A-4,R²-21,R³-7), (I-P3778,A-4,R²-25,R³-4), (I-P3779,A-4,R²-25,R³-5),
(I-P3646,A-4,R²-21,R³-8), (I-P3647,A-4,R²-21,R³-9), (I-P3780,A-4,R²-25,R³-6), (I-P3781,A-4,R²-25,R³-7),
(I-P3648,A-4,R²-21,R³-10), (I-P3649,A-4,R²-21,R³-11), (I-P3782,A-4,R²-25,R³-8), (I-P3783,A-4,R²-25,R³-9),
(I-P3650,A-4,R²-21,R³-12), (I-P3651,A-4,R²-21,R³-13), (I-P3784,A-4,R²-25,R³-10), (I-P3785,A-4,R²-25,R³-11),
(I-P3652,A-4,R²-21,R³-14), (I-P3653,A-4,R²-21,R³-15), (I-P3786,A-4,R²-25,R³-12), (I-P3787,A-4,R²-25,R³-13),
(I-P3654,A-4,R²-21,R³-16), (I-P3655,A-4,R²-21,R³-17), (I-P3788,A-4,R²-25,R³-14), (I-P3789,A-4,R²-25,R³-15),
(I-P3656,A-4,R²-21,R³-18), (I-P3657,A-4,R²-21,R³-19), (I-P3790,A-4,R²-25,R³-16), (I-P3791,A-4,R²-25,R³-17),
(I-P3658,A-4,R²-21,R³-20), (I-P3659,A-4,R²-21,R³-21), (I-P3792,A-4,R²-25,R³-18), (I-P3793,A-4,R²-25,R³-19),
(I-P3660,A-4,R²-21,R³-22), (I-P3661,A-4,R²-21,R³-23), (I-P3794,A-4,R²-25,R³-20), (I-P3795,A-4,R²-25,R³-21),
(I-P3662,A-4,R²-21,R³-24), (I-P3663,A-4,R²-21,R³-25), (I-P3796,A-4,R²-25,R³-22), (I-P3797,A-4,R²-25,R³-23),
(I-P3664,A-4,R²-21,R³-26), (I-P3665,A-4,R²-21,R³-27), (I-P3798,A-4,R²-25,R³-24), (I-P3799,A-4,R²-25,R³-25),
(I-P3666,A-4,R²-21,R³-28), (I-P3667,A-4,R²-21,R³-29), (I-P3800,A-4,R²-25,R³-26), (I-P3801,A-4,R²-25,R³-27),
(I-P3668,A-4,R²-21,R³-30), (I-P3669,A-4,R²-21,R³-31), (I-P3802,A-4,R²-25,R³-28), (I-P3803,A-4,R²-25,R³-29),
(I-P3670,A-4,R²-21,R³-32), (I-P3671,A-4,R²-21,R³-33), (I-P3804,A-4,R²-25,R³-30), (I-P3805,A-4,R²-25,R³-31),
(I-P3672,A-4,R²-21,R³-34), (I-P3673,A-4,R²-22,R³-1), (I-P3806,A-4,R²-25,R³-32), (I-P3807,A-4,R²-25,R³-33),
(I-P3674,A-4,R²-22,R³-2), (I-P3675,A-4,R²-22,R³-3), (I-P3808,A-4,R²-25,R³-34), (I-P3809,A-4,R²-26,R³-1),
(I-P3676,A-4,R²-22,R³-4), (I-P3677,A-4,R²-22,R³-5), (I-P3810,A-4,R²-26,R³-2), (I-P3811,A-4,R²-26,R³-3), (I-P3812,A-4,R²-26,R³-4), (I-P3813,A-4,R²-26,R³-5), (I-P3946,A-5,R²-1,R³-2), (I-P3947,A-5,R²-1,R³-3),
(I-P3814,A-4,R²-26,R³-6), (I-P3815,A-4,R²-26,R³-7), (I-P3948,A-5,R²-1,R³-4), (I-P3949,A-5,R²-1,R³-5),
(I-P3816,A-4,R²-26,R³-8), (I-P3817,A-4,R²-26,R³-9), (I-P3950,A-5,R²-1,R³-6), (I-P3951,A-5,R²-1,R³-7),
(I-P3818,A-4,R²-26,R³-10), (I-P3819,A-4,R²-26,R³-11), (I-P3952,A-5,R²-1,R³-8), (I-P3953,A-5,R²-1,R³-9),
(I-P3820,A-4,R²-26,R³-12), (I-P3821,A-4,R²-26,R³-13), (I-P3954,A-5,R²-1,R³-10), (I-P3955,A-5,R²-1,R³-11),
(I-P3822,A-4,R²-26,R³-14), (I-P3823,A-4,R²-26,R³-15), (I-P3956,A-5,R²-1,R³-12), (I-P3957,A-5,R²-1,R³-13),
(I-P3824,A-4,R²-26,R³-16), (I-P3825,A-4,R²-26,R³-17), (I-P3958,A-5,R²-1,R³-14), (I-P3959,A-5,R²-1,R³-15),
(I-P3826,A-4,R²-26,R³-18), (I-P3827,A-4,R²-26,R³-19), (I-P3960,A-5,R²-1,R³-16), (I-P3961,A-5,R²-1,R³-17),
(I-P3828,A-4,R²-26,R³-20), (I-P3829,A-4,R²-26,R³-21), (I-P3962,A-5,R²-1,R³-18), (I-P3963,A-5,R²-1,R³-19),
(I-P3830,A-4,R²-26,R³-22), (I-P3831,A-4,R²-26,R³-23), (I-P3964,A-5,R²-1,R³-20), (I-P3965,A-5,R²-1,R³-21),
(I-P3832,A-4,R²-26,R³-24), (I-P3833,A-4,R²-26,R³-25), (I-P3966,A-5,R²-1,R³-22), (I-P3967,A-5,R²-1,R³-23),
(I-P3834,A-4,R²-26,R³-26), (I-P3835,A-4,R²-26,R³-27), (I-P3968,A-5,R²-1,R³-24), (I-P3969,A-5,R²-1,R³-25),
(I-P3836,A-4,R²-26,R³-28), (I-P3837,A-4,R²-26,R³-29), (I-P3970,A-5,R²-1,R³-26), (I-P3971,A-5,R²-1,R³-27),
(I-P3838,A-4,R²-26,R³-30), (I-P3839,A-4,R²-26,R³-31), (I-P3972,A-5,R²-1,R³-28), (I-P3973,A-5,R²-1,R³-29),
(I-P3840,A-4,R²-26,R³-32), (I-P3841,A-4,R²-26,R³-33), (I-P3974,A-5,R²-1,R³-30), (I-P3975,A-5,R²-1,R³-31),
(I-P3842,A-4,R²-26,R³-34), (I-P3843,A-4,R²-27,R³-1), (I-P3976,A-5,R²-1,R³-32), (I-P3977,A-5,R²-1,R³-33),
(I-P3844,A-4,R²-27,R³-2), (I-P3845,A-4,R²-27,R³-3), (I-P3978,A-5,R²-1,R³-34), (I-P3979,A-5,R²-2,R³-1),
(I-P3846,A-4,R²-27,R³-4), (I-P3847,A-4,R²-27,R³-5), (I-P3980,A-5,R²-2,R³-2), (I-P3981,A-5,R²-2,R³-3),
(I-P3848,A-4,R²-27,R³-6), (I-P3849,A-4,R²-27,R³-7), (I-P3982,A-5,R²-2,R³-4), (I-P3983,A-5,R²-2,R³-5),
(I-P3850,A-4,R²-27,R³-8), (I-P3851,A-4,R²-27,R³-9), (I-P3984,A-5,R²-2,R³-6), (I-P3985,A-5,R²-2,R³-7),
(I-P3852,A-4,R²-27,R³-10), (I-P3853,A-4,R²-27,R³-11), (I-P3986,A-5,R²-2,R³-8), (I-P3987,A-5,R²-2,R³-9),
(I-P3854,A-4,R²-27,R³-12), (I-P3855,A-4,R²-27,R³-13), (I-P3988,A-5,R²-2,R³-10), (I-P3989,A-5,R²-2,R³-11),
(I-P3856,A-4,R²-27,R³-14), (I-P3857,A-4,R²-27,R³-15), (I-P3990,A-5,R²-2,R³-12), (I-P3991,A-5,R²-2,R³-13),
(I-P3858,A-4,R²-27,R³-16), (I-P3859,A-4,R²-27,R³-17), (I-P3992,A-5,R²-2,R³-14), (I-P3993,A-5,R²-2,R³-15),
(I-P3860,A-4,R²-27,R³-18), (I-P3861,A-4,R²-27,R³-19), (I-P3994,A-5,R²-2,R³-16), (I-P3995,A-5,R²-2,R³-17),
(I-P3862,A-4,R²-27,R³-20), (I-P3863,A-4,R²-27,R³-21), (I-P3996,A-5,R²-2,R³-18), (I-P3997,A-5,R²-2,R³-19),
(I-P3864,A-4,R²-27,R³-22), (I-P3865,A-4,R²-27,R³-23), (I-P3998,A-5,R²-2,R³-20), (I-P3999,A-5,R²-2,R³-21),
(I-P3866,A-4,R³-27,R³-24), (I-P3867,A-4,R²-27,R³-25), (I-P4000,A-5,R²-2,R³-22), (I-P4001,A-5,R²-2,R³-23),
(I-P3868,A-4,R²-27,R³-26), (I-P3869,A-4,R²-27,R³-27), (I-P4002,A-5,R²-2,R³-24), (I-P4003,A-5,R²-2,R³-25),
(I-P3870,A-4,R²-27,R³-28), (I-P3871,A-4,R²-27,R³-29), (I-P4004,A-5,R²-2,R³-26), (I-P4005,A-5,R²-2,R³-27),
(I-P3872,A-4,R²-27,R³-30), (I-P3873,A-4,R²-27,R³-31), (I-P4006,A-5,R²-2,R³-28), (I-P4007,A-5,R²-2,R³-29),
(I-P3874,A-4,R²-27,R³-32), (I-P3875,A-4,R²-27,R³-33), (I-P4008,A-5,R²-2,R³-30), (I-P4009,A-5,R²-2,R³-31),
(I-P3876,A-4,R²-27,R³-34), (I-P3877,A-4,R²-28,R³-1), (I-P4010,A-5,R²-2,R³-32), (I-P4011,A-5,R²-2,R³-33),
(I-P3878,A-4,R²-28,R³-2), (I-P3879,A-4,R²-28,R³-3), (I-P4012,A-5,R²-2,R³-34), 1), (I-P4014,A-5,R²-3,R³-2),
(I-P3880,A-4,R²-28,R³-4), (I-P3881,A-4,R²-28,R³-5), (I-P4015,A-5,R²-3,R³-3), (I-P4016,A-5,R²-3,R³-4),
(I-P3882,A-4,R²-28,R³-6), (I-P3883,A-4,R²-28,R³-7), (I-P4017,A-5,R²-3,R³-5), (I-P4018,A-5,R²-3,R³-6),
(I-P3884,A-4,R²-28,R³-8), (I-P3885,A-4,R²-28,R³-9), (I-P4019,A-5,R²-3,R³-7), (I-P4020,A-5,R²-3,R³-8),
(I-P3886,A-4,R²-28,R³-10), (I-P3887,A-4,R²-28,R³-11), (I-P4021,A-5,R²-3,R³-9), (I-P4022,A-5,R²-3,R³-10),
(I-P3888,A-4,R²-28,R³-12), (I-P3889,A-4,R²-28,R³-13), (I-P4023,A-5,R²-3,R³-11), (I-P4024,A-5,R²-3,R³-12),
(I-P3890,A-4,R²-28,R³-14), (I-P3891,A-4,R²-28,R³-15), (I-P4025,A-5,R²-3,R³-13), (I-P4026,A-5,R²-3,R³-14),
(I-P3892,A-4,R²-28,R³-16), (I-P3893,A-4,R²-28,R³-17), (I-P4027,A-5,R²-3,R³-15), (I-P4028,A-5,R²-3,R³-16),
(I-P3894,A-4,R²-28,R³-18), (I-P3895,A-4,R²-28,R³-19), (I-P4029,A-5,R²-3,R³-17), (I-P4030,A-5,R²-3,R³-18),
(I-P3896,A-4,R²-28,R³-20), (I-P3897,A-4,R²-28,R³-21), (I-P4031,A-5,R²-3,R³-19), (I-P4032,A-5,R²-3,R³-20),
(I-P3898,A-4,R²-28,R³-22), (I-P3899,A-4,R²-28,R³-23), (I-P4033,A-5,R²-3,R³-21), (I-P4034,A-5,R²-3,R³-22),
(I-P3900,A-4,R²-28,R³-24), (I-P3901,A-4,R²-28,R³-25), (I-P4035,A-5,R²-3,R³-23), (I-P4036,A-5,R²-3,R³-24),
(I-P3902,A-4,R²-28,R³-26), (I-P3903,A-4,R²-28,R³-27), (I-P4037,A-5,R²-3,R³-25), (I-P4038,A-5,R²-3,R³-26),
(I-P3904,A-4,R²-28,R³-28), (I-P3905,A-4,R²-28,R³-29), (I-P4039,A-5,R²-3,R³-27), (I-P4040,A-5,R²-3,R³-28),
(I-P3906,A-4,R²-28,R³-30), (I-P3907,A-4,R²-28,R³-31), (I-P4041,A-5,R²-3,R³-29), (I-P4042,A-5,R²-3,R³-30),
(I-P3908,A-4,R²-28,R³-32), (I-P3909,A-4,R²-28,R³-33), (I-P4043,A-5,R²-3,R³-31), (I-P4044,A-5,R²-3,R³-32),
(I-P3910,A-4,R²-28,R³-24), (I-P3911,A-4,R²-29,R³-1), (I-P4045,A-5,R²-3,R³-33), (I-P4046,A-5,R²-3,R³-34),
(I-P3912,A-4,R²-29,R³-2), (I-P3913,A-4,R²-29,R³-3), (I-P4047,A-5,R²-4,R³-1), (I-P4048,A-5,R²-4,R³-2),
(I-P3914,A-4,R²-29,R³-4), (I-P3915,A-4,R²-29,R³-5), (I-P4049,A-5,R²-4,R³-3), (I-P4050,A-5,R²-4,R³-4),
(I-P3916,A-4,R²-29,R³-6), (I-P3917,A-4,R²-29,R³-7), (I-P4051,A-5,R²-4,R³-5), (I-P4052,A-5,R²-4,R³-6),
(I-P3918,A-4,R²-29,R³-8), (I-P3919,A-4,R²-29,R³-9), (I-P4053,A-5,R²-4,R³-7), (I-P4054,A-5,R²-4,R³-8),
(I-P3920,A-4,R²-29,R³-10), (I-P3921,A-4,R²-29,R³-11), (I-P4055,A-5,R²-4,R³-9), (I-P4056,A-5,R²-4,R³-10),
(I-P3922,A-4,R²-29,R³-12), (I-P3923,A-4,R²-29,R³-13), (I-P4057,A-5,R²-4,R³-11), (I-P4058,A-5,R²-4,R³-12),
(I-P3924,A-4,R²-29,R³-14), (I-P3925,A-4,R²-29,R³-15), (I-P4059,A-5,R²-4,R³-13), (I-P4060,A-5,R²-4,R³-14),
(I-P3926,A-4,R²-29,R³-16), (I-P3927,A-4,R²-29,R³-17), (I-P4061,A-5,R²-4,R³-15), (I-P4062,A-5,R²-4,R³-16),
(I-P3928,A-4,R²-29,R³-18), (I-P3929,A-4,R²-29,R³-19), (I-P4063,A-5,R²-4,R³-17), (I-P4064,A-5,R²-4,R³-18),
(I-P3930,A-4,R²-29,R³-20), (I-P3931,A-4,R²-29,R³-21), (I-P4065,A-5,R²-4,R³-19), (I-P4066,A-5,R²-4,R³-20),
(I-P3932,A-4,R²-29,R³-22), (I-P3933,A-4,R²-29,R³-23), (I-P4067,A-5,R²-4,R³-21), (I-P4068,A-5,R²-4,R³-22),
(I-P3934,A-4,R²-29,R³-24), (I-P3935,A-4,R²-29,R³-25), (I-P4069,A-5,R²-4,R³-23), (I-P4070,A-5,R²-4,R³-24),
(I-P3936,A-4,R²-29,R³-26), (I-P3937,A-4,R²-29,R³-27), (I-P4071,A-5,R²-4,R³-25), (I-P4072,A-5,R²-4,R³-26),
(I-P3938,A-4,R²-29,R³-28), (I-P3939,A-4,R²-29,R³-29), (I-P4073,A-5,R²-4,R³-27), (I-P4074,A-5,R²-4,R³-28),
(I-P3940,A-4,R²-29,R³-30), (I-P3941,A-4,R²-29,R³-31), (I-P4075,A-5,R²-4,R³-29), (I-P4076,A-5,R²-4,R³-30),
(I-P3942,A-4,R²-29,R³-32), (I-P3943,A-4,R²-29,R³-33), (I-P4077,A-5,R²-4,R³-31), (I-P4078,A-5,R²-4,R³-32),
(I-P3944,A-4,R²-29,R³-34), (I-P3945,A-5,R²-1,R³-1), (I-P4079,A-5,R²-4,R³-33), (I-P4080,A-5,R²-4,R³-34), (I-P4081,A-5,$R^2$-5,$R^3$-1), (I-P4082,A-5,$R^2$-5,$R^3$-2), (I-P4215,A-5,$R^2$-8,$R^3$-33), (I-P4216,A-5,$R^2$-8,$R^3$-34),
(I-P4083,A-5,$R^2$-5,$R^3$-3), (I-P4084,A-5,$R^2$-5,$R^3$-4), (I-P4217,A-5,$R^2$-9,$R^3$-1), (I-P4218,A-5,$R^2$-9,$R^3$-2),
(I-P4085,A-5,$R^2$-5,$R^3$-5), (I-P4086,A-5,$R^2$-5,$R^3$-6), (I-P4219,A-5,$R^2$-9,$R^3$-3), (I-P4220,A-5,$R^2$-9,$R^3$-4),
(I-P4087,A-5,$R^2$-5,$R^3$-7), (I-P4088,A-5,$R^2$-5,$R^3$-8), (I-P4221,A-5,$R^2$-9,$R^3$-5), (I-P4222,A-5,$R^2$-9,$R^3$-6),
(I-P4089,A-5,$R^2$-5,$R^3$-9), (I-P4090,A-5,$R^2$-5,$R^3$-10), (I-P4223,A-5,$R^2$-9,$R^3$-7), (I-P4224,A-5,$R^2$-9,$R^3$-8),
(I-P4091,A-5,$R^2$-5,$R^3$-11), (I-P4092,A-5,$R^2$-5,$R^3$-12), (I-P4225,A-5,$R^2$-9,$R^3$-9), (I-P4226,A-5,$R^2$-9,$R^3$-10),
(I-P4093,A-5,$R^2$-5,$R^3$-13), (I-P4094,A-5,$R^2$-5,$R^3$-14), (I-P4227,A-5,$R^2$-9,$R^3$-11), (I-P4228,A-5,$R^2$-9,$R^3$-12),
(I-P4095,A-5,$R^2$-5,$R^3$-15), (I-P4096,A-5,$R^2$-5,$R^3$-16), (I-P4229,A-5,$R^2$-9,$R^3$-13), (I-P4230,A-5,$R^2$-9,$R^3$-14),
(I-P4097,A-5,$R^2$-5,$R^3$-17), (I-P4098,A-5,$R^2$-5,$R^3$-18), (I-P4231,A-5,$R^2$-9,$R^3$-15), (I-P4232,A-5,$R^2$-9,$R^3$-16),
(I-P4099,A-5,$R^2$-5,$R^3$-19), (I-P4100,A-5,$R^2$-5,$R^3$-20), (I-P4233,A-5,$R^2$-9,$R^3$-17), (I-P4234,A-5,$R^2$-9,$R^3$-18),
(I-P4101,A-5,$R^2$-5,$R^3$-21), (I-P4102,A-5,$R^2$-5,$R^3$-22), (I-P4235,A-5,$R^2$-9,$R^3$-19), (I-P4236,A-5,$R^2$-9,$R^3$-20),
(I-P4103,A-5,$R^2$-5,$R^3$-23), (I-P4104,A-5,$R^2$-5,$R^3$-24), (I-P4237,A-5,$R^2$-9,$R^3$-21), (I-P4238,A-5,$R^2$-9,$R^3$-22),
(I-P4105,A-5,$R^2$-5,$R^3$-25), (I-P4106,A-5,$R^2$-5,$R^3$-26), (I-P4239,A-5,$R^2$-9,$R^3$-23), (I-P4240,A-5,$R^2$-9,$R^3$-24),
(I-P4107,A-5,$R^2$-5,$R^3$-27), (I-P4108,A-5,$R^2$-5,$R^3$-28), (I-P4241,A-5,$R^2$-9,$R^3$-25), (I-P4242,A-5,$R^2$-9,$R^3$-26),
(I-P4109,A-5,$R^2$-5,$R^3$-29), (I-P4110,A-5,$R^2$-5,$R^3$-30), (I-P4243,A-5,$R^2$-9,$R^3$-27), (I-P4244,A-5,$R^2$-9,$R^3$-28),
(I-P4111,A-5,$R^2$-5,$R^3$-31), (I-P4112,A-5,$R^2$-5,$R^3$-32), (I-P4245,A-5,$R^2$-9,$R^3$-29), (I-P4246,A-5,$R^2$-9,$R^3$-30),
(I-P4113,A-5,$R^2$-5,$R^3$-33), (I-P4114,A-5,$R^2$-5,$R^3$-34), (I-P4247,A-5,$R^2$-9,$R^3$-31), (I-P4248,A-5,$R^2$-9,$R^3$-32),
(I-P4115,A-5,$R^2$-6,$R^3$-1), (I-P4116,A-5,$R^2$-6,$R^3$-2), (I-P4249,A-5,$R^2$-9,$R^3$-33), (I-P4250,A-5,$R^2$-9,$R^3$-34),
(I-P4117,A-5,$R^2$-6,$R^3$-3), (I-P4118,A-5,$R^2$-6,$R^3$-4), (I-P4251,A-5,$R^2$-10,$R^3$-1), (I-P4252,A-5,$R^2$-10,$R^3$-2),
(I-P4119,A-5,$R^2$-6,$R^3$-5), (I-P4120,A-5,$R^2$-6,$R^3$-6), (I-P4253,A-5,$R^2$-10,$R^3$-3), (I-P4254,A-5,$R^2$-10,$R^3$-4),
(I-P4121,A-5,$R^2$-6,$R^3$-7), (I-P4122,A-5,$R^2$-6,$R^3$-8), (I-P4255,A-5,$R^2$-10,$R^3$-5), (I-P4256,A-5,$R^2$-10,$R^3$-6),
(I-P4123,A-5,$R^2$-6,$R^3$-9), (I-P4124,A-5,$R^2$-6,$R^3$-10), (I-P4257,A-5,$R^2$-10,$R^3$-7), (I-P4258,A-5,$R^2$-10,$R^3$-8),
(I-P4125,A-5,$R^2$-6,$R^3$-11), (I-P4126,A-5,$R^2$-6,$R^3$-12), (I-P4259,A-5,$R^2$-10,$R^3$-9), (I-P4260,A-5,$R^2$-10,$R^3$-10),
(I-P4127,A-5,$R^2$-6,$R^3$-13), (I-P4128,A-5,$R^2$-6,$R^3$-14), (I-P4261,A-5,$R^2$-10,$R^3$-11), (I-P4262,A-5,$R^2$-10,$R^3$-12),
(I-P4129,A-5,$R^2$-6,$R^3$-15), (I-P4130,A-5,$R^2$-6,$R^3$-16), (I-P4263,A-5,$R^2$-10,$R^3$-13), (I-P4264,A-5,$R^2$-10,$R^3$-14),
(I-P4131,A-5,$R^2$-6,$R^3$-17), (I-P4132,A-5,$R^2$-6,$R^3$-18), (I-P4265,A-5,$R^2$-10,$R^3$-15), (I-P4266,A-5,$R^2$-10,$R^3$-16),
(I-P4133,A-5,$R^2$-6,$R^3$-19), (I-P4134,A-5,$R^2$-6,$R^3$-20), (I-P4267,A-5,$R^2$-10,$R^3$-17), (I-P4268,A-5,$R^2$-10,$R^3$-18),
(I-P4135,A-5,$R^2$-6,$R^3$-21), (I-P4136,A-5,$R^2$-6,$R^3$-22), (I-P4269,A-5,$R^2$-10,$R^3$-19), (I-P4270,A-5,$R^2$-10,$R^3$-20),
(I-P4137,A-5,$R^2$-6,$R^3$-23), (I-P4138,A-5,$R^2$-6,$R^3$-24), (I-P4271,A-5,$R^2$-10,$R^3$-21), (I-P4272,A-5,$R^2$-10,$R^3$-22),
(I-P4139,A-5,$R^2$-6,$R^3$-25), (I-P4140,A-5,$R^2$-6,$R^3$-26), (I-P4273,A-5,$R^2$-10,$R^3$-23), (I-P4274,A-5,$R^2$-10,$R^3$-24),
(I-P4141,A-5,$R^2$-6,$R^3$-27), (I-P4142,A-5,$R^2$-6,$R^3$-28), (I-P4275,A-5,$R^2$-10,$R^3$-25), (I-P4276,A-5,$R^2$-10,$R^3$-26),
(I-P4143,A-5,$R^2$-6,$R^3$-29), (I-P4144,A-5,$R^2$-6,$R^3$-30), (I-P4277,A-5,$R^2$-10,$R^3$-27), (I-P4278,A-5,$R^2$-10,$R^3$-28),
(I-P4145,A-5,$R^2$-6,$R^3$-31), (I-P4146,A-5,$R^2$-6,$R^3$-32), (I-P4279,A-5,$R^2$-10,$R^3$-29), (I-P4280,A-5,$R^2$-10,$R^3$-30),
(I-P4147,A-5,$R^2$-6,$R^3$-33), (I-P4148,A-5,$R^2$-6,$R^3$-34), (I-P4281,A-5,$R^2$-10,$R^3$-31), (I-P4282,A-5,$R^2$-10,$R^3$-32),
(I-P4149,A-5,$R^2$-7,$R^3$-1), (I-P4150,A-5,$R^2$-7,$R^3$-2), (I-P4283,A-5,$R^2$-10,$R^3$-33), (I-P4284,A-5,$R^2$-10,$R^3$-34),
(I-P4151,A-5,$R^2$-7,$R^3$-3), (I-P4152,A-5,$R^2$-7,$R^3$-4), (I-P4285,A-5,$R^2$-11,$R^3$-1), (I-P4286,A-5,$R^2$-11,$R^3$-2),
(I-P4153,A-5,$R^2$-7,$R^3$-5), (I-P4154,A-5,$R^2$-7,$R^3$-6), (I-P4287,A-5,$R^2$-11,$R^3$-3), (I-P4288,A-5,$R^2$-11,$R^3$-4),
(I-P4155,A-5,$R^2$-7,$R^3$-7), (I-P4156,A-5,$R^2$-7,$R^3$-8), (I-P4289,A-5,$R^2$-11,$R^3$-5), (I-P4290,A-5,$R^2$-11,$R^3$-6),
(I-P4157,A-5,$R^2$-7,$R^3$-9), (I-P4158,A-5,$R^2$-7,$R^3$-10), (I-P4291,A-5,$R^2$-11,$R^3$-7), (I-P4292,A-5,$R^2$-11,$R^3$-8),
(I-P4159,A-5,$R^2$-7,$R^3$-11), (I-P4160,A-5,$R^2$-7,$R^3$-12), (I-P4293,A-5,$R^2$-11,$R^3$-9), (I-P4294,A-5,$R^2$-11,$R^3$-10),
(I-P4161,A-5,$R^2$-7,$R^3$-13), (I-P4162,A-5,$R^2$-7,$R^3$-14), (I-P4295,A-5,$R^2$-11,$R^3$-11), (I-P4296,A-5,$R^2$-11,$R^3$-12),
(I-P4163,A-5,$R^2$-7,$R^3$-15), (I-P4164,A-5,$R^2$-7,$R^3$-16), (I-P4297,A-5,$R^2$-11,$R^3$-13), (I-P4298,A-5,$R^2$-11,$R^3$-14),
(I-P4165,A-5,$R^2$-7,$R^3$-17), (I-P4166,A-5,$R^2$-7,$R^3$-18), (I-P4299,A-5,$R^2$-11,$R^3$-15), (I-P4300,A-5,$R^2$-11,$R^3$-16),
(I-P4167,A-5,$R^2$-7,$R^3$-19), (I-P4168,A-5,$R^2$-7,$R^3$-20), (I-P4301,A-5,$R^2$-11,$R^3$-17), (I-P4302,A-5,$R^2$-11,$R^3$-18),
(I-P4169,A-5,$R^2$-7,$R^3$-21), (I-P4170,A-5,$R^2$-7,$R^3$-22), (I-P4303,A-5,$R^2$-11,$R^3$-19), (I-P4304,A-5,$R^2$-11,$R^3$-20),
(I-P4171,A-5,$R^2$-7,$R^3$-23), (I-P4172,A-5,$R^2$-7,$R^3$-24), (I-P4305,A-5,$R^2$-11,$R^3$-21), (I-P4306,A-5,$R^2$-11,$R^3$-22),
(I-P4173,A-5,$R^2$-7,$R^3$-25), (I-P4174,A-5,$R^2$-7,$R^3$-26), (I-P4307,A-5,$R^2$-11,$R^3$-23), (I-P4308,A-5,$R^2$-11,$R^3$-24),
(I-P4175,A-5,$R^2$-7,$R^3$-27), (I-P4176,A-5,$R^2$-7,$R^3$-28), (I-P4309,A-5,$R^2$-11,$R^3$-25), (I-P4310,A-5,$R^2$-11,$R^3$-26),
(I-P4177,A-5,$R^2$-7,$R^3$-29), (I-P4178,A-5,$R^2$-7,$R^3$-30), (I-P4311,A-5,$R^2$-11,$R^3$-27), (I-P4312,A-5,$R^2$-11,$R^3$-28),
(I-P4179,A-5,$R^2$-7,$R^3$-31), (I-P4180,A-5,$R^2$-7,$R^3$-32), (I-P4313,A-5,$R^2$-11,$R^3$-29), (I-P4314,A-5,$R^2$-11,$R^3$-30),
(I-P4181,A-5,$R^2$-7,$R^3$-33), (I-P4182,A-5,$R^2$-7,$R^3$-34), (I-P4315,A-5,$R^2$-11,$R^3$-31), (I-P4316,A-5,$R^2$-11,$R^3$-32),
(I-P4183,A-5,$R^2$-8,$R^3$-1), (I-P4184,A-5,$R^2$-8,$R^3$-2), (I-P4317,A-5,$R^2$-11,$R^3$-33), (I-P4318,A-5,$R^2$-11,$R^3$-34),
(I-P4185,A-5,$R^2$-8,$R^3$-3), (I-P4186,A-5,$R^2$-8,$R^3$-4), (I-P4319,A-5,$R^2$-12,$R^3$-1), (I-P4320,A-5,$R^2$-12,$R^3$-2),
(I-P4187,A-5,$R^2$-8,$R^3$-5), (I-P4188,A-5,$R^2$-8,$R^3$-6), (I-P4321,A-5,$R^2$-12,$R^3$-3), (I-P4322,A-5,$R^2$-12,$R^3$-4),
(I-P4189,A-5,$R^2$-8,$R^3$-7), (I-P4190,A-5,$R^2$-8,$R^3$-8), (I-P4323,A-5,$R^2$-12,$R^3$-5), (I-P4324,A-5,$R^2$-12,$R^3$-6),
(I-P4191,A-5,$R^2$-8,$R^3$-9), (I-P4192,A-5,$R^2$-8,$R^3$-10), (I-P4325,A-5,$R^2$-12,$R^3$-7), (I-P4326,A-5,$R^2$-12,$R^3$-8),
(I-P4193,A-5,$R^2$-8,$R^3$-11), (I-P4194,A-5,$R^2$-8,$R^3$-12), (I-P4327,A-5,$R^2$-12,$R^3$-9), (I-P4328,A-5,$R^2$-12,$R^3$-10),
(I-P4195,A-5,$R^2$-8,$R^3$-13), (I-P4196,A-5,$R^2$-8,$R^3$-14), (I-P4329,A-5,$R^2$-12,$R^3$-11), (I-P4330,A-5,$R^2$-12,$R^3$-12),
(I-P4197,A-5,$R^2$-8,$R^3$-15), (I-P4198,A-5,$R^2$-8,$R^3$-16), (I-P4331,A-5,$R^2$-12,$R^3$-13), (I-P4332,A-5,$R^2$-12,$R^3$-14),
(I-P4199,A-5,$R^2$-8,$R^3$-17), (I-P4200,A-5,$R^2$-8,$R^3$-18), (I-P4333,A-5,$R^2$-12,$R^3$-15), (I-P4334,A-5,$R^2$-12,$R^3$-16),
(I-P4201,A-5,$R^2$-8,$R^3$-19), (I-P4202,A-5,$R^2$-8,$R^3$-20), (I-P4335,A-5,$R^2$-12,$R^3$-17), (I-P4336,A-5,$R^2$-12,$R^3$-18),
(I-P4203,A-5,$R^2$-8,$R^3$-21), (I-P4204,A-5,$R^2$-8,$R^3$-22), (I-P4337,A-5,$R^2$-12,$R^3$-19), (I-P4338,A-5,$R^2$-12,$R^3$-20),
(I-P4205,A-5,$R^2$-8,$R^3$-23), (I-P4206,A-5,$R^2$-8,$R^3$-24), (I-P4339,A-5,$R^2$-12,$R^3$-21), (I-P4340,A-5,$R^2$-12,$R^3$-22),
(I-P4207,A-5,$R^2$-8,$R^3$-25), (I-P4208,A-5,$R^2$-8,$R^3$-26), (I-P4341,A-5,$R^2$-12,$R^3$-23), (I-P4342,A-5,$R^2$-12,$R^3$-24),
(I-P4209,A-5,$R^2$-8,$R^3$-27), (I-P4210,A-5,$R^2$-8,$R^3$-28), (I-P4343,A-5,$R^2$-12,$R^3$-25), (I-P4344,A-5,$R^2$-12,$R^3$-26),
(I-P4211,A-5,$R^2$-8,$R^3$-29), (I-P4212,A-5,$R^2$-8,$R^3$-30), (I-P4345,A-5,$R^2$-12,$R^3$-27), (I-P4346,A-5,$R^2$-12,$R^3$-28),
(I-P4213,A-5,$R^2$-8,$R^3$-31), (I-P4214,A-5,$R^2$-8,$R^3$-32), (I-P4347,A-5,$R^2$-12,$R^3$-29), (I-P4348,A-5,$R^2$-12,$R^3$-30), (I-P4349,A-5,R²-12,R³-31), (I-P4350,A-5,R²-12,R³-32), (I-P4483,A-5,R²-16,R³-29), (I-P4484,A-5,R²-16,R³-30),
(I-P4351,A-5,R²-12,R³-33), (I-P4352,A-5,R²-12,R³-34), (I-P4485,A-5,R²-16,R³-31), (I-P4486,A-5,R²-16,R³-32),
(I-P4353,A-5,R²-13,R³-1), (I-P4354,A-5,R²-13,R³-2), (I-P4487,A-5,R²-16,R³-33), (I-P4488,A-5,R²-16,R³-34),
(I-P4355,A-5,R²-13,R³-3), (I-P4356,A-5,R²-13,R³-4), (I-P4489,A-5,R²-17,R³-1), (I-P4490,A-5,R²-17,R³-2),
(I-P4357,A-5,R²-13,R³-5), (I-P4358,A-5,R²-13,R³-6), (I-P4491,A-5,R²-17,R³-3), (I-P4492,A-5,R²-17,R³-4),
(I-P4359,A-5,R²-13,R³-7), (I-P4360,A-5,R²-13,R³-8), (I-P4493,A-5,R²-17,R³-5), (I-P4494,A-5,R²-17,R³-6),
(I-P4361,A-5,R²-13,R³-9), (I-P4362,A-5,R²-13,R³-10), (I-P4495,A-5,R²-17,R³-7), (I-P4496,A-5,R²-17,R³-8),
(I-P4363,A-5,R²-13,R³-11), (I-P4364,A-5,R²-13,R³-12), (I-P4497,A-5,R²-17,R³-9), (I-P4498,A-5,R²-17,R³-10),
(I-P4365,A-5,R²-13,R³-13), (I-P4366,A-5,R²-13,R³-14), (I-P4499,A-5,R²-17,R³-11), (I-P4500,A-5,R²-17,R³-12),
(I-P4367,A-5,R²-13,R³-15), (I-P4368,A-5,R²-13,R³-16), (I-P4501,A-5,R²-17,R³-13), (I-P4502,A-5,R²-17,R³-14),
(I-P4369,A-5,R²-13,R³-17), (I-P4370,A-5,R²-13,R³-18), (I-P4503,A-5,R²-17,R³-15), (I-P4504,A-5,R²-17,R³-16),
(I-P4371,A-5,R²-13,R³-19), (I-P4372,A-5,R²-13,R³-20), (I-P4505,A-5,R²-17,R³-17), (I-P4506,A-5,R²-17,R³-18),
(I-P4373,A-5,R²-13,R³-21), (I-P4374,A-5,R²-13,R³-22), (I-P4507,A-5,R²-17,R³-19), (I-P4508,A-5,R²-17,R³-20),
(I-P4375,A-5,R²-13,R³-23), (I-P4376,A-5,R²-13,R³-24), (I-P4509,A-5,R²-17,R³-21), (I-P4510,A-5,R²-17,R³-22),
(I-P4377,A-5,R²-13,R³-25), (I-P4378,A-5,R²-13,R³-26), (I-P4511,A-5,R²-17,R³-23), (I-P4512,A-5,R²-17,R³-24),
(I-P4379,A-5,R²-13,R³-27), (I-P4380,A-5,R²-13,R³-28), (I-P4513,A-5,R²-17,R³-25), (I-P4514,A-5,R²-17,R³-26),
(I-P4381,A-5,R²-13,R³-29), (I-P4382,A-5,R²-13,R³-30), (I-P4515,A-5,R²-17,R³-27), (I-P4516,A-5,R²-17,R³-28),
(I-P4383,A-5,R²-13,R³-31), (I-P4384,A-5,R²-13,R³-32), (I-P4517,A-5,R²-17,R³-29), (I-P4518,A-5,R²-17,R³-30),
(I-P4385,A-5,R²-13,R³-33), (I-P4386,A-5,R²-13,R³-34), (I-P4519,A-5,R²-17,R³-31), (I-P4520,A-5,R²-17,R³-32),
(I-P4387,A-5,R²-14,R³-1), (I-P4388,A-5,R²-14,R³-2), (I-P4521,A-5,R²-17,R³-33), (I-P4522,A-5,R²-17,R³-34),
(I-P4389,A-5,R²-14,R³-3), (I-P4390,A-5,R²-14,R³-4), (I-P4523,A-5,R²-18,R³-1), (I-P4524,A-5,R²-18,R³-2),
(I-P4391,A-5,R²-14,R³-5), (I-P4392,A-5,R²-14,R³-6), (I-P4525,A-5,R²-18,R³-3), (I-P4526,A-5,R²-18,R³-4),
(I-P4393,A-5,R²-14,R³-7), (I-P4394,A-5,R²-14,R³-8), (I-P4527,A-5,R²-18,R³-5), (I-P4528,A-5,R²-18,R³-6),
(I-P4395,A-5,R²-14,R³-9), (I-P4396,A-5,R²-14,R³-10), (I-P4529,A-5,R²-18,R³-7), (I-P4530,A-5,R²-18,R³-8),
(I-P4397,A-5,R²-14,R³-11), (I-P4398,A-5,R²-14,R³-12), (I-P4531,A-5,R²-18,R³-9), (I-P4532,A-5,R²-18,R³-10),
(I-P4399,A-5,R²-14,R³-13), (I-P4400,A-5,R²-14,R³-14), (I-P4533,A-5,R²-18,R³-11), (I-P4534,A-5,R²-18,R³-12),
(I-P4401,A-5,R²-14,R³-15), (I-P4402,A-5,R²-14,R³-16), (I-P4535,A-5,R²-18,R³-13), (I-P4536,A-5,R²-18,R³-14),
(I-P4403,A-5,R²-14,R³-17), (I-P4404,A-5,R²-14,R³-18), (I-P4537,A-5,R²-18,R³-15), (I-P4538,A-5,R²-18,R³-16),
(I-P4405,A-5,R²-14,R³-19), (I-P4406,A-5,R²-14,R³-20), (I-P4539,A-5,R²-18,R³-17), (I-P4540,A-5,R²-18,R³-18),
(I-P4407,A-5,R²-14,R³-21), (I-P4408,A-5,R²-14,R³-22), (I-P4541,A-5,R²-18,R³-19), (I-P4542,A-5,R²-18,R³-20),
(I-P4409,A-5,R²-14,R³-23), (I-P4410,A-5,R²-14,R³-24), (I-P4543,A-5,R²-18,R³-21), (I-P4544,A-5,R²-18,R³-22),
(I-P4411,A-5,R²-14,R³-25), (I-P4412,A-5,R²-14,R³-26), (I-P4545,A-5,R²-18,R³-23), (I-P4546,A-5,R²-18,R³-24),
(I-P4413,A-5,R²-14,R³-27), (I-P4414,A-5,R²-14,R³-28), (I-P4547,A-5,R²-18,R³-25), (I-P4548,A-5,R²-18,R³-26),
(I-P4415,A-5,R²-14,R³-29), (I-P4416,A-5,R²-14,R³-30), (I-P4549,A-5,R²-18,R³-27), (I-P4550,A-5,R²-18,R³-28),
(I-P4417,A-5,R²-14,R³-31), (I-P4418,A-5,R²-14,R³-32), (I-P4551,A-5,R²-18,R³-29), (I-P4552,A-5,R²-18,R³-30),
(I-P4419,A-5,R²-14,R³-33), (I-P4420,A-5,R²714,R³-34), (I-P4553,A-5,R²-18,R³-31), (I-P4554,A-5,R²-18,R³-32),
(I-P4421,A-5,R²-15,R³-1), (I-P4422,A-5,R²-15,R³-2), (I-P4555,A-5,R²-18,R³-33), (I-P4556,A-5,R²-18,R³-34),
(I-P4423,A-5,R²-15,R³-3), (I-P4424,A-5,R²-15,R³-4), (I-P4557,A-5,R²-19,R³-1), (I-P4558,A-5,R²-19,R³-2),
(I-P4425,A-5,R²-15,R³-5), (I-P4426,A-5,R²-15,R³-6), (I-P4559,A-5,R²-19,R³-3), (I-P4560,A-5,R²-19,R³-4),
(I-P4427,A-5,R²-15,R³-7), (I-P4428,A-5,R²-15,R³-8), (I-P4561,A-5,R²-19,R³-5), (I-P4562,A-5,R²-19,R³-6),
(I-P4429,A-5,R²-15,R³-9), (I-P4430,A-5,R²-15,R³-10), (I-P4563,A-5,R²-19,R³-7), (I-P4564,A-5,R²-19,R³-8),
(I-P4431,A-5,R²-15,R³-11), (I-P4432,A-5,R²-15,R³-12), (I-P4565,A-5,R²-19,R³-9), (I-P4566,A-5,R²-19,R³-10),
(I-P4433,A-5,R²-15,R³-13), (I-P4434,A-5,R²-15,R³-14), (I-P4567,A-5,R²-19,R³-11), (I-P4568,A-5,R²-19,R³-12),
(I-P4435,A-5,R²-15,R³-15), (I-P4436,A-5,R²-15,R³-16), (I-P4569,A-5,R²-19,R³-13), (I-P4570,A-5,R²-19,R³-14),
(I-P4437,A-5,R²-15,R³-17), (I-P4438,A-5,R²-15,R³-18), (I-P4571,A-5,R²-19,R³-15), (I-P4572,A-5,R²-19,R³-16),
(I-P4439,A-5,R²-15,R³-19), (I-P4440,A-5,R²-15,R³-20), (I-P4573,A-5,R²-19,R³-17), (I-P4574,A-5,R²-19,R³-18),
(I-P4441,A-5,R²-15,R³-21), (I-P4442,A-5,R²-15,R³-22), (I-P4575,A-5,R²-19,R³-19), (I-P4576,A-5,R²-19,R³-20),
(I-P4443,A-5,R²-15,R³-23), (I-P4444,A-5,R²-15,R³-24), (I-P4577,A-5,R²-19,R³-21), (I-P4578,A-5,R²-19,R³-22),
(I-P4445,A-5,R²-15,R³-25), (I-P4446,A-5,R²-15,R³-26), (I-P4579,A-5,R²-19,R³-23), (I-P4580,A-5,R²-19,R³-24),
(I-P4447,A-5,R²-15,R³-27), (I-P4448,A-5,R²-15,R³-28), (I-P4581,A-5,R²-19,R³-25), (I-P4582,A-5,R²-19,R³-26),
(I-P4449,A-5,R²-15,R³-29), (I-P4450,A-5,R²-15,R³-30), (I-P4583,A-5,R²-19,R³-27), (I-P4584,A-5,R²-19,R³-28),
(I-P4451,A-5,R²-15,R³-31), (I-P4452,A-5,R²-15,R³-32), (I-P4585,A-5,R²-19,R³-29), (I-P4586,A-5,R²-19,R³-30),
(I-P4453,A-5,R²-15,R³-33), (I-P4454,A-5,R²-15,R³-34), (I-P4587,A-5,R²-19,R³-31), (I-P4588,A-5,R²-19,R³-32),
(I-P4455,A-5,R²-16,R³-1), (I-P4456,A-5,R²-16,R³-2), (I-P4589,A-5,R²-19,R³-33), (I-P4590,A-5,R²-19,R³-34),
(I-P4457,A-5,R²-16,R³-3), (I-P4458,A-5,R²-16,R³-4), (I-P4591,A-5,R²-20,R³-1), (I-P4592,A-5,R²-20,R³-2),
(I-P4459,A-5,R²-16,R³-5), (I-P4460,A-5,R²-16,R³-6), (I-P4593,A-5,R²-20,R³-3), (I-P4594,A-5,R²-20,R³-4),
(I-P4461,A-5,R²-16,R³-7), (I-P4462,A-5,R²-16,R³-8), (I-P4595,A-5,R²-20,R³-5), (I-P4596,A-5,R²-20,R³-6),
(I-P4463,A-5,R²-16,R³-9), (I-P4464,A-5,R²-16,R³-10), (I-P4597,A-5,R²-20,R³-7), (I-P4598,A-5,R²-20,R³-8),
(I-P4465,A-5,R²-16,R³-11), (I-P4466,A-5,R²-16,R³-12), (I-P4599,A-5,R²-20,R³-9), (I-P4600,A-5,R²-20,R³-10),
(I-P4467,A-5,R²-16,R³-13), (I-P4468,A-5,R²-16,R³-14), (I-P4601,A-5,R²-20,R³-11), (I-P4602,A-5,R²-20,R³-12),
(I-P4469,A-5,R²-16,R³-15), (I-P4470,A-5,R²-16,R³-16), (I-P4603,A-5,R²-20,R³-13), (I-P4604,A-5,R²-20,R³-14),
(I-P4471,A-5,R²-16,R³-17), (I-P4472,A-5,R²-16,R³-18), (I-P4605,A-5,R²-20,R³-15), (I-P4606,A-5,R²-20,R³-16),
(I-P4473,A-5,R²-16,R³-19), (I-P4474,A-5,R²-16,R³-20), (I-P4607,A-5,R²-20,R³-17), (I-P4608,A-5,R²-20,R³-18),
(I-P4475,A-5,R²-16,R³-21), (I-P4476,A-5,R²-16,R³-22), (I-P4609,A-5,R²-20,R³-19), (I-P4610,A-5,R²-20,R³-20),
(I-P4477,A-5,R²-16,R³-23), (I-P4478,A-5,R²-16,R³-24), (I-P4611,A-5,R²-20,R³-21), (I-P4612,A-5,R²-20,R³-22),
(I-P4479,A-5,R²-16,R³-25), (I-P4480,A-5,R²-16,R³-26), (I-P4613,A-5,R²-20,R³-23), (I-P4614,A-5,R²-20,R³-24),
(I-P4481,A-5,R²-16,R³-27), (I-P4482,A-5,R²-16,R³-28), (I-P4615,A-5,R²-20,R³-25), (I-P4616,A-5,R²-20,R³-26), (I-P4617,A-5,R²-20,R³-27), (I-P4618,A-5,R²-20,R³-28), (I-P4751,A-5,R²-24,R³-25), (I-P4752,A-5,R²-24,R³-26),
(I-P4619,A-5,R²-20,R³-29), (I-P4620,A-5,R²-20,R³-30), (I-P4753,A-5,R²-24,R³-27), (I-P4754,A-5,R²-24,R³-28),
(I-P4621,A-5,R²-20,R³-31), (I-P4622,A-5,R²-20,R³-32), (I-P4755,A-5,R²-24,R³-29), (I-P4756,A-5,R²-24,R³-30),
(I-P4623,A-5,R²-20,R³-33), (I-P4624,A-5,R²-20,R³-34), (I-P4757,A-5,R²-24,R³-31), (I-P4758,A-5,R²-24,R³-32),
(I-P4625,A-5,R²-21,R³-1), (I-P4626,A-5,R²-21,R³-2), (I-P4759,A-5,R²-24,R³-33), (I-P4760,A-5,R²-24,R³-34),
(I-P4627,A-5,R²-21,R³-3), (I-P4628,A-5,R²-21,R³-4), (I-P4761,A-5,R²-25,R³-1), (I-P4762,A-5,R²-25,R³-2),
(I-P4629,A-5,R²-21,R³-5), (I-P4630,A-5,R²-21,R³-6), (I-P4763,A-5,R²-25,R³-3), (I-P4764,A-5,R²-25,R³-4),
(I-P4631,A-5,R²-21,R³-7), (I-P4632,A-5,R²-21,R³-8), (I-P4765,A-5,R²-25,R³-5), (I-P4766,A-5,R²-25,R³-6),
(I-P4633,A-5,R²-21,R³-9), (I-P4634,A-5,R²-21,R³-10), (I-P4767,A-5,R²-25,R³-7), (I-P4768,A-5,R²-25,R³-8),
(I-P4635,A-5,R²-21,R³-11), (I-P4636,A-5,R²-21,R³-12), (I-P4769,A-5,R²-25,R³-9), (I-P4770,A-5,R²-25,R³-10),
(I-P4637,A-5,R²-21,R³-13), (I-P4638,A-5,R²-21,R³-14), (I-P4771,A-5,R²-25,R³-11), (I-P4772,A-5,R²-25,R³-12),
(I-P4639,A-5,R²-21,R³-15), (I-P4640,A-5,R²-21,R³-16), (I-P4773,A-5,R²-25,R³-13), (I-P4774,A-5,R²-25,R³-14),
(I-P4641,A-5,R²-21,R³-17), (I-P4642,A-5,R²-21,R³-18), (I-P4775,A-5,R²-25,R³-15), (I-P4776,A-5,R²-25,R³-16),
(I-P4643,A-5,R²-21,R³-19), (I-P4644,A-5,R²-21,R³-20), (I-P4777,A-5,R²-25,R³-17), (I-P4778,A-5,R²-25,R³-18),
(I-P4645,A-5,R²-21,R³-21), (I-P4646,A-5,R²-21,R³-22), (I-P4779,A-5,R²-25,R³-19), (I-P4780,A-5,R²-25,R³-20),
(I-P4647,A-5,R²-21,R³-23), (I-P4648,A-5,R²-21,R³-24), (I-P4781,A-5,R²-25,R³-21), (I-P4782,A-5,R²-25,R³-22),
(I-P4649,A-5,R²-21,R³-25), (I-P4650,A-5,R²-21,R³-26), (I-P4783,A-5,R²-25,R³-23), (I-P4784,A-5,R²-25,R³-24),
(I-P4651,A-5,R²-21,R³-27), (I-P4652,A-5,R²-21,R³-28), (I-P4785,A-5,R²-25,R³-25), (I-P4786,A-5,R²-25,R³-26),
(I-P4653,A-5,R²-21,R³-29), (I-P4654,A-5,R²-21,R³-30), (I-P4787,A-5,R²-25,R³-27), (I-P4788,A-5,R²-25,R³-28),
(I-P4655,A-5,R²-21,R³-31), (I-P4656,A-5,R²-21,R³-32), (I-P4789,A-5,R²-25,R³-29), (I-P4790,A-5,R²-25,R³-30),
(I-P4657,A-5,R²-21,R³-33), (I-P4658,A-5,R²-21,R³-34), (I-P4791,A-5,R²-25,R³-31), (I-P4792,A-5,R²-25,R³-32),
(I-P4659,A-5,R²-22,R³-1), (I-P4660,A-5,R²-22,R³-2), (I-P4793,A-5,R²-25,R³-33), (I-P4794,A-5,R²-25,R³-34),
(I-P4661,A-5,R²-22,R³-3), (I-P4662,A-5,R²-22,R³-4), (I-P4795,A-5,R²-26,R³-1), (I-P4796,A-5,R²-26,R³-2),
(I-P4663,A-5,R²-22,R³-5), (I-P4664,A-5,R²-22,R³-6), (I-P4797,A-5,R²-26,R³-3), (I-P4798,A-5,R²-26,R³-4),
(I-P4665,A-5,R²-22,R³-7), (I-P4666,A-5,R²-22,R³-8), (I-P4799,A-5,R²-26,R³-5), (I-P4800,A-5,R²-26,R³-6),
(I-P4667,A-5,R²-22,R³-9), (I-P4668,A-5,R²-22,R³-10), (I-P4801,A-5,R²-26,R³-7), (I-P4802,A-5,R²-26,R³-8),
(I-P4669,A-5,R²-22,R³-11), (I-P4670,A-5,R²-22,R³-12), (I-P4803,A-5,R²-26,R³-9), (I-P4804,A-5,R²-26,R³-10),
(I-P4671,A-5,R²-22,R³-13), (I-P4672,A-5,R²-22,R³-14), (I-P4805,A-5,R²-26,R³-11), (I-P4806,A-5,R²-26,R³-12),
(I-P4673,A-5,R²-22,R³-15), (I-P4674,A-5,R²-22,R³-16), (I-P4807,A-5,R²-26,R³-13), (I-P4808,A-5,R²-26,R³-14),
(I-P4675,A-5,R²-22,R³-17), (I-P4676,A-5,R²-22,R³-18), (I-P4809,A-5,R²-26,R³-15), (I-P4810,A-5,R²-26,R³-16),
(I-P4677,A-5,R²-22,R³-19), (I-P4678,A-5,R²-22,R³-20), (I-P4811,A-5,R²-26,R³-17), (I-P4812,A-5,R²-26,R³-18),
(I-P4679,A-5,R²-22,R³-21), (I-P4680,A-5,R²-22,R³-22), (I-P4813,A-5,R²-26,R³-19), (I-P4814,A-5,R²-26,R³-20),
(I-P4681,A-5,R²-22,R³-23), (I-P4682,A-5,R²-22,R³-24), (I-P4815,A-5,R²-26,R³-21), (I-P4816,A-5,R²-26,R³-22),
(I-P4683,A-5,R²-22,R³-25), (I-P4684,A-5,R²-22,R³-26), (I-P4817,A-5,R²-26,R³-23), (I-P4818,A-5,R²-26,R³-24),
(I-P4685,A-5,R²-22,R³-27), (I-P4686,A-5,R²-22,R³-28), (I-P4819,A-5,R²-26,R³-25), (I-P4820,A-5,R²-26,R³-26),
(I-P4687,A-5,R²-22,R³-29), (I-P4688,A-5,R²-22,R³-30), (I-P4821,A-5,R²-26,R³-27), (I-P4822,A-5,R²-26,R³-28),
(I-P4689,A-5,R²-22,R³-31), (I-P4690,A-5,R²-22,R³-32), (I-P4823,A-5,R²-26,R³-29), (I-P4824,A-5,R²-26,R³-30),
(I-P4691,A-5,R²-22,R³-33), (I-P4692,A-5,R²-22,R³-34), (I-P4825,A-5,R²-26,R³-31), (I-P4826,A-5,R²-26,R³-32),
(I-P4693,A-5,R²-23,R³-1), (I-P4694,A-5,R²-23,R³-2), (I-P4827,A-5,R²-26,R³-33), (I-P4828,A-5,R²-26,R³-34),
(I-P4695,A-5,R²-23,R³-3), (I-P4696,A-5,R²-23,R³-4), (I-P4829,A-5,R²-27,R³-1), (I-P4830,A-5,R²-27,R³-2),
(I-P4697,A-5,R²-23,R³-5), (I-P4698,A-5,R²-23,R³-6), (I-P4831,A-5,R²-27,R³-3), (I-P4832,A-5,R²-27,R³-4),
(I-P4699,A-5,R²-23,R³-7), (I-P4700,A-5,R²-23,R³-8), (I-P4833,A-5,R²-27,R³-5), (I-P4834,A-5,R²-27,R³-6),
(I-P4701,A-5,R²-23,R³-9), (I-P4702,A-5,R²-23,R³-10), (I-P4835,A-5,R²-27,R³-7), (I-P4836,A-5,R²-27,R³-8),
(I-P4703,A-5,R²-23,R³-11), (I-P4704,A-5,R²-23,R³-12), (I-P4837,A-5,R²-27,R³-9), (I-P4838,A-5,R²-27,R³-10),
(I-P4705,A-5,R²-23,R³-13), (I-P4706,A-5,R²-23,R³-14), (I-P4839,A-5,R²-27,R³-11), (I-P4840,A-5,R²-27,R³-12),
(I-P4707,A-5,R²-23,R³-15), (I-P4708,A-5,R²-23,R³-16), (I-P4841,A-5,R²-27,R³-13), (I-P4842,A-5,R²-27,R³-14),
(I-P4709,A-5,R²-23,R³-17), (I-P4710,A-5,R²-23,R³-18), (I-P4843,A-5,R²-27,R³-15), (I-P4844,A-5,R²-27,R³-16),
(I-P4711,A-5,R²-23,R³-19), (I-P4712,A-5,R²-23,R³-20), (I-P4845,A-5,R²-27,R³-17), (I-P4846,A-5,R²-27,R³-18),
(I-P4713,A-5,R²-23,R³-21), (I-P4714,A-5,R²-23,R³-22), (I-P4847,A-5,R²-27,R³-19), (I-P4848,A-5,R²-27,R³-20),
(I-P4715,A-5,R²-23,R³-23), (I-P4716,A-5,R²-23,R³-24), (I-P4849,A-5,R²-27,R³-21), (I-P4850,A-5,R²-27,R³-22),
(I-P4717,A-5,R²-23,R³-25), (I-P4718,A-5,R²-23,R³-26), (I-P4851,A-5,R²-27,R³-23), (I-P4852,A-5,R²-27,R³-24),
(I-P4719,A-5,R²-23,R³-27), (I-P4720,A-5,R²-23,R³-28), (I-P4853,A-5,R²-27,R³-25), (I-P4854,A-5,R²-27,R³-26),
(I-P4721,A-5,R²-23,R³-29), (I-P4722,A-5,R²-23,R³-30), (I-P4855,A-5,R²-27,R³-27), (I-P4856,A-5,R²-27,R³-28),
(I-P4723,A-5,R²-23,R³-31), (I-P4724,A-5,R²-23,R³-32), (I-P4857,A-5,R²-27,R³-29), (I-P4858,A-5,R²-27,R³-30),
(I-P4725,A-5,R²-23,R³-33), (I-P4726,A-5,R²-23,R³-34), (I-P4859,A-5,R²-27,R³-31), (I-P4860,A-5,R²-27,R³-32),
(I-P4727,A-5,R²-24,R³-1), (I-P4728,A-5,R²-24,R³-2), (I-P4861,A-5,R²-27,R³-33), (I-P4862,A-5,R²-27,R³-34),
(I-P4729,A-5,R²-24,R³-3), (I-P4730,A-5,R²-24,R³-4), (I-P4863,A-5,R²-28,R³-1), (I-P4864,A-5,R²-28,R³-2),
(I-P4731,A-5,R²-24,R³-5), (I-P4732,A-5,R²-24,R³-6), (I-P4865,A-5,R²-28,R³-3), (I-P4866,A-5,R²-28,R³-4),
(I-P4733,A-5,R²-24,R³-7), (I-P4734,A-5,R²-24,R³-8), (I-P4867,A-5,R²-28,R³-5), (I-P4868,A-5,R²-28,R³-6),
(I-P4735,A-5,R²-24,R³-9), (I-P4736,A-5,R²-24,R³-10), (I-P4869,A-5,R²-28,R³-7), (I-P4870,A-5,R²-28,R³-8),
(I-P4737,A-5,R²-24,R³-11), (I-P4738,A-5,R²-24,R³-12), (I-P4871,A-5,R²-28,R³-9), (I-P4872,A-5,R²-28,R³-10),
(I-P4739,A-5,R²-24,R³-13), (I-P4740,A-5,R²-24,R³-14), (I-P4873,A-5,R²-28,R³-11), (I-P4874,A-5,R²-28,R³-12),
(I-P4741,A-5,R²-24,R³-15), (I-P4742,A-5,R²-24,R³-16), (I-P4875,A-5,R²-28,R³-13), (I-P4876,A-5,R²-28,R³-14),
(I-P4743,A-5,R²-24,R³-17), (I-P4744,A-5,R²-24,R³-18), (I-P4877,A-5,R²-28,R³-15), (I-P4878,A-5,R²-28,R³-16),
(I-P4745,A-5,R²-24,R³-19), (I-P4746,A-5,R²-24,R³-20), (I-P4879,A-5,R²-28,R³-17), (I-P4880,A-5,R²-28,R³-18),
(I-P4747,A-5,R²-24,R³-21), (I-P4748,A-5,R²-24,R³-22), (I-P4881,A-5,R²-28,R³-19), (I-P4882,A-5,R²-28,R³-20),
(I-P4749,A-5,R²-24,R³-23), (I-P4750,A-5,R²-24,R³-24), (I-P4883,A-5,R²-28,R³-21), (I-P4884,A-5,R²-28,R³-22), (I-P4885,A-5,R²-28,R³-23), (I-P4886,A-5,R²-28,R³-24), (I-P5019,A-6,R²-3,R³-21), (I-P5020,A-6,R²-3,R³-22),
(I-P4887,A-5,R²-28,R³-25), (I-P4888,A-5,R²-28,R³-26), (I-P5021,A-6,R²-3,R³-23), (I-P5022,A-6,R²-3,R³-24),
(I-P4889,A-5,R²-28,R³-27), (I-P4890,A-5,R²-28,R³-28), (I-P5023,A-6,R²-3,R³-25), (I-P5024,A-6,R²-3,R³-26),
(I-P4891,A-5,R²-28,R³-29), (I-P4892,A-5,R²-28,R³-30), (I-P5025,A-6,R²-3,R³-27), (I-P5026,A-6,R²-3,R³-28),
(I-P4893,A-5,R²-28,R³-31), (I-P4894,A-5,R²-28,R³-32), (I-P5027,A-6,R²-3,R³-29), (I-P5028,A-6,R²-3,R³-30),
(I-P4895,A-5,R²-28,R³-33), (I-P4896,A-5,R²-28,R³-34), (I-P5029,A-6,R²-3,R³-31), (I-P5030,A-6,R²-3,R³-32),
(I-P4897,A-5,R²-29,R³-1), (I-P4898,A-5,R²-29,R³-2), (I-P5031,A-6,R²-3,R³-33), (I-P5032,A-6,R²-3,R³-34),
(I-P4899,A-5,R²-29,R³-3), (I-P4900,A-5,R²-29,R³-4), (I-P5033,A-6,R²-4,R³-1), (I-P5034,A-6,R²-4,R³-2),
(I-P4901,A-5,R²-29,R³-5), (I-P4902,A-5,R²-29,R³-6), (I-P5035,A-6,R²-4,R³-3), (I-P5036,A-6,R²-4,R³-4),
(I-P4903,A-5,R²-29,R³-7), (I-P4904,A-5,R²-29,R³-8), (I-P5037,A-6,R²-4,R³-5), (I-P5038,A-6,R²-4,R³-6),
(I-P4905,A-5,R²-29,R³-9), (I-P4906,A-5,R²-29,R³-10), (I-P5039,A-6,R²-4,R³-7), (I-P5040,A-6,R²-4,R³-8),
(I-P4907,A-5,R²-29,R³-11), (I-P4908,A-5,R²-29,R³-12), (I-P5041,A-6,R²-4,R³-9), (I-P5042,A-6,R²-4,R³-10),
(I-P4909,A-5,R²-29,R³-13), (I-P4910,A-5,R²-29,R³-14), (I-P5043,A-6,R²-4,R³-11), (I-P5044,A-6,R²-4,R³-12),
(I-P4911,A-5,R²-29,R³-15), (I-P4912,A-5,R²-29,R³-16), (I-P5045,A-6,R²-4,R³-13), (I-P5046,A-6,R²-4,R³-14),
(I-P4913,A-5,R²-29,R³-17), (I-P4914,A-5,R²-29,R³-18), (I-P5047,A-6,R²-4,R³-15), (I-P5048,A-6,R²-4,R³-16),
(I-P4915,A-5,R²-29,R³-19), (I-P4916,A-5,R²-29,R³-20), (I-P5049,A-6,R²-4,R³-17), (I-P5050,A-6,R²-4,R³-18),
(I-P4917,A-5,R²-29,R³-21), (I-P4918,A-5,R²-29,R³-22), (I-P5051,A-6,R²-4,R³-19), (I-P5052,A-6,R²-4,R³-20),
(I-P4919,A-5,R²-29,R³-23), (I-P4920,A-5,R²-29,R³-24), (I-P5053,A-6,R²-4,R³-21), (I-P5054,A-6,R²-4,R³-22),
(I-P4921,A-5,R²-29,R³-25), (I-P4922,A-5,R²-29,R³-26), (I-P5055,A-6,R²-4,R³-23), (I-P5056,A-6,R²-4,R³-24),
(I-P4923,A-5,R²-29,R³-27), (I-P4924,A-5,R²-29,R³-28), (I-P5057,A-6,R²-4,R³-25), (I-P5058,A-6,R²-4,R³-26),
(I-P4925,A-5,R²-29,R³-29), (I-P4926,A-5,R²-29,R³-30), (I-P5059,A-6,R²-4,R³-27), (I-P5060,A-6,R²-4,R³-28),
(I-P4927,A-5,R²-29,R³-31), (I-P4928,A-5,R²-29,R³-32), (I-P5061,A-6,R²-4,R³-29), (I-P5062,A-6,R²-4,R³-30),
(I-P4929,A-5,R²-29,R³-33), (I-P4930,A-5,R²-29,R³-34), (I-P5063,A-6,R²-4,R³-31), (I-P5064,A-6,R²-4,R³-32),
(I-P4931,A-6,R²-1,R³-1), (I-P4932,A-6,R²-1,R³-2), (I-P5065,A-6,R²-4,R³-33), (I-P5066,A-6,R²-4,R³-34),
(I-P4933,A-6,R²-1,R³-3), (I-P4934,A-6,R²-1,R³-4), (I-P5067,A-6,R²-5,R³-1), (I-P5068,A-6,R²-5,R³-2),
(I-P4935,A-6,R²-1,R³-5), (I-P4936,A-6,R²-1,R³-6), (I-P5069,A-6,R²-5,R³-3), (I-P5070,A-6,R²-5,R³-4),
(I-P4937,A-6,R²-1,R³-7), (I-P4938,A-6,R²-1,R³-8), (I-P5071,A-6,R²-5,R³-5), (I-P5072,A-6,R²-5,R³-6),
(I-P4939,A-6,R²-1,R³-9), (I-P4940,A-6,R²-1,R³-10), (I-P5073,A-6,R²-5,R³-7), (I-P5074,A-6,R²-5,R³-8),
(I-P4941,A-6,R²-1,R³-11), (I-P4942,A-6,R²-1,R³-12), (I-P5075,A-6,R²-5,R³-9), (I-P5076,A-6,R²-5,R³-10),
(I-P4943,A-6,R²-1,R³-13), (I-P4944,A-6,R²-1,R³-14), (I-P5077,A-6,R²-5,R³-11), (I-P5078,A-6,R²-5,R³-12),
(I-P4945,A-6,R²-1,R³-15), (I-P4946,A-6,R²-1,R³-16), (I-P5079,A-6,R²-5,R³-13), (I-P5080,A-6,R²-5,R³-14),
(I-P4947,A-6,R²-1,R³-17), (I-P4948,A-6,R²-1,R³-18), (I-P5081,A-6,R²-5,R³-15), (I-P5082,A-6,R²-5,R³-16),
(I-P4949,A-6,R²-1,R³-19), (I-P4950,A-6,R²-1,R³-20), (I-P5083,A-6,R²-5,R³-17), (I-P5084,A-6,R²-5,R³-18),
(I-P4951,A-6,R²-1,R³-21), (I-P4952,A-6,R²-1,R³-22), (I-P5085,A-6,R²-5,R³-19), (I-P5086,A-6,R²-5,R³-20),
(I-P4953,A-6,R²-1,R³-23), (I-P4954,A-6,R²-1,R³-24), (I-P5087,A-6,R²-5,R³-21), (I-P5088,A-6,R²-5,R³-22),
(I-P4955,A-6,R²-1,R³-25), (I-P4956,A-6,R²-1,R³-26), (I-P5089,A-6,R²-5,R³-23), (I-P5090,A-6,R²-5,R³-24),
(I-P4957,A-6,R²-1,R³-27), (I-P4958,A-6,R²-1,R³-28), (I-P5091,A-6,R²-5,R³-25), (I-P5092,A-6,R²-5,R³-26),
(I-P4959,A-6,R²-1,R³-29), (I-P4960,A-6,R²-1,R³-30), (I-P5093,A-6,R²-5,R³-27), (I-P5094,A-6,R²-5,R³-28),
(I-P4961,A-6,R²-1,R³-31), (I-P4962,A-6,R²-1,R³-32), (I-P5095,A-6,R²-5,R³-29), (I-P5096,A-6,R²-5,R³-30),
(I-P4963,A-6,R²-1,R³-33), (I-P4964,A-6,R²-1,R³-34), (I-P5097,A-6,R²-5,R³-31), (I-P5098,A-6,R²-5,R³-32),
(I-P4965,A-6,R²-2,R³-1), (I-P4966,A-6,R²-2,R³-2), (I-P5099,A-6,R²-5,R³-33), (I-P5100,A-6,R²-5,R³-34),
(I-P4967,A-6,R²-2,R³-3), (I-P4968,A-6,R²-2,R³-4), (I-P5101,A-6,R²-6,R³-1), (I-P5102,A-6,R²-6,R³-2),
(I-P4969,A-6,R²-2,R³-5), (I-P4970,A-6,R²-2,R³-6), (I-P5103,A-6,R²-6,R³-3), (I-P5104,A-6,R²-6,R³-4),
(I-P4971,A-6,R²-2,R³-7), (I-P4972,A-6,R²-2,R³-8), (I-P5105,A-6,R²-6,R³-5), (I-P5106,A-6,R²-6,R³-6),
(I-P4973,A-6,R²-2,R³-9), (I-P4974,A-6,R²-2,R³-10), (I-P5107,A-6,R²-6,R³-7), (I-P5108,A-6,R²-6,R³-8),
(I-P4975,A-6,R²-2,R³-11), (I-P4976,A-6,R²-2,R³-12), (I-P5109,A-6,R²-6,R³-9), (I-P5110,A-6,R²-6,R³-10),
(I-P4977,A-6,R²-2,R³-13), (I-P4978,A-6,R²-2,R³-14), (I-P5111,A-6,R²-6,R³-11), (I-P5112,A-6,R²-6,R³-12),
(I-P4979,A-6,R²-2,R³-15), (I-P4980,A-6,R²-2,R³-16), (I-P5113,A-6,R²-6,R³-13), (I-P5114,A-6,R²-6,R³-14),
(I-P4981,A-6,R²-2,R³-17), (I-P4982,A-6,R²-2,R³-18), (I-P5115,A-6,R²-6,R³-15), (I-P5116,A-6,R²-6,R³-16),
(I-P4983,A-6,R²-2,R³-19), (I-P4984,A-6,R²-2,R³-20), (I-P5117,A-6,R²-6,R³-17), (I-P5118,A-6,R²-6,R³-18),
(I-P4985,A-6,R²-2,R³-21), (I-P4986,A-6,R²-2,R³-22), (I-P5119,A-6,R²-6,R³-19), (I-P5120,A-6,R²-6,R³-20),
(I-P4987,A-6,R²-2,R³-23), (I-P4988,A-6,R²-2,R³-24), (I-P5121,A-6,R²-6,R³-21), (I-P5122,A-6,R²-6,R³-22),
(I-P4989,A-6,R²-2,R³-25), (I-P4990,A-6,R²-2,R³-26), (I-P5123,A-6,R²-6,R³-23), (I-P5124,A-6,R²-6,R³-24),
(I-P4991,A-6,R²-2,R³-27), (I-P4992,A-6,R²-2,R³-28), (I-P5125,A-6,R²-6,R³-25), (I-P5126,A-6,R²-6,R³-26),
(I-P4993,A-6,R²-2,R³-29), (I-P4994,A-6,R²-2,R³-30), (I-P5127,A-6,R²-6,R³-27), (I-P5128,A-6,R²-6,R³-28),
(I-P4995,A-6,R²-2,R³-31), (I-P4996,A-6,R²-2,R³-32), (I-P5129,A-6,R²-6,R³-29), (I-P5130,A-6,R²-6,R³-30),
(I-P4997,A-6,R²-2,R³-33), (I-P4998,A-6,R²-2,R³-34), (I-P5131,A-6,R²-6,R³-31), (I-P5132,A-6,R²-6,R³-32),
(I-P4999,A-6,R²-3,R³-1), (I-P5000,A-6,R²-3,R³-2), (I-P5133,A-6,R²-6,R³-33), (I-P5134,A-6,R²-6,R³-34),
(I-P5001,A-6,R²-3,R³-3), (I-P5002,A-6,R²-3,R³-4), (I-P5135,A-6,R²-7,R³-1), (I-P5136,A-6,R²-7,R³-2),
(I-P5003,A-6,R²-3,R³-5), (I-P5004,A-6,R²-3,R³-6), (I-P5137,A-6,R²-7,R³-3), (I-P5138,A-6,R²-7,R³-4),
(I-P5005,A-6,R²-3,R³-7), (I-P5006,A-6,R²-3,R³-8), (I-P5139,A-6,R²-7,R³-5), (I-P5140,A-6,R²-7,R³-6),
(I-P5007,A-6,R²-3,R³-9), (I-P5008,A-6,R²-3,R³-10), (I-P5141,A-6,R²-7,R³-7), (I-P5142,A-6,R²-7,R³-8),
(I-P5009,A-6,R²-3,R³-11), (I-P5010,A-6,R²-3,R³-12), (I-P5143,A-6,R²-7,R³-9), (I-P5144,A-6,R²-7,R³-10),
(I-P5011,A-6,R²-3,R³-13), (I-P5012,A-6,R²-3,R³-14), (I-P5145,A-6,R²-7,R³-11), (I-P5146,A-6,R²-7,R³-12),
(I-P5013,A-6,R²-3,R³-15), (I-P5014,A-6,R²-3,R³-16), (I-P5147,A-6,R²-7,R³-13), (I-P5148,A-6,R²-7,R³-14),
(I-P5015,A-6,R²-3,R³-17), (I-P5016,A-6,R²-3,R³-18), (I-P5149,A-6,R²-7,R³-15), (I-P5150,A-6,R²-7,R³-16),
(I-P5017,A-6,R²-3,R³-19), (I-P5018,A-6,R²-3,R³-20), (I-P5151,A-6,R²-7,R³-17), (I-P5152,A-6,R²-7,R³-18)

(I-P5153,A-6,R²-7,R³-19), (I-P5154,A-6,R²-7,R³-20), (I-P5287,A-6,R²-11,R³-17), (I-P5288,A-6,R²-11,R³-18),
(I-P5155,A-6,R²-7,R³-21), (I-P5156,A-6,R²-7,R³-22), (I-P5289,A-6,R²-11,R³-19), (I-P5290,A-6,R²-11,R³-20),
(I-P5157,A-6,R²-7,R³-23), (I-P5158,A-6,R²-7,R³-24), (I-P5291,A-6,R²-11,R³-21), (I-P5292,A-6,R²-11,R³-22),
(I-P5159,A-6,R²-7,R³-25), (I-P5160,A-6,R²-7,R³-26), (I-P5293,A-6,R²-11,R³-23), (I-P5294,A-6,R²-11,R³-24),
(I-P5161,A-6,R²-7,R³-27), (I-P5162,A-6,R²-7,R³-28), (I-P5295,A-6,R²-11,R³-25), (I-P5296,A-6,R²-11,R³-26),
(I-P5163,A-6,R²-7,R³-29), (I-P5164,A-6,R²-7,R³-30), (I-P5297,A-6,R²-11,R³-27), (I-P5298,A-6,R²-11,R³-28),
(I-P5165,A-6,R²-7,R³-31), (I-P5166,A-6,R²-7,R³-32), (I-P5299,A-6,R²-11,R³-29), (I-P5300,A-6,R²-11,R³-30),
(I-P5167,A-6,R²-7,R³-33), (I-P5168,A-6,R²-7,R³-34), (I-P5301,A-6,R²-11,R³-31), (I-P5302,A-6,R²-11,R³-32),
(I-P5169,A-6,R²-8,R³-1), (I-P5170,A-6,R²-8,R³-2), (I-P5303,A-6,R²-11,R³-33), (I-P5304,A-6,R²-11,R³-34),
(I-P5171,A-6,R²-8,R³-3), (I-P5172,A-6,R²-8,R³-4), (I-P5305,A-6,R²-12,R³-1), (I-P5306,A-6,R²-12,R³-2),
(I-P5173,A-6,R²-8,R³-5), (I-P5174,A-6,R²-8,R³-6), (I-P5307,A-6,R²-12,R³-3), (I-P5308,A-6,R²-12,R³-4),
(I-P5175,A-6,R²-8,R³-7), (I-P5176,A-6,R²-8,R³-8), (I-P5309,A-6,R²-12,R³-5), (I-P5310,A-6,R²-12,R³-6),
(I-P5177,A-6,R²-8,R³-9), (I-P5178,A-6,R²-8,R³-10), (I-P5311,A-6,R²-12,R³-7), (I-P5312,A-6,R²-12,R³-8),
(I-P5179,A-6,R²-8,R³-11), (I-P5180,A-6,R²-8,R³-12), (I-P5313,A-6,R²-12,R³-9), (I-P5314,A-6,R²-12,R³-10),
(I-P5181,A-6,R²-8,R³-13), (I-P5182,A-6,R²-8,R³-14), (I-P5315,A-6,R²-12,R³-11), (I-P5316,A-6,R²-12,R³-12),
(I-P5183,A-6,R²-8,R³-15), (I-P5184,A-6,R²-8,R³-16), (I-P5317,A-6,R²-12,R³-13), (I-P5318,A-6,R²-12,R³-14),
(I-P5185,A-6,R²-8,R³-17), (I-P5186,A-6,R²-8,R³-18), (I-P5319,A-6,R²-12,R³-15), (I-P5320,A-6,R²-12,R³-16),
(I-P5187,A-6,R²-8,R³-19), (I-P5188,A-6,R²-8,R³-20), (I-P5321,A-6,R²-12,R³-17), (I-P5322,A-6,R²-12,R³-18),
(I-P5189,A-6,R²-8,R³-21), (I-P5190,A-6,R²-8,R³-22), (I-P5323,A-6,R²-12,R³-19), (I-P5324,A-6,R²-12,R³-20),
(I-P5191,A-6,R²-8,R³-23), (I-P5192,A-6,R²-8,R³-24), (I-P5325,A-6,R²-12,R³-21), (I-P5326,A-6,R²-12,R³-22),
(I-P5193,A-6,R²-8,R³-25), (I-P5194,A-6,R²-8,R³-26), (I-P5327,A-6,R²-12,R³-23), (I-P5328,A-6,R²-12,R³-24),
(I-P5195,A-6,R²-8,R³-27), (I-P5196,A-6,R²-8,R³-28), (I-P5329,A-6,R²-12,R³-25), (I-P5330,A-6,R²-12,R³-26),
(I-P5197,A-6,R²-8,R³-29), (I-P5198,A-6,R²-8,R³-30), (I-P5331,A-6,R²-12,R³-27), (I-P5332,A-6,R²-12,R³-28),
(I-P5199,A-6,R²-8,R³-31), (I-P5200,A-6,R²-8,R³-32), (I-P5333,A-6,R²-12,R³-29), (I-P5334,A-6,R²-12,R³-30),
(I-P5201,A-6,R²-8,R³-33), (I-P5202,A-6,R²-8,R³-34), (I-P5335,A-6,R²-12,R³-31), (I-P5336,A-6,R²-12,R³-32),
(I-P5203,A-6,R²-9,R³-1), (I-P5204,A-6,R²-9,R³-2), (I-P5337,A-6,R²-12,R³-33), (I-P5338,A-6,R²-12,R³-34),
(I-P5205,A-6,R²-9,R³-3), (I-P5206,A-6,R²-9,R³-4), (I-P5339,A-6,R²-13,R³-1), (I-P5340,A-6,R²-13,R³-2),
(I-P5207,A-6,R²-9,R³-5), (I-P5208,A-6,R²-9,R³-6), (I-P5341,A-6,R²-13,R³-3), (I-P5342,A-6,R²-13,R³-4),
(I-P5209,A-6,R²-9,R³-7), (I-P5210,A-6,R²-9,R³-8), (I-P5343,A-6,R²-13,R³-5), (I-P5344,A-6,R²-13,R³-6),
(I-P5211,A-6,R²-9,R³-9), (I-P5212,A-6,R²-9,R³-10), (I-P5345,A-6,R²-13,R³-7), (I-P5346,A-6,R²-13,R³-8),
(I-P5213,A-6,R²-9,R³-11), (I-P5214,A-6,R²-9,R³-12), (I-P5347,A-6,R²-13,R³-9), (I-P5348,A-6,R²-13,R³-10),
(I-P5215,A-6,R²-9,R³-13), (I-P5216,A-6,R²-9,R³-14), (I-P5349,A-6,R²-13,R³-11), (I-P5350,A-6,R²-13,R³-12),
(I-P5217,A-6,R²-9,R³-15), (I-P5218,A-6,R²-9,R³-16), (I-P5351,A-6,R²-13,R³-13), (I-P5352,A-6,R²-13,R³-14),
(I-P5219,A-6,R²-9,R³-17), (I-P5220,A-6,R²-9,R³-18), (I-P5353,A-6,R²-13,R³-15), (I-P5354,A-6,R²-13,R³-16),
(I-P5221,A-6,R²-9,R³-19), (I-P5222,A-6,R²-9,R³-20), (I-P5355,A-6,R²-13,R³-17), (I-P5356,A-6,R²-13,R³-18),
(I-P5223,A-6,R²-9,R³-21), (I-P5224,A-6,R²-9,R³-22), (I-P5357,A-6,R²-13,R³-19), (I-P5358,A-6,R²-13,R³-20),
(I-P5225,A-6,R²-9,R³-23), (I-P5226,A-6,R²-9,R³-24), (I-P5359,A-6,R²-13,R³-21), (I-P5360,A-6,R²-13,R³-22),
(I-P5227,A-6,R²-9,R³-25), (I-P5228,A-6,R²-9,R³-26), (I-P5361,A-6,R²-13,R³-23), (I-P5362,A-6,R²-13,R³-24),
(I-P5229,A-6,R²-9,R³-27), (I-P5230,A-6,R²-9,R³-28), (I-P5363,A-6,R²-13,R³-25), (I-P5364,A-6,R²-13,R³-26),
(I-P5231,A-6,R²-9,R³-29), (I-P5232,A-6,R²-9,R³-30), (I-P5365,A-6,R²-13,R³-27), (I-P5366,A-6,R²-13,R³-28),
(I-P5233,A-6,R²-9,R³-31), (I-P5234,A-6,R²-9,R³-32), (I-P5367,A-6,R²-13,R³-29), (I-P5368,A-6,R²-13,R³-30),
(I-P5235,A-6,R²-9,R³-33), (I-P5236,A-6,R²-9,R³-34), (I-P5369,A-6,R²-13,R³-31), (I-P5370,A-6,R²-13,R³-32),
(I-P5237,A-6,R²-10,R³-1), (I-P5238,A-6,R²-10,R³-2), (I-P5371,A-6,R²-13,R³-33), (I-P5372,A-6,R²-13,R³-34),
(I-P5239,A-6,R²-10,R³-3), (I-P5240,A-6,R²-10,R³-4), (I-P5373,A-6,R²-14,R³-1), (I-P5374,A-6,R²-14,R³-2),
(I-P5241,A-6,R²-10,R³-5), (I-P5242,A-6,R²-10,R³-6), (I-P5375,A-6,R²-14,R³-3), (I-P5376,A-6,R²-14,R³-4),
(I-P5243,A-6,R²-10,R³-7), (I-P5244,A-6,R²-10,R³-8), (I-P5377,A-6,R²-14,R³-5), (I-P5378,A-6,R²-14,R³-6),
(I-P5245,A-6,R²-10,R³-9), (I-P5246,A-6,R²-10,R³-10), (I-P5379,A-6,R²-14,R³-7), (I-P5380,A-6,R²-14,R³-8),
(I-P5247,A-6,R²-10,R³-11), (I-P5248,A-6,R²-10,R³-12), (I-P5381,A-6,R²-14,R³-9), (I-P5382,A-6,R²-14,R³-10),
(I-P5249,A-6,R²-10,R³-13), (I-P5250,A-6,R²-10,R³-14), (I-P5383,A-6,R²-14,R³-11), (I-P5384,A-6,R²-14,R³-12),
(I-P5251,A-6,R²-10,R³-15), (I-P5252,A-6,R²-10,R³-16), (I-P5385,A-6,R²-14,R³-13), (I-P5386,A-6,R²-14,R³-14),
(I-P5253,A-6,R²-10,R³-17), (I-P5254,A-6,R²-10,R³-18), (I-P5387,A-6,R²-14,R³-15), (I-P5388,A-6,R²-14,R³-16),
(I-P5255,A-6,R²-10,R³-19), (I-P5256,A-6,R²-10,R³-20), (I-P5389,A-6,R²-14,R³-17), (I-P5390,A-6,R²-14,R³-18),
(I-P5257,A-6,R²-10,R³-21), (I-P5258,A-6,R²-10,R³-22), (I-P5391,A-6,R²-14,R³-19), (I-P5392,A-6,R²-14,R³-20),
(I-P5259,A-6,R²-10,R³-23), (I-P5260,A-6,R²-10,R³-24), (I-P5393,A-6,R²-14,R³-21), (I-P5394,A-6,R²-14,R³-22),
(I-P5261,A-6,R²-10,R³-25), (I-P5262,A-6,R²-10,R³-26), (I-P5395,A-6,R²-14,R³-23), (I-P5396,A-6,R²-14,R³-24),
(I-P5263,A-6,R²-10,R³-27), (I-P5264,A-6,R²-10,R³-28), (I-P5397,A-6,R²-14,R³-25), (I-P5398,A-6,R²-14,R³-26),
(I-P5265,A-6,R²-10,R³-29), (I-P5266,A-6,R²-10,R³-30), (I-P5399,A-6,R²-14,R³-27), (I-P5400,A-6,R²-14,R³-28),
(I-P5267,A-6,R²-10,R³-31), (I-P5268,A-6,R²-10,R³-32), (I-P5401,A-6,R²-14,R³-29), (I-P5402,A-6,R²-14,R³-30),
(I-P5269,A-6,R²-10,R³-33), (I-P5270,A-6,R²-10,R³-34), (I-P5403,A-6,R²-14,R³-31), (I-P5404,A-6,R²-14,R³-32),
(I-P5271,A-6,R²-11,R³-1), (I-P5272,A-6,R²-11,R³-2), (I-P5405,A-6,R²-14,R³-33), (I-P5406,A-6,R²-14,R³-34),
(I-P5273,A-6,R²-11,R³-3), (I-P5274,A-6,R²-11,R³-4), (I-P5407,A-6,R²-15,R³-1), (I-P5408,A-6,R²-15,R³-2),
(I-P5275,A-6,R²-11,R³-5), (I-P5276,A-6,R²-11,R³-6), (I-P5409,A-6,R²-15,R³-3), (I-P5410,A-6,R²-15,R³-4),
(I-P5277,A-6,R²-11,R³-7), (I-P5278,A-6,R²-11,R³-8), (I-P5411,A-6,R²-15,R³-5), (I-P5412,A-6,R²-15,R³-6),
(I-P5279,A-6,R²-11,R³-9), (I-P5280,A-6,R²-11,R³-10), (I-P5413,A-6,R²-15,R³-7), (I-P5414,A-6,R²-15,R³-8),
(I-P5281,A-6,R²-11,R³-11), (I-P5282,A-6,R²-11,R³-12), (I-P5415,A-6,R²-15,R³-9), (I-P5416,A-6,R²-15,R³-10),
(I-P5283,A-6,R²-11,R³-13), (I-P5284,A-6,R²-11,R³-14), (I-P5417,A-6,R²-15,R³-11), (I-P5418,A-6,R²-15,R³-12),
(I-P5285,A-6,R²-11,R³-15), (I-P5286,A-6,R²-11,R³-16), (I-P5419,A-6,R²-15,R³-13), (I-P5420,A-6,R²-15,R³-14), (I-P5421,A-6,$R^2$-15,$R^3$-15), (I-P5422,A-6,$R^2$-15,$R^3$-16), (I-P5556,A-6,$R^2$-19,$R^3$-14), (I-P5557,A-6,$R^2$-19,$R^3$-15),
(I-P5423,A-6,$R^2$-15,$R^3$-17), (I-P5424,A-6,$R^2$-15,$R^3$-18), (I-P5558,A-6,$R^2$-19,$R^3$-16), (I-P5559,A-6,$R^2$-19,$R^3$-17),
(I-P5425,A-6,$R^2$-15,$R^3$-19), (I-P5426,A-6,$R^2$-15,$R^3$-20), (I-P5560,A-6,$R^2$-19,$R^3$-18), (I-P5561,A-6,$R^2$-19,$R^3$-19),
(I-P5427,A-6,$R^2$-15,$R^3$-21), (I-P5428,A-6,$R^2$-15,$R^3$-22), (I-P5562,A-6,$R^2$-19,$R^3$-20), (I-P5563,A-6,$R^2$-19,$R^3$-21),
(I-P5429,A-6,$R^2$-15,$R^3$-23), (I-P5430,A-6,$R^2$-15,$R^3$-24), (I-P5564,A-6,$R^2$-19,$R^3$-22), (I-P5565,A-6,$R^2$-19,$R^3$-23),
(I-P5431,A-6,$R^2$-15,$R^3$-25), (I-P5432,A-6,$R^2$-15,$R^3$-26), (I-P5566,A-6,$R^2$-19,$R^3$-24), (I-P5567,A-6,$R^2$-19,$R^3$-25),
(I-P5433,A-6,$R^2$-15,$R^3$-27), (I-P5434,A-6,$R^2$-15,$R^3$-28), (I-P5568,A-6,$R^2$-19,$R^3$-26), (I-P5569,A-6,$R^2$-19,$R^3$-27),
(I-P5435,A-6,$R^2$-15,$R^3$-29), (I-P5436,A-6,$R^2$-15,$R^3$-30), (I-P5570,A-6,$R^2$-19,$R^3$-28), (I-P5571,A-6,$R^2$-19,$R^3$-29),
(I-P5437,A-6,$R^2$-15,$R^3$-31), (I-P5438,A-6,$R^2$-15,$R^3$-32), (I-P5572,A-6,$R^2$-19,$R^3$-30), (I-P5573,A-6,$R^2$-19,$R^3$-31),
(I-P5439,A-6,$R^2$-15,$R^3$-33), (I-P5440,A-6,$R^2$-15,$R^3$-34), (I-P5574,A-6,$R^2$-19,$R^3$-32), (I-P5575,A-6,$R^2$-19,$R^3$-33),
(I-P5441,A-6,$R^2$-16,$R^3$-1), (I-P5442,A-6,$R^2$-16,$R^3$-2), (I-P5576,A-6,$R^2$-19,$R^3$-34), (I-P5577,A-6,$R^2$-20,$R^3$-1),
(I-P5443,A-6,$R^2$-16,$R^3$-3), (I-P5444,A-6,$R^2$-16,$R^3$-4), (I-P5578,A-6,$R^2$-20,$R^3$-2), (I-P5579,A-6,$R^2$-20,$R^3$-3),
(I-P5445,A-6,$R^2$-16,$R^3$-5), (I-P5446,A-6,$R^2$-16,$R^3$-6), (I-P5580,A-6,$R^2$-20,$R^3$-4), (I-P5581,A-6,$R^2$-20,$R^3$-5),
(I-P5447,A-6,$R^2$-16,$R^3$-7), (I-P5448,A-6,$R^2$-16,$R^3$-8), (I-P5582,A-6,$R^2$-20,$R^3$-6), (I-P5583,A-6,$R^2$-20,$R^3$-7),
(I-P5449,A-6,$R^2$-16,$R^3$-9), (I-P5450,A-6,$R^2$-16,$R^3$-10), (I-P5584,A-6,$R^2$-20,$R^3$-8), (I-P5585,A-6,$R^2$-20,$R^3$-9),
(I-P5451,A-6,$R^2$-16,$R^3$-11), (I-P5452,A-6,$R^2$-16,$R^3$-12), (I-P5586,A-6,$R^2$-20,$R^3$-10), (I-P5587,A-6,$R^2$-20,$R^3$-11),
(I-P5453,A-6,$R^2$-16,$R^3$-13), (I-P5454,A-6,$R^2$-16,$R^3$-14), (I-P5588,A-6,$R^2$-20,$R^3$-12), (I-P5589,A-6,$R^2$-20,$R^3$-13),
(I-P5455,A-6,$R^2$-16,$R^3$-15), (I-P5456,A-6,$R^2$-16,$R^3$-16), (I-P5590,A-6,$R^2$-20,$R^3$-14), (I-P5591,A-6,$R^2$-20,$R^3$-15),
(I-P5457,A-6,$R^2$-16,$R^3$-17), (I-P5458,A-6,$R^2$-16,$R^3$-18), (I-P5592,A-6,$R^2$-20,$R^3$-16), (I-P5593,A-6,$R^2$-20,$R^3$-17),
(I-P5459,A-6,$R^2$-16,$R^3$-19), (I-P5460,A-6,$R^2$-16,$R^3$-20), (I-P5594,A-6,$R^2$-20,$R^3$-18), (I-P5595,A-6,$R^2$-20,$R^3$-19),
(I-P5461,A-6,$R^2$-16,$R^3$-21), (I-P5462,A-6,$R^2$-16,$R^3$-22), (I-P5596,A-6,$R^2$-20,$R^3$-20), (I-P5597,A-6,$R^2$-20,$R^3$-21),
(I-P5463,A-6,$R^2$-16,$R^3$-23), (I-P5464,A-6,$R^2$-16,$R^3$-24), (I-P5598,A-6,$R^2$-20,$R^3$-22), (I-P5599,A-6,$R^2$-20,$R^3$-23),
(I-P5465,A-6,$R^2$-16,$R^3$-25), (I-P5466,A-6,$R^2$-16,$R^3$-26), (I-P5600,A-6,$R^2$-20,$R^3$-24), (I-P5601,A-6,$R^2$-20,$R^3$-25),
(I-P5467,A-6,$R^2$-16,$R^3$-27), (I-P5468,A-6,$R^2$-16,$R^3$-28), (I-P5602,A-6,$R^2$-20,$R^3$-26), (I-P5603,A-6,$R^2$-20,$R^3$-27),
(I-P5469,A-6,$R^2$-16,$R^3$-29), (I-P5470,A-6,$R^2$-16,$R^3$-30), (I-P5604,A-6,$R^2$-20,$R^3$-28), (I-P5605,A-6,$R^2$-20,$R^3$-29),
(I-P5471,A-6,$R^2$-16,$R^3$-31), (I-P5472,A-6,$R^2$-16,$R^3$-32), (I-P5606,A-6,$R^2$-20,$R^3$-30), (I-P5607,A-6,$R^2$-20,$R^3$-31),
(I-P5473,A-6,$R^2$-16,$R^3$-33), (I-P5474,A-6,$R^2$-16,$R^3$-34), (I-P5608,A-6,$R^2$-20,$R^3$-32), (I-P5609,A-6,$R^2$-20,$R^3$-33),
(I-P5475,A-6,$R^2$-17,$R^3$-1), (I-P5476,A-6,$R^2$-17,$R^3$-2), (I-P5610,A-6,$R^2$-20,$R^3$-34), (I-P5611,A-6,$R^2$-21,$R^3$-1),
(I-P5477,A-6,$R^2$-17,$R^3$-3), (I-P5478,A-6,$R^2$-17,$R^3$-4), (I-P5612,A-6,$R^2$-21,$R^3$-2), (I-P5613,A-6,$R^2$-21,$R^3$-3),
(I-P5479,A-6,$R^2$-17,$R^3$-5), (I-P5480,A-6,$R^2$-17,$R^3$-6), (I-P5614,A-6,$R^2$-21,$R^3$-4), (I-P5615,A-6,$R^2$-21,$R^3$-5),
(I-P5481,A-6,$R^2$-17,$R^3$-7), (I-P5482,A-6,$R^2$-17,$R^3$-8), (I-P5616,A-6,$R^2$-21,$R^3$-6), (I-P5617,A-6,$R^2$-21,$R^3$-7),
(I-P5483,A-6,$R^2$-17,$R^3$-9), (I-P5484,A-6,$R^2$-17,$R^3$-10), (I-P5618,A-6,$R^2$-21,$R^3$-8), (I-P5619,A-6,$R^2$-21,$R^3$-9),
(I-P5485,A-6,$R^2$-17,$R^3$-11), (I-P5486,A-6,$R^2$-17,$R^3$-12), (I-P5620,A-6,$R^2$-21,$R^3$-10), (I-P5621,A-6,$R^2$-21,$R^3$-11),
(I-P5487,A-6,$R^2$-17,$R^3$-13), (I-P5488,A-6,$R^2$-17,$R^3$-14), (I-P5622,A-6,$R^2$-21,$R^3$-12), (I-P5623,A-6,$R^2$-21,$R^3$-13),
(I-P5489,A-6,$R^2$-17,$R^3$-15), (I-P5490,A-6,$R^2$-17,$R^3$-16), (I-P5624,A-6,$R^2$-21,$R^3$-14), (I-P5625,A-6,$R^2$-21,$R^3$-15),
(I-P5491,A-6,$R^2$-17,$R^3$-17), (I-P5492,A-6,$R^2$-17,$R^3$-18), (I-P5626,A-6,$R^2$-21,$R^3$-16), (I-P5627,A-6,$R^2$-21,$R^3$-17),
(I-P5493,A-6,$R^2$-17,$R^3$-19), (I-P5494,A-6,$R^2$-17,$R^3$-20), (I-P5628,A-6,$R^2$-21,$R^3$-18), (I-P5629,A-6,$R^2$-21,$R^3$-19),
(I-P5495,A-6,$R^2$-17,$R^3$-21), (I-P5496,A-6,$R^2$-17,$R^3$-22), (I-P5630,A-6,$R^2$-21,$R^3$-20), (I-P5631,A-6,$R^2$-21,$R^3$-21),
(I-P5497,A-6,$R^2$-17,$R^3$-23), (I-P5498,A-6,$R^2$-17,$R^3$-24), (I-P5632,A-6,$R^2$-21,$R^3$-22), (I-P5633,A-6,$R^2$-21,$R^3$-23),
(I-P5499,A-6,$R^2$-17,$R^3$-25), (I-P5500,A-6,$R^2$-17,$R^3$-26), (I-P5634,A-6,$R^2$-21,$R^3$-24), (I-P5635,A-6,$R^2$-21,$R^3$-25),
(I-P5502,A-6,$R^2$-17,$R^3$-28), (I-P5503,A-6,$R^2$-17,$R^3$-29), (I-P5636,A-6,$R^2$-21,$R^3$-26), (I-P5637,A-6,$R^2$-21,$R^3$-27),
(I-P5504,A-6,$R^2$-17,$R^3$-30), (I-P5505,A-6,$R^2$-17,$R^3$-31), (I-P5638,A-6,$R^2$-21,$R^3$-28), (I-P5639,A-6,$R^2$-21,$R^3$-29),
(I-P5506,A-6,$R^2$-17,$R^3$-32), (I-P5507,A-6,$R^2$-17,$R^3$-33), (I-P5640,A-6,$R^2$-21,$R^3$-30), (I-P5641,A-6,$R^2$-21,$R^3$-31),
(I-P5508,A-6,$R^2$-17,$R^3$-34), (I-P5509,A-6,$R^2$-18,$R^3$-1), (I-P5642,A-6,$R^2$-21,$R^3$-32), (I-P5643,A-6,$R^2$-21,$R^3$-33),
(I-P5510,A-6,$R^2$-18,$R^3$-2), (I-P5511,A-6,$R^2$-18,$R^3$-3), (I-P5644,A-6,$R^2$-21,$R^3$-34), (I-P5645,A-6,$R^2$-22,$R^3$-1),
(I-P5512,A-6,$R^2$-18,$R^3$-4), (I-P5513,A-6,$R^2$-18,$R^3$-5), (I-P5646,A-6,$R^2$-22,$R^3$-2), (I-P5647,A-6,$R^2$-22,$R^3$-3),
(I-P5514,A-6,$R^2$-18,$R^3$-6), (I-P5515,A-6,$R^2$-18,$R^3$-7), (I-P5648,A-6,$R^2$-22,$R^3$-4), (I-P5649,A-6,$R^2$-22,$R^3$-5),
(I-P5516,A-6,$R^2$-18,$R^3$-8), (I-P5517,A-6,$R^2$-18,$R^3$-9), (I-P5650,A-6,$R^2$-22,$R^3$-6), (I-P5651,A-6,$R^2$-22,$R^3$-7),
(I-P5518,A-6,$R^2$-18,$R^3$-10), (I-P5519,A-6,$R^2$-18,$R^3$-11), (I-P5652,A-6,$R^2$-22,$R^3$-8), (I-P5653,A-6,$R^2$-22,$R^3$-9),
(I-P5520,A-6,$R^2$-18,$R^3$-12), (I-P5521,A-6,$R^2$-18,$R^3$-13), (I-P5654,A-6,$R^2$-22,$R^3$-10), (I-P5655,A-6,$R^2$-22,$R^3$-11),
(I-P5522,A-6,$R^2$-18,$R^3$-14), (I-P5523,A-6,$R^2$-18,$R^3$-15), (I-P5656,A-6,$R^2$-22,$R^3$-12), (I-P5657,A-6,$R^2$-22,$R^3$-13),
(I-P5524,A-6,$R^2$-18,$R^3$-16), (I-P5525,A-6,$R^2$-18,$R^3$-17), (I-P5658,A-6,$R^2$-22,$R^3$-14), (I-P5659,A-6,$R^2$-22,$R^3$-15),
(I-P5526,A-6,$R^2$-18,$R^3$-18), (I-P5527,A-6,$R^2$-18,$R^3$-19), (I-P5660,A-6,$R^2$-22,$R^3$-16), (I-P5661,A-6,$R^2$-22,$R^3$-17),
(I-P5528,A-6,$R^2$-18,$R^3$-20), (I-P5529,A-6,$R^2$-18,$R^3$-21), (I-P5662,A-6,$R^2$-22,$R^3$-18), (I-P5663,A-6,$R^2$-22,$R^3$-19),
(I-P5530,A-6,$R^2$-18,$R^3$-22), (I-P553 1A-6,$R^2$-18,$R^3$-23), (I-P5664,A-6,$R^2$-22,$R^3$-20), (I-P5665,A-6,$R^2$-22,$R^3$-21),
(I-P5532,A-6,$R^2$-18,$R^3$-24), (I-P5533,A-6,$R^2$-18,$R^3$-25), (I-P5666,A-6,$R^2$-22,$R^3$-22), (I-P5667,A-6,$R^2$-22,$R^3$-23),
(I-P5534,A-6,$R^2$-18,$R^3$-26), (I-P5535,A-6,$R^2$-18,$R^3$-27), (I-P5668,A-6,$R^2$-22,$R^3$-24), (I-P5669,A-6,$R^2$-22,$R^3$-25),
(I-P5536,A-6,$R^2$-18,$R^3$-28), (I-P5537,A-6,$R^2$-18,$R^3$-29), (I-P5670,A-6,$R^2$-22,$R^3$-26), (I-P5671,A-6,$R^2$-22,$R^3$-27),
(I-P5538,A-6,$R^2$-18,$R^3$-30), (I-P5539,A-6,$R^2$-18,$R^3$-31), (I-P5672,A-6,$R^2$-22,$R^3$-28), (I-P5673,A-6,$R^2$-22,$R^3$-29),
(I-P5540,A-6,$R^2$-18,$R^3$-32), (I-P5541,A-6,$R^2$-18,$R^3$-33), (I-P5674,A-6,$R^2$-22,$R^3$-30), (I-P5675,A-6,$R^2$-22,$R^3$-31),
(I-P5542,A-6,$R^2$-18,$R^3$-34), (I-P5543,A-6,$R^2$-19,$R^3$-1), (I-P5676,A-6,$R^2$-22,$R^3$-32), (I-P5677,A-6,$R^2$-22,$R^3$-33),
(I-P5544,A-6,$R^2$-19,$R^3$-2), (I-P5545,A-6,$R^2$-19,$R^3$-3), (I-P5678,A-6,$R^2$-22,$R^3$-34), (I-P5679,A-6,$R^2$-23,$R^3$-1),
(I-P5546,A-6,$R^2$-19,$R^3$-4), (I-P5547,A-6,$R^2$-19,$R^3$-5), (I-P5680,A-6,$R^2$-23,$R^3$-2), (I-P5681,A-6,$R^2$-23,$R^3$-3),
(I-P5548,A-6,$R^2$-19,$R^3$-6), (I-P5549,A-6,$R^2$-19,$R^3$-7), (I-P5682,A-6,$R^2$-23,$R^3$-4), (I-P5683,A-6,$R^2$-23,$R^3$-5),
(I-P5550,A-6,$R^2$-19,$R^3$-8), (I-P5551,A-6,$R^2$-19,$R^3$-9), (I-P5684,A-6,$R^2$-23,$R^3$-6), (I-P5685,A-6,$R^2$-23,$R^3$-7),
(I-P5552,A-6,$R^2$-19,$R^3$-10), (I-P5553,A-6,$R^2$-19,$R^3$-11), (I-P5686,A-6,$R^2$-23,$R^3$-8), (I-P5687,A-6,$R^2$-23,$R^3$-9),
(I-P5554,A-6,$R^2$-19,$R^3$-12), (I-P5555,A-6,$R^2$-19,$R^3$-13), (I-P5688,A-6,$R^2$-23,$R^3$-10), (I-P5689,A-6,$R^2$-23,$R^3$-11), (I-P5690,A-6,R²-23,R³-12), (I-P5691,A-6,R²-23,R³-13), (I-P5824,A-6,R²-27,R³-10), (I-P5825,A-6,R²-27,R³-11),
(I-P5692,A-6,R²-23,R³-14), (I-P5693,A-6,R²-23,R³-15), (I-P5826,A-6,R²-27,R³-12), (I-P5827,A-6,R²-27,R³-13),
(I-P5694,A-6,R²-23,R³-16), (I-P5695,A-6,R²-23,R³-17), (I-P5828,A-6,R²-27,R³-14), (I-P5829,A-6,R²-27,R³-15),
(I-P5696,A-6,R²-23,R³-18), (I-P5697,A-6,R²-23,R³-19), (I-P5830,A-6,R²-27,R³-16), (I-P5831,A-6,R²-27,R³-17),
(I-P5698,A-6,R²-23,R³-20), (I-P5699,A-6,R²-23,R³-21), (I-P5832,A-6,R²-27,R³-18), (I-P5833,A-6,R²-27,R³-19),
(I-P5700,A-6,R²-23,R³-22), (I-P5701,A-6,R²-23,R³-23), (I-P5834,A-6,R²-27,R³-20), (I-P5835,A-6,R²-27,R³-21),
(I-P5702,A-6,R²-23,R³-24), (I-P5703,A-6,R²-23,R³-25), (I-P5836,A-6,R²-27,R³-22), (I-P5837,A-6,R²-27,R³-23),
(I-P5704,A-6,R²-23,R³-26), (I-P5705,A-6,R²-23,R³-27), (I-P5838,A-6,R²-27,R³-24), (I-P5839,A-6,R²-27,R³-25),
(I-P5706,A-6,R²-23,R³-28), (I-P5707,A-6,R²-23,R³-29), (I-P5840,A-6,R²-27,R³-26), (I-P5841,A-6,R²-27,R³-27),
(I-P5708,A-6,R²-23,R³-30), (I-P5709,A-6,R²-23,R³-31), (I-P5842,A-6,R²-27,R³-28), (I-P5843,A-6,R²-27,R³-29),
(I-P5710,A-6,R²-23,R³-32), (I-P5711,A-6,R²-23,R³-33), (I-P5844,A-6,R²-27,R³-30), (I-P5845,A-6,R²-27,R³-31),
(I-P5712,A-6,R²-23,R³-34), (I-P5713,A-6,R²-24,R³-1), (I-P5846,A-6,R²-27,R³-32), (I-P5847,A-6,R²-27,R³-33),
(I-P5714,A-6,R²-24,R³-2), (I-P5715,A-6,R²-24,R³-3), (I-P5848,A-6,R²-27,R³-34), (I-P5849,A-6,R²-28,R³-1),
(I-P5716,A-6,R²-24,R³-4), (I-P5717,A-6,R²-24,R³-5), (I-P5850,A-6,R²-28,R³-2), (I-P5851,A-6,R²-28,R³-3),
(I-P5718,A-6,R²-24,R³-6), (I-P5719,A-6,R²-24,R³-7), (I-P5852,A-6,R²-28,R³-4), (I-P5853,A-6,R²-28,R³-5),
(I-P5720,A-6,R²-24,R³-8), (I-P5721,A-6,R²-24,R³-9), (I-P5854,A-6,R²-28,R³-6), (I-P5855,A-6,R²-28,R³-7),
(I-P5722,A-6,R²-24,R³-10), (I-P5723,A-6,R²-24,R³-11), (I-P5856,A-6,R²-28,R³-8), (I-P5857,A-6,R²-28,R³-9),
(I-P5724,A-6,R²-24,R³-12), (I-P5725,A-6,R²-24,R³-13), (I-P5858,A-6,R²-28,R³-10), (I-P5859,A-6,R²-28,R³-11),
(I-P5726,A-6,R²-24,R³-14), (I-P5727,A-6,R²-24,R³-15), (I-P5860,A-6,R²-28,R³-12), (I-P5861,A-6,R²-28,R³-13),
(I-P5728,A-6,R²-24,R³-16), (I-P5729,A-6,R²-24,R³-17), (I-P5862,A-6,R²-28,R³-14), (I-P5863,A-6,R²-28,R³-15),
(I-P5730,A-6,R²-24,R³-18), (I-P5731,A-6,R²-24,R³-19), (I-P5864,A-6,R²-28,R³-16), (I-P5865,A-6,R²-28,R³-17),
(I-P5732,A-6,R²-24,R³-20), (I-P5733,A-6,R²-24,R³-21), (I-P5866,A-6,R²-28,R³-18), (I-P5867,A-6,R²-28,R³-19),
(I-P5734,A-6,R²-24,R³-22), (I-P5735,A-6,R²-24,R³-23), (I-P5868,A-6,R²-28,R³-20), (I-P5869,A-6,R²-28,R³-21),
(I-P5736,A-6,R²-24,R³-24), (I-P5737,A-6,R²-24,R³-25), (I-P5870,A-6,R²-28,R³-22), (I-P5871,A-6,R²-28,R³-23),
(I-P5738,A-6,R²-24,R³-26), (I-P5739,A-6,R²-24,R³-27), (I-P5872,A-6,R²-28,R³-24), (I-P5873,A-6,R²-28,R³-25),
(I-P5740,A-6,R²-24,R³-28), (I-P5741,A-6,R²-24,R³-29), (I-P5874,A-6,R²-28,R³-26), (I-P5875,A-6,R²-28,R³-27),
(I-P5742,A-6,R²-24,R³-30), (I-P5743,A-6,R²-24,R³-31), (I-P5876,A-6,R²-28,R³-28), (I-P5877,A-6,R²-28,R³-29),
(I-P5744,A-6,R²-24,R³-32), (I-P5745,A-6,R²-24,R³-33), (I-P5878,A-6,R²-28,R³-30), (I-P5879,A-6,R²-28,R³-31),
(I-P5746,A-6,R²-24,R³-34), (I-P5747,A-6,R²-25,R³-1), (I-P5880,A-6,R²-28,R³-32), (I-P5881,A-6,R²-28,R³-33),
(I-P5748,A-6,R²-25,R³-2), (I-P5749,A-6,R²-25,R³-3), (I-P5882,A-6,R²-28,R³-34), (I-P5883,A-6,R²-29,R³-1),
(I-P5750,A-6,R²-25,R³-4), (I-P5751,A-6,R²-25,R³-5), (I-P5884,A-6,R²-29,R³-2), (I-P5885,A-6,R²-29,R³-3),
(I-P5752,A-6,R²-25,R³-6), (I-P5753,A-6,R²-25,R³-7), (I-P5886,A-6,R²-29,R³-4), (I-P5887,A-6,R²-29,R³-5),
(I-P5754,A-6,R²-25,R³-8), (I-P5755,A-6,R²-25,R³-9), (I-P5888,A-6,R²-29,R³-6), (I-P5889,A-6,R²-29,R³-7),
(I-P5756,A-6,R²-25,R³-10), (I-P5757,A-6,R²-25,R³-11), (I-P5890,A-6,R²-29,R³-8), (I-P5891,A-6,R²-29,R³-9),
(I-P5758,A-6,R²-25,R³-12), (I-P5759,A-6,R²-25,R³-13), (I-P5892,A-6,R²-29,R³-10), (I-P5893,A-6,R²-29,R³-11),
(I-P5760,A-6,R²-25,R³-14), (I-P5761,A-6,R²-25,R³-15), (I-P5894,A-6,R²-29,R³-12), (I-P5895,A-6,R²-29,R³-13),
(I-P5762,A-6,R²-25,R³-16), (I-P5763,A-6,R²-25,R³-17), (I-P5896,A-6,R²-29,R³-14), (I-P5897,A-6,R²-29,R³-15),
(I-P5764,A-6,R²-25,R³-18), (I-P5765,A-6,R²-25,R³-19), (I-P5898,A-6,R²-29,R³-16), (I-P5899,A-6,R²-29,R³-17),
(I-P5766,A-6,R²-25,R³-20), (I-P5767,A-6,R²-25,R³-21), (I-P5900,A-6,R²-29,R³-18), (I-P5901,A-6,R²-29,R³-19),
(I-P5768,A-6,R²-25,R³-22), (I-P5769,A-6,R²-25,R³-23), (I-P5902,A-6,R²-29,R³-20), (I-P5903,A-6,R²-29,R³-21),
(I-P5770,A-6,R²-25,R³-24), (I-P5771,A-6,R²-25,R³-25), (I-P5904,A-6,R²-29,R³-22), (I-P5905,A-8,R²-29,R³-23),
(I-P5772,A-6,R²-25,R³-26), (I-P5773,A-6,R²-25,R³-27), (I-P5906,A-6,R²-29,R³-24), (I-P5907,A-6,R²-29,R³-25),
(I-P5774,A-6,R²-25,R³-28), (I-P5775,A-6,R²-25,R³-29), (I-P5908,A-6,R²-29,R³-26), (I-P5909,A-6,R²-29,R³-27),
(I-P5776,A-6,R²-25,R³-30), (I-P5777,A-6,R²-25,R³-31), (I-P5910,A-6,R²-29,R³-28), (I-P5911,A-6,R²-29,R³-29),
(I-P5778,A-6,R²-25,R³-32), (I-P5779,A-6,R²-25,R³-33), (I-P5912,A-6,R²-29,R³-30), (I-P5913,A-6,R²-29,R³-31),
(I-P5780,A-6,R²-25,R³-34), (I-P5781,A-6,R²-26,R³-1), (I-P5914,A-6,R²-29,R³-32), (I-P5915,A-6,R²-29,R³-33),
(I-P5782,A-6,R²-26,R³-2), (I-P5783,A-6,R²-26,R³-3), (I-P5916,A-6,R²-29,R³-34), (I-P5917,A-7,R²-1,R³-1),
(I-P5784,A-6,R²-26,R³-4), (I-P5785,A-6,R²-26,R³-5), (I-P5918,A-7,R²-1,R³-2), (I-P5919,A-7,R²-1,R³-3),
(I-P5786,A-6,R²-26,R³-6), (I-P5787,A-6,R²-26,R³-7), (I-P5920,A-7,R²-1,R³-4), (I-P5921,A-7,R²-1,R³-5),
(I-P5788,A-6,R²-26,R³-8), (I-P5789,A-6,R²-26,R³-9), (I-P5922,A-7,R²-1,R³-6), (I-P5923,A-7,R²-1,R³-7),
(I-P5790,A-6,R²-26,R³-10), (I-P5791,A-6,R²-26,R³-11), (I-P5924,A-7,R²-1,R³-8), (I-P5925,A-7,R²-1,R³-9),
(I-P5792,A-6,R²-26,R³-12), (I-P5793,A-6,R²-26,R³-13), (I-P5926,A-7,R²-1,R³-10), (I-P5927,A-7,R²-1,R³-11),
(I-P5794,A-6,R²-26,R³-14), (I-P5795,A-6,R²-26,R³-15), (I-P5928,A-7,R²-1,R³-12), (I-P5929,A-7,R²-1,R³-13),
(I-P5796,A-6,R²-26,R³-16), (I-P5797,A-6,R²-26,R³-17), (I-P5930,A-7,R²-1,R³-14), (I-P5931,A-7,R²-1,R³-15),
(I-P5798,A-6,R²-26,R³-18), (I-P5799,A-6,R²-26,R³-19), (I-P5932,A-7,R²-1,R³-16), (I-P5933,A-7,R²-1,R³-17),
(I-P5800,A-6,R²-26,R³-20), (I-P5801,A-6,R²-26,R³-21), (I-P5934,A-7,R²-1,R³-18), (I-P5935,A-7,R²-1,R³-19),
(I-P5802,A-6,R²-26,R³-22), (I-P5803,A-6,R²-26,R³-23), (I-P5936,A-7,R²-1,R³-20), (I-P5937,A-7,R²-1,R³-21),
(I-P5804,A-6,R²-26,R³-24), (I-P5805,A-6,R²-26,R³-25), (I-P5938,A-7,R²-1,R³-22), (I-P5939,A-7,R²-1,R³-23),
(I-P5806,A-6,R²-26,R³-26), (I-P5807,A-6,R²-26,R³-27), (I-P5940,A-7,R²-1,R³-24), (I-P5941,A-7,R²-1,R³-25),
(I-P5808,A-6,R²-26,R³-28), (I-P5809,A-6,R²-26,R³-29), (I-P5942,A-7,R²-1,R³-26), (I-P5943,A-7,R²-1,R³-27),
(I-P5810,A-6,R²-26,R³-30), (I-P5811,A-6,R²-26,R³-31), (I-P5944,A-7,R²-1,R³-28), (I-P5945,A-7,R²-1,R³-29),
(I-P5812,A-6,R²-26,R³-32), (I-P5813,A-6,R²-26,R³-33), (I-P5946,A-7,R²-1,R³-30), (I-P5947,A-7,R²-1,R³-31),
(I-P5814,A-6,R²-26,R³-34), (I-P5815,A-6,R²-27,R³-1), (I-P5948,A-7,R²-1,R³-32), (I-P5949,A-7,R²-1,R³-33),
(I-P5816,A-6,R²-27,R³-2), (I-P5817,A-6,R²-27,R³-3), (I-P5950,A-7,R²-1,R³-34), (I-P5951,A-7,R²-2,R³-1),
(I-P5818,A-6,R²-27,R³-4), (I-P5819,A-6,R²-27,R³-5), (I-P5952,A-7,R²-2,R³-2), (I-P5953,A-7,R²-2,R³-3),
(I-P5820,A-6,R²-27,R³-6), (I-P5821,A-6,R²-27,R³-7), (I-P5954,A-7,R²-2,R³-4), (I-P5955,A-7,R²-2,R³-5),
(I-P5822,A-6,R²-27,R³-8), (I-P5823,A-6,R²-27,R³-9), (I-P5956,A-7,R²-2,R³-6), (I-P5957,A-7,R²-2,R³-7), (I-P5958,A-7,R²-2,R³-8), (I-P5959,A-7,R²-2,R³-9), (I-P6092,A-7,R²-6,R³-6), (I-P6093,A-7,R²-6,R³-7),
(I-P5960,A-7,R²-2,R³-10), (I-P5961,A-7,R²-2,R³-11), (I-P6094,A-7,R²-6,R³-8), (I-P6095,A-7,R²-6,R³-9),
(I-P5962,A-7,R²-2,R³-12), (I-P5963,A-7,R²-2,R³-13), (I-P6096,A-7,R²-6,R³-10), (I-P6097,A-7,R²-6,R³-11),
(I-P5964,A-7,R²-2,R³-14), (I-P5965,A-7,R²-2,R³-15), (I-P6098,A-7,R²-6,R³-12), (I-P6099,A-P6100,A-7,R²-6,R³-
(I-P5966,A-7,R²-2,R³-16), (I-P5967,A-7,R²-2,R³-17), 14), (I-P6101,A-7,R²-6,R³-15), (I-P6102,A-7,R²-6,R³-16),
(I-P5968,A-7,R²-2,R³-18), (I-P5969,A-7,R²-2,R³-19), (I-P6103,A-7,R²-6,R³-17), (I-P6104,A-7,R²-6,R³-18),
(I-P5970,A-7,R²-2,R³-20), (I-P5971,A-7,R²-2,R³-21), (I-P6105,A-7,R²-6,R³-19), (I-P6106,A-7,R²-6,R³-20),
(I-P5972,A-7,R²-2,R³-22), (I-P5973,A-7,R²-2,R³-23), (I-P6107,A-7,R²-6,R³-21), (I-P6108,A-7,R²-6,R³-22),
(I-P5974,A-7,R²-2,R³-24), (I-P5975,A-7,R²-2,R³-25), (I-P6109,A-7,R²-6,R³-23), (I-P6110,A-7,R²-6,R³-24),
(I-P5976,A-7,R²-2,R³-26), (I-P5977,A-7,R²-2,R³-27), (I-P6111,A-7,R²-6,R³-25), (I-P6112,A-7,R²-6,R³-26),
(I-P5978,A-7,R²-2,R³-28), (I-P5979,A-7,R²-2,R³-29), (I-P6113,A-7,R²-6,R³-27), (I-P6114,A-7,R²-6,R³-28),
(I-P5980,A-7,R²-2,R³-30), (I-P5981,A-7,R²-2,R³-31), (I-P6115,A-7,R²-6,R³-29), (I-P6116,A-7,R²-6,R³-30),
(I-P5982,A-7,R²-2,R³-32), (I-P5983,A-7,R²-2,R³-33), (I-P6117,A-7,R²-6,R³-31), (I-P6118,A-7,R²-6,R³-32),
(I-P5984,A-7,R²-2,R³-34), (I-P5985,A-7,R²-3,R³-1), (I-P6119,A-7,R²-6,R³-33), (I-P6120,A-7,R²-6,R³-34),
(I-P5986,A-7,R²-3,R³-2), (I-P5987,A-7,R²-3,R³-3), (I-P6121,A-7,R²-7,R³-1), (I-P6122,A-7,R²-7,R³-2),
(I-P5988,A-7,R²-3,R³-4), (I-P5989,A-7,R²-3,R³-5), (I-P6123,A-7,R²-7,R³-3), (I-P6124,A-7,R²-7,R³-4),
(I-P5990,A-7,R²-3,R³-6), (I-P5991,A-7,R²-3,R³-7), (I-P6125,A-7,R²-7,R³-5), (I-P6126,A-7,R²-7,R³-6),
(I-P5992,A-7,R²-3,R³-8), (I-P5993,A-7,R²-3,R³-9), (I-P6127,A-7,R²-7,R³-7), (I-P6128,A-7,R²-7,R³-8),
(I-P5994,A-7,R²-3,R³-10), (I-P5995,A-7,R²-3,R³-11), (I-P6129,A-7,R²-7,R³-9), (I-P6130,A-7,R²-7,R³-10),
(I-P5996,A-7,R²-3,R³-12), (I-P5997,A-7,R²-3,R³-13), (I-P6131,A-7,R²-7,R³-11), (I-P6132,A-7,R²-7,R³-12),
(I-P5998,A-7,R²-3,R³-14), (I-P5999,A-7,R²-3,R³-15), (I-P6133,A-7,R²-7,R³-13), (I-P6134,A-7,R²-7,R³-14),
(I-P6000,A-7,R²-3,R³-16), (I-P6001,A-7,R²-3,R³-17), (I-P6135,A-7,R²-7,R³-15), (I-P6136,A-7,R²-7,R³-16),
(I-P6002,A-7,R²-3,R³-18), (I-P6003,A-7,R²-3,R³-19), (I-P6137,A-7,R²-7,R³-17), (I-P6138,A-7,R²-7,R³-18),
(I-P6004,A-7,R²-3,R³-20), (I-P6005,A-7,R²-3,R³-21), (I-P6139,A-7,R²-7,R³-19), (I-P6140,A-7,R²-7,R³-20),
(I-P6006,A-7,R²-3,R³-22), (I-P6007,A-7,R²-3,R³-23), (I-P6141,A-7,R²-7,R³-21), (I-P6142,A-7,R²-7,R³-22),
(I-P6008,A-7,R²-3,R³-24), (I-P6009,A-7,R²-3,R³-25), (I-P6143,A-7,R²-7,R³-23), (I-P6144,A-7,R²-7,R³-24),
(I-P6010,A-7,R²-3,R³-26), (I-P6011,A-7,R²-3,R³-27), (I-P6145,A-7,R²-7,R³-25), (I-P6146,A-7,R²-7,R³-26),
(I-P6012,A-7,R²-3,R³-28), (I-P6013,A-7,R²-3,R³-29), (I-P6147,A-7,R²-7,R³-27), (I-P6148,A-7,R²-7,R³-28),
(I-P6014,A-7,R²-3,R³-30), (I-P6015,A-7,R²-3,R³-31), (I-P6149,A-7,R²-7,R³-29), (I-P6150,A-7,R²-7,R³-30),
(I-P6016,A-7,R²-3,R³-32), (I-P6017,A-7,R²-3,R³-33), (I-P6151,A-7,R²-7,R³-31), (I-P6152,A-7,R²-7,R³-32),
(I-P6018,A-7,R²-3,R³-34), (I-P6019,A-7,R²-4,R³-1), (I-P6153,A-7,R²-7,R³-33), (I-P6154,A-7,R²-7,R³-34),
(I-P6020,A-7,R²-4,R³-2), (I-P6021,A-7,R²-4,R³-3), (I-P6155,A-7,R²-8,R³-1), (I-P6156,A-7,R²-8,R³-2),
(I-P6022,A-7,R²-4,R³-4), (I-P6023,A-7,R²-4,R³-5), (I-P6157,A-7,R²-8,R³-3), (I-P6158,A-7,R²-8,R³-4),
(I-P6024,A-7,R²-4,R³-6), (I-P6025,A-7,R²-4,R³-7), (I-P6159,A-7,R²-8,R³-5), (I-P6160,A-7,R²-8,R³-6),
(I-P6026,A-7,R²-4,R³-8), (I-P6027,A-7,R²-4,R³-9), (I-P6161,A-7,R²-8,R³-7), (I-P6162,A-7,R²-8,R³-8),
(I-P6028,A-7,R²-4,R³-10), (I-P6029,A-7,R²-4,R³-11), (I-P6163,A-7,R²-8,R³-9), (I-P6164,A-7,R²-8,R³-10),
(I-P6030,A-7,R²-4,R³-12), (I-P6031,A-7,R²-4,R³-13), (I-P6165,A-7,R²-8,R³-11), (I-P6166,A-7,R²-8,R³-12),
(I-P6032,A-7,R²-4,R³-14), (I-P6033,A-7,R²-4,R³-15), (I-P6167,A-7,R²-8,R³-13), (I-P6168,A-7,R²-8,R³-14),
(I-P6034,A-7,R²-4,R³-16), (I-P6035,A-7,R²-4,R³-17), (I-P6169,A-7,R²-8,R³-15), (I-P6170,A-7,R²-8,R³-16),
(I-P6036,A-7,R²-4,R³-18), (I-P6037,A-7,R²-4,R³-19), (I-P6171,A-7,R²-8,R³-17), (I-P6172,A-7,R²-8,R³-18),
(I-P6038,A-7,R²-4,R³-20), (I-P6039,A-7,R²-4,R³-21), (I-P6173,A-7,R²-8,R³-19), (I-P6174,A-7,R²-8,R³-20),
(I-P6040,A-7,R²-4,R³-22), (I-P6041,A-7,R²-4,R³-23), (I-P6175,A-7,R²-8,R³-21), (I-P6176,A-7,R²-8,R³-22),
(I-P6042,A-7,R²-4,R³-24), (I-P6043,A-7,R²-4,R³-25), (I-P6177,A-7,R²-8,R³-23), (I-P6178,A-7,R²-8,R³-24),
(I-P6044,A-7,R²-4,R³-26), (I-P6045,A-7,R²-4,R³-27), (I-P6179,A-7,R²-8,R³-25), (I-P6180,A-7,R²-8,R³-26),
(I-P6046,A-7,R²-4,R³-28), (I-P6047,A-7,R²-4,R³-29), (I-P6181,A-7,R²-8,R³-27), (I-P6182,A-7,R²-8,R³-28),
(I-P6048,A-7,R²-4,R³-30), (I-P6049,A-7,R²-4,R³-31), (I-P6183,A-7,R²-8,R³-29), (I-P6184,A-7,R²-8,R³-30),
(I-P6050,A-7,R²-4,R³-32), (I-P6051,A-7,R²-4,R³-33), (I-P6185,A-7,R²-8,R³-31), (I-P6186,A-7,R²-8,R³-32),
(I-P6052,A-7,R²-4,R³-34), (I-P6053,A-7,R²-5,R³-1), (I-P6187,A-7,R²-8,R³-33), (I-P6188,A-7,R²-8,R³-34),
(I-P6054,A-7,R²-5,R³-2), (I-P6055,A-7,R²-5,R³-3), (I-P6189,A-7,R²-9,R³-1), (I-P6190,A-7,R²-9,R³-2),
(I-P6056,A-7,R²-5,R³-4), (I-P6057,A-7,R²-5,R³-5), (I-P6191,A-7,R²-9,R³-3), (I-P6192,A-7,R²-9,R³-4),
(I-P6058,A-7,R²-5,R³-6), (I-P6059,A-7,R²-5,R³-7), (I-P6193,A-7,R²-9,R³-5), (I-P6194,A-7,R²-9,R³-6),
(I-P6060,A-7,R²-5,R³-8), (I-P6061,A-7,R²-5,R³-9), (I-P6195,A-7,R²-9,R³-7), (I-P6196,A-7,R²-9,R³-8),
(I-P6062,A-7,R²-5,R³-10), (I-P6063,A-7,R²-5,R³-11), (I-P6197,A-7,R²-9,R³-9), (I-P6198,A-7,R²-9,R³-10),
(I-P6064,A-7,R²-5,R³-12), (I-P6065,A-7,R²-5,R³-13), (I-P6199,A-7,R²-9,R³-11), (I-P6200,A-7,R²-9,R³-12),
(I-P6066,A-7,R²-5,R³-14), (I-P6067,A-7,R²-5,R³-15), (I-P6201,A-7,R²-9,R³-13), (I-P6202,A-7,R²-9,R³-14),
(I-P6068,A-7,R²-5,R³-16), (I-P6069,A-7,R²-5,R³-17), (I-P6203,A-7,R²-9,R³-15), (I-P6204,A-7,R²-9,R³-16),
(I-P6070,A-7,R²-5,R³-18), (I-P6071,A-7,R²-5,R³-19), (I-P6205,A-7,R²-9,R³-17), (I-P6206,A-7,R²-9,R³-18),
(I-P6072,A-7,R²-5,R³-20), (I-P6073,A-7,R²-5,R³-21), (I-P6207,A-7,R²-9,R³-19), (I-P6208,A-7,R²-9,R³-20),
(I-P6074,A-7,R²-5,R³-22), (I-P6075,A-7,R²-5,R³-23), (I-P6209,A-7,R²-9,R³-21), (I-P6210,A-7,R²-9,R³-22),
(I-P6076,A-7,R²-5,R³-24), (I-P6077,A-7,R²-5,R³-25), (I-P6211,A-7,R²-9,R³-23), (I-P6212,A-7,R²-9,R³-24),
(I-P6078,A-7,R²-5,R³-26), (I-P6079,A-7,R²-5,R³-27), (I-P6213,A-7,R²-9,R³-25), (I-P6214,A-7,R²-9,R³-26),
(I-P6080,A-7,R²-5,R³-28), (I-P6081,A-7,R²-5,R³-29), (I-P6215,A-7,R²-9,R³-27), (I-P6216,A-7,R²-9,R³-28),
(I-P6082,A-7,R²-5,R³-30), (I-P6083,A-7,R²-5,R³-31), (I-P6217,A-7,R²-9,R³-29), (I-P6218,A-7,R²-9,R³-30),
(I-P6084,A-7,R²-5,R³-32), (I-P6085,A-7,R²-5,R³-33), (I-P6219,A-7,R²-9,R³-31), (I-P6220,A-7,R²-9,R³-32),
(I-P6086,A-7,R²-5,R³-34), (I-P6087,A-7,R²-6,R³-1), (I-P6221,A-7,R²-9,R³-33), (I-P6222,A-7,R²-9,R³-34),
(I-P6088,A-7,R²-6,R³-2), (I-P6089,A-7,R²-6,R³-3), (I-P6223,A-7,R²-10,R³-1), (I-P6224,A-7,R²-10,R³-2),
(I-P6090,A-7,R²-6,R³-4), (I-P6091,A-7,R²-6,R³-5), (I-P6225,A-7,R²-10,R³-3), (I-P6226,A-7,R²-10,R³-4), (I-P6227,A-7,R²-10,R³-5), (I-P6228,A-7,R²-10,R³-6), (I-P6361,A-7,R²-14,R³-3), (I-P6362,A-7,R²-14,R³-4),
(I-P6229,A-7,R²-10,R³-7), (I-P6230,A-7,R²-10,R³-8), (I-P6363,A-7,R²-14,R³-5), (I-P6364,A-7,R²-14,R³-6),
(I-P6231,A-7,R²-10,R³-9), (I-P6232,A-7,R²-10,R³-10), (I-P6365,A-7,R²-14,R³-7), (I-P6366,A-7,R²-14,R³-8),
(I-P6233,A-7,R²-10,R³-11), (I-P6234,A-7,R²-10,R³-12), (I-P6367,A-7,R²-14,R³-9), (I-P6368,A-7,R²-14,R³-10),
(I-P6235,A-7,R²-10,R³-13), (I-P6236,A-7,R²-10,R³-14), (I-P6369,A-7,R²-14,R³-11), (I-P6370,A-7,R²-14,R³-12),
(I-P6237,A-7,R²-10,R³-15), (I-P6238,A-7,R²-10,R³-16), (I-P6371,A-7,R²-14,R³-13), (I-P6372,A-7,R²-14,R³-14),
(I-P6239,A-7,R²-10,R³-17), (I-P6240,A-7,R²-10,R³-18), (I-P6373,A-7,R²-14,R³-15), (I-P6374,A-7,R²-14,R³-16),
(I-P6241,A-7,R²-10,R³-19), (I-P6242,A-7,R²-10,R³-20), (I-P6375,A-7,R²-14,R³-17), (I-P6376,A-7,R²-14,R³-18),
(I-P6243,A-7,R²-10,R³-21), (I-P6244,A-7,R²-10,R³-22), (I-P6377,A-7,R²-14,R³-19), (I-P6378,A-7,R²-14,R³-20),
(I-P6245,A-7,R²-10,R³-23), (I-P6246,A-7,R²-10,R³-24), (I-P6379,A-7,R²-14,R³-21), (I-P6380,A-7,R²-14,R³-22),
(I-P6247,A-7,R²-10,R³-25), (I-P6248,A-7,R²-10,R³-26), (I-P6381,A-7,R²-14,R³-23), (I-P6382,A-7,R²-14,R³-24),
(I-P6249,A-7,R²-10,R³-27), (I-P6250,A-7,R²-10,R³-28), (I-P6383,A-7,R²-14,R³-25), (I-P6384,A-7,R²-14,R³-26),
(I-P6251,A-7,R²-10,R³-29), (I-P6252,A-7,R²-10,R³-30), (I-P6385,A-7,R²-14,R³-27), (I-P6386,A-7,R²-14,R³-28),
(I-P6253,A-7,R²-10,R³-31), (I-P6254,A-7,R²-10,R³-32), (I-P6387,A-7,R²-14,R³-29), (I-P6388,A-7,R²-14,R³-30),
(I-P6255,A-7,R²-10,R³-33), (I-P6256,A-7,R²-10,R³-34), (I-P6389,A-7,R²-14,R³-31), (I-P6390,A-7,R²-14,R³-32),
(I-P6257,A-7,R²-11,R³-1), (I-P6258,A-7,R²-11,R³-2), (I-P6391,A-7,R²-14,R³-33), (I-P6392,A-7,R²-14,R³-34),
(I-P6259,A-7,R²-11,R³-3), (I-P6260,A-7,R²-11,R³-4), (I-P6393,A-7,R²-15,R³-1), (I-P6394,A-7,R²-15,R³-2),
(I-P6261,A-7,R²-11,R³-5), (I-P6262,A-7,R²-11,R³-6), (I-P6395,A-7,R²-15,R³-3), (I-P6396,A-7,R²-15,R³-4),
(I-P6263,A-7,R²-11,R³-7), (I-P6264,A-7,R²-11,R³-8), (I-P6397,A-7,R²-15,R³-5), (I-P6398,A-7,R²-15,R³-6),
(I-P6265,A-7,R²-11,R³-9), (I-P6266,A-7,R²-11,R³-10), (I-P6399,A-7,R²-15,R³-7), (I-P6400,A-7,R²-15,R³-8),
(I-P6267,A-7,R²-11,R³-11), (I-P6268,A-7,R²-11,R³-12), (I-P6401,A-7,R²-15,R³-9), (I-P6402,A-7,R²-15,R³-10),
(I-P6269,A-7,R²-11,R³-13), (I-P6270,A-7,R²-11,R³-14), (I-P6403,A-7,R²-15,R³-11), (I-P6404,A-7,R²-15,R³-12),
(I-P6271,A-7,R²-11,R³-15), (I-P6272,A-7,R²-11,R³-16), (I-P6405,A-7,R²-15,R³-13), (I-P6406,A-7,R²-15,R³-14),
(I-P6273,A-7,R²-11,R³-17), (I-P6274,A-7,R²-11,R³-18), (I-P6407,A-7,R²-15,R³-15), (I-P6408,A-7,R²-15,R³-16),
(I-P6275,A-7,R²-11,R³-19), (I-P6276,A-7,R²-11,R³-20), (I-P6409,A-7,R²-15,R³-17), (I-P6410,A-7,R²-15,R³-18),
(I-P6277,A-7,R²-11,R³-21), (I-P6278,A-7,R²-11,R³-22), (I-P6411,A-7,R²-15,R³-19), (I-P6412,A-7,R²-15,R³-20),
(I-P6279,A-7,R²-11,R³-23), (I-P6280,A-7,R²-11,R³-24), (I-P6413,A-7,R²-15,R³-21), (I-P6414,A-7,R²-15,R³-22),
(I-P6281,A-7,R²-11,R³-25), (I-P6282,A-7,R²-11,R³-26), (I-P6415,A-7,R²-15,R³-23), (I-P6416,A-7,R²-15,R³-24),
(I-P6283,A-7,R²-11,R³-27), (I-P6284,A-7,R²-11,R³-28), (I-P6417,A-7,R²-15,R³-25), (I-P6418,A-7,R²-15,R³-26),
(I-P6285,A-7,R²-11,R³-29), (I-P6286,A-7,R²-11,R³-30), (I-P6419,A-7,R²-15,R³-27), (I-P6420,A-7,R²-15,R³-28),
(I-P6287,A-7,R²-11,R³-31), (I-P6288,A-7,R²-11,R³-32), (I-P6421,A-7,R²-15,R³-29), (I-P6422,A-7,R²-15,R³-30),
(I-P6289,A-7,R²-11,R³-33), (I-P6290,A-7,R²-11,R³-34), (I-P6423,A-7,R²-15,R³-31), (I-P6424,A-7,R²-15,R³-32),
(I-P6291,A-7,R²-12,R³-1), (I-P6292,A-7,R²-12,R³-2), (I-P6425,A-7,R²-15,R³-33), (I-P6426,A-7,R²-15,R³-34),
(I-P6293,A-7,R²-12,R³-3), (I-P6294,A-7,R²-12,R³-4), (I-P6427,A-7,R²-16,R³-1), (I-P6428,A-7,R²-16,R³-2),
(I-P6295,A-7,R²-12,R³-5), (I-P6296,A-7,R²-12,R³-6), (I-P6429,A-7,R²-16,R³-3), (I-P6430,A-7,R²-16,R³-4),
(I-P6297,A-7,R²-12,R³-7), (I-P6298,A-7,R²-12,R³-8), (I-P6431,A-7,R²-16,R³-5), (I-P6432,A-7,R²-16,R³-6),
(I-P6299,A-7,R²-12,R³-9), (I-P6300,A-7,R²-12,R³-10), (I-P6433,A-7,R²-16,R³-7), (I-P6434,A-7,R²-16,R³-8),
(I-P6301,A-7,R²-12,R³-11), (I-P6302,A-7,R²-12,R³-12), (I-P6435,A-7,R²-16,R³-9), (I-P6436,A-7,R²-16,R³-10),
(I-P6303,A-7,R²-12,R³-13), (I-P6304,A-7,R²-12,R³-14), (I-P6437,A-7,R²-16,R³-11), (I-P6438,A-7,R²-16,R³-12),
(I-P6305,A-7,R²-12,R³-15), (I-P6306,A-7,R²-12,R³-16), (I-P6439,A-7,R²-16,R³-13), (I-P6440,A-7,R²-16,R³-14),
(I-P6307,A-7,R²-12,R³-17), (I-P6308,A-7,R²-12,R³-18), (I-P6441,A-7,R²-16,R³-15), (I-P6442,A-7,R²-16,R³-16),
(I-P6309,A-7,R²-12,R³-19), (I-P6310,A-7,R²-12,R³-20), (I-P6443,A-7,R²-16,R³-17), (I-P6444,A-7,R²-16,R³-18),
(I-P6311,A-7,R²-12,R³-21), (I-P6312,A-7,R²-12,R³-22), (I-P6445,A-7,R²-16,R³-19), (I-P6446,A-7,R²-16,R³-20),
(I-P6313,A-7,R²-12,R³-23), (I-P6314,A-7,R²-12,R³-24), (I-P6447,A-7,R²-16,R³-21), (I-P6448,A-7,R²-16,R³-22),
(I-P6315,A-7,R²-12,R³-25), (I-P6316,A-7,R²-12,R³-26), (I-P6449,A-7,R²-16,R³-23), (I-P6450,A-7,R²-16,R³-24),
(I-P6317,A-7,R²-12,R³-27), (I-P6318,A-7,R²-12,R³-28), (I-P6451,A-7,R²-16,R³-25), (I-P6452,A-7,R²-16,R³-26),
(I-P6319,A-7,R²-12,R³-29), (I-P6320,A-7,R²-12,R³-30), (I-P6453,A-7,R²-16,R³-27), (I-P6454,A-7,R²-16,R³-28),
(I-P6321,A-7,R²-12,R³-31), (I-P6322,A-7,R²-12,R³-32), (I-P6455,A-7,R²-16,R³-29), (I-P6456,A-7,R²-16,R³-30),
(I-P6323,A-7,R²-12,R³-33), (I-P6324,A-7,R²-12,R³-34), (I-P6457,A-7,R²-16,R³-31), (I-P6458,A-7,R²-16,R³-32),
(I-P6325,A-7,R²-13,R³-1), (I-P6326,A-7,R²-13,R³-2), (I-P6459,A-7,R²-16,R³-33), (I-P6460,A-7,R²-16,R³-34),
(I-P6327,A-7,R²-13,R³-3), (I-P6328,A-7,R²-13,R³-4), (I-P6461,A-7,R²-17,R³-1), (I-P6462,A-7,R²-17,R³-2),
(I-P6329,A-7,R²-13,R³-5), (I-P6330,A-7,R²-13,R³-6), (I-P6463,A-7,R²-17,R³-3), (I-P6464,A-7,R²-17,R³-4),
(I-P6331,A-7,R²-13,R³-7), (I-P6332,A-7,R²-13,R³-8), (I-P6465,A-7,R²-17,R³-5), (I-P6466,A-7,R²-17,R³-6),
(I-P6333,A-7,R²-13,R³-9), (I-P6334,A-7,R²-13,R³-10), (I-P6467,A-7,R²-17,R³-7), (I-P6468,A-7,R²-17,R³-8),
(I-P6335,A-7,R²-13,R³-11), (I-P6336,A-7,R²-13,R³-12), (I-P6469,A-7,R²-17,R³-9), (I-P6470,A-7,R²-17,R³-10),
(I-P6337,A-7,R²-13,R³-13), (I-P6338,A-7,R²-13,R³-14), (I-P6471,A-7,R²-17,R³-11), (I-P6472,A-7,R²-17,R³-12),
(I-P6339,A-7,R²-13,R³-15), (I-P6340,A-7,R²-13,R³-16), (I-P6473,A-7,R²-17,R³-13), (I-P6474,A-7,R²-17,R³-14),
(I-P6341,A-7,R²-13,R³-17), (I-P6342,A-7,R²-13,R³-18), (I-P6475,A-7,R²-17,R³-15), (I-P6476,A-7,R²-17,R³-16),
(I-P6343,A-7,R²-13,R³-19), (I-P6344,A-7,R²-13,R³-20), (I-P6477,A-7,R²-17,R³-17), (I-P6478,A-7,R²-17,R³-18),
(I-P6345,A-7,R²-13,R³-21), (I-P6346,A-7,R²-13,R³-22), (I-P6479,A-7,R²-17,R³-19), (I-P6480,A-7,R²-17,R³-20),
(I-P6347,A-7,R²-13,R³-23), (I-P6348,A-7,R²-13,R³-24), (I-P6481,A-7,R²-17,R³-21), (I-P6482,A-7,R²-17,R³-22),
(I-P6349,A-7,R²-13,R³-25), (I-P6350,A-7,R²-13,R³-26), (I-P6483,A-7,R²-17,R³-23), (I-P6484,A-7,R²-17,R³-24),
(I-P6351,A-7,R²-13,R³-27), (I-P6352,A-7,R²-13,R³-28), (I-P6485,A-7,R²-17,R³-25), (I-P6486,A-7,R²-17,R³-26),
(I-P6353,A-7,R²-13,R³-29), (I-P6354,A-7,R²-13,R³-30), (I-P6487,A-7,R²-17,R³-27), (I-P6488,A-7,R²-17,R³-28),
(I-P6355,A-7,R²-13,R³-31), (I-P6356,A-7,R²-13,R³-32), (I-P6489,A-7,R²-17,R³-29), (I-P6490,A-7,R²-17,R³-30),
(I-P6357,A-7,R²-13,R³-33), (I-P6358,A-7,R²-13,R³-34), (I-P6491,A-7,R²-17,R³-31), (I-P6492,A-7,R²-17,R³-32),
(I-P6359,A-7,R²-14,R³-1), (I-P6360,A-7,R²-14,R³-2), (I-P6493,A-7,R²-17,R³-33), (I-P6494,A-7,R²-17,R³-34), (I-P6495,A-7,R²-18,R³-1), (I-P6496,A-7,R²-18,R³-2), (I-P6629,A-7,R²-21,R³-33), (I-P6630,A-7,R²-21,R³-34),
(I-P6497,A-7,R²-18,R³-3), (I-P6498,A-7,R²-18,R³-4), (I-P6631,A-7,R²-22,R³-1), (I-P6632,A-7,R²-22,R³-2),
(I-P6499,A-7,R²-18,R³-5), (I-P6500,A-7,R²-18,R³-6), (I-P6633,A-7,R²-22,R³-3), (I-P6634,A-7,R²-22,R³-4),
(I-P6501,A-7,R²-18,R³-7), (I-P6502,A-7,R²-18,R³-8), (I-P6635,A-7,R²-22,R³-5), (I-P6636,A-7,R²-22,R³-6),
(I-P6503,A-7,R²-18,R³-9), (I-P6504,A-7,R²-18,R³-10), (I-P6637,A-7,R²-22,R³-7), (I-P6638,A-7,R²-22,R³-8),
(I-P6505,A-7,R²-18,R³-11), (I-P6506,A-7,R²-18,R³-12), (I-P6639,A-7,R²-22,R³-9), (I-P6640,A-7,R²-22,R³-10),
(I-P6507,A-7,R²-18,R³-13), (I-P6508,A-7,R²-18,R³-14), (I-P6641,A-7,R²-22,R³-11), (I-P6642,A-7,R²-22,R³-12),
(I-P6509,A-7,R²-18,R³-15), (I-P6510,A-7,R²-18,R³-16), (I-P6643,A-7,R²-22,R³-13), (I-P6644,A-7,R²-22,R³-14),
(I-P6511,A-7,R²-18,R³-17), (I-P6512,A-7,R²-18,R³-18), (I-P6645,A-7,R²-22,R³-15), (I-P6646,A-7,R²-22,R³-16),
(I-P6513,A-7,R²-18,R³-19), (I-P6514,A-7,R²-18,R³-20), (I-P6647,A-7,R²-22,R³-17), (I-P6648,A-7,R²-22,R³-18),
(I-P6515,A-7,R²-18,R³-21), (I-P6516,A-7,R²-18,R³-22), (I-P6649,A-7,R²-22,R³-19), (I-P6650,A-7,R²-22,R³-20),
(I-P6517,A-7,R²-18,R³-23), (I-P6518,A-7,R²-18,R³-24), (I-P6651,A-7,R²-22,R³-21), (I-P6652,A-7,R²-22,R³-22),
(I-P6519,A-7,R²-18,R³-25), (I-P6520,A-7,R²-18,R³-26), (I-P6653,A-7,R²-22,R³-23), (I-P6654,A-7,R²-22,R³-24),
(I-P6521,A-7,R²-18,R³-27), (I-P6522,A-7,R²-18,R³-28), (I-P6655,A-7,R²-22,R³-25), (I-P6656,A-7,R²-22,R³-26),
(I-P6523,A-7,R²-18,R³-29), (I-P6524,A-7,R²-18,R³-30), (I-P6657,A-7,R²-22,R³-27), (I-P6658,A-7,R²-22,R³-28),
(I-P6525,A-7,R²-18,R³-31), (I-P6526,A-7,R²-18,R³-32), (I-P6659,A-7,R²-22,R³-29), (I-P6660,A-7,R²-22,R³-30),
(I-P6527,A-7,R²-18,R³-33), (I-P6528,A-7,R²-18,R³-34), (I-P6661,A-7,R²-22,R³-31), (I-P6662,A-7,R²-22,R³-32),
(I-P6529,A-7,R²-19,R³-1), (I-P6530,A-7,R²-19,R³-2), (I-P6663,A-7,R²-22,R³-33), (I-P6664,A-7,R²-22,R³-34),
(I-P6531,A-7,R²-19,R³-3), (I-P6532,A-7,R²-19,R³-4), (I-P6665,A-7,R²-23,R³-1), (I-P6666,A-7,R²-23,R³-2),
(I-P6533,A-7,R²-19,R³-5), (I-P6534,A-7,R²-19,R³-6), (I-P6667,A-7,R²-23,R³-3), (I-P6668,A-7,R²-23,R³-4),
(I-P6535,A-7,R²-19,R³-7), (I-P6536,A-7,R²-19,R³-8), (I-P6669,A-7,R²-23,R³-5), (I-P6670,A-7,R²-23,R³-6),
(I-P6537,A-7,R²-19,R³-9), (I-P6538,A-7,R²-19,R³-10), (I-P6671,A-7,R²-23,R³-7), (I-P6672,A-7,R²-23,R³-8),
(I-P6539,A-7,R²-19,R³-11), (I-P6540,A-7,R²-19,R³-12), (I-P6673,A-7,R²-23,R³-9), (I-P6674,A-7,R²-23,R³-10),
(I-P6541,A-7,R²-19,R³-13), (I-P6542,A-7,R²-19,R³-14), (I-P6675,A-7,R²-23,R³-11), (I-P6676,A-7,R²-23,R³-12),
(I-P6543,A-7,R²-19,R³-15), (I-P6544,A-7,R²-19,R³-16), (I-P6677,A-7,R²-23,R³-13), (I-P6678,A-7,R²-23,R³-14),
(I-P6545,A-7,R²-19,R³-17), (I-P6546,A-7,R²-19,R³-18), (I-P6679,A-7,R²-23,R³-15), (I-P6680,A-7,R²-23,R³-16),
(I-P6547,A-7,R²-19,R³-19), (I-P6548,A-7,R²-19,R³-20), (I-P6681,A-7,R²-23,R³-17), (I-P6682,A-7,R²-23,R³-18),
(I-P6549,A-7,R²-19,R³-21), (I-P6550,A-7,R²-19,R³-22), (I-P6683,A-7,R²-23,R³-19), (I-P6684,A-7,R²-23,R³-20),
(I-P6551,A-7,R²-19,R³-23), (I-P6552,A-7,R²-19,R³-24), (I-P6685,A-7,R²-23,R³-21), (I-P6686,A-7,R²-23,R³-22),
(I-P6553,A-7,R²-19,R³-25), (I-P6554,A-7,R²-19,R³-26), (I-P6687,A-7,R²-23,R³-23), (I-P6688,A-7,R²-23,R³-24),
(I-P6555,A-7,R²-19,R³-27), (I-P6556,A-7,R²-19,R³-28), (I-P6689,A-7,R²-23,R³-25), (I-P6690,A-7,R²-23,R³-26),
(I-P6557,A-7,R²-19,R³-29), (I-P6558,A-7,R²-19,R³-30), (I-P6691,A-7,R²-23,R³-27), (I-P6692,A-7,R²-23,R³-28),
(I-P6559,A-7,R²-19,R³-31), (I-P6560,A-7,R²-19,R³-32), (I-P6693,A-7,R²-23,R³-29), (I-P6694,A-7,R²-23,R³-30),
(I-P6561,A-7,R²-19,R³-33), (I-P6562,A-7,R²-19,R³-34), (I-P6695,A-7,R²-23,R³-31), (I-P6696,A-7,R²-23,R³-32),
(I-P6563,A-7,R²-20,R³-1), (I-P6564,A-7,R²-20,R³-2), (I-P6697,A-7,R²-23,R³-33), (I-P6698,A-7,R²-23,R³-34),
(I-P6565,A-7,R²-20,R³-3), (I-P6566,A-7,R²-20,R³-4), (I-P6699,A-7,R²-24,R³-1), (I-P6700,A-7,R²-24,R³-2),
(I-P6567,A-7,R²-20,R³-5), (I-P6568,A-7,R²-20,R³-6), (I-P6701,A-7,R²-24,R³-3), (I-P6702,A-7,R²-24,R³-4),
(I-P6569,A-7,R²-20,R³-7), (I-P6570,A-7,R²-20,R³-8), (I-P6703,A-7,R²-24,R³-5), (I-P6704,A-7,R²-24,R³-6),
(I-P6571,A-7,R²-20,R³-9), (I-P6572,A-7,R²-20,R³-10), (I-P6705,A-7,R²-24,R³-7), (I-P6706,A-7,R²-24,R³-8),
(I-P6573,A-7,R²-20,R³-11), (I-P6574,A-7,R²-20,R³-12), (I-P6707,A-7,R²-24,R³-9), (I-P6708,A-7,R²-24,R³-10),
(I-P6575,A-7,R²-20,R³-13), (I-P6576,A-7,R²-20,R³-14), (I-P6709,A-7,R²-24,R³-11), (I-P6710,A-7,R²-24,R³-12),
(I-P6577,A-7,R²-20,R³-15), (I-P6578,A-7,R²-20,R³-16), (I-P6711,A-7,R²-24,R³-13), (I-P6712,A-7,R²-24,R³-14),
(I-P6579,A-7,R²-20,R³-17), (I-P6580,A-7,R²-20,R³-18), (I-P6713,A-7,R²-24,R³-15), (I-P6714,A-7,R²-24,R³-16),
(I-P6581,A-7,R²-20,R³-19), (I-P6582,A-7,R²-20,R³-20), (I-P6715,A-7,R²-24,R³-17), (I-P6716,A-7,R²-24,R³-18),
(I-P6583,A-7,R²-20,R³-21), (I-P6584,A-7,R²-20,R³-22), (I-P6717,A-7,R²-24,R³-19), (I-P6718,A-7,R²-24,R³-20),
(I-P6585,A-7,R²-20,R³-23), (I-P6586,A-7,R²-20,R³-24), (I-P6719,A-7,R²-24,R³-21), (I-P6720,A-7,R²-24,R³-22),
(I-P6587,A-7,R²-20,R³-25), (I-P6588,A-7,R²-20,R³-26), (I-P6721,A-7,R²-24,R³-23), (I-P6722,A-7,R²-24,R³-24),
(I-P6589,A-7,R²-20,R³-27), (I-P6590,A-7,R²-20,R³-28), (I-P6723,A-7,R²-24,R³-25), (I-P6724,A-7,R²-24,R³-26),
(I-P6591,A-7,R²-20,R³-29), (I-P6592,A-7,R²-20,R³-30), (I-P6725,A-7,R²-24,R³-27), (I-P6726,A-7,R²-24,R³-28),
(I-P6593,A-7,R²-20,R³-31), (I-P6594,A-7,R²-20,R³-32), (I-P6727,A-7,R²-24,R³-29), (I-P6728,A-7,R²-24,R³-30),
(I-P6595,A-7,R²-20,R³-33), (I-P6596,A-7,R²-20,R³-34), (I-P6729,A-7,R²-24,R³-31), (I-P6730,A-7,R²-24,R³-32),
(I-P6597,A-7,R²-21,R³-1), (I-P6598,A-7,R²-21,R³-2), (I-P6731,A-7,R²-24,R³-33), (I-P6732,A-7,R²-24,R³-34),
(I-P6599,A-7,R²-21,R³-3), (I-P6600,A-7,R²-21,R³-4), (I-P6733,A-7,R²-25,R³-1), (I-P6734,A-7,R²-25,R³-2),
(I-P6601,A-7,R²-21,R³-5), (I-P6602,A-7,R²-21,R³-6), (I-P6735,A-7,R²-25,R³-3), (I-P6736,A-7,R²-25,R³-4),
(I-P6603,A-7,R²-21,R³-7), (I-P6604,A-7,R²-21,R³-8), (I-P6737,A-7,R²-25,R³-5), (I-P6738,A-7,R²-25,R³-6),
(I-P6605,A-7,R²-21,R³-9), (I-P6606,A-7,R²-21,R³-10), (I-P6739,A-7,R²-25,R³-7), (I-P6740,A-7,R²-25,R³-8),
(I-P6607,A-7,R²-21,R³-11), (I-P6608,A-7,R²-21,R³-12), (I-P6741,A-7,R²-25,R³-9), (I-P6742,A-7,R²-25,R³-10),
(I-P6609,A-7,R²-21,R³-13), (I-P6610,A-7,R²-21,R³-14), (I-P6743,A-7,R²-25,R³-11), (I-P6744,A-7,R²-25,R³-12),
(I-P6611,A-7,R²-21,R³-15), (I-P6612,A-7,R²-21,R³-16), (I-P6745,A-7,R²-25,R³-13), (I-P6746,A-7,R²-25,R³-14),
(I-P6613,A-7,R²-21,R³-17), (I-P6614,A-7,R²-21,R³-18), (I-P6747,A-7,R²-25,R³-15), (I-P6748,A-7,R²-25,R³-16),
(I-P6615,A-7,R²-21,R³-19), (I-P6616,A-7,R²-21,R³-20), (I-P6749,A-7,R²-25,R³-17), (I-P6750,A-7,R²-25,R³-18),
(I-P6617,A-7,R²-21,R³-21), (I-P6618,A-7,R²-21,R³-22), (I-P6751,A-7,R²-25,R³-19), (I-P6752,A-7,R²-25,R³-20),
(I-P6619,A-7,R²-21,R³-23), (I-P6620,A-7,R²-21,R³-24), (I-P6753,A-7,R²-25,R³-21), (I-P6754,A-7,R²-25,R³-22),
(I-P6621,A-7,R²-21,R³-25), (I-P6622,A-7,R²-21,R³-26), (I-P6755,A-7,R²-25,R³-23), (I-P6756,A-7,R²-25,R³-24),
(I-P6623,A-7,R²-21,R³-27), (I-P6624,A-7,R²-21,R³-28), (I-P6757,A-7,R²-25,R³-25), (I-P6758,A-7,R²-25,R³-26),
(I-P6625,A-7,R²-21,R³-29), (I-P6626,A-7,R²-21,R³-30), (I-P6759,A-7,R²-25,R³-27), (I-P6760,A-7,R²-25,R³-28),
(I-P6627,A-7,R²-21,R³-31), (I-P6628,A-7,R²-21,R³-32), (I-P6761,A-7,R²-25,R³-29), (I-P6762,A-7,R²-25,R³-30), (I-P6763,A-7,R²-25,R³-31), (I-P6764,A-7,R²-25,R³-32), (I-P6897,A-7,R²-29,R³-29), (I-P6898,A-7,R²-29,R³-30),
(I-P6765,A-7,R²-25,R³-33), (I-P6766,A-7,R²-25,R³-34), (I-P6899,A-7,R²-29,R³-31), (I-P6900,A-7,R²-29,R³-32),
(I-P6767,A-7,R²-26,R³-1), (I-P6768,A-7,R²-26,R³-2), (I-P6901,A-7,R²-29,R³-33), (I-P6902,A-7,R²-29,R³-34),
(I-P6769,A-7,R²-26,R³-3), (I-P6770,A-7,R²-26,R³-4), (I-P6903,A-8,R²-1,R³-1), (I-P6904,A-8,R²-1,R³-2),
(I-P6771,A-7,R²-26,R³-5), (I-P6772,A-7,R²-26,R³-6), (I-P6905,A-8,R²-1,R³-3), (I-P6906,A-8,R²-1,R³-4),
(I-P6773,A-7,R²-26,R³-7), (I-P6774,A-7,R²-26,R³-8), (I-P6907,A-8,R²-1,R³-5), (I-P6908,A-8,R²-1,R³-6),
(I-P6775,A-7,R²-26,R³-9), (I-P6776,A-7,R²-26,R³-10), (I-P6909,A-8,R²-1,R³-7), (I-P6910,A-8,R²-1,R³-8),
(I-P6777,A-7,R²-26,R³-11), (I-P6778,A-7,R²-26,R³-12), (I-P6911,A-8,R²-1,R³-9), (I-P6912,A-8,R²-1,R³-10),
(I-P6779,A-7,R²-26,R³-13), (I-P6780,A-7,R²-26,R³-14), (I-P6913,A-8,R²-1,R³-11), (I-P6914,A-8,R²-1,R³-12),
(I-P6781,A-7,R²-26,R³-15), (I-P6782,A-7,R²-26,R³-16), (I-P6915,A-8,R²-1,R³-13), (I-P6916,A-8,R²-1,R³-14),
(I-P6783,A-7,R²-26,R³-17), (I-P6784,A-7,R²-26,R³-18), (I-P6917,A-8,R²-1,R³-15), (I-P6918,A-8,R²-1,R³-16),
(I-P6785,A-7,R²-26,R³-19), (I-P6786,A-7,R²-26,R³-20), (I-P6919,A-8,R²-1,R³-17), (I-P6920,A-8,R²-1,R³-18),
(I-P6787,A-7,R²-26,R³-21), (I-P6788,A-7,R²-26,R³-22), (I-P6921,A-8,R²-1,R³-19), (I-P6922,A-8,R²-1,R³-20),
(I-P6789,A-7,R²-26,R³-23), (I-P6790,A-7,R²-26,R³-24), (I-P6923,A-8,R²-1,R³-21), (I-P6924,A-8,R²-1,R³-22),
(I-P6791,A-7,R²-26,R³-25), (I-P6792,A-7,R²-26,R³-26), (I-P6925,A-8,R²-1,R³-23), (I-P6926,A-8,R²-1,R³-24),
(I-P6793,A-7,R²-26,R³-27), (I-P6794,A-7,R²-26,R³-28), (I-P6927,A-8,R²-1,R³-25), (I-P6928,A-8,R²-1,R³-26),
(I-P6795,A-7,R²-26,R³-29), (I-P6796,A-7,R²-26,R³-30), (I-P6929,A-8,R²-1,R³-27), (I-P6930,A-8,R²-1,R³-28),
(I-P6797,A-7,R²-26,R³-31), (I-P6798,A-7,R²-26,R³-32), (I-P6931,A-8,R²-1,R³-29), (I-P6932,A-8,R²-1,R³-30),
(I-P6799,A-7,R²-26,R³-33), (I-P6800,A-7,R²-26,R³-34), (I-P6933,A-8,R²-1,R³-31), (I-P6934,A-8,R²-1,R³-32),
(I-P6801,A-7,R²-27,R³-1), (I-P6802,A-7,R²-27,R³-2), (I-P6935,A-8,R²-1,R³-33), (I-P6936,A-8,R²-1,R³-34),
(I-P6803,A-7,R²-27,R³-3), (I-P6804,A-7,R²-27,R³-4), (I-P6937,A-8,R²-2,R³-1), (I-P6938,A-8,R²-2,R³-2),
(I-P6805,A-7,R²-27,R³-5), (I-P6806,A-7,R²-27,R³-6), (I-P6939,A-8,R²-2,R³-3), (I-P6940,A-8,R²-2,R³-4),
(I-P6807,A-7,R²-27,R³-7), (I-P6808,A-7,R²-27,R³-8), (I-P6941,A-8,R²-2,R³-5), (I-P6942,A-8,R²-2,R³-6),
(I-P6809,A-7,R²-27,R³-9), (I-P6810,A-7,R²-27,R³-10), (I-P6943,A-8,R²-2,R³-7), (I-P6944,A-8,R²-2,R³-8),
(I-P6811,A-7,R²-27,R³-11), (I-P6812,A-7,R²-27,R³-12), (I-P6945,A-8,R²-2,R³-9), (I-P6946,A-8,R²-2,R³-10),
(I-P6813,A-7,R²-27,R³-13), (I-P6814,A-7,R²-27,R³-14), (I-P6947,A-8,R²-2,R³-11), (I-P6948,A-8,R²-2,R³-12),
(I-P6815,A-7,R²-27,R³-15), (I-P6816,A-7,R²-27,R³-16), (I-P6949,A-8,R²-2,R³-13), (I-P6950,A-8,R²-2,R³-14),
(I-P6817,A-7,R²-27,R³-17), (I-P6818,A-7,R²-27,R³-18), (I-P6951,A-8,R²-2,R³-15), (I-P6952,A-8,R²-2,R³-16),
(I-P6819,A-7,R²-27,R³-19), (I-P6820,A-7,R²-27,R³-20), (I-P6953,A-8,R²-2,R³-17), (I-P6954,A-8,R²-2,R³-18),
(I-P6821,A-7,R²-27,R³-21), (I-P6822,A-7,R²-27,R³-22), (I-P6955,A-8,R²-2,R³-19), (I-P6956,A-8,R²-2,R³-20),
(I-P6823,A-7,R²-27,R³-23), (I-P6824,A-7,R²-27,R³-24), (I-P6957,A-8,R²-2,R³-21), (I-P6958,A-8,R²-2,R³-22),
(I-P6825,A-7,R²-27,R³-25), (I-P6826,A-7,R²-27,R³-26), (I-P6959,A-8,R²-2,R³-23), (I-P6960,A-8,R²-2,R³-24),
(I-P6827,A-7,R²-27,R³-27), (I-P6828,A-7,R²-27,R³-28), (I-P6961,A-8,R²-2,R³-25), (I-P6962,A-8,R²-2,R³-26),
(I-P6829,A-7,R²-27,R³-29), (I-P6830,A-7,R²-27,R³-30), (I-P6963,A-8,R²-2,R³-27), (I-P6964,A-8,R²-2,R³-28),
(I-P6831,A-7,R²-27,R³-31), (I-P6832,A-7,R²-27,R³-32), (I-P6965,A-8,R²-2,R³-29), (I-P6966,A-8,R²-2,R³-30),
(I-P6833,A-7,R²-27,R³-33), (I-P6834,A-7,R²-27,R³-34), (I-P6967,A-8,R²-2,R³-31), (I-P6968,A-8,R²-2,R³-32),
(I-P6835,A-7,R²-28,R³-1), (I-P6836,A-7,R²-28,R³-2), (I-P6969,A-8,R²-2,R³-33), (I-P6970,A-8,R²-2,R³-34),
(I-P6837,A-7,R²-28,R³-3), (I-P6838,A-7,R²-28,R³-4), (I-P6971,A-8,R²-3,R³-1), (I-P6972,A-8,R²-3,R³-2),
(I-P6839,A-7,R²-28,R³-5), (I-P6840,A-7,R²-28,R³-6), (I-P6973,A-8,R²-3,R³-3), (I-P6974,A-8,R²-3,R³-4),
(I-P6841,A-7,R²-28,R³-7), (I-P6842,A-7,R²-28,R³-8), (I-P6975,A-8,R²-3,R³-5), (I-P6976,A-8,R²-3,R³-6),
(I-P6843,A-7,R²-28,R³-9), (I-P6844,A-7,R²-28,R³-10), (I-P6977,A-8,R²-3,R³-7), (I-P6978,A-8,R²-3,R³-8),
(I-P6845,A-7,R²-28,R³-11), (I-P6846,A-7,R²-28,R³-12), (I-P6979,A-8,R²-3,R³-9), (I-P6980,A-8,R²-3,R³-10),
(I-P6847,A-7,R²-28,R³-13), (I-P6848,A-7,R²-28,R³-14), (I-P6981,A-8,R²-3,R³-11), (I-P6982,A-8,R²-3,R³-12),
(I-P6849,A-7,R²-28,R³-15), (I-P6850,A-7,R²-28,R³-16), (I-P6983,A-8,R²-3,R³-13), (I-P6984,A-8,R²-3,R³-14),
(I-P6851,A-7,R²-28,R³-17), (I-P6852,A-7,R²-28,R³-18), (I-P6985,A-8,R²-3,R³-15), (I-P6986,A-8,R²-3,R³-16),
(I-P6853,A-7,R²-28,R³-19), (I-P6854,A-7,R²-28,R³-20), (I-P6987,A-8,R²-3,R³-17), (I-P6988,A-8,R²-3,R³-18),
(I-P6855,A-7,R²-28,R³-21), (I-P6856,A-7,R²-28,R³-22), (I-P6989,A-8,R²-3,R³-19), (I-P6990,A-8,R²-3,R³-20),
(I-P6857,A-7,R²-28,R³-23), (I-P6858,A-7,R²-28,R³-24), (I-P6991,A-8,R²-3,R³-21), (I-P6992,A-8,R²-3,R³-22),
(I-P6859,A-7,R²-28,R³-25), (I-P6860,A-7,R²-28,R³-26), (I-P6993,A-8,R²-3,R³-23), (I-P6994,A-8,R²-3,R³-24),
(I-P6861,A-7,R²-28,R³-27), (I-P6862,A-7,R²-28,R³-28), (I-P6995,A-8,R²-3,R³-25), (I-P6996,A-8,R²-3,R³-26),
(I-P6863,A-7,R²-28,R³-29), (I-P6864,A-7,R²-28,R³-30), (I-P6997,A-8,R²-3,R³-27), (I-P6998,A-8,R²-3,R³-28),
(I-P6865,A-7,R²-28,R³-31), (I-P6866,A-7,R²-28,R³-32), (I-P6999,A-8,R²-3,R³-29), (I-P7000,A-8,R²-3,R³-30),
(I-P6867,A-7,R²-28,R³-33), (I-P6868,A-7,R²-28,R³-34), (I-P7001,A-8,R²-3,R³-31), (I-P7002,A-8,R²-3,R³-32),
(I-P6869,A-7,R²-29,R³-1), (I-P6870,A-7,R²-29,R³-2), (I-P7003,A-8,R²-3,R³-33), (I-P7004,A-8,R²-3,R³-34),
(I-P6871,A-7,R²-29,R³-3), (I-P6872,A-7,R²-29,R³-4), (I-P7005,A-8,R²-4,R³-1), (I-P7006,A-8,R²-4,R³-2),
(I-P6873,A-7,R²-29,R³-5), (I-P6874,A-7,R²-29,R³-6), (I-P7007,A-8,R²-4,R³-3), (I-P7008,A-8,R²-4,R³-4),
(I-P6875,A-7,R²-29,R³-7), (I-P6876,A-7,R²-29,R³-8), (I-P7009,A-8,R²-4,R³-5), (I-P7010,A-8,R²-4,R³-6),
(I-P6877,A-7,R²-29,R³-9), (I-P6878,A-7,R²-29,R³-10), (I-P7011,A-8,R²-4,R³-7), (I-P7012,A-8,R²-4,R³-8),
(I-P6879,A-7,R²-29,R³-11), (I-P6880,A-7,R²-29,R³-12), (I-P7013,A-8,R²-4,R³-9), (I-P7014,A-8,R²-4,R³-10),
(I-P6881,A-7,R²-29,R³-13), (I-P6882,A-7,R²-29,R³-14), (I-P7015,A-8,R²-4,R³-11), (I-P7016,A-8,R²-4,R³-12),
(I-P6883,A-7,R²-29,R³-15), (I-P6884,A-7,R²-29,R³-16), (I-P7017,A-8,R²-4,R³-13), (I-P7018,A-8,R²-4,R³-14),
(I-P6885,A-7,R²-29,R³-17), (I-P6886,A-7,R²-29,R³-18), (I-P7019,A-8,R²-4,R³-15), (I-P7020,A-8,R²-4,R³-16),
(I-P6887,A-7,R²-29,R³-19), (I-P6888,A-7,R²-29,R³-20), (I-P7021,A-8,R²-4,R³-17), (I-P7022,A-8,R²-4,R³-18),
(I-P6889,A-7,R²-29,R³-21), (I-P6890,A-7,R²-29,R³-22), (I-P7023,A-8,R²-4,R³-19), (I-P7024,A-8,R²-4,R³-20),
(I-P6891,A-7,R²-29,R³-23), (I-P6892,A-7,R²-29,R³-24), (I-P7025,A-8,R²-4,R³-21), (I-P7026,A-8,R²-4,R³-22),
(I-P6893,A-7,R²-29,R³-25), (I-P6894,A-7,R²-29,R³-26), (I-P7027,A-8,R²-4,R³-23), (I-P7028,A-8,R²-4,R³-24),
(I-P6895,A-7,R²-29,R³-27), (I-P6896,A-7,R²-29,R³-28), (I-P7029,A-8,R²-4,R³-25), (I-P7030,A-8,R²-4,R³-26), (I-P7031,A-8,R²-4,R³-27), (I-P7032,A-8,R²-4,R³-28), (I-P7165,A-8,R²-8,R³-25), (I-P7166,A-8,R²-8,R³-26),
(I-P7033,A-8,R²-4,R³-29), (I-P7034,A-8,R²-4,R³-30), (I-P7167,A-8,R²-8,R³-27), (I-P7168,A-8,R²-8,R³-28),
(I-P7035,A-8,R²-4,R³-31), (I-P7036,A-8,R²-4,R³-32), (I-P7169,A-8,R²-8,R³-29), (I-P7170,A-8,R²-8,R³-30),
(I-P7037,A-8,R²-4,R³-33), (I-P7038,A-8,R²-4,R³-34), (I-P7171,A-8,R²-8,R³-31), (I-P7172,A-8,R²-8,R³-32),
(I-P7039,A-8,R²-5,R³-1), (I-P7040,A-8,R²-5,R³-2), (I-P7173,A-8,R²-8,R³-33), (I-P7174,A-8,R²-8,R³-34),
(I-P7041,A-8,R²-5,R³-3), (I-P7042,A-8,R²-5,R³-4), (I-P7175,A-8,R²-9,R³-1), (I-P7176,A-8,R²-9,R³-2),
(I-P7043,A-8,R²-5,R³-5), (I-P7044,A-8,R²-5,R³-6), (I-P7177,A-8,R²-9,R³-3), (I-P7178,A-8,R²-9,R³-4),
(I-P7045,A-8,R²-5,R³-7), (I-P7046,A-8,R²-5,R³-8), (I-P7179,A-8,R²-9,R³-5), (I-P7180,A-8,R²-9,R³-6),
(I-P7047,A-8,R²-5,R³-9), (I-P7048,A-8,R²-5,R³-10), (I-P7181,A-8,R²-9,R³-7), (I-P7182,A-8,R²-9,R³-8),
(I-P7049,A-8,R²-5,R³-11), (I-P7050,A-8,R²-5,R³-12), (I-P7183,A-8,R²-9,R³-9), (I-P7184,A-8,R²-9,R³-10),
(I-P7051,A-8,R²-5,R³-13), (I-P7052,A-8,R²-5,R³-14), (I-P7185,A-8,R²-9,R³-11), (I-P7186,A-8,R²-9,R³-12),
(I-P7053,A-8,R²-5,R³-15), (I-P7054,A-8,R²-5,R³-16), (I-P7187,A-8,R²-9,R³-13), (I-P7188,A-8,R²-9,R³-14),
(I-P7055,A-8,R²-5,R³-17), (I-P7056,A-8,R²-5,R³-18), (I-P7189,A-8,R²-9,R³-15), (I-P7190,A-8,R²-9,R³-16),
(I-P7057,A-8,R²-5,R³-19), (I-P7058,A-8,R²-5,R³-20), (I-P7191,A-8,R²-9,R³-17), (I-P7192,A-8,R²-9,R³-18),
(I-P7059,A-8,R²-5,R³-21), (I-P7060,A-8,R²-5,R³-22), (I-P7193,A-8,R²-9,R³-19), (I-P7194,A-8,R²-9,R³-20),
(I-P7061,A-8,R²-5,R³-23), (I-P7062,A-8,R²-5,R³-24), (I-P7195,A-8,R²-9,R³-21), (I-P7196,A-8,R²-9,R³-22),
(I-P7063,A-8,R²-5,R³-25), (I-P7064,A-8,R²-5,R³-26), (I-P7197,A-8,R²-9,R³-23), (I-P7198,A-8,R²-9,R³-24),
(I-P7065,A-8,R²-5,R³-27), (I-P7066,A-8,R²-5,R³-28), (I-P7199,A-8,R²-9,R³-25), (I-P7200,A-8,R²-9,R³-26),
(I-P7067,A-8,R²-5,R³-29), (I-P7068,A-8,R²-5,R³-30), (I-P7201,A-8,R²-9,R³-27), (I-P7202,A-8,R²-9,R³-28),
(I-P7069,A-8,R²-5,R³-31), (I-P7070,A-8,R²-5,R³-32), (I-P7203,A-8,R²-9,R³-29), (I-P7204,A-8,R²-9,R³-30),
(I-P7071,A-8,R²-5,R³-33), (I-P7072,A-8,R²-5,R³-34), (I-P7205,A-8,R²-9,R³-31), (I-P7206,A-8,R²-9,R³-32),
(I-P7073,A-8,R²-6,R³-1), (I-P7074,A-8,R²-6,R³-2), (I-P7207,A-8,R²-9,R³-33), (I-P7208,A-8,R²-9,R³-34),
(I-P7075,A-8,R²-6,R³-3), (I-P7076,A-8,R²-6,R³-4), (I-P7209,A-8,R²-10,R³-1), (I-P7210,A-8,R²-10,R³-2),
(I-P7077,A-8,R²-6,R³-5), (I-P7078,A-8,R²-6,R³-6), (I-P7211,A-8,R²-10,R³-3), (I-P7212,A-8,R²-10,R³-4),
(I-P7079,A-8,R²-6,R³-7), (I-P7080,A-8,R²-6,R³-8), (I-P7213,A-8,R²-10,R³-5), (I-P7214,A-8,R²-10,R³-6),
(I-P7081,A-8,R²-6,R³-9), (I-P7082,A-8,R²-6,R³-10), (I-P7215,A-8,R²-10,R³-7), (I-P7216,A-8,R²-10,R³-8),
(I-P7083,A-8,R²-6,R³-11), (I-P7084,A-8,R²-6,R³-12), (I-P7217,A-8,R²-10,R³-9), (I-P7218,A-8,R²-10,R³-10),
(I-P7085,A-8,R²-6,R³-13), (I-P7086,A-8,R²-6,R³-14), (I-P7219,A-8,R²-10,R³-11), (I-P7220,A-8,R²-10,R³-12),
(I-P7087,A-8,R²-6,R³-15), (I-P7088,A-8,R²-6,R³-16), (I-P7221,A-8,R²-10,R³-13), (I-P7222,A-8,R²-10,R³-14),
(I-P7089,A-8,R²-6,R³-17), (I-P7090,A-8,R²-6,R³-18), (I-P7223,A-8,R²-10,R³-15), (I-P7224,A-8,R²-10,R³-16),
(I-P7091,A-8,R²-6,R³-19), (I-P7092,A-8,R²-6,R³-20), (I-P7225,A-8,R²-10,R³-17), (I-P7226,A-8,R²-10,R³-18),
(I-P7093,A-8,R²-6,R³-21), (I-P7094,A-8,R²-6,R³-22), (I-P7227,A-8,R²-10,R³-19), (I-P7228,A-8,R²-10,R³-20),
(I-P7095,A-8,R²-6,R³-23), (I-P7096,A-8,R²-6,R³-24), (I-P7229,A-8,R²-10,R³-21), (I-P7230,A-8,R²-10,R³-22),
(I-P7097,A-8,R²-6,R³-25), (I-P7098,A-8,R²-6,R³-26), (I-P7231,A-8,R²-10,R³-23), (I-P7232,A-8,R²-10,R³-24),
(I-P7099,A-8,R²-6,R³-27), (I-P7100,A-8,R²-6,R³-28), (I-P7233,A-8,R²-10,R³-25), (I-P7234,A-8,R²-10,R³-26),
(I-P7101,A-8,R²-6,R³-29), (I-P7102,A-8,R²-6,R³-30), (I-P7235,A-8,R²-10,R³-27), (I-P7236,A-8,R²-10,R³-28),
(I-P7103,A-8,R²-6,R³-31), (I-P7104,A-8,R²-6,R³-32), (I-P7237,A-8,R²-10,R³-29), (I-P7238,A-8,R²-10,R³-30),
(I-P7105,A-8,R²-6,R³-33), (I-P7106,A-8,R²-6,R³-34), (I-P7239,A-8,R²-10,R³-31), (I-P7240,A-8,R²-10,R³-32),
(I-P7107,A-8,R²-7,R³-1), (I-P7108,A-8,R²-7,R³-2), (I-P7241,A-8,R²-10,R³-33), (I-P7242,A-8,R²-10,R³-34),
(I-P7109,A-8,R²-7,R³-3), (I-P7110,A-8,R²-7,R³-4), (I-P7243,A-8,R²-11,R³-1), (I-P7244,A-8,R²-11,R³-2),
(I-P7111,A-8,R²-7,R³-5), (I-P7112,A-8,R²-7,R³-6), (I-P7245,A-8,R²-11,R³-3), (I-P7246,A-8,R²-11,R³-4),
(I-P7113,A-8,R²-7,R³-7), (I-P7114,A-8,R²-7,R³-8), (I-P7247,A-8,R²-11,R³-5), (I-P7248,A-8,R²-11,R³-6),
(I-P7115,A-8,R²-7,R³-9), (I-P7116,A-8,R²-7,R³-10), (I-P7249,A-8,R²-11,R³-7), (I-P7250,A-8,R²-11,R³-8),
(I-P7117,A-8,R²-7,R³-11), (I-P7118,A-8,R²-7,R³-12), (I-P7251,A-8,R²-11,R³-9), (I-P7252,A-8,R²-11,R³-10),
(I-P7119,A-8,R²-7,R³-13), (I-P7120,A-8,R²-7,R³-14), (I-P7253,A-8,R²-11,R³-11), (I-P7254,A-8,R²-11,R³-12),
(I-P7121,A-8,R²-7,R³-15), (I-P7122,A-8,R²-7,R³-16), (I-P7255,A-8,R²-11,R³-13), (I-P7256,A-8,R²-11,R³-14),
(I-P7123,A-8,R²-7,R³-17), (I-P7124,A-8,R²-7,R³-18), (I-P7257,A-8,R²-11,R³-15), (I-P7258,A-8,R²-11,R³-16),
(I-P7125,A-8,R²-7,R³-19), (I-P7126,A-8,R²-7,R³-20), (I-P7259,A-8,R²-11,R³-17), (I-P7260,A-8,R²-11,R³-18),
(I-P7127,A-8,R²-7,R³-21), (I-P7128,A-8,R²-7,R³-22), (I-P7261,A-8,R²-11,R³-19), (I-P7262,A-8,R²-11,R³-20),
(I-P7129,A-8,R²-7,R³-23), (I-P7130,A-8,R²-7,R³-24), (I-P7263,A-8,R²-11,R³-21), (I-P7264,A-8,R²-11,R³-22),
(I-P7131,A-8,R²-7,R³-25), (I-P7132,A-8,R²-7,R³-26), (I-P7265,A-8,R²-11,R³-23), (I-P7266,A-8,R²-11,R³-24),
(I-P7133,A-8,R²-7,R³-27), (I-P7134,A-8,R²-7,R³-28), (I-P7267,A-8,R²-11,R³-25), (I-P7268,A-8,R²-11,R³-26),
(I-P7135,A-8,R²-7,R³-29), (I-P7136,A-8,R²-7,R³-30), (I-P7269,A-8,R²-11,R³-27), (I-P7270,A-8,R²-11,R³-28),
(I-P7137,A-8,R²-7,R³-31), (I-P7138,A-8,R²-7,R³-32), (I-P7271,A-8,R²-11,R³-29), (I-P7272,A-8,R²-11,R³-30),
(I-P7139,A-8,R²-7,R³-33), (I-P7140,A-8,R²-7,R³-34), (I-P7273,A-8,R²-11,R³-31), (I-P7274,A-8,R²-11,R³-32),
(I-P7141,A-8,R²-8,R³-1), (I-P7142,A-8,R²-8,R³-2), (I-P7275,A-8,R²-11,R³-33), (I-P7276,A-8,R²-11,R³-34),
(I-P7143,A-8,R²-8,R³-3), (I-P7144,A-8,R²-8,R³-4), (I-P7277,A-8,R²-12,R³-1), (I-P7278,A-8,R²-12,R³-2),
(I-P7145,A-8,R²-8,R³-5), (I-P7146,A-8,R²-8,R³-6), (I-P7279,A-8,R²-12,R³-3), (I-P7280,A-8,R²-12,R³-4),
(I-P7147,A-8,R²-8,R³-7), (I-P7148,A-8,R²-8,R³-8), (I-P7281,A-8,R²-12,R³-5), (I-P7282,A-8,R²-12,R³-6),
(I-P7149,A-8,R²-8,R³-9), (I-P7150,A-8,R²-8,R³-10), (I-P7283,A-8,R²-12,R³-7), (I-P7284,A-8,R²-12,R³-8),
(I-P7151,A-8,R²-8,R³-11), (I-P7152,A-8,R²-8,R³-12), (I-P7285,A-8,R²-12,R³-9), (I-P7286,A-8,R²-12,R³-10),
(I-P7153,A-8,R²-8,R³-13), (I-P7154,A-8,R²-8,R³-14), (I-P7287,A-8,R²-12,R³-11), (I-P7288,A-8,R²-12,R³-12),
(I-P7155,A-8,R²-8,R³-15), (I-P7156,A-8,R²-8,R³-16), (I-P7289,A-8,R²-12,R³-13), (I-P7290,A-8,R²-12,R³-14),
(I-P7157,A-8,R²-8,R³-17), (I-P7158,A-8,R²-8,R³-18), (I-P7291-8,R²-12,R³-15), (I-P7292,A-8,R²-12,R³-16),
(I-P7159,A-8,R²-8,R³-19), (I-P7160,A-8,R²-8,R³-20), (I-P7293,A-8,R²-12,R³-17), (I-P7294,A-8,R²-12,R³-18),
(I-P7161,A-8,R²-8,R³-21), (I-P7162,A-8,R²-8,R³-22), (I-P7295,A-8,R²-12,R³-19), (I-P7296,A-8,R²-12,R³-20),
(I-P7163,A-8,R²-8,R³-23), (I-P7164,A-8,R²-8,R³-24), (I-P7297,A-8,R²-12,R³-21), (I-P7298,A-8,R²-12,R³-22), (I-P7299,A-8,$R^2$-12,$R^3$-23), (I-P7300,A-8,$R^2$-12,$R^3$-24), (I-P7434,A-8,$R^2$-16,$R^3$-22), (I-P7435,A-8,$R^2$-16,$R^3$-23),
(I-P7301,A-8,$R^2$-12,$R^3$-25), (I-P7302,A-8,$R^2$-12,$R^3$-26), (I-P7436,A-8,$R^2$-16,$R^3$-24), (I-P7437,A-8,$R^2$-16,$R^3$-25),
(I-P7303,A-8,$R^2$-12,$R^3$-27), (I-P7304,A-8,$R^2$-12,$R^3$-28), (I-P7438,A-8,$R^2$-16,$R^3$-26), (I-P7439,A-8,$R^2$-16,$R^3$-27),
(I-P7305,A-8,$R^2$-12,$R^3$-29), (I-P7306,A-8,$R^2$-12,$R^3$-30), (I-P7440,A-8,$R^2$-16,$R^3$-28), (I-P7441,A-8,$R^2$-16,$R^3$-29),
(I-P7307,A-8,$R^2$-12,$R^3$-31), (I-P7308,A-8,$R^2$-12,$R^3$-32), (I-P7442,A-8,$R^2$-16,$R^3$-30), (I-P7443,A-8,$R^2$-16,$R^3$-31),
(I-P7309,A-8,$R^2$-12,$R^3$-33), (I-P7310,A-8,$R^2$-12,$R^3$-34), (I-P7444,A-8,$R^2$-16,$R^3$-32), (I-P7445,A-8,$R^2$-16,$R^3$-33),
(I-P7311,A-8,$R^2$-13,$R^3$-1), (I-P7312,A-8,$R^2$-13,$R^3$-2), (I-P7446,A-8,$R^2$-16,$R^3$-34), (I-P7447,A-8,$R^2$-17,$R^3$-1),
(I-P7313,A-8,$R^2$-13,$R^3$-3), (I-P7314,A-8,$R^2$-13,$R^3$-4), (I-P7448,A-8,$R^2$-17,$R^3$-2), (I-P7449,A-8,$R^2$-17,$R^3$-3),
(I-P7315,A-8,$R^2$-13,$R^3$-5), (I-P7316,A-8,$R^2$-13,$R^3$-6), (I-P7450,A-8,$R^2$-17,$R^3$-4), (I-P7451,A-8,$R^2$-17,$R^3$-5),
(I-P7317,A-8,$R^2$-13,$R^3$-7), (I-P7318,A-8,$R^2$-13,$R^3$-8), (1-P7452,A-8,$R^2$-17,$R^3$-6), (I-P7453,A-8,$R^2$-17,$R^3$-7),
(I-P7319,A-8,$R^2$-13,$R^3$-9), (I-P7320,A-8,$R^2$-13,$R^3$-10), (I-P7454,A-8,$R^2$-17,$R^3$-8), (I-P7455,A-8,$R^2$-17,$R^3$-9),
(I-P7321,A-8,$R^2$-13,$R^3$-11), (I-P7322,A-8,$R^2$-13,$R^3$-12), (I-P7456,A-8,$R^2$-17,$R^3$-10), (I-P7457,A-8,$R^2$-17,$R^3$-11),
(I-P7323,A-8,$R^2$-13,$R^3$-13), (I-P7324,A-8,$R^2$-13,$R^3$-14), (I-P7458,A-8,$R^2$-17,$R^3$-12), (I-P7459,A-8,$R^2$-17,$R^3$-13),
(I-P7325,A-8,$R^2$-13,$R^3$-15), (I-P7326,A-8,$R^2$-13,$R^3$-16), (I-P7460,A-8,$R^2$-17,$R^3$-14), (I-P7461,A-8,$R^2$-17,$R^3$-15),
(I-P7327,A-8,$R^2$-13,$R^3$-17), (I-P7328,A-8,$R^2$-13,$R^3$-18), (I-P7462,A-8,$R^2$-17,$R^3$-16), (I-P7463,A-8,$R^2$-17,$R^3$-17),
(I-P7329,A-8,$R^2$-13,$R^3$-19), (I-P7330,A-8,$R^2$-13,$R^3$-20), (I-P7464,A-8,$R^2$-17,$R^3$-18), (I-P7465,A-8,$R^2$-17,$R^3$-19),
(I-P7331,A-8,$R^2$-13,$R^3$-21), (I-P7332,A-8,$R^2$-13,$R^3$-22), (I-P7466,A-8,$R^2$-17,$R^3$-20), (I-P7467,A-8,$R^2$-17,$R^3$-21),
(I-P7333,A-8,$R^2$-13,$R^3$-23), (I-P7334,A-8,$R^2$-13,$R^3$-24), (I-P7468,A-8,$R^2$-17,$R^3$-22), (I-P7469,A-8,$R^2$-17,$R^3$-23),
(I-P7335,A-8,$R^2$-13,$R^3$-25), (I-P7336,A-8,$R^2$-13,$R^3$-26), (I-P7470,A-8,$R^2$-17,$R^3$-24), (I-P7471,A-8,$R^2$-17,$R^3$-25),
(I-P7337,A-8,$R^2$-13,$R^3$-27), (I-P7338,A-8,$R^2$-13,$R^3$-28), (I-P7472,A-8,$R^2$-17,$R^3$-26), (I-P7473,A-8,$R^2$-17,$R^3$-27),
(I-P7339,A-8,$R^2$-13,$R^3$-29), (I-P7340,A-8,$R^2$-13,$R^3$-30), (I-P7474,A-8,$R^2$-17,$R^3$-28), (I-P7475,A-8,$R^2$-17,$R^3$-29),
(I-P7341,A-8,$R^2$-13,$R^3$-31), (I-P7342,A-8,$R^2$-13,$R^3$-32), (I-P7476,A-8,$R^2$-17,$R^3$-30), (I-P7477,A-8,$R^2$-17,$R^3$-31),
(I-P7343,A-8,$R^2$-13,$R^3$-33), (I-P7344,A-8,$R^2$-13,$R^3$-34), (I-P7478,A-8,$R^2$-17,$R^3$-32), (I-P7479,A-8,$R^2$-17,$R^3$-33),
(I-P7345,A-8,$R^2$-14,$R^3$-1), (I-P7346,A-8,$R^2$-14,$R^3$-2), (I-P7480,A-8,$R^2$-17,$R^3$-34), (I-P7481,A-8,$R^2$-18,$R^3$-1),
(I-P7347,A-8,$R^2$-14,$R^3$-3), (I-P7348,A-8,$R^2$-14,$R^3$-4), (I-P7482,A-8,$R^2$-18,$R^3$-2), (I-P7483,A-8,$R^2$-18,$R^3$-3),
(I-P7349,A-8,$R^2$-14,$R^3$-5), (I-P7350,A-8,$R^2$-14,$R^3$-6), (I-P7484,A-8,$R^2$-18,$R^3$-4), (I-P7485,A-8,$R^2$-18,$R^3$-5),
(I-P7351,A-8,$R^2$-14,$R^3$-7), (I-P7352,A-8,$R^2$-14,$R^3$-8), (I-P7486,A-8,$R^2$-18,$R^3$-6), (I-P7487,A-8,$R^2$-18,$R^3$-7),
(I-P7353,A-P7354,A-8,$R^2$-14,$R^3$-10), (I-P7355,A-8,$R^2$-14,$R^3$-11), (I-P7488,A-8,$R^2$-18,$R^3$-8), (I-P7489,A-8,$R^2$-18,$R^3$-9),
(I-P7356,A-8,$R^2$-14,$R^3$-12), (I-P7357,A-8,$R^2$-14,$R^3$-13), (I-P7490,A-8,$R^2$-18,$R^3$-10), (I-P7491,A-8,$R^2$-18,$R^3$-11),
(I-P7358,A-8,$R^2$-14,$R^3$-14), (I-P7359,A-8,$R^2$-14,$R^3$-15), (I-P7492,A-8,$R^2$-18,$R^3$-12), (I-P7493,A-8,$R^2$-18,$R^3$-13),
(I-P7360,A-8,$R^2$-14,$R^3$-16), (I-P7361,A-8,$R^2$-14,$R^3$-17), (I-P7494,A-8,$R^2$-18,$R^3$-14), (I-P7495,A-8,$R^2$-18,$R^3$-15),
(I-P7362,A-8,$R^2$-14,$R^3$-18), (I-P7363,A-8,$R^2$-14,$R^3$-19), (I-P7496,A-8,$R^2$-18,$R^3$-16), (I-P7497,A-8,$R^2$-18,$R^3$-17),
(I-P7364,A-8,$R^2$-14,$R^3$-20), (I-P7365,A-8,$R^2$-14,$R^3$-21), (I-P7498,A-8,$R^2$-18,$R^3$-18), (I-P7499,A-8,$R^2$-18,$R^3$-19),
(I-P7366,A-8,$R^2$-14,$R^3$-22), (I-P7367,A-8,$R^2$-14,$R^3$-23), (I-P7500,A-8,$R^2$-18,$R^3$-20), (I-P7501,A-8,$R^2$-18,$R^3$-21),
(I-P7368,A-8,$R^2$-14,$R^3$-24), (I-P7369,A-8,$R^2$-14,$R^3$-25), (I-P7502,A-8,$R^2$-18,$R^3$-22), (I-P7503,A-8,$R^2$-18,$R^3$-23),
(I-P7370,A-8,$R^2$-14,$R^3$-26), (I-P7371,A-8,$R^2$-14,$R^3$-27), (I-P7504,A-8,$R^2$-18,$R^3$-24), (I-P7505,A-8,$R^2$-18,$R^3$-25),
(I-P7372,A-8,$R^2$-14,$R^3$-28), (I-P7373,A-8,$R^2$-14,$R^3$-29), (I-P7506,A-8,$R^2$-18,$R^3$-26), (I-P7507,A-8,$R^2$-18,$R^3$-27),
(I-P7374,A-8,$R^2$-14,$R^3$-30), (I-P7375,A-8,$R^2$-14,$R^3$-31), (I-P7508,A-8,$R^2$-18,$R^3$-28), (I-P7509,A-8,$R^2$-18,$R^3$-29),
(I-P7376,A-8,$R^2$-14,$R^3$-32), (I-P7377,A-8,$R^2$-14,$R^3$-33), (I-P7510,A-8,$R^2$-18,$R^3$-30), (I-P7511,A-8,$R^2$-18,$R^3$-31),
(I-P7378,A-8,$R^2$-14,$R^3$-34), (I-P7379,A-8,$R^2$-15,$R^3$-1), (I-P7512,A-8,$R^2$-18,$R^3$-32), (I-P7513,A-8,$R^2$-18,$R^3$-33),
(I-P7380,A-8,$R^2$-15,$R^3$-2), (I-P7381,A-8,$R^2$-15,$R^3$-3), (I-P7514,A-8,$R^2$-18,$R^3$-34), (I-P7515,A-8,$R^2$-19,$R^3$-1),
(I-P7382,A-8,$R^2$-15,$R^3$-4), (I-P7383,A-8,$R^2$-15,$R^3$-5), (I-P7516,A-8,$R^2$-19,$R^3$-2), (I-P7517,A-8,$R^2$-19,$R^3$-3),
(I-P7384,A-8,$R^2$-15,$R^3$-6), (I-P7385,A-8,$R^2$-15,$R^3$-7), (I-P7518,A-8,$R^2$-19,$R^3$-4), (I-P7519,A-8,$R^2$-19,$R^3$-5),
(I-P7386,A-8,$R^2$-15,$R^3$-8), (I-P7387,A-8,$R^2$-15,$R^3$-9), (I-P7520,A-8,$R^2$-19,$R^3$-6), (I-P7521,A-8,$R^2$-19,$R^3$-7),
(I-P7388,A-8,$R^2$-15,$R^3$-10), (I-P7389,A-8,$R^2$-15,$R^3$-11), (I-P7522,A-8,$R^2$-19,$R^3$-8), (I-P7523,A-8,$R^2$-19,$R^3$-9),
(I-P7390,A-8,$R^2$-15,$R^3$-12), (I-P7391,A-8,$R^2$-15,$R^3$-13), (I-P7524,A-8,$R^2$-19,$R^3$-10), (I-P7525,A-8,$R^2$-19,$R^3$-11),
(I-P7392,A-8,$R^2$-15,$R^3$-14), (I-P7393,A-8,$R^2$-15,$R^3$-15), (I-P7526,A-8,$R^2$-19,$R^3$-12), (I-P7527,A-8,$R^2$-19,$R^3$-13),
(I-P7394,A-8,$R^2$-15,$R^3$-16), (I-P7395,A-8,$R^2$-15,$R^3$-17), (I-P7528,A-8,$R^2$-19,$R^3$-14), (I-P7529,A-8,$R^2$-19,$R^3$-15),
(I-P7396,A-8,$R^2$-15,$R^3$-18), (I-P7397,A-8,$R^2$-15,$R^3$-19), (I-P7530,A-8,$R^2$-19,$R^3$-16), (I-P7531,A-8,$R^2$-19,$R^3$-17),
(I-P7398,A-8,$R^2$-15,$R^3$-20), (I-P7399,A-8,$R^2$-15,$R^3$-21), (I-P7532,A-8,$R^2$-19,$R^3$-18), (I-P7533,A-8,$R^2$-19,$R^3$-19),
(I-P7400,A-8,$R^2$-15,$R^3$-22), (I-P7401,A-8,$R^2$-15,$R^3$-23), (I-P7534,A-8,$R^2$-19,$R^3$-20), (I-P7535,A-8,$R^2$-19,$R^3$-21),
(I-P7402,A-8,$R^2$-15,$R^3$-24), (I-P7403,A-8,$R^2$-15,$R^3$-25), (I-P7536,A-8,$R^2$-19,$R^3$-22), (I-P7537,A-8,$R^2$-19,$R^3$-23),
(I-P7404,A-8,$R^2$-15,$R^3$-26), (I-P7405,A-8,$R^2$-15,$R^3$-27), (I-P7538,A-8,$R^2$-19,$R^3$-24), (I-P7539,A-8,$R^2$-19,$R^3$-25),
(I-P7406,A-8,$R^2$-15,$R^3$-28), (I-P7407,A-8,$R^2$-15,$R^3$-29), (I-P7540,A-8,$R^2$-19,$R^3$-26), (I-P7541,A-8,$R^2$-19,$R^3$-27),
(I-P7408,A-8,$R^2$-15,$R^3$-30), (I-P7409,A-8,$R^2$-15,$R^3$-31), (I-P7542,A-8,$R^2$-19,$R^3$-28), (I-P7543,A-8,$R^2$-19,$R^3$-29),
(I-P7410,A-8,$R^2$-15,$R^3$-32), (I-P7411,A-8,$R^2$-15,$R^3$-33), (I-P7544,A-8,$R^2$-19,$R^3$-30), (I-P7545,A-8,$R^2$-19,$R^3$-31),
(I-P7412,A-8,$R^2$-15,$R^3$-34), (I-P7413,A-8,$R^2$-16,$R^3$-1), (I-P7546,A-8,$R^2$-19,$R^3$-32), (I-P7547,A-8,$R^2$-19,$R^3$-33),
(I-P7414,A-8,$R^2$-16,$R^3$-2), (I-P7415,A-8,$R^2$-16,$R^3$-3), (I-P7548,A-8,$R^2$-19,$R^3$-34), (I-P7549,A-8,$R^2$-20,$R^3$-1),
(I-P7416,A-8,$R^2$-16,$R^3$-4), (I-P7417,A-8,$R^2$-16,$R^3$-5), (I-P7550,A-8,$R^2$-20,$R^3$-2), (I-P7551,A-8,$R^2$-20,$R^3$-3),
(I-P7418,A-8,$R^2$-16,$R^3$-6), (I-P7419,A-8,$R^2$-16,$R^3$-7), (I-P7552,A-8,$R^2$-20,$R^3$-4), (I-P7553,A-8,$R^2$-20,$R^3$-5),
(I-P7420,A-8,$R^2$-16,$R^3$-8), (I-P7421,A-8,$R^2$-16,$R^3$-9), (I-P7554,A-8,$R^2$-20,$R^3$-6), (I-P7555,A-8,$R^2$-20,$R^3$-7),
(I-P7422,A-8,$R^2$-16,$R^3$-10), (I-P7423,A-8,$R^2$-16,$R^3$-11), (I-P7556,A-8,$R^2$-20,$R^3$-8), (I-P7557,A-8,$R^2$-20,$R^3$-9),
(I-P7424,A-8,$R^2$-16,$R^3$-12), (I-P7425,A-8,$R^2$-16,$R^3$-13), (I-P7558,A-8,$R^2$-20,$R^3$-10), (I-P7559,A-8,$R^2$-20,$R^3$-11),
(I-P7426,A-8,$R^2$-16,$R^3$-14), (I-P7427,A-8,$R^2$-16,$R^3$-15), (I-P7560,A-8,$R^2$-20,$R^3$-12), (I-P7561,A-8,$R^2$-20,$R^3$-13),
(I-P7428,A-8,$R^2$-16,$R^3$-16), (I-P7429,A-8,$R^2$-16,$R^3$-17), (I-P7562,A-8,$R^2$-20,$R^3$-14), (I-P7563,A-8,$R^2$-20,$R^3$-15),
(I-P7430,A-8,$R^2$-16,$R^3$-18), (I-P7431,A-8,$R^2$-16,$R^3$-19), (I-P7564,A-8,$R^2$-20,$R^3$-16), (I-P7565,A-8,$R^2$-20,$R^3$-17),
(I-P7432,A-8,$R^2$-16,$R^3$-20), (I-P7433,A-8,$R^2$-16,$R^3$-21), (I-P7566,A-8,$R^2$-20,$R^3$-18), (I-P7567,A-8,$R^2$-20,$R^3$-19), (I-P7568,A-8,R²-20,R³-20), (I-P7569,A-8,R²-20,R³-21), (I-P7702,A-8,R²-24,R³-18), (I-P7703,A-8,R²-24,R³-19),
(I-P7570,A-8,R²-20,R³-22), (I-P7571,A-8,R²-20,R³-23), (I-P7704,A-8,R²-24,R³-20), (I-P7705,A-8,R²-24,R³-21),
(I-P7572,A-8,R²-20,R³-24), (I-P7573,A-8,R²-20,R³-25), (I-P7706,A-8,R²-24,R³-22), (I-P7707,A-8,R²-24,R³-23),
(I-P7574,A-8,R²-20,R³-26), (I-P7575,A-8,R²-20,R³-27), (I-P7708,A-8,R²-24,R³-24), (I-P7709,A-8,R²-24,R³-25),
(I-P7576,A-8,R²-20,R³-28), (I-P7577,A-8,R²-20,R³-29), (I-P7710,A-8,R²-24,R³-26), (I-P7711,A-8,R²-24,R³-27),
(I-P7578,A-8,R²-20,R³-30), (I-P7579,A-8,R²-20,R³-31), (I-P7712,A-8,R²-24,R³-28), (I-P7713,A-8,R²-24,R³-29),
(I-P7580,A-8,R²-20,R³-32), (I-P7581,A-8,R²-20,R³-33), (I-P7714,A-8,R²-24,R³-30), (I-P7715,A-8,R²-24,R³-31),
(I-P7582,A-8,R²-20,R³-34), (I-P7583,A-8,R²-21,R³-1), (I-P7716,A-8,R²-24,R³-32), (I-P7717,A-8,R²-24,R³-33),
(I-P7584,A-8,R²-21,R³-2), (I-P7585,A-8,R²-21,R³-3), (I-P7718,A-8,R²-24,R³-34), (I-P7719,A-8,R²-25,R³-1),
(I-P7586,A-8,R²-21,R³-4), (I-P7587,A-8,R²-21,R³-5), (I-P7720,A-8,R²-25,R³-2), (I-P7721,A-8,R²-25,R³-3),
(I-P7588,A-8,R²-21,R³-6), (I-P7589,A-8,R²-21,R³-7), (I-P7722,A-8,R²-25,R³-4), (I-P7723,A-8,R²-25,R³-5),
(I-P7590,A-8,R²-21,R³-8), (I-P7591,A-8,R²-21,R³-9), (I-P7724,A-8,R²-25,R³-6), (I-P7725,A-8,R²-25,R³-7),
(I-P7592,A-8,R²-21,R³-10), (I-P7593,A-8,R²-21,R³-11), (I-P7726,A-8,R²-25,R³-8), (I-P7727,A-8,R²-25,R³-9),
(I-P7594,A-8,R²-21,R³-12), (I-P7595,A-8,R²-21,R³-13), (I-P7728,A-8,R²-25,R³-10), (I-P7729,A-8,R²-25,R³-11),
(I-P7596,A-8,R²-21,R³-14), (I-P7597,A-8,R²-21,R³-15), (I-P7730,A-8,R²-25,R³-12), (I-P7731,A-8,R²-25,R³-13),
(I-P7598,A-8,R²-21,R³-16), (I-P7599,A-8,R²-21,R³-17), (I-P7732,A-8,R²-25,R³-14), (I-P7733,A-8,R²-25,R³-15),
(I-P7600,A-8,R²-21,R³-18), (I-P7601,A-8,R²-21,R³-19), (I-P7734,A-8,R²-25,R³-16), (I-P7735,A-8,R²-25,R³-17),
(I-P7602,A-8,R²-21,R³-20), (I-P7603,A-8,R²-21,R³-21), (I-P7736,A-8,R²-25,R³-18), (I-P7737,A-8,R²-25,R³-19),
(I-P7604,A-8,R²-21,R³-22), (I-P7605,A-8,R²-21,R³-23), (I-P7738,A-8,R²-25,R³-20), (I-P7739,A-8,R²-25,R³-21),
(I-P7606,A-8,R²-21,R³-24), (I-P7607,A-8,R²-21,R³-25), (I-P7740,A-8,R²-25,R³-22), (I-P7741,A-8,R²-25,R³-23),
(I-P7608,A-8,R²-21,R³-26), (I-P7609,A-8,R²-21,R³-27), (I-P7742,A-8,R²-25,R³-24), (I-P7743,A-8,R²-25,R³-25),
(I-P7610,A-8,R²-21,R³-28), (I-P7611,A-8,R²-21,R³-29), (I-P7744,A-8,R²-25,R³-26), (I-P7745,A-8,R²-25,R³-27),
(I-P7612,A-8,R²-21,R³-30), (I-P7613,A-8,R²-21,R³-31), (I-P7746,A-8,R²-25,R³-28), (I-P7747,A-8,R²-25,R³-29),
(I-P7614,A-8,R²-21,R³-32), (I-P7615,A-8,R²-21,R³-33), (I-P7748,A-8,R²-25,R³-30), (I-P7749,A-8,R²-25,R³-31),
(I-P7616,A-8,R²-21,R³-34), (I-P7617,A-8,R²-22,R³-1), (I-P7750,A-8,R²-25,R³-32), (I-P7751,A-8,R²-25,R³-33),
(I-P7618,A-8,R²-22,R³-2), (I-P7619,A-8,R²-22,R³-3), (I-P7752,A-8,R²-25,R³-34), (I-P7753,A-8,R²-26,R³-1),
(I-P7620,A-8,R²-22,R³-4), (I-P7621,A-8,R²-22,R³-5), (I-P7754,A-8,R²-26,R³-2), (I-P7755,A-8,R²-26,R³-3),
(I-P7622,A-8,R²-22,R³-6), (I-P7623,A-8,R²-22,R³-7), (I-P7756,A-8,R²-26,R³-4), (I-P7757,A-8,R²-26,R³-5),
(I-P7624,A-8,R²-22,R³-8), (I-P7625,A-8,R²-22,R³-9), (I-P7758,A-8,R²-26,R³-6), (I-P7759,A-8,R²-26,R³-7),
(I-P7626,A-8,R²-22,R³-10), (I-P7627,A-8,R²-22,R³-11), (I-P7760,A-8,R²-26,R³-8), (I-P7761,A-8,R²-26,R³-9),
(I-P7628,A-8,R²-22,R³-12), (I-P7629,A-8,R²-22,R³-13), (I-P7762,A-8,R²-26,R³-10), (I-P7763,A-8,R²-26,R³-11),
(I-P7630,A-8,R²-22,R³-14), (I-P7631,A-8,R²-22,R³-15), (I-P7764,A-8,R²-26,R³-12), (I-P7765,A-8,R²-26,R³-13),
(I-P7632,A-8,R²-22,R³-16), (I-P7633,A-8,R²-22,R³-17), (I-P7766,A-8,R²-26,R³-14), (I-P7767,A-8,R²-26,R³-15),
(I-P7634,A-8,R²-22,R³-18), (I-P7635,A-8,R²-22,R³-19), (I-P7768,A-8,R²-26,R³-16), (I-P7769,A-8,R²-26,R³-17),
(I-P7636,A-8,R²-22,R³-20), (I-P7637,A-8,R²-22,R³-21), (I-P7770,A-8,R²-26,R³-18), (I-P7771,A-8,R²-26,R³-19),
(I-P7638,A-8,R²-22,R³-22), (I-P7639,A-8,R²-22,R³-23), (I-P7772,A-8,R²-26,R³-20), (I-P7773,A-8,R²-26,R³-21),
(I-P7640,A-8,R²-22,R³-24), (I-P7641,A-8,R²-22,R³-25), (I-P7774,A-8,R²-26,R³-22), (I-P7775,A-8,R²-26,R³-23),
(I-P7642,A-8,R²-22,R³-26), (I-P7643,A-8,R²-22,R³-27), (I-P7776,A-8,R²-26,R³-24), (I-P7777,A-8,R²-26,R³-25),
(I-P7644,A-8,R²-22,R³-28), (I-P7645,A-8,R²-22,R³-29), (I-P7778,A-8,R²-26,R³-26), (I-P7779,A-8,R²-26,R³-27),
(I-P7646,A-8,R²-22,R³-30), (I-P7647,A-8,R²-22,R³-31), (I-P7780,A-8,R²-26,R³-28), (I-P7781,A-8,R²-26,R³-29),
(I-P7648,A-8,R²-22,R³-32), (I-P7649,A-8,R²-22,R³-33), (I-P7782,A-8,R²-26,R³-30), (I-P7783,A-8,R²-26,R³-31),
(I-P7650,A-8,R²-22,R³-34), (I-P7651,A-8,R²-23,R³-1), (I-P7784,A-8,R²-26,R³-32), (I-P7785,A-8,R²-26,R³-33),
(I-P7652,A-8,R²-23,R³-2), (I-P7653,A-8,R²-23,R³-3), (I-P7786,A-8,R²-26,R³-34), (I-P7787,A-8,R²-27,R³-1),
(I-P7654,A-8,R²-23,R³-4), (I-P7655,A-8,R²-23,R³-5), (I-P7788,A-8,R²-27,R³-2), (I-P7789,A-8,R²-27,R³-3),
(I-P7656,A-8,R²-23,R³-6), (I-P7657,A-8,R²-23,R³-7), (I-P7790,A-8,R²-27,R³-4), (I-P7791,A-8,R²-27,R³-5),
(I-P7658,A-8,R²-23,R³-8), (I-P7659,A-8,R²-23,R³-9), (I-P7792,A-8,R²-27,R³-6), (I-P7793,A-8,R²-27,R³-7),
(I-P7660,A-8,R²-23,R³-10), (I-P7661,A-8,R²-23,R³-11), (I-P7794,A-8,R²-27,R³-8), (I-P7795,A-8,R²-27,R³-9),
(I-P7662,A-8,R²-23,R³-12), (I-P7663,A-8,R²-23,R³-13), (I-P7796,A-8,R²-27,R³-10), (I-P7797,A-8,R²-27,R³-11),
(I-P7664,A-8,R²-23,R³-14), (I-P7665,A-8,R²-23,R³-15), (I-P7798,A-8,R²-27,R³-12), (I-P7799,A-8,R²-27,R³-13),
(I-P7666,A-8,R²-23,R³-16), (I-P7667,A-8,R²-23,R³-17), (I-P7800,A-8,R²-27,R³-14), (I-P7801,A-8,R²-27,R³-15),
(I-P7668,A-8,R²-23,R³-18), (I-P7669,A-8,R²-23,R³-19), (I-P7802,A-8,R²-27,R³-16), (I-P7803,A-8,R²-27,R³-17),
(I-P7670,A-8,R²-23,R³-20), (I-P7671,A-8,R²-23,R³-21), (I-P7804,A-8,R²-27,R³-18), (I-P7805,A-8,R²-27,R³-19),
(I-P7672,A-8,R²-23,R³-22), (I-P7673,A-8,R²-23,R³-23), (I-P7806,A-8,R²-27,R³-20), (I-P7807,A-8,R²-27,R³-21),
(I-P7674,A-8,R²-23,R³-24), (I-P7675,A-8,R²-23,R³-25), (I-P7808,A-8,R²-27,R³-22), (I-P7809,A-8,R²-27,R³-23),
(I-P7676,A-8,R²-23,R³-26), (I-P7677,A-8,R²-23,R³-27), (I-P7810,A-8,R²-27,R³-24), (I-P7811,A-8,R²-27,R³-25),
(I-P7678,A-8,R²-23,R³-28), (I-P7679,A-8,R²-23,R³-29), (I-P7812,A-8,R²-27,R³-26), (I-P7813,A-8,R²-27,R³-27),
(I-P7680,A-8,R²-23,R³-30), (I-P7681,A-8,R²-23,R³-31), (I-P7814,A-8,R²-27,R³-28), (I-P7815,A-8,R²-27,R³-29),
(I-P7682,A-8,R²-23,R³-32), (I-P7683,A-8,R²-23,R³-33), (I-P7816,A-8,R²-27,R³-30), (I-P7817,A-8,R²-27,R³-31),
(I-P7684,A-8,R²-23,R³-34), (I-P7685,A-8,R²-24,R³-1), (I-P7818,A-8,R²-27,R³-32), (I-P7819,A-8,R²-27,R³-33),
(I-P7686,A-8,R²-24,R³-2), (I-P7687,A-8,R²-24,R³-3), (I-P7820,A-8,R²-27,R³-34), (I-P7821,A-8,R²-28,R³-1),
(I-P7688,A-8,R²-24,R³-4), (I-P7689,A-8,R²-24,R³-5), (I-P7822,A-8,R²-28,R³-2), (I-P7823,A-8,R²-28,R³-3),
(I-P7690,A-8,R²-24,R³-6), (I-P7691,A-8,R²-24,R³-7), (I-P7824,A-8,R²-28,R³-4), (I-P7825,A-8,R²-28,R³-5),
(I-P7692,A-8,R²-24,R³-8), (I-P7693,A-8,R²-24,R³-9), (I-P7826,A-8,R²-28,R³-6), (I-P7827,A-8,R²-28,R³-7),
(I-P7694,A-8,R²-24,R³-10), (I-P7695,A-8,R²-24,R³-11), (I-P7828,A-8,R²-28,R³-8), (I-P7829,A-8,R²-28,R³-9),
(I-P7696,A-8,R²-24,R³-12), (I-P7697,A-8,R²-24,R³-13), (I-P7830,A-8,R²-28,R³-10), (I-P7831,A-8,R²-28,R³-11),
(I-P7698,A-8,R²-24,R³-14), (I-P7699,A-8,R²-24,R³-15), (I-P7832,A-8,R²-28,R³-12), (I-P7833,A-8,R²-28,R³-13),
(I-P7700,A-8,R²-24,R³-16), (I-P7701,A-8,R²-24,R³-17), (I-P7834,A-8,R²-28,R³-14), (I-P7835,A-8,R²-28,R³-15), (I-P7836,A-8,R²-28,R³-16), (I-P7837,A-8,R²-28,R³-17), (I-P7970,A-9,R²-3,R³-14), (I-P7971,A-9,R²-3,R³-15),
(I-P7838,A-8,R²-28,R³-18), (I-P7839,A-8,R²-28,R³-19), (I-P7972,A-9,R²-3,R³-16), (I-P7973,A-9,R²-3,R³-17),
(I-P7840,A-8,R²-28,R³-20), (I-P7841,A-8,R²-28,R³-21), (I-P7974,A-9,R²-3,R³-18), (I-P7975,A-9,R²-3,R³-19),
(I-P7842,A-8,R²-28,R³-22), (I-P7843,A-8,R²-28,R³-23), (I-P7976,A-9,R²-3,R³-20), (I-P7977,A-9,R²-3,R³-21),
(I-P7844,A-8,R²-28,R³-24), (I-P7845,A-8,R²-28,R³-25), (I-P7978,A-9,R²-3,R³-22), (I-P7979,A-9,R²-3,R³-23),
(I-P7846,A-8,R²-28,R³-26), (I-P7847,A-8,R²-28,R³-27), (I-P7980,A-9,R²-3,R³-24), (I-P7981,A-9,R²-3,R³-25),
(I-P7848,A-8,R²-28,R³-28), (I-P7849,A-8,R²-28,R³-29), (I-P7982,A-9,R²-3,R³-26), (I-P7983,A-9,R²-3,R³-27),
(I-P7850,A-8,R²-28,R³-30), (I-P7851,A-8,R²-28,R³-31), (I-P7984,A-9,R²-3,R³-28), (I-P7985,A-9,R²-3,R³-29),
(I-P7852,A-8,R²-28,R³-32), (I-P7853,A-8,R²-28,R³-33), (I-P7986,A-9,R²-3,R³-30), (I-P7987,A-9,R²-3,R³-31),
(I-P7854,A-8,R²-28,R³-34), (I-P7855,A-8,R²-29,R³-1), (I-P7988,A-9,R²-3,R³-32), (I-P7989,A-9,R²-3,R³-33),
(I-P7856,A-8,R²-29,R³-2), (I-P7857,A-8,R²-29,R³-3), (I-P7990,A-9,R²-3,R³-34), (I-P7991,A-9,R²-4,R³-1),
(I-P7858,A-8,R²-29,R³-4), (I-P7859,A-8,R²-29,R³-5), (I-P7992,A-9,R²-4,R³-2), (I-P7993,A-9,R²-4,R³-3),
(I-P7860,A-8,R²-29,R³-6), (I-P7861,A-8,R²-29,R³-7), (I-P7994,A-9,R²-4,R³-4), (I-P7995,A-9,R²-4,R³-5),
(I-P7862,A-8,R²-29,R³-8), (I-P7863,A-8,R²-29,R³-9), (I-P7996,A-9,R²-4,R³-6), (I-P7997,A-9,R²-4,R³-7),
(I-P7864,A-8,R²-29,R³-10), (I-P7865,A-8,R²-29,R³-11), (I-P7998,A-9,R²-4,R³-8), (I-P7999,A-9,R²-4,R³-9),
(I-P7866,A-8,R²-29,R³-12), (I-P7867,A-8,R²-29,R³-13), (I-P8000,A-9,R²-4,R³-10), (I-P8001,A-9,R²-4,R³-11),
(I-P7868,A-8,R²-29,R³-14), (I-P7869,A-8,R²-29,R³-15), (I-P8002,A-9,R²-4,R³-12), (I-P8003,A-9,R²-4,R³-13),
(I-P7870,A-8,R²-29,R³-16), (I-P7871,A-8,R²-29,R³-17), (I-P8004,A-9,R²-4,R³-14), (I-P8005,A-9,R²-4,R³-15),
(I-P7872,A-8,R²-29,R³-18), (I-P7873,A-8,R²-29,R³-19), (I-P8006,A-9,R²-4,R³-16), (I-P8007,A-9,R²-4,R³-17),
(I-P7874,A-8,R²-29,R³-20), (I-P7875,A-8,R²-29,R³-21), (I-P8008,A-9,R²-4,R³-18), (I-P8009,A-9,R²-4,R³-19),
(I-P7876,A-8,R²-29,R³-22), (I-P7877,A-8,R²-29,R³-23), (I-P8010,A-9,R²-4,R³-20), (I-P8011,A-9,R²-4,R³-21),
(I-P7878,A-8,R²-29,R³-24), (I-P7879,A-8,R²-29,R³-25), (I-P8012,A-9,R²-4,R³-22), (I-P8013,A-9,R²-4,R³-23),
(I-P7880,A-8,R²-29,R³-26), (I-P7881,A-8,R²-29,R³-27), (I-P8014,A-9,R²-4,R³-24), (I-P8015,A-9,R²-4,R³-25),
(I-P7882,A-8,R²-29,R³-28), (I-P7883,A-8,R²-29,R³-29), (I-P8016,A-9,R²-4,R³-26), (I-P8017,A-9,R²-4,R³-27),
(I-P7884,A-8,R²-29,R³-30), (I-P7885,A-8,R²-29,R³-31), (I-P8018,A-9,R²-4,R³-28), (I-P8019,A-9,R²-4,R³-29),
(I-P7886,A-8,R²-29,R³-32), (I-P7887,A-8,R²-29,R³-33), (I-P8020,A-9,R²-4,R³-30), (I-P8021,A-9,R²-4,R³-31),
(I-P7888,A-8,R²-29,R³-34), (I-P7889,A-9,R²-1,R³-1), (I-P8022,A-9,R²-4,R³-32), (I-P8023,A-9,R²-4,R³-33),
(I-P7890,A-9,R²-1,R³-2), (I-P7891,A-9,R²-1,R³-3), (I-P8024,A-9,R²-4,R³-34), (I-P8025,A-9,R²-5,R³-1),
(I-P7892,A-9,R²-1,R³-4), (I-P7893,A-9,R²-1,R³-5), (I-P8026,A-9,R²-5,R³-2), (I-P8027,A-9,R²-5,R³-3),
(I-P7894,A-9,R²-1,R³-6), (I-P7895,A-9,R²-1,R³-7), (I-P8028,A-9,R²-5,R³-4), (I-P8029,A-9,R²-5,R³-5),
(I-P7896,A-9,R²-1,R³-8), (I-P7897,A-9,R²-1,R³-9), (I-P8030,A-9,R²-5,R³-6), (I-P8031,A-9,R²-5,R³-7),
(I-P7898,A-9,R²-1,R³-10), (I-P7899,A-9,R²-1,R³-11), (I-P8032,A-9,R²-5,R³-8), (I-P8033,A-9,R²-5,R³-9),
(I-P7900,A-9,R²-1,R³-12), (I-P7901,A-9,R²-1,R³-13), (I-P8034,A-9,R²-5,R³-10), (I-P8035,A-9,R²-5,R³-11),
(I-P7902,A-9,R²-1,R³-14), (I-P7903,A-9,R²-1,R³-15), (I-P8036,A-9,R²-5,R³-12), (I-P8037,A-9,R²-5,R³-13),
(I-P7904,A-9,R²-1,R³-16), (I-P7905,A-9,R²-1,R³-17), (I-P8038,A-9,R²-5,R³-14), (I-P8039,A-9,R²-5,R³-15),
(I-P7906,A-9,R²-1,R³-18), (I-P7907,A-9,R²-1,R³-19), (I-P8040,A-9,R²-5,R³-10, (I-P8041,A-9,R²-5,R³-17),
(I-P7908,A-9,R²-1,R³-20), (I-P7909,A-9,R²-1,R³-21), (I-P8042,A-9,R²-5,R³-18), (I-P8043,A-9,R²-5,R³-19),
(I-P7910,A-9,R²-1,R³-22), (I-P7911,A-9,R²-1,R³-23), (I-P8044,A-9,R²-5,R³-20), (I-P8045,A-9,R²-5,R³-21),
(I-P7912,A-9,R²-1,R³-24), (I-P7913,A-9,R²-1,R³-25), (I-P8046,A-9,R²-5,R³-22), (I-P8047,A-9,R²-5,R³-23),
(I-P7914,A-9,R²-1,R³-26), (I-P7915,A-9,R²-1,R³-27), (I-P8048,A-9,R²-5,R³-24), (I-P8049,A-9,R²-5,R³-25),
(I-P7916,A-9,R²-1,R³-28), (I-P7917,A-9,R²-1,R³-29), (I-P8050,A-9,R²-5,R³-26), (I-P8051,A-9,R²-5,R³-27),
(I-P7918,A-9,R²-1,R³-30), (I-P7919,A-9,R²-1,R³-31), (I-P8052,A-9,R²-5,R³-28), (I-P8053,A-9,R²-5,R³-29),
(I-P7920,A-9,R²-1,R³-32), (I-P7921,A-9,R²-1,R³-33), (I-P8054,A-9,R²-5,R³-30), (I-P8055,A-9,R²-5,R³-31),
(I-P7922,A-9,R²-1,R³-34), (I-P7923,A-9,R²-2,R³-1), (I-P8056,A-9,R²-5,R³-32), (1-P8057,A-9,R²-5,R³-33),
(I-P7924,A-9,R²-2,R³-2), (I-P7925,A-9,R²-2,R³-3), (I-P8058,A-9,R²-5,R³-34), (I-P8059,A-9,R²-6,R³-1),
(I-P7926,A-9,R²-2,R³-4), (I-P7927,A-9,R²-2,R³-5), (I-P8060,A-9,R²-6,R³-2), (I-P8061,A-9,R²-6,R³-3),
(I-P7928,A-9,R²-2,R³-6), (I-P7929,A-9,R²-2,R³-7), (I-P8062,A-9,R²-6,R³-4), (I-P8063,A-9,R²-6,R³-5),
(I-P7930,A-9,R²-2,R³-8), (I-P7931,A-9,R²-2,R³-9), (I-P8064,A-9,R²-6,R³-6), (I-P8065,A-9,R²-6,R³-7),
(I-P7932,A-9,R²-2,R³-10), (I-P7933,A-9,R²-2,R³-11), (I-P8066,A-9,R²-6,R³-8), (I-P8067,A-9,R²-6,R³-9),
(I-P7934,A-9,R²-2,R³-12), (I-P7935,A-9,R²-2,R³-13), (I-P8068,A-9,R²-6,R³-10), (I-P8069,A-9,R²-6,R³-11),
(I-P7936,A-9,R²-2,R³-14), (I-P7937,A-9,R²-2,R³-15), (I-P8070,A-9,R²-6,R³-12), (I-P8071,A-9,R²-6,R³-13),
(I-P7938,A-9,R²-2,R³-16), (I-P7939,A-9,R²-2,R³-17), (I-P8072,A-9,R²-6,R³-14), (I-P8073,A-9,R²-6,R³-15),
(I-P7940,A-9,R²-2,R³-18), (I-P7941,A-9,R²-2,R³-19), (I-P8074,A-9,R²-6,R³-16), (I-P8075,A-9,R²-6,R³-17),
(I-P7942,A-9,R²-2,R³-20), (I-P7943,A-9,R²-2,R³-21), (I-P8076,A-9,R²-6,R³-18), (I-P8077,A-9,R²-6,R³-19),
(I-P7944,A-9,R²-2,R³-22), (I-P7945,A-9,R²-2,R³-23), (I-P8078,A-9,R²-6,R³-20), (I-P8079,A-9,R²-6,R³-21),
(I-P7946,A-9,R²-2,R³-24), (I-P7947,A-9,R²-2,R³-25), (I-P8080,A-9,R²-6,R³-22), (I-P8081,A-9,R²-6,R³-23),
(I-P7948,A-9,R²-2,R³-26), (I-P7949,A-9,R²-2,R³-27), (I-P8082,A-9,R²-6,R³-24), (I-P8083,A-9,R²-6,R³-25),
(I-P7950,A-9,R²-2,R³-28), (I-P7951,A-9,R²-2,R³-29), (I-P8084,A-9,R²-6,R³-26), (I-P8085,A-9,R²-6,R³-27),
(I-P7952,A-9,R²-2,R³-30), (I-P7953,A-9,R²-2,R³-31), (I-P8086,A-9,R²-6,R³-28), (I-P8087,A-9,R²-6,R³-29),
(I-P7954,A-9,R²-2,R³-32), (I-P7955,A-9,R²-2,R³-33), (I-P8088,A-9,R²-6,R³-30), (I-P8089,A-9,R²-6,R³-31),
(I-P7956,A-9,R²-2,R³-34), (I-P7957,A-9,R²-3,R³-1), (I-P8090,A-9,R²-6,R³-32), (I-P8091,A-9,R²-6,R³-33),
(I-P7958,A-9,R²-3,R³-2), (I-P7959,A-9,R²-3,R³-3), (I-P8092,A-9,R²-6,R³-34), (I-P8093,A-9,R²-7,R³-1),
(I-P7960,A-9,R²-3,R³-4), (I-P7961,A-9,R²-3,R³-5), (I-P8094,A-9,R²-7,R³-2), (I-P8095,A-9,R²-7,R³-3),
(I-P7962,A-9,R²-3,R³-6), (I-P7963,A-9,R²-3,R³-7), (I-P8096,A-9,R²-7,R³-4), (I-P8097,A-9,R²-7,R³-5),
(I-P7964,A-9,R²-3,R³-8), (I-P7965,A-9,R²-3,R³-9), (I-P8098,A-9,R²-7,R³-6), (I-P8099,A-9,R²-7,R³-7),
(I-P7966,A-9,R²-3,R³-10), (I-P7967,A-9,R²-3,R³-11), (I-P8100,A-9,R²-7,R³-8), (I-P8101,A-9,R²-7,R³-9),
(I-P7968,A-9,R²-3,R³-12), (I-P7969,A-9,R²-3,R³-13), (I-P8102,A-9,R²-7,R³-10), (I-P8103,A-9,R²-7,R³-11), (I-P8104,A-9,R²-7,R³-12), (I-P8105,A-9,R²-7,R³-13), (I-P8238,A-9,R²-11,R³-10), (I-P8239,A-9,R²-11,R³-11),
(I-P8106,A-9,R²-7,R³-14), (I-P8107,A-9,R²-7,R³-15), (I-P8240,A-9,R²-11,R³-12), (I-P8241,A-9,R²-11,R³-13),
(I-P8108,A-9,R²-7,R³-16), (I-P8109,A-9,R²-7,R³-17), (I-P8242,A-9,R²-11,R³-14), (I-P8243,A-9,R²-11,R³-15),
(I-P8110,A-9,R²-7,R³-18), (I-P8111,A-9,R²-7,R³-19), (I-P8244,A-9,R²-11,R³-16), (I-P8245,A-9,R²-11,R³-17),
(I-P8112,A-9,R²-7,R³-20), (I-P8113,A-9,R²-7,R³-21), (I-P8246,A-9,R²-11,R³-18), (I-P8247,A-9,R²-11,R³-19),
(I-P8114,A-9,R²-7,R³-22), (I-P8115,A-9,R²-7,R³-23), (I-P8248,A-9,R²-11,R³-20), (I-P8249,A-9,R²-11,R³-21),
(I-P8116,A-9,R²-7,R³-24), (I-P8117,A-9,R²-7,R³-25), (I-P8250,A-9,R²-11,R³-22), (I-P8251,A-9,R²-11,R³-23),
(I-P8118,A-9,R²-7,R³-26), (I-P8119,A-9,R²-7,R³-27), (I-P8252,A-9,R²-11,R³-24), (I-P8253,A-9,R²-11,R³-25),
(I-P8120,A-9,R²-7,R³-28), (I-P8121,A-9,R²-7,R³-29), (I-P8254,A-9,R²-11,R³-26), (I-P8255,A-9,R²-11,R³-27),
(I-P8122,A-9,R²-7,R³-30), (I-P8123,A-9,R²-7,R³-31), (I-P8256,A-9,R²-11,R³-28), (I-P8257,A-9,R²-11,R³-29),
(I-P8124,A-9,R²-7,R³-32), (I-P8125,A-9,R²-7,R³-33), (I-P8258,A-9,R²-11,R³-30), (I-P8259,A-9,R²-11,R³-31),
(I-P8126,A-9,R²-7,R³-34), (I-P8127,A-9,R²-8,R³-1), (I-P8260,A-9,R²-11,R³-32), (I-P8261,A-9,R²-11,R³-33),
(I-P8128,A-9,R²-8,R³-2), (I-P8129,A-9,R²-8,R³-3), (I-P8262,A-9,R²-11,R³-34), (I-P8263,A-9,R²-12,R³-1),
(I-P8130,A-9,R²-8,R³-4), (I-P8131,A-9,R²-8,R³-5), (I-P8264,A-9,R²-12,R³-2), (I-P8265,A-9,R²-12,R³-3),
(I-P8132,A-9,R²-8,R³-6), (I-P8133,A-9,R²-8,R³-7), (I-P8266,A-9,R²-12,R³-4), (I-P8267,A-9,R²-12,R³-5),
(I-P8134,A-9,R²-8,R³-8), (I-P8135,A-9,R²-8,R³-9), (I-P8268,A-9,R²-12,R³-6), (I-P8269,A-9,R²-12,R³-7),
(I-P8136,A-9,R²-8,R³-10), (I-P8137,A-9,R²-8,R³-11), (I-P8270,A-9,R²-12,R³-8), (I-P8271,A-9,R²-12,R³-9),
(I-P8138,A-9,R²-8,R³-12), (I-P8139,A-9,R²-8,R³-13), (I-P8272,A-9,R²-12,R³-10), (I-P8273,A-9,R²-12,R³-11),
(I-P8140,A-9,R²-8,R³-14), (I-P8141,A-9,R²-8,R³-15), (I-P8274,A-9,R²-12,R³-12), (I-P8275,A-9,R²-12,R³-13),
(I-P8142,A-9,R²-8,R³-16), (I-P8143,A-9,R²-8,R³-17), (I-P8276,A-9,R²-12,R³-14), (I-P8277,A-9,R²-12,R³-15),
(I-P8144,A-9,R²-8,R³-18), (I-P8145,A-9,R²-8,R³-19), (I-P8278,A-9,R²-12,R³-16), (I-P8279,A-9,R²-12,R³-17),
(I-P8146,A-9,R²-8,R³-20), (I-P8147,A-9,R²-8,R³-21), (I-P8280,A-9,R²-12,R³-18), (I-P8281,A-9,R²-12,R³-19),
(I-P8148,A-9,R²-8,R³-22), (I-P8149,A-9,R²-8,R³-23), (I-P8282,A-9,R²-12,R³-20), (I-P8283,A-9,R²-12,R³-21),
(I-P8150,A-9,R²-8,R³-24), (I-P8151,A-9,R²-8,R³-25), (I-P8284,A-9,R²-12,R³-22), (I-P8285,A-9,R²-12,R³-23),
(I-P8152,A-9,R²-8,R³-26), (I-P8153,A-9,R²-8,R³-27), (I-P8286,A-9,R²-12,R³-24), (I-P8287,A-9,R²-12,R³-25),
(I-P8154,A-9,R²-8,R³-28), (I-P8155,A-9,R²-8,R³-29), (I-P8288,A-9,R²-12,R³-26), (I-P8289,A-9,R²-12,R³-27),
(I-P8156,A-9,R²-8,R³-30), (I-P8157,A-9,R²-8,R³-31), (I-P8290,A-9,R²-12,R³-28), (I-P8291,A-9,R²-12,R³-29),
(I-P8158,A-9,R²-8,R³-32), (I-P8159,A-9,R²-8,R³-33), (I-P8292,A-9,R²-12,R³-30), (I-P8293,A-9,R²-12,R³-31),
(I-P8160,A-9,R²-8,R³-34), (I-P8161,A-9,R²-9,R³-1), (I-P8294,A-9,R²-12,R³-32), (I-P8295,A-9,R²-12,R³-33),
(I-P8162,A-9,R²-9,R³-2), (I-P8163,A-9,R²-9,R³-3), (I-P8296,A-9,R²-12,R³-34), (I-P8297,A-9,R²-13,R³-1),
(I-P8164,A-9,R²-9,R³-4), (I-P8165,A-9,R²-9,R³-5), (I-P8298,A-9,R²-13,R³-2), (I-P8299,A-9,R²-13,R³-3),
(I-P8166,A-9,R²-9,R³-6), (I-P8167,A-9,R²-9,R³-7), (I-P8300,A-9,R²-13,R³-4), (I-P8301,A-9,R²-13,R³-5),
(I-P8168,A-9,R²-9,R³-8), (I-P8169,A-9,R²-9,R³-9), (I-P8302,A-9,R²-13,R³-6), (I-P8303,A-9,R²-13,R³-7),
(I-P8170,A-9,R²-9,R³-10), (I-P8171,A-9,R²-9,R³-11), (I-P8304,A-9,R²-13,R³-8), (I-P8305,A-9,R²-13,R³-9),
(I-P8172,A-9,R²-9,R³-12), (I-P8173,A-9,R²-9,R³-13), (I-P8306,A-9,R²-13,R³-10), (I-P8307,A-9,R²-13,R³-11),
(I-P8174,A-9,R²-9,R³-14), (I-P8175,A-9,R²-9,R³-15), (I-P8308,A-9,R²-13,R³-12), (I-P8309,A-9,R²-13,R³-13),
(I-P8176,A-9,R²-9,R³-16), (I-P8177,A-9,R²-9,R³-17), (I-P8310,A-9,R²-13,R³-14), (I-P8311,A-9,R²-13,R³-15),
(I-P8178,A-9,R²-9,R³-18), (I-P8179,A-9,R²-9,R³-19), (I-P8312,A-9,R²-13,R³-16), (I-P8313,A-9,R²-13,R³-17),
(1-P8180,A-9,R²-9,R³-20), (I-P8181,A-9,R²-9,R³-21), (I-P8314,A-9,R²-13,R³-18), (I-P8315,A-9,R²-13,R³-19),
(I-P8182,A-9,R²-9,R³-22), (I-P8183,A-9,R²-9,R³-23), (I-P8316,A-9,R²-13,R³-20), (I-P8317,A-9,R²-13,R³-21),
(I-P8184,A-9,R²-9,R³-24), (I-P8185,A-9,R²-9,R³-25), (I-P8318,A-9,R²-13,R³-22), (I-P8319,A-9,R²-13,R³-23),
(I-P8186,A-9,R²-9,R³-26), (I-P8187,A-9,R²-9,R³-27), (I-P8320,A-9,R²-13,R³-24), (I-P8321,A-9,R²-13,R³-25),
(I-P8188,A-9,R²-9,R³-28), (I-P8189,A-9,R²-9,R³-29), (I-P8322,A-9,R²-13,R³-26), (I-P8323,A-9,R²-13,R³-27),
(I-P8190,A-9,R²-9,R³-30), (I-P8191,A-9,R²-9,R³-31), (I-P8324,A-9,R²-13,R³-28), (I-P8325,A-9,R²-13,R³-29),
(I-P8192,A-9,R²-9,R³-32), (I-P8193,A-9,R²-9,R³-33), (I-P8326,A-9,R²-13,R³-30), (I-P8327,A-9,R²-13,R³-31),
(I-P8194,A-9,R²-9,R³-34), (I-P8195,A-9,R²-10,R³-1), (I-P8328,A-9,R²-13,R³-32), (I-P8329,A-9,R²-13,R³-33),
(I-P8196,A-9,R²-10,R³-2), (I-P8197,A-9,R²-10,R³-3), (I-P8330,A-9,R²-13,R³-34), (I-P8331,A-9,R²-14,R³-1),
(I-P8198,A-9,R²-10,R³-4), (I-P8199,A-9,R²-10,R³-5), (I-P8332,A-9,R²-14,R³-2), (I-P8333,A-9,R²-14,R³-3),
(I-P8200,A-9,R²-10,R³-6), (I-P8201,A-9,R²-10,R³-7), (I-P8334,A-9,R²-14,R³-4), (I-P8335,A-9,R²-14,R³-5),
(I-P8202,A-9,R²-10,R³-8), (I-P8203,A-9,R²-10,R³-9), (I-P8336,A-9,R²-14,R³-6), (I-P8337,A-9,R²-14,R³-7),
(I-P8204,A-9,R²-10,R³-10), (I-P8205,A-9,R²-10,R³-11), (I-P8338,A-9,R²-14,R³-8), (I-P8339,A-9,R²-14,R³-9),
(I-P8206,A-9,R²-10,R³-12), (I-P8207,A-9,R²-10,R³-13), (I-P8340,A-9,R²-14,R³-10), (I-P8341,A-9,R²-14,R³-11),
(I-P8208,A-9,R²-10,R³-14), (I-P8209,A-9,R²-10,R³-15), (I-P8342,A-9,R²-14,R³-12), (I-P8343,A-9,R²-14,R³-13),
(I-P8210,A-9,R²-10,R³-16), (I-P8211,A-9,R²-10,R³-17), (I-P8344,A-9,R²-14,R³-14), (I-P8345,A-9,R²-14,R³-15),
(I-P8212,A-9,R²-10,R³-18), (I-P8213,A-9,R²-10,R³-19), (I-P8346,A-9,R²-14,R³-16), (I-P8347,A-9,R²-14,R³-17),
(I-P8214,A-9,R²-10,R³-20), (I-P8215,A-9,R²-10,R³-21), (I-P8348,A-9,R²-14,R³-18), (I-P8349,A-9,R²-14,R³-19),
(I-P8216,A-9,R²-10,R³-22), (I-P8217,A-9,R²-10,R³-23), (I-P8350,A-9,R²-14,R³-20), (I-P8351,A-9,R²-14,R³-21),
(I-P8218,A-9,R²-10,R³-24), (I-P8219,A-9,R²-10,R³-25), (I-P8352,A-9,R²-14,R³-22), (I-P8353,A-9,R²-14,R³-23),
(I-P8220,A-9,R²-10,R³-26), (I-P8221,A-9,R²-10,R³-27), (I-P8354,A-9,R²-14,R³-24), (I-P8355,A-9,R²-14,R³-25),
(I-P8222,A-9,R²-10,R³-28), (I-P8223,A-9,R²-10,R³-29), (I-P8356,A-9,R²-14,R³-26), (I-P8357,A-9,R²-14,R³-27),
(I-P8224,A-9,R²-10,R³-30), (I-P8225,A-9,R²-10,R³-31), (I-P8358,A-9,R²-14,R³-28), (I-P8359,A-9,R²-14,R³-29),
(I-P8226,A-9,R²-10,R³-32), (I-P8227,A-9,R²-10,R³-33), (I-P8360,A-9,R²-14,R³-30), (I-P8361,A-9,R²-14,R³-31),
(I-P8228,A-9,R²-10,R³-34), (I-P8229,A-9,R²-11,R³-1), (I-P8362,A-9,R²-14,R³-32), (I-P8363,A-9,R²-14,R³-33),
(I-P8230,A-9,R²-11,R³-2), (I-P8231,A-9,R²-11,R³-3), (I-P8364,A-9,R²-14,R³-34), (I-P8365,A-9,R²-15,R³-1),
(I-P8232,A-9,R²-11,R³-4), (I-P8233,A-9,R²-11,R³-5), (I-P8366,A-9,R²-15,R³-2), (I-P8367,A-9,R²-15,R³-3),
(I-P8234,A-9,R²-11,R³-6), (I-P8235,A-9,R²-11,R³-7), (I-P8368,A-9,R²-15,R³-4), (I-P8369,A-9,R²-15,R³-5),
(I-P8236,A-9,R²-11,R³-8), (I-P8237,A-9,R²-11,R³-9), (I-P8370,A-9,R²-15,R³-6), (I-P8371,A-9,R²-15,R³-7), (I-P8372,A-9,R²-15,R³-8), (I-P8373,A-9,R²-15,R³-9), (I-P8506,A-9,R²-19,R³-6), (I-P8507,A-9,R²-19,R³-7),
(I-P8374,A-9,R²-15,R³-10), (I-P8375,A-9,R²-15,R³-11), (I-P8508,A-9,R²-19,R³-8), (I-P8509,A-9,R²-19,R³-9),
(I-P8376,A-9,R²-15,R³-12), (I-P8377,A-9,R²-15,R³-13), (I-P8510,A-9,R²-19,R³-10), (I-P8511,A-9,R²-19,R³-11),
(I-P8378,A-9,R²-15,R³-14), (I-P8379,A-9,R²-15,R³-15), (I-P8512,A-9,R²-19,R³-12), (I-P8513,A-9,R²-19,R³-13),
(I-P8380,A-9,R²-15,R³-16), (I-P8381,A-9,R²-15,R³-17), (I-P8514,A-9,R²-19,R³-14), (I-P8515,A-9,R²-19,R³-15),
(I-P8382,A-9,R²-15,R³-18), (I-P8383,A-9,R²-15,R³-19), (I-P8516,A-9,R²-19,R³-16), (I-P8517,A-9,R²-19,R³-17),
(I-P8384,A-9,R²-15,R³-20), (I-P8385,A-9,R²-15,R³-21), (I-P8518,A-9,R²-19,R³-18), (I-P8519,A-9,R²-19,R³-19),
(I-P8386,A-9,R²-15,R³-22), (I-P8387,A-9,R²-15,R³-23), (I-P8520,A-9,R²-19,R³-20), (I-P8521,A-9,R²-19,R³-21),
(I-P8388,A-9,R²-15,R³-24), (I-P8389,A-9,R²-15,R³-25), (I-P8522,A-9,R²-19,R³-22), (I-P8523,A-9,R²-19,R³-23),
(I-P8390,A-9,R²-15,R³-26), (I-P8391,A-9,R²-15,R³-27), (I-P8524,A-9,R²-19,R³-24), (I-P8525,A-9,R²-19,R³-25),
(I-P8392,A-9,R²-15,R³-28), (I-P8393,A-9,R²-15,R³-29), (I-P8526,A-9,R²-19,R³-26), (I-P8527,A-9,R²-19,R³-27),
(I-P8394,A-9,R²-15,R³-30), (I-P8395,A-9,R²-15,R³-31), (I-P8528,A-9,R²-19,R³-28), (I-P8529,A-9,R²-19,R³-29),
(I-P8396,A-9,R²-15,R³-32), (I-P8397,A-9,R²-15,R³-33), (I-P8530,A-9,R²-19,R³-30), (I-P8531,A-9,R²-19,R³-31),
(I-P8398,A-9,R²-15,R³-34), (I-P8399,A-9,R²-16,R³-1), (I-P8532,A-9,R²-19,R³-32), (I-P8533,A-9,R²-19,R³-33),
(I-P8400,A-9,R²-16,R³-2), (I-P8401,A-9,R²-16,R³-3), (I-P8534,A-9,R²-19,R³-34), (I-P8535,A-9,R²-20,R³-1),
(I-P8402,A-9,R²-16,R³-4), (I-P8403,A-9,R²-16,R³-5), (I-P8536,A-9,R²-20,R³-2), (I-P8537,A-9,R²-20,R³-3),
(I-P8404,A-9,R²-16,R³-6), (I-P8405,A-9,R²-16,R³-7), (I-P8538,A-9,R²-20,R³-4), (I-P8539,A-9,R²-20,R³-5),
(I-P8406,A-9,R²-16,R³-8), (I-P8407,A-9,R²-16,R³-9), (I-P8540,A-9,R²-20,R³-6), (I-P8541,A-9,R²-20,R³-7),
(I-P8408,A-9,R²-16,R³-10), (I-P8409,A-9,R²-16,R³-11), (I-P8542,A-9,R²-20,R³-8), (I-P8543,A-9,R²-20,R³-9),
(I-P8410,A-9,R²-16,R³-12), (I-P8411,A-9,R²-16,R³-13), (I-P8544,A-9,R²-20,R³-10), (I-P8545,A-9,R²-20,R³-11),
(I-P8412,A-9,R²-16,R³-14), (I-P8413,A-9,R²-16,R³-15), (I-P8546,A-9,R²-20,R³-12), (I-P8547,A-9,R²-20,R³-13),
(I-P8414,A-9,R²-16,R³-16), (I-P8415,A-9,R²-16,R³-17), (I-P8548,A-9,R²-20,R³-14), (I-P8549,A-9,R²-20,R³-15),
(I-P8416,A-9,R²-16,R³-18), (I-P8417,A-9,R²-16,R³-19), (I-P8550,A-9,R²-20,R³-16), (I-P8551,A-9,R²-20,R³-17),
(I-P8418,A-9,R²-16,R³-20), (I-P8419,A-9,R²-16,R³-21), (I-P8552,A-9,R²-20,R³-18), (I-P8553,A-9,R²-20,R³-19),
(I-P8420,A-9,R²-16,R³-22), (I-P8421,A-9,R²-16,R³-23), (I-P8554,A-9,R²-20,R³-20), (I-P8555,A-9,R²-20,R³-21),
(I-P8422,A-9,R²-16,R³-24), (I-P8423,A-9,R²-16,R³-25), (I-P8556,A-9,R²-20,R³-22), (I-P8557,A-9,R²-20,R³-23),
(I-P8424,A-9,R²-16,R³-26), (I-P8425,A-9,R²-16,R³-27), (I-P8558,A-9,R²-20,R³-24), (I-P8559,A-9,R²-20,R³-25),
(I-P8426,A-9,R²-16,R³-28), (I-P8427,A-9,R²-16,R³-29), (I-P8560,A-9,R²-20,R³-26), (I-P8561,A-9,R²-20,R³-27),
(I-P8428,A-9,R²-16,R³-30), (I-P8429,A-9,R²-16,R³-31), (I-P8562,A-9,R²-20,R³-28), (I-P8563,A-9,R²-20,R³-29),
(I-P8430,A-9,R²-16,R³-32), (I-P8431,A-9,R²-16,R³-33), (I-P8564,A-9,R²-20,R³-30), (I-P8565,A-9,R²-20,R³-31),
(I-P8432,A-9,R²-16,R³-34), (I-P8433,A-9,R²-17,R³-1), (I-P8566,A-9,R²-20,R³-32), (I-P8567,A-9,R²-20,R³-33),
(I-P8434,A-9,R²-17,R³-2), (I-P8435,A-9,R²-17,R³-3), (I-P8568,A-9,R²-20,R³-34), (I-P8569,A-9,R²-21,R³-1),
(I-P8436,A-9,R²-17,R³-4), (I-P8437,A-9,R²-17,R³-5), (I-P8570,A-9,R²-21,R³-2), (I-P8571,A-9,R²-21,R³-3),
(I-P8438,A-9,R²-17,R³-6), (I-P8439,A-9,R²-17,R³-7), (I-P8572,A-9,R²-21,R³-4), (I-P8573,A-9,R²-21,R³-5),
(I-P8440,A-9,R²-17,R³-8), (I-P8441,A-9,R²-17,R³-9), (I-P8574,A-9,R²-21,R³-6), (I-P8575,A-9,R²-21,R³-7),
(I-P8442,A-9,R²-17,R³-10), (I-P8443,A-9,R²-17,R³-11), (I-P8576,A-9,R²-21,R³-8), (I-P8577,A-9,R²-21,R³-9),
(I-P8444,A-9,R²-17,R³-12), (I-P8445,A-9,R²-17,R³-13), (I-P8578,A-9,R²-21,R³-10), (I-P8579,A-9,R²-21,R³-11),
(I-P8446,A-9,R²-17,R³-14), (I-P8447,A-9,R²-17,R³-15), (I-P8580,A-9,R²-21,R³-12), (I-P8581,A-9,R²-21,R³-13),
(I-P8448,A-9,R²-17,R³-16), (I-P8449,A-9,R²-17,R³-17), (I-P8582,A-9,R²-21,R³-14), (I-P8583,A-9,R²-21,R³-15),
(I-P8450,A-9,R²-17,R³-18), (I-P8451,A-9,R²-17,R³-19), (I-P8584,A-9,R²-21,R³-16), (I-P8585,A-9,R²-21,R³-17),
(I-P8452,A-9,R²-17,R³-20), (I-P8453,A-9,R²-17,R³-21), (I-P8586,A-9,R²-21,R³-18), (I-P8587,A-9,R²-21,R³-19),
(I-P8454,A-9,R²-17,R³-22), (I-P8455,A-9,R²-17,R³-23), (I-P8588,A-9,R²-21,R³-20), (I-P8589,A-9,R²-21,R³-21),
(I-P8456,A-9,R²-17,R³-24), (I-P8457,A-9,R²-17,R³-25), (I-P8590,A-9,R²-21,R³-22), (I-P8591,A-9,R²-21,R³-23),
(I-P8458,A-9,R²-17,R³-26), (I-P8459,A-9,R²-17,R³-27), (I-P8592,A-9,R²-21,R³-24), (I-P8593,A-9,R²-21,R³-25),
(I-P8460,A-9,R²-17,R³-28), (I-P8461,A-9,R²-17,R³-29), (I-P8594,A-9,R²-21,R³-26), (I-P8595,A-9,R²-21,R³-27),
(I-P8462,A-9,R²-17,R³-30), (I-P8463,A-9,R²-17,R³-31), (I-P8596,A-9,R²-21,R³-28), (I-P8597,A-9,R²-21,R³-29),
(I-P8464,A-9,R²-17,R³-32), (I-P8465,A-9,R²-17,R³-33), (I-P8598,A-9,R²-21,R³-30), (I-P8599,A-9,R²-21,R³-31),
(I-P8466,A-9,R²-17,R³-34), (I-P8467,A-9,R²-18,R³-1), (I-P8600,A-9,R²-21,R³-32), (I-P8601,A-9,R²-21,R³-33),
(I-P8468,A-9,R²-18,R³-2), (I-P8469,A-9,R²-18,R³-3), (I-P8602,A-9,R²-21,R³-34), (I-P8603,A-9,R²-22,R³-1),
(I-P8470,A-9,R²-18,R³-4), (I-P8471,A-9,R²-18,R³-5), (I-P8604,A-9,R²-22,R³-2), (I-P8605,A-9,R²-22,R³-3),
(I-P8472,A-9,R²-18,R³-6), (I-P8473,A-9,R²-18,R³-7), (I-P8606,A-9,R²-22,R³-4), (I-P8607,A-9,R²-22,R³-5),
(I-P8474,A-9,R²-18,R³-8), (I-P8475,A-9,R²-18,R³-9), (I-P8608,A-9,R²-22,R³-6), (I-P8609,A-9,R²-22,R³-7),
(I-P8476,A-9,R²-18,R³-10), (I-P8477,A-9,R²-18,R³-11), (I-P8610,A-9,R²-22,R³-8), (I-P8611,A-9,R²-22,R³-9),
(I-P8478,A-9,R²-18,R³-12), (I-P8479,A-9,R²-18,R³-13), (I-P8612,A-9,R²-22,R³-10), (I-P8613,A-9,R²-22,R³-11),
(I-P8480,A-9,R²-18,R³-14), (I-P8481,A-9,R²-18,R³-15), (I-P8614,A-9,R²-22,R³-12), (I-P8615,A-9,R²-22,R³-13),
(I-P8482,A-9,R²-18,R³-16), (I-P8483,A-9,R²-18,R³-17), (I-P8616,A-9,R²-22,R³-14), (I-P8617,A-9,R²-22,R³-15),
(I-P8484,A-9,R²-18,R³-18), (I-P8485,A-9,R²-18,R³-19), (I-P8618,A-9,R²-22,R³-16), (I-P8619,A-9,R²-22,R³-17),
(I-P8486,A-9,R²-18,R³-20), (I-P8487,A-9,R²-18,R³-21), (I-P8620,A-9,R²-22,R³-18), (I-P8621,A-9,R²-22,R³-19),
(I-P8488,A-9,R²-18,R³-22), (I-P8489,A-9,R²-18,R³-23), (I-P8622,A-9,R²-22,R³-20), (I-P8623,A-9,R²-22,R³-21),
(I-P8490,A-9,R²-18,R³-24), (I-P8491,A-9,R²-18,R³-25), (I-P8624,A-9,R²-22,R³-22), (I-P8625,A-9,R²-22,R³-23),
(I-P8492,A-9,R²-18,R³-26), (I-P8493,A-9,R²-18,R³-27), (I-P8626,A-9,R²-22,R³-24), (I-P8627,A-9,R²-22,R³-25),
(I-P8494,A-9,R²-18,R³-28), (I-P8495,A-9,R²-18,R³-29), (I-P8628,A-9,R²-22,R³-26), (I-P8629,A-9,R²-22,R³-27),
(I-P8496,A-9,R²-18,R³-30), (I-P8497,A-9,R²-18,R³-31), (I-P8630,A-9,R²-22,R³-28), (I-P8631,A-9,R²-22,R³-29),
(I-P8498,A-9,R²-18,R³-32), (I-P8499,A-9,R²-18,R³-33), (I-P8632,A-9,R²-22,R³-30), (I-P8633,A-9,R²-22,R³-31),
(I-P8500,A-9,R²-18,R³-34), (I-P8501,A-9,R²-19,R³-1), (I-P8634,A-9,R²-22,R³-32), (I-P8635,A-9,R²-22,R³-33),
(I-P8502,A-9,R²-19,R³-2), (I-P8503,A-9,R²-19,R³-3), (I-P8636,A-9,R²-22,R³-34), (I-P8637,A-9,R²-23,R³-1),
(I-P8504,A-9,R²-19,R³-4), (I-P8505,A-9,R²-19,R³-5), (I-P8638,A-9,R²-23,R³-2), (I-P8639,A-9,R²-23,R³-3), (I-P8640,A-9,R²-23,R³-4), (I-P8641,A-9,R²-23,R³-5), (I-P8774,A-9,R²-27,R³-2), (I-P8775,A-9,R²-27,R³-3),
(I-P8642,A-9,R²-23,R³-6), (I-P8643,A-9,R²-23,R³-7), (I-P8776,A-9,R²-27,R³-4), (I-P8777,A-9,R²-27,R³-5),
(I-P8644,A-9,R²-23,R³-8), (I-P8645,A-9,R²-23,R³-9), (I-P8778,A-9,R²-27,R³-6), (I-P8779,A-9,R²-27,R³-7),
(I-P8646,A-9,R²-23,R³-10), (I-P8647,A-9,R²-23,R³-11), (I-P8780,A-9,R²-27,R³-8), (I-P8781,A-9,R²-27,R³-9),
(I-P8648,A-9,R²-23,R³-12), (I-P8649,A-9,R²-23,R³-13), (I-P8782,A-9,R²-27,R³-10), (I-P8783,A-9,R²-27,R³-11),
(I-P8650,A-9,R²-23,R³-14), (I-P8651,A-9,R²-23,R³-15), (I-P8784,A-9,R²-27,R³-12), (I-P8785,A-9,R²-27,R³-13),
(I-P8652,A-9,R²-23,R³-16), (I-P8653,A-9,R²-23,R³-17), (I-P8786,A-9,R²-27,R³-14), (I-P8787,A-9,R²-27,R³-15),
(I-P8654,A-9,R²-23,R³-18), (I-P8655,A-9,R²-23,R³-19), (I-P8788,A-9,R²-27,R³-16), (I-P8789,A-9,R²-27,R³-17),
(I-P8656,A-9,R²-23,R³-20), (I-P8657,A-9,R²-23,R³-21), (I-P8790,A-9,R²-27,R³-18), (I-P8791,A-9,R²-27,R³-19),
(I-P8658,A-9,R²-23,R³-22), (I-P8659,A-9,R²-23,R³-23), (I-P8792,A-9,R²-27,R³-20), (I-P8793,A-9,R²-27,R³-21),
(I-P8660,A-9,R²-23,R³-24), (I-P8661,A-9,R²-23,R³-25), (I-P8794,A-9,R²-27,R³-22), (I-P8795,A-9,R²-27,R³-23),
(I-P8662,A-9,R²-23,R³-26), (I-P8663,A-9,R²-23,R³-27), (I-P8796,A-9,R²-27,R³-24), (I-P8797,A-9,R²-27,R³-25),
(I-P8664,A-9,R²-23,R³-28), (I-P8665,A-9,R²-23,R³-29), (I-P8798,A-9,R²-27,R³-26), (I-P8799,A-9,R²-27,R³-27),
(I-P8666,A-9,R²-23,R³-30), (I-P8667,A-9,R²-23,R³-31), (I-P8800,A-9,R²-27,R³-28), (I-P8801,A-9,R²-27,R³-29),
(I-P8668,A-9,R²-23,R³-32), (I-P8669,A-9,R²-23,R³-33), (I-P8802,A-9,R²-27,R³-30), (I-P8803,A-9,R²-27,R³-31),
(I-P8670,A-9,R²-23,R³-34), (I-P8671,A-9,R²-24,R³-1), (I-P8804,A-9,R²-27,R³-32), (I-P8805,A-9,R²-27,R³-33),
(I-P8672,A-9,R²-24,R³-2), (I-P8673,A-9,R²-24,R³-3), (I-P8806,A-9,R²-27,R³-34), (I-P8807,A-9,R²-28,R³-1),
(I-P8674,A-9,R²-24,R³-4), (I-P8675,A-9,R²-24,R³-5), (I-P8808,A-9,R²-28,R³-2), (I-P8809,A-9,R²-28,R³-3),
(I-P8676,A-9,R²-24,R³-6), (I-P8677,A-9,R²-24,R³-7), (I-P8810,A-9,R²-28,R³-4), (I-P8811,A-9,R²-28,R³-5),
(I-P8678,A-9,R²-24,R³-8), (I-P8679,A-9,R²-24,R³-9), (I-P8812,A-9,R²-28,R³-6), (I-P8813,A-9,R²-28,R³-7),
(I-P8680,A-9,R²-24,R³-10), (I-P868 LA-9,R²-24,R³-11), (I-P8814,A-9,R²-28,R³-8), (I-P8815,A-9,R²-28,R³-9),
(I-P8682,A-9,R²-24,R³-12), (I-P8683,A-9,R²-24,R³-13), (I-P8816,A-9,R²-28,R³-10), (I-P8817,A-9,R²-28,R³-11),
(I-P8684,A-9,R²-24,R³-14), (I-P8685,A-9,R²-24,R³-15), (I-P8818,A-9,R²-28,R³-12), (I-P8819,A-9,R²-28,R³-13),
(I-P8686,A-9,R²-24,R³-16), (I-P8687,A-9,R²-24,R³-17), (I-P8820,A-9,R²-28,R³-14), (I-P8821,A-9,R²-28,R³-15),
(I-P8688,A-9,R²-24,R³-18), (I-P8689,A-9,R²-24,R³-19), (I-P8822,A-9,R²-28,R³-16), (I-P8823,A-9,R²-28,R³-17),
(I-P8690,A-9,R²-24,R³-20), (I-P8691,A-9,R²-24,R³-21), (I-P8824,A-9,R²-28,R³-18), (I-P8825,A-9,R²-28,R³-19),
(I-P8692,A-9,R²-24,R³-22), (I-P8693,A-9,R²-24,R³-23), (I-P8826,A-9,R²-28,R³-20), (I-P8827,A-9,R²-28,R³-21),
(I-P8694,A-9,R²-24,R³-24), (I-P8695,A-9,R²-24,R³-25), (I-P8828,A-9,R²-28,R³-22), (I-P8829,A-9,R²-28,R³-23),
(I-P8696,A-9,R²-24,R³-26), (I-P8697,A-9,R²-24,R³-27), (I-P8830,A-9,R²-28,R³-24), (I-P8831,A-9,R²-28,R³-25),
(I-P8698,A-9,R²-24,R³-28), (I-P8699,A-9,R²-24,R³-29), (I-P8832,A-9,R²-28,R³-26), (I-P8833,A-9,R²-28,R³-27),
(I-P8700,A-9,R²-24,R³-30), (I-P8701,A-9,R²-24,R³-31), (I-P8834,A-9,R²-28,R³-28), (I-P8835,A-9,R²-28,R³-29),
(I-P8702,A-9,R²-24,R³-32), (I-P8703,A-9,R²-24,R³-33), (I-P8836,A-9,R²-28,R³-30), (I-P8837,A-9,R²-28,R³-31),
(I-P8704,A-9,R²-24,R³-34), (I-P8705,A-9,R²-25,R³-1), (I-P8838,A-9,R²-28,R³-32), (I-P8839,A-9,R²-28,R³-33),
(I-P8706,A-9,R²-25,R³-2), (I-P8707,A-9,R²-25,R³-3), (I-P8840,A-9,R²-28,R³-34), (I-P8841,A-9,R²-29,R³-1),
(I-P8708,A-9,R²-25,R³-4), (I-P8709,A-9,R²-25,R³-5), (I-P8842,A-9,R²-29,R³-2), (I-P8843,A-9,R²-29,R³-3),
(I-P8710,A-9,R²-25,R³-6), (I-P8711,A-9,R²-25,R³-7), (I-P8844,A-9,R²-29,R³-4), (I-P8845,A-9,R²-29,R³-5),
(I-P8712,A-9,R²-25,R³-8), (I-P8713,A-9,R²-25,R³-9), (I-P8846,A-9,R²-29,R³-6), (I-P8847,A-9,R²-29,R³-7),
(I-P8714,A-9,R²-25,R³-10), (I-P8715,A-9,R²-25,R³-11), (I-P8848,A-9,R²-29,R³-8), (I-P8849,A-9,R²-29,R³-9),
(I-P8716,A-9,R²-25,R³-12), (I-P8717,A-9,R²-25,R³-13), (I-P8850,A-9,R²-29,R³-10), (I-P8851,A-9,R²-29,R³-11),
(I-P8718,A-9,R²-25,R³-14), (I-P8719,A-9,R²-25,R³-15), (I-P8852,A-9,R²-29,R³-12), (I-P8853,A-9,R²-29,R³-13),
(I-P8720,A-9,R²-25,R³-16), (I-P8721,A-9,R²-25,R³-17), (I-P8854,A-9,R²-29,R³-14), (I-P8855,A-9,R²-29,R³-15),
(I-P8722,A-9,R²-25,R³-18), (I-P8723,A-9,R²-25,R³-19), (I-P8856,A-9,R²-29,R³-16), (I-P8857,A-9,R²-29,R³-17),
(I-P8724,A-9,R²-25,R³-20), (I-P8725,A-9,R²-25,R³-21), (I-P8858,A-9,R²-29,R³-18), (I-P8859,A-9,R²-29,R³-19),
(I-P8726,A-9,R²-25,R³-22), (I-P8727,A-9,R²-25,R³-23), (I-P8860,A-9,R²-29,R³-20), (I-P8861,A-9,R²-29,R³-21),
(I-P8728,A-9,R²-25,R³-24), (I-P8729,A-9,R²-25,R³-25), (I-P8862,A-9,R²-29,R³-22), (I-P8863,A-9,R²-29,R³-23),
(I-P8730,A-9,R²-25,R³-26), (I-P8731,A-9,R²-25,R³-27), (I-P8864,A-9,R²-29,R³-24), (I-P8865,A-9,R²-29,R³-25),
(I-P8732,A-9,R²-25,R³-28), (I-P8733,A-9,R²-25,R³-29), (I-P8866,A-9,R²-29,R³-26), (I-P8867,A-9,R²-29,R³-27),
(I-P8734,A-9,R²-25,R³-30), (I-P8735,A-9,R²-25,R³-31), (I-P8868,A-9,R²-29,R³-28), (I-P8869,A-9,R²-29,R³-29),
(I-P8736,A-9,R²-25,R³-32), (I-P8737,A-9,R²-25,R³-33), (I-P8870,A-9,R²-29,R³-30), (I-P8871,A-9,R²-29,R³-31),
(I-P8738,A-9,R²-25,R³-34), (I-P8739,A-9,R²-26,R³-1), (I-P8872,A-9,R²-29,R³-32), (I-P8873,A-9,R²-29,R³-33),
(I-P8740,A-9,R²-26,R³-2), (I-P8741,A-9,R²-26,R³-3), (I-P8874,A-9,R²-29,R³-34), (I-P8875,A-10,R²-1,R³-1),
(I-P8742,A-9,R²-26,R³-4), (I-P8743,A-9,R²-26,R³-5), (I-P8876,A-10,R²-1,R³-2), (I-P8877,A-10,R²-1,R³-3),
(I-P8744,A-9,R²-26,R³-6), (I-P8745,A-9,R²-26,R³-7), (I-P8878,A-10,R²-1,R³-4), (I-P8879,A-10,R²-1,R³-5),
(I-P8746,A-9,R²-26,R³-8), (I-P8747,A-9,R²-26,R³-9), (I-P8880,A-10,R²-1,R³-6), (I-P8881,A-10,R²-1,R³-7),
(I-P8748,A-9,R²-26,R³-10), (I-P8749,A-9,R²-26,R³-11), (I-P8882,A-10,R²-1,R³-8), (I-P8883,A-10,R²-1,R³-9),
(I-P8750,A-9,R²-26,R³-12), (I-P8751,A-9,R²-26,R³-13), (I-P8884,A-10,R²-1,R³-10), (I-P8885,A-10,R²-1,R³-11),
(I-P8752,A-9,R²-26,R³-14), (I-P8753,A-9,R²-26,R³-15), (I-P8886,A-10,R²-1,R³-12), (I-P8887,A-10,R²-1,R³-13),
(I-P8754,A-9,R²-26,R³-16), (I-P8755,A-9,R²-26,R³-17), (I-P8888,A-10,R²-1,R³-14), (I-P8889,A-10,R²-1,R³-15),
(I-P8756,A-9,R²-26,R³-18), (I-P8757,A-9,R²-26,R³-19), (I-P8890,A-10,R²-1,R³-16), (I-P8891,A-10,R²-1,R³-17),
(I-P8758,A-9,R²-26,R³-20), (I-P8759,A-9,R²-26,R³-21), (I-P8892,A-10,R²-1,R³-18), (I-P8893,A-10,R²-1,R³-19),
(I-P8760,A-9,R²-26,R³-22), (I-P876 LA-9,R²-26,R³-23), (I-P8894,A-10,R²-1,R³-20), (I-P8895,A-10,R²-1,R³-21),
(I-P8762,A-9,R²-26,R³-24), (I-P8763,A-9,R²-26,R³-25), (I-P8896,A-10,R²-1,R³-22), (I-P8897,A-10,R²-1,R³-23),
(I-P8764,A-9,R²-26,R³-26), (I-P8765,A-9,R²-26,R³-27), (I-P8898,A-10,R²-1,R³-24), (I-P8899,A-10,R²-1,R³-25),
(I-P8766,A-9,R²-26,R³-28), (I-P8767,A-9,R²-26,R³-29), (I-P8900,A-10,R²-1,R³-26), (I-P8901,A-10,R²-1,R³-27),
(I-P8768,A-9,R²-26,R³-30), (I-P8769,A-9,R²-26,R³-31), (I-P8902,A-10,R²-1,R³-28), (I-P8903,A-10,R²-1,R³-29),
(I-P8770,A-9,R²-26,R³-32), (I-P8771,A-9,R²-26,R³-33), (I-P8904,A-10,R²-1,R³-30), (I-P8905,A-10,R²-1,R³-31),
(I-P8772,A-9,R²-26,R³-34), (I-P8773,A-9,R²-27,R³-1), (I-P8906,A-10,R²-1,R³-32), (I-P8907,A-10,R²-1,R³-33), (I-P8908,A-10,R²-1,R³-34), (I-P8909,A-10,R²-2,R³-1), (I-P9042,A-10,R²-5,R³-32), (I-P9043,A-10,R²-5,R³-33),
(I-P8910,A-10,R²-2,R³-2), (I-P8911,A-10,R²-2,R³-3), (I-P9044,A-10,R²-5,R³-34), (I-P9045,A-10,R²-6,R³-1),
(I-P8912,A-10,R²-2,R³-4), (I-P8913,A-10,R²-2,R³-5), (I-P9046,A-10,R²-6,R³-2), (I-P9047,A-10,R²-6,R³-3),
(I-P8914,A-10,R²-2,R³-6), (I-P8915,A-10,R²-2,R³-7), (I-P9048,A-10,R²-6,R³-4), (I-P9049,A-10,R²-6,R³-5),
(I-P8916,A-10,R²-2,R³-8), (I-P8917,A-10,R²-2,R³-9), (I-P9050,A-10,R²-6,R³-6), (I-P9051,A-10,R²-6,R³-7),
(I-P8918,A-10,R²-2,R³-10), (I-P8919,A-10,R²-2,R³-11), (I-P9052,A-10,R²-6,R³-8), (I-P9053,A-10,R²-6,R³-9),
(I-P8920,A-10,R²-2,R³-12), (I-P8921,A-10,R²-2,R³-13), (I-P9054,A-10,R²-6,R³-10), (I-P9055,A-10,R²-6,R³-11),
(I-P8922,A-10,R²-2,R³-14), (I-P8923,A-10,R²-2,R³-15), (I-P9056,A-10,R²-6,R³-12), (I-P9057,A-10,R²-6,R³-13),
(I-P8924,A-10,R²-2,R³-16), (I-P8925,A-10,R²-2,R³-17), (I-P9058,A-10,R²-6,R³-14), (I-P9059,A-10,R²-6,R³-15),
(I-P8926,A-10,R²-2,R³-18), (I-P8927,A-10,R²-2,R³-19), (I-P9060,A-10,R²-6,R³-16), (I-P9061,A-10,R²-6,R³-17),
(I-P8928,A-10,R²-2,R³-20), (I-P8929,A-10,R²-2,R³-21), (I-P9062,A-10,R²-6,R³-18), (I-P9063,A-10,R²-6,R³-19),
(I-P8930,A-10,R²-2,R³-22), (I-P8931,A-10,R²-2,R³-23), (I-P9064,A-10,R²-6,R³-20), (I-P9065,A-10,R²-6,R³-21),
(I-P8932,A-10,R²-2,R³-24), (I-P8933,A-10,R²-2,R³-25), (I-P9066,A-10,R²-6,R³-22), (I-P9067,A-10,R²-6,R³-23),
(I-P8934,A-10,R²-2,R³-26), (I-P8935,A-10,R²-2,R³-27), (I-P9068,A-10,R²-6,R³-24), (I-P9069,A-10,R²-6,R³-25),
(I-P8936,A-10,R²-2,R³-28), (I-P8937,A-10,R²-2,R³-29), (I-P9070,A-10,R²-6,R³-26), (I-P9071,A-10,R²-6,R³-27),
(I-P8938,A-10,R²-2,R³-30), (I-P8939,A-10,R²-2,R³-31), (I-P9072,A-10,R²-6,R³-28), (I-P9073,A-10,R²-6,R³-29),
(I-P8940,A-10,R²-2,R³-32), (I-P8941,A-10,R²-2,R³-33), (I-P9074,A-10,R²-6,R³-30), (I-P9075,A-10,R²-6,R³-31),
(I-P8942,A-10,R²-2,R³-34), (I-P8943,A-10,R²-3,R³-1), (I-P9076,A-10,R²-6,R³-32), (I-P9077,A-10,R²-6,R³-33),
(I-P8944,A-10,R²-3,R³-2), (I-P8945,A-10,R²-3,R³-3), (I-P9078,A-10,R²-6,R³-34), (I-P9079,A-10,R²-7,R³-1),
(I-P8946,A-10,R²-3,R³-4), (I-P8947,A-10,R²-3,R³-5), (I-P9080,A-10,R²-7,R³-2), (I-P9081,A-10,R²-7,R³-3),
(I-P8948,A-10,R²-3,R³-6), (I-P8949,A-10,R²-3,R³-7), (I-P9082,A-10,R²-7,R³-4), (I-P9083,A-10,R²-7,R³-5),
(I-P8950,A-10,R²-3,R³-8), (I-P8951,A-10,R²-3,R³-9), (I-P9084,A-10,R²-7,R³-6), (I-P9085,A-10,R²-7,R³-7),
(I-P8952,A-10,R²-3,R³-10), (I-P8953,A-10,R²-3,R³-11), (I-P9086,A-10,R²-7,R³-8), (I-P9087,A-10,R²-7,R³-9),
(I-P8954,A-10,R²-3,R³-12), (I-P8955,A-10,R²-3,R³-13), (I-P9088,A-10,R²-7,R³-10), (I-P9089,A-10,R²-7,R³-11),
(I-P8956,A-10,R²-3,R³-14), (I-P8957,A-10,R²-3,R³-15), (I-P9090,A-10,R²-7,R³-12), (I-P9091,A-10,R²-7,R³-13),
(I-P8958,A-10,R²-3,R³-16), (I-P8959,A-10,R²-3,R³-17), (I-P9092,A-10,R²-7,R³-14), (I-P9093,A-10,R²-7,R³-15),
(I-P8960,A-10,R²-3,R³-18), (I-P8961,A-10,R²-3,R³-19), (I-P9094,A-10,R²-7,R³-16), (I-P9095,A-10,R²-7,R³-17),
(I-P8962,A-10,R²-3,R³-20), (I-P8963,A-10,R²-3,R³-21), (I-P9096,A-10,R²-7,R³-18), (I-P9097,A-10,R²-7,R³-19),
(I-P8964,A-10,R²-3,R³-22), (I-P8965,A-10,R²-3,R³-23), (I-P9098,A-10,R²-7,R³-20), (I-P9099,A-10,R²-7,R³-21),
(I-P8966,A-10,R²-3,R³-24), (I-P8967,A-10,R²-3,R³-25), (I-P9100,A-10,R²-7,R³-22), (I-P9101,A-10,R²-7,R³-23),
(I-P8968,A-10,R²-3,R³-26), (I-P8969,A-10,R²-3,R³-27), (I-P9102,A-10,R²-7,R³-24), (I-P9103,A-10,R²-7,R³-25),
(I-P8970,A-10,R²-3,R³-28), (I-P8971,A-10,R²-3,R³-29), (I-P9104,A-10,R²-7,R³-26), (I-P9105,A-10,R²-7,R³-27),
(I-P8972,A-10,R²-3,R³-30), (I-P8973,A-10,R²-3,R³-31), (I-P9106,A-10,R²-7,R³-28), (I-P9107,A-10,R²-7,R³-29),
(I-P8974,A-10,R²-3,R³-32), (I-P8975,A-10,R²-3,R³-33), (I-P9108,A-10,R²-7,R³-30), (I-P9109,A-10,R²-7,R³-31),
(I-P8976,A-10,R²-3,R³-34), (I-P8977,A-10,R²-4,R³-1), (I-P9110,A-10,R²-7,R³-32), (I-P9111,A-10,R²-7,R³-33),
(I-P8978,A-10,R²-4,R³-2), (I-P8979,A-10,R²-4,R³-3), (I-P9112,A-10,R²-7,R³-34), (I-P9113,A-10,R²-8,R³-1),
(I-P8980,A-10,R²-4,R³-4), (I-P8981,A-10,R²-4,R³-5), (I-P9114,A-10,R²-8,R³-2), (I-P9115,A-10,R²-8,R³-3),
(I-P8982,A-10,R²-4,R³-6), (I-P8983,A-10,R²-4,R³-7), (I-P9116,A-10,R²-8,R³-4), (I-P9117,A-10,R²-8,R³-5),
(I-P8984,A-10,R²-4,R³-8), (I-P8985,A-10,R²-4,R³-9), (I-P9118,A-10,R²-8,R³-6), (I-P9119,A-10,R²-8,R³-7),
(I-P8986,A-10,R²-4,R³-10), (I-P8987,A-10,R²-4,R³-11), (I-P9120,A-10,R²-8,R³-8), (I-P9121,A-10,R²-8,R³-9),
(I-P8988,A-10,R²-4,R³-12), (I-P8989,A-10,R²-4,R³-13), (I-P9122,A-10,R²-8,R³-10), (I-P9123,A-10,R²-8,R³-11),
(I-P8990,A-10,R²-4,R³-14), (I-P8991,A-10,R²-4,R³-15), (I-P9124,A-10,R²-8,R³-12), (I-P9125,A-10,R²-8,R³-13),
(I-P8992,A-10,R²-4,R³-16), (I-P8993,A-10,R²-4,R³-17), (I-P9126,A-10,R²-8,R³-14), (I-P9127,A-10,R²-8,R³-15),
(I-P8994,A-10,R²-4,R³-18), (I-P8995,A-10,R²-4,R³-19), (I-P9128,A-10,R²-8,R³-16), (I-P9129,A-10,R²-8,R³-17),
(I-P8996,A-10,R²-4,R³-20), (I-P8997,A-10,R²-4,R³-21), (I-P9130,A-10,R²-8,R³-18), (I-P9131,A-10,R²-8,R³-19),
(I-P8998,A-10,R²-4,R³-22), (I-P8999,A-10,R²-4,R³-23), (I-P9132,A-10,R²-8,R³-20), (I-P9133,A-10,R²-8,R³-21),
(I-P9000,A-10,R²-4,R³-24), (I-P9001,A-10,R²-4,R³-25), (I-P9134,A-10,R²-8,R³-22), (I-P9135,A-10,R²-8,R³-23),
(I-P9002,A-10,R²-4,R³-26), (I-P9003,A-10,R²-4,R³-27), (I-P9136,A-10,R²-8,R³-24), (I-P9137,A-10,R²-8,R³-25),
(I-P9004,A-10,R²-4,R³-28), (I-P9005,A-10,R²-4,R³-29), (I-P9138,A-10,R²-8,R³-26), (I-P9139,A-10,R²-8,R³-27),
(I-P9006,A-10,R²-4,R³-30), (I-P9007,A-10,R²-4,R³-31), (I-P9140,A-10,R²-8,R³-28), (I-P9141,A-10,R²-8,R³-29),
(I-P9008,A-10,R²-4,R³-32), (I-P9009,A-10,R²-4,R³-33), (I-P9142,A-10,R²-8,R³-30), (I-P9143,A-10,R²-8,R³-31),
(I-P9010,A-10,R²-4,R³-34), (I-P9011,A-10,R²-5,R³-1), (I-P9144,A-10,R²-8,R³-32), (I-P9145,A-10,R²-8,R³-33),
(I-P9012,A-10,R²-5,R³-2), (I-P9013,A-10,R²-5,R³-3), (I-P9146,A-10,R²-8,R³-34), (I-P9147,A-10,R²-9,R³-1),
(I-P9014,A-10,R²-5,R³-4), (I-P9015,A-10,R²-5,R³-5), (I-P9148,A-10,R²-9,R³-2), (I-P9149,A-10,R²-9,R³-3),
(I-P9016,A-10,R²-5,R³-6), (I-P9017,A-10,R²-5,R³-7), (I-P9150,A-10,R²-9,R³-4), (I-P9151,A-10,R²-9,R³-5),
(I-P9018,A-10,R²-5,R³-8), (I-P9019,A-10,R²-5,R³-9), (I-P9152,A-10,R²-9,R³-6), (I-P9153,A-10,R²-9,R³-7),
(I-P9020,A-10,R²-5,R³-10), (I-P9021,A-10,R²-5,R³-11), (I-P9154,A-10,R²-9,R³-8), (I-P9155,A-10,R²-9,R³-9),
(I-P9022,A-10,R²-5,R³-12), (I-P9023,A-10,R²-5,R³-13), (I-P9156,A-10,R²-9,R³-10), (I-P9157,A-10,R²-9,R³-11),
(I-P9024,A-10,R²-5,R³-14), (I-P9025,A-10,R²-5,R³-15), (I-P9158,A-10,R²-9,R³-12), (I-P9159,A-10,R²-9,R³-13),
(I-P9026,A-10,R²-5,R³-16), (I-P9027,A-10,R²-5,R³-17), (I-P9160,A-10,R²-9,R³-14), (I-P9161,A-10,R²-9,R³-15),
(I-P9028,A-10,R²-5,R³-18), (I-P9029,A-10,R²-5,R³-19), (I-P9162,A-10,R²-9,R³-16), (I-P9163,A-10,R²-9,R³-17),
(I-P9030,A-10,R²-5,R³-20), (I-P9031,A-10,R²-5,R³-21), (I-P9164,A-10,R²-9,R³-18), (I-P9165,A-10,R²-9,R³-19),
(I-P9032,A-10,R²-5,R³-22), (I-P9033,A-10,R²-5,R³-23), (I-P9166,A-10,R²-9,R³-20), (I-P9167,A-10,R²-9,R³-21),
(I-P9034,A-10,R²-5,R³-24), (I-P9035,A-10,R²-5,R³-25), (I-P9168,A-10,R²-9,R³-22), (I-P9169,A-10,R²-9,R³-23),
(I-P9036,A-10,R²-5,R³-26), (I-P9037,A-10,R²-5,R³-27), (I-P9170,A-10,R²-9,R³-24), (I-P9171,A-10,R²-9,R³-25),
(I-P9038,A-10,R²-5,R³-28), (I-P9039,A-10,R²-5,R³-29), (I-P9172,A-10,R²-9,R³-26), (I-P9173,A-10,R²-9,R³-27),
(I-P9040,A-10,R²-5,R³-30), (I-P9041,A-10,R²-5,R³-31), (I-P9174,A-10,R²-9,R³-28), (I-P9175,A-10,R²-9,R³-29), (I-P9176,A-10,$R^2$-9,$R^3$-30), (I-P9177,A-10,$R^2$-9,$R^3$-31),
(I-P9178,A-10,$R^2$-9,$R^3$-32), (I-P9179,A-10,$R^2$-9,$R^3$-33),
(I-P9180,A-10,$R^2$-9,$R^3$-34), (I-P9181,A-10,$R^2$-10,$R^3$-1),
(I-P9182,A-10,$R^2$-10,$R^3$-2), (I-P9183,A-10,$R^2$-10,$R^3$-3),
(I-P9184,A-10,$R^2$-10,$R^3$-4), (I-P9185,A-10,$R^2$-10,$R^3$-5),
(I-P9186,A-10,$R^2$-10,$R^3$-6), (I-P9187,A-10,$R^2$-10,$R^3$-7),
(I-P9188,A-10,$R^2$-10,$R^3$-8), (I-P9189,A-10,$R^2$-10,$R^3$-9),
(I-P9190,A-10,$R^2$-10,$R^3$-10), (I-P9191,A-10,$R^2$-10,$R^3$-11),
(I-P9192,A-10,$R^2$-10,$R^3$-12), (I-P9193,A-10,$R^2$-10,$R^3$-13),
(I-P9194,A-10,$R^2$-10,$R^3$-14), (I-P9195,A-10,$R^2$-10,$R^3$-15),
(I-P9196,A-10,$R^2$-10,$R^3$-16), (I-P9197,A-10,$R^2$-10,$R^3$-17),
(I-P9198,A-10,$R^2$-10,$R^3$-18), (I-P9199,A-10,$R^2$-10,$R^3$-19),
(I-P9200,A-10,$R^2$-10,$R^3$-20), (I-P9201,A-10,$R^2$-10,$R^3$-21),
(I-P9202,A-10,$R^2$-10,$R^3$-22), (I-P9203,A-10,$R^2$-10,$R^3$-23),
(I-P9204,A-10,$R^2$-10,$R^3$-24), (I-P9205,A-10,$R^2$-10,$R^3$-25),
(I-P9206,A-10,$R^2$-10,$R^3$-26), (I-P9207,A-10,$R^2$-10,$R^3$-27),
(I-P9208,A-10,$R^2$-10,$R^3$-28), (I-P9209,A-10,$R^2$-10,$R^3$-29),
(I-P9210,A-10,$R^2$-10,$R^3$-30), (I-P9211,A-10,$R^2$-10,$R^3$-31),
(I-P9212,A-10,$R^2$-10,$R^3$-32), (I-P9213,A-10,$R^2$-10,$R^3$-33),
(I-P9214,A-10,$R^2$-10,$R^3$-34), (I-P9215,A-10,$R^2$-11,$R^3$-1),
(I-P9216,A-10,$R^2$-11,$R^3$-2), (I-P9217,A-10,$R^2$-11,$R^3$-3),
(I-P9218,A-10,$R^2$-11,$R^3$-4), (I-P9219,A-10,$R^2$-11,$R^3$-5),
(I-P9220,A-10,$R^2$-11,$R^3$-6), (I-P9221,A-10,$R^2$-11,$R^3$-7),
(I-P9222,A-10,$R^2$-11,$R^3$-8), (I-P9223,A-10,$R^2$-11,$R^3$-9),
(I-P9224,A-10,$R^2$-11,$R^3$-10), (I-P9225,A-10,$R^2$-11,$R^3$-11),
(I-P9226,A-10,$R^2$-11,$R^3$-12), (I-P9227,A-10,$R^2$-11,$R^3$-13),
(I-P9228,A-10,$R^2$-11,$R^3$-14), (I-P9229,A-10,$R^2$-11,$R^3$-15),
(I-P9230,A-10,$R^2$-11,$R^3$-16), (I-P9231,A-10,$R^2$-11,$R^3$-17),
(I-P9232,A-10,$R^2$-11,$R^3$-18), (I-P9233,A-10,$R^2$-11,$R^3$-19),
(I-P9234,A-10,$R^2$-11,$R^3$-20), (I-P9235,A-10,$R^2$-11,$R^3$-21),
(I-P9236,A-10,$R^2$-11,$R^3$-22), (I-P9237,A-10,$R^2$-11,$R^3$-23),
(I-P9238,A-10,$R^2$-11,$R^3$-24), (I-P9239,A-10,$R^2$-11,$R^3$-25),
(I-P9240,A-10,$R^2$-11,$R^3$-26), (I-P9241,A-10,$R^2$-11,$R^3$-27),
(I-P9242,A-10,$R^2$-11,$R^3$-28), (I-P9243,A-10,$R^2$-11,$R^3$-29),
(I-P9244,A-10,$R^2$-11,$R^3$-30), (I-P9245,A-10,$R^2$-11,$R^3$-31),
(I-P9246,A-10,$R^2$-11,$R^3$-32), (I-P9247,A-10,$R^2$-11,$R^3$-33),
(I-P9248,A-10,$R^2$-11,$R^3$-34), (I-P9249,A-10,$R^2$-12,$R^3$-1),
(I-P9250,A-10,$R^2$-12,$R^3$-2), (I-P9251,A-10,$R^2$-12,$R^3$-3),
(I-P9252,A-10,$R^2$-12,$R^3$-4), (I-P9253,A-10,$R^2$-12,$R^3$-5),
(I-P9254,A-10,$R^2$-12,$R^3$-6), (I-P9255,A-10,$R^2$-12,$R^3$-7),
(I-P9256,A-10,$R^2$-12,$R^3$-8), (I-P9257,A-10,$R^2$-12,$R^3$-9),
(I-P9258,A-10,$R^2$-12,$R^3$-10), (I-P9259,A-10,$R^2$-12,$R^3$-11),
(I-P9260,A-10,$R^2$-12,$R^3$-12), (I-P9261,A-10,$R^2$-12,$R^3$-13),
(I-P9262,A-10,$R^2$-12,$R^3$-14), (I-P9263,A-10,$R^2$-12,$R^3$-15),
(I-P9264,A-10,$R^2$-12,$R^3$-16), (I-P9265,A-10,$R^2$-12,$R^3$-17),
(I-P9266,A-10,$R^2$-12,$R^3$-18), (I-P9267,A-10,$R^2$-12,$R^3$-19),
(I-P9268,A-10,$R^2$-12,$R^3$-20), (I-P9269,A-10,$R^2$-12,$R^3$-21),
(I-P9270,A-10,$R^2$-12,$R^3$-22), (I-P9271,A-10,$R^2$-12,$R^3$-23),
(I-P9272,A-10,$R^2$-12,$R^3$-24), (I-P9273,A-10,$R^2$-12,$R^3$-25),
(I-P9274,A-10,$R^2$-12,$R^3$-26), (I-P9275,A-10,$R^2$-12,$R^3$-27),
(I-P9276,A-10,$R^2$-12,$R^3$-28), (I-P9277,A-10,$R^2$-12,$R^3$-29),
(I-P9278,A-10,$R^2$-12,$R^3$-30), (I-P9279,A-10,$R^2$-12,$R^3$-31),
(I-P9280,A-10,$R^2$-12,$R^3$-32), (I-P9281,A-10,$R^2$-12,$R^3$-33),
(I-P9282,A-10,$R^2$-12,$R^3$-34), (I-P9283,A-10,$R^2$-13,$R^3$-1),
(I-P9284,A-10,$R^2$-13,$R^3$-2), (I-P9285,A-10,$R^2$-13,$R^3$-3),
(I-P9286,A-10,$R^2$-13,$R^3$-4), (I-P9287,A-10,$R^2$-13,$R^3$-5),
(I-P9288,A-10,$R^2$-13,$R^3$-6), (I-P9289,A-10,$R^2$-13,$R^3$-7),
(I-P9290,A-10,$R^2$-13,$R^3$-8), (I-P9291,A-10,$R^2$-13,$R^3$-9),
(I-P9292,A-10,$R^2$-13,$R^3$-10), (I-P9293,A-10,$R^2$-13,$R^3$-11),
(I-P9294,A-10,$R^2$-13,$R^3$-12), (I-P9295,A-10,$R^2$-13,$R^3$-13),
(I-P9296,A-10,$R^2$-13,$R^3$-14), (I-P9297,A-10,$R^2$-13,$R^3$-15),
(I-P9298,A-10,$R^2$-13,$R^3$-16), (I-P9299,A-10,$R^2$-13,$R^3$-17),
(I-P9300,A-10,$R^2$-13,$R^3$-18), (I-P9301,A-10,$R^2$-13,$R^3$-19),
(I-P9302,A-10,$R^2$-13,$R^3$-20), (I-P9303,A-10,$R^2$-13,$R^3$-21),
(I-P9304,A-10,$R^2$-13,$R^3$-22), (I-P9305,A-10,$R^2$-13,$R^3$-23),
(I-P9306,A-10,$R^2$-13,$R^3$-24), (I-P9307,A-10,$R^2$-13,$R^3$-25),
(I-P9308,A-10,$R^2$-13,$R^3$-26), (I-P9309,A-10,$R^2$-13,$R^3$-27),
(I-P9310,A-10,$R^2$-13,$R^3$-28), (I-P9311,A-10,$R^2$-13,$R^3$-29),
(I-P9312,A-10,$R^2$-13,$R^3$-30), (I-P9313,A-10,$R^2$-13,$R^3$-31),
(I-P9314,A-10,$R^2$-13,$R^3$-32), (I-P9315,A-10,$R^2$-13,$R^3$-33),
(I-P9316,A-10,$R^2$-13,$R^3$-34), (I-P9317,A-10,$R^2$-14,$R^3$-1),
(I-P9318,A-10,$R^2$-14,$R^3$-2), (I-P9319,A-10,$R^2$-14,$R^3$-3),
(I-P9320,A-10,$R^2$-14,$R^3$-4), (I-P9321,A-10,$R^2$-14,$R^3$-5),
(I-P9322,A-10,$R^2$-14,$R^3$-6), (I-P9323,A-10,$R^2$-14,$R^3$-7),
(I-P9324,A-10,$R^2$-14,$R^3$-8), (I-P9325,A-10,$R^2$-14,$R^3$-9),
(I-P9326,A-10,$R^2$-14,$R^3$-10), (I-P9327,A-10,$R^2$-14,$R^3$-11),
(I-P9328,A-10,$R^2$-14,$R^3$-12), (I-P9329,A-10,$R^2$-14,$R^3$-13),
(I-P9330,A-10,$R^2$-14,$R^3$-14), (I-P9331,A-10,$R^2$-14,$R^3$-15),
(I-P9332,A-10,$R^2$-14,$R^3$-16), (I-P9333,A-10,$R^2$-14,$R^3$-17),
(I-P9334,A-10,$R^2$-14,$R^3$-18), (I-P9335,A-10,$R^2$-14,$R^3$-19),
(I-P9336,A-10,$R^2$-14,$R^3$-20), (I-P9337,A-10,$R^2$-14,$R^3$-21),
(I-P9338,A-10,$R^2$-14,$R^3$-22), (I-P9339,A-10,$R^2$-14,$R^3$-23),
(I-P9340,A-10,$R^2$-14,$R^3$-24), (I-P9341,A-10,$R^2$-14,$R^3$-25),
(I-P9342,A-10,$R^2$-14,$R^3$-26), (I-P9343,A-10,$R^2$-14,$R^3$-27),
(I-P9344,A-10,$R^2$-14,$R^3$-28), (I-P9345,A-10,$R^2$-14,$R^3$-29),
(I-P9346,A-10,$R^2$-14,$R^3$-30), (I-P9347,A-10,$R^2$-14,$R^3$-31),
(I-P9348,A-10,$R^2$-14,$R^3$-32), (I-P9349,A-10,$R^2$-14,$R^3$-33),
(I-P9350,A-10,$R^2$-14,$R^3$-34), (I-P9351,A-10,$R^2$-15,$R^3$-1),
(I-P9352,A-10,$R^2$-15,$R^3$-2), (I-P9353,A-10,$R^2$-15,$R^3$-3),
(I-P9354,A-10,$R^2$-15,$R^3$-4), (I-P9355,A-10,$R^2$-15,$R^3$-5),
(I-P9356,A-10,$R^2$-15,$R^3$-6), (I-P9357,A-10,$R^2$-15,$R^3$-7),
(I-P9358,A-10,$R^2$-15,$R^3$-8), (I-P9359,A-10,$R^2$-15,$R^3$-9),
(I-P9360,A-10,$R^2$-15,$R^3$-10), (I-P9361,A-10,$R^2$-15,$R^3$-11),
(I-P9362,A-10,$R^2$-15,$R^3$-12), (I-P9363,A-10,$R^2$-15,$R^3$-13),
(I-P9364,A-10,$R^2$-15,$R^3$-14), (I-P9365,A-10,$R^2$-15,$R^3$-15),
(I-P9366,A-10,$R^2$-15,$R^3$-16), (I-P9367,A-10,$R^2$-15,$R^3$-17),
(I-P9368,A-10,$R^2$-15,$R^3$-18), (I-P9369,A-10,$R^2$-15,$R^3$-19),
(I-P9370,A-10,$R^2$-15,$R^3$-20), (I-P9371,A-10,$R^2$-15,$R^3$-21),
(I-P9372,A-10,$R^2$-15,$R^3$-22), (I-P9373,A-10,$R^2$-15,$R^3$-23),
(I-P9374,A-10,$R^2$-15,$R^3$-24), (I-P9375,A-10,$R^2$-15,$R^3$-25),
(I-P9376,A-10,$R^2$-15,$R^3$-26), (I-P9377,A-10,$R^2$-15,$R^3$-27),
(I-P9378,A-10,$R^2$-15,$R^3$-28), (I-P9379,A-10,$R^2$-15,$R^3$-29),
(I-P9380,A-10,$R^2$-15,$R^3$-30), (I-P9381,A-10,$R^2$-15,$R^3$-31),
(I-P9382,A-10,$R^2$-15,$R^3$-32), (I-P9383,A-10,$R^2$-15,$R^3$-33),
(I-P9384,A-10,$R^2$-15,$R^3$-34), (I-P9385,A-10,$R^2$-16,$R^3$-1),
(I-P9386,A-10,$R^2$-16,$R^3$-2), (I-P9387,A-10,$R^2$-16,$R^3$-3),
(I-P9388,A-10,$R^2$-16,$R^3$-4), (I-P9389,A-10,$R^2$-16,$R^3$-5),
(I-P9390,A-10,$R^2$-16,$R^3$-6), (I-P9391,A-10,$R^2$-16,$R^3$-7),
(I-P9392,A-10,$R^2$-16,$R^3$-8), (I-P9393,A-10,$R^2$-16,$R^3$-9),
(I-P9394,A-10,$R^2$-16,$R^3$-10), (I-P9395,A-10,$R^2$-16,$R^3$-11),
(I-P9396,A-10,$R^2$-16,$R^3$-12), (I-P9397,A-10,$R^2$-16,$R^3$-13),
(I-P9398,A-10,$R^2$-16,$R^3$-14), (I-P9399,A-10,$R^2$-16,$R^3$-15),
(I-P9400,A-10,$R^2$-16,$R^3$-16), (I-P9401,A-10,$R^2$-16,$R^3$-17),
(I-P9402,A-10,$R^2$-16,$R^3$-18), (I-P9403,A-10,$R^2$-16,$R^3$-19),
(I-P9404,A-10,$R^2$-16,$R^3$-20), (I-P9405,A-10,$R^2$-16,$R^3$-21),
(I-P9406,A-10,$R^2$-16,$R^3$-22), (I-P9407,A-10,$R^2$-16,$R^3$-23),
(I-P9408,A-10,$R^2$-16,$R^3$-24), (I-P9409,A-10,$R^2$-16,$R^3$-25),
(I-P9410,A-10,$R^2$-16,$R^3$-26), (I-P9411,A-10,$R^2$-16,$R^3$-27),
(I-P9412,A-10,$R^2$-16,$R^3$-28), (I-P9413,A-10,$R^2$-16,$R^3$-29),
(I-P9414,A-10,$R^2$-16,$R^3$-30), (I-P9415,A-10,$R^2$-16,$R^3$-31),
(I-P9416,A-10,$R^2$-16,$R^3$-32), (I-P9417,A-10,$R^2$-16,$R^3$-33),
(I-P9418,A-10,$R^2$-16,$R^3$-34), (I-P9419,A-10,$R^2$-17,$R^3$-1),
(I-P9420,A-10,$R^2$-17,$R^3$-2), (I-P9421,A-10,$R^2$-17,$R^3$-3),
(I-P9422,A-10,$R^2$-17,$R^3$-4), (I-P9423,A-10,$R^2$-17,$R^3$-5),
(I-P9424,A-10,$R^2$-17,$R^3$-6), (I-P9425,A-10,$R^2$-17,$R^3$-7),
(I-P9426,A-10,$R^2$-17,$R^3$-8), (I-P9427,A-10,$R^2$-17,$R^3$-9),
(I-P9428,A-10,$R^2$-17,$R^3$-10), (I-P9429,A-10,$R^2$-17,$R^3$-11),
(I-P9430,A-10,$R^2$-17,$R^3$-12), (I-P9431,A-10,$R^2$-17,$R^3$-13),
(I-P9432,A-10,$R^2$-17,$R^3$-14), (I-P9433,A-10,$R^2$-17,$R^3$-15),
(I-P9434,A-10,$R^2$-17,$R^3$-16), (I-P9435,A-10,$R^2$-17,$R^3$-17),
(I-P9436,A-10,$R^2$-17,$R^3$-18), (I-P9437,A-10,$R^2$-17,$R^3$-19),
(I-P9438,A-10,$R^2$-17,$R^3$-20), (I-P9439,A-10,$R^2$-17,$R^3$-21),
(I-P9440,A-10,$R^2$-17,$R^3$-22), (I-P9441,A-10,$R^2$-17,$R^3$-23),
(I-P9442,A-10,$R^2$-17,$R^3$-24), (I-P9443,A-10,$R^2$-17,$R^3$-25), (I-P9444,A-10,$R^2$-17,$R^3$-26), (I-P9445,A-10,$R^2$-17,$R^3$-27),
(I-P9446,A-10,$R^2$-17,$R^3$-28), (I-P9447,A-10,$R^2$-17,$R^3$-29),
(I-P9448,A-10,$R^2$-17,$R^3$-30), (I-P9449,A-10,$R^2$-17,$R^3$-31),
(I-P9450,A-10,$R^2$-17,$R^3$-32), (I-P9451,A-10,$R^2$-17,$R^3$-33),
(I-P9452,A-10,$R^2$-17,$R^3$-34), (I-P9453,A-10,$R^2$-18,$R^3$-1),
(I-P9454,A-10,$R^2$-18,$R^3$-2), (I-P9455,A-10,$R^2$-18,$R^3$-3),
(I-P9456,A-10,$R^2$-18,$R^3$-4), (I-P9457,A-10,$R^2$-18,$R^3$-5),
(I-P9458,A-10,$R^2$-18,$R^3$-6), (I-P9459,A-10,$R^2$-18,$R^3$-7),
(I-P9460,A-10,$R^2$-18,$R^3$-8), (I-P9461,A-10,$R^2$-18,$R^3$-9),
(I-P9462,A-10,$R^2$-18,$R^3$-10), (I-P9463,A-10,$R^2$-18,$R^3$-11),
(I-P9464,A-10,$R^2$-18,$R^3$-12), (I-P9465,A-10,$R^2$-18,$R^3$-13),
(I-P9466,A-10,$R^2$-18,$R^3$-14), (I-P9467,A-10,$R^2$-18,$R^3$-15),
(I-P9468,A-10,$R^2$-18,$R^3$-16), (I-P9469,A-10,$R^2$-18,$R^3$-17),
(I-P9470,A-10,$R^2$-18,$R^3$-18), (I-P9471,A-10,$R^2$-18,$R^3$-19),
(I-P9472,A-10,$R^2$-18,$R^3$-20), (I-P9473,A-10,$R^2$-18,$R^3$-21),
(I-P9474,A-10,$R^2$-18,$R^3$-22), (I-P9475,A-10,$R^2$-18,$R^3$-23),
(I-P9476,A-10,$R^2$-18,$R^3$-24), (I-P9477,A-10,$R^2$-18,$R^3$-25),
(I-P9478,A-10,$R^2$-18,$R^3$-26), (I-P9479,A-10,$R^2$-18,$R^3$-27),
(I-P9480,A-10,$R^2$-18,$R^3$-28), (I-P9481,A-10,$R^2$-18,$R^3$-29),
(I-P9482,A-10,$R^2$-18,$R^3$-30), (I-P9483,A-10,$R^2$-18,$R^3$-31),
(I-P9484,A-10,$R^2$-18,$R^3$-32), (I-P9485,A-10,$R^2$-18,$R^3$-33),
(I-P9486,A-10,$R^2$-18,$R^3$-34), (I-P9487,A-10,$R^2$-19,$R^3$-1),
(I-P9488,A-10,$R^2$-19,$R^3$-2), (I-P9489,A-10,$R^2$-19,$R^3$-3),
(I-P9490,A-10,$R^2$-19,$R^3$-4), (I-P9491,A-10,$R^2$-19,$R^3$-5),
(I-P9492,A-10,$R^2$-19,$R^3$-6), (I-P9493,A-10,$R^2$-19,$R^3$-7),
(I-P9494,A-10,$R^2$-19,$R^3$-8), (I-P9495,A-10,$R^2$-19,$R^3$-9),
(I-P9496,A-10,$R^2$-19,$R^3$-10), (I-P9497,A-10,$R^2$-19,$R^3$-11),
(I-P9498,A-10,$R^2$-19,$R^3$-12), (I-P9499,A-10,$R^2$-19,$R^3$-13),
(I-P9500,A-10,$R^2$-19,$R^3$-14), (I-P9501,A-10,$R^2$-19,$R^3$-15),
(I-P9502,A-10,$R^2$-19,$R^3$-16), (I-P9503,A-10,$R^2$-19,$R^3$-17),
(I-P9504,A-10,$R^2$-19,$R^3$-18), (I-P9505,A-10,$R^2$-19,$R^3$-19),
(I-P9506,A-10,$R^2$-19,$R^3$-20), (I-P9507,A-10,$R^2$-19,$R^3$-21),
(I-P9508,A-10,$R^2$-19,$R^3$-22), (I-P9509,A-10,$R^2$-19,$R^3$-23),
(I-P9510,A-10,$R^2$-19,$R^3$-24), (I-P9511,A-10,$R^2$-19,$R^3$-25),
(I-P9512,A-10,$R^2$-19,$R^3$-26), (I-P9513,A-10,$R^2$-19,$R^3$-27),
(I-P9514,A-10,$R^2$-19,$R^3$-28), (I-P9515,A-10,$R^2$-19,$R^3$-29),
(I-P9516,A-10,$R^2$-19,$R^3$-30), (I-P9517,A-10,$R^2$-19,$R^3$-31),
(I-P9518,A-10,$R^2$-19,$R^3$-32), (I-P9519,A-10,$R^2$-19,$R^3$-33),
(I-P9520,A-10,$R^2$-19,$R^3$-34), (I-P9521,A-10,$R^2$-20,$R^3$-1),
(I-P9522,A-10,$R^2$-20,$R^3$-2), (I-P9523,A-10,$R^2$-20,$R^3$-3),
(I-P9524,A-10,$R^2$-20,$R^3$-4), (I-P9525,A-10,$R^2$-20,$R^3$-5),
(I-P9526,A-10,$R^2$-20,$R^3$-6), (I-P9527,A-10,$R^2$-20,$R^3$-7),
(I-P9528,A-10,$R^2$-20,$R^3$-8), (I-P9529,A-10,$R^2$-20,$R^3$-9),
(I-P9530,A-10,$R^2$-20,$R^3$-10), (I-P9531,A-10,$R^2$-20,$R^3$-11),
(I-P9532,A-10,$R^2$-20,$R^3$-12), (I-P9533,A-10,$R^2$-20,$R^3$-13),
(I-P9534,A-10,$R^2$-20,$R^3$-14), (I-P9535,A-10,$R^2$-20,$R^3$-15),
(I-P9536,A-10,$R^2$-20,$R^3$-16), (I-P9537,A-10,$R^2$-20,$R^3$-17),
(I-P9538,A-10,$R^2$-20,$R^3$-18), (I-P9539,A-10,$R^2$-20,$R^3$-19),
(I-P9540,A-10,$R^2$-20,$R^3$-20), (I-P9541,A-10,$R^2$-20,$R^3$-21),
(I-P9542,A-10,$R^2$-20,$R^3$-22), (I-P9543,A-10,$R^2$-20,$R^3$-23),
(I-P9544,A-10,$R^2$-20,$R^3$-24), (I-P9545,A-10,$R^2$-20,$R^3$-25),
(I-P9546,A-10,$R^2$-20,$R^3$-26), (I-P9547,A-10,$R^2$-20,$R^3$-27),
(I-P9548,A-10,$R^2$-20,$R^3$-28), (I-P9549,A-10,$R^2$-20,$R^3$-29),
(I-P9550,A-10,$R^2$-20,$R^3$-30), (I-P9551,A-10,$R^2$-20,$R^3$-31),
(I-P9552,A-10,$R^2$-20,$R^3$-32), (I-P9553,A-10,$R^2$-20,$R^3$-33),
(I-P9554,A-10,$R^2$-20,$R^3$-34), (I-P9555,A-10,$R^2$-21,$R^3$-1),
(I-P9556,A-10,$R^2$-21,$R^3$-2), (I-P9557,A-10,$R^2$-21,$R^3$-3),
(I-P9558,A-10,$R^2$-21,$R^3$-4), (I-P9559,A-10,$R^2$-21,$R^3$-5),
(I-P9560,A-10,$R^2$-21,$R^3$-6), (I-P9561,A-10,$R^2$-21,$R^3$-7),
(I-P9562,A-10,$R^2$-21,$R^3$-8), (I-P9563,A-10,$R^2$-21,$R^3$-9),
(I-P9564,A-10,$R^2$-21,$R^3$-10), (I-P9565,A-10,$R^2$-21,$R^3$-11),
(I-P9566,A-10,$R^2$-21,$R^3$-12), (I-P9567,A-10,$R^2$-21,$R^3$-13),
(I-P9568,A-10,$R^2$-21,$R^3$-14), (I-P9569,A-10,$R^2$-21,$R^3$-15),
(I-P9570,A-10,$R^2$-21,$R^3$-16), (I-P9571,A-10,$R^2$-21,$R^3$-17),
(I-P9572,A-10,$R^2$-21,$R^3$-18), (I-P9573,A-10,$R^2$-21,$R^3$-19),
(I-P9574,A-10,$R^2$-21,$R^3$-20), (I-P9575,A-10,$R^2$-21,$R^3$-21),
(I-P9576,A-10,$R^2$-21,$R^3$-22), (I-P9577,A-10,$R^2$-21,$R^3$-23),
(I-P9578,A-10,$R^2$-21,$R^3$-24), (I-P9579,A-10,$R^2$-21,$R^3$-25),
(I-P9580,A-10,$R^2$-21,$R^3$-26), (I-P9581,A-10,$R^2$-21,$R^3$-27),
(I-P9582,A-10,$R^2$-21,$R^3$-28), (I-P9583,A-10,$R^2$-21,$R^3$-29),
(I-P9584,A-10,$R^2$-21,$R^3$-30), (I-P9585,A-10,$R^2$-21,$R^3$-31),
(I-P9586,A-10,$R^2$-21,$R^3$-32), (I-P9587,A-10,$R^2$-21,$R^3$-33),
(I-P9588,A-10,$R^2$-21,$R^3$-34), (I-P9589,A-10,$R^2$-22,$R^3$-1),
(I-P9590,A-10,$R^2$-22,$R^3$-2), (I-P9591,A-10,$R^2$-22,$R^3$-3),
(I-P9592,A-10,$R^2$-22,$R^3$-4), (I-P9593,A-10,$R^2$-22,$R^3$-5),
(I-P9594,A-10,$R^2$-22,$R^3$-6), (I-P9595,A-10,$R^2$-22,$R^3$-7),
(I-P9596,A-10,$R^2$-22,$R^3$-8), (I-P9597,A-10,$R^2$-22,$R^3$-9),
(I-P9598,A-10,$R^2$-22,$R^3$-10), (I-P9599,A-10,$R^2$-22,$R^3$-11),
(I-P9600,A-10,$R^2$-22,$R^3$-12), (I-P9601,A-10,$R^2$-22,$R^3$-13),
(I-P9602,A-10,$R^2$-22,$R^3$-14), (I-P9603,A-10,$R^2$-22,$R^3$-15),
(I-P9604,A-10,$R^2$-22,$R^3$-16), (I-P9605,A-10,$R^2$-22,$R^3$-17),
(I-P9606,A-10,$R^2$-22,$R^3$-18), (I-P9607,A-10,$R^2$-22,$R^3$-19),
(I-P9608,A-10,$R^2$-22,$R^3$-20), (I-P9609,A-10,$R^2$-22,$R^3$-21),
(I-P9610,A-10,$R^2$-22,$R^3$-22), (I-P9611,A-10,$R^2$-22,$R^3$-23),
(I-P9612,A-10,$R^2$-22,$R^3$-24), (I-P9613,A-10,$R^2$-22,$R^3$-25),
(I-P9614,A-10,$R^2$-22,$R^3$-26), (I-P9615,A-10,$R^2$-22,$R^3$-27),
(I-P9616,A-10,$R^2$-22,$R^3$-28), (I-P9617,A-10,$R^2$-22,$R^3$-29),
(I-P9618,A-10,$R^2$-22,$R^3$-30), (I-P9619,A-10,$R^2$-22,$R^3$-31),
(I-P9620,A-10,$R^2$-22,$R^3$-32), (I-P9621,A-10,$R^2$-22,$R^3$-33),
(I-P9622,A-10,$R^2$-22,$R^3$-34), (I-P9623,A-10,$R^2$-23,$R^3$-1),
(I-P9624,A-10,$R^2$-23,$R^3$-2), (I-P9625,A-10,$R^2$-23,$R^3$-3),
(I-P9626,A-10,$R^2$-23,$R^3$-4), (I-P9627,A-10,$R^2$-23,$R^3$-5),
(I-P9628,A-10,$R^2$-23,$R^3$-6), (I-P9629,A-10,$R^2$-23,$R^3$-7),
(I-P9630,A-10,$R^2$-23,$R^3$-8), (I-P9631,A-10,$R^2$-23,$R^3$-9),
(I-P9632,A-10,$R^2$-23,$R^3$-10), (I-P9633,A-10,$R^2$-23,$R^3$-11),
(I-P9634,A-10,$R^2$-23,$R^3$-12), (I-P9635,A-10,$R^2$-23,$R^3$-13),
(I-P9636,A-10,$R^2$-23,$R^3$-14), (I-P9637,A-10,$R^2$-23,$R^3$-15),
(I-P9638,A-10,$R^2$-23,$R^3$-16), (I-P9639,A-10,$R^2$-23,$R^3$-17),
(I-P9640,A-10,$R^2$-23,$R^3$-18), (I-P9641,A-10,$R^2$-23,$R^3$-19),
(I-P9642,A-10,$R^2$-23,$R^3$-20), (I-P9643,A-10,$R^2$-23,$R^3$-21),
(I-P9644,A-10,$R^2$-23,$R^3$-22), (I-P9645,A-10,$R^2$-23,$R^3$-23),
(I-P9646,A-10,$R^2$-23,$R^3$-24), (I-P9647,A-10,$R^2$-23,$R^3$-25),
(I-P9648,A-10,$R^2$-23,$R^3$-26), (I-P9649,A-10,$R^2$-23,$R^3$-27),
(I-P9650,A-10,$R^2$-23,$R^3$-28), (I-P9651,A-10,$R^2$-23,$R^3$-29),
(I-P9652,A-10,$R^2$-23,$R^3$-30), (I-P9653,A-10,$R^2$-23,$R^3$-31),
(I-P9654,A-10,$R^2$-23,$R^3$-32), (I-P9655,A-10,$R^2$-23,$R^3$-33),
(I-P9656,A-10,$R^2$-23,$R^3$-34), (I-P9657,A-10,$R^2$-24,$R^3$-1),
(I-P9658,A-10,$R^2$-24,$R^3$-2), (I-P9659,A-10,$R^2$-24,$R^3$-3),
(I-P9660,A-10,$R^2$-24,$R^3$-4), (I-P9661,A-10,$R^2$-24,$R^3$-5),
(I-P9662,A-10,$R^2$-24,$R^3$-6), (I-P9663,A-10,$R^2$-24,$R^3$-7),
(I-P9664,A-10,$R^2$-24,$R^3$-8), (I-P9665,A-10,$R^2$-24,$R^3$-9),
(I-P9666,A-10,$R^2$-24,$R^3$-10), (I-P9667,A-10,$R^2$-24,$R^3$-11),
(I-P9668,A-10,$R^2$-24,$R^3$-12), (I-P9669,A-10,$R^2$-24,$R^3$-13),
(I-P9670,A-10,$R^2$-24,$R^3$-14), (I-P9671,A-10,$R^2$-24,$R^3$-15),
(I-P9672,A-10,$R^2$-24,$R^3$-16), (I-P9673,A-10,$R^2$-24,$R^3$-17),
(I-P9674,A-10,$R^2$-24,$R^3$-18), (I-P9675,A-10,$R^2$-24,$R^3$-19),
(I-P9676,A-10,$R^2$-24,$R^3$-20), (I-P9677,A-10,$R^2$-24,$R^3$-21),
(I-P9678,A-10,$R^2$-24,$R^3$-22), (I-P9679,A-10,$R^2$-24,$R^3$-23),
(I-P9680,A-10,$R^2$-24,$R^3$-24), (I-P9681,A-10,$R^2$-24,$R^3$-25),
(I-P9682,A-10,$R^2$-24,$R^3$-26), (I-P9683,A-10,$R^2$-24,$R^3$-27),
(I-P9684,A-10,$R^2$-24,$R^3$-28), (I-P9685,A-10,$R^2$-24,$R^3$-29),
(I-P9686,A-10,$R^2$-24,$R^3$-30), (I-P9687,A-10,$R^2$-24,$R^3$-31),
(I-P9688,A-10,$R^2$-24,$R^3$-32), (I-P9689,A-10,$R^2$-24,$R^3$-33),
(I-P9690,A-10,$R^2$-24,$R^3$-34), (I-P9691,A-10,$R^2$-25,$R^3$-1),
(I-P9692,A-10,$R^2$-25,$R^3$-2), (I-P9693,A-10,$R^2$-25,$R^3$-3),
(I-P9694,A-10,$R^2$-25,$R^3$-4), (I-P9695,A-10,$R^2$-25,$R^3$-5),
(I-P9696,A-10,$R^2$-25,$R^3$-6), (I-P9697,A-10,$R^2$-25,$R^3$-7),
(I-P9698,A-10,$R^2$-25,$R^3$-8), (I-P9699,A-10,$R^2$-25,$R^3$-9),
(I-P9700,A-10,$R^2$-25,$R^3$-10), (I-P9701,A-10,$R^2$-25,$R^3$-11),
(I-P9702,A-10,$R^2$-25,$R^3$-12), (I-P9703,A-10,$R^2$-25,$R^3$-13),
(I-P9704,A-10,$R^2$-25,$R^3$-14), (I-P9705,A-10,$R^2$-25,$R^3$-15),
(I-P9706,A-10,$R^2$-25,$R^3$-16), (I-P9707,A-10,$R^2$-25,$R^3$-17),
(I-P9708,A-10,$R^2$-25,$R^3$-18), (I-P9709,A-10,$R^2$-25,$R^3$-19),
(I-P9710,A-10,$R^2$-25,$R^3$-20), (I-P9711,A-10,$R^2$-25,$R^3$-21), (I-P9712,A-10,R²-25,R³-22), (I-P9713,A-10,R²-25,R³-23),
(I-P9714,A-10,R²-25,R³-24), (I-P9715,A-10,R²-25,R³-25),
(I-P9716,A-10,R²-25,R³-26), (I-P9717,A-10,R²-25,R³-27),
(I-P9718,A-10,R²-25,R³-28), (I-P9719,A-10,R²-25,R³-29),
(I-P9720,A-10,R²-25,R³-30), (I-P9721,A-10,R²-25,R³-31),
(I-P9722,A-10,R²-25,R³-32), (I-P9723,A-10,R²-25,R³-33),
(I-P9724,A-10,R²-25,R³-34), (I-P9725,A-10,R²-26,R³-1),
(I-P9726,A-10,R²-26,R³-2), (I-P9727,A-10,R²-26,R³-3),
(I-P9728,A-10,R²-26,R³-4), (I-P9729,A-10,R²-26,R³-5),
(I-P9730,A-10,R²-26,R³-6), (I-P9731,A-10,R²-26,R³-7),
(I-P9732,A-10,R²-26,R³-8), (I-P9733,A-10,R²-26,R³-9),
(I-P9734,A-10,R²-26,R³-10), (I-P9735,A-10,R²-26,R³-11),
(I-P9736,A-10,R²-26,R³-12), (I-P9737,A-10,R²-26,R³-13),
(I-P9738,A-10,R²-26,R³-14), (I-P9739,A-10,R²-26,R³-15),
(I-P9740,A-10,R²-26,R³-16), (I-P9741,A-10,R²-26,R³-17),
(I-P9742,A-10,R²-26,R³-18), (I-P9743,A-10,R²-26,R³-19),
(I-P9744,A-10,R²-26,R³-20), (I-P9745,A-10,R²-26,R³-21),
(I-P9746,A-10,R²-26,R³-22), (I-P9747,A-10,R²-26,R³-23),
(I-P9748,A-10,R²-26,R³-24), (I-P9749,A-10,R²-26,R³-25),
(I-P9750,A-10,R²-26,R³-26), (I-P9751,A-10,R²-26,R³-27),
(I-P9752,A-10,R²-26,R³-28), (I-P9753,A-10,R²-26,R³-29),
(I-P9754,A-10,R²-26,R³-30), (I-P9755,A-10,R²-26,R³-31),
(I-P9756,A-10,R²-26,R³-32), (I-P9757,A-10,R²-26,R³-33),
(I-P9758,A-10,R²-26,R³-34), (I-P9759,A-10,R²-27,R³-1),
(I-P9760,A-10,R²-27,R³-2), (I-P9761,A-10,R²-27,R³-3),
(I-P9762,A-10,R²-27,R³-4), (I-P9763,A-10,R²-27,R³-5),
(I-P9764,A-10,R²-27,R³-6), (I-P9765,A-10,R²-27,R³-7),
(I-P9766,A-10,R²-27,R³-8), (I-P9767,A-10,R²-27,R³-9),
(I-P9768,A-10,R²-27,R³-10), (I-P9769,A-10,R²-27,R³-11),
(I-P9770,A-10,R²-27,R³-12), (I-P9771,A-10,R²-27,R³-13),
(I-P9772,A-10,R²-27,R³-14), (I-P9773,A-10,R²-27,R³-15),
(I-P9774,A-10,R²-27,R³-16), (I-P9775,A-10,R²-27,R³-17),
(I-P9776,A-10,R²-27,R³-18), (I-P9777,A-10,R²-27,R³-19),
(I-P9778,A-10,R²-27,R³-20), (I-P9779,A-10,R²-27,R³-21),
(I-P9780,A-10,R²-27,R³-22), (I-P9781,A-10,R²-27,R³-23),
(I-P9782,A-10,R²-27,R³-24), (I-P9783,A-10,R²-27,R³-25),
(I-P9784,A-10,R²-27,R³-26), (I-P9785,A-10,R²-27,R³-27),
(I-P9786,A-10,R²-27,R³-28), (I-P9787,A-10,R²-27,R³-29),
(I-P9788,A-10,R²-27,R³-30), (I-P9789,A-10,R²-27,R³-31),
(I-P9790,A-10,R²-27,R³-32), (I-P9791,A-10,R²-27,R³-33),
(I-P9792,A-10,R²-27,R³-34), (I-P9793,A-10,R²-28,R³-1),
(I-P9794,A-10,R²-28,R³-2), (I-P9795,A-10,R²-28,R³-3),
(I-P9796,A-10,R²-28,R³-4), (I-P9797,A-10,R²-28,R³-5),
(I-P9798,A-10,R²-28,R³-6), (I-P9799,A-10,R²-28,R³-7),
(I-P9800,A-10,R²-28,R³-8), (I-P9801,A-10,R²-28,R³-9),
(I-P9802,A-10,R²-28,R³-10), (I-P9803,A-10,R²-28,R³-11),
(I-P9804,A-10,R²-28,R³-12), (I-P9805,A-10,R²-28,R³-13),
(I-P9806,A-10,R²-28,R³-14), (I-P9807,A-10,R²-28,R³-15),
(I-P9808,A-10,R²-28,R³-16), (I-P9809,A-10,R²-28,R³-17),
(I-P9810,A-10,R²-28,R³-18), (I-P9811,A-10,R²-28,R³-19),
(I-P9812,A-10,R²-28,R³-20), (I-P9813,A-10,R²-28,R³-21),
(I-P9814,A-10,R²-28,R³-22), (I-P9815,A-10,R²-28,R³-23),
(I-P9816,A-10,R²-28,R³-24), (I-P9817,A-10,R²-28,R³-25),
(I-P9818,A-10,R²-28,R³-26), (I-P9819,A-10,R²-28,R³-27),
(I-P9820,A-10,R²-28,R³-28), (I-P9821,A-10,R²-28,R³-29),
(I-P9822,A-10,R²-28,R³-30), (I-P9823,A-10,R²-28,R³-31),
(I-P9824,A-10,R²-28,R³-32), (I-P9825,A-10,R²-28,R³-33),
(I-P9826,A-10,R²-28,R³-34), (I-P9827,A-10,R²-29,R³-1),
(I-P9828,A-10,R²-29,R³-2), (I-P9829,A-10,R²-29,R³-3),
(I-P9830,A-10,R²-29,R³-4), (I-P9831,A-10,R²-29,R³-5),
(I-P9832,A-10,R²-29,R³-6), (I-P9833,A-10,R²-29,R³-7),
(I-P9834,A-10,R²-29,R³-8), (I-P9835,A-10,R²-29,R³-9),
(I-P9836,A-10,R²-29,R³-10), (I-P9837,A-10,R²-29,R³-11),
(I-P9838,A-10,R²-29,R³-12), (I-P9839,A-10,R²-29,R³-13),
(I-P9840,A-10,R²-29,R³-14), (I-P9841,A-10,R²-29,R³-15),
(I-P9842,A-10,R²-29,R³-16), (I-P9843,A-10,R²-29,R³-17),
(I-P9844,A-10,R²-29,R³-18), (I-P9845,A-10,R²-29,R³-19),
(I-P9846,A-10,R²-29,R³-20), (I-P9847,A-10,R²-29,R³-21),
(I-P9848,A-10,R²-29,R³-22), (I-P9849,A-10,R²-29,R³-23),
(I-P9850,A-10,R²-29,R³-24), (I-P9851,A-10,R²-29,R³-25),
(I-P9852,A-10,R²-29,R³-26), (I-P9853,A-10,R²-29,R³-27),
(I-P9854,A-10,R²-29,R³-28), (I-P9855,A-10,R²-29,R³-29),
(I-P9856,A-10,R²-29,R³-30), (I-P9857,A-10,R²-29,R³-31),
(I-P9858,A-10,R²-29,R³-32), (I-P9859,A-10,R²-29,R³-33),
(I-P9860,A-10,R²-29,R³-34), (I-P9861,A-11,R²-1,R³-1),
(I-P9862,A-11,R²-1,R³-2), (I-P9863,A-11,R²-1,R³-3),
(I-P9864,A-11,R²-1,R³-4), (I-P9865,A-11,R²-1,R³-5),
(I-P9866,A-11,R²-1,R³-6), (I-P9867,A-11,R²-1,R³-7),
(I-P9868,A-11,R²-1,R³-8), (I-P9869,A-11,R²-1,R³-9),
(I-P9870,A-11,R²-1,R³-10), (I-P9871,A-11,R²-1,R³-11),
(I-P9872,A-11,R²-1,R³-12), (I-P9873,A-11,R²-1,R³-13),
(I-P9874,A-11,R²-1,R³-14), (I-P9875,A-11,R²-1,R³-15),
(I-P9876,A-11,R²-1,R³-16), (I-P9877,A-11,R²-1,R³-17),
(I-P9878,A-11,R²-1,R³-18), (I-P9879,A-11,R²-1,R³-19),
(I-P9880,A-11,R²-1,R³-20), (I-P9881,A-11,R²-1,R³-21),
(I-P9882,A-11,R²-1,R³-22), (I-P9883,A-11,R²-1,R³-23),
(I-P9884,A-11,R²-1,R³-24), (I-P9885,A-11,R²-1,R³-25),
(I-P9886,A-11,R²-1,R³-26), (I-P9887,A-11,R²-1,R³-27),
(I-P9888,A-11,R²-1,R³-28), (I-P9889,A-11,R²-1,R³-29),
(I-P9890,A-11,R²-1,R³-30), (I-P9891,A-11,R²-1,R³-31),
(I-P9892,A-11,R²-1,R³-32), (I-P9893,A-11,R²-1,R³-33),
(I-P9894,A-11,R²-1,R³-34), (I-P9895,A-11,R²-2,R³-1),
(I-P9896,A-11,R²-2,R³-2), (I-P9897,A-11,R²-2,R³-3),
(I-P9898,A-11,R²-2,R³-4), (I-P9899,A-11,R²-2,R³-5),
(I-P9900,A-11,R²-2,R³-6), (I-P9901,A-11,R²-2,R³-7),
(I-P9902,A-11,R²-2,R³-8), (I-P9903,A-11,R²-2,R³-9),
(I-P9904,A-11,R²-2,R³-10), (I-P9905,A-11,R²-2,R³-11),
(I-P9906,A-11,R²-2,R³-12), (I-P9907,A-11,R²-2,R³-13),
(I-P9908,A-11,R²-2,R³-14), (I-P9909,A-11,R²-2,R³-15),
(I-P9910,A-11,R²-2,R³-16), (I-P9911,A-11,R²-2,R³-17),
(I-P9912,A-11,R²-2,R³-18), (I-P9913,A-11,R²-2,R³-19),
(I-P9914,A-11,R²-2,R³-20), (I-P9915,A-11,R²-2,R³-21),
(I-P9916,A-11,R²-2,R³-22), (I-P9917,A-11,R²-2,R³-23),
(I-P9918,A-11,R²-2,R³-24), (I-P9919,A-11,R²-2,R³-25),
(I-P9920,A-11,R²-2,R³-26), (I-P9921,A-11,R²-2,R³-27),
(I-P9922,A-11,R²-2,R³-28), (I-P9923,A-11,R²-2,R³-29),
(I-P9924,A-11,R²-2,R³-30), (I-P9925,A-11,R²-2,R³-31),
(I-P9926,A-11,R²-2,R³-32), (I-P9927,A-11,R²-2,R³-33),
(I-P9928,A-11,R²-2,R³-34), (I-P9929,A-11,R²-3,R³-1),
(I-P9930,A-11,R²-3,R³-2), (I-P9931,A-11,R²-3,R³-3),
(I-P9932,A-11,R²-3,R³-4), (I-P9933,A-11,R²-3,R³-5),
(I-P9934,A-11,R²-3,R³-6), (I-P9935,A-11,R²-3,R³-7),
(I-P9936,A-11,R²-3,R³-8), (I-P9937,A-11,R²-3,R³-9),
(I-P9938,A-11,R²-3,R³-10), (I-P9939,A-11,R²-3,R³-11),
(I-P9940,A-11,R²-3,R³-12), (I-P9941,A-11,R²-3,R³-13),
(I-P9942,A-11,R²-3,R³-14), (I-P9943,A-11,R²-3,R³-15),
(I-P9944,A-11,R²-3,R³-16), (I-P9945,A-11,R²-3,R³-17),
(I-P9946,A-11,R²-3,R³-18), (I-P9947,A-11,R²-3,R³-19),
(I-P9948,A-11,R²-3,R³-20), (I-P9949,A-11,R²-3,R³-21),
(I-P9950,A-11,R²-3,R³-22), (I-P9951,A-11,R²-3,R³-23),
(I-P9952,A-11,R²-3,R³-24), (I-P9953,A-11,R²-3,R³-25),
(I-P9954,A-11,R²-3,R³-26), (I-P9955,A-11,R²-3,R³-27),
(I-P9956,A-11,R²-3,R³-28), (I-P9957,A-11,R²-3,R³-29),
(I-P9958,A-11,R²-3,R³-30), (I-P9959,A-11,R²-3,R³-31),
(I-P9960,A-11,R²-3,R³-32), (I-P9961,A-11,R²-3,R³-33),
(I-P9962,A-11,R²-3,R³-34), (I-P9963,A-11,R²-4,R³-1),
(I-P9964,A-11,R²-4,R³-2), (I-P9965,A-11,R²-4,R³-3),
(I-P9966,A-11,R²-4,R³-4), (I-P9967,A-11,R²-4,R³-5),
(I-P9968,A-11,R²-4,R³-6), (I-P9969,A-11,R²-4,R³-7),
(I-P9970,A-11,R²-4,R³-8), (I-P9971,A-11,R²-4,R³-9),
(I-P9972,A-11,R²-4,R³-10), (I-P9973,A-11,R²-4,R³-11),
(I-P9974,A-11,R²-4,R³-12), (I-P9975,A-11,R²-4,R³-13),
(I-P9976,A-11,R²-4,R³-14), (I-P9977,A-11,R²-4,R³-15),
(I-P9978,A-11,R²-4,R³-16), (I-P9979,A-11,R²-4,R³-17), (I-P9980,A-11,$R^2$-4,$R^3$-18), (I-P9981,A-11,$R^2$-4,$R^3$-19),
(I-P9982,A-11,$R^2$-4,$R^3$-20), (I-P9983,A-11,$R^2$-4,$R^3$-21),
(I-P9984,A-11,$R^2$-4,$R^3$-22), (I-P9985,A-11,$R^2$-4,$R^3$-23),
(I-P9986,A-11,$R^2$-4,$R^3$-24), (I-P9987,A-11,$R^2$-4,$R^3$-25),
(I-P9988,A-11,$R^2$-4,$R^3$-26), (I-P9989,A-11,$R^2$-4,$R^3$-27),
(I-P9990,A-11,$R^2$-4,$R^3$-28), (I-P9991,A-11,$R^2$-4,$R^3$-29),
(I-P9992,A-11,$R^2$-4,$R^3$-30), (I-P9993,A-11,$R^2$-4,$R^3$-31),
(I-P9994,A-11,$R^2$-4,$R^3$-32), (I-P9995,A-11,$R^2$-4,$R^3$-33),
(I-P9996,A-11,$R^2$-4,$R^3$-34), (I-P9997,A-11,$R^2$-5,$R^3$-1),
(I-P9998,A-11,$R^2$-5,$R^3$-2), (I-P9999,A-11,$R^2$-5,$R^3$-3),
(I-P10000,A-11,$R^2$-5,$R^3$-4), (I-P10001,A-11,$R^2$-5,$R^3$-5),
(I-P10002,A-11,$R^2$-5,$R^3$-6), (I-P10003,A-11,$R^2$-5,$R^3$-7),
(I-P10004,A-11,$R^2$-5,$R^3$-8), (I-P10005,A-11,$R^2$-5,$R^3$-9),
(I-P10006,A-11,$R^2$-5,$R^3$-10), (I-P10007,A-11,$R^2$-5,$R^3$-11),
(I-P10008,A-11,$R^2$-5,$R^3$-12), (I-P10009,A-11,$R^2$-5,$R^3$-13),
(I-P10010,A-11,$R^2$-5,$R^3$-14), (I-P10011,A-11,$R^2$-5,$R^3$-15),
(I-P10012,A-11,$R^2$-5,$R^3$-16), (I-P10013,A-11,$R^2$-5,$R^3$-17),
(I-P10014,A-11,$R^2$-5,$R^3$-18), (I-P10015,A-11,$R^2$-5,$R^3$-19),
(I-P10016,A-11,$R^2$-5,$R^3$-20), (I-P10017,A-11,$R^2$-5,$R^3$-21),
(I-P10018,A-11,$R^2$-5,$R^3$-22), (I-P10019,A-11,$R^2$-5,$R^3$-23),
(I-P10020,A-11,$R^2$-5,$R^3$-24), (I-P10021,A-11,$R^2$-5,$R^3$-25),
(I-P10022,A-11,$R^2$-5,$R^3$-26), (I-P10023,A-11,$R^2$-5,$R^3$-27),
(I-P10024,A-11,$R^2$-5,$R^3$-28), (I-P10025,A-11,$R^2$-5,$R^3$-29),
(I-P10026,A-11,$R^2$-5,$R^3$-30), (I-P10027,A-11,$R^2$-5,$R^3$-31),
(I-P10028,A-11,$R^2$-5,$R^3$-32), (I-P10029,A-11,$R^2$-5,$R^3$-33),
(I-P10030,A-11,$R^2$-5,$R^3$-34), (I-P10031,A-11,$R^2$-6,$R^3$-1),
(I-P10032,A-11,$R^2$-6,$R^3$-2), (I-P10033,A-11,$R^2$-6,$R^3$-3),
(I-P10034,A-11,$R^2$-6,$R^3$-4), (I-P10035,A-11,$R^2$-6,$R^3$-5),
(I-P10036,A-11,$R^2$-6,$R^3$-6), (I-P10037,A-11,$R^2$-6,$R^3$-7),
(I-P10038,A-11,$R^2$-6,$R^3$-8), (I-P10039,A-11,$R^2$-6,$R^3$-9),
(I-P10040,A-11,$R^2$-6,$R^3$-10), (I-P10041,A-11,$R^2$-6,$R^3$-11),
(I-P10042,A-11,$R^2$-6,$R^3$-12), (I-P10043,A-11,$R^2$-6,$R^3$-13),
(I-P10044,A-11,$R^2$-6,$R^3$-14), (I-P10045,A-11,$R^2$-6,$R^3$-15),
(I-P10046,A-11,$R^2$-6,$R^3$-16), (I-P10047,A-11,$R^2$-6,$R^3$-17),
(I-P10048,A-11,$R^2$-6,$R^3$-18), (I-P10049,A-11,$R^2$-6,$R^3$-19),
(I-P10050,A-11,$R^2$-6,$R^3$-20), (I-P10051,A-11,$R^2$-6,$R^3$-21),
(I-P10052,A-11,$R^2$-6,$R^3$-22), (I-P10053,A-11,$R^2$-6,$R^3$-23),
(I-P10054,A-11,$R^2$-6,$R^3$-24), (I-P10055,A-11,$R^2$-6,$R^3$-25),
(I-P10056,A-11,$R^2$-6,$R^3$-26), (I-P10057,A-11,$R^2$-6,$R^3$-27),
(I-P10058,A-11,$R^2$-6,$R^3$-28), (I-P10059,A-11,$R^2$-6,$R^3$-29),
(I-P10060,A-11,$R^2$-6,$R^3$-30), (I-P10061,A-11,$R^2$-6,$R^3$-31),
(I-P10062,A-11,$R^2$-6,$R^3$-32), (I-P10063,A-11,$R^2$-6,$R^3$-33),
(I-P10064,A-11,$R^2$-6,$R^3$-34), (I-P10065,A-11,$R^2$-7,$R^3$-1),
(I-P10066,A-11,$R^2$-7,$R^3$-2), (I-P10067,A-11,$R^2$-7,$R^3$-3),
(I-P10068,A-11,$R^2$-7,$R^3$-4), (I-P10069,A-11,$R^2$-7,$R^3$-5),
(I-P10070,A-11,$R^2$-7,$R^3$-6), (I-P10071,A-11,$R^2$-7,$R^3$-7),
(I-P10072,A-11,$R^2$-7,$R^3$-8), (I-P10073,A-11,$R^2$-7,$R^3$-9),
(I-P10074,A-11,$R^2$-7,$R^3$-10), (I-P10075,A-11,$R^2$-7,$R^3$-11),
(I-P10076,A-11,$R^2$-7,$R^3$-12), (I-P10077,A-11,$R^2$-7,$R^3$-13),
(I-P10078,A-11,$R^2$-7,$R^3$-14), (I-P10079,A-11,$R^2$-7,$R^3$-15),
(I-P10080,A-11,$R^2$-7,$R^3$-16), (I-P10081,A-11,$R^2$-7,$R^3$-17),
(I-P10082,A-11,$R^2$-7,$R^3$-18), (I-P10083,A-11,$R^2$-7,$R^3$-19),
(I-P10084,A-11,$R^2$-7,$R^3$-20), (I-P10085,A-11,$R^2$-7,$R^3$-21),
(I-P10086,A-11,$R^2$-7,$R^3$-22), (I-P10087,A-11,$R^2$-7,$R^3$-23),
(I-P10088,A-11,$R^2$-7,$R^3$-24), (I-P10089,A-11,$R^2$-7,$R^3$-25),
(I-P10090,A-11,$R^2$-7,$R^3$-26), (I-P10091,A-11,$R^2$-7,$R^3$-27),
(I-P10092,A-11,$R^2$-7,$R^3$-28), (I-P10093,A-11,$R^2$-7,$R^3$-29),
(I-P10094,A-11,$R^2$-7,$R^3$-30), (I-P10095,A-11,$R^2$-7,$R^3$-31),
(I-P10096,A-11,$R^2$-7,$R^3$-32), (I-P10097,A-11,$R^2$-7,$R^3$-33),
(I-P10098,A-11,$R^2$-7,$R^3$-34), (I-P10099,A-11,$R^2$-8,$R^3$-1),
(I-P10100,A-11,$R^2$-8,$R^3$-2), (I-P10101,A-11,$R^2$-8,$R^3$-3),
(I-P10102,A-11,$R^2$-8,$R^3$-4), (I-P10103,A-11,$R^2$-8,$R^3$-5),
(I-P10104,A-11,$R^2$-8,$R^3$-6), (I-P10105,A-11,$R^2$-8,$R^3$-7),
(I-P10106,A-11,$R^2$-8,$R^3$-8), (I-P10107,A-11,$R^2$-8,$R^3$-9),
(I-P10108,A-11,$R^2$-8,$R^3$-10), (I-P10109,A-11,$R^2$-8,$R^3$-11),
(I-P10110,A-11,$R^2$-8,$R^3$-12), (I-P10111,A-11,$R^2$-8,$R^3$-13),
(I-P10112,A-11,$R^2$-8,$R^3$-14), (I-P10113,A-11,$R^2$-8,$R^3$-15),
(I-P10114,A-11,$R^2$-8,$R^3$-16), (I-P10115,A-11,$R^2$-8,$R^3$-17),
(I-P10116,A-11,$R^2$-8,$R^3$-18), (I-P10117,A-11,$R^2$-8,$R^3$-19),
(I-P10118,A-11,$R^2$-8,$R^3$-20), (I-P10119,A-11,$R^2$-8,$R^3$-21),
(I-P10120,A-11,$R^2$-8,$R^3$-22), (I-P10121,A-11,$R^2$-8,$R^3$-23),
(I-P10122,A-11,$R^2$-8,$R^3$-24), (I-P10123,A-11,$R^2$-8,$R^3$-25),
(I-P10124,A-11,$R^2$-8,$R^3$-26), (I-P10125,A-11,$R^2$-8,$R^3$-27),
(I-P10126,A-11,$R^2$-8,$R^3$-28), (I-P10127,A-11,$R^2$-8,$R^3$-29),
(I-P10128,A-11,$R^2$-8,$R^3$-30), (I-P10129,A-11,$R^2$-8,$R^3$-31),
(I-P10130,A-11,$R^2$-8,$R^3$-32), (I-P10131,A-11,$R^2$-8,$R^3$-33),
(I-P10132,A-11,$R^2$-8,$R^3$-34), (I-P10133,A-11,$R^2$-9,$R^3$-1),
(I-P10134,A-11,$R^2$-9,$R^3$-2), (I-P10135,A-11,$R^2$-9,$R^3$-3),
(I-P10136,A-11,$R^2$-9,$R^3$-4), (I-P10137,A-11,$R^2$-9,$R^3$-5),
(I-P10138,A-11,$R^2$-9,$R^3$-6), (I-P10139,A-11,$R^2$-9,$R^3$-7),
(I-P10140,A-11,$R^2$-9,$R^3$-8), (I-P10141,A-11,$R^2$-9,$R^3$-9),
(I-P10142,A-11,$R^2$-9,$R^3$-10), (I-P10143,A-11,$R^2$-9,$R^3$-11),
(I-P10144,A-11,$R^2$-9,$R^3$-12), (I-P10145,A-11,$R^2$-9,$R^3$-13),
(I-P10146,A-11,$R^2$-9,$R^3$-14), (I-P10147,A-11,$R^2$-9,$R^3$-15),
(I-P10148,A-11,$R^2$-9,$R^3$-16), (I-P10149,A-11,$R^2$-9,$R^3$-17),
(I-P10150,A-11,$R^2$-9,$R^3$-18), (I-P10151,A-11,$R^2$-9,$R^3$-19),
(I-P10152,A-11,$R^2$-9,$R^3$-20), (I-P10153,A-11,$R^2$-9,$R^3$-21),
(I-P10154,A-11,$R^2$-9,$R^3$-22), (I-P10155,A-11,$R^2$-9,$R^3$-23),
(I-P10156,A-11,$R^2$-9,$R^3$-24), (I-P10157,A-11,$R^2$-9,$R^3$-25),
(I-P10158,A-11,$R^2$-9,$R^3$-26), (I-P10159,A-11,$R^2$-9,$R^3$-27),
(I-P10160,A-11,$R^2$-9,$R^3$-28), (I-P10161,A-11,$R^2$-9,$R^3$-29),
(I-P10162,A-11,$R^2$-9,$R^3$-30), (I-P10163,A-11,$R^2$-9,$R^3$-31),
(I-P10164,A-11,$R^2$-9,$R^3$-32), (I-P10165,A-11,$R^2$-9,$R^3$-33),
(I-P10166,A-11,$R^2$-9,$R^3$-34), (I-P10167,A-11,$R^2$-10,$R^3$-1),
(I-P10168,A-11,$R^2$-10,$R^3$-2), (I-P10169,A-11,$R^2$-10,$R^3$-3),
(I-P10170,A-11,$R^2$-10,$R^3$-4), (I-P10171,A-11,$R^2$-10,$R^3$-5),
(I-P10172,A-11,$R^2$-10,$R^3$-6), (I-P10173,A-11,$R^2$-10,$R^3$-7),
(I-P10174,A-11,$R^2$-10,$R^3$-8), (I-P10175,A-11,$R^2$-10,$R^3$-9),
(I-P10176,A-11,$R^2$-10,$R^3$-10), (I-P10177,A-11,$R^2$-10,$R^3$-11), (I-P10178,A-11,$R^2$-10,$R^3$-12), (I-P10179,A-11,$R^2$-10,$R^3$-13), (I-P10180,A-11,$R^2$-10,$R^3$-14), (I-P10181,A-11,$R^2$-10,$R^3$-15), (I-P10182,A-11,$R^2$-10,$R^3$-16), (I-P10183,A-11,$R^2$-10,$R^3$-17), (I-P10184,A-11,$R^2$-10,$R^3$-18), (I-P10185,A-11,$R^2$-10,$R^3$-19), (I-P10186,A-11,$R^2$-10,$R^3$-20), (I-P10187,A-11,$R^2$-10,$R^3$-21), (I-P10188,A-11,$R^2$-10,$R^3$-22), (I-P10189,A-11,$R^2$-10,$R^3$-23), (I-P10190,A-11,$R^2$-10,$R^3$-24), (I-P10191,A-11,$R^2$-10,$R^3$-25), (I-P10192,A-11,$R^2$-10,$R^3$-26), (I-P10193,A-11,$R^2$-10,$R^3$-27), (I-P10194,A-11,$R^2$-10,$R^3$-28), (I-P10195,A-11,$R^2$-10,$R^3$-29), (I-P10196,A-11,$R^2$-10,$R^3$-30), (I-P10197,A-11,$R^2$-10,$R^3$-31), (I-P10198,A-11,$R^2$-10,$R^3$-32), (I-P10199,A-11,$R^2$-10,$R^3$-33), (I-P10200,A-11,$R^2$-10,$R^3$-34), (I-P10201,A-11,$R^2$-11,$R^3$-1),
(I-P10202,A-11,$R^2$-11,$R^3$-2), (I-P10203,A-11,$R^2$-11,$R^3$-3),
(I-P10204,A-11,$R^2$-11,$R^3$-4), (I-P10205,A-11,$R^2$-11,$R^3$-5),
(I-P10206,A-11,$R^2$-11,$R^3$-6), (I-P10207,A-11,$R^2$-11,$R^3$-7),
(I-P10208,A-11,$R^2$-11,$R^3$-8), (I-P10209,A-11,$R^2$-11,$R^3$-9),
(I-P10210,A-11,$R^2$-11,$R^3$-10), (I-P10211,A-11,$R^2$-11,$R^3$-11), (I-P10212,A-11,$R^2$-11,$R^3$-12), (I-P10213,A-11,$R^2$-11,$R^3$-13), (I-P10214,A-11,$R^2$-11,$R^3$-14), (I-P10215,A-11,$R^2$-11,$R^3$-15), (I-P10216,A-11,$R^2$-11,$R^3$-16), (I-P10217,A-11,$R^2$-11,$R^3$-17), (I-P10218,A-11,$R^2$-11,$R^3$-18), (I-P10219,A-11,$R^2$-11,$R^3$-19), (I-P10220,A-11,$R^2$-11,$R^3$-20), (I-P10221,A-11,$R^2$-11,$R^3$-21), (I-P10222,A-11,$R^2$-11,$R^3$-22), (I-P10223,A-11,$R^2$-11,$R^3$-23), (I-P10224,A-11,$R^2$-11,$R^3$-24), (I-P10225,A-11,$R^2$-11,$R^3$-25), (I-P10226,A-11,$R^2$-11,$R^3$-26), (I-P10227,A-11,$R^2$-11,$R^3$-27), (I-P10228,A-11,$R^2$-11,$R^3$-28), (I-P10229,A-11,$R^2$-11,$R^3$-29), (I-P10230,A-11,$R^2$-11,$R^3$-30), (I-P10231,A-11,$R^2$-11,$R^3$-31), (I-P10232,A-11,$R^2$-11,$R^3$-32), (I-P10233,A-11,$R^2$-11,$R^3$-33), (I-P10234,A-11,$R^2$-11,$R^3$-34), (I-P10235,A-11,$R^2$-12,$R^3$-1),
(I-P10236,A-11,$R^2$-12,$R^3$-2), (I-P10237,A-11,$R^2$-12,$R^3$-3),
(I-P10238,A-11,$R^2$-12,$R^3$-4), (I-P10239,A-11,$R^2$-12,$R^3$-5),
(I-P10240,A-11,$R^2$-12,$R^3$-6), (I-P10241,A-11,$R^2$-12,$R^3$-7),
(I-P10242,A-11,$R^2$-12,$R^3$-8), (I-P10243,A-11,$R^2$-12,$R^3$-9), (I-P10244,A-11,R²-12,R³-10), (I-P10245,A-11,R²-12,R³-11), (I-P10246,A-11,R²-12,R³-12), (I-P10247,A-11,R²-12,R³-13), (I-P10248,A-11,R²-12,R³-14), (I-P10249,A-11,R²-12,R³-15), (I-P10250,A-11,R²-12,R³-16), (I-P10251,A-11,R²-12,R³-17), (I-P10252,A-11,R²-12,R³-18), (I-P10253,A-11,R²-12,R³-19), (I-P10254,A-11,R²-12,R³-20), (I-P10255,A-11,R²-12,R³-21), (I-P10256,A-11,R²-12,R³-22), (I-P10257,A-11,R²-12,R³-23), (I-P10258,A-11,R²-12,R³-24), (I-P10259,A-11,R²-12,R³-25), (I-P10260,A-11,R²-12,R³-26), (I-P10261,A-11,R²-12,R³-27), (I-P10262,A-11,R²-12,R³-28), (I-P10263,A-11,R²-12,R³-29), (I-P10264,A-11,R²-12,R³-30), (I-P10265,A-11,R²-12,R³-31), (I-P10266,A-11,R²-12,R³-32), (I-P10267,A-11,R²-12,R³-33), (I-P10268,A-11,R²-12,R³-34), (I-P10269,A-11,R²-13,R³-1), (I-P10270,A-11,R²-13,R³-2), (I-P10271,A-11,R²-13,R³-3), (I-P10272,A-11,R²-13,R³-4), (I-P10273,A-11,R²-13,R³-5), (I-P10274,A-11,R²-13,R³-6), (I-P10275,A-11,R²-13,R³-7), (I-P10276,A-11,R²-13,R³-8), (I-P10277,A-11,R²-13,R³-9), (I-P10278,A-11,R²-13,R³-10), (I-P10279,A-11,R²-13,R³-11), (I-P10280,A-11,R²-13,R³-12), (I-P10281,A-11,R²-13,R³-13), (I-P10282,A-11,R²-13,R³-14), (I-P10283,A-11,R²-13,R³-15), (I-P10284,A-11,R²-13,R³-16), (I-P10285,A-11,R²-13,R³-17), (I-P10286,A-11,R²-13,R³-18), (I-P10287,A-11,R²-13,R³-19), (I-P10288,A-11,R²-13,R³-20), (I-P10289,A-11,R²-13,R³-21), (I-P10290,A-11,R²-13,R³-22), (I-P10291,A-11,R²-13,R³-23), (I-P10292,A-11,R²-13,R³-24), (I-P10293,A-11,R²-13,R³-25), (I-P10294,A-11,R²-13,R³-26), (I-P10295,A-11,R²-13,R³-27), (I-P10296,A-11,R²-13,R³-28), (I-P10297,A-11,R²-13,R³-29), (I-P10298,A-11,R²-13,R³-30), (I-P10299,A-11,R²-13,R³-31), (I-P10300,A-11,R²-13,R³-32), (I-P10301,A-11,R²-13,R³-33), (I-P10302,A-11,R²-13,R³-34), (I-P10303,A-11,R²-14,R³-1), (I-P10304,A-11,R²-14,R³-2), (I-P10305,A-11,R²-14,R³-3), (I-P10306,A-11,R²-14,R³-4), (I-P10307,A-11,R²-14,R³-5), (I-P10308,A-11,R²-14,R³-6), (I-P10309,A-11,R²-14,R³-7), (I-P10310,A-11,R²-14,R³-8), (I-P10311,A-11,R²-14,R³-9), (I-P10312,A-11,R²-14,R³-10), (I-P10313,A-11,R²-14,R³-11), (I-P10314,A-11,R²-14,R³-12), (I-P10315,A-11,R²-14,R³-13), (I-P10316,A-11,R²-14,R³-14), (I-P10317,A-11,R²-14,R³-15), (I-P10318,A-11,R²-14,R³-16), (I-P10319,A-11,R²-14,R³-17), (I-P10320,A-11,R²-14,R³-18), (I-P10321,A-11,R²-14,R³-19), (I-P10322,A-11,R²-14,R³-20), (I-P10323,A-11,R²-14,R³-21), (I-P10324,A-11,R²-14,R³-22), (I-P10325,A-11,R²-14,R³-23), (I-P10326,A-11,R²-14,R³-24), (I-P10327,A-11,R²-14,R³-25), (I-P10328,A-11,R²-14,R³-26), (I-P10329,A-11,R²-14,R³-27), (I-P10330,A-11,R²-14,R³-28), (I-P10331,A-11,R²-14,R³-29), (I-P10332,A-11,R²-14,R³-30), (I-P10333,A-11,R²-14,R³-31), (I-P10334,A-11,R²-14,R³-32), (I-P10335,A-11,R²-14,R³-33), (I-P10336,A-11,R²-14,R³-34), (I-P10337,A-11,R²-15,R³-1), (I-P10338,A-11,R²-15,R³-2), (I-P10339,A-11,R²-15,R³-3), (I-P10340,A-11,R²-15,R³-4), (I-P10341,A-11,R²-15,R³-5), (I-P10342,A-11,R²-15,R³-6), (I-P10343,A-11,R²-15,R³-7), (I-P10344,A-11,R²-15,R³-8), (I-P10345,A-11,R²-15,R³-9), (I-P10346,A-11,R²-15,R³-10), (I-P10347,A-11,R²-15,R³-11), (I-P10348,A-11,R²-15,R³-12), (I-P10349,A-11,R²-15,R³-13), (I-P10350,A-11,R²-15,R³-14), (I-P10351,A-11,R²-15,R³-15), (I-P10352,A-11,R²-15,R³-16), (I-P10353,A-11,R²-15,R³-17), (I-P10354,A-11,R²-15,R³-18), (I-P10355,A-11,R²-15,R³-19), (I-P10356,A-11,R²-15,R³-20), (I-P10357,A-11,R²-15,R³-21), (I-P10358,A-11,R²-15,R³-22), (I-P10359,A-11,R²-15,R³-23), (I-P10360,A-11,R²-15,R³-24), (I-P10361,A-11,R²-15,R³-25), (I-P10362,A-11,R²-15,R³-26), (I-P10363,A-11,R²-15,R³-27), (I-P10364,A-11,R²-15,R³-28), (I-P10365,A-11,R²-15,R³-29), (I-P10366,A-11,R²-15,R³-30), (I-P10367,A-11,R²-15,R³-31), (I-P10368,A-11,R²-15,R³-32), (I-P10369,A-11,R²-15,R³-33), (I-P10370,A-11,R²-15,R³-34), (I-P10371,A-11,R²-16,R³-1), (I-P10372,A-11,R²-16,R³-2), (I-P10373,A-11,R²-16,R³-3), (I-P10374,A-11,R²-16,R³-4), (I-P10375,A-11,R²-16,R³-5), (I-P10376,A-11,R²-16,R³-6), (I-P10377,A-11,R²-16,R³-7), (I-P10378,A-11,R²-16,R³-8), (I-P10379,A-11,R²-16,R³-9), (I-P10380,A-11,R²-16,R³-10), (I-P10381,A-11,R²-16,R³-11), (I-P10382,A-11,R²-16,R³-12), (I-P10383,A-11,R²-16,R³-13), (I-P10384,A-11,R²-16,R³-14), (I-P10385,A-11,R²-16,R³-15), (I-P10386,A-11,R²-16,R³-16), (I-P10387,A-11,R²-16,R³-17), (I-P10388,A-11,R²-16,R³-18), (I-P10389,A-11,R²-16,R³-19), (I-P10390,A-11,R²-16,R³-20), (I-P10391,A-11,R²-16,R³-21), (I-P10392,A-11,R²-16,R³-22), (I-P10393,A-11,R²-16,R³-23), (I-P10394,A-11,R²-16,R³-24), (I-P10395,A-11,R²-16,R³-25), (I-P10396,A-11,R²-16,R³-26), (I-P10397,A-11,R²-16,R³-27), (I-P10398,A-11,R²-16,R³-28), (I-P10399,A-11,R²-16,R³-29), (I-P10400,A-11,R²-16,R³-30), (I-P10401,A-11,R²-16,R³-31), (I-P10402,A-11,R²-16,R³-32), (I-P10403,A-11,R²-16,R³-33), (I-P10404,A-11,R²-16,R³-34), (I-P10405,A-11,R²-17,R³-1), (I-P10406,A-11,R²-17,R³-2), (I-P10407,A-11,R²-17,R³-3), (I-P10408,A-11,R²-17,R³-4), (I-P10409,A-11,R²-17,R³-5), (I-P10410,A-11,R²-17,R³-6), (I-P10411,A-11,R²-17,R³-7), (I-P10412,A-11,R²-17,R³-8), (I-P10413,A-11,R²-17,R³-9), (I-P10414,A-11,R²-17,R³-10), (I-P10415,A-11,R²-17,R³-11), (I-P10416,A-11,R²-17,R³-12), (I-P10417,A-11,R²-17,R³-13), (I-P10418,A-11,R²-17,R³-14), (I-P10419,A-11,R²-17,R³-15), (I-P10420,A-11,R²-17,R³-16), (I-P10421,A-11,R²-17,R³-17), (I-P10422,A-11,R²-17,R³-18), (I-P10423,A-11,R²-17,R³-19), (I-P10424,A-11,R²-17,R³-20), (I-P10425,A-11,R²-17,R³-21), (I-P10426,A-11,R²-17,R³-22), (I-P10427,A-11,R²-17,R³-23), (I-P10428,A-11,R²-17,R³-24), (I-P10429,A-11,R²-17,R³-25), (I-P10430,A-11,R²-17,R³-26), (I-P10431,A-11,R²-17,R³-27), (I-P10432,A-11,R²-17,R³-28), (I-P10433,A-11,R²-17,R³-29), (I-P10434,A-11,R²-17,R³-30), (I-P10435,A-11,R²-17,R³-31), (I-P10436,A-11,R²-17,R³-32), (I-P10437,A-11,R²-17,R³-33), (I-P10438,A-11,R²-17,R³-34), (I-P10439,A-11,R²-18,R³-1), (I-P10440,A-11,R²-18,R³-2), (I-P10441,A-11,R²-18,R³-3), (I-P10442,A-11,R²-18,R³-4), (I-P10443,A-11,R²-18,R³-5), (I-P10444,A-11,R²-18,R³-6), (I-P10445,A-11,R²-18,R³-7), (I-P10446,A-11,R²-18,R³-8), (I-P10447,A-11,R²-18,R³-9), (I-P10448,A-11,R²-18,R³-10), (I-P10449,A-11,R²-18,R³-11), (I-P10450,A-11,R²-18,R³-12), (I-P10451,A-11,R²-18,R³-13), (I-P10452,A-11,R²-18,R³-14), (I-P10453,A-11,R²-18,R³-15), (I-P10454,A-11,R²-18,R³-16), (I-P10455,A-11,R²-18,R³-17), (I-P10456,A-11,R²-18,R³-18), (I-P10457,A-11,R²-18,R³-19), (I-P10458,A-11,R²-18,R³-20), (I-P10459,A-11,R²-18,R³-21), (I-P10460,A-11,R²-18,R³-22), (I-P10461,A-11,R²-18,R³-23), (I-P10462,A-11,R²-18,R³-24), (I-P10463,A-11,R²-18,R³-25), (I-P10464,A-11,R²-18,R³-26), (I-P10465,A-11,R²-18,R³-27), (I-P10466,A-11,R²-18,R³-28), (I-P10467,A-11,R²-18,R³-29), (I-P10468,A-11,R²-18,R³-30), (I-P10469,A-11,R²-18,R³-31), (I-P10470,A-11,R²-18,R³-32), (I-P10471,A-11,R²-18,R³-33), (I-P10472,A-11,R²-18,R³-34), (I-P10473,A-11,R²-19,R³-1), (I-P10474,A-11,R²-19,R³-2), (I-P10475,A-11,R²-19,R³-3), (I-P10476,A-11,R²-19,R³-4), (I-P10477,A-11,R²-19,R³-5), (I-P10478,A-11,R²-19,R³-6), (I-P10479,A-11,R²-19,R³-7), (I-P10480,A-11,R²-19,R³-8), (I-P10481,A-11,R²-19,R³-9), (I-P10482,A-11,R²-19,R³-10), (I-P 10483,A-11,R²-19,R³-11), (I-P10484,A-11,R²-19,R³-12), (I-P10485,A-11,R²-19,R³-13), (I-P10486,A-11,R²-19,R³-14), (I-P10487,A-11,R²-19,R³-15), (I-P10488,A-11,R²-19,R³-16), (I-P10489,A-11,R²-19,R³-17), (I-P10490,A-11,R²-19,R³-18), (I-P10491,A-11,R²-19,R³-19), (I-P10492,A-11,R²-19,R³-20), (I-P10493,A-11,R²-19,R³-21), (I-P10494,A-11,R²-19,R³-22), (I-P10495,A-11,R²-19,R³-23), (I-P10496,A-11,R²-19,R³-

24), (I-P10497,A-11,$R^2$-19,$R^3$-25), (I-P10498,A-11,$R^2$-19, $R^3$-26), (I-P10499,A-11,$R^2$-19,$R^3$-27), (I-P10500,A-11,$R^2$-19,$R^3$-28), (I-P10501,A-11,$R^2$-19,$R^3$-29), (I-P10502,A-11, $R^2$-19,$R^3$-30), (I-P10503,A-11,$R^2$-19,$R^3$-31), (I-P10504,A-11,$R^2$-19,$R^3$-32), (I-P10505,A-11,$R^2$-19,$R^3$-33), (I-P10506, A-11,$R^2$-19,$R^3$-34), (I-P10507,A-11,$R^2$-20,$R^3$-1), (I-P10508,A-11,$R^2$-20,$R^3$-2), (I-P10509,A-11,$R^2$-20,$R^3$-3), (I-P10510,A-11,$R^2$-20,$R^3$-4), (I-P10511,A-11,$R^2$-20,$R^3$-5), (I-P10512,A-11,$R^2$-20,$R^3$-6), (I-P10513,A-11,$R^2$-20,$R^3$-7), (I-P10514,A-11,$R^2$-20,$R^3$-8), (I-P10515,A-11,$R^2$-20,$R^3$-9), (I-P10516,A-11,$R^2$-20,$R^3$-10), (I-P10517,A-11,$R^2$-20,$R^3$-11), (I-P10518,A-11,$R^2$-20,$R^3$-12), (I-P10519,A-11,$R^2$-20, $R^3$-13), (I-P10520,A-11,$R^2$-20,$R^3$-14), (I-P10521,A-11,$R^2$-20,$R^3$-15), (I-P10522,A-11,$R^2$-20,$R^3$-16), (I-P10523,A-11, $R^2$-20,$R^3$-17), (I-P10524,A-11,$R^2$-20,$R^3$-18), (I-P10525,A-11,$R^2$-20,$R^3$-19), (I-P10526,A-11,$R^2$-20,$R^3$-20), (I-P10527, A-11,$R^2$-20,$R^3$-21), (I-P10528,A-11,$R^2$-20,$R^3$-22), (I-P10529,A-11,$R^2$-20,$R^3$-23), (I-P10530,A-11,$R^2$-20,$R^3$-24), (I-P10531,A-11,$R^2$-20,$R^3$-25), (I-P10532,A-11,$R^2$-20, $R^3$-26), (I-P10533,A-11,$R^2$-20,$R^3$-27), (I-P10534,A-11,$R^2$-20,$R^3$-28), (I-P10535,A-11,$R^2$-20,$R^3$-29), (I-P10536,A-11, $R^2$-20,$R^3$-30), (I-P10537,A-11,$R^2$-20,$R^3$-31), (I-P10538,A-11,$R^2$-20,$R^3$-32), (I-P10539,A-11,$R^2$-20,$R^3$-33), (I-P10540, A-11,$R^2$-20,$R^3$-34), (I-P10541,A-11,$R^2$-21,$R^3$-1), (I-P10542,A-11,$R^2$-21,$R^3$-2), (I-P10543,A-11,$R^2$-21,$R^3$-3), (I-P10544,A-11,$R^2$-21,$R^3$-4), (I-P10545,A-11,$R^2$-21,$R^3$-5), (I-P10546,A-11,$R^2$-21,$R^3$-6), (I-P10547,A-11,$R^2$-21,$R^3$-7), (I-P10548,A-11,$R^2$-21,$R^3$-8), (I-P10549,A-11,$R^2$-21,$R^3$-9), (I-P10550,A-11,$R^2$-21,$R^3$-10), (I-P10551,A-11,$R^2$-21,$R^3$-11), (I-P10552,A-11,$R^2$-21,$R^3$-12), (I-P10553,A-11,$R^2$-21, $R^3$-13), (I-P10554,A-11,$R^2$-21,$R^3$-14), (I-P10555,A-11,$R^2$-21,$R^3$-15), (I-P10556,A-11,$R^2$-21,$R^3$-16), (I-P10557,A-11, $R^2$-21,$R^3$-17), (I-P10558,A-11,$R^2$-21,$R^3$-18), (I-P10559,A-11,$R^2$-21,$R^3$-19), (I-P10560,A-11,$R^2$-21,$R^3$-20), (I-P10561, A-11,$R^2$-21,$R^3$-21), (I-P10562,A-11,$R^2$-21,$R^3$-22), (I-P10563,A-11,$R^2$-21,$R^3$-23), (I-P10564,A-11,$R^2$-21,$R^3$-24), (I-P10565,A-11,$R^2$-21,$R^3$-25), (I-P10566,A-11,$R^2$-21, $R^3$-26), (I-P10567,A-11,$R^2$-21,$R^3$-27), (I-P10568,A-11,$R^2$-21,$R^3$-28), (I-P10569,A-11,$R^2$-21,$R^3$-29), (I-P10570,A-11, $R^2$-21,$R^3$-30), (I-P10571,A-11,$R^2$-21,$R^3$-31), (I-P10572,A-11,$R^2$-21,$R^3$-32), (I-P10573,A-11,$R^2$-21,$R^3$-33), (I-P10574, A-11,$R^2$-21,$R^3$-34), (I-P10575,A-11,$R^2$-22,$R^3$-1), (I-P10576,A-11,$R^2$-22,$R^3$-2), (I-P10577,A-11,$R^2$-22,$R^3$-3), (I-P10578,A-11,$R^2$-22,$R^3$-4), (I-P10579,A-11,$R^2$-22,$R^3$-5), (I-P10580,A-11,$R^2$-22,$R^3$-6), (I-P10581,A-11,$R^2$-22,$R^3$-7), (I-P10582,A-11,$R^2$-22,$R^3$-8), (I-P10583,A-11,$R^2$-22,$R^3$-9), (I-P10584,A-11,$R^2$-22,$R^3$-10), (I-P10585,A-11,$R^2$-22,$R^3$-11), (I-P10586,A-11,$R^2$-22,$R^3$-12), (I-P10587,A-11,$R^2$-22, $R^3$-13), (I-P10588,A-11,$R^2$-22,$R^3$-14), (I-P10589,A-11,$R^2$-22,$R^3$-15), (I-P10590,A-11,$R^2$-22,$R^3$-16), (I-P10591,A-11, $R^2$-22,$R^3$-17), (I-P10592,A-11,$R^2$-22,$R^3$-18), (I-P10593,A-11,$R^2$-22,$R^3$-19), (I-P10594,A-11,$R^2$-22,$R^3$-20), (I-P10595, A-11,$R^2$-22,$R^3$-21), (I-P10596,A-11,$R^2$-22,$R^3$-22), (I-P10597,A-11,$R^2$-22,$R^3$-23), (I-P10598,A-11,$R^2$-22,$R^3$-24), (I-P10599,A-11,$R^2$-22,$R^3$-25), (I-P10600,A-11,$R^2$-22, $R^3$-26), (I-P10601,A-11,$R^2$-22,$R^3$-27), (I-P10602,A-11,$R^2$-22,$R^3$-28), (I-P10603,A-11,$R^2$-22,$R^3$-29), (I-P10604,A-11, $R^2$-22,$R^3$-30), (I-P10605,A-11,$R^2$-22,$R^3$-31), (I-P10606,A-11,$R^2$-22,$R^3$-32), (I-P10607,A-11,$R^2$-22,$R^3$-33), (I-P10608, A-11,$R^2$-22,$R^3$-34), (I-P10609,A-11,$R^2$-23,$R^3$-1), (I-P10610,A-11,$R^2$-23,$R^3$-2), (I-P10611,A-11,$R^2$-23,$R^3$-3), (I-P10612,A-11,$R^2$-23,$R^3$-4), (I-P10613,A-11,$R^2$-23,$R^3$-5), (I-P10614,A-11,$R^2$-23,$R^3$-6), (I-P10615,A-11,$R^2$-23,$R^3$-7), (I-P10616,A-11,$R^2$-23,$R^3$-8), (I-P10617,A-11,$R^2$-23,$R^3$-9), (I-P10618,A-11,$R^2$-23,$R^3$-10), (I-P10619,A-11,$R^2$-23,$R^3$-11), (I-P10620,A-11,$R^2$-23,$R^3$-12), (I-P10621,A-11,$R^2$-23, $R^3$-13), (I-P10622,A-11,$R^2$-23,$R^3$-14), (I-P10623,A-11,$R^2$-23,$R^3$-15), (I-P10624,A-11,$R^2$-23,$R^3$-16), (I-P10625,A-11, $R^2$-23,$R^3$-17), (I-P10626,A-11,$R^2$-23,$R^3$-18), (I-P10627,A-11,$R^2$-23,$R^3$-19), (I-P10628,A-11,$R^2$-23,$R^3$-20), (I-P10629, A-11,$R^2$-23,$R^3$-21), (I-P10630,A-11,$R^2$-23,$R^3$-22), (I-P10631,A-11,$R^2$-23,$R^3$-23), (I-P10632,A-11,$R^2$-23,$R^3$-24), (I-P10633,A-11,$R^2$-23,$R^3$-25), (I-P10634,A-11,$R^2$-23, $R^3$-26), (I-P10635,A-11,$R^2$-23,$R^3$-27), (I-P10636,A-11,$R^2$-23,$R^3$-28), (I-P10637,A-11,$R^2$-23,$R^3$-29), (I-P10638,A-11, $R^2$-23,$R^3$-30), (I-P10639,A-11,$R^2$-23,$R^3$-31), (I-P10640,A-11,$R^2$-23,$R^3$-32), (I-P10641,A-11,$R^2$-23,$R^3$-33), (I-P10642, A-11,$R^2$-23,$R^3$-34), (I-P10643,A-11,$R^2$-24,$R^3$-1), (I-P10644,A-11,$R^2$-24,$R^3$-2), (I-P10645,A-11,$R^2$-24,$R^3$-3), (I-P10646,A-11,$R^2$-24,$R^3$-4), (I-P10647,A-11,$R^2$-24,$R^3$-5), (I-P10648,A-11,$R^2$-24,$R^3$-6), (I-P10649,A-11,$R^2$-24,$R^3$-7), (I-P10650,A-11,$R^2$-24,$R^3$-8), (I-P10651,A-11,$R^2$-24,$R^3$-9), (I-P10652,A-11,$R^2$-24,$R^3$-10), (I-P10653,A-11,$R^2$-24,$R^3$-11), (I-P10654,A-11,$R^2$-24,$R^3$-12), (I-P10655,A-11,$R^2$-24, $R^3$-13), (I-P10656,A-11,$R^2$-24,$R^3$-14), (I-P10657,A-11,$R^2$-24,$R^3$-15), (I-P10658,A-11,$R^2$-24,$R^3$-16), (I-P10659,A-11, $R^2$-24,$R^3$-17), (I-P10660,A-11,$R^2$-24,$R^3$-18), (I-P10661,A-11,$R^2$-24,$R^3$-19), (I-P10662,A-11,$R^2$-24,$R^3$-20), (I-P10663, A-11,$R^2$-24,$R^3$-21), (I-P10664,A-11,$R^2$-24,$R^3$-22), (I-P10665,A-11,$R^2$-24,$R^3$-23), (I-P10666,A-11,$R^2$-24,$R^3$-24), (I-P10667,A-11,$R^2$-24,$R^3$-25), (I-P10668,A-11,$R^2$-24, $R^3$-26), (I-P10669,A-11,$R^2$-24,$R^3$-27), (I-P10670,A-11,$R^2$-24,$R^3$-28), (I-P10671,A-11,$R^2$-24,$R^3$-29), (I-P10672,A-11, $R^2$-24,$R^3$-30), (I-P10673,A-11,$R^2$-24,$R^3$-31), (I-P10674,A-11,$R^2$-24,$R^3$-32), (I-P10675,A-11,$R^2$-24,$R^3$-33), (I-P10676, A-11,$R^2$-24,$R^3$-34), (I-P10677,A-11,$R^2$-25,$R^3$-1), (I-P10678,A-11,$R^2$-25,$R^3$-2), (I-P10679,A-11,$R^2$-25,$R^3$-3), (I-P10680,A-11,$R^2$-25,$R^3$-4), (I-P10681,A-11,$R^2$-25,$R^3$-5), (I-P10682,A-11,$R^2$-25,$R^3$-6), (I-P10683,A-11,$R^2$-25,$R^3$-7), (I-P10684,A-11,$R^2$-25,$R^3$-8), (I-P10685,A-11,$R^2$-25,$R^3$-9), (I-P10686,A-11,$R^2$-25,$R^3$-10), (I-P10687,A-11,$R^2$-25,$R^3$-11) (I-P10688,A-11,$R^2$-25,$R^3$-12), (I-P10689,A-11,$R^2$-25, $R^3$-13), (I-P10690,A-11,$R^2$-25,$R^3$-14), (I-P10691,A-11,$R^2$-25,$R^3$-15), (I-P10692,A-11,$R^2$-25,$R^3$-16), (I-P10693,A-11, $R^2$-25,$R^3$-17), (I-P10694,A-11,$R^2$-25,$R^3$-18), (I-P10695,A-11,$R^2$-25,$R^3$-19), (I-P10696,A-11,$R^2$-25,$R^3$-20), (I-P10697, A-11,$R^2$-25,$R^3$-21), (I-P10698,A-11,$R^2$-25,$R^3$-22), (I-P10699,A-11,$R^2$-25,$R^3$-23), (I-P10700,A-11,$R^2$-25,$R^3$-24), (I-P10701,A-11,$R^2$-25,$R^3$-25), (I-P10702,A-11,$R^2$-25, $R^3$-26), (I-P10703,A-11,$R^2$-25,$R^3$-27), (I-P10704,A-11,$R^2$-25,$R^3$-28), (I-P10705,A-11,$R^2$-25,$R^3$-29), (I-P10706,A-11, $R^2$-25,$R^3$-30), (I-P10707,A-11,$R^2$-25,$R^3$-31), (I-P10708,A-11,$R^2$-25,$R^3$-32), (I-P10709,A-11,$R^2$-25,$R^3$-33), (I-P10710, A-11,$R^2$-25,$R^3$-34), (I-P10711,A-11,$R^2$-26,$R^3$-1), (I-P10712,A-11,$R^2$-26,$R^3$-2), (I-P10713,A-11,$R^2$-26,$R^3$-3), (I-P10714,A-11,$R^2$-26,$R^3$-4), (I-P10715,A-11,$R^2$-26,$R^3$-5), (I-P10716,A-11,$R^2$-26,$R^3$-6), (I-P10717,A-11,$R^2$-26,$R^3$-7), (I-P10718,A-11,$R^2$-26,$R^3$-8), (I-P10719,A-11,$R^2$-26,$R^3$-9), (I-P10720,A-11,$R^2$-26,$R^3$-10), (I-P10721,A-11,$R^2$-26,$R^3$-11), (I-P10722,A-11,$R^2$-26,$R^3$-12), (I-P10723,A-11,$R^2$-26, $R^3$-13), (I-P10724,A-11,$R^2$-26,$R^3$-14), (I-P10725,A-11,$R^2$-26,$R^3$-15), (I-P10726,A-11,$R^2$-26,$R^3$-16), (I-P10727,A-11, $R^2$-26,$R^3$-17), (I-P10728,A-11,$R^2$-26,$R^3$-18), (I-P10729,A-11,$R^2$-26,$R^3$-19), (I-P10730,A-11,$R^2$-26,$R^3$-20), (I-P10731, A-11,$R^2$-26,$R^3$-21), (I-P10732,A-11,$R^2$-26,$R^3$-22), (I-P10733,A-11,$R^2$-26,$R^3$-23), (I-P10734,A-11,$R^2$-26,$R^3$-24), (I-P10735,A-11,$R^2$-26,$R^3$-25), (I-P10736,A-11,$R^2$-26, $R^3$-26), (I-P10737,A-11,$R^2$-26,$R^3$-27), (I-P10738,A-11,$R^2$-26,$R^3$-28), (I-P10739,A-11,$R^2$-26,$R^3$-29), (I-P10740,A-11, $R^2$-26,$R^3$-30), (I-P10741,A-11,$R^2$-26,$R^3$-31), (I-P10742,A-11,$R^2$-26,$R^3$-32), (I-P10743,A-11,$R^2$-26,$R^3$-33), (I-P10744, A-11,$R^2$-26,$R^3$-34), (I-P10745,A-11,$R^2$-27,$R^3$-1), (I-P10746,A-11,$R^2$-27,$R^3$-2), (I-P10747,A-11,$R^2$-27,$R^3$-3), (I-P10748,A-11,$R^2$-27,$R^3$-4), (I-P10749,A-11,$R^2$-27,$R^3$-5), (I-P10750,A-11,R²-27,R³-6), (I-P10751,A-11,R²-27,R³-7), (I-P10752,A-11,R²-27,R³-8), (I-P10753,A-11,R²-27,R³-9), (I-P10754,A-11,R²-27,R³-10), (I-P10755,A-11,R²-27,R³-11), (I-P10756,A-11,R²-27,R³-12), (I-P10757,A-11,R²-27,R³-13), (I-P10758,A-11,R²-27,R³-14), (I-P10759,A-11,R²-27,R³-15), (I-P10760,A-11,R²-27,R³-16), (I-P10761,A-11,R²-27,R³-17), (I-P10762,A-11,R²-27,R³-18), (I-P10763,A-11,R²-27,R³-19), (I-P10764,A-11,R²-27,R³-20), (I-P10765,A-11,R²-27,R³-21), (I-P10766,A-11,R²-27,R³-22), (I-P10767,A-11,R²-27,R³-23), (I-P10768,A-11,R²-27,R³-24), (I-P10769,A-11,R²-27,R³-25), (I-P10770,A-11,R²-27,R³-26), (I-P10771,A-11,R²-27,R³-27), (I-P10772,A-11,R²-27,R³-28), (I-P10773,A-11,R²-27,R³-29), (I-P10774,A-11,R²-27,R³-30), (I-P10775,A-11,R²-27,R³-31), (I-P10776,A-11,R²-27,R³-32), (I-P10777,A-11,R²-27,R³-33), (I-P10778,A-11,R²-27,R³-34), (I-P10779,A-11,R²-28,R³-1), (I-P10780,A-11,R²-28,R³-2), (I-P10781,A-11,R²-28,R³-3), (I-P10782,A-11,R²-28,R³-4), (I-P10783,A-11,R²-28,R³-5), (I-P10784,A-11,R²-28,R³-6), (I-P10785,A-11,R²-28,R³-7), (I-P10786,A-11,R²-28,R³-8), (I-P10787,A-11,R²-28,R³-9), (I-P10788,A-11,R²-28,R³-10), (I-P10789,A-11,R²-28,R³-11), (I-P10790,A-11,R²-28,R³-12), (I-P10791,A-11,R²-28,R³-13), (I-P10792,A-11,R²-28,R³-14), (I-P10793,A-11,R²-28,R³-15), (I-P10794,A-11,R²-28,R³-16), (I-P10795,A-11,R²-28,R³-17), (I-P10796,A-11,R²-28,R³-18), (I-P10797,A-11,R²-28,R³-19), (I-P10798,A-11,R²-28,R³-20), (I-P10799,A-11,R²-28,R³-21), (I-P10800,A-11,R²-28,R³-22), (I-P10801,A-11,R²-28,R³-23), (I-P10802,A-11,R²-28,R³-24), (I-P10803,A-11,R²-28,R³-25), (I-P10804,A-11,R²-28,R³-26), (I-P10805,A-11,R²-28,R³-27), (I-P10806,A-11,R²-28,R³-28), (I-P10807,A-11,R²-28,R³-29), (I-P10808,A-11,R²-28,R³-30), (I-P10809,A-11,R²-28,R³-31), (I-P10810,A-11,R²-28,R³-32), (I-P10811,A-11,R²-28,R³-33), (I-P10812,A-11,R²-28,R³-34), (I-P10813,A-11,R²-29,R³-1), (I-P10814,A-11,R²-29,R³-2), (I-P10815,A-11,R²-29,R³-3), (I-P10816,A-11,R²-29,R³-4), (I-P10817,A-11,R²-29,R³-5), (I-P10818,A-11,R²-29,R³-6), (I-P10819,A-11,R²-29,R³-7), (I-P10820,A-11,R²-29,R³-8), (I-P10821,A-11,R²-29,R³-9), (I-P10822,A-11,R²-29,R³-10), (I-P10823,A-11,R²-29,R³-11), (I-P10824,A-11,R²-29,R³-12), (I-P10825,A-11,R²-29,R³-13), (I-P10826,A-11,R²-29,R³-14), (I-P10827,A-11,R²-29,R³-15), (I-P10828,A-11,R²-29,R³-16), (I-P10838,A-11,R²-29,R³-26), (I-P10839,A-11,R²-29,R³-27), (I-P10840,A-11,R²-29,R³-28), (I-P10841,A-11,R²-29,R³-29), (I-P10842,A-11,R²-29,R³-30), (I-P10843,A-11,R²-29,R³-31), (I-P10844,A-11,R²-29,R³-32), (I-P10845,A-11,R²-29,R³-33), (I-P10846,A-11,R²-29,R³-34), (I-P10847,A-12,R²-1,R³-1), (I-P10848,A-12,R²-1,R³-2), (I-P10849,A-12,R²-1,R³-3), (I-P10850,A-12,R²-1,R³-4), (I-P10851,A-12,R²-1,R³-5), (I-P10852,A-12,R²-1,R³-6), (I-P10853,A-12,R²-1,R³-7), (I-P10854,A-12,R²-1,R³-8), (I-P10855,A-12,R²-1,R³-9), (I-P10856,A-12,R²-1,R³-10), (I-P10857,A-12,R²-1,R³-11), (I-P10858,A-12,R²-1,R³-12), (I-P10859,A-12,R²-1,R³-13), (I-P10860,A-12,R²-1,R³-14), (I-P10861,A-12,R²-1,R³-15), (I-P10862,A-12,R²-1,R³-16), (I-P10863,A-12,R²-1,R³-17), (I-P10864,A-12,R²-1,R³-18), (I-P10865,A-12,R²-1,R³-19), (I-P10866,A-12,R²-1,R³-20), (I-P10867,A-12,R²-1,R³-21), (I-P10868,A-12,R²-1,R³-22), (I-P10869,A-12,R²-1,R³-23), (I-P10870,A-12,R²-1,R³-24), (I-P10871,A-12,R²-1,R³-25), (I-P10872,A-12,R²-1,R³-26), (I-P10873,A-12,R²-1,R³-27), (I-P10874,A-12,R²-1,R³-28), (I-P10875,A-12,R²-1,R³-29), (I-P10876,A-12,R²-1,R³-30), (I-P10877,A-12,R²-1,R³-31), (I-P10878,A-12,R²-1,R³-32), (I-P10879,A-12,R²-1,R³-33), (I-P10880,A-12,R²-1,R³-34), (I-P10881,A-12,R²-2,R³-1), (I-P10882,A-12,R²-2,R³-2), (I-P10883,A-12,R²-2,R³-3), (I-P10884,A-12,R²-2,R³-4), (I-P10885,A-12,R²-2,R³-5), (I-P10886,A-12,R²-2,R³-6), (I-P10887,A-12,R²-2,R³-7), (I-P10888,A-12,R²-2,R³-8), (I-P10889,A-12,R²-2,R³-9), (I-P10890,A-12,R²-2,R³-10), (I-P10891,A-12,R²-2,R³-11), (I-P10892,A-12,R²-2,R³-12), (I-P10893,A-12,R²-2,R³-13), (I-P10894,A-12,R²-2,R³-14), (I-P10895,A-12,R²-2,R³-15), (I-P10896,A-12,R²-2,R³-16), (I-P10897,A-12,R²-2,R³-17), (I-P10898,A-12,R²-2,R³-18), (I-P10899,A-12,R²-2,R³-19), (I-P10900,A-12,R²-2,R³-20), (I-P10901,A-12,R²-2,R³-21), (I-P10902,A-12,R²-2,R³-22), (I-P10903,A-12,R²-2,R³-23), (I-P10904,A-12,R²-2,R³-24), (I-P10905,A-12,R²-2,R³-25), (I-P10906,A-12,R²-2,R³-26), (I-P10907,A-12,R²-2,R³-27), (I-P10908,A-12,R²-2,R³-28), (I-P10909,A-12,R²-2,R³-29), (I-P10910,A-12,R²-2,R³-30), (I-P10911,A-12,R²-2,R³-31), (I-P10912,A-12,R²-2,R³-32), (I-P10913,A-12,R²-2,R³-33), (I-P10914,A-12,R²-2,R³-34), (I-P10915,A-12,R²-3,R³-1), (I-P10916,A-12,R²-3,R³-2), (I-P10917,A-12,R²-3,R³-3), (I-P10918,A-12,R²-3,R³-4), (I-P10919,A-12,R²-3,R³-5), (I-P10920,A-12,R²-3,R³-6), (I-P10921,A-12,R²-3,R³-7), (I-P10922,A-12,R²-3,R³-8), (I-P10923,A-12,R²-3,R³-9), (I-P10924,A-12,R²-3,R³-10), (I-P10925,A-12,R²-3,R³-11), (I-P10926,A-12,R²-3,R³-12), (I-P10927,A-12,R²-3,R³-13), (I-P10928,A-12,R²-3,R³-14), (I-P10929,A-12,R²-3,R³-15), (I-P10930,A-12,R²-3,R³-16), (I-P10931,A-12,R²-3,R³-17), (I-P10932,A-12,R²-3,R³-18), (I-P10933,A-12,R²-3,R³-19), (I-P10934,A-12,R²-3,R³-20), (I-P10935,A-12,R²-3,R³-21), (I-P10936,A-12,R²-3,R³-22), (I-P10937,A-12,R²-3,R³-23), (I-P10938,A-12,R²-3,R³-24), (I-P10939,A-12,R²-3,R³-25), (I-P10940,A-12,R²-3,R³-26), (I-P10941,A-12,R²-3,R³-27), (I-P10942,A-12,R²-3,R³-28), (I-P10943,A-12,R²-3,R³-29), (I-P10944,A-12,R²-3,R³-30), (I-P10945,A-12,R²-3,R³-31), (I-P10946,A-12,R²-3,R³-32), (I-P10947,A-12,R²-3,R³-33), (I-P10948,A-12,R²-3,R³-34), (I-P10949,A-12,R²-4,R³-1), (I-P10950,A-12,R²-4,R³-2), (I-P10951,A-12,R²-4,R³-3), (I-P10952,A-12,R²-4,R³-4), (I-P10953,A-12,R²-4,R³-5), (I-P10954,A-12,R²-4,R³-6), (I-P10955,A-12,R²-4,R³-7), (I-P10956,A-12,R²-4,R³-8), (I-P10957,A-12,R²-4,R³-9), (I-P10958,A-12,R²-4,R³-10), (I-P10959,A-12,R²-4,R³-11), (I-P10960,A-12,R²-4,R³-12), (I-P10961,A-12,R²-4,R³-13), (I-P10962,A-12,R²-4,R³-14), (I-P10963,A-12,R²-4,R³-15), (I-P10964,A-12,R²-4,R³-16), (I-P10965,A-12,R²-4,R³-17), (I-P10966,A-12,R²-4,R³-18), (I-P10967,A-12,R²-4,R³-19), (I-P10968,A-12,R²-4,R³-20), (I-P10969,A-12,R²-4,R³-21), (I-P10970,A-12,R²-4,R³-22), (I-P10971,A-12,R²-4,R³-23), (I-P10972,A-12,R²-4,R³-24), (I-P10973,A-12,R²-4,R³-25), (I-P10974,A-12,R²-4,R³-26), (I-P10975,A-12,R²-4,R³-27), (I-P10976,A-12,R²-4,R³-28), (I-P10977,A-12,R²-4,R³-29), (I-P10978,A-12,R²-4,R³-30), (I-P10979,A-12,R²-4,R³-31), (I-P10980,A-12,R²-4,R³-32), (I-P10981,A-12,R²-4,R³-33), (I-P10982,A-12,R²-4,R³-34), (I-P10983,A-12,R²-5,R³-1), (I-P10984,A-12,R²-5,R³-2), (I-P10985,A-12,R²-5,R³-3), (I-P10986,A-12,R²-5,R³-4), (I-P10987,A-12,R²-5,R³-5), (I-P10988,A-12,R²-5,R³-6), (I-P10989,A-12,R²-5,R³-7), (I-P10990,A-12,R²-5,R³-8), (I-P10991,A-12,R²-5,R³-9), (I-P10992,A-12,R²-5,R³-10), (I-P10993,A-12,R²-5,R³-11), (I-P10994,A-12,R²-5,R³-12), (I-P10995,A-12,R²-5,R³-13), (I-P10996,A-12,R²-5,R³-14), (I-P10997,A-12,R²-5,R³-15), (I-P10998,A-12,R²-5,R³-16), (I-P10999,A-12,R²-5,R³-17), (I-P11000,A-12,R²-5,R³-18), (I-P11001,A-12,R²-5,R³-19), (I-P11002,A-12,R²-5,R³-20), (I-P11003,A-12,R²-5,R³-21), (I-P11004,A-12,R²-5,R³-22), (I-P11005,A-12,R²-5,R³-23), (I-P11006,A-12,R²-5,R³-24), (I-P11007,A-12,R²-5,R³-25), (I-P11008,A-12,R²-5,R³-26), (I-P11009,A-12,R²-5,R³-27), (I-P11010,A-12,R²-5,R³-28), (I-P11011,A-12,R²-5,R³-29), (I-P11012,A-12,R²-5,R³-30), (I-P11013,A-12,R²-5,R³-31), (I-P11014,A-12,R²-5,R³-32), (I-P11015,A-12,R²-5,R³-33), (I-P11016,A-12,R²-5,R³-34), (I-P11017,A-12,R²-6,R³-1), (I-P11018,A-12,R²-6,R³-2), (I-P11019,A-12,R²-6,R³-3), (I-P11020,A-12,R²-6,R³-4), (I-P11021,A-12,R²-6,

R³-5), (I-P11022,A-12,R²-6,R³-6), (I-P11023,A-12,R²-6, R³-7), (I-P11024,A-12,R²-6,R³-8), (I-P11025,A-12,R²-6, R³-9), (I-P11026,A-12,R²-6,R³-10), (I-P11027,A-12,R²-6, R³-11), (I-P11028,A-12,R²-6,R³-12), (I-P11029,A-12,R²-6, R³-13), (I-P11030,A-12,R²-6,R³-14), (I-P11031,A-12,R²-6, R³-15), (I-P11032,A-12,R²-6,R³-16), (I-P11033,A-12,R²-6, R³-17), (I-P11034,A-12,R²-6,R³-18), (I-P11035,A-12,R²-6, R³-19), (I-P11036,A-12,R²-6,R³-20), (I-P11037,A-12,R²-6, R³-21), (I-P11038,A-12,R²-6,R³-22), (I-P11039,A-12,R²-6, R³-23), (I-P11040,A-12,R²-6,R³-24), (I-P11041,A-12,R²-6, R³-25), (I-P11042,A-12,R²-6,R³-26), (I-P11043,A-12,R²-6, R³-27), (I-P11044,A-12,R²-6,R³-28), (I-P11045,A-12,R²-6, R³-29), (I-P11046,A-12,R²-6,R³-30), (I-P11047,A-12,R²-6, R³-31), (I-P11048,A-12,R²-6,R³-32), (I-P11049,A-12,R²-6, R³-33), (I-P11050,A-12,R²-6,R³-34), (I-P11051,A-12,R²-7, R³-1), (I-P11052,A-12,R²-7,R³-2), (I-P11053,A-12,R²-7, R³-3), (I-P11054,A-12,R²-7,R³-4), (I-P11055,A-12,R²-7, R³-5), (I-P11056,A-12,R²-7,R³-6), (I-P11057,A-12,R²-7, R³-7), (I-P11058,A-12,R²-7,R³-8), (I-P11059,A-12,R²-7, R³-9), (I-P11060,A-12,R²-7,R³-10), (I-P11061,A-12,R²-7, R³-11), (I-P11062,A-12,R²-7,R³-12), (I-P11063,A-12,R²-7, R³-13), (I-P11064,A-12,R²-7,R³-14), (I-P11065,A-12,R²-7, R³-15), (I-P11066,A-12,R²-7,R³-16), (I-P11067,A-12,R²-7, R³-17), (I-P11068,A-12,R²-7,R³-18), (I-P11069,A-12,R²-7, R³-19), (I-P11070,A-12,R²-7,R³-20), (I-P11071,A-12,R²-7, R³-21), (I-P11072,A-12,R²-7,R³-22), (I-P11073,A-12,R²-7, R³-23), (I-P11074,A-12,R²-7,R³-24), (I-P11075,A-12,R²-7, R³-25), (I-P11076,A-12,R²-7,R³-26), (I-P11077,A-12,R²-7, R³-27), (I-P11078,A-12,R²-7,R³-28), (I-P11079,A-12,R²-7, R³-29), (I-P11080,A-12,R²-7,R³-30), (I-P11081,A-12,R²-7, R³-31), (I-P11082,A-12,R²-7,R³-32), (I-P11083,A-12,R²-7, R³-33), (I-P11084,A-12,R²-7,R³-34), (I-P11085,A-12,R²-8, R³-1), (I-P11086,A-12,R²-8,R³-2), (I-P11087,A-12,R²-8, R³-3), (I-P11088,A-12,R²-8,R³-4), (I-P11089,A-12,R²-8, R³-5), (I-P11090,A-12,R²-8,R³-6), (I-P11091,A-12,R²-8, R³-7), (I-P11092,A-12,R²-8,R³-8), (I-P11093,A-12,R²-8, R³-9), (I-P11094,A-12,R²-8,R³-10), (I-P11095,A-12,R²-8, R³-11), (I-P11096,A-12,R²-8,R³-12), (I-P11097,A-12,R²-8, R³-13), (I-P11098,A-12,R²-8,R³-14), (I-P11099,A-12,R²-8, R³-15), (I-P11100,A-12,R²-8,R³-16), (I-P11101,A-12,R²-8, R³-17), (I-P11102,A-12,R²-8,R³-18), (I-P11103,A-12,R²-8, R³-19), (I-P11104,A-12,R²-8,R³-20), (I-P11105,A-12,R²-8, R³-21), (I-P11106,A-12,R²-8,R³-22), (I-P11107,A-12,R²-8, R³-23), (I-P11108,A-12,R²-8,R³-24), (I-P11109,A-12,R²-8, R³-25), (I-P11110,A-12,R²-8,R³-26), (I-P11111,A-12,R²-8, R³-27), (I-P11112,A-12,R²-8,R³-28), (I-P11113,A-12,R²-8, R³-29), (I-P11114,A-12,R²-8,R³-30), (I-P11115,A-12,R²-8, R³-31), (I-P11116,A-12,R²-8,R³-32), (I-P11117,A-12,R²-8, R³-33), (I-P11118,A-12,R²-8,R³-34), (I-P11119,A-12,R²-9, R³-1), (I-P11120,A-12,R²-9,R³-2), (I-P11121,A-12,R²-9, R³-3), (I-P11122,A-12,R²-9,R³-4), (I-P11123,A-12,R²-9, R³-5), (I-P11124,A-12,R²-9,R³-6), (I-P11125,A-12,R²-9, R³-7), (I-P11126,A-12,R²-9,R³-8), (I-P11127,A-12,R²-9, R³-9), (I-P11128,A-12,R²-9,R³-10), (I-P11129,A-12,R²-9, R³-11), (I-P11130,A-12,R²-9,R³-12), (I-P11131,A-12,R²-9, R³-13), (I-P11132,A-12,R²-9,R³-14), (I-P11133,A-12,R²-9, R³-15), (I-P11134,A-12,R²-9,R³-16), (I-P11135,A-12,R²-9, R³-17), (I-P11136,A-12,R²-9,R³-18), (I-P11137,A-12,R²-9, R³-19), (I-P11138,A-12,R²-9,R³-20), (I-P11139,A-12,R²-9, R³-21), (I-P11140,A-12,R²-9,R³-22), (I-P11141,A-12,R²-9, R³-23), (I-P11142,A-12,R²-9,R³-24), (I-P11143,A-12,R²-9, R³-25), (I-P11144,A-12,R²-9,R³-26), (I-P11145,A-12,R²-9, R³-27), (I-P11146,A-12,R²-9,R³-28), (I-P11147,A-12,R²-9, R³-29), (I-P11148,A-12,R²-9,R³-30), (I-P11149,A-12,R²-9, R³-31), (I-P11150,A-12,R²-9,R³-32), (I-P11151,A-12,R²-9, R³-33), (I-P11152,A-12,R²-9,R³-34), (I-P11153,A-12,R²-10,R³-1), (I-P11154,A-12,R²-10,R³-2), (I-P11155,A-12,R²-10,R³-3), (I-P11156,A-12,R²-10,R³-4), (I-P11157,A-12,R²-10,R³-5), (I-P11158,A-12,R²-10,R³-6), (I-P11159,A-12,R²-10,R³-7), (I-P11160,A-12,R²-10,R³-8), (I-P11161,A-12,R²-10,R³-9), (I-P11162,A-12,R²-10,R³-10), (I-P11163,A-12,R²-10,R³-11), (I-P11164,A-12,R²-10,R³-12), (I-P11165,A-12,R²-10,R³-13), (I-P11166,A-12,R²-10,R³-14), (I-P11167,A-12,R²-10,R³-15), (I-P11168,A-12,R²-10,R³-16), (I-P11169,A-12,R²-10,R³-17), (I-P11170,A-12,R²-10,R³-18), (I-P11171,A-12,R²-10,R³-19), (I-P11172,A-12,R²-10,R³-20), (I-P11173,A-12,R²-10,R³-21), (I-P11174,A-12,R²-10,R³-22), (I-P11175,A-12,R²-10,R³-23), (I-P11176,A-12,R²-10,R³-24), (I-P11177,A-12,R²-10,R³-25), (I-P11178,A-12,R²-10,R³-26), (I-P11179,A-12,R²-10,R³-27), (I-P11180,A-12,R²-10,R³-28), (I-P11181,A-12,R²-10,R³-29), (I-P11182,A-12,R²-10,R³-30), (I-P11183,A-12,R²-10,R³-31), (I-P11184,A-12,R²-10,R³-32), (I-P11185,A-12,R²-10,R³-33), (I-P11186,A-12,R²-10,R³-34), (I-P11187,A-12,R²-11,R³-1), (I-P11188,A-12,R²-11,R³-2), (I-P11189,A-12,R²-11,R³-3), (I-P11190,A-12,R²-11,R³-4), (I-P11191,A-12,R²-11,R³-5), (I-P11192,A-12,R²-11,R³-6), (I-P11193,A-12,R²-11,R³-7), (I-P11194,A-12,R²-11,R³-8), (I-P11195,A-12,R²-11,R³-9), (I-P11196,A-12,R²-11,R³-10), (I-P11197,A-12,R²-11,R³-11), (I-P11198,A-12,R²-11,R³-12), (I-P11199,A-12,R²-11,R³-13), (I-P11200,A-12,R²-11,R³-14), (I-P11201,A-12,R²-11,R³-15), (I-P11202,A-12,R²-11,R³-16), (I-P11203,A-12,R²-11,R³-17), (I-P11204,A-12,R²-11,R³-18), (I-P11205,A-12,R²-11,R³-19), (I-P11206,A-12,R²-11,R³-20), (I-P11207,A-12,R²-11,R³-21), (I-P11208,A-12,R²-11,R³-22), (I-P11209,A-12,R²-11,R³-23), (I-P11210,A-12,R²-11,R³-24), (I-P11211,A-12,R²-11,R³-25), (I-P11212,A-12,R²-11,R³-26), (I-P11213,A-12,R²-11,R³-27), (I-P11214,A-12,R²-11,R³-28), (I-P11215,A-12,R²-11,R³-29), (I-P11216,A-12,R²-11,R³-30), (I-P11217,A-12,R²-11,R³-31), (I-P11218,A-12,R²-11,R³-32), (I-P11219,A-12,R²-11,R³-33), (I-P11220,A-12,R²-11,R³-34), (I-P11221,A-12,R²-12,R³-1), (I-P11222,A-12,R²-12,R³-2), (I-P11223,A-12,R²-12,R³-3), (I-P11224,A-12,R²-12,R³-4), (I-P11225,A-12,R²-12,R³-5), (I-P11226,A-12,R²-12,R³-6), (I-P11227,A-12,R²-12,R³-7), (I-P11228,A-12,R²-12,R³-8), (I-P11229,A-12,R²-12,R³-9), (I-P11230,A-12,R²-12,R³-10), (I-P11231,A-12,R²-12,R³-11), (I-P11232,A-12,R²-12,R³-12), (I-P11233,A-12,R²-12,R³-13), (I-P11234,A-12,R²-12,R³-14), (I-P11235,A-12,R²-12,R³-15), (I-P11236,A-12,R²-12,R³-16), (I-P11237,A-12,R²-12,R³-17), (I-P11238,A-12,R²-12,R³-18), (I-P11239,A-12,R²-12,R³-19), (I-P11240,A-12,R²-12,R³-20), (I-P11241,A-12,R²-12,R³-21), (I-P11242,A-12,R²-12,R³-22), (I-P11243,A-12,R²-12,R³-23), (I-P11244,A-12,R²-12,R³-24), (I-P11245,A-12,R²-12,R³-25), (I-P11246,A-12,R²-12,R³-26), (I-P11247,A-12,R²-12,R³-27), (I-P11248,A-12,R²-12,R³-28), (I-P11249,A-12,R²-12,R³-29), (I-P11250,A-12,R²-12,R³-30), (I-P11251,A-12,R²-12,R³-31), (I-P11252,A-12,R²-12,R³-32), (I-P11253,A-12,R²-12,R³-33), (I-P11254,A-12,R²-12,R³-34), (I-P11255,A-12,R²-13,R³-1), (I-P11256,A-12,R²-13,R³-2), (I-P11257,A-12,R²-13,R³-3), (I-P11258,A-12,R²-13,R³-4), (I-P11259,A-12,R²-13,R³-5), (I-P11260,A-12,R²-13,R³-6), (I-P11261,A-12,R²-13,R³-7), (I-P11262,A-12,R²-13,R³-8), (I-P11263,A-12,R²-13,R³-9), (I-P11264,A-12,R²-13,R³-10), (I-P11265,A-12,R²-13,R³-11), (I-P11266,A-12,R²-13,R³-12), (I-P11267,A-12,R²-13,R³-13), (I-P11268,A-12,R²-13,R³-14), (I-P11269,A-12,R²-13,R³-15), (I-P11270,A-12,R²-13,R³-16), (I-P11271,A-12,R²-13,R³-17), (I-P11272,A-12,R²-13,R³-18), (I-P11273,A-12,R²-13,R³-19), (I-P11274,A-12,R²-13,R³-20), (I-P11275,A-12,R²-13,R³-21), (I-P11276,A-12,R²-13,R³-22), (I-P11277,A-12,R²-13,R³-23), (I-P11278,A-12,R²-13,R³-24), (I-P11279,A-12,R²-13,R³-25), (I-P11280,A-12,R²-13,R³-26), (I-P11281,A-12,R²-13,R³-27), (I-P11282,

A-12,R²-13,R³-28), (I-P11283,A-12,R²-13,R³-29), (I-P11284,A-12,R²-13,R³-30), (I-P11285,A-12,R²-13,R³-31), (I-P11286,A-12,R²-13,R³-32), (I-P11287,A-12,R²-13,R³-33), (I-P11288,A-12,R²-13,R³-34), (I-P11289,A-12,R²-14,R³-1), (I-P11290,A-12,R²-14,R³-2), (I-P11291,A-12,R²-14,R³-3), (I-P11292,A-12,R²-14,R³-4), (I-P11293,A-12,R²-14,R³-5), (I-P11294,A-12,R²-14,R³-6), (I-P11295,A-12,R²-14,R³-7), (I-P11296,A-12,R²-14,R³-8), (I-P11297,A-12,R²-14,R³-9), (I-P11298,A-12,R²-14,R³-10), (I-P11299,A-12,R²-14,R³-11), (I-P11300,A-12,R²-14,R³-12), (I-P11301,A-12,R²-14,R³-13), (I-P11302,A-12,R²-14,R³-14), (I-P11303,A-12,R²-14,R³-15), (I-P11304,A-12,R²-14,R³-16), (I-P11305,A-12,R²-14,R³-17), (I-P11306,A-12,R²-14,R³-18), (I-P11307,A-12,R²-14,R³-19), (I-P11308,A-12,R²-14,R³-20), (I-P11309,A-12,R²-14,R³-21), (I-P11310,A-12,R²-14,R³-22), (I-P11311,A-12,R²-14,R³-23), (I-P11312,A-12,R²-14,R³-24), (I-P11313,A-12,R²-14,R³-25), (I-P11314,A-12,R²-14,R³-26), (I-P11315,A-12,R²-14,R³-27), (I-P11316,A-12,R²-14,R³-28), (I-P11317,A-12,R²-14,R³-29), (I-P11318,A-12,R²-14,R³-30), (I-P11319,A-12,R²-14,R³-31), (I-P11320,A-12,R²-14,R³-32), (I-P11321,A-12,R²-14,R³-33), (I-P11322,A-12,R²-14,R³-34), (I-P11323,A-12,R²-15,R³-1), (I-P11324,A-12,R²-15,R³-2), (I-P11325,A-12,R²-15,R³-3), (I-P11326,A-12,R²-15,R³-4), (I-P11327,A-12,R²-15,R³-5), (I-P11328,A-12,R²-15,R³-6), (I-P11329,A-12,R²-15,R³-7), (I-P11330,A-12,R²-15,R³-8), (I-P11331,A-12,R²-15,R³-9), (I-P11332,A-12,R²-15,R³-10), (I-P11333,A-12,R²-15,R³-11), (I-P11334,A-12,R²-15,R³-12), (I-P11335,A-12,R²-15,R³-13), (I-P11336,A-12,R²-15,R³-14), (I-P11337,A-12,R²-15,R³-15), (I-P11338,A-12,R²-15,R³-16), (I-P11339,A-12,R²-15,R³-17), (I-P11340,A-12,R²-15,R³-18), (I-P11341,A-12,R²-15,R³-19), (I-P11342,A-12,R²-15,R³-20), (I-P11343,A-12,R²-15,R³-21), (I-P11344,A-12,R²-15,R³-22), (I-P11345,A-12,R²-15,R³-23), (I-P11346,A-12,R²-15,R³-24), (I-P11347,A-12,R²-15,R³-25), (I-P11348,A-12,R²-15,R³-26), (I-P11349,A-12,R²-15,R³-27), (I-P11350,A-12,R²-15,R³-28), (I-P11351,A-12,R²-15,R³-29), (I-P11352,A-12,R²-15,R³-30), (I-P11353,A-12,R²-15,R³-31), (I-P11354,A-12,R²-15,R³-32), (I-P11355,A-12,R²-15,R³-33), (I-P11356,A-12,R²-15,R³-34), (I-P11357,A-12,R²-16,R³-1), (I-P11358,A-12,R²-16,R³-2), (I-P11359,A-12,R²-16,R³-3), (I-P11360,A-12,R²-16,R³-4), (I-P11361,A-12,R²-16,R³-5), (I-P11362,A-12,R²-16,R³-6), (I-P11363,A-12,R²-16,R³-7), (I-P11364,A-12,R²-16,R³-8), (I-P11365,A-12,R²-16,R³-9), (I-P11366,A-12,R²-16,R³-10), (I-P11367,A-12,R²-16,R³-11), (I-P11368,A-12,R²-16,R³-12), (I-P11369,A-12,R²-16,R³-13), (I-P11370,A-12,R²-16,R³-14), (I-P11371,A-12,R²-16,R³-15), (I-P11372,A-12,R²-16,R³-16), (I-P11373,A-12,R²-16,R³-17), (I-P11374,A-12,R²-16,R³-18), (I-P11375,A-12,R²-16,R³-19), (I-P11376,A-12,R²-16,R³-20), (I-P11377,A-12,R²-16,R³-21), (I-P11378,A-12,R²-16,R³-22), (I-P11379,A-12,R²-16,R³-23), (I-P11380,A-12,R²-16,R³-24), (I-P11381,A-12,R²-16,R³-25), (I-P11382,A-12,R²-16,R³-26), (I-P11383,A-12,R²-16,R³-27), (I-P11384,A-12,R²-16,R³-28), (I-P11385,A-12,R²-16,R³-29), (I-P11386,A-12,R²-16,R³-30), (I-P11387,A-12,R²-16,R³-31), (I-P11388,A-12,R²-16,R³-32), (I-P11389,A-12,R²-16,R³-33), (I-P11390,A-12,R²-16,R³-34), (I-P11391,A-12,R²-17,R³-1), (I-P11392,A-12,R²-17,R³-2), (I-P11393,A-12,R²-17,R³-3), (I-P11394,A-12,R²-17,R³-4), (I-P11395,A-12,R²-17,R³-5), (I-P11396,A-12,R²-17,R³-6), (I-P11397,A-12,R²-17,R³-7), (I-P11398,A-12,R²-17,R³-8), (I-P11399,A-12,R²-17,R³-9), (I-P11400,A-12,R²-17,R³-10), (I-P11401,A-12,R²-17,R³-11), (I-P11402,A-12,R²-17,R³-12), (I-P11403,A-12,R²-17,R³-13), (I-P11404,A-12,R²-17,R³-14), (I-P11405,A-12,R²-17,R³-15), (I-P11406,A-12,R²-17,R³-16), (I-P11407,A-12,R²-17,R³-17), (I-P11408,A-12,R²-17,R³-18), (I-P11409,A-12,R²-17,R³-19), (I-P11410,A-12,R²-17,R³-20), (I-P11411,A-12,R²-17,R³-21), (I-P11412,A-12,R²-17,R³-22), (I-P11413,A-12,R²-17,R³-23), (I-P11414,A-12,R²-17,R³-24), (I-P11415,A-12,R²-17,R³-25), (I-P11416,A-12,R²-17,R³-26), (I-P11417,A-12,R²-17,R³-27), (I-P11418,A-12,R²-17,R³-28), (I-P11419,A-12,R²-17,R³-29), (I-P11420,A-12,R²-17,R³-30), (I-P11421,A-12,R²-17,R³-31), (I-P11422,A-12,R²-17,R³-32), (I-P11423,A-12,R²-17,R³-33), (I-P11424,A-12,R²-17,R³-34), (I-P11425,A-12,R²-18,R³-1), (I-P11426,A-12,R²-18,R³-2), (I-P11427,A-12,R²-18,R³-3), (I-P11428,A-12,R²-18,R³-4), (I-P11429,A-12,R²-18,R³-5), (I-P11430,A-12,R²-18,R³-6), (I-P11431,A-12,R²-18,R³-7), (I-P11432,A-12,R²-18,R³-8), (I-P11433,A-12,R²-18,R³-9), (I-P11434,A-12,R²-18,R³-10), (I-P11435,A-12,R²-18,R³-11), (I-P11436,A-12,R²-18,R³-12), (I-P11437,A-12,R²-18,R³-13), (I-P11438,A-12,R²-18,R³-14), (I-P11439,A-12,R²-18,R³-15), (I-P11440,A-12,R²-18,R³-16), (I-P11441,A-12,R²-18,R³-17), (I-P11442,A-12,R²-18,R³-18), (I-P11443,A-12,R²-18,R³-19), (I-P11444,A-12,R²-18,R³-20), (I-P11445,A-12,R²-18,R³-21), (I-P11446,A-12,R²-18,R³-22), (I-P11447,A-12,R²-18,R³-23), (I-P11448,A-12,R²-18,R³-24), (I-P11449,A-12,R²-18,R³-25), (I-P11450,A-12,R²-18,R³-26), (I-P11451,A-12,R²-18,R³-27), (I-P11452,A-12,R²-18,R³-28), (I-P11453,A-12,R²-18,R³-29), (I-P11454,A-12,R²-18,R³-30), (I-P11455,A-12,R²-18,R³-31), (I-P11456,A-12,R²-18,R³-32), (I-P11457,A-12,R²-18,R³-33), (I-P11458,A-12,R²-18,R³-34), (I-P11459,A-12,R²-19,R³-1), (I-P11460,A-12,R²-19,R³-2), (I-P11461,A-12,R²-19,R³-3), (I-P11462,A-12,R²-19,R³-4), (I-P11463,A-12,R²-19,R³-5), (I-P11464,A-12,R²-19,R³-6), (I-P11465,A-12,R²-19,R³-7), (I-P11466,A-12,R²-19,R³-8), (I-P11467,A-12,R²-19,R³-9), (I-P11468,A-12,R²-19,R³-10), (I-P11469,A-12,R²-19,R³-11), (I-P11470,A-12,R²-19,R³-12), (I-P11471,A-12,R²-19,R³-13), (I-P11472,A-12,R²-19,R³-14), (I-P11473,A-12,R²-19,R³-15), (I-P11474,A-12,R²-19,R³-16), (I-P11475,A-12,R²-19,R³-17), (I-P11476,A-12,R²-19,R³-18), (I-P11477,A-12,R²-19,R³-19), (I-P11478,A-12,R²-19,R³-20), (I-P11479,A-12,R²-19,R³-21), (I-P11480,A-12,R²-19,R³-22), (I-P11481,A-12,R²-19,R³-23), (I-P11482,A-12,R²-19,R³-24), (I-P11483,A-12,R²-19,R³-25), (I-P11484,A-12,R²-19,R³-26), (I-P11485,A-12,R²-19,R³-27), (I-P11486,A-12,R²-19,R³-28), (I-P11487,A-12,R²-19,R³-29), (I-P11488,A-12,R²-19,R³-30), (I-P11489,A-12,R²-19,R³-31), (I-P11490,A-12,R²-19,R³-32), (I-P11491,A-12,R²-19,R³-33), (I-P11492,A-12,R²-20,R³-34), (I-P11493,A-12,R²-20,R³-1), (I-P11494,A-12,R²-20,R³-2), (I-P11495,A-12,R²-20,R³-3), (I-P11496,A-12,R²-20,R³-4), (I-P11497,A-12,R²-20,R³-5), (I-P11498,A-12,R²-20,R³-6), (I-P11499,A-12,R²-20,R³-7), (I-P11500,A-12,R²-20,R³-8), (I-P11501,A-12,R²-20,R³-9), (I-P11502,A-12,R²-20,R³-10), (I-P11503,A-12,R²-20,R³-11), (I-P11504,A-12,R²-20,R³-12), (I-P11505,A-12,R²-20,R³-13), (I-P11506,A-12,R²-20,R³-14), (I-P11507,A-12,R²-20,R³-15), (I-P11508,A-12,R²-20,R³-16), (I-P11509,A-12,R²-20,R³-17), (I-P11510,A-12,R²-20,R³-18), (I-P11511,A-12,R²-20,R³-19), (I-P11512,A-12,R²-20,R³-20), (I-P11513,A-12,R²-20,R³-21), (I-P11514,A-12,R²-20,R³-22), (I-P11515,A-12,R²-20,R³-23), (I-P11516,A-12,R²-20,R³-24), (I-P11517,A-12,R²-20,R³-25), (I-P11518,A-12,R²-20,R³-26), (I-P11519,A-12,R²-20,R³-27), (I-P11520,A-12,R²-20,R³-28), (I-P11521,A-12,R²-20,R³-29), (I-P11522,A-12,R²-20,R³-30), (I-P11523,A-12,R²-20,R³-31), (I-P11521,A-12,R²-20,R³-32), (I-P11525,A-12,R²-20,R³-33), (I-P11526,A-12,R²-20,R³-34), (I-P11527,A-12,R²-21,R³-1), I-P11528,A-12,R²-21,R³-2), (I-P11529,A-12,R²-21,R³-3), (I-P11530,A-12,R²-21,R³-4), (I-P11531,A-12,R²-21,R³-5), (I-P11532,A-12,R²-21,R³-6), (I-P11533,A-12,R²-21,R³-7), I-P11534,A-12,R²-21,R³-8), (I-P11535,A-12,

R²-21,R³-9), (I-P11536, A-12,R²-21,R³-10), (I-P11537,A-12,R²-21,R³-11), (I-P11538,A-12,R²-21,R³-12), (I-P11539, A-12,R²-21,R³-13), (I-P11540,A-12,R²-21,R³-14), (I-P11541,A-12,R²-21,R³-15), (I-P11542, A-12,R²-21,R³-16), (I-P11543,A-12,R²-21,R³-17), (I-P11544,A-12,R²-21, R³-18), (I-P11545, A-12,R²-21,R³-19), (I-P11546,A-12,R²-21,R³-20), (I-P11547,A-12,R²-21,R³-21), (I-P11548, A-12, R²-21,R³-22), (I-P11549,A-12,R²-21,R³-23), (I-P11550,A-12,R²-21,R³-24), (I-P11551, A-12,R²-21,R³-25), (I-P11552, A-12,R²-21,R³-26), (I-P11553,A-12,R²-21,R³-27), (I-P11554, A-12,R²-21,R³-28), (I-P11555,A-12,R²-21,R³-29), (I-P11556,A-12,R²-21,R³-30), (I-P11557, A-12,R²-21, R³-31), (I-P11558,A-12,R²-21,R³-32), (I-P11559,A-12,R²-21,R³-33), (I-P11560, A-12,R²-21,R³-34), (I-P11561,A-12, R²-22,R³-1), (I-P11562,A-12,R²-22,R³-2), (I-P11563, A-12, R²-22,R³-3), (I-P11564,A-12,R²-22,R³-4), (I-P11565,A-12, R²-22,R³-5), (I-P11566, A-12,R²-22,R³-6), (I-P11567,A-12, R²-22,R³-7), (I-P11568,A-12,R²-22,R³-8), (I-P11569, A-12, R²-22,R³-9), (I-P11570,A-12,R²-22,R³-10), (I-P11571,A-12,R²-22,R³-11), (I-P11572, A-12,R²-22,R³-12), (I-P11573, A-12,R²-22,R³-13), (I-P11574,A-12,R²-22,R³-14), (I-P11575, A-12, R²-22,R³-15), (I-P11576,A-12,R²-22,R³-16), (I-P11577,A-12,R²-22,R³-17), (I-P11578, A-12,R²-22, R³-18), (I-P11579,A-12,R²-22,R³-19), (I-P11580,A-12,R²-22,R³-20), (I-P11581, A-12,R²-22,R³-21), (I-P11582,A-12, R²-22,R³-22), (I-P11583,A-12,R²-22,R³-23), (I-P11584, A-12,R²-22,R³-24), (I-P11585,A-12,R²-22,R³-25), (I-P11586,A-12,R²-22,R³-26), (I-P11587, A-12,R²-22,R³-27), (I-P11588,A-12,R²-22,R³-28), (I-P11589,A-12,R²-22, R³-29), (I-P11590, A-12,R²-22,R³-30), (I-P11591,A-12,R²-22,R³-31), (I-P11592,A-12,R²-22,R³-32), (I-P11593, A-12, R²-22,R³-33), (I-P11594,A-12,R²-22,R³-34), (I-P11595,A-12,R²-23,R³-1), (I-P11596, A-12,R²-23,R³-2), (I-P11597,A-12,R²-23,R³-3), (I-P11598,A-12,R²-23,R³-4), (I-P11599, A-12,R²-23,R³-5), (I-P11600,A-12,R²-23,R³-6), (I-P11601, A-12,R²-23,R³-7), (I-P11602,A-12,R²-23,R³-8), (I-P11603, A-12,R²-23,R³-9), (I-P11604,A-12,R²-23,R³-10), (I-P11605, A-12,R²-23,R³-11), (I-P11606,A-12,R²-23,R³-12), (I-P11607,A-12,R²-23,R³-13), (I-P11608, A-12,R²-23, R³-14), (I-P11609,A-12,R²-23,R³-15), (I-P11610,A-12,R²-23,R³-16), (I-P11611, A-12,R²-23,R³-17), (I-P11612,A-12, R²-23,R³-18), (I-P11613,A-12,R²-23,R³-19), (I-P11614, A-12,R²-23,R³-20), (I-P11615,A-12,R²-23,R³-21), (I-P11616,A-12,R²-23,R³-22), (I-P11617, A-12,R²-23,R³-23), (I-P11618,A-12,R²-23,R³-24), (I-P11619,A-12,R²-23, R³-25), (I-P11620, A-12,R²-23,R³-26), (I-P11621,A-12,R²-23,R³-27), (I-P11622,A-12,R²-23,R³-28), (I-P11623, A-12, R²-23,R³-29), (I-P11624,A-12,R²-23,R³-30), (I-P11625,A-12,R²-23,R³-31), (I-P11626, A-12,R²-23,R³-32), (I-P11627, A-12,R²-23,R³-33), (I-P11628,A-12,R²-23,R³-34), (I-P11629, A-12,R²-24,R³-1), (I-P11630,A-12,R²-24,R³-2), (I-P11631,A-12,R²-24,R³-3), (I-P11632, A-12,R²-24,R³-4), (I-P11635,A-12,R²-24,R³-5), (I-P11634,A-12,R²-24,R³-6), (I-P11626, A-12,R²-24,R³-7), (I-P11638,A-12,R²-24,R³-8), (I-P11637,A-12,R²-24,R³-9), (I-P11626, A-12,R²-24,R³-10), (I-P11639,A-12,R²-24,R³-11), (I-P11640,A-12,R²-24, R³-12), (I-P11641, A-12,R²-24,R³-13), (I-P11624,A-12,R²-24,R³-14), (I-P11643,A-12,R²-24,R³-15), (I-P11644, A-12, R²-23,R³-16), (I-P11645,A-12,R²-24,R³-17), (I-P11656,A-12,R²-24,R³-18), (I-P11647,A-12,R²-24,R³-19), (I-P11648, A-12,R²-24,R³-20), (I-P11649,A-12,R²-24,R³-21), (I-P11650, A-12,R²-24,R³-22), (I-P11651,A-12,R²-24,R³-23), (I-P11652,A-12,R²-24,R³-24), (I-P11653, A-12,R²-24, R³-25), (I-P11654,A-12,R²-24,R³-26), (I-P11655,A-12,R²-24,R³-27), (I-P11656, A-12,R²-24,R³-28), (I-P11657,A-12, R²-24,R³-29), (I-P11658,A-12,R²-24,R³-30), (I-P11569, A-12,R²-24,R³-31), (I-P11660,A-12,R²-24,R³-32), (I-P11661,A-12,R²-24,R³-33), (I-P11662, A-12,R²-24,R³-34), (I-P11663,A-12,R²-25,R³-1), (I-P11664,A-12,R²-25, R³-2), (I-P11665, A-12,R²-25,R³-3), (I-P11666,A-12,R²-25, R³-4), (I-P11667,A-12,R²-25,R³-5), (I-P11668, A-12,R²-25, R³-6), (I-P11669,A-12,R²-25,R³-7), (I-P11670,A-12,R²-25, R³-8), (I-P11671, A-12,R²-25,R³-9), (I-P11672,A-12,R²-25, R³-10), (I-P11673,A-12,R²-25,R³-11), (I-P11674, A-12,R²-25,R³-12), (I-P11675,A-12,R²-25,R³-13), (I-P11676,A-12, R²-25,R³-14), (I-P11677, A-12,R²-25,R³-15), (I-P11678,A-12,R²-25,R³-16), (I-P11679,A-12,R²-25,R³-17), (I-P11680, A-12,R²-25,R³-18), (I-P11681,A-12,R²-25,R³-19), (I-P11682,A-12,R²-25,R³-20), (I-P11683, A-12,R²-25,R³-21), (I-P11684,A-12,R²-25,R³-22), (I-P11685,A-12,R²-25, R³-23), (I-P11686, A-12,R²-25,R³-24), (I-P11687,A-12,R²-25,R³-25), (I-P11688,A-12,R²-25,R³-26), (I-P11689, A-12, R²-25,R³-32), (I-P11690,A-12,R²-25,R³-28), (I-P11691,A-12,R²-25,R³-29), (I-P11692, A-12,R²-25,R³-32), (I-P11693, A-12,R²-25,R³-31), (I-P11694,A-12,R²-25,R³-32), (I-P11695, A-12,R²-25,R³-32), (I-P11696,A-12,R²-25,R³-34), (I-P11697,A-12,R²-26,R³-1), (I-P11698, A-12,R²-26, R³-32), (I-P11699,A-12,R²-26,R³-3), (I-P11700,A-12,R²-26,R³-4), (I-P11701, A-12,R²-26,R³-32), (I-P11702,A-12, R²-26,R³-6), (I-P11703,A-12,R²-26,R³-7), (I-P11704, A-12, R²-26,R³-8), (I-P11705, A-12,R²-26,R³-9), (I-P11706,A-12, R²-26,R³-10), (I-P11707, A-12,R²-26,R³-11), (I-P11708,A-12,R²-26,R³-12), (I-P11709,A-12,R²-26,R³-13), (I-P11710, A-12,R²-26,R³-14), (I-P11711,A-12,R²-26,R³-15), (I-P11712,A-12,R²-26,R³-16), (I-P11713, A-12,R²-26,R³-17), (I-P11714,A-12,R²-26,R³-18), (I-P11715,A-12,R²-26, R³-19), (I-P11716, A-12,R²-26,R³-20), (I-P11717,A-12,R²-26,R³-21), (I-P11718,A-12,R²-26,R³-22), (I-P11719, A-12, R²-26,R³-23), (I-P11720,A-12,R²-26,R³-24), (I-P11721,A-12,R²-26,R³-25), (I-P11722, A-12,R²-26,R³-26), (I-P11723, A-12,R²-26,R³-27), (I-P11724,A-12,R²-26,R³-28), (I-P11725, A-12,R²-26,R³-29), (I-P11726,A-12,R²-26,R³-30), (I-P11727,A-12,R²-26,R³-31), (I-P11728, A-12,R²-26, R³-32), (I-P11729,A-12,R²-26,R³-33), (I-P11730,A-12,R²-26,R³-34), (I-P11731, A-12,R²-27,R³-1), (I-P11732,A-12, R²-27,R³-2), (I-P11733,A-12,R²-27,R³-3), (I-P11734, A-12, R²-27,R³-4), (I-P11735,A-12,R²-27,R³-5), (I-P11736,A-12, R²-27,R³-6), (I-P11737,A-12,R²-27,R³-7), (I-P11738,A-12, R²-27,R³-8), (I-P11739,A-12,R²-27,R³-9), (I-P11740, A-12, R²-27,R³-10), (I-P11741,A-12,R²-27,R³-11), (I-P11742,A-12,R²-27,R³-12), (I-P11743, A-12,R²-27,R³-13), (I-P11744, A-12,R²-27,R³-14), (I-P11745,A-12,R²-27,R³-15), (I-P11746, A-12, R²-27,R³-16), (I-P11747,A-12,R²-27,R³-17), (I-P11748,A-12,R²-27,R³-18), (I-P11749, A-12,R²-27, R³-19), (I-P11750,A-12,R²-27,R³-20), (I-P11751,A-12,R²-27,R³-21), (I-P11752, A-12,R²-27,R³-22), (I-P11753,A-12, R²-27,R³-23), (I-P11754,A-12,R²-27,R³-24), (I-P11755, A-12,R²-27,R³-25), (I-P11756,A-12,R²-27,R³-26), (I-P11757,A-12,R²-27,R³-27), (I-P11758, A-12,R²-27,R³-28), (I-P11759,A-12,R²-27,R³-29), (I-P11760,A-12,R²-27, R³-30), (I-P11761, A-12,R²-27,R³-31), (I-P11762,A-12,R²-27,R³-32), (I-P11763,A-12,R²-27,R³-33), (I-P11764, A-12, R²-27,R³-34), (I-P11765,A-12,R²-28,R³-1), (I-P11766,A-12,R²-28,R³-2), (I-P11767,A-12,R²-28,R³-3), (I-P11768,A-12,R²-28,R³-4), (I-P11769,A-12,R²-28,R³-5), (I-P11770, A-12,R²-28,R³-6), (I-P11771,A-12,R²-28,R³-7), (I-P11772, A-12,R²-28,R³-8), (I-P11773, A-12,R²-28,R³-9), (I-P11774, A-12,R²-28,R³-10), (I-P11775,A-12,R²-28,R³-12), (I-P11776, A-12, R²-28,R³-12), (I-P11777,A-12,R²-28,R³-13), (I-P11778,A-12,R²-28,R³-15), (I-P11779, A-12,R²-28, R³-15), (I-P11780,A-12,R²-28,R³-16), (I-P11781,A-12,R²-28,R³-18), (I-P11782,A-12,R²-28,R³-18), (I-P11783,A-12, R²-28,R³-19), (I-P11784,A-12,R²-28,R³-21), (I-P11785, A-12,R²-28,R³-21), (I-P11786,A-12,R²-28,R³-22), (I-P11787,A-12,R²-28,R³-24), (I-P11788, A-12,R²-28,R³-24), (I-P11789,A-12,R²-28,R³-25), (I-P11790,A-12,R²-28,R³-26), (I-P11791, A-12,R²-28,R³-27), (I-P11792,A-12,R²-28,R³-28), (I-P11793,A-12,R²-28,R³-29), (I-P11794, A-12,R²-28,R³-30), (I-P11795,A-12,R²-28,R³-31), (I-P11796,A-12,R²-28,R³-32), (I-P11797, A-12,R²-28,R³-33), (I-P11798, A-12,R²-28,R³-34), (I-P11799,A-12,R²-29,R³-1), (I-P11800, A-12,R²-29,R³-2), (I-P11801,A-12,R²-29,R³-3), (I-P11802,A-12,R²-29,R³-4), (I-P11803, A-12,R²-29,R³-5), (I-P11804,A-12,R²-29,R³-6), (I-P11805,A-12,R²-29,R³-7), (I-P11806, A-12,R²-29,R³-8), (I-P11807,A-12,R²-29,R³-9), (I-P11808,A-12,R²-29,R³-10), (I-P11809, A-12,R²-29,R³-11), (I-P11810,A-12,R²-29,R³-12), (I-P11811,A-12,R²-29,R³-13), (I-P11812, A-12,R²-29,R³-14), (I-P11813,A-12,R²-29,R³-15), (I-P11815,A-12,R²-29,R³-16), (I-P11815, A-12,R²-29,R³-17), (I-P11816,A-12,R²-29,R³-18), (I-P11818,A-12,R²-29,R³-19), (I-P11815, A-12,R²-29,R³-20), (I-P11819, A-12,R²-29,R³-21), (I-P11820,A-12,R²-29,R³-22), (I-P11821, A-12,R²-29,R³-23), (I-P11822,A-12,R²-29,R³-24), (I-P11823,A-12,R²-29,R³-25), (I-P11824, A-12,R²-29,R³-26), (I-P11825,A-12,R²-29,R³-27), (I-P11826,A-12,R²-29,R³-28), (I-P11827, A-12,R²-29,R³-29), (I-P11828,A-12,R²-29,R³-30), (I-P11829,A-12,R²-29,R³-31), (I-P11830, A-12,R²-29,R³-32), (I-P11831,A-12,R²-29,R³-33), (I-P11832,A-12,R²-29,R³-34), (I-P11833, A-13,R²-1,R³-1), (I-P11834,A-13,R²-1,R³-2), (I-P11835,A-13,R²-1,R³-3), (I-P11836, A-13,R²-1,R³-4), (I-P11837,A-13,R²-1,R³-5), (I-P11838,A-13,R²-1,R³-6), (I-P11839, A-13,R²-1,R³-7), (I-P11840,A-13,R²-1,R³-8), (I-P11841,A-13,R²-1,R³-9), (I-P11842, A-13,R²-1,R³-10), (I-P11843,A-13,R²-1,R³-11), (I-P11844,A-13,R²-1,R³-12), (I-P11845, A-13,R²-1,R³-13), (I-P11846,A-13,R²-1,R³-14), (I-P11847,A-13,R²-1,R³-15), (I-P11848, A-13,R²-1,R³-16), (I-P11849,A-13,R²-1,R³-17), (I-P11850,A-13,R²-1,R³-18), (I-P11851, A-13,R²-1,R³-19), (I-P11852,A-13,R²-1,R³-20), (I-P11853,A-13,R²-1,R³-21), (I-P11854, A-13,R²-1,R³-22), (I-P11855,A-13,R²-1,R³-23), (I-P11856,A-13,R²-1,R³-24), (I-P11857, A-13,R²-1,R³-25), (I-P11858,A-13,R²-1,R³-26), (I-P11859,A-13,R²-1,R³-27), (I-P11860, A-13,R²-1,R³-28), (I-P11861,A-13,R²-1,R³-29), (I-P11862,A-13,R²-1,R³-30), (I-P11863, A-13,R²-1,R³-31), (I-P11864,A-13,R²-1,R³-32), (I-P11865,A-13,R²-1,R³-33), (I-P11866, A-13,R²-1,R³-34), (I-P11867,A-13,R²-2,R³-1), (I-P11868,A-13,R²-2,R³-2), (I-P11869, A-13,R²-1,R³-3), (I-P11870,A-13,R²-2,R³-4), (I-P11871,A-13,R²-2,R³-5), (I-P11872, A-13,R²-2,R³-6), (I-P11873,A-13,R²-2,R³-7), (I-P11874,A-13,R²-2,R³-8), (I-P11875, A-13,R²-2,R³-9), (I-P11876,A-13,R²-2,R³-10), (I-P11877,A-13,R²-2,R³-11), (I-P11878, A-13,R²-2,R³-12), (I-P11879,A-13,R²-2,R³-13), (I-P11880,A-13,R²-2,R³-14), (I-P11881, A-13,R²-2,R³-15), (I-P11882,A-13,R²-2,R³-16), (I-P11883,A-13,R²-2,R³-17), (I-P11884, A-13,R²-2,R³-18), (I-P11885,A-13,R²-2,R³-19), (I-P11886,A-13,R²-2,R³-20), (I-P11887, A-13,R²-2,R³-21), (I-P11888,A-13,R²-2,R³-22), (I-P11889,A-13,R²-2,R³-23), (I-P11890, A-13,R²-2,R³-24), (I-P11891,A-13,R²-2,R³-25), (I-P11892,A-13,R²-2,R³-26), (I-P11893, A-13,R²-2,R³-27), (I-P11894,A-13,R²-2,R³-28), (I-P11895,A-13,R²-2,R³-29), (I-P11896, A-13,R²-2,R³-30), (I-P11897,A-13,R²-2,R³-31), (I-P11898,A-13,R²-2,R³-32), (I-P11899, A-13,R²-2,R³-33), (I-P11900, A-13,R²-2,R³-34), (I-P11901,A-13,R²-3,R³-1), (I-P11902, A-13,R²-3,R³-2), (I-P11903,A-13,R²-3,R³-3), (I-P11904,A-13,R²-3,R³-4), (I-P11905, A-13,R²-3,R³-5), (I-P11906,A-13,R²-3,R³-6), (I-P11907,A-13,R²-3,R³-7), (I-P11908, A-13,R²-3,R³-8), (I-P11909,A-13,R²-3,R³-9), (I-P11910,A-13,R²-3,R³-10), (I-P11911, A-13,R²-3,R³-11), (I-P11912,A-13,R²-3,R³-12), (I-P11913,A-13,R²-3,R³-13), (I-P11914, A-13,R²-3,R³-14), (I-P11915,A-13,R²-3,R³-15), (I-P11916,A-13,R²-3,R³-16), (I-P11917, A-13,R²-3,R³-17), (I-P11918,A-13,R²-3,R³-18), (I-P11919,A-13,R²-3,R³-19), (I-P11920, A-13,R²-3,R³-20), (I-P11921,A-13,R²-3,R³-21), (I-P11922,A-13,R²-3,R³-22), (I-P11923, A-13,R²-3,R³-4), (I-P11924,A-13,R²-3,R³-24), (I-P11925,A-13,R²-3,R³-25), (I-P11926, A-13,R²-3,R³-4), (I-P11927,A-13,R²-3,R³-27), (I-P11928,A-13,R²-3,R³-28), (I-P11929, A-13,R²-3,R³-4), (I-P11930,A-13,R²-3,R³-30), (I-P11931,A-13,R²-3,R³-31), (I-P11932, A-13,R²-3,R³-4), (I-P11933,A-13,R²-3,R³-33), (I-P11934,A-13,R²-3,R³-34), (I-P11935, A-13,R²-4,R³-4), (I-P11936,A-13,R²-4,R³-2), (I-P11937,A-13,R²-4,R³-3), (I-P11938, A-13,R²-4,R³-4), (I-P11939,A-13,R²-4,R³-3), (I-P11940,A-13,R²-4,R³-6), (I-P11941, A-13,R²-4,R³-7), (I-P11942,A-13,R²-4,R³-8), (I-P11943,A-13,R²-4,R³-9), (I-P11944, A-13,R²-4,R³-10), (I-P11945,A-13,R²-4,R³-11), (I-P11946,A-13,R²-4,R³-12), (I-P11947, A-13,R²-4,R³-13), (I-P11948,A-13,R²-4,R³-14), (I-P11949,A-13,R²-4,R³-15), (I-P11950, A-13,R²-4,R³-16), (I-P11951,A-13,R²-4,R³-17), (I-P11952,A-13,R²-4,R³-18), (I-P11953, A-13,R²-4,R³-19), (I-P11954,A-13,R²-4,R³-20), (I-P11955,A-13,R²-4,R³-21), (I-P11956, A-13,R²-4,R³-22), (I-P11957,A-13,R²-4,R³-23), (I-P11958,A-13,R²-4,R³-24), (I-P11959, A-13,R²-4,R³-25), (I-P11960,A-13,R²-4,R³-26), (I-P11961,A-13,R²-4,R³-27), (I-P11962, A-13,R²-4,R³-28), (I-P11963,A-13,R²-4,R³-29), (I-P11964,A-13,R²-4,R³-30), (I-P11965, A-13,R²-4,R³-31), (I-P11966,A-13,R²-4,R³-32), (I-P11967,A-13,R²-4,R³-33), (I-P11968, A-13,R²-4,R³-34), (I-P11969,A-13,R²-5,R³-1), (I-P11970,A-13,R²-5,R³-2), (I-P11971, A-13,R²-5,R³-3), (I-P11972,A-13,R²-5,R³-4), (I-P11973,A-13,R²-5,R³-5), (I-P11974, A-13,R²-5,R³-6), (I-P11975,A-13,R²-5,R³-7), (I-P11976,A-13,R²-5,R³-8), (I-P11977, A-13,R²-5,R³-9), (I-P11978,A-13,R²-5,R³-10), (I-P11979,A-13,R²-5,R³-11), (I-P11980, A-13,R²-5,R³-12), (I-P11981,A-13,R²-5,R³-13), (I-P11982,A-13,R²-5,R³-14), (I-P11983, A-13,R²-5,R³-15), (I-P11984,A-13,R²-5,R³-16), (I-P11985,A-13,R²-5,R³-17), (I-P11986, A-13,R²-5,R³-18), (I-P11987,A-13,R²-5,R³-19), (I-P11988,A-13,R²-5,R³-20), (I-P11989, A-13,R²-5,R³-21), (I-P11990,A-13,R²-5,R³-22), (I-P11991,A-13,R²-5,R³-23), (I-P11992, A-13,R²-5,R³-24), (I-P11993,A-13,R²-5,R³-25), (I-P11994,A-13,R²-5,R³-26), (I-P11995, A-13,R²-5,R³-27), (I-P11996,A-13,R²-5,R³-28), (I-P11997,A-13,R²-5,R³-29), (I-P11998, A-13,R²-5,R³-30), (I-P11999,A-13,R²-5,R³-31), (I-P12000,A-13,R²-5,R³-32), (I-P12001, A-13,R²-5,R³-33), (I-P12002,A-13,R²-5,R³-34), (I-P12003,A-13,R²-6,R³-1), (I-P12004, A-13,R²-6,R³-2), (I-P12005,A-13,R²-6,R³-3), (I-P12006,A-13,R²-6,R³-4), (I-P12007, A-13,R²-6,R³-5), (I-P12008,A-13,R²-6,R³-6), (I-P12009,A-13,R²-6,R³-7), (I-P12010, A-13,R²-6,R³-8), (I-P12011,A-13,R²-6,R³-9), (I-P12012,A-13,R²-6,R³-10), (I-P12013,A-13,R²-6,R³-11), (I-P12014,A-13,R²-6,R³-12), (I-P12015,A-13,R²-6,R³-13), (I-P12016, A-13,R²-6,R³-14), (I-P12017,A-13,R²-6,R³-15), (I-P12018,A-13,R²-6,R³-16), (I-P12019, A-13,R²-6,R³-17), (I-P12020,A-13,R²-6,R³-18), (I-P12021, A-13,R²-6,R³-19), (I-P12022, A-13,R²-6,R³-20), (I-P12023,A-13,R²-6,R³-21), (I-P12024,A-13,R²-6,R³-22), (I-P12025, A-13,R²-6,R³-23), (I-P12026,A-13,R²-6,R³-24), (I-P12027,A-13,R²-6,R³-25), (I-P12028, A-13,R²-6,R³-26), (I-P12029,A-13,R²-6,R³-27), (I-P12030,A-13,R²-6,R³-28), (I-P12031, A-13,R²-6,R³-29), (I-P12032,A-13,R²-6,R³-30), (I-P12033,A-13,R²-6,R³-31), (I-P12034, A-13,R²-6,R³-32), (I-P12035,A-13,R²-6,R³-33), (I-P12036,A-13,R²-6,R³-34), (I-P12037, A-13,R²-7,R³-1), (I-P12038,A-13,R²-7,R³-2), (I-P12039,A-13,R²-7,R³-3), (I-P12040, A-13,R²-7,R³-4), (I-P12041,A-13,R²-7,R³-5), (I-P12042,A-13,R²-7,R³-6), (I-P12043, A-13,R²-7,R³-7), (I-P12044,A-13,R²-7,R³-8), (I-P12045,A-13,R²-7,R³-9), (I-P12046, A-13,R²-7,R³-10), (I-P12047,A-13,R²-7,R³-11), (I-P12048,A-13,R²-7,R³-12), (I-P12049,A-13,R²-7,R³-13), (I-P12050,A-13,R²-7,R³-14), (I-P12051,A-13,R²-7,R³-15), (I-P12052, A-13,$R^2$-7,$R^3$-16), (I-P12053,A-13,$R^2$-7,$R^3$-17), (I-P12054,A-13,$R^2$-7,$R^3$-18), (I-P12055, A-13,$R^2$-7,$R^3$-19), (I-P12056,A-13,$R^2$-7,$R^3$-20), (I-P12057,A-13,$R^2$-7,$R^3$-21), (I-P12058, A-13,$R^2$-7,$R^3$-22), (I-P12059,A-13,$R^2$-7,$R^3$-23), (I-P12060,A-13,$R^2$-7,$R^3$-24), (I-P12061, A-13,$R^2$-7,$R^3$-25), (I-P12062,A-13,$R^2$-7,$R^3$-26), (I-P12063,A-13,$R^2$-7,$R^3$-27), (I-P12064, A-13,$R^2$-7,$R^3$-28), (I-P12065,A-13,$R^2$-7,$R^3$-29), (I-P12066,A-13,$R^2$-7,$R^3$-30), (I-P12067, A-13,$R^2$-7,$R^3$-31), (I-P12068,A-13,$R^2$-7,$R^3$-32), (I-P12069,A-13,$R^2$-8,$R^3$-33), (I-P12070, A-13,$R^2$-7,$R^3$-34), (I-P12071,A-13,$R^2$-8,$R^3$-1), (I-P12072,A-13,$R^2$-8,$R^3$-2), (I-P12073, A-13,$R^2$-8,$R^3$-3), (I-P12074,A-13,$R^2$-8,$R^3$-4), (I-P12075,A-13,$R^2$-8,$R^3$-5), (I-P12076, A-13,$R^2$-8,$R^3$-6), (I-P12077,A-13,$R^2$-8,$R^3$-7), (I-P12078,A-13,$R^2$-8,$R^3$-8), (I-P12079, A-13,$R^2$-8,$R^3$-9), (I-P12080,A-13,$R^2$-8,$R^3$-10), (I-P12081,A-13,$R^2$-8,$R^3$-11), (I-P12082, A-13,$R^2$-8,$R^3$-12), (I-P12083,A-13,$R^2$-8,$R^3$-13), (I-P12084,A-13,$R^2$-8,$R^3$-14), (I-P12085, A-13,$R^2$-8,$R^3$-15), (I-P12086,A-13,$R^2$-8,$R^3$-16), (I-P12087,A-13,$R^2$-8,$R^3$-17), (I-P12088, A-13,$R^2$-8,$R^3$-18), (I-P12089,A-13,$R^2$-8,$R^3$-19), (I-P12090,A-13,$R^2$-8,$R^3$-20), (I-P12091, A-13,$R^2$-8,$R^3$-21), (I-P12092,A-13,$R^2$-8,$R^3$-22), (I-P12093,A-13,$R^2$-8,$R^3$-23), (I-P12094, A-13,$R^2$-8,$R^3$-24), (I-P12095,A-13,$R^2$-8,$R^3$-25), (I-P12096,A-13,$R^2$-8,$R^3$-26), (I-P12097, A-13,$R^2$-8,$R^3$-27), (I-P12098,A-13,$R^2$-8,$R^3$-28), (I-P12099,A-13,$R^2$-8,$R^3$-29), (I-P12100, A-13,$R^2$-8,$R^3$-30), (I-P12101,A-13,$R^2$-8,$R^3$-31), (I-P12102,A-13,$R^2$-8,$R^3$-32), (I-P12102, A-13,$R^2$-8,$R^3$-33), (I-P12104,A-13,$R^2$-8,$R^3$-34), (I-P12105,A-13,$R^2$-9,$R^3$-1), (I-P12106, A-13,$R^2$-9,$R^3$-2), (I-P12107,A-13,$R^2$-9,$R^3$-3), (I-P12108,A-13,$R^2$-9,$R^3$-4), (I-P12109, A-13,$R^2$-9,$R^3$-5), (I-P12110,A-13,$R^2$-9,$R^3$-6), (I-P12111,A-13,$R^2$-9,$R^3$-7), (I-P12112, A-13,$R^2$-9,$R^3$-8), (I-P12113,A-13,$R^2$-9,$R^3$-9), (I-P12114,A-13,$R^2$-9,$R^3$-10), (I-P12115, A-13,$R^2$-9,$R^3$-11), (I-P12116,A-13,$R^2$-9,$R^3$-12), (I-P12117,A-13,$R^2$-9,$R^3$-13), (I-P12118, A-13,$R^2$-9,$R^3$-14), (I-P12119,A-13,$R^2$-9,$R^3$-15), (I-P12120,A-13,$R^2$-9,$R^3$-16), (I-P12121, A-13,$R^2$-9,$R^3$-17), (I-P12122,A-13,$R^2$-9,$R^3$-18), (I-P12123,A-13,$R^2$-9,$R^3$-19), (I-P12124, A-13,$R^2$-9,$R^3$-20), (I-P12125,A-13,$R^2$-9,$R^3$-21), (I-P12126,A-13,$R^2$-9,$R^3$-22), (I-P12127, A-13,$R^2$-9,$R^3$-33), (I-P12128,A-13,$R^2$-9,$R^3$-24), (I-P12129,A-13,$R^2$-9,$R^3$-25), (I-P12130, A-13,$R^2$-9,$R^3$-26), (I-P12131,A-13,$R^2$-9,$R^3$-27), (I-P12132,A-13,$R^2$-9,$R^3$-28), (I-P12133, A-13,$R^2$-9,$R^3$-29), (I-P12134,A-13,$R^2$-9,$R^3$-30), (I-P12135,A-13,$R^2$-9,$R^3$-31), (I-P12136, A-13,$R^2$-9,$R^3$-32), (I-P12137,A-13,$R^2$-9,$R^3$-33), (I-P12138,A-13,$R^2$-9,$R^3$-34), (I-P12139, A-13,$R^2$-10,$R^3$-1), (I-P12140,A-13,$R^2$-10,$R^3$-2), (I-P12141,A-13,$R^2$-10,$R^3$-3), (I-P12142, A-13,$R^2$-10,$R^3$-4), (I-P12143,A-13,$R^2$-10,$R^3$-5), (I-P12144,A-13,$R^2$-10,$R^3$-6), (I-P12145, A-13,$R^2$-10,$R^3$-7), (I-P12146,A-13,$R^2$-10,$R^3$-8), (I-P12147,A-13,$R^2$-10,$R^3$-9), (I-P12148, A-13,$R^2$-10,$R^3$-10), (I-P12149,A-13,$R^2$-10,$R^3$-11), (I-P12150,A-13,$R^2$-10,$R^3$-12), (I-P12151, A-13,$R^2$-10,$R^3$-13), (I-P12152,A-13,$R^2$-10,$R^3$-14), (I-P12153,A-13,$R^2$-10,$R^3$-15), (I-P12154, A-13,$R^2$-10,$R^3$-16), (I-P12155,A-13,$R^2$-10,$R^3$-17), (I-P12156,A-13,$R^2$-10,$R^3$-18), (I-P12157, A-13,$R^2$-10,$R^3$-19), (I-P12158,A-13,$R^2$-10,$R^3$-20), (I-P12159,A-13,$R^2$-10,$R^3$-21), (I-P12160, A-13,$R^2$-10,$R^3$-22), (I-P12161,A-13,$R^2$-10,$R^3$-23), (I-P12162,A-13,$R^2$-10,$R^3$-24), (I-P12163, A-13,$R^2$-10,$R^3$-25), (I-P12164,A-13,$R^2$-10,$R^3$-26), (I-P12165,A-13,$R^2$-10,$R^3$-27), (I-P12166, A-13,$R^2$-10,$R^3$-28), (I-P12167,A-13,$R^2$-10,$R^3$-29), (I-P12168,A-13,$R^2$-10,$R^3$-30), (I-P12169,A-13,$R^2$-10,$R^3$-31), (I-P12170, A-13,$R^2$-10,$R^3$-32), (I-P12171,A-13,$R^2$-10,$R^3$-33), (I-P12172, A-13,$R^2$-10,$R^3$-34), (I-P12173,A-13,$R^2$-11,$R^3$-1), (I-P12174,A-13,$R^2$-11,$R^3$-2), (I-P12175, A-13,$R^2$-11,$R^3$-3), (I-P12176,A-13,$R^2$-11,$R^3$-4), (I-P12177,A-13,$R^2$-11,$R^3$-5), (I-P12178, A-13,$R^2$-11,$R^3$-6), (I-P12179,A-13,$R^2$-11,$R^3$-7), (I-P12180,A-13,$R^2$-11,$R^3$-8), (I-P12181, A-13,$R^2$-11,$R^3$-9), (I-P12182,A-13,$R^2$-11,$R^3$-10), (I-P12183,A-13,$R^2$-11,$R^3$-11), (I-P12184, A-13,$R^2$-11,$R^3$-12), (I-P12185,A-13,$R^2$-11,$R^3$-13), (I-P12186,A-13,$R^2$-11,$R^3$-14), (I-P12187, A-13,$R^2$-11,$R^3$-15), (I-P12188,A-13,$R^2$-11,$R^3$-16), (I-P12189,A-13,$R^2$-11,$R^3$-17), (I-P12190, A-13,$R^2$-11,$R^3$-18), (I-P12191, A-13,$R^2$-11,$R^3$-19), (I-P12192,A-13,$R^2$-11,$R^3$-20), (I-P12193, A-13,$R^2$-11,$R^3$-21), (I-P12194,A-13,$R^2$-11,$R^3$-22), (I-P12195,A-13,$R^2$-11,$R^3$-23), (I-P12196, A-13,$R^2$-11,$R^3$-24), (I-P12197,A-13,$R^2$-11,$R^3$-25), (I-P12198,A-13,$R^2$-11,$R^3$-26), (I-P12199, A-13,$R^2$-11,$R^3$-27), (I-P12200,A-13,$R^2$-11,$R^3$-28), (I-P12201,A-13,$R^2$-11,$R^3$-29), (I-P12202, A-13,$R^2$-11,$R^3$-30), (I-P12203,A-13,$R^2$-11,$R^3$-31), (I-P12204,A-13,$R^2$-11,$R^3$-33), (I-P12205, A-13,$R^2$-11,$R^3$-33), (I-P12206,A-13,$R^2$-11,$R^3$-34), (I-P12207,A-13,$R^2$-12,$R^3$-1), (I-P12208, A-13,$R^2$-12,$R^3$-2), (I-P12209,A-13,$R^2$-12,$R^3$-3), (I-P12210,A-13,$R^2$-12,$R^3$-4), (I-P12211, A-13,$R^2$-12,$R^3$-5), (I-P12212,A-13,$R^2$-12,$R^3$-6), (I-P12213,A-13,$R^2$-12,$R^3$-7), (I-P12214, A-13,$R^2$-12,$R^3$-8), (I-P12215,A-13,$R^2$-12,$R^3$-9), (I-P12216,A-13,$R^2$-12,$R^3$-10), (I-P12217, A-13,$R^2$-12,$R^3$-11), (I-P12218,A-13,$R^2$-12,$R^3$-12), (I-P12219,A-13,$R^2$-12,$R^3$-13), (I-P12220, A-13,$R^2$-12,$R^3$-14), (I-P12221,A-13,$R^2$-12,$R^3$-15), (I-P12222,A-13,$R^2$-12,$R^3$-16), (I-P12223, A-13,$R^2$-12,$R^3$-17), (I-P12224,A-13,$R^2$-12,$R^3$-18), (I-P12225,A-13,$R^2$-12,$R^3$-19), (I-P12226, A-13,$R^2$-12,$R^3$-20), (I-P12227,A-13,$R^2$-12,$R^3$-21), (I-P12228,A-13,$R^2$-12,$R^3$-22), (I-P12229, A-13,$R^2$-12,$R^3$-23), (I-P12230,A-13,$R^2$-12,$R^3$-24), (I-P12231,A-13,$R^2$-12,$R^3$-25), (I-P12232, A-13,$R^2$-12,$R^3$-26), (I-P12233,A-13,$R^2$-12,$R^3$-27), (I-P12234,A-13,$R^2$-12,$R^3$-28), (I-P12235,A-13,$R^2$-12,$R^3$-29), (I-P12236, A-13,$R^2$-12,$R^3$-30), (I-P12237,A-13,$R^2$-12,$R^3$-31), (I-P12238, A-13,$R^2$-12,$R^3$-32), (I-P12239,A-13,$R^2$-12,$R^3$-33), (I-P12240,A-13,$R^2$-12,$R^3$-34), (I-P12241, A-13,$R^2$-12,$R^3$-1), (I-P12242,A-13,$R^2$-13,$R^3$-2), (I-P12243,A-13,$R^2$-13,$R^3$-3), (I-P12244, A-13,$R^2$-13,$R^3$-4), (I-P12245,A-13,$R^2$-12,$R^3$-5), (I-P12246,A-13,$R^2$-12,$R^3$-6), (I-P12247, A-13,$R^2$-12,$R^3$-7), (I-P12248,A-13,$R^2$-12,$R^3$-8), (I-P12249,A-13,$R^2$-12,$R^3$-9), (I-P12250, A-13,$R^2$-12,$R^3$-10), (I-P12251,A-13,$R^2$-12,$R^3$-11), (I-P12252,A-13,$R^2$-12,$R^3$-12), (I-P12253, A-13,$R^2$-12,$R^3$-13), (I-P12254,A-13,$R^2$-12,$R^3$-14), (I-P12255,A-13,$R^2$-12,$R^3$-15), (I-P12256, A-13,$R^2$-12,$R^3$-16), (I-P12257, A-13,$R^2$-12,$R^3$-17), (I-P12258,A-13,$R^2$-12,$R^3$-18), (I-P12259, A-13,$R^2$-12,$R^3$-19), (I-P12260,A-13,$R^2$-12,$R^3$-20), (I-P12261,A-13,$R^2$-12,$R^3$-21), (I-P12262, A-13,$R^2$-12,$R^3$-22), (I-P12263,A-13,$R^2$-12,$R^3$-23), (I-P12264,A-13,$R^2$-12,$R^3$-24), (I-P12265, A-13,$R^2$-12,$R^3$-25), (I-P12266,A-13,$R^2$-12,$R^3$-26), (I-P12267,A-13,$R^2$-12,$R^3$-27), (I-P12268, A-13,$R^2$-12,$R^3$-28), (I-P12269,A-13,$R^2$-12,$R^3$-29), (I-P12270,A-13,$R^2$-12,$R^3$-30), (I-P12271, A-13,$R^2$-12,$R^3$-31), (I-P12272,A-13,$R^2$-12,$R^3$-32), (I-P12273,A-13,$R^2$-12,$R^3$-33), (I-P12274, A-13,$R^2$-12,$R^3$-34), (I-P12275,A-13,$R^2$-14,$R^3$-1), (I-P12276,A-13,$R^2$-14,$R^3$-2), (I-P12277,A-13,$R^2$-14,$R^3$-3), (I-P12278,A-13,$R^2$-14,$R^3$-4), (I-P12279,A-13,$R^2$-14,$R^3$-5), (I-P12280, A-13,$R^2$-14,$R^3$-6), (I-P12281,A-13,$R^2$-14,$R^3$-7), (I-P12282,A-13,$R^2$-14,$R^3$-8), (I-P12283, A-13,$R^2$-14,$R^3$-9), (I-P12284,A-13,$R^2$-14,$R^3$-10), (I-P12285,A-13,$R^2$-14,$R^3$-11), (I-P12286, A-13,$R^2$-14,$R^3$-12), (I-P12287,A-13,$R^2$-14,$R^3$-13), (I-P12288,A-13,$R^2$-14,$R^3$-14), (I-P12289, A-13,$R^2$-14,$R^3$-15), (I-P12290,A-13,$R^2$-14,$R^3$-16), (I-P12291,A-13,$R^2$-14,$R^3$-17), (I-P12292, A-13,$R^2$-14,$R^3$-18), (I-P12293,A-13,$R^2$-14,$R^3$-19), (I-P12294,A-13,$R^2$-14,$R^3$-20), (I-P12295, A-13,$R^2$-14,$R^3$-21), (I-P12296,A-13,$R^2$-14,$R^3$-22), (I-P12297,A-13,$R^2$-14,$R^3$-23), (I-P12298, A-13,$R^2$-14,$R^3$-24), (I-P12299,A-13,$R^2$-14,$R^3$-25), (I-P12300,A-13,$R^2$-14,$R^3$-26), (I-P12301, A-13,$R^2$-14,$R^3$-27), (I-P12302, A-13,$R^2$-14,$R^3$-28), (I-P12303,A-13,$R^2$-14,$R^3$-29), (I-P12304, A-13,$R^2$-14,$R^3$-30), (I-P12305,A-13,$R^2$-14,$R^3$-31), (I-P12306,A-13,$R^2$-14,$R^3$-32), (I-P12307, A-13,$R^2$-14,$R^3$-33), (I-P12308,A-13,$R^2$-14,$R^3$-34), (I-P12309,A-13,$R^2$-

15,R³-1), (I-P12310, A-13,R²-15,R³-2), (I-P12311,A-13,R²-14,R³-3), (I-P12312,A-13,R²-15,R³-4), (I-P12313, A-13,R²-15,R³-5), (I-P12314,A-13,R²-15,R³-6), (I-P12315,A-13,R²-15,R³-7), (I-P12316, A-13,R²-15,R³-8), (I-P12317,A-13,R²-15,R³-9), (I-P12318,A-13,R²-15,R³-10), (I-P12319, A-13, R²-15,R³-11), (I-P12320,A-13,R²-15,R³-12), (I-P12321,A-13,R²-15,R³-13), (I-P12322, A-13,R²-15,R³-14), (I-P12323, A-13,R²-15,R³-15), (I-P12324,A-13,R²-15,R³-16), (I-P12325, A-13,R²-15,R³-17), (I-P12326,A-13,R²-15,R³-18), (I-P12327,A-13,R²-15,R³-19), (I-P12328, A-13,R²-15, R³-20), (I-P12329,A-13,R²-15,R³-21), (I-P12330,A-13,R²-15,R³-22), (I-P12331, A-13,R²-15,R³-23), (I-P12332,A-13, R²-15,R³-24), (I-P12333,A-13,R²-15,R³-25), (I-P12334, A-13,R²-15,R³-26), (I-P12335,A-13,R²-15,R³-27), (I-P12336,A-13,R²-15,R³-28), (I-P12337, A-13,R²-15,R³-29), (I-P12338,A-13,R²-15,R³-30), (I-P12339,A-13,R²-15, R³-31), (I-P12340, A-13,R²-15,R³-32), (I-P12341,A-13,R²-15,R³-33), (I-P12342,A-13,R²-15,R³-34), (I-P12343, A-13, R²-16,R³-1), (I-P12344,A-13,R²-16,R³-2), (I-P12345,A-13, R²-16,R³-3), (I-P12346, A-13,R²-16,R³-4), (I-P12347,A-13, R²-16,R³-5), (I-P12348,A-13,R²-16,R³-6), (I-P12349, A-13, R²-16,R³-7), (I-P12350,A-13,R²-16,R³-8), (I-P12351,A-13, R²-16,R³-9), (I-P12352, A-13,R²-16,R³-10), (I-P12353,A-13,R²-16,R³-11), (I-P12354,A-13,R²-16,R³-12), (I-P12355, A-13,R²-16,R³-13), (I-P12356,A-13,R²-16,R³-14), (I-P12357,A-13,R²-16,R³-15), (I-P12358, A-13,R²-16,R³-16), (I-P12359,A-13,R²-16,R³-17), (I-P12360,A-13,R²-16, R³-18), (I-P12361, A-13,R²-16,R³-19), (I-P12362,A-13,R²-16,R³-20), (I-P12363,A-13,R²-16,R³-21), (I-P12364, A-13, R²-16,R³-22), (I-P12365,A-13,R²-16,R³-23), (I-P12366,A-13,R²-16,R³-24), (I-P12367, A-13,R²-16,R³-25), (I-P12368, A-13,R²-16,R³-26), (I-P12369,A-13,R²-16,R³-27), (I-P12370, A-13,R²-16,R³-28), (I-P12371,A-13,R²-16,R³-29), (I-P12372,A-13,R²-16,R³-30), (I-P12373, A-13,R²-16, R³-31), (I-P12374,A-13,R²-16,R³-32), (I-P12375,A-13,R²-16,R³-33), (I-P12376, A-13,R²-16,R³-34), (I-P12377,A-13, R²-17,R³-1), (I-P12378,A-13,R²-17,R³-2), (I-P12379, A-13, R²-17,R³-3), (I-P12380,A-13,R²-17,R³-4), (I-P12381,A-13, R²-17,R³-5), (I-P12382,A-13,R²-17,R³-6), (I-P12383,A-13, R²-17,R³-7), (I-P12384,A-13,R²-17,R³-8), (I-P12385, A-13, R²-17,R³-9), (I-P12386,A-13,R²-17,R³-10), (I-P12387,A-13,R²-17,R³-11), (I-P12388, A-13,R²-17,R³-12), (I-P12389, A-13,R²-17,R³-13), (I-P12390,A-13,R²-17,R³-14), (I-P12391, A-13,R²-17,R³-15), (I-P12392,A-13,R²-17,R³-16), (I-P12393,A-13,R²-17,R³-17), (I-P12394, A-13,R²-17, R³-18), (I-P12395,A-13,R²-17,R³-19), (I-P12396,A-13,R²-17,R³-20), (I-P12397, A-13,R²-17,R³-21), (I-P12398,A-13, R²-17,R³-22), (I-P12399,A-13,R²-17,R³-23), (I-P12400, A-13,R²-17,R³-24), (I-P12401,A-13,R²-17,R³-25), (I-P12402,A-13,R²-17,R³-26), (I-P12403, A-13,R²-17,R³-27), (I-P12404,A-13,R²-17,R³-28), (I-P12405,A-13,R²-17, R³-29), (I-P12406, A-13,R²-17,R³-30), (I-P12407,A-13,R²-17,R³-31), (I-P12408,A-13,R²-17,R³-32), (I-P12409, A-13, R²-17,R³-33), (I-P12410,A-13,R²-17,R³-34), (I-P12411,A-13,R²-18,R³-1), (I-P12412, A-13,R²-18,R³-2), (I-P12413,A-13,R²-18,R³-3), (I-P12414,A-13,R²-18,R³-4), (I-P12415, A-13,R²-18,R³-5), (I-P12416,A-13,R²-18,R³-6), (I-P12417, A-13,R²-18,R³-7), (I-P12418, A-13,R²-18,R³-8), (I-P12419, A-13,R²-18,R³-9), (I-P12420,A-13,R²-18,R³-10), (I-P12421, A-13,R²-18,R³-11), (I-P12422,A-13,R²-18,R³-12), (I-P12423,A-13,R²-18,R³-13), (I-P12424, A-13,R²-18, R³-14), (I-P12425,A-13,R²-18,R³-15), (I-P12426,A-13,R²-18,R³-16), (I-P12427,A-13,R²-18,R³-17), (I-P12428,A-13, R²-18,R³-18), (I-P12429,A-13,R²-18,R³-19), (I-P12430, A-13,R²-18,R³-20), (I-P12431,A-13,R²-18,R³-21), (I-P12432,A-13,R²-18,R³-22), (I-P12433, A-13,R²-18,R³-23), (I-P12434,A-13,R²-18,R³-24), (I-P12435,A-13,R²-18, R³-25), (I-P12436, A-13,R²-18,R³-26), (I-P12437,A-13,R²-18,R³-27), (I-P12438,A-13,R²-18,R³-28), (I-P12439, A-13, R²-18,R³-29), (I-P12440,A-13,R²-18,R³-30), (I-P12441,A-13,R²-18,R³-31), (I-P12442, A-13,R²-18,R³-32), (I-P12443, A-13,R²-18,R³-33), (I-P12444,A-13,R²-18,R³-34), (I-P12445, A-13,R²-19,R³-1), (I-P12446,A-13,R²-19,R³-2), (I-P12447,A-13,R²-19,R³-3), (I-P12448, A-13,R²-19,R³-4), (I-P12449,A-13,R²-19,R³-5), (I-P12450,A-13,R²-19,R³-6), (I-P12451, A-13,R²-19,R³-7), (I-P12452,A-13,R²-19,R³-8), (I-P12453,A-13,R²-19,R³-9), (I-P12454, A-13,R²-19,R³-10), (I-P12455,A-13,R²-19,R³-11), (I-P12456,A-13,R²-19, R³-12), (I-P12457, A-13,R²-19,R³-13), (I-P12458,A-13,R²-19,R³-14), (I-P12459,A-13,R²-19,R³-15), (I-P12460, A-13, R²-19,R³-16), (I-P12461,A-13,R²-19,R³-17), (I-P12462,A-13,R²-12,R³-18), (I-P12463, A-13,R²-12,R³-19), (I-P12464, A-13,R²-19,R³-20), (I-P12465,A-13,R²-19,R³-21), (I-P12466, A-13,R²-19,R³-22), (I-P12467,A-13,R²-19,R³-23), (I-P12468,A-13,R²-19,R³-24), (I-P12469, A-13,R²-19, R³-25), (I-P12470,A-13,R²-19,R³-26), (I-P12471,A-13,R²-19,R³-27), (I-P12472, A-13,R²-19,R³-28), (I-P12473,A-13, R²-19,R³-29), (I-P12474,A-13,R²-19,R³-30), (I-P12475, A-13,R²-19,R³-31), (I-P12476,A-13,R²-19,R³-32), (I-P12477,A-13,R²-19,R³-33), (I-P12478, A-13,R²-19,R³-34), (I-P12479,A-13,R²-20,R³-1), (I-P12480,A-13,R²-20, R³-2), (I-P12481, A-13,R²-20,R³-3), (I-P12482,A-13,R²-20, R³-4), (I-P12483,A-13,R²-20,R³-5), (I-P12484, A-13,R²-20, R³-6), (I-P12485,A-13,R²-20,R³-7), (I-P12486,A-13,R²-20, R³-8), (I-P12487, A-13,R²-20,R³-9), (I-P12488,A-13,R²-20, R³-10), (I-P12489,A-13,R²-20,R³-11), (I-P12490, A-13,R²-20,R³-12), (I-P12491,A-13,R²-20,R³-13), (I-P12492,A-13, R²-20,R³-14), (I-P12493, A-13,R²-20,R³-15), (I-P12494,A-13,R²-20,R³-16), (I-P12495,A-13,R²-20,R³-17), (I-P12496, A-13,R²-20,R³-18), (I-P12497,A-13,R²-20,R³-19), (I-P12498,A-13,R²-20,R³-20), (I-P12499, A-13,R²-20,R³-21), (I-P12500,A-13,R²-20,R³-22), (I-P12501,A-13,R²-20, R³-23), (I-P12502, A-13,R²-20,R³-24), (I-P12503,A-13,R²-20,R³-25), (I-P12504,A-13,R²-20,R³-26), (I-P12505, A-13, R²-20,R³-27), (I-P12506,A-13,R²-20,R³-28), (I-P12507,A-13,R²-20,R³-29), (I-P12508, A-13,R²-20,R³-30), (I-P12509, A-13,R²-20,R³-31), (I-P12510,A-13,R²-20,R³-32), (I-P12511, A-13,R²-20,R³-33), (I-P12512,A-13,R²-20,R³-34), (I-P12513,A-13,R²-21,R³-1), (I-P12514, A-13,R²-21, R³-2), (I-P12515,A-13,R²-21,R³-3), (I-P12516,A-13,R²-21, R³-4), (I-P12517, A-13,R²-21,R³-5), (I-P12518,A-13,R²-21, R³-6), (I-P12519,A-13,R²-21,R³-7), (I-P12520, A-13,R²-21, R³-8), (I-P12521,A-13,R²-21,R³-9), (I-P12522,A-13,R²-21, R³-10), (I-P12523, A-13,R²-21,R³-11), (I-P12524,A-13,R²-21,R³-12), (I-P12525,A-13,R²-21,R³-13), (I-P12526, A-13, R²-21,R³-14), (I-P12527,A-13,R²-21,R³-15), (I-P12528,A-13,R²-21,R³-16), (I-P12529, A-13,R²-21,R³-17), (I-P12530, A-13,R²-21,R³-18), (I-P12531,A-13,R²-21,R³-19), (I-P12532, A-13,R²-21,R³-20), (I-P12533,A-13,R²-21,R³-21), (I-P12534,A-13,R²-21,R³-22), (I-P12535, A-13,R²-21, R³-23), (I-P12536,A-13,R²-21,R³-24), (I-P12537,A-13,R²-21,R³-25), (I-P12538, A-13,R²-21,R³-26), (I-P12539,A-13, R²-21,R³-27), (I-P12540,A-13,R²-21,R³-28), (I-P12541, A-13,R²-21,R³-29), (I-P12542,A-13,R²-21,R³-30), (I-P12543,A-13,R²-21,R³-31), (I-P12544, A-13,R²-21,R³-32), (I-P12545,A-13,R²-21,R³-33), (I-P12546,A-13,R²-21, R³-34), (I-P12547, A-13,R²-22,R³-1), (I-P12548,A-13,R²-22,R³-2), (I-P12549,A-13,R²-22,R³-3), (I-P12550, A-13,R²-22,R³-4), (I-P12551,A-13,R²-22,R³-5), (I-P12552,A-13, R²-22,R³-6), (I-P12553, A-13,R²-22,R³-7), (I-P12554,A-13, R²-22,R³-8), (I-P12555,A-13,R²-22,R³-9), (I-P12556, A-13, R²-22,R³-10), (I-P12557,A-13,R²-22,R³-11), (I-P12558, A-13,R²-22,R³-12), (I-P12559, A-13,R²-22,R³-13), (I-P12560,A-13,R²-22,R³-14), (I-P12561,A-13,R²-22,R³-15), (I-P12562,

A-13,R²-22,R³-16), (I-P12563,A-13,R²-22,R³-17), (I-P12564,A-13,R²-22,R³-18), (I-P12565, A-13,R²-22,R³-19), (I-P12566,A-13,R²-22,R³-20), (I-P12567,A-13,R²-22,R³-21), (I-P12568, A-13,R²-22,R³-22), (I-P12569,A-13,R²-22,R³-23), (I-P12570,A-13,R²-22,R³-24), (I-P12571, A-13,R²-22,R³-25), (I-P12572,A-13,R²-22,R³-26), (I-P12573,A-13,R²-22,R³-27), (I-P12574, A-13,R²-22,R³-28), (I-P12575,A-13,R²-22,R³-29), (I-P12576,A-13,R²-22,R³-30), (I-P12577, A-13,R²-22,R³-31), (I-P12578,A-13,R²-22,R³-32), (I-P12579,A-13,R²-22,R³-33), (I-P12580, A-13,R²-22,R³-34), (I-P12581,A-13,R²-23,R³-1), (I-P12582,A-13,R²-23,R³-2), (I-P12583, A-13,R²-23,R³-3), (I-P12584,A-13,R²-23,R³-4), (I-P12585,A-13,R²-23,R³-5), (I-P12586, A-13,R²-23,R³-6), (I-P12587,A-13,R²-23,R³-7), (I-P12588,A-13,R²-23,R³-8), (I-P12589, A-13,R²-23,R³-9), (I-P12590,A-13,R²-23,R³-10), (I-P12591,A-13,R²-23,R³-11), (I-P12592, A-13,R²-23,R³-12), (I-P12503,A-13,R²-23,R³-13), (I-P12594,A-13,R²-23,R³-14), (I-P12595, A-13,R²-23,R³-15), (I-P12596, A-13,R²-23,R³-16), (I-P12597,A-13,R²-23,R³-17), (I-P12598, A-13,R²-23,R³-18), (I-P12599,A-13,R²-23,R³-19), (I-P12600,A-13,R²-23,R³-20), (I-P12601, A-13,R²-23,R³-21), (I-P12602,A-13,R²-23,R³-22), (I-P12603,A-13,R²-23,R³-23), (I-P12604, A-13,R²-23,R³-24), (I-P12605,A-13,R²-23,R³-25), (I-P12606,A-13,R²-23,R³-26), (I-P12607, A-13,R²-23,R³-27), (I-P12608,A-13,R²-23,R³-28), (I-P12609,A-13,R²-23,R³-29), (I-P12610, A-13,R²-23,R³-30), (I-P12611,A-13,R²-23,R³-31), (I-P12612,A-13,R²-23,R³-32), (I-P12613, A-13,R²-23,R³-33), (I-P12614,A-13,R²-23,R³-34), (I-P12615,A-13,R²-24,R³-1), (I-P12616, A-13,R²-24,R³-2), (I-P12617,A-13,R²-24,R³-3), (I-P12618,A-13,R²-24,R³-4), (I-P12619, A-13,R²-24,R³-5), (I-P12620,A-13,R²-24,R³-6), (I-P12621,A-13,R²-24,R³-7), (I-P12622, A-13,R²-24,R³-8), (I-P12623,A-13,R²-24,R³-9), (I-P12624,A-13,R²-24,R³-10), (I-P12625, A-13,R²-24,R³-11), (I-P12626,A-13,R²-24,R³-12), (I-P12627,A-13,R²-24,R³-13), (I-P12628, A-13,R²-24,R³-14), (I-P12629,A-13,R²-24,R³-15), (I-P12630,A-13,R²-24,R³-16), (I-P12631, A-13,R²-24,R³-17), (I-P12632,A-13,R²-24,R³-18), (I-P12633,A-13,R²-24,R³-19), (I-P12634, A-13,R²-24,R³-20), (I-P12635,A-13,R²-24,R³-21), (I-P12636,A-13,R²-24,R³-22), (I-P12637, A-13,R²-24,R³-23), (I-P12638,A-13,R²-24,R³-24), (I-P12639,A-13,R²-24,R³-25), (I-P12640, A-13,R²-24,R³-26), (I-P12641,A-13,R²-24,R³-27), (I-P12642,A-13,R²-24,R³-28), (I-P12643, A-13,R²-24,R³-29), (I-P12644,A-13,R²-24,R³-30), (I-P12645,A-13,R²-24,R³-31), (I-P12646, A-13,R²-24,R³-32), (I-P12647,A-13,R²-24,R³-33), (I-P12648,A-13,R²-24,R³-34), (I-P12649, A-13,R²-25,R³-1), (I-P12650,A-13,R²-25,R³-2), (I-P12651,A-13,R²-25,R³-3), (I-P12652, A-13,R²-25,R³-4), (I-P12653,A-13,R²-25,R³-5), (I-P12654,A-13,R²-25,R³-6), (I-P12655,A-13,R²-25,R³-7), (I-P12656,A-13,R²-25,R³-8), (I-P12657,A-13,R²-25,R³-9), (I-P12658, A-13,R²-25,R³-10), (I-P12659,A-13,R²-25,R³-11), (I-P12660,A-13,R²-25,R³-12), (I-P12661, A-13,R²-25,R³-13), (I-P12662, A-13,R²-25,R³-14), (I-P12663,A-13,R²-25,R³-15), (I-P12664, A-13,R²-25,R³-16), (I-P12665,A-13,R²-25,R³-17), (I-P12666,A-13,R²-25,R³-18), (I-P12667, A-13,R²-25,R³-19), (I-P12668,A-13,R²-25,R³-20), (I-P12669,A-13,R²-25,R³-21), (I-P12670, A-13,R²-25,R³-22), (I-P12671,A-13,R²-25,R³-23), (I-P12672,A-13,R²-25,R³-24), (I-P12673, A-13,R²-25,R³-25), (I-P12674,A-13,R²-25,R³-26), (I-P12675,A-13,R²-25,R³-27), (I-P12676, A-13,R²-25,R³-28), (I-P12677,A-13,R²-25,R³-29), (I-P12678,A-13,R²-25,R³-30), (I-P12679, A-13,R²-25,R³-31), (I-P12680,A-13,R²-25,R³-32), (I-P12681,A-13,R²-25,R³-33), (I-P12682, A-13,R²-25,R³-34), (I-P12683,A-13,R²-26,R³-1), (I-P12684,A-13,R²-26,R³-2), (I-P12685, A-13,R²-26,R³-3), (I-P12686,A-13,R²-26,R³-4), (I-P12687,A-13,R²-26,R³-5), (I-P12688, A-13,R²-26,R³-6), (I-P12689,A-13,R²-26,R³-7), (I-P12690, A-13,R²-26,R³-8), (I-P12691, A-13,R²-26,R³-9), (I-P12692, A-13,R²-26,R³-10), (I-P12693,A-13,R²-26,R³-11), (I-P12694, A-13,R²-26,R³-12), (I-P12695,A-13,R²-26,R³-13), (I-P12696,A-13,R²-26,R³-14), (I-P12697, A-13,R²-26,R³-15), (I-P12698,A-13,R²-26,R³-16), (I-P12699,A-13,R²-26,R³-17), (I-P12700, A-13,R²-26,R³-18), (I-P12701,A-13,R²-26,R³-19), (I-P12702,A-13,R²-26,R³-20), (I-P12703, A-13,R²-26,R³-21), (I-P12704,A-13,R²-26,R³-22), (I-P12705,A-13,R²-26,R³-23), (I-P12706, A-13,R²-26,R³-24), (I-P12707,A-13,R²-26,R³-25), (I-P12708,A-13,R²-26,R³-26), (I-P12709, A-13,R²-26,R³-27), (I-P12710,A-13,R²-26,R³-28), (I-P12711,A-13,R²-26,R³-29), (I-P12712, A-13,R²-26,R³-30), (I-P12713,A-13,R²-26,R³-31), (I-P12714,A-13,R²-26,R³-32), (I-P12715, A-13,R²-26,R³-33), (I-P12716, A-13,R²-26,R³-34), (I-P12717,A-13,R²-27,R³-1), (I-P12718, A-13,R²-27,R³-2), (I-P12719,A-13,R²-27,R³-3), (I-P12720,A-13,R²-27,R³-4), (I-P12721, A-13,R²-27,R³-5), (I-P12722,A-13,R²-27,R³-6), (I-P12723,A-13,R²-27,R³-7), (I-P12724, A-13,R²-27,R³-8), (I-P12725,A-13,R²-27,R³-9), (I-P12726,A-13,R²-27,R³-10), (I-P12727, A-13,R²-27,R³-11), (I-P12728,A-13,R²-27,R³-12), (I-P12729,A-13,R²-27,R³-13), (I-P12730, A-13,R²-27,R³-14), (I-P12731,A-13,R²-27,R³-15), (I-P12732,A-13,R²-27,R³-16), (I-P12733, A-13,R²-27,R³-17), (I-P12734,A-13,R²-27,R³-18), (I-P12735,A-13,R²-27,R³-19), (I-P12736,A-13,R²-27,R³-20), (I-P12737, A-13,R²-27,R³-21), (I-P12738,A-13,R²-27,R³-22), (I-P12739, A-13,R²-27,R³-23), (I-P12740,A-13,R²-27,R³-24), (I-P12741,A-13,R²-27,R³-25), (I-P12742, A-13,R²-27,R³-26), (I-P12743,A-13,R²-27,R³-27), (I-P12744,A-13,R²-27,R³-28), (I-P12745, A-13,R²-27,R³-29), (I-P12746,A-13,R²-27,R³-30), (I-P12747,A-13,R²-27,R³-31), (I-P12748, A-13,R²-27,R³-32), (I-P12749,A-13,R²-27,R³-33), (I-P12750,A-13,R²-27,R³-34), (I-P12751, A-13,R²-28,R³-1), (I-P12752,A-13,R²-28,R³-2), (I-P12753,A-13,R²-28,R³-3), (I-P12754, A-13,R²-28,R³-4), (I-P12755,A-13,R²-28,R³-5), (I-P12756,A-13,R²-28,R³-6), (I-P12757, A-13,R²-28,R³-7), (I-P12758,A-13,R²-28,R³-8), (I-P12759,A-13,R²-28,R³-9), (I-P12760, A-13,R²-28,R³-10), (I-P12761,A-13,R²-28,R³-11), (I-P12762,A-13,R²-28,R³-12), (I-P12763, A-13,R²-28,R³-13), (I-P12764,A-13,R²-28,R³-14), (I-P12765,A-13,R²-28,R³-15), (I-P12766, A-13,R²-28,R³-16), (I-P12767,A-13,R²-28,R³-17), (I-P12768,A-13,R²-28,R³-18), (I-P12769, A-13,R²-28,R³-19), (I-P12770,A-13,R²-28,R³-20), (I-P12771,A-13,R²-28,R³-21), (I-P12772, A-13,R²-28,R³-22), (I-P12773,A-13,R²-28,R³-23), (I-P12774,A-13,R²-28,R³-24), (I-P12775, A-13,R²-28,R³-25), (I-P12776,A-13,R²-28,R³-26), (I-P12777,A-13,R²-28,R³-27), (I-P12778, A-13,R²-28,R³-28), (I-P12779,A-13,R²-28,R³-29), (I-P12780,A-13,R²-28,R³-30), (I-P12781, A-13,R²-28,R³-31), (I-P12782, A-13,R²-28,R³-32), (I-P12783,A-13,R²-28,R³-33), (I-P12784, A-13,R²-28,R³-34), (I-P12785,A-13,R²-29,R³-1), (I-P12786,A-13,R²-29,R³-2), (I-P12787,A-13,R²-29,R³-3), (I-P12788,A-13,R²-29,R³-4), (I-P12789,A-13,R²-29,R³-5), (I-P12790, A-13,R²-29,R³-6), (I-P12791,A-13,R²-29,R³-7), (I-P12792,A-13,R²-29,R³-8), (I-P12793,A-13,R²-29,R³-9), (I-P12794,A-13,R²-29,R³-10), (I-P12795,A-13,R²-29,R³-11), (I-P12796, A-13,R²-29,R³-12), (I-P12797,A-13,R²-29,R³-13), (I-P12798,A-13,R²-29,R³-14), (I-P12799, A-13,R²-29,R³-15), (I-P12800,A-13,R²-29,R³-16), (I-P12801,A-13,R²-29,R³-17), (I-P12802, A-13,R²-29,R³-18), (I-P12803, A-13,R²-29,R³-19), (I-P12804,A-13,R²-29,R³-20), (I-P12805, A-13,R²-29,R³-21), (I-P12806,A-13,R²-29,R³-22), (I-P12807,A-13,R²-29,R³-23), (I-P12808, A-13,R²-29,R³-24), (I-P12809,A-13,R²-29,R³-25), (I-P12810,A-13,R²-29,R³-26), (I-P12811, A-13,R²-29,R³-27), (I-P12812,A-13,R²-29,R³-28), (I-P12813,A-13,R²-29,R³-29), (I-P12814,

A-13,R²-29,R³-30), (I-P12815,A-13,R²-29,R³-31), (I-P12816,A-13,R²-29,R³-32), (I-P12817, A-13,R²-29,R³-33), (I-P12818,A-13,R²-29,R³-34), (I-P12819,A-14,R²-1,R³-1), (I-P12820, A-14,R²-1,R³-2), (I-P12821,A-14,R²-1,R³-3), (I-P12822,A-14,R²-1,R³-4), (I-P12823, A-14,R²-1,R³-5), (I-P12824,A-14,R²-1,R³-6), (I-P12825,A-14,R²-1,R³-7), (I-P12826, A-14,R²-1,R³-8), (I-P12827,A-14,R²-1,R³-9), (I-P12828,A-14,R²-1,R³-10), (I-P12829, A-14,R²-1,R³-11), (I-P12830,A-14,R²-1,R³-12), (I-P12831,A-14,R²-1,R³-13), (I-P12832, A-14,R²-1,R³-14), (I-P12833,A-14,R²-1,R³-15), (I-P12834,A-14,R²-1,R³-16), (I-P12835, A-14,R²-1,R³-17), (I-P12836,A-14,R²-1,R³-18), (I-P12837,A-14,R²-1,R³-19), (I-P12838,A-14,R²-1,R³-20), (I-P12839,A-14,R²-1,R³-21), (I-P12840,A-14,R²-1,R³-22), (I-P12841, A-14,R²-1,R³-23), (I-P12842,A-14,R²-1,R³-24), (I-P12843,A-14,R²-1,R³-25), (I-P12844,A-14,R²-1,R³-26), (I-P12845,A-14,R²-1,R³-27), (I-P12846,A-14,R²-1,R³-28), (I-P12847,A-14,R²-1,R³-29), (I-P12848,A-14,R²-1,R³-30), (I-P12849,A-14,R²-1,R³-31), (I-P12850, A-14,R²-1,R³-32), (I-P12851,A-14,R²-1,R³-33), (I-P12852,A-14,R²-1,R³-34), (I-P12853,A-14,R²-2,R³-1), (I-P12854,A-14,R²-2,R³-2), (I-P12855,A-14,R²-2,R³-3), (I-P12856, A-14,R²-2,R³-4), (I-P12857,A-14,R²-2,R³-5), (I-P12858,A-14,R²-2,R³-6), (I-P12859, A-14,R²-2,R³-7), (I-P12860,A-14,R²-2,R³-8), (I-P12861,A-14,R²-2,R³-9), (I-P12862, A-14,R²-2,R³-10), (I-P12863,A-14,R²-2,R³-11), (I-P12864,A-14,R²-2,R³-12), (I-P12865,A-14,R²-2,R³-13), (I-P12866,A-14,R²-2,R³-14), (I-P12867,A-14,R²-2,R³-15), (I-P12868,A-14,R²-2,R³-16), (I-P12869,A-14,R²-2,R³-17), (I-P12870,A-14,R²-2,R³-18), (I-P12871, A-14,R²-2,R³-19), (I-P12872,A-14,R²-2,R³-20), (I-P12873,A-14,R²-2,R³-21), (I-P12874, A-14,R²-2,R³-22), (I-P12875,A-14,R²-2,R³-23), (I-P12876,A-14,R²-2,R³-24), (I-P12877,A-14,R²-2,R³-25), (I-P12878,A-14,R²-2,R³-26), (I-P12879,A-14,R²-2,R³-27), (I-P12880, A-14,R²-2,R³-28), (I-P12881,A-14,R²-2,R³-29), (I-P12882,A-14,R²-2,R³-30), (I-P12883,A-14,R²-2,R³-31), (I-P12884,A-14,R²-2,R³-32), (I-P12885,A-14,R²-2,R³-33), (I-P12886, A-14,R²-2,R³-34), (I-P12887,A-14,R²-3,R³-1), (I-P12888,A-14,R²-3,R³-2), (I-P12889, A-14,R²-3,R³-3), (I-P12890,A-14,R²-3,R³-4), (I-P12891,A-14,R²-3,R³-5), (I-P12892, A-14,R²-3,R³-6), (I-P12893,A-14,R²-3,R³-7), (I-P12894,A-14,R²-3,R³-8), (I-P12895, A-14,R²-3,R³-9), (I-P12896,A-14,R²-3,R³-10), (I-P12897,A-14,R²-3,R³-11), (I-P12898,A-14,R²-3,R³-12), (I-P12899,A-14,R²-3,R³-13), (I-P12900,A-14,R²-3,R³-14), (I-P12901,A-14,R²-3,R³-15), (I-P12902,A-14,R²-3,R³-16), (I-P12903,A-14,R²-3,R³-17), (I-P12904,A-14,R²-3,R³-18), (I-P12905,A-14,R²-3,R³-19), (I-P12906,A-14,R²-3,R³-20), (I-P12907,A-14,R²-3,R³-21), (I-P12908,A-14,R²-3,R³-22), (I-P12909,A-14,R²-3,R³-23), (I-P12910,A-14,R²-3,R³-24), (I-P12911,A-14,R²-3,R³-25), (I-P12912,A-14,R²-3,R³-26), (I-P12913,A-14,R²-3,R³-27), (I-P12914,A-14,R²-3,R³-28), (I-P12915,A-14,R²-3,R³-29), (I-P12916,A-14,R²-3,R³-30), (I-P12917,A-14,R²-3,R³-31), (I-P12918,A-14,R²-3,R³-32), (I-P12919,A-14,R²-3,R³-33), (I-P12920,A-14,R²-3,R³-34), (I-P12921,A-14,R²-4,R³-1), (I-P12922, A-14,R²-4,R³-2), (I-P12923,A-14,R²-4,R³-3), (I-P12924,A-14,R²-4,R³-4), (I-P12925,A-14,R²-4,R³-5), (I-P12926,A-14,R²-4,R³-6), (I-P12927,A-14,R²-4,R³-7), (I-P12928, A-14,R²-4,R³-8), (I-P12929,A-14,R²-4,R³-9), (I-P12930,A-14,R²-4,R³-10), (I-P12931, A-14,R²-4,R³-11), (I-P12932,A-14,R²-4,R³-12), (I-P12933,A-14,R²-4,R³-13), (I-P12934,A-14,R²-4,R³-14), (I-P12935,A-14,R²-4,R³-15), (I-P12936,A-14,R²-4,R³-16), (I-P12937,A-14,R²-4,R³-17), (I-P12938,A-14,R²-4,R³-18), (I-P12939,A-14,R²-4,R³-19), (I-P12940,A-14,R²-4,R³-20), (I-P12941,A-14,R²-4,R³-21), (I-P12942,A-14,R²-4,R³-22), (I-P12943,A-14,R²-4,R³-23), (I-P12944,A-14,R²-4,R³-24), (I-P12945,A-14,R²-4,R³-25), (I-P12946,A-14,R²-4,R³-26), (I-P12947,A-14,R²-4,R³-27), (I-P12948,A-14,R²-4,R³-28), (I-P12949, A-14,R²-4,R³-29), (I-P12950,A-14,R²-4,R³-30), (I-P12951,A-14,R²-4,R³-31), (I-P12952, A-14,R²-4,R³-32), (I-P12953,A-14,R²-4,R³-33), (I-P12954,A-14,R²-4,R³-34), (I-P12955,A-14,R²-5,R³-1), (I-P12956,A-14,R²-5,R³-2), (I-P12957,A-14,R²-5,R³-3), (I-P12958, A-14,R²-5,R³-4), (I-P12959,A-14,R²-5,R³-5), (I-P12960,A-14,R²-5,R³-6), (I-P12961, A-14,R²-5,R³-7), (I-P12962,A-14,R²-5,R³-8), (I-P12963,A-14,R²-5,R³-9), (I-P12964, A-14,R²-5,R³-10), (I-P12965,A-14,R²-5,R³-11), (I-P12966,A-14,R²-5,R³-12), (I-P12967, A-14,R²-5,R³-13), (I-P12968,A-14,R²-5,R³-14), (I-P12969,A-14,R²-5,R³-15), (I-P12970, A-14,R²-5,R³-16), (I-P12971,A-14,R²-5,R³-17), (I-P12972,A-14,R²-5,R³-18), (I-P12973,A-14,R²-5,R³-19), (I-P12974,A-14,R²-5,R³-20), (I-P12975,A-14,R²-5,R³-21), (I-P12976, A-14,R²-5,R³-22), (I-P12977,A-14,R²-5,R³-23), (I-P12978,A-14,R²-5,R³-24), (I-P12979,A-14,R²-5,R³-25), (I-P12980,A-14,R²-5,R³-26), (I-P12981,A-14,R²-5,R³-27), (I-P12982,A-14,R²-5,R³-28), (I-P12983,A-14,R²-5,R³-29), (I-P12984,A-14,R²-5,R³-30), (I-P12985,A-14,R²-5,R³-31), (I-P12986,A-14,R²-5,R³-32), (I-P12987,A-14,R²-5,R³-33), (I-P12988,A-14,R²-5,R³-34), (I-P12989,A-14,R²-6,R³-1), (I-P12990,A-14,R²-6,R³-2), (I-P12991, A-14,R²-6,R³-3), (I-P12992,A-14,R²-6,R³-4), (I-P12993,A-14,R²-6,R³-5), (I-P12994, A-14,R²-6,R³-6), (I-P12995,A-14,R²-6,R³-7), (I-P12996,A-14,R²-6,R³-8), (I-P12997, A-14,R²-6,R³-9), (I-P12998,A-14,R²-6,R³-10), (I-P12999,A-14,R²-6,R³-11), (I-P13000, A-14,R²-6,R³-12), (I-P13001,A-14,R²-6,R³-13), (I-P13002,A-14,R²-6,R³-14), (I-P13003, A-14,R²-6,R³-15), (I-P13004,A-14,R²-6,R³-16), (I-P13005,A-14,R²-6,R³-17), (I-P13006,A-14,R²-6,R³-18), (I-P13007,A-14,R²-6,R³-19), (I-P13008,A-14,R²-6,R³-20), (I-P13009,A-14,R²-6,R³-21), (I-P13010,A-14,R²-6,R³-22), (I-P13011,A-14,R²-6,R³-23), (I-P13012, A-14,R²-6,R³-24), (I-P13013,A-14,R²-6,R³-25), (I-P13014,A-14,R²-6,R³-26), (I-P13015, A-14,R²-6,R³-27), (I-P13016,A-14,R²-6,R³-28), (I-P13017,A-14,R²-6,R³-29), (I-P13018, A-14,R²-6,R³-30), (I-P13019,A-14,R²-6,R³-31), (I-P13020,A-14,R²-6,R³-32), (I-P13021, A-14,R²-6,R³-33), (I-P13022,A-14,R²-6,R³-34), (I-P13023,A-14,R²-7,R³-1), (I-P13024, A-14,R²-7,R³-2), (I-P13025,A-14,R²-7,R³-3), (I-P13026,A-14,R²-7,R³-4), (I-P13027, A-14,R²-7,R³-5), (I-P13028,A-14,R²-7,R³-6), (I-P13029,A-14,R²-7,R³-7), (I-P13030, A-14,R²-7,R³-8), (I-P13031,A-14,R²-7,R³-9), (I-P13032,A-14,R²-7,R³-10), (I-P13033, A-14,R²-7,R³-11), (I-P13034,A-14,R²-7,R³-12), (I-P13035,A-14,R²-7,R³-13), (I-P13036, A-14,R²-7,R³-14), (I-P13037,A-14,R²-7,R³-15), (I-P13038,A-14,R²-7,R³-16), (I-P13039,A-14,R²-7,R³-17), (I-P13040,A-14,R²-7,R³-18), (I-P13041,A-14,R²-7,R³-19), (I-P13042,A-14,R²-7,R³-20), (I-P13043,A-14,R²-7,R³-21), (I-P13044,A-14,R²-7,R³-22), (I-P13045,A-14,R²-7,R³-23), (I-P13046,A-14,R²-7,R³-24), (I-P13047,A-14,R²-7,R³-25), (I-P13048, A-14,R²-7,R³-26), (I-P13049,A-14,R²-7,R³-27), (I-P13050,A-14,R²-7,R³-28), (I-P13051,A-14,R²-7,R³-29), (I-P13052,A-14,R²-7,R³-30), (I-P13053,A-14,R²-7,R³-31), (I-P13054, A-14,R²-7,R³-32), (I-P13055,A-14,R²-7,R³-33), (I-P13056,A-14,R²-7,R³-34), (I-P13057, A-14,R²-8,R³-1), (I-P13058,A-14,R²-8,R³-2), (I-P13059,A-14,R²-8,R³-3), (I-P13060, A-14,R²-8,R³-4), (I-P13061,A-14,R²-8,R³-5), (I-P13062,A-14,R²-8,R³-6), (I-P13063, A-14,R²-8,R³-7), (I-P13064,A-14,R²-8,R³-8), (I-P13065,A-14,R²-8,R³-9), (I-P13066,A-14,R²-8,R³-10), (I-P13067,A-14,R²-8,R³-11), (I-P13068,A-14,R²-8,R³-12), (I-P13069,A-14,R²-8,R³-13), (I-P13070,A-14,R²-8,R³-14), (I-P13071,A-14,R²-8,R³-15), (I-P13072, A-14,R²-8,R³-16), (I-P13073,A-14,R²-8,R³-17), (I-P13074,A-14,R²-8,R³-18), (I-P13075,A-14,R²-8,R³-19), (I-P13076,A-14,R²-8,R³-20), (I-P13077,A-14,R²-8,R³-21), (I-P13078, A-14,R²-8,R³-22), (I-P13079,A-14,R²-8,R³-23), (I-P13080,A-14,R²-8,R³-24), (I-P13081, A-14,R²-8, (I-P13082,A-14,R²-8,R³-25), (I-P13082,A-14,R²-8,R³-26), (I-P13083,A-14,R²-8,R³-27), (I-P13084,A-14,R²-8,R³-28), (I-P13085,A-14,R²-8,R³-29), (I-P13086,A-14,R²-8,R³-30), (I-P13087,A-14,R²-8,R³-31), (I-P13088,A-14,R²-8,R³-32), (I-P13089,A-14,R²-8,R³-33), (I-P13090,A-14,R²-8,R³-34), (I-P13091,A-14,R²-9,R³-1), (I-P13092,A-14,R²-9,R³-2), (I-P13093,A-14,R²-9,R³-3), (I-P13094,A-14,R²-9,R³-4), (I-P13095,A-14,R²-9,R³-5), (I-P13096,A-14,R²-9,R³-6), (I-P13097,A-14,R²-9,R³-7), (I-P13098,A-14,R²-9,R³-8), (I-P13099,A-14,R²-9,R³-9), (I-P13100,A-14,R²-9,R³-10), (I-P13101,A-14,R²-9,R³-11), (I-P13102,A-14,R²-9,R³-12), (I-P13103,A-14,R²-9,R³-13), (I-P13104,A-14,R²-9,R³-14), (I-P13105,A-14,R²-9,R³-15), (I-P13106,A-14,R²-9,R³-16), (I-P13107,A-14,R²-9,R³-17), (I-P13108,A-14,R²-9,R³-18), (I-P13109,A-14,R²-9,R³-19), (I-P13110,A-14,R²-9,R³-20), (I-P13111,A-14,R²-9,R³-21), (I-P13112,A-14,R²-9,R³-22), (I-P13113,A-14,R²-9,R³-23), (I-P13114,A-14,R²-9,R³-24), (I-P13115,A-14,R²-9,R³-25), (I-P13116,A-14,R²-9,R³-26), (I-P13117,A-14,R²-9,R³-27), (I-P13118,A-14,R²-9,R³-28), (I-P13119,A-14,R²-9,R³-29), (I-P13120,A-14,R²-9,R³-30), (I-P13121,A-14,R²-9,R³-31), (I-P13122,A-14,R²-9,R³-32), (I-P13123,A-14,R²-9,R³-33), (I-P13124,A-14,R²-9,R³-34), (I-P13125,A-14,R²-10,R³-1), (I-P13126,A-14,R²-10,R³-2), (I-P13127,A-14,R²-10,R³-3), (I-P13128,A-14,R²-10,R³-4), (I-P13129,A-14,R²-10,R³-5), (I-P13130,A-14,R²-10,R³-6), (I-P13131,A-14,R²-10,R³-7), (I-P13132,A-14,R²-10,R³-8), (I-P13133,A-14,R²-10,R³-9), (I-P13134,A-14,R²-10,R³-10), (I-P13135,A-14,R²-10,R³-11), (I-P13136,A-14,R²-10,R³-12), (I-P13137,A-14,R²-10,R³-13), (I-P13138,A-14,R²-10,R³-14), (I-P13121,A-14,R²-10,R³-15), (I-P13122,A-14,R²-10,R³-16), (I-P13123, A-14,R²-10,R³-17), (I-P13143,A-14,R²-10,R³-18), (I-P13143,A-14,R²-10,R³-19), (I-P13144, A-14,R²-10,R³-20), (I-P13145,A-14,R²-10,R³-21), (I-P13146,A-14,R²-10,R³-22), (I-P13147, A-14,R²-10,R³-23), (I-P13148,A-14,R²-10,R³-24), (I-P13149,A-14,R²-10,R³-25), (I-P13150,A-14,R²-10,R³-26), (I-P13151,A-14,R²-10,R³-27), (I-P13152,A-14,R²-10,R³-28), (I-P13153, A-14,R²-10,R³-29), (I-P13154,A-14,R²-10,R³-30), (I-P13155,A-14,R²-10,R³-31), (I-P13156, A-14,R²-10,R³-32), (I-P13157,A-14,R²-10,R³-33), (I-P13158,A-14,R²-11,R³-34), (I-P13159, A-14,R²-11,R³-1), (I-P13160,A-14,R²-11,R³-2), (I-P13161,A-14,R²-11,R³-3), (I-P13162,A-14,R²-11,R³-4), (I-P13163,A-14,R²-11,R³-5), (I-P13164,A-14,R²-11,R³-6), (I-P13165,A-14,R²-11,R³-7), (I-P13166,A-14,R²-11,R³-8), (I-P13167,A-14,R²-11,R³-9), (I-P13168, A-14,R²-11,R³-10), (I-P13169,A-14,R²-11,R³-11), (I-P13170,A-14,R²-11,R³-12), (I-P13171, A-14,R²-11,R³-13), (I-P13172,A-14,R²-11,R³-14), (I-P13173,A-14,R²-11,R³-15), (I-P13174, A-14,R²-11,R³-16), (I-P13175,A-14,R²-11,R³-17), (I-P13176,A-14,R²-11,R³-18), (I-P13177, A-14,R²-11,R³-19), (I-P13178,A-14,R²-11,R³-20), (I-P13179,A-14,R²-11,R³-21), (I-P13180, A-14,R²-11,R³-22), (I-P13181,A-14,R²-11,R³-23), (I-P13182,A-14,R²-11,R³-34), (I-P13183, A-14,R²-11,R³-25), (I-P13184, A-14,R²-11,R³-26), (I-P13185,A-14,R²-11,R³-27), (I-P13186, A-14,R²-11,R³-28), (I-P13187,A-14,R²-11,R³-29), (I-P13188,A-14,R²-11,R³-30), (I-P13189, A-14,R²-11,R³-31), (I-P13190,A-14,R²-11,R³-32), (I P13191,A-14,R²-11,R³-33), (I-P13192, A-14,R²-11,R³-34), (I-P13193,A-14,R²-12,R³-1), (I-P13194,A-14,R²-12,R³-2), (I-P13195,A-14,R²-12,R³-3), (I-P13196,A-14,R²-12,R³-4), (I-P13197,A-14,R²-12,R³-5), (I-P13198, A-14,R²-12,R³-6), (I-P13199,A-14,R²-12,R³-7), (I-P13200,A-14,R²-12,R³-8), (I-P13201, A-14,R²-12,R³-9), (I-P13202,A-14,R²-12,R³-10), (I-P13203,A-14,R²-12,R³-11), (I-P13204, A-14,R²-12,R³-12), (I-P13205, A-14,R²-12,R³-13), (I-P13206,A-14,R²-12,R³-14), (I-P13207, A-14,R²-12,R³-15), (I-P13208,A-14,R²-12,R³-16), (I-P13209,A-14,R²-12,R³-17), (I-P13210, A-14,R²-12,R³-18), (I-P13211,A-14,R²-12,R³-19), (I-P13212,A-14,R²-12,R³-20), (I-P13213, A-14,R²-12,R³-21), (I-P13214,A-14,R²-12,R³-22), (I-P13215,A-14,R²-12,R³-23), (I-P13216, A-14,R²-12,R³-24), (I-P13217,A-14,R²-12,R³-25), (I-P13218,A-14,R²-12,R³-26), (I-P13219, A-14,R²-12,R³-27), (I-P13220,A-14,R²-12,R³-28), (I-P13221,A-14,R²-12,R³-29), (I-P13222, A-14,R²-12,R³-30), (I-P13223,A-14,R²-12,R³-31), (I-P13224,A-14,R²-12,R³-32), (I-P13225, A-14,R²-12,R³-33), (I-P13226,A-14,R²-12,R³-34), (I-P13227,A-14,R²-13,R³-1), (I-P13228, A-14,R²-13,R³-2), (I-P13229,A-14,R²-13,R³-3), (I-P13230,A-14,R²-13,R³-4), (I-P13231, A-14,R²-13,R³-5), (I-P13232,A-14,R²-13,R³-6), (I-P13233, A-14,R²-13,R³-7), (I-P13234, A-14,R²-13,R³-8), (I-P13235, A-14,R²-13,R³-9), (I-P13236,A-14,R²-13,R³-10), (I-P13237, A-14,R²-13,R³-11), (I-P13238,A-14,R²-13,R³-12), (I-P13239,A-14,R²-13,R³-13), (I-P13240, A-14,R²-13,R³-14), (I-P13241,A-14,R²-13,R³-15), (I-P13242,A-14,R²-13,R³-16), (I-P13243, A-14,R²-13,R³-17), (I-P13244,A-14,R²-13,R³-18), (I-P13245,A-14,R²-13,R³-19), (I-P13246, A-14,R²-13,R³-20), (I-P13247,A-14,R²-13,R³-21), (I-P13248,A-14,R²-13,R³-22), (I-P13249, A-14,R²-13,R³-23), (I-P13250,A-14,R²-13,R³-24), (I-P13251,A-14,R²-13,R³-25), (I-P13252, A-14,R²-13,R³-26), (I-P13253,A-14,R²-13,R³-27), (I-P13254,A-14,R²-13,R³-28), (I-P13255, A-14,R²-13,R³-29), (I-P13256,A-14,R²-13,R³-30), (I-P13257,A-14,R²-13,R³-31), (I-P13258,A-14,R²-13,R³-32), (I-P13259, A-14,R²-13,R³-33), (I-P13260,A-14,R²-14,R³-34), (I-P13261, A-14,R²-14,R³-1), (I-P13262,A-14,R²-14,R³-2), (I-P13262,A-14,R²-14,R³-3), (I-P13264, A-14,R²-14,R³-4), (I-P13265,A-14,R²-14,R³-5), (I-P13266,A-14,R²-14,R³-6), (I-P13267, A-14,R²-14,R³-7), (I-P13268,A-14,R²-14,R³-8), (I-P13269,A-14,R²-14,R³-9), (I-P13270, A-14,R²-14,R³-10), (I-P13271,A-14,R²-14,R³-11), (I-P13272,A-14,R²-14,R³-12), (I-P13273, A-14,R²-14,R³-13), (I-P13274,A-14,R²-14,R³-14), (I-P13275,A-14,R²-14,R³-15), (I-P13276, A-14,R²-14,R³-16), (I-P13277,A-14,R²-14,R³-17), (I-P13278,A-14,R²-14,R³-18), (I-P13279, A-14,R²-14,R³-19), (I-P13280, A-14,R²-14,R³-20), (I-P13281,A-14,R²-14,R³-21), (I-P13282, A-14,R²-14,R³-22), (I-P13283,A-14,R²-14,R³-23), (I-P13284,A-14,R²-14,R³-24), (I-P13285, A-14,R²-14,R³-25), (I-P13286,A-14,R²-14,R³-26), (I-P13287,A-14,R²-14,R³-27), (I-P13288, A-14,R²-14,R³-78), (I-P13289,A-14,R²-14,R³-29), (I-P13290,A-14,R²-15,R³-30), (I-P13291, A-14,R²-14,R³-31), (I-P13292,A-14,R²-14,R³-32), (I-P13293,A-14,R²-15,R³-33), (I-P13294, A-14,R²-14,R³-34), (I-P13295,A-14,R²-15,R³-1), (I-P13296,A-14,R²-15,R³-2), (I-P13297, A-14,R²-15,R³-3), (I-P13298,A-14,R²-15,R³-4), (I-P13299,A-14,R²-15,R³-5), (I-P13300,A-14,R²-15,R³-6), (I-P13301,A-14,R²-15,R³-7), (I-P13302,A-14,R²-15,R³-8), (I-P13303,A-14,R²-15,R³-9), (I-P13304,A-14,R²-15,R³-10), (I-P13305,A-14,R²-15,R³-11), (I-P13306,A-14,R²-15,R³-12), (I-P13307,A-14,R²-15,R³-13), (I-P13308,A-14,R²-15,R³-14), (I-P13309, A-14,R²-15,R³-15), (I-P13310,A-14,R²-15,R³-16), (I-P13311,A-14,R²-15,R³-17), (I-P13312, A-14,R²-15,R³-18), (I-P13313,A-14,R²-15,R³-19), (I-P13314,A-14,R²-15,R³-20), (I-P13315, A-14,R²-15,R³-21), (I-P13316,A-14,R²-15,R³-22), (I-P13317,A-14,R²-15,R³-23), (I-P13318, A-14,R²-15,R³-24), (I-P13319,A-14,R²-15,R³-25), (I-P13320,A-14,R²-15,R³-26), (I-P13321, A-14,R²-15,R³-27), (I-P13322,A-14,R²-15,R³-28), (I-P13323,A-14,R²-15,R³-29), (I-P13324,A-14,R²-15,R³-30), (I-P13325, A-14,R²-15,R³-31), (I-P13326,A-14,R²-15,R³-32), (I-P13327, A-14,R²-15,R³-33), (I-P13328,A-14,R²-15,R³-34), (I-P13329,A-14,R²-16,R³-1), (I-P13330, A-14,R²-16,R³-3), (I-P13331,A-14,R²-16,R³-4), (I-P13332,A-14,R²-16,R³-5), (I-P13333,A-14,R²-16,R³-6), (I-P13334,A-14,R²-16,R³-7), (I-P13335,A-14,R²-16,R³-8), (I-P13336, A-14,R²-16,

R³-8), (I-P13337,A-14,R²-15,R³-9), (I-P13338,A-14,R²-16, R³-10), (I-P13339, A-14,R²-16,R³-11), (I-P13340,A-14,R²-15,R³-12), (I-P13341,A-14,R²-16,R³-13), (I-P13342, A-14, R²-16,R³-14), (I-P13343,A-14,R²-15,R³-15), (I-P13344,A-14,R²-16,R³-16), (I-P13345, A-14,R²-16,R³-17), (I-P13346, A-14,R²-15,R³-18), (I-P13347,A-14,R²-16,R³-19), (I-P13348, A-14,R²-16,R³-20), (I-P13349,A-14,R²-15,R³-21), (I-P13350,A-14,R²-16,R³-22), (I-P13351, A-14,R²-16, R³-23), (I-P13352,A-14,R²-15,R³-24), (I-P13353,A-14,R²-16,R³-25), (I-P13354, A-14,R²-16,R³-26), (I-P13355,A-14, R²-15,R³-27), (I-P13356,A-14,R²-16,R³-28), (I-P13357, A-14,R²-16,R³-29), (I-P13358,A-14,R²-15,R³-30), (I-P13359,A-14,R²-16,R³-31), (I-P13360, A-14,R²-16,R³-32), (I-P13361,A-14,R²-15,R³-33), (I-P13362,A-14,R²-16, R³-34), (I-P13363, A-14,R²-16,R³-1), (I-P13364,A-14,R²-17,R³-2), (I-P13365,A-14,R²-17,R³-3), (I-P13366, A-14,R²-17,R³-4), (I-P13367,A-14,R²-17,R³-5), (I-P13368,A-14,R²-17,R³-6), (I-P13369, A-14,R²-17,R³-7), (I-P13370,A-14,R²-17,R³-8), (I-P13371,A-14,R²-17,R³-9), (I-P13372, A-14,R²-17,R³-10), (I-P13373,A-14,R²-17,R³-11), (I-P13374,A-14, R²-17,R³-12), (I-P13375, A-14,R²-17,R³-13), (I-P13376,A-14,R²-17,R³-14), (I-P13377,A-14,R²-17,R³-15), (I-P13378, A-14,R²-17,R³-16), (I-P13379,A-14,R²-17,R³-17), (I-P13380,A-14,R²-17,R³-18), (I-P13381, A-14,R²-17,R³-19), (I-P13382,A-14,R²-17,R³-20), (I-P13383,A-14,R²-17, R³-21), (I-P13384, A-14,R²-17,R³-22), (I-P13385,A-14,R²-17,R³-23), (I-P13386,A-14,R²-17,R³-24), (I-P13387, A-14, R²-17,R³-25), (I-P13388,A-14,R²-17,R³-26), (I-P13389,A-14,R²-17,R³-27), (I-P13390, A-14,R²-17,R³-28), (I-P13391, A-14,R²-17,R³-29), (I-P13392,A-14,R²-17,R³-30), (I-P13393, A-14,R²-17,R³-31), (I-P13394,A-14,R²-17,R³-32), (I-P13395,A-14,R²-17,R³-33), (I-P13396, A-14,R²-17, R³-34), (I-P13397,A-14,R²-18,R³-1), (I-P13398,A-14,R²-18,R³-2), (I-P13399,A-14,R²-18,R³-3), (I-P13400,A-14,R²-18,R³-4), (I-P13401,A-14,R²-18,R³-5), (I-P13402, A-14,R²-18,R³-6), (I-P13403,A-14,R²-18,R³-7), (I-P13404,A-14,R²-18,R³-8), (I-P13405, A-14,R²-18,R³-9), (I-P13406,A-14,R²-18,R³-10), (I-P13407,A-14,R²-18,R³-11), (I-P13408, A-14, R²-18,R³-12), (I-P13409,A-14,R²-18,R³-13), (I-P13410,A-14,R²-18,R³-14), (I-P13411, A-14,R²-18,R³-15), (I-P13412, A-14,R²-18,R³-16), (I-P13413,A-14,R²-18,R³-17), (I-P13414, A-14,R²-18,R³-18), (I-P13415,A-14,R²-18,R³-19), (I-P13416,A-14,R²-18,R³-20), (I-P13417, A-14,R²-18, R³-21), (I-P13418,A-14,R²-18,R³-22), (I-P13419,A-14,R²-18,R³-23), (I-P13420, A-14,R²-18,R³-24), (I-P13421,A-14, R²-18,R³-25), (I-P13422,A-14,R²-18,R³-26), (I-P13423, A-14,R²-18,R³-27), (I-P13424,A-14,R²-18,R³-28), (I-P13425,A-14,R²-18,R³-29), (I-P13426, A-14,R²-18,R³-30), (I-P13427,A-14,R²-18,R³-31), (I-P13428,A-14,R²-18, R³-32), (I-P13429, A-14,R²-18,R³-33), (I-P13430,A-14,R²-18,R³-34), (I-P13343,A-14,R²-19,R³-1), (I-P13432, A-14,R²-19,R³-2), (I-P13433,A-14,R²-19,R³-3), (I-P13434,A-14,R²-19,R³-4), (I-P13435,A-14,R²-19,R³-5), (I-P13436,A-14,R²-19,R³-6), (I-P13437,A-14,R²-19,R³-7), (I-P13438, A-14,R²-19,R³-8), (I-P13439,A-14,R²-19,R³-9), (I-P13440,A-14,R²-19,R³-10), (I-P13441, A-14,R²-19,R³-11), (I-P13442,A-14, R²-19,R³-12), (I-P13443,A-14,R²-19,R³-13), (I-P13444, A-14,R²-19,R³-14), (I-P13445,A-14,R²-19,R³-15), (I-P13446,A-14,R²-19,R³-16), (I-P13447, A-14,R²-19,R³-17), (I-P13448,A-14,R²-19,R³-18), (I-P13449,A-14,R²-19, R³-19), (I-P13450, A-14,R²-19,R³-20), (I-P13451,A-14,R²-19,R³-21), (I-P13452,A-14,R²-19,R³-22), (I-P13453, A-14, R²-19,R³-23), (I-P13454,A-14,R²-19,R³-24), (I-P13455,A-14,R²-19,R³-25), (I-P13456, A-14,R²-19,R³-26), (I-P13457, A-14,R²-19,R³-27), (I-P13458,A-14,R²-19,R³-28), (I-P13459, A-14,R²-19,R³-29), (I-P13460,A-14,R²-19,R³-30), (I-P13461,A-14,R²-19,R³-31), (I-P13462, A-14,R²-19, R³-32), (I-P13463,A-14,R²-19,R³-33), (I-P13464,A-14,R²-19,R³-34), (I-P13465, A-14,R²-20,R³-1), (I-P13466,A-14, R²-20,R³-2), (I-P13467,A-14,R²-20,R³-3), (I-P13468, A-14, R²-20,R³-4), (I-P13469,A-14,R²-20,R³-5), (I-P13470,A-14, R²-20,R³-6), (I-P13471, A-14,R²-20,R³-7), (I-P13472,A-14, R²-20,R³-8), (I-P13473,A-14,R²-20,R³-9), (I-P13474, A-14, R²-20,R³-10), (I-P13475,A-14,R²-20,R³-11), (I-P13476,A-14,R²-20,R³-12), (I-P13477, A-14,R²-20,R³-13), (I-P13478, A-14,R²-20,R³-14), (I-P13479,A-14,R²-20,R³-15), (I-P13480, A-14,R²-20,R³-16), (I-P13481,A-14,R²-20,R³-17), (I-P13482,A-14,R²-20,R³-18), (I-P13483, A-14,R²-20, R³-19), (I-P13484,A-14,R²-20,R³-20), (I-P13485,A-14,R²-20,R³-21), (I-P13486, A-14,R²-20,R³-22), (I-P13487,A-14, R²-20,R³-23), (I-P13488,A-14,R²-20,R³-24), (I-P13489, A-14,R²-20,R³-25), (I-P13490,A-14,R²-20,R³-26), (I-P13491,A-14,R²-20,R³-27), (I-P13492, A-14,R²-20,R³-28), (I-P13493,A-14,R²-20,R³-29), (I-P13494,A-14,R²-20, R³-30), (I-P13495, A-14,R²-20,R³-31), (I-P13496,A-14,R²-20,R³-32), (I-P13497,A-14,R²-20,R³-33), (I-P13498, A-14, R²-20,R³-34), (I-P13499,A-14,R²-21,R³-1), (I-P13500,A-14,R²-21,R³-2), (I-P13501, A-14,R²-21,R³-3), (I-P13502,A-14,R²-21,R³-4), (I-P13503,A-14,R²-21,R³-5), (I-P13504, A-14,R²-21,R³-6), (I-P13505,A-14,R²-21,R³-7), (I-P13506, A-14,R²-21,R³-8), (I-P13507,A-14,R²-21,R³-9), (I-P13508, A-14,R²-21,R³-10), (I-P13509,A-14,R²-21,R³-11), (I-P13510, A-14,R²-21,R³-12), (I-P13511,A-14,R²-21,R³-13), (I-P13512,A-14,R²-21,R³-14), (I-P13513, A-14,R²-21, R³-15), (I-P13514,A-14,R²-21,R³-16), (I-P13515,A-14,R²-21,R³-17), (I-P13516, A-14,R²-21,R³-18), (I-P13517,A-14, R²-21,R³-19), (I-P13518,A-14,R²-21,R³-20), (I-P13519, A-14,R²-21,R³-21), (I-P13520,A-14,R²-21,R³-22), (I-P13521,A-14,R²-21,R³-23), (I-P13522, A-14,R²-21,R³-24), (I-P13523,A-14,R²-21,R³-25), (I-P13524,A-14,R²-21, R³-26), (I-P13525, A-14,R²-21,R³-27), (I-P13526,A-14,R²-21,R³-28), (I-P13527,A-14,R²-21,R³-29), (I-P13528, A-14, R²-21,R³-30), (I-P13529,A-14,R²-21,R³-31), (I-P13530,A-14,R²-21,R³-32), (I-P13531, A-14,R²-21,R³-33), (I-P13532, A-14,R²-21,R³-34), (I-P13533,A-14,R²-22,R³-1), (I-P13534, A-14,R²-22,R³-2), (I-P13535,A-14,R²-22,R³-3), (I-P13536,A-14,R²-22,R³-4), (I-P13537, A-14,R²-22,R³-5), (I-P13538,A-14,R²-22,R³-6), (I-P13539,A-14,R²-22,R³-7), (I-P13540, A-14,R²-22,R³-8), (I-P13541,A-14,R²-22,R³-9), (I-P13542, A-14,R²-22,R³-10), (I-P13543, A-14,R²-22,R³-11), (I-P13544,A-14,R²-22,R³-12), (I-P13545,A-14,R²-22, R³-13), (I-P13546, A-14,R²-22,R³-14), (I-P13547,A-14,R²-22,R³-15), (I-P13548,A-14,R²-22,R³-16), (I-P13549, A-14, R²-22,R³-17), (I-P13550,A-14,R²-22,R³-18), (I-P13551,A-14,R²-22,R³-19), (I-P13552, A-14,R²-22,R³-20), (I-P13553, A-14,R²-22,R³-21), (I-P13554,A-14,R²-22,R³-22), (I-P13555, A-14,R²-22,R³-23), (I-P13556,A-14,R²-22,R³-24), (I-P13557,A-14,R²-22,R³-25), (I-P13558, A-14,R²-22, R³-26), (I-P13559,A-14,R²-22,R³-27), (I-P13560,A-14,R²-22,R³-28), (I-P13561, A-14,R²-22,R³-29), (I-P13562,A-14, R²-22,R³-30), (I-P13563,A-14,R²-22,R³-31), (I-P13564, A-14,R²-22,R³-32), (I-P13565,A-14,R²-22,R³-33), (I-P13566,A-14,R²-22,R³-34), (I-P13567, A-14,R²-23,R³-1), (I-P13568,A-14,R²-23,R³-2), (I-P13569,A-14,R²-23,R³-3), (I-P13570, A-14,R²-23,R³-4), (I-P13571,A-14,R²-23,R³-5), (I-P13572,A-14,R²-23,R³-6), (I-P13573, A-14,R²-23,R³-7), (I-P13574,A-14,R²-23,R³-8), (I-P13575,A-14,R²-23,R³-9), (I-P13576, A-14,R²-23,R³-10), (I-P13577,A-14,R²-23, R³-11), (I-P13578,A-14,R²-23,R³-12), (I-P13579, A-14,R²-23,R³-13), (I-P13580,A-14,R²-23,R³-14), (I-P13581,A-14, R²-23,R³-15), (I-P13582, A-14,R²-23,R³-16), (I-P13583,A-14,R²-23,R³-17), (I-P13584,A-14,R²-23,R³-18), (I-P13585, A-14,R²-23,R³-19), (I-P13586,A-14,R²-23,R³-20), (I-P13587,A-14,R²-23,R³-21), (I-P13588, A-14,R²-23,R³-

22), (I-P13589,A-14,$R^2$-23,$R^3$-23), (I-P13590,A-14,$R^2$-23,$R^3$-24), (I-P13591, A-14,$R^2$-23,$R^3$-25), (I-P13592,A-14,$R^2$-23,$R^3$-26), (I-P13593,A-14,$R^2$-23,$R^3$-27), (I-P13594, A-14,$R^2$-23,$R^3$-28), (I-P13595,A-14,$R^2$-23,$R^3$-29), (I-P13596,A-14,$R^2$-23,$R^3$-30), (I-P13597, A-14,$R^2$-23,$R^3$-31), (I-P13598, A-14,$R^2$-23,$R^3$-32), (I-P13599,A-14,$R^2$-24,$R^3$-33), (I-P13600, A-14,$R^2$-23,$R^3$-34), (I-P13601,A-14,$R^2$-24,$R^3$-1), (I-P13602,A-14,$R^2$-24,$R^3$-2), (I-P13603, A-14,$R^2$-24,$R^3$-3), (I-P13604,A-14,$R^2$-24,$R^3$-4), (I-P13605,A-14,$R^2$-24,$R^3$-5), (I-P13606, A-14,$R^2$-24,$R^3$-6), (I-P13607,A-14,$R^2$-24,$R^3$-7), (I-P13608,A-14,$R^2$-24,$R^3$-8), (I-P13609, A-14,$R^2$-24,$R^3$-9), (I-P135610,A-14,$R^2$-24,$R^3$-10), (I-P13611,A-14,$R^2$-24,$R^3$-11), (I-P13612, A-14,$R^2$-24,$R^3$-12), (I-P13613,A-14,$R^2$-24,$R^3$-13), (I-P13614,A-14,$R^2$-24,$R^3$-14), (I-P13615, A-14,$R^2$-24,$R^3$-15), (I-P13616,A-14,$R^2$-24,$R^3$-16), (I-P13617,A-14,$R^2$-24,$R^3$-17), (I-P13618, A-14,$R^2$-24,$R^3$-18), (I-P13619, A-14,$R^2$-24,$R^3$-19), (I-P13620,A-14,$R^2$-24,$R^3$-20), (I-P13621, A-14,$R^2$-24,$R^3$-21), (I-P13622,A-14,$R^2$-24,$R^3$-22), (I-P13623,A-14,$R^2$-24,$R^3$-23), (I-P13624, A-14,$R^2$-24,$R^3$-24), (I-P13625,A-14,$R^2$-24,$R^3$-25), (I-P13626,A-14,$R^2$-24,$R^3$-26), (I-P13627, A-14,$R^2$-24,$R^3$-27), (I-P13628,A-14,$R^2$-24,$R^3$-28), (I-P13629,A-14,$R^2$-24,$R^3$-29), (I-P13630, A-14,$R^2$-24,$R^3$-30), (I-P13631,A-14,$R^2$-24,$R^3$-31), (I-P13632,A-14,$R^2$-24,$R^3$-32), (I-P13633, A-14,$R^2$-24,$R^3$-33), (I-P13634,A-14,$R^2$-24,$R^3$-34), (I-P13635,A-14,$R^2$-25,$R^3$-1), (I-P13636, A-14,$R^2$-25,$R^3$-2), (I-P13637,A-14,$R^2$-25,$R^3$-3), (I-P13638,A-14,$R^2$-25,$R^3$-4), (I-P13639, A-14,$R^2$-25,$R^3$-5), (I-P13640,A-14,$R^2$-25,$R^3$-6), (I-P13641,A-14,$R^2$-25,$R^3$-7), (I-P13642, A-14,$R^2$-25,$R^3$-8), (I-P13643,A-14,$R^2$-25,$R^3$-9), (I-P13644,A-14,$R^2$-25,$R^3$-10), (I-P13645, A-14,$R^2$-25,$R^3$-11), (I-P13646,A-14,$R^2$-25,$R^3$-12), (I-P13647,A-14,$R^2$-25,$R^3$-13), (I-P13648, A-14,$R^2$-25,$R^3$-14), (I-P13649,A-14,$R^2$-25,$R^3$-15), (I-P13650,A-14,$R^2$-25,$R^3$-16), (I-P13651, A-14,$R^2$-25,$R^3$-17), (I-P13652,A-14,$R^2$-25,$R^3$-18), (I-P13653,A-14,$R^2$-25,$R^3$-19), (I-P13654, A-14,$R^2$-25,$R^3$-20), (I-P13655,A-14,$R^2$-25,$R^3$-21), (I-P13656,A-14,$R^2$-25,$R^3$-22), (I-P13657, A-14,$R^2$-25,$R^3$-23), (I-P13658,A-14,$R^2$-25,$R^3$-24), (I-P13659,A-14,$R^2$-25,$R^3$-25), (I-P13660, A-14,$R^2$-25,$R^3$-26), (I-P13661,A-14,$R^2$-25,$R^3$-27), (I-P13662,A-14,$R^2$-25,$R^3$-28), (I-P13663, A-14,$R^2$-25,$R^3$-29), (I-P13664, A-14,$R^2$-25,$R^3$-30), (I-P13665,A-14,$R^2$-25,$R^3$-31), (I-P13666, A-14,$R^2$-25,$R^3$-32), (I-P13667,A-14,$R^2$-25,$R^3$-33), (I-P13668,A-14,$R^2$-25,$R^3$-34), (I-P13669, A-14,$R^2$-26,$R^3$-1), (I-P13670,A-14,$R^2$-26,$R^3$-2), (I-P13671,A-14,$R^2$-26,$R^3$-3), (I-P13672, A-14,$R^2$-26,$R^3$-4), (I-P13673,A-14,$R^2$-26,$R^3$-5), (I-P13674,A-14,$R^2$-26,$R^3$-6), (I-P13675, A-14,$R^2$-26,$R^3$-7), (I-P13676,A-14,$R^2$-26,$R^3$-8), (I-P13677,A-14,$R^2$-26,$R^3$-9), (I-P13678, A-14,$R^2$-26,$R^3$-10), (I-P13679,A-14,$R^2$-26,$R^3$-11), (I-P13680,A-14,$R^2$-26,$R^3$-12), (I-P13681, A-14,$R^2$-26,$R^3$-13), (I-P13682,A-14,$R^2$-26,$R^3$-14), (I-P13683,A-14,$R^2$-26,$R^3$-15), (I-P13684, A-14,$R^2$-26,$R^3$-16), (I-P13685, A-14,$R^2$-26,$R^3$-17), (I-P13686,A-14,$R^2$-26,$R^3$-16), (I-P13687, A-14,$R^2$-26,$R^3$-19), (I-P13688,A-14,$R^2$-26,$R^3$-20), (I-P13689,A-14,$R^2$-26,$R^3$-21), (I-P13690, A-14,$R^2$-26,$R^3$-22), (I-P13691,A-14,$R^2$-26,$R^3$-23), (I-P13692,A-14,$R^2$-26,$R^3$-24), (I-P13693, A-14,$R^2$-26,$R^3$-25), (I-P13694,A-14,$R^2$-26,$R^3$-26), (I-P13695,A-14,$R^2$-26,$R^3$-27), (I-P13696, A-14,$R^2$-26,$R^3$-28), (I-P13697,A-14,$R^2$-26,$R^3$-29), (I-P13698,A-14,$R^2$-26,$R^3$-30), (I-P13699, A-14,$R^2$-26,$R^3$-31), (I-P13700,A-14,$R^2$-26,$R^3$-32), (I-P13701,A-14,$R^2$-26,$R^3$-33), (I-P13702, A-14,$R^2$-26,$R^3$-34), (I-P13703,A-14,$R^2$-27,$R^3$-1), (I-P13704,A-14,$R^2$-27,$R^3$-2), (I-P13705, A-14,$R^2$-27,$R^3$-3), (I-P13706,A-14,$R^2$-27,$R^3$-4), (I-P13707,A-14,$R^2$-27,$R^3$-5), (I-P13708, A-14,$R^2$-27,$R^3$-6), (I-P13709,A-14,$R^2$-27,$R^3$-7), (I-P13710,A-14,$R^2$-27,$R^3$-8), (I-P13711, A-14,$R^2$-27,$R^3$-9), (I-P13712,A-14,$R^2$-27,$R^3$-10), (I-P13713,A-14,$R^2$-27,$R^3$-11), (I-P13714, A-14,$R^2$-27,$R^3$-12), (I-P13715,A-14,$R^2$-27,$R^3$-13), (I-P13716,A-14,$R^2$-27,$R^3$-14), (I-P13717, A-14,$R^2$-27,$R^3$-15), (I-P13718,A-14,$R^2$-27,$R^3$-16), (I-P13719,A-14,$R^2$-27,$R^3$-17), (I-P13720, A-14,$R^2$-27,$R^3$-18), (I-P13721,A-14,$R^2$-27,$R^3$-19), (I-P13722,A-14,$R^2$-27,$R^3$-20), (I-P13723, A-14,$R^2$-27,$R^3$-21), (I-P13724,A-14,$R^2$-27,$R^3$-22), (I-P13725,A-14,$R^2$-27,$R^3$-23), (I-P13726, A-14,$R^2$-27,$R^3$-24), (I-P13727,A-14,$R^2$-27,$R^3$-25), (I-P13728,A-14,$R^2$-27,$R^3$-26), (I-P13729,A-14,$R^2$-27,$R^3$-27), (I-P13730, A-14,$R^2$-27,$R^3$-28), (I-P13731,A-14,$R^2$-27,$R^3$-29), (I-P13732, A-14,$R^2$-27,$R^3$-30), (I-P13733,A-14,$R^2$-27,$R^3$-31), (I-P13734,A-14,$R^2$-27,$R^3$-32), (I-P13735, A-14,$R^2$-27,$R^3$-33), (I-P13736,A-14,$R^2$-27,$R^3$-34), (I-P13737,A-14,$R^2$-28,$R^3$-1), (I-P13738, A-14,$R^2$-28,$R^3$-2), (I-P13739,A-14,$R^2$-28,$R^3$-3), (I-P13740,A-14,$R^2$-28,$R^3$-4), (I-P13751, A-14,$R^2$-28,$R^3$-5), (I-P13742,A-14,$R^2$-28,$R^3$-6), (I-P13743,A-14,$R^2$-28,$R^3$-7), (I-P13744, A-14,$R^2$-28,$R^3$-8), (I-P13745,A-14,$R^2$-28,$R^3$-9), (I-P13746,A-14,$R^2$-28,$R^3$-10), (I-P13747, A-14,$R^2$-28,$R^3$-11), (I-P13748,A-14,$R^2$-28,$R^3$-12), (I-P13749,A-14,$R^2$-28,$R^3$-13), (I-P13750, A-14,$R^2$-28,$R^3$-14), (I-P13751, A-14,$R^2$-28,$R^3$-15), (I-P13752,A-14,$R^2$-28,$R^3$-16), (I-P13753, A-14,$R^2$-28,$R^3$-17), (I-P13754,A-14,$R^2$-28,$R^3$-18), (I-P13755,A-14,$R^2$-28,$R^3$-19), (I-P13756, A-14,$R^2$-28,$R^3$-20), (I-P13757,A-14,$R^2$-28,$R^3$-21), (I-P13758,A-14,$R^2$-28,$R^3$-22), (I-P13759, A-14,$R^2$-28,$R^3$-23), (I-P13760,A-14,$R^2$-28,$R^3$-24), (I-P13761,A-14,$R^2$-28,$R^3$-25), (I-P13762, A-14,$R^2$-28,$R^3$-26), (I-P13763,A-14,$R^2$-28,$R^3$-27), (I-P13764,A-14,$R^2$-28,$R^3$-28), (I-P13765, A-14,$R^2$-28,$R^3$-29), (I-P13766,A-14,$R^2$-28,$R^3$-30), (I-P13767,A-14,$R^2$-28,$R^3$-31), (I-P13768, A-14,$R^2$-28,$R^3$-32), (I-P13769,A-14,$R^2$-28,$R^3$-33), (I-P13770,A-14,$R^2$-28,$R^3$-34), (I-P13771, A-14,$R^2$-29,$R^3$-1), (I-P13772,A-14,$R^2$-29,$R^3$-2), (I-P13773,A-14,$R^2$-29,$R^3$-3), (I-P13774, A-14,$R^2$-29,$R^3$-4), (I-P13775,A-14,$R^2$-29,$R^3$-5), (I-P13776,A-14,$R^2$-29,$R^3$-6), (I-P13777, A-14,$R^2$-29,$R^3$-7), (I-P13778,A-14,$R^2$-29,$R^3$-8), (I-P13779,A-4,$R^2$-29,$R^3$-9), (I-P13780, A-14,$R^2$-29,$R^3$-10), (I-P13781,A-14,$R^2$-29,$R^3$-11), (I-P13782,A-14,$R^2$-29,$R^3$-12), (I-P13783, A-14,$R^2$-29,$R^3$-13), (I-P13784,A-14,$R^2$-29,$R^3$-14), (I-P13785,A-14,$R^2$-29,$R^3$-15), (I-P13786, A-14,$R^2$-29,$R^3$-16), (I-P13787,A-14,$R^2$-29,$R^3$-17), (I-P13788,A-14,$R^2$-29,$R^3$-18), (I-P13789, A-14,$R^2$-29,$R^3$-19), (I-P13790,A-14,$R^2$-29,$R^3$-20), (I-P13791,A-14,$R^2$-29,$R^3$-21), (I-P13792, A-14,$R^2$-29,$R^3$-22), (I-P13793,A-14,$R^2$-29,$R^3$-23), (I-P13794,A-14,$R^2$-29,$R^3$-24), (I-P13795, A-14,$R^2$-29,$R^3$-25), (I-P13796, A-14,$R^2$-29,$R^3$-26), (I-P13797,A-14,$R^2$-29,$R^3$-27), (I-P13798, A-14,$R^2$-29,$R^3$-28), (I-P13799,A-14,$R^2$-29,$R^3$-29), (I-P13800,A-14,$R^2$-29,$R^3$-30), (I-P13801, A-14,$R^2$-29,$R^3$-31), (I-P13802,A-14,$R^2$-29,$R^3$-32), (I-P13803,A-14,$R^2$-29,$R^3$-33), (I-P13804, A-14,$R^2$-29,$R^3$-34), (I-P13805,A-15,$R^2$-1,$R^3$-1), (I-P13806,A-15,$R^2$-1,$R^3$-2), (I-P13807, A-15,$R^2$-1,$R^3$-3), (I-P13808,A-15,$R^2$-1,$R^3$-4), (I-P13809,A-15,$R^2$-1,$R^3$-5), (I-P13810, A-15,$R^2$-1,$R^3$-6), (I-P13811,A-15,$R^2$-1,$R^3$-7), (I-P13812,A-15,$R^2$-1,$R^3$-8), (I-P13813, A-15,$R^2$-1,$R^3$-9), (I-P13814,A-15,$R^2$-1,$R^3$-10), (I-P13815,A-15,$R^2$-1,$R^3$-11), (I-P13816, A-15,$R^2$-1,$R^3$-12), (I-P13817,A-15,$R^2$-1,$R^3$-13), (I-P13818,A-15,$R^2$-1,$R^3$-14), (I-P13819, A-15,$R^2$-1,$R^3$-15), (I-P13820,A-15,$R^2$-1,$R^3$-16), (I-P13821,A-15,$R^2$-1,$R^3$-17), (I-P13822,A-15,$R^2$-1,$R^3$-18), (I-P13823,A-15,$R^2$-1,$R^3$-19), (I-P13824,A-15,$R^2$-1,$R^3$-20), (I-P13825,A-15,$R^2$-1,$R^3$-21), (I-P13826,A-15,$R^2$-1,$R^3$-22), (I-P13827,A-15,$R^2$-1,$R^3$-23), (I-P13828,A-15,$R^2$-1,$R^3$-24), (I-P13829,A-15,$R^2$-1,$R^3$-25), (I-P13830,A-15,$R^2$-1,$R^3$-26), (I-P13831,A-15,$R^2$-1,$R^3$-27), (I-P13832,A-15,$R^2$-1,$R^3$-28), (I-P13833,A-15,$R^2$-1,$R^3$-29), (I-P13834,A-15,$R^2$-1,$R^3$-30), (I-P13835,A-15,$R^2$-1,$R^3$-31), (I-P13836,A-15,$R^2$-1,$R^3$-32), (I-P13837,A-15,$R^2$-1,$R^3$-33), (I-P13838,A-15,$R^2$-1,$R^3$-34), (I-P13839,A-15,$R^2$-2,$R^3$-1), (I-P13840, A-15,$R^2$-2,$R^3$-2), (I-P13841,A-15,$R^2$-2,$R^3$-3), (I-P13842,A-15,$R^2$-2,$R^3$-4), (I-P13843, A-15, $R^2$-2,$R^3$-5), (I-P13844,A-15,$R^2$-2,$R^3$-6), (I-P13845,A-15, $R^2$-2,$R^3$-7), (I-P13846, A-15,$R^2$-2,$R^3$-8), (I-P13847,A-15, $R^2$-2,$R^3$-9), (I-P13848,A-15,$R^2$-2,$R^3$-10), (I-P13849, A-15, $R^2$-2,$R^3$-11), (I-P13850,A-15,$R^2$-2,$R^3$-12), (I-P13851,A-15, $R^2$-2,$R^3$-13), (I-P13852,A-15,$R^2$-2,$R^3$-14), (I-P13853,A-15, $R^2$-2,$R^3$-15), (I-P13854,A-15,$R^2$-2,$R^3$-16), (I-P13855,A-15, $R^2$-2,$R^3$-17), (I-P13856,A-15,$R^2$-2,$R^3$-18), (I-P13857,A-15, $R^2$-2,$R^3$-19), (I-P13858, A-15,$R^2$-2,$R^3$-20), (I-P13859,A-15, $R^2$-2,$R^3$-21), (I-P13860,A-15,$R^2$-2,$R^3$-22), (I-P13861, A-15, $R^2$-2,$R^3$-23), (I-P13862,A-15,$R^2$-2,$R^3$-24), (I-P13863,A-15, $R^2$-2,$R^3$-25), (I-P13864, A-15,$R^2$-2,$R^3$-26), (I-P13865,A-15, $R^2$-2,$R^3$-27), (I-P13866,A-15,$R^2$-2,$R^3$-28), (I-P13867,A-15, $R^2$-2,$R^3$-29), (I-P13868,A-15,$R^2$-2,$R^3$-30), (I-P13869,A-15, $R^2$-2,$R^3$-31), (I-P13870, A-15,$R^2$-2,$R^3$-32), (I-P13871,A-15, $R^2$-2,$R^3$-33), (I-P13872,A-15,$R^2$-3,$R^3$-34), (I-P13873, A-15, $R^2$-3,$R^3$-1), (I-P13874,A-15,$R^2$-3,$R^3$-2), (I-P13875,A-15, $R^2$-3,$R^3$-3), (I-P13876, A-15,$R^2$-3,$R^3$-4), (I-P13877,A-15, $R^2$-3,$R^3$-5), (I-P13878,A-15,$R^2$-3,$R^3$-6), (I-P13879, A-15, $R^2$-3,$R^3$-7), (I-P13880,A-15,$R^2$-2,$R^3$-8), (I-P13881,A-15, $R^2$-3,$R^3$-9), (I-P13882, A-15,$R^2$-3,$R^3$-10), (I-P13883,A-15, $R^2$-2,$R^3$-11), (I-P13884,A-15,$R^2$-3,$R^3$-12), (I-P13885,A-15, $R^2$-3,$R^3$-13), (I-P13886,A-15,$R^2$-2,$R^3$-14), (I-P13887,A-15, $R^2$-3,$R^3$-15), (I-P13888, A-15,$R^2$-3,$R^3$-16), (I-P13889,A-15, $R^2$-2,$R^3$-17), (I-P13890,A-15,$R^2$-3,$R^3$-18), (I-P13891,A-15, $R^2$-3,$R^3$-19), (I-P13892,A-15,$R^2$-2,$R^3$-20), (I-P13892,A-15, $R^2$-3,$R^3$-21), (I-P13894, A-15,$R^2$-3,$R^3$-22), (I-P13895,A-15, $R^2$-2,$R^3$-23), (I-P13896,A-15,$R^2$-3,$R^3$-24), (I-P13897,A-15, $R^2$-3,$R^3$-25), (I-P13898,A-15,$R^2$-2,$R^3$-26), (I-P13899,A-15, $R^2$-3,$R^3$-27), (I-P13900, A-15,$R^2$-3,$R^3$-28), (I-P13901,A-15, $R^2$-2,$R^3$-29), (I-P13902,A-15,$R^2$-3,$R^3$-30), (I-P13903, A-15, $R^2$-3,$R^3$-31), (I-P13904,A-15,$R^2$-2,$R^3$-32), (I-P13905,A-15, $R^2$-3,$R^3$-33), (I-P13906, A-15,$R^2$-3,$R^3$-34), (I-P13907,A-15, $R^2$-4,$R^3$-1), (I-P13908,A-15,$R^2$-4,$R^3$-2), (I-P13909, A-15, $R^2$-4,$R^3$-3), (I-P13910,A-15,$R^2$-4,$R^3$-4), (I-P13911,A-15, $R^2$-4,$R^3$-5), (I-P13912, A-15,$R^2$-4,$R^3$-6), (I-P13913,A-15, $R^2$-4,$R^3$-7), (I-P13914,A-15,$R^2$-4,$R^3$-8), (I-P13915, A-15, $R^2$-4,$R^3$-9), (I-P13916,A-15,$R^2$-4,$R^3$-10), (I-P13917,A-15, $R^2$-4,$R^3$-11), (I-P13918, A-15,$R^2$-4,$R^3$-12), (I-P13919,A-15, $R^2$-4,$R^3$-13), (I-P13920,A-15,$R^2$-4,$R^3$-14), (I-P13921,A-15, $R^2$-4,$R^3$-15), (I-P13922,A-15,$R^2$-4,$R^3$-16), (I-P13923,A-15, $R^2$-4,$R^3$-17), (I-P13924, A-15,$R^2$-4,$R^3$-18), (I-P13925,A-15, $R^2$-4,$R^3$-19), (I-P13926,A-15,$R^2$-4,$R^3$-20), (I-P13927, A-15, $R^2$-4,$R^3$-21), (I-P13928,A-15,$R^2$-4,$R^3$-22), (I-P13929, A-15, $R^2$-4,$R^3$-23), (I-P13930, A-15,$R^2$-4,$R^3$-24), (I-P13931,A-15, $R^2$-4,$R^3$-25), (I-P13932,A-15,$R^2$-4,$R^3$-26), (I-P13933, A-15, $R^2$-4,$R^3$-27), (I-P13934,A-15,$R^2$-4,$R^3$-28), (I-P13935,A-15, $R^2$-4,$R^3$-29), (I-P13936, A-15,$R^2$-4,$R^3$-30), (I-P13937,A-15, $R^2$-4,$R^3$-31), (I-P13938,A-15,$R^2$-4,$R^3$-32), (I-P13939,A-15, $R^2$-4,$R^3$-33), (I-P13940,A-15,$R^2$-4,$R^3$-34), (I-P13941,A-15, $R^2$-5,$R^3$-1), (I-P13942, A-15,$R^2$-5,$R^3$-2), (I-P13943,A-15, $R^2$-5,$R^3$-3), (I-P13944,A-15,$R^2$-5,$R^3$-4), (I-P13945, A-15, $R^2$-5,$R^3$-5), (I-P13946,A-15,$R^2$-5,$R^3$-6), (I-P13947,A-15, $R^2$-5,$R^3$-7), (I-P13948, A-15,$R^2$-5,$R^3$-8), (I-P13949,A-15, $R^2$-5,$R^3$-9), (I-P13950,A-15,$R^2$-5,$R^3$-10), (I-P13951, A-15, $R^2$-5,$R^3$-11), (I-P13952,A-15,$R^2$-5,$R^3$-12), (I-P13953,A-15, $R^2$-5,$R^3$-13), (I-P13954,A-15,$R^2$-5,$R^3$-14), (I-P13955,A-15, $R^2$-5,$R^3$-15), (I-P13956,A-15,$R^2$-5,$R^3$-16), (I-P13957,A-15, $R^2$-5,$R^3$-17), (I-P13958,A-15,$R^2$-5,$R^3$-18), (I-P13959,A-15, $R^2$-5,$R^3$-19), (I-P13960, A-15,$R^2$-5,$R^3$-20), (I-P13961,A-15, $R^2$-5,$R^3$-21), (I-P13962,A-15,$R^2$-5,$R^3$-22), (I-P13963, A-15, $R^2$-5,$R^3$-23), (I-P13964,A-15,$R^2$-5,$R^3$-24), (I-P13965,A-15, $R^2$-5,$R^3$-25), (I-P13966,A-15,$R^2$-5,$R^3$-26), (I-P13967,A-15, $R^2$-5,$R^3$-27), (I-P13968,A-15,$R^2$-5,$R^3$-28), (I-P13969,A-15, $R^2$-5,$R^3$-29), (I-P13970, A-15,$R^2$-5,$R^3$-30), (I-P13971,A-15, $R^2$-5,$R^3$-31), (I-P13972,A-15,$R^2$-5,$R^3$-32), (I-P13973,A-15, $R^2$-5,$R^3$-33), (I-P13974,A-15,$R^2$-5,$R^3$-34), (I-P13975,A-15, $R^2$-6,$R^3$-1), (I-P13976,A-15,$R^2$-6,$R^3$-2), (I-P13977,A-15, $R^2$-6,$R^3$-3), (I-P13978, A-15,$R^2$-6,$R^3$-4), (I-P13979,A-15, $R^2$-6,$R^3$-5), (I-P13980,A-15,$R^2$-6,$R^3$-6), (I-P13981, A-15, $R^2$-6,$R^3$-7), (I-P13982,A-15,$R^2$-6,$R^3$-8), (I-P13983,A-15, $R^2$-6,$R^3$-9), (I-P13984, A-15,$R^2$-6,$R^3$-10), (I-P13985,A-15, $R^2$-6,$R^3$-11), (I-P13986,A-15,$R^2$-6,$R^3$-12), (I-P13987,A-15, $R^2$-6,$R^3$-13), (I-P13988,A-15,$R^2$-6,$R^3$-14), (I-P13989,A-15, $R^2$-6,$R^3$-15), (I-P13990, A-15,$R^2$-6,$R^3$-16), (I-P13991,A-15, $R^2$-6,$R^3$-17), (I-P13992,A-15,$R^2$-6,$R^3$-18), (I-P13993, A-15, $R^2$-6,$R^3$-19), (I-P13994,A-15,$R^2$-6,$R^3$-20), (I-P13995,A-15, $R^2$-6,$R^3$-21), (I-P13996, A-15,$R^2$-6,$R^3$-22), (I-P13997,A-15, $R^2$-6,$R^3$-23), (I-P13998,A-15,$R^2$-6,$R^3$-24), (I-P13999,A-15, $R^2$-6,$R^3$-25), (I-P14000,A-15,$R^2$-6,$R^3$-26), (I-P14001,A-15, $R^2$-6,$R^3$-27), (I-P14002, A-15,$R^2$-6,$R^3$-28), (I-P14003,A-15, $R^2$-6,$R^3$-29), (I-P14004,A-15,$R^2$-6,$R^3$-30), (I-P14005,A-15, $R^2$-6,$R^3$-31), (I-P14006,A-15,$R^2$-6,$R^3$-32), (I-P14007,A-15, $R^2$-6,$R^3$-33), (I-P14008,A-15,$R^2$-6,$R^3$-34), (I-P14009,A-15, $R^2$-7,$R^3$-1), (I-P14010,A-15,$R^2$-7,$R^3$-2), (I-P14011, A-15, $R^2$-7,$R^3$-3), (I-P14012,A-15,$R^2$-7,$R^3$-4), (I-P14013,A-15, $R^2$-7,$R^3$-5), (I-P14014, A-15,$R^2$-7,$R^3$-6), (I-P14015,A-15, $R^2$-7,$R^3$-7), (I-P14016,A-15,$R^2$-7,$R^3$-8), (I-P14017, A-15, $R^2$-7,$R^3$-9), (I-P14018,A-15,$R^2$-7,$R^3$-10), (I-P14019,A-15, $R^2$-7,$R^3$-11), (I-P14020, A-15,$R^2$-7,$R^3$-12), (I-P14021,A-15, $R^2$-7,$R^3$-13), (I-P14022,A-15,$R^2$-7,$R^3$-14), (I-P14023,A-15, $R^2$-7,$R^3$-15), (I-P14024,A-15,$R^2$-7,$R^3$-16), (I-P14025,A-15, $R^2$-7,$R^3$-17), (I-P14026, A-15,$R^2$-7,$R^3$-18), (I-P14027,A-15, $R^2$-7,$R^3$-19), (I-P14028,A-15,$R^2$-7,$R^3$-20), (I-P14029,A-15, $R^2$-7,$R^3$-21), (I-P14030,A-15,$R^2$-7,$R^3$-22), (I-P14031,A-15, $R^2$-7,$R^3$-23), (I-P14032, A-15,$R^2$-7,$R^3$-24), (I-P14033,A-15, $R^2$-7,$R^3$-25), (I-P14034,A-15,$R^2$-7,$R^3$-26), (I-P14035,A-15, $R^2$-7,$R^3$-27), (I-P14036,A-15,$R^2$-7,$R^3$-28), (I-P14037,A-15, $R^2$-7,$R^3$-29), (I-P14038, A-15,$R^2$-7,$R^3$-30), (I-P14039,A-15, $R^2$-7,$R^3$-31), (I-P14040,A-15,$R^2$-7,$R^3$-32), (I-P14041, A-15, $R^2$-7,$R^3$-33), (I-P14042,A-15,$R^2$-7,$R^3$-34), (I-P14043,A-15, $R^2$-8,$R^3$-1), (I-P14044, A-15,$R^2$-8,$R^3$-2), (I-P14045,A-15, $R^2$-8,$R^3$-3), (I-P14046,A-15,$R^2$-8,$R^3$-4), (I-P14047, A-15, $R^2$-8,$R^3$-5), (I-P14048,A-15,$R^2$-8,$R^3$-6), (I-P14049,A-15, $R^2$-8,$R^3$-7), (I-P14050, A-15,$R^2$-8,$R^3$-8), (I-P14051,A-15, $R^2$-8,$R^3$-9), (I-P14052,A-15,$R^2$-8,$R^3$-10), (I-P14053, A-15, $R^2$-8,$R^3$-11), (I-P14054,A-15,$R^2$-8,$R^3$-12), (I-P14055,A-15, $R^2$-8,$R^3$-13), (I-P14056,A-15,$R^2$-8,$R^3$-14), (I-P14057,A-15, $R^2$-8,$R^3$-15), (I-P14058,A-15,$R^2$-8,$R^3$-16), (I-P14059,A-15, $R^2$-8,$R^3$-17), (I-P14060,A-15,$R^2$-8,$R^3$-18), (I-P14061,A-15, $R^2$-8,$R^3$-19), (I-P14062, A-15,$R^2$-8,$R^3$-20), (I-P14063,A-15, $R^2$-8,$R^3$-21), (I-P14064,A-15,$R^2$-8,$R^3$-22), (I-P14065, A-15, $R^2$-8,$R^3$-23), (I-P14066,A-15,$R^2$-8,$R^3$-24), (I-P14067,A-15, $R^2$-8,$R^3$-25), (I-P14068,A-15,$R^2$-8,$R^3$-26), (I-P14069,A-15, $R^2$-8,$R^3$-27), (I-P14070,A-15,$R^2$-8,$R^3$-28), (I-P14071,A-15, $R^2$-8,$R^3$-29), (I-P14072,A-15,$R^2$-8,$R^3$-30), (I-P14073,A-15, $R^2$-8,$R^3$-31), (I-P14074, A-15,$R^2$-8,$R^3$-32), (I-P14075,A-15, $R^2$-8,$R^3$-33), (I-P14076,A-15,$R^2$-8,$R^3$-34), (I-P14077,A-15, $R^2$-9,$R^3$-1), (I-P14078,A-15,$R^2$-9,$R^3$-2), (I-P14079, A-15, $R^2$-9,$R^3$-3), (I-P14080, A-15,$R^2$-9,$R^3$-4), (I-P14081,A-15, $R^2$-9,$R^3$-5), (I-P14082,A-15,$R^2$-9,$R^3$-6), (I-P14083, A-15, $R^2$-9,$R^3$-7), (I-P14084,A-15,$R^2$-9,$R^3$-8), (I-P14085,A-15, $R^2$-9,$R^3$-9), (I-P14086, A-15,$R^2$-9,$R^3$-10), (I-P14087,A-15, $R^2$-9,$R^3$-11), (I-P14088,A-15,$R^2$-9,$R^3$-12), (I-P14089,A-15, $R^2$-9,$R^3$-13), (I-P14090,A-15,$R^2$-9,$R^3$-14), (I-P14091,A-15, $R^2$-9,$R^3$-15), (I-P14092,A-15,$R^2$-9,$R^3$-16), (I-P14093,A-15, $R^2$-9,$R^3$-17), (I-P14094,A-15,$R^2$-9,$R^3$-18), (I-P14095, A-15, $R^2$-9,$R^3$-19), (I-P14096,A-15,$R^2$-9,$R^3$-20), (I-P14097,A-15, $R^2$-9,$R^3$-21), (I-P14098,A-15,$R^2$-9,$R^3$-22), (I-P14099,A-15, $R^2$-9,$R^3$-23), (I-P14100,A-15,$R^2$-9,$R^3$-24), (I-P14101,A-15, $R^2$-9,$R^3$-25), (I-P14102,A-15,$R^2$-9,$R^3$-26), (I-P14103,A-15, $R^2$-9,$R^3$-27), (I-P14104,A-15,$R^2$-9,$R^3$-28), (I-P14105,A-15, $R^2$-9,$R^3$-29), (I-P14106,A-15,$R^2$-9,$R^3$-30), (I-P14107,A-15, $R^2$-9,$R^3$-31), (I-P14108,A-15,$R^2$-9,$R^3$-32), (I-P14109,A-15, $R^2$-9,$R^3$-33), (I-P14110, A-15,$R^2$-9,$R^3$-34), (I-P14111, A-15, $R^2$-10,$R^3$-1), (I-P14112,A-15,$R^2$-10,$R^3$-2), (I-P14113, A-15, $R^2$-10,$R^3$-3), (I-P14114,A-15,$R^2$-10,$R^3$-4), (I-P14115,A-15, $R^2$-10,$R^3$-5), (I-P14116, A-15,$R^2$-10,$R^3$-6), (I-P14117,A-15, $R^2$-10,$R^3$-7), (I-P14118, A-15,$R^2$-10,$R^3$-8), (I-P14119, A-15, $R^2$-10,$R^3$-9), (I-P14120,A-15,$R^2$-10,$R^3$-10), (I-P14121,A-15,$R^2$-10,$R^3$-11), (I-P14122, A-15,$R^2$-10,$R^3$-12), (I-P14123, A-15,$R^2$-10,$R^3$-13), (I-P14124,A-15,$R^2$-10,$R^3$-14), (I-P14125, A-15,$R^2$-10,$R^3$-15), (I-P14126,A-15,$R^2$-10,$R^3$-16), (I-P14127,A-15,$R^2$-10,$R^3$-17), (I-P14128, A-15,$R^2$-10, $R^3$-18), (I-P14129,A-15,$R^2$-10,$R^3$-19), (I-P14130,A-15,$R^2$-10,$R^3$-20), (I-P14131, A-15,$R^2$-10,$R^3$-21), (I-P14132,A-15, $R^2$-10,$R^3$-22), (I-P14133,A-15,$R^2$-10,$R^3$-23), (I-P14134, A-15,$R^2$-10,$R^3$-24), (I-P14135,A-15,$R^2$-10,$R^3$-25), (I-P14136,A-15,$R^2$-10,$R^3$-26), (I-P14137, A-15,$R^2$-10,$R^3$-27), (I-P14138,A-15,$R^2$-10,$R^3$-28), (I-P14139,A-15,$R^2$-10, $R^3$-29), (I-P14140, A-15,$R^2$-10,$R^3$-30), (I-P14141,A-15,$R^2$-10,$R^3$-31), (I-P14142,A-15,$R^2$-10,$R^3$-32), (I-P14143, A-15, $R^2$-10,$R^3$-33), (I-P14144,A-15,$R^2$-10,$R^3$-34), (I-P14145,A-15,$R^2$-11,$R^3$-1), (I-P14146, A-15,$R^2$-11,$R^3$-2), (I-P14147,A-15,$R^2$-11,$R^3$-3), (I-P14148,A-15,$R^2$-11,$R^3$-4), (I-P14149, A-15,$R^2$-11,$R^3$-5), (I-P14150,A-15,$R^2$-11,$R^3$-6), (I-P14151, A-15,$R^2$-11,$R^3$-7), (I-P14152, A-15,$R^2$-11,$R^3$-8), (I-P14153, A-15,$R^2$-11,$R^3$-9), (I-P14154,A-15,$R^2$-11,$R^3$-10), (I-P14155, A-15,$R^2$-11,$R^3$-11), (I-P14156,A-15,$R^2$-11,$R^3$-12), (I-P14157,A-15,$R^2$-11,$R^3$-13), (I-P14158, A-15,$R^2$-11, $R^3$-14), (I-P14159,A-15,$R^2$-11,$R^3$-15), (I-P14160,A-15,$R^2$-11,$R^3$-16), (I-P14161, A-15,$R^2$-11,$R^3$-17), (I-P14162,A-15, $R^2$-11,$R^3$-18), (I-P14163, A-15,$R^2$-11,$R^3$-19), (I-P14164, A-15,$R^2$-11,$R^3$-20), (I-P14165,A-15,$R^2$-11,$R^3$-21), (I-P14166,A-15,$R^2$-11,$R^3$-22), (I-P14167, A-15,$R^2$-11,$R^3$-23), (I-P14168,A-15,$R^2$-11,$R^3$-24), (I-P14169,A-15,$R^2$-11, $R^3$-25), (I-P14170, A-15,$R^2$-11,$R^3$-26), (I-P14171,A-15,$R^2$-11,$R^3$-27), (I-P14172,A-15,$R^2$-11,$R^3$-28), (I-P14173, A-15, $R^2$-11,$R^3$-29), (I-P14174,A-15,$R^2$-11,$R^3$-30), (I-P14175,A-15,$R^2$-11,$R^3$-31), (I-P14176,A-15,$R^2$-11,$R^3$-32), (I-P14177, A-15,$R^2$-11,$R^3$-33), (I-P14178,A-15,$R^2$-11,$R^3$-34), (I-P14179, A-15,$R^2$-12,$R^3$-1), (I-P14180,A-15,$R^2$-12,$R^3$-2), (I-P14181,A-15,$R^2$-12,$R^3$-3), (I-P14182, A-15,$R^2$-12,$R^3$-4), (I-P14183,A-15,$R^2$-12,$R^3$-5), (I-P14184, A-15,$R^2$-12,$R^3$-6), (I-P14185, A-15,$R^2$-12,$R^3$-7), (I-P14186,A-15,$R^2$-12,$R^3$-8), (I-P14187,A-15,$R^2$-12,$R^3$-9), (I-P14188, A-15,$R^2$-12,$R^3$-10), (I-P14189,A-15,$R^2$-12,$R^3$-11), (I-P14190,A-15,$R^2$-12, $R^3$-12), (I-P14191, A-15,$R^2$-12,$R^3$-13), (I-P14192,A-15,$R^2$-12,$R^3$-14), (I-P14193,A-15,$R^2$-12,$R^3$-15), (I-P14194, A-15, $R^2$-12,$R^3$-16), (I-P14195,A-15,$R^2$-12,$R^3$-17), (I-P14196,A-15,$R^2$-12,$R^3$-18), (I-P14197, A-15,$R^2$-12,$R^3$-19), (I-P14198, A-15,$R^2$-12,$R^3$-20), (I-P14199,A-15,$R^2$-12,$R^3$-21), (I-P14200, A-15,$R^2$-12,$R^3$-22), (I-P14201,A-15,$R^2$-12,$R^3$-23), (I-P14202,A-15,$R^2$-12,$R^3$-24), (I-P14203, A-15,$R^2$-12, $R^3$-25), (I-P14204,A-15,$R^2$-12,$R^3$-26), (I-P14205,A-15,$R^2$-12,$R^3$-27), (I-P14206, A-15,$R^2$-12,$R^3$-28), (I-P14207,A-15, $R^2$-12,$R^3$-29), (I-P14208,A-15,$R^2$-12,$R^3$-30), (I-P14209, A-15,$R^2$-12,$R^3$-31), (I-P14210,A-15,$R^2$-12,$R^3$-32), (I-P14211,A-15,$R^2$-12,$R^3$-33), (I-P14212, A-15,$R^2$-12,$R^3$-34), (I-P14213,A-15,$R^2$-13,$R^3$-1), (I-P14214,A-15,$R^2$-13, $R^3$-2), (I-P14215,A-15,$R^2$-13,$R^3$-3), (I-P14216,A-15,$R^2$-13, $R^3$-4), (I-P14217,A-15,$R^2$-13,$R^3$-5), (I-P14218, A-15,$R^2$-13, $R^3$-6), (I-P14219,A-15,$R^2$-13,$R^3$-7), (I-P14220,A-15,$R^2$-13, $R^3$-8), (I-P14221,A-15,$R^2$-13,$R^3$-9), (I-P14222,A-15,$R^2$-13, $R^3$-10), (I-P14223,A-15,$R^2$-13,$R^3$-11), (I-P14224, A-15,$R^2$-13,$R^3$-12), (I-P14225,A-15,$R^2$-13,$R^3$-13), (I-P14226,A-15, $R^2$-13,$R^3$-14), (I-P14227,A-15,$R^2$-13,$R^3$-15), (I-P14228,A-15,$R^2$-13,$R^3$-16), (I-P14229,A-15,$R^2$-13,$R^3$-17), (I-P14230, A-15,$R^2$-13,$R^3$-18), (I-P14231,A-15,$R^2$-13,$R^3$-19), (I-P14232,A-15,$R^2$-13,$R^3$-20), (I-P14233, A-15,$R^2$-13,$R^3$-21), (I-P14234,A-15,$R^2$-13,$R^3$-22), (I-P14235,A-15,$R^2$-13, $R^3$-23), (I-P14236, A-15,$R^2$-13,$R^3$-24), (I-P14237,A-15,$R^2$-13,$R^3$-25), (I-P14238,A-15,$R^2$-13,$R^3$-26), (I-P14239, A-15, $R^2$-13,$R^3$-27), (I-P14240,A-15,$R^2$-13,$R^3$-28), (I-P14241,A-15,$R^2$-13,$R^3$-29), (I-P14242, A-15,$R^2$-13,$R^3$-30), (I-P14243, A-15,$R^2$-13,$R^3$-31), (I-P14244,A-15,$R^2$-13,$R^3$-32), (I-P14245, A-15,$R^2$-13,$R^3$-33), (I-P14246,A-15,$R^2$-13,$R^3$-34), (I-P14247,A-15,$R^2$-14,$R^3$-1), (I-P14248, A-15,$R^2$-14, $R^3$-2), (I-P14249,A-15,$R^2$-14,$R^3$-3), (I-P14250,A-15,$R^2$-14, $R^3$-4), (I-P14251, A-15,$R^2$-14,$R^3$-5), (I-P14252,A-15,$R^2$-14, $R^3$-6), (I-P14253,A-15,$R^2$-14,$R^3$-7), (I-P14254, A-15,$R^2$-14, $R^3$-8), (I-P14255,A-15,$R^2$-14,$R^3$-9), (I-P14256,A-15,$R^2$-14, $R^3$-10), (I-P14257, A-15,$R^2$-14,$R^3$-11), (I-P14258,A-15,$R^2$-14,$R^3$-12), (I-P14259,A-15,$R^2$-14,$R^3$-13), (I-P14269, A-15, $R^2$-14,$R^3$-14), (I-P14261,A-15,$R^2$-14,$R^3$-15), (I-P14262,A-15,$R^2$-14,$R^3$-16), (I-P14263, A-15,$R^2$-14,$R^3$-17), (I-P14264, A-15,$R^2$-14,$R^3$-18), (I-P14265,A-15,$R^2$-14,$R^3$-19), (I-P14266, A-15,$R^2$-14,$R^3$-20), (I-P14267,A-15,$R^2$-14,$R^3$-21), (I-P14268,A-15,$R^2$-14,$R^3$-22), (I-P14269, A-15,$R^2$-14, $R^3$-23), (I-P14270,A-15,$R^2$-14,$R^3$-24), (I-P14271,A-15,$R^2$-14,$R^3$-25), (I-P14272, A-15,$R^2$-14,$R^3$-26), (I-P14273,A-15, $R^2$-14,$R^3$-27), (I-P14274,A-15,$R^2$-14,$R^3$-28), (I-P14275, A-15,$R^2$-14,$R^3$-29), (I-P14276,A-15,$R^2$-14,$R^3$-30), (I-P14277,A-15,$R^2$-14,$R^3$-31), (I-P14278, A-15,$R^2$-14,$R^3$-32), (I-P14279,A-15,$R^2$-14,$R^3$-33), (I-P14280,A-15,$R^2$-14, $R^3$-34), (I-P14281, A-15,$R^2$-15,$R^3$-1), (I-P14282,A-15,$R^2$-15,$R^3$-2), (I-P14283,A-15,$R^2$-15,$R^3$-3), (I-P14284,A-15, $R^2$-15,$R^3$-4), (I-P14285,A-15,$R^2$-15,$R^3$-5), (I-P14286,A-15, $R^2$-15,$R^3$-6), (I-P14287,A-15,$R^2$-15,$R^3$-7), (I-P14288,A-15, $R^2$-15,$R^3$-8), (I-P14289,A-15,$R^2$-15,$R^3$-9), (I-P14291, A-15, $R^2$-15,$R^3$-10), (I-P14291,A-15,$R^2$-15,$R^3$-11), (I-P14292,A-15, $R^2$-15,$R^3$-12), (I-P14293, A-15,$R^2$-15,$R^3$-13), (I-P14294,A-15,$R^2$-15,$R^3$-14), (I-P14295,A-15,$R^2$-15,$R^3$-15), (I-P14296, A-15,$R^2$-15,$R^3$-16), (I-P14297,A-15,$R^2$-15,$R^3$-17), (I-P14298,A-15,$R^2$-15,$R^3$-18), (I-P14299, A-15,$R^2$-15,$R^3$-19), (I-P14300,A-15,$R^2$-15,$R^3$-20), (I-P14301,A-15,$R^2$-15, $R^3$-21), (I-P14302, A-15,$R^2$-15,$R^3$-22), (I-P14303,A-15,$R^2$-15,$R^3$-23), (I-P14304,A-15,$R^2$-15,$R^3$-24), (I-P14305, A-15, $R^2$-15,$R^3$-25), (I-P14306,A-15,$R^2$-15,$R^3$-26), (I-P14307,A-15,$R^2$-15,$R^3$-27), (I-P14308, A-15,$R^2$-15,$R^3$-28), (I-P14309, A-15,$R^2$-15,$R^3$-29), (I-P14310,A-15,$R^2$-15,$R^3$-30), (I-P14311, A-15,$R^2$-15,$R^3$-31), (I-P14312,A-15,$R^2$-15,$R^3$-32), (I-P14313,A-15,$R^2$-15,$R^3$-33), (I-P14314, A-15,$R^2$-15, $R^3$-34), (I-P14315,A-15,$R^2$-16,$R^3$-1), (I-P14316,A-15,$R^2$-16,$R^3$-2), (I-P14317, A-15,$R^2$-16,$R^3$-3), (I-P14318,A-15,$R^2$-16,$R^3$-4), (I-P14319,A-15,$R^2$-16,$R^3$-5), (I-P14320, A-15,$R^2$-16,$R^3$-6), (I-P14321,A-15,$R^2$-16,$R^3$-7), (I-P14322,A-15,$R^2$-16,$R^3$-8), (I-P14323, A-15,$R^2$-15,$R^3$-9), (I-P14324,A-15,$R^2$-16,$R^3$-10), (I-P14325,A-15,$R^2$-16,$R^3$-11), (I-P14326, A-15, $R^2$-16,$R^3$-12), (I-P14327,A-15,$R^2$-16,$R^3$-13), (I-P14328,A-15,$R^2$-16,$R^3$-14), (I-P14329,A-15,$R^2$-16,$R^3$-15), (I-P14330, A-15,$R^2$-16,$R^3$-16), (I-P14331,A-15,$R^2$-16,$R^3$-17), (I-P14332, A-15,$R^2$-16,$R^3$-18), (I-P14333,A-15,$R^2$-16,$R^3$-19), (I-P14334,A-15,$R^2$-16,$R^3$-20), (I-P14335, A-15,$R^2$-16, $R^3$-21), (I-P14336,A-15,$R^2$-16,$R^3$-22), (I-P14337,A-15,$R^2$-16,$R^3$-23), (I-P14338, A-15,$R^2$-16,$R^3$-24), (I-P14339,A-15, $R^2$-16,$R^3$-25), (I-P14340,A-15,$R^2$-16,$R^3$-26), (I-P14341, A-15,$R^2$-16,$R^3$-27), (I-P14342,A-15,$R^2$-16,$R^3$-28), (I-P14343,A-15,$R^2$-16,$R^3$-29), (I-P14344, A-15,$R^2$-16,$R^3$-30), (I-P14345,A-15,$R^2$-16,$R^3$-31), (I-P14346,A-15,$R^2$-16, $R^3$-32), (I-P14347, A-15,$R^2$-16,$R^3$-33), (I-P14348,A-15,$R^2$-16,$R^3$-34), (I-P14349,A-15,$R^2$-17,$R^3$-1), (I-P14350, A-15, $R^2$-17,$R^3$-2), (I-P14351,A-15,$R^2$-17,$R^3$-3), (I-P14352,A-15, $R^2$-17,$R^3$-4), (I-P14353, A-15,$R^2$-17,$R^3$-5), (I-P14354, A-15, $R^2$-17,$R^3$-6), (I-P14355,A-15,$R^2$-17,$R^3$-7), (I-P14356, A-15, $R^2$-17,$R^3$-8), (I-P14357,A-15,$R^2$-17,$R^3$-9), (I-P14358,A-15, $R^2$-17,$R^3$-10), (I-P14359, A-15,$R^2$-17,$R^3$-11), (I-P14360,A-15,$R^2$-17,$R^3$-12), (I-P14361,A-15,$R^2$-17,$R^3$-13), (I-P14362, A-15,$R^2$-17,$R^3$-14), (I-P14363,A-15,$R^2$-17,$R^3$-15), (I-P14364,A-15,$R^2$-17,$R^3$-16), (I-P14365, A-15,$R^2$-17,$R^3$-17), (I-P14366,A-15,$R^2$-17,$R^3$-18), (I-P14367,A-15,$R^2$-17,$R^3$-19), (I-P14368, A-15,$R^2$-17,$R^3$-20), (I-P14369,A-15,$R^2$-17,$R^3$-21), (I-P14370,A-15,$R^2$-17,$R^3$-22), (I-P14371, A-15,$R^2$-17,$R^3$-23), (I-P14372,A-15,$R^2$-17,$R^3$-24), (I-P14373,A-15,$R^2$-17,$R^3$-25), (I-P14374, A-15,$R^2$-17,$R^3$-26), (I-P14375, A-15,$R^2$-17,$R^3$-27), (I-P14376,A-15,$R^2$-17,$R^3$-28), (I-P14377, A-15,$R^2$-17,$R^3$-29), (I-P14378,A-15,$R^2$-17,$R^3$-30), (I-P14379,A-15,$R^2$-17,$R^3$-31), (I-P14380, A-15,$R^2$-17,$R^3$-32), (I-P14381,A-15,$R^2$-17,$R^3$-33), (I-P14382,A-15,$R^2$-17,$R^3$-34), (I-P14383, A-15,$R^2$-18,$R^3$-1), (I-P14384,A-15,$R^2$-18,$R^3$-2), (I-P14385,A-15,$R^2$-18,$R^3$-3), (I-P14386, A-15,$R^2$-18,$R^3$-4), (I-P14387,A-15,$R^2$-18,$R^3$-5), (I-P14388,A-15,$R^2$-18,$R^3$-6), (I-P14389,A-15,$R^2$-18,$R^3$-7), (I-P14390,A-15,$R^2$-18,$R^3$-8), (I-P14391,A-15,$R^2$-18,$R^3$-9), (I-P14392, A-15,$R^2$-18,$R^3$-10), (I-P14393,A-15,$R^2$-18,$R^3$-11), (I-P14394,A-15,$R^2$-18,$R^3$-12), (I-P14395, A-15,$R^2$-18,$R^3$-13), (I-P14396, A-15,$R^2$-18,$R^3$-14), (I-P14397,A-15,$R^2$-18,$R^3$-15), (I-P14398, A-15,$R^2$-18,$R^3$-16), (I-P14399,A-15,$R^2$-18,$R^3$-17), (I-P14400,A-15,$R^2$-18,$R^3$-18), (I-P14401, A-15,$R^2$-18,$R^3$-19), (I-P14402,A-15,$R^2$-18,$R^3$-20), (I-P14403,A-15,$R^2$-18,$R^3$-21), (I-P14404, A-15,$R^2$-18,$R^3$-22), (I-P14405,A-15,$R^2$-18,$R^3$-23), (I-P14406,A-15,$R^2$-18,$R^3$-24), (I-P14407, A-15,$R^2$-18,$R^3$-25), (I-P14408,A-15,$R^2$-18,$R^3$-26), (I-P14409,A-15,$R^2$-18,$R^3$-27), (I-P14410, A-15,$R^2$-18,$R^3$-28), (I-P14411,A-15,$R^2$-18,$R^3$-29), (I-P14412,A-15,$R^2$-18,$R^3$-30), (I-P14413, A-15,$R^2$-18,$R^3$-31), (I-P14414,A-15,$R^2$-18,$R^3$-32), (I-P14415,A-15,$R^2$-18,$R^3$-33), (I-P14416, A-15,$R^2$-18,$R^3$-34), (I-P14417,A-15,$R^2$-19,$R^3$-1), (I-P14418,A-15,$R^2$-19,$R^3$-2), (I-P14419, A-15,$R^2$-19,$R^3$-3), (I-P14420,A-15,$R^2$-19,$R^3$-4), (I-P14421,A-15,$R^2$-19,$R^3$-5), (I-P14422, A-15,$R^2$-19,$R^3$-6), (I-P14423,A-15,$R^2$-19,$R^3$-7), (I-P14424, A-15,$R^2$-19,$R^3$-8), (I-P14425, A-15,$R^2$-19,$R^3$-9), (I-P14426, A-15,$R^2$-19,$R^3$-10), (I-P14427,A-15,$R^2$-19,$R^3$-11), (I-P14428, A-15,$R^2$-19,$R^3$-12), (I-P14429,A-15,$R^2$-19,$R^3$-13), (I-P14430,A-15,$R^2$-19,$R^3$-14), (I-P14431, A-15,$R^2$-19,$R^3$-15), (I-P14432,A-15,$R^2$-19,$R^3$-16), (I-P14433,A-15,$R^2$-19,$R^3$-17), (I-P14434, A-15,$R^2$-19,$R^3$-18), (I-P14435,A-15,$R^2$-19,$R^3$-19), (I-P14436,A-15,$R^2$-19,$R^3$-20), (I-P14437, A-15,$R^2$-19,$R^3$-21), (I-P14438,A-15,$R^2$-19,$R^3$-22), (I-P14439,A-15,$R^2$-19,$R^3$-23), (I-P14440, A-15,$R^2$-19,$R^3$-24), (I-P14441,A-15,$R^2$-19,$R^3$-25), (I-P14442,A-15,$R^2$-19,$R^3$-26), (I-P14443, A-15,$R^2$-19,$R^3$-27), (I-P14444,A-15,$R^2$-19,$R^3$-28), (I-P14445,A-15,$R^2$-19,$R^3$-29), (I-P14446, A-15,$R^2$-19,$R^3$-30), (I-P14447,A-15,$R^2$-19,$R^3$-31), (I-P14448,A-15,$R^2$-19,$R^3$-32), (I-P14449, A-15,$R^2$-19,$R^3$-33), (I-P14450,A-15,$R^2$-19,$R^3$-34), (I-P14451,A-15,$R^2$-20,$R^3$-1), (I-P14452, A-15,$R^2$-20,$R^3$-2), (I-P14453,A-15,$R^2$-20,$R^3$-3), (I-P14454,A-15,$R^2$-20,$R^3$-4), (I-P14455, A-15,$R^2$-20,$R^3$-5), (I-P14456,A-15,$R^2$-20,$R^3$-6), (I-P14457,A-15,$R^2$-20,$R^3$-7), (I-P14458, A-15,$R^2$-20,$R^3$-8), (I-P14459,A-15,$R^2$-20,$R^3$-9), (I-P14460,A-15,$R^2$-20,$R^3$-10), (I-P14461, A-15,$R^2$-20,$R^3$-11), (I-P14462,A-15,$R^2$-20,$R^3$-12), (I-P14463,A-15,$R^2$-20,$R^3$-13), (I-P14464, A-15,$R^2$-20,$R^3$-14), (I-P14465,A-15,$R^2$-20,$R^3$-15), (I-P14466,A-15,$R^2$-20,$R^3$-16), (I-P14467, A-15,$R^2$-20,$R^3$-17), (I-P14468,A-15,$R^2$-20,$R^3$-18), (I-P14469,A-15,$R^2$-20,$R^3$-19), (I-P14470, A-15,$R^2$-20,$R^3$-20), (I-P14471,A-15,$R^2$-20,$R^3$-21), (I-P14472,A-15,$R^2$-20,$R^3$-22), (I-P14473, A-15,$R^2$-20,$R^3$-23), (I-P14474,A-15,$R^2$-20,$R^3$-24), (I-P14475,A-15,$R^2$-20,$R^3$-25), (I-P14476, A-15,$R^2$-20,$R^3$-26), (I-P14477,A-15,$R^2$-20,$R^3$-27), (I-P14478,A-15,$R^2$-20,$R^3$-28), (I-P14479, A-15,$R^2$-20,$R^3$-29), (I-P14480, A-15,$R^2$-20,$R^3$-30), (I-P14481,A-15,$R^2$-20,$R^3$-31), (I-P14482, A-15,$R^2$-20,$R^3$-32), (I-P14483, A-15,$R^2$-20,$R^3$-33), (I-P14484,A-15,$R^2$-20,$R^3$-34), (I-P14485, A-15,$R^2$-21,$R^3$-1), (I-P14486,A-15,$R^2$-21,$R^3$-2), (I-P14487, A-15,$R^2$-21,$R^3$-3), (I-P14488, A-15,$R^2$-21,$R^3$-4), (I-P14489,A-15,$R^2$-21,$R^3$-5), (I-P14490,A-15,$R^2$-21,$R^3$-6), (I-P14491, A-15,$R^2$-21,$R^3$-7), (I-P14492,A-15,$R^2$-21,$R^3$-8), (I-P14493,A-15,$R^2$-21,$R^3$-9), (I-P14494, A-15,$R^2$-21,$R^3$-10), (I-P14495,A-15,$R^2$-21,$R^3$-11), (I-P14496,A-15,$R^2$-21,$R^3$-12), (I-P14497, A-15,$R^2$-21,$R^3$-13), (I-P14498,A-15,$R^2$-21,$R^3$-14), (I-P14499,A-15,$R^2$-21,$R^3$-15), (I-P14500, A-15,$R^2$-21,$R^3$-16), (I-P14501, A-15,$R^2$-21,$R^3$-17), (I-P14502,A-15,$R^2$-21,$R^3$-18), (I-P14503, A-15,$R^2$-21,$R^3$-19), (I-P14504,A-15,$R^2$-21,$R^3$-20), (I-P14505,A-15,$R^2$-21,$R^3$-21), (I-P14506, A-15,$R^2$-21,$R^3$-22), (I-P14507,A-15,$R^2$-21,$R^{10}$-23), (I-P14508,A-15,$R^2$-21,$R^3$-24), (I-P14509, A-15,$R^2$-21,$R^3$-25), (I-P14510,A-15,$R^2$-21,$R^3$-26), (I-P14511,A-15,$R^2$-21,$R^3$-27), (I-P14512, A-15,$R^2$-21,$R^3$-28), (I-P14513,A-15,$R^2$-21,$R^3$-29), (I-P14514,A-15,$R^2$-21,$R^3$-30), (I-P14515, A-15,$R^2$-21,$R^3$-31), (I-P14516,A-15,$R^2$-21,$R^3$-32), (I-P14517,A-15,$R^2$-21,$R^3$-33), (I-P14518, A-15,$R^2$-21,$R^3$-34), (I-P14519,A-15,$R^2$-22,$R^3$-1), (I-P14520,A-15,$R^2$-22,$R^3$-2), (I-P14521, A-15,$R^2$-22,$R^3$-3), (I-P14522,A-15,$R^2$-22,$R^3$-4), (I-P14523,A-15,$R^2$-22,$R^3$-5), (I-P14524, A-15,$R^2$-22,$R^3$-6), (I-P14525,A-15,$R^2$-22,$R^3$-7), (I-P14526,A-15,$R^2$-22,$R^3$-8), (I-P14527, A-15,$R^2$-22,$R^3$-9), (I-P14528,A-15,$R^2$-22,$R^3$-10), (I-P14529,A-15,$R^2$-22,$R^3$-11), (I-P14530, A-15,$R^2$-22,$R^3$-12), (I-P14531,A-15,$R^2$-22,$R^3$-13), (I-P14532,A-15,$R^2$-22,$R^3$-14), (I-P14533, A-15,$R^2$-22,$R^3$-15), (I-P14534,A-15,$R^2$-22,$R^3$-16), (I-P14535,A-15,$R^2$-22,$R^3$-17), (I-P14536, A-15,$R^2$-22,$R^3$-18), (I-P14537,A-15,$R^2$-22,$R^3$-19), (I-P14538,A-15,$R^2$-22,$R^3$-20), (I-P14539, A-15,$R^2$-22,$R^3$-21), (I-P14540,A-15,$R^2$-22,$R^3$-22), (I-P14541,A-15,$R^2$-22,$R^3$-23), (I-P14542, A-15,$R^2$-22,$R^3$-24), (I-P14543,A-15,$R^2$-22,$R^3$-25), (I-P14544,A-15,$R^2$-22,$R^3$-26), (I-P14545,A-15,$R^2$-22,$R^3$-27), (I-P14546, A-15,$R^2$-22,$R^3$-28), (I-P14547,A-15,$R^2$-22,$R^3$-29), (I-P14548, A-15,$R^2$-22,$R^3$-30), (I-P14549,A-15,$R^2$-22,$R^3$-31), (I-P14550,A-15,$R^2$-22,$R^3$-32), (I-P14551, A-15,$R^2$-22,$R^3$-33), (I-P14552,A-15,$R^2$-22,$R^3$-34), (I-P14553,A-15,$R^2$-23,$R^3$-1), (I-P14554,A-15,$R^2$-23,$R^3$-2), (I-P14455,A-15,$R^2$-23,$R^3$-3), (I-P14556,A-15,$R^2$-23,$R^3$-4), (I-P14557,A-15,$R^2$-23,$R^3$-5), (I-P14558,A-15,$R^2$-23,$R^3$-6), (I-P14559,A-15,$R^2$-23,$R^3$-7), (I-P14560,A-15,$R^2$-23,$R^3$-8), (I-P14561,A-15,$R^2$-23,$R^3$-9), (I-P14562,A-15,$R^2$-23,$R^3$-10), (I-P14563, A-15,$R^2$-23,$R^3$-11), (I-P14564,A-15,$R^2$-23,$R^3$-12), (I-P14565,A-15,$R^2$-23,$R^3$-13), (I-P14566, A-15,$R^2$-23,$R^3$-14), (I-P14567, A-15,$R^2$-23,$R^3$-15), (I-P14568,A-15,$R^2$-23,$R^3$-16), (I-P14569, A-15,$R^2$-23,$R^3$-17), (I-P14570,A-15,$R^2$-23,$R^3$-18), (I-P14571,A-15,$R^2$-23,$R^3$-19), (I-P14572, A-15,$R^2$-23,$R^3$-20), (I-P14573,A-15,$R^2$-23,$R^3$-21), (I-P14574,A-15,$R^2$-23,$R^3$-22), (I-P14575, A-15,$R^2$-23,$R^3$-23), (I-P14576,A-15,$R^2$-23,$R^3$-24), (I-P14577,A-15,$R^2$-23,$R^3$-25), (I-P14578, A-15,$R^2$-23,$R^3$-26), (I-P14579,A-15,$R^2$-23,$R^3$-27), (I-P14580,A-15,$R^2$-23,$R^3$-28), (I-P14581, A-15,$R^2$-23,$R^3$-29), (I-P14582,A-15,$R^2$-23,$R^3$-30), (I-P14583,A-15,$R^2$-23,$R^3$-31), (I-P14584, A-15,$R^2$-23,$R^3$-32), (I-P14585,A-15,$R^2$-23,$R^3$-33), (I-P14586,A-15,$R^2$-23,$R^3$-34), (I-P14587, A-15,$R^2$-24,$R^3$-1), (I-P14588,A-15,$R^2$-24,$R^3$-2), (I-P14589,A-15,$R^2$-24,$R^3$-3), (I-P14590, A-15,$R^2$-24,$R^3$-4), (I-P14591, A-15,$R^2$-24,$R^3$-5), (I-P14592,A-15,$R^2$-24,$R^3$-6), (I-P14593, A-15,$R^2$-24,$R^3$-7), (I-P14594,A-15,$R^2$-24,$R^3$-8), (I-P14595,A-15,$R^2$-24,$R^3$-9), (I-P14596, A-15,$R^2$-24,$R^3$-10), (I-P14597,A-15,$R^2$-24,$R^3$-11), (I-P14598,A-15,$R^2$-24,$R^3$-12), (I-P14599, A-15,$R^2$-24,$R^3$-13), (I-P14600,A-15,$R^2$-24,$R^3$-14), (I-P14601,A-15,$R^2$-24,$R^3$-15), (I-P14602, A-15,$R^2$-24,$R^3$-16), (I-P14603,A-15,$R^2$-24,$R^3$-17), (I-P14604,A-15,$R^2$-24,$R^3$-18), (I-P14605, A-15,$R^2$-24,$R^3$-19), (I-P14606,A-15,$R^2$-24,$R^3$-20), (I-P14607,A-15,$R^2$-24,$R^3$-21), (I-P14608, A-15,$R^2$-24,$R^3$-22), (I-P14609,A-15,$R^2$-24,$R^3$-23), (I-P14610,A-15,$R^2$-24,$R^3$-24), (I-P14611, A-15,$R^2$-24,$R^3$-25), (I-P14612, A-15,$R^2$-24,$R^3$-26), (I-P14613,A-15,$R^2$-24,$R^3$-27), (I-P14614, A-15,$R^2$-24,$R^3$-28), (I-P14615,A-15,$R^2$-24,$R^3$-

29), (I-P14616,A-15,$R^2$-24,$R^3$-30), (I-P14617, A-15,$R^2$-24, $R^3$-31), (I-P14618,A-15,$R^2$-24,$R^3$-32), (I-P14619,A-15,$R^2$-24,$R^3$-33), (I-P14620, A-15,$R^2$-24,$R^3$-34), (I-P14621,A-15, $R^2$-25,$R^3$-1), (I-P14622,A-15,$R^2$-25,$R^3$-2), (I-P14623, A-15, $R^2$-25,$R^3$-3), (I-P14624,A-15,$R^2$-25,$R^3$-4), (I-P14625,A-15, $R^2$-25,$R^3$-5), (I-P14626, A-15,$R^2$-25,$R^3$-6), (I-P14627,A-15, $R^2$-25,$R^3$-7), (I-P14628,A-15,$R^2$-25,$R^3$-8), (I-P14629, A-15, $R^2$-25,$R^3$-9), (I-P14630,A-15,$R^2$-25,$R^3$-10), (I-P14631,A-15,$R^2$-25,$R^3$-11), (I-P14632, A-15,$R^2$-25,$R^3$-12), (I-P14633, A-15,$R^2$-25,$R^3$-13), (I-P14634,A-15,$R^2$-25,$R^3$-14), (I-P14635, A-15,$R^2$-25,$R^3$-15), (I-P14636,A-15,$R^2$-25,$R^3$-16), (I-P14637,A-15,$R^2$-25,$R^3$-17), (I-P14638, A-15,$R^2$-25, $R^3$-18), (I-P14639,A-15,$R^2$-25,$R^3$-19), (I-P14640,A-15,$R^2$-25,$R^3$-20), (I-P14641, A-15,$R^2$-25,$R^3$-21), (I-P14642,A-15, $R^2$-25,$R^3$-22), (I-P14643,A-15,$R^2$-25,$R^3$-23), (I-P14644, A-15,$R^2$-25,$R^3$-24), (I-P14645,A-15,$R^2$-25,$R^3$-25), (I-P14646,A-15,$R^2$-25,$R^3$-26), (I-P14647, A-15,$R^2$-25,$R^3$-27), (I-P14648,A-15,$R^2$-25,$R^3$-28), (I-P14649,A-15,$R^2$-25, $R^3$-29), (I-P14650, A-15,$R^2$-25,$R^3$-30), (I-P14651,A-15,$R^2$-25,$R^3$-31), (I-P14652,A-15,$R^2$-25,$R^3$-32), (I-P14653, A-15, $R^2$-25,$R^3$-33), (I-P14654,A-15,$R^2$-25,$R^3$-34), (I-P14655,A-15,$R^2$-26,$R^3$-1), (I-P14656, A-15,$R^2$-26,$R^3$-2), (I-P14657,A-15,$R^2$-26,$R^3$-3), (I-P14658,A-15,$R^2$-26,$R^3$-4), (I-P14659, A-15,$R^2$-26,$R^3$-5), (I-P14660,A 15,$R^2$-26,$R^3$-6), (I-P14661,A 15,$R^2$-26,$R^3$-7), (I-P14662, A-15,$R^2$-26,$R^3$-8), (I-P14663,A-15,$R^2$-26,$R^3$-9), (I-P14664,A-15,$R^2$-26,$R^3$-10), (I-P14665, A-15,$R^2$-26,$R^3$-11), (I-P14666,A-15,$R^2$-26,$R^3$-12), (I-P14667,A-15,$R^2$-26,$R^3$-13), (I-P14668, A-15,$R^2$-26,$R^3$-14), (I-P14669,A-15,$R^2$-26,$R^3$-15), (I-P14670,A-15, $R^2$-26,$R^3$-16), (I-P14671, A-15,$R^2$-26,$R^3$-17), (I-P14672,A-15,$R^2$-26,$R^3$-18), (I-P14673,A-15,$R^2$-26,$R^3$-19), (I-P14674, A-15,$R^2$-26,$R^3$-20), (I-P14675,A-15,$R^2$-26,$R^3$-21), (I-P14676,A-15,$R^2$-26,$R^3$-22), (I-P14677, A-15,$R^2$-26,$R^3$-23), (I-P14678,A-15,$R^2$-26,$R^3$-24), (I-P14679,A-15,$R^2$-26, $R^3$-25), (I-P14680, A-15,$R^2$-26,$R^3$-26), (I-P14681,A-15,$R^2$-26,$R^3$-27), (I-P14682,A-15,$R^2$-26,$R^3$-28), (I-P14683, A-15, $R^2$-26,$R^3$-29), (I-P14684,A-15,$R^2$-26,$R^3$-30), (I-P14685,A-15,$R^2$-26,$R^3$-31), (I-P14686, A-15,$R^2$-26,$R^3$-32), (I-P14687, A-15,$R^2$-26,$R^3$-33), (I-P14688,A-15,$R^2$-26,$R^3$-34), (I-P14689, A-15,$R^2$-27,$R^3$-1), (I-P14690,A-15,$R^2$-27,$R^3$-2), (I-P14691,A-15,$R^2$-27,$R^3$-3), (I-P14692, A-15,$R^2$-27,$R^3$-4), (I-P14693, A-15,$R^2$-27,$R^3$-5), (I-P14694,A-15,$R^2$-27,$R^3$-6), (I-P14695, A-15,$R^2$-27,$R^3$-7), (I-P14696,A-15,$R^2$-27,$R^3$-8), (I-P14697,A-15,$R^2$-27,$R^3$-9), (I-P14698, A-15,$R^2$-27,$R^3$-10), (I-P14699,A-15,$R^2$-27,$R^3$-11), (I-P14700,A-15,$R^2$-27, $R^3$-12), (I-P14701, A-15,$R^2$-27,$R^3$-13), (I-P14702,A-15,$R^2$-27,$R^3$-14), (I-P14703,A-15,$R^2$-27,$R^3$-15), (I-P14704, A-15, $R^2$-27,$R^3$-16), (I-P14705,A-15,$R^2$-27,$R^3$-17), (I-P14706,A-15,$R^2$-27,$R^3$-18), (I-P14707, A-15,$R^2$-27,$R^3$-19), (I-P14708, A-15,$R^2$-27,$R^3$-20), (I-P14709,A-15,$R^2$-27,$R^3$-21), (I-P14710, A-15,$R^2$-27,$R^3$-22), (I-P14711,A-15,$R^2$-27,$R^3$-23), (I-P14712,A-15,$R^2$-27,$R^3$-24), (I-P14713, A-15,$R^2$-27, $R^3$-25), (I-P14714,A-15,$R^2$-27,$R^3$-26), (I-P14715,A-15,$R^2$-27,$R^3$-27), (I-P14716, A-15,$R^2$-27,$R^3$-28), (I-P14717,A-15, $R^2$-27,$R^3$-29), (I-P14718,A-15,$R^2$-27,$R^3$-30), (I-P14719, A-15,$R^2$-27,$R^3$-31), (I-P14720, A-15,$R^2$-27,$R^3$-32), (I-P14721,A-15,$R^2$-27,$R^3$-33), (I-P14722, A-15,$R^2$-27,$R^3$-34), (I-P14723,A-15,$R^2$-28,$R^3$-1), (I-P14724,A-15,$R^2$-28, $R^3$-2), (I-P14725,A-15,$R^2$-28,$R^3$-3), (I-P14726,A-15,$R^2$-28, $R^3$-4), (I-P14727,A-15,$R^2$-28,$R^3$-5), (I-P14728, A-15,$R^2$-28, $R^3$-6), (I-P14729,A-15,$R^2$-28,$R^3$-7), (I-P14730,A-15,$R^2$-28, $R^3$-8), (I-P14731, A-15,$R^2$-28,$R^3$-9), (I-P14732,A-15,$R^2$-28, $R^3$-10), (I-P14733,A-15,$R^2$-28,$R^3$-11), (I-P14734, A-15,$R^2$-28,$R^3$-12), (I-P14735,A-15,$R^2$-28,$R^3$-13), (I-P14736,A-15, $R^2$-28,$R^3$-14), (I-P14737, A-15,$R^2$-28,$R^3$-15), (I-P14738,A-15,$R^2$-28,$R^3$-16), (I-P14739,A-15,$R^2$-28,$R^3$-17), (I-P14740, A-15,$R^2$-28,$R^3$-18), (I-P14741,A-15,$R^2$-28,$R^3$-19), (I-P14742,A-15,$R^2$-28,$R^3$-20), (I-P14743, A-15,$R^2$-28,$R^3$-21), (I-P14744,A-15,$R^2$-28,$R^3$-22), (I-P14745,A-15,$R^2$-28, $R^3$-23), (I-P14746, A-15,$R^2$-28,$R^3$-24), (I-P14747,A-15,$R^2$-28,$R^3$-25), (I-P14748,A-15,$R^2$-28,$R^3$-26), (I-P14749, A-15, $R^2$-28,$R^3$-27), (I-P14750,A-15,$R^2$-28,$R^3$-28), (I-P14751,A-15,$R^2$-28,$R^3$-29), (I-P14752, A-15,$R^2$-28,$R^3$-30), (I-P14753, A-15,$R^2$-28,$R^3$-31), (I-P14754,A-15,$R^2$-28,$R^3$-32), (I-P14755, A-15,$R^2$-28,$R^3$-33), (I-P14756,A-15,$R^2$-28,$R^3$-34), (I-P14757,A-15,$R^2$-29,$R^3$-1), (I-P14758, A-15,$R^2$-29, $R^3$-2), (I-P14759,A-15,$R^2$-29,$R^3$-3), (I-P14760,A-15,$R^2$-29, $R^3$-4), (I-P14761,A-15,$R^2$-29,$R^3$-5), (I-P14762,A-15,$R^2$-29, $R^3$-6), (I-P14763,A-15,$R^2$-29,$R^3$-7), (I-P14764,A-15,$R^2$-29, $R^3$-8), (I-P14765,A-15,$R^2$-29,$R^3$-9), (I-P14766,A-15,$R^2$-29, $R^3$-10), (I-P14767, A-15,$R^2$-29,$R^3$-11), (I-P14768,A-15,$R^2$-29,$R^3$-12), (I-P14769,A-15,$R^2$-29,$R^3$-13), (I-P14770, A-15, $R^2$-29,$R^3$-14), (I-P14771,A-15,$R^2$-29,$R^3$-15), (I-P14772,A-15,$R^2$-29,$R^3$-16), (I-P14773, A-15,$R^2$-29,$R^3$-17), (I-P14774, A-15,$R^2$-29,$R^3$-18), (I-P14775,A-15,$R^2$-29,$R^3$-19), (I-P14776, A-15,$R^2$-29,$R^3$-20), (I-P14777,A-15,$R^2$-29,$R^3$-21), (I-P14778,A-15,$R^2$-29,$R^3$-22), (I-P14779, A-15,$R^2$-29, $R^3$-23), (I-P14780,A-15,$R^2$-29,$R^3$-24), (I-P14781,A-15,$R^2$-29,$R^3$-25), (I-P14782, A-15,$R^2$-29,$R^3$-26), (I-P14783,A-15, $R^2$-29,$R^3$-27), (I-P14784,A-15,$R^2$-29,$R^3$-28), (I-P14785, A-15,$R^2$-29,$R^3$-29), (I-P14786,A-15,$R^2$-29,$R^3$-30), (I-P14787,A-15,$R^2$-29,$R^3$-31), (I-P14788, A-15,$R^2$-29,$R^3$-32), (I-P14789,A-15,$R^2$-29,$R^3$-33), (I-P14790,A-15,$R^2$-29, $R^3$-34), (I-P14791, A-16,$R^2$-1,$R^3$-1), (I-P14792,A-16,$R^2$-1, $R^3$-2), (I-P14793,A-16,$R^2$-1,$R^3$-3), (I-P14794, A-16,$R^2$-1, $R^3$-4), (I-P14795,A-16,$R^2$-1,$R^3$-5), (I-P14796,A-16,$R^2$-1, $R^3$-6), (I-P14797, A-16,$R^2$-1,$R^3$-7), (I-P14798,A-16,$R^2$-1, $R^3$-8), (I-P14799,A-16,$R^2$-1,$R^3$-9), (I-P14800, A-16,$R^2$-1, $R^3$-10), (I-P14801,A-16,$R^2$-1,$R^3$-11), (I-P14802,A-16,$R^2$-1, $R^3$-12), (I-P14803, A-16,$R^2$-1,$R^3$-13), (I-P14804,A-16,$R^2$-1, $R^3$-14), (I-P14805,A-16,$R^2$-1,$R^3$-15), (I-P14806,A-16,$R^2$-1, $R^3$-16), (I-P14807,A-16,$R^2$-1,$R^3$-17), (I-P14808,A-16,$R^2$-1, $R^3$-18), (I-P14809, A-16,$R^2$-1,$R^3$-19), (I-P14810,A-16,$R^2$-1, $R^3$-20), (I-P14811,A-16,$R^2$-1,$R^3$-21), (I-P14812, A-16,$R^2$-1, $R^3$-22), (I-P14813,A-16,$R^2$-1,$R^3$-23), (I-P14814,A-16,$R^2$-1, $R^3$-24), (I-P14815, A-16,$R^2$-1,$R^3$-25), (I-P14816,A-16,$R^2$-1, $R^3$-26), (I-P14817,A-16,$R^2$-1,$R^3$-27), (I-P14818, A-16,$R^2$-1, $R^3$-28), (I-P14819,A-16,$R^2$-1,$R^3$-29), (I-P14820, A-16,$R^2$-1, $R^3$-30), (I-P14821, A-16, $R^2$-1,$R^3$-31), (I-P14822,A-16,$R^2$-1,$R^3$-32), (I-P14823,A-16,$R^2$-1,$R^3$-33), (I-P14824, A-16,$R^2$-1,$R^3$-34), (I-P14825,A-16,$R^2$-2,$R^3$-1), (I-P14826,A-16,$R^2$-2, $R^3$-2), (I-P14827, A-16,$R^2$-2,$R^3$-3), (I-P14828,A-16,$R^2$-2, $R^3$-4), (I-P14829,A-16,$R^2$-2,$R^3$-5), (I-P14830, A-16,$R^2$-2, $R^3$-6), (I-P14831,A-16,$R^2$-2,$R^3$-7), (I-P14832,A-16,$R^2$-2, $R^3$-8), (I-P14833, A-16,$R^2$-2,$R^3$-9), (I-P14834,A-16,$R^2$-2, $R^3$-10), (I-P14835,A-16,$R^2$-2,$R^3$-11), (I-P14836, A-16,$R^2$-2, $R^3$-12), (I-P14837,A-16,$R^2$-2,$R^3$-13), (I-P14838,A-16,$R^2$-2, $R^3$-14), (I-P14839, A-16,$R^2$-2,$R^3$-15), (I-P14840,A-16,$R^2$-2, $R^3$-16), (I-P14841,A-16,$R^2$-2,$R^3$-17), (I-P14842, A-16,$R^2$-2, $R^3$-18), (I-P14843,A-16,$R^2$-2,$R^3$-19), (I-P14844,A-16,$R^2$-2, $R^3$-20), (I-P14845, A-16,$R^2$-2,$R^3$-21), (I-P14846,A-16,$R^2$-2, $R^3$-22), (I-P14847,A-16,$R^2$-2,$R^3$-23), (I-P14848, A-16,$R^2$-2, $R^3$-24), (I-P14849,A-16,$R^2$-2,$R^3$-25), (I-P14850,A-16,$R^2$-2, $R^3$-26), (I-P14851, A-16,$R^2$-2,$R^3$-27), (I-P14852, A-16,$R^2$-2, $R^3$-28), (I-P14853,A-16,$R^2$-2,$R^3$-29), (I-P14854, A-16,$R^2$-2, $R^3$-30), (I-P14855,A-16,$R^2$-2,$R^3$-31), (I-P14856, A-16,$R^2$-2, $R^3$-32), (I-P14857,A-16,$R^2$-2,$R^3$-33), (I-P14858, A-16,$R^2$-2, $R^3$-34), (I-P14859,A-16,$R^2$-3,$R^3$-1), (I-P14860, A-16,$R^2$-3, $R^2$-2), (I-P14861,A-16,$R^2$-3,$R^3$-3), (I-P14862,A-16,$R^2$-3, $R^3$-4), (I-P14863, A-16,$R^2$-3,$R^3$-5), (I-P14864,A-16,$R^2$-3, $R^3$-6), (I-P14865,A-16,$R^2$-3,$R^3$-7), (I-P14866, A-16,$R^2$-3, $R^3$-8), (I-P14867,A-16,$R^2$-3,$R^3$-9), (I-P14868,A-16,$R^2$-3, $R^3$-10), (I-P14869,A-16,$R^2$-3,$R^3$-11), (I-P14870,A-16,$R^2$-3, $R^3$-12), (I-P14871,A-16,$R^2$-3,$R^3$-13), (I-P14872, A-16,$R^2$-3,

R³-14), (I-P14873,A-16,R²-3,R³-15), (I-P14874,A-16,R²-3, R³-16), (I-P14875,A-16,R²-3,R³-17), (I-P14876,A-16,R²-3, R³-18), (I-P14877,A-16,R²-3,R³-19), (I-P14878,A-16,R²-3, R³-20), (I-P14879,A-16,R²-3,R³-21), (I-P14880,A-16,R²-3, R³-22), (I-P14881,A-16,R²-3,R³-23), (I-P14882,A-16,R²-3, R³-24), (I-P14883,A-16,R²-3,R³-25), (I-P14884,A-16,R²-3, R³-26), (I-P14885,A-16,R²-3,R³-27), (I-P14886,A-16,R²-3, R³-28), (I-P14887,A-16,R²-3,R³-29), (I-P14888,A-16,R²-3, R³-30), (I-P14889,A-16,R²-3,R³-31), (I-P14890, A-16,R²-3, R³-32), (I-P14891,A-16,R²-3,R³-33), (I-P14892,A-16,R²-3, R³-34), (I-P14893, A-16,R²-4,R³-1), (I-P14894,A-16,R²-4, R³-2), (I-P14895,A-16,R²-4,R³-3), (I-P14896, A-16,R²-4, R³-4), (I-P14897,A-16,R²-4,R³-5), (I-P14898,A-16,R²-4, R³-6), (I-P14899, A-16,R²-4,R³-7), (I-P14900,A-16,R²-4, R³-8), (I-P14901,A-16,R²-4,R³-9), (I-P14902, A-16,R²-4, R³-10), (I-P14903,A-16,R²-4,R³-11), (I-P14904,A-16,R²-4, R³-12), (I-P14905,A-16,R²-4,R³-13), (I-P14906,A-16,R²-4, R³-14), (I-P14907,A-16,R²-4,R³-15), (I-P14908, A-16,R²-4, R³-16), (I-P14909,A-16,R²-4,R³-17), (I-P14910,A-16,R²-4, R³-18), (I-P14911, A-16,R²-4,R³-19), (I-P14912,A-16,R²-4, R³-20), (I-P14913,A-16,R²-4,R³-21), (I-P14914, A-16,R²-4, R³-22), (I-P14915,A-16,R²-4,R³-23), (I-P14916,A-16,R²-4, R³-24), (I-P14917, A-16,R²-4,R³-25), (I-P14918,A-16,R²-4, R³-26), (I-P14919,A-16,R²-4,R³-27), (I-P14920, A-16,R²-4, R³-28), (I-P14921,A-16,R²-4,R³-29), (I-P14922, A-16,R²-4, R³-30), (I-P14923,A-16,R²-4,R³-31), (I-P14924,A-16,R²-4, R³-32), (I-P14925,A-16,R²-4,R³-33), (I-P14926, A-16,R²-4, R³-34), (I-P14927,A-16,R²-5,R³-1), (I-P14928,A-16,R²-5, R³-2), (I-P14929, A-16,R²-5,R³-3), (I-P14930,A-16,R²-5, R³-4), (I-P14931,A-16,R²-5,R³-5), (I-P14932, A-16,R²-5, R³-6), (I-P14933,A-16,R²-5,R³-7), (I-P14934,A-16,R²-5, R³-8), (I-P14935, A-16,R²-5,R³-9), (I-P14936,A-16,R²-5, R³-10), (I-P14937,A-16,R²-5,R³-11), (I-P14938,A-16,R²-5, R³-12), (I-P14939,A-16,R²-5,R³-13), (I-P14940,A-16,R²-5, R³-14), (I-P14941,A-16,R²-5,R³-15), (I-P14942,A-16,R²-5, R³-16), (I-P14943,A-16,R²-5,R³-17), (I-P14944,A-16,R²-5, R³-18), (I-P14945,A-16,R²-5,R³-19), (I-P14946,A-16,R²-5, R³-20), (I-P14947, A-16,R²-5,R³-21), (I-P14948,A-16,R²-5, R³-22), (I-P14949,A-16,R²-5,R³-23), (I-P14950,A-16,R²-5, R³-24), (I-P14951,A-16,R²-5,R³-25), (I-P14952,A-16,R²-5, R³-26), (I-P14953, A-16,R²-5,R³-27), (I-P14954,A-16,R²-5, R³-28), (I-P14955,A-16,R²-5,R³-29), (I-P14956,A-16,R²-5, R³-30), (I-P14957,A-16,R²-5,R³-31), (I-P14958,A-16,R²-5, R³-32), (I-P14959, A-16,R²-5,R³-33), (I-P14960,A-16,R²-5, R³-34), (I-P14961,A-16,R²-6,R³-1), (I-P14962, A-16,R²-6, R³-2), (I-P14963,A-16,R²-6,R³-3), (I-P14964,A-16,R²-6, R³-4), (I-P14965, A-16,R²-6,R³-5), (I-P14966,A-16,R²-6, R³-6), (I-P14967,A-16,R²-6,R³-7), (I-P14968, A-16,R²-6, R³-8), (I-P14969,A-16,R²-6,R³-9), (I-P14970,A-16,R²-6, R³-10), (I-P14971,A-16,R²-6,R³-11), (I-P14972,A-16,R²-6, R³-12), (I-P14973,A-16,R²-6,R³-13), (I-P14974,A-16,R²-6, R³-14), (I-P14975,A-16,R²-6,R³-15), (I-P14976,A-16,R²-6, R³-16), (I-P14977,A-16,R²-6,R³-17), (I-P14978,A-16,R²-6, R³-18), (I-P14979,A-16,R²-6,R³-19), (I-P14980,A-16,R²-6, R³-20), (I-P14981,A-16,R²-6,R³-21), (I-P14982,A-16,R²-6, R³-22), (I-P14983,A-16,R²-6,R³-23), (I-P14984,A-16,R²-6, R³-24), (I-P14985,A-16,R²-6,R³-25), (I-P14986,A-16,R²-6, R³-26), (I-P14987,A-16,R²-6,R³-27), (I-P14988,A-16,R²-6, R³-28), (I-P14989,A-16,R²-6,R³-29), (I-P14990,A-16,R²-6, R³-30), (I-P14991,A-16,R²-6,R³-31), (I-P14992,A-16,R²-6, R³-32), (I-P14993,A-16,R²-6,R³-33), (I-P14994,A-16,R²-6, R³-34), (I-P14995, A-16,R²-7,R³-1), (I-P14996,A-16,R²-7, R³-2), (I-P14997,A-16,R²-7,R³-3), (I-P14998, A-16,R²-7, R³-4), (I-P14999,A-16,R²-7,R³-5), (I-P15000,A-16,R²-7, R³-6), (I-P15001, A-16,R²-7,R³-7), (I-P15002,A-16,R²-7, R³-8), (I-P15003,A-16,R²-7,R³-9), (I-P15004, A-16,R²-7, R³-10), (I-P15005,A-16,R²-7,R³-11), (I-P15006,A-16,R²-7, R³-12), (I-P15007, A-16,R²-7,R³-13), (I-P15008,A-16,R²-7, R³-14), (I-P15009,A-16,R²-7,R³-15), (I-P15010, A-16,R²-7, R³-16), (I-P15011,A-16,R²-7,R³-17), (I-P15012,A-16,R²-7, R³-18), (I-P15013, A-16,R²-7,R³-19), (I-P15014,A-16,R²-7, R³-20), (I-P15015,A-16,R²-7,R³-21), (I-P15016, A-16,R²-7, R³-22), (I-P15017,A-16,R²-7,R³-23), (I-P15018,A-16,R²-7, R³-24), (I-P15019, A-16,R²-7,R³-25), (I-P15020, A-16,R²-7, R³-26), (I-P15021,A-16,R²-7,R³-27), (I-P15022, A-16,R²-7, R³-28), (I-P15023,A-16,R²-7,R³-29), (I-P15024,A-16,R²-7, R³-30), (I-P15025, A-16,R²-7,R³-31), (I-P15026,A-16,R²-7, R³-32), (I-P15027,A-16,R²-7,R³-33), (I-P15028,A-16,R²-7, R³-34), (I-P15029,A-16,R²-8,R³-1), (I-P15030,A-16,R²-8, R³-2), (I-P15031, A-16,R²-8,R³-3), (I-P15032,A-16,R²-8, R³-4), (I-P15033,A-16,R²-8,R³-5), (I-P15034, A-16,R²-8, R³-6), (I-P15035,A-16,R²-8,R³-7), (I-P15036,A-16,R²-8, R³-8), (I-P15037, A-16,R²-8,R³-9), (I-P15038,A-16,R²-8, R³-10), (I-P15039,A-16,R²-8,R³-11), (I-P15040, A-16,R²-8, R³-12), (I-P15041,A-16,R²-8,R³-13), (I-P15042,A-16,R²-8, R³-14), (I-P15043, A-16,R²-8,R³-15), (I-P15044,A-16,R²-8, R³-16), (I-P15045,A-16,R²-8,R³-17), (I-P15046,A-16,R²-8, R³-18), (I-P15047,A-16,R²-8,R³-19), (I-P15048,A-16,R²-8, R³-20), (I-P15049, A-16,R²-8,R³-21), (I-P15050,A-16,R²-8, R³-22), (I-P15051,A-16,R²-8,R³-23), (I-P15052, A-16,R²-8, R³-24), (I-P15053,A-16,R²-8,R³-25), (I-P15054,A-16,R²-8, R³-26), (I-P15055, A-16,R²-8,R³-27), (I-P15056,A-16,R²-8, R³-28), (I-P15057,A-16,R²-8,R³-29), (I-P15058,A-16,R²-8, R³-30), (I-P15059,A-16,R²-8,R³-31), (I-P15060,A-16,R²-8, R³-32), (I-P15061, A-16,R²-8,R³-33), (I-P15062,A-16,R²-8, R³-34), (I-P15063,A-16,R²-9,R³-1), (I-P15064, A-16,R²-9, R³-2), (I-P15065,A-16,R²-9,R³-3), (I-P15066,A-16,R²-9, R³-4), (I-P15067, A-16,R²-9,R³-5), (I-P15068,A-16,R²-9, R³-6), (I-P15069,A-16,R²-9,R³-7), (I-P15070, A-16,R²-9, R³-8), (I-P15071,A-16,R²-9,R³-9), (I-P15072,A-16,R²-9, R³-10), (I-P15073, A-16,R²-9,R³-11), (I-P15074,A-16,R²-9, R³-12), (I-P15075,A-16,R²-9,R³-13), (I-P15076, A-16,R²-9, R³-14), (I-P15077,A-16,R²-9,R³-15), (I-P15078,A-16,R²-9, R³-16), (I-P15079, A-16,R²-9,R³-17), (I-P15080,A-16,R²-9, R³-18), (I-P15081,A-16,R²-9,R³-19), (I-P15082,A-16,R²-9, R³-20), (I-P15083,A-16,R²-9,R³-21), (I-P15084,A-16,R²-9, R³-22), (I-P15085, A-16,R²-9,R³-23), (I-P15086,A-16,R²-9, R³-24), (I-P15087,A-16,R²-9,R³-25), (I-P15088, A-16,R²-9, R³-26), (I-P15089,A-16,R²-9,R³-27), (I-P15090,A-16,R²-9, R³-28), (I-P15091, A-16,R²-9,R³-29), (I-P15092,A-16,R²-9, R³-30), (I-P15093,A-16,R²-9,R³-31), (I-P15094, A-16,R²-9, R³-32), (I-P15095,A-16,R²-9,R³-33), (I-P15096,A-16,R²-9, R³-34), (I-P15097, A-16,R²-10,R³-1), (I-P15098,A-16,R²-10,R³-2), (I-P15099,A-16,R²-10,R³-3), (I-P15100,A-16,R²-10,R³-4), (I-P15101,A-16,R²-10,R³-5), (I-P15102,A-16,R²-10,R³-6), (I-P15103, A-16,R²-10,R³-7), (I-P15104,A-16,R²-10,R³-8), (I-P15105,A-16,R²-10,R³-9), (I-P15106, A-16,R²-10,R³-10), (I-P15107,A-16,R²-10,R³-11), (I-P15108,A-16, R²-10,R³-12), (I-P15109, A-16,R²-10,R³-13), (I-P15110,A-16,R²-10,R³-14), (I-P15111,A-16,R²-10,R³-15), (I-P15112, A-16,R²-10,R³-16), (I-P15113,A-16,R²-10,R³-17), (I-P15114,A-16,R²-10,R³-18), (I-P15115, A-16,R²-10,R³-19), (I-P15116,A-16,R²-10,R³-20), (I-P15117,A-16,R²-10, R³-21), (I-P15118, A-16,R²-10,R³-22), (I-P15119,A-16,R²-10,R³-23), (I-P15120, A-16,R²-10,R³-24), (I-P15121, A-16, R²-10,R³-25), (I-P15122,A-16,R²-10,R³-26), (I-P15123,A-16,R²-10,R³-27), (I-P15124, A-16,R²-10,R³-28), (I-P15125, A-16,R²-10,R³-29), (I-P15126,A-16,R²-10,R³-30), (I-P15127, A-16,R²-10,R³-31), (I-P15128,A-16,R²-10,R³-32), (I-P15129,A-16,R²-10,R³-33), (I-P15130, A-16,R²-10, R³-34), (I-P15131,A-16,R²-11,R³-1), (I-P15132,A-16,R²-11,R³-2), (I-P15133, A-16,R²-11,R³-3), (I-P15134,A-16,R²-11,R³-4), (I-P15135,A-16,R²-11,R³-5), (I-P15136,A-16,R²-11,R³-6), (I-P15137,A-16,R²-11,R³-7), (I-P15138,A-16,R²-

11,R³-8), (I-P15139,A-16,R²-11,R³-9), (I-P15140,A-16,R²-11,R³-10), (I-P15141,A-16,R²-11,R³-11), (I-P15143, A-16,R²-11,R³-12), (I-P15143,A-16,R²-11,R³-13), (I-P15144,A-16,R²-11,R³-14), (I-P15145, A-16,R²-11,R³-15), (I-P15146, A-16,R²-11,R³-16), (I-P15147,A-16,R²-11,R³-17), (I-P15148, A-16,R²-11,R³-18), (I-P15149,A-16,R²-11,R³-19), (I-P15150,A-16,R²-11,R³-20), (I-P15151, A-16,R²-11,R³-21), (I-P15152,A-16,R²-11,R³-22), (I-P15153,A-16,R²-11,R³-23), (I-P15154, A-16,R²-11,R³-24), (I-P15155,A-16,R²-11,R³-25), (I-P15156,A-16,R²-11,R³-26), (I-P15157, A-16,R²-11,R³-27), (I-P15158,A-16,R²-11,R³-28), (I-P15159,A-16,R²-11,R³-29), (I-P15160, A-16,R²-11,R³-30), (I-P15161,A-16,R²-11,R³-31), (I-P15162,A-16,R²-11,R³-32), (I-P15163, A-16,R²-11,R³-33), (I-P15164,A-16,R²-11,R³-34), (I-P15165,A-16,R²-12,R³-1), (I-P15166, A-16,R²-12,R³-2), (I-P15167,A-16,R²-12,R³-3), (I-P15168,A-16,R²-12,R³-4), (I-P15169, A-16,R²-12,R³-5), (I-P15170,A-16,R²-12,R³-6), (I-P15171,A-16,R²-12,R³-7), (I-P15172, A-16,R²-12,R³-8), (I-P15173,A-16,R²-12,R³-9), (I-P15174,A-16,R²-12,R³-10), (I-P15175, A-16,R²-12,R³-11), (I-P15176,A-16,R²-12,R³-12), (I-P15177,A-16,R²-12,R³-13), (I-P15178, A-16,R²-12,R³-14), (I-P15179,A-16,R²-12,R³-15), (I-P15180,A-16,R²-12,R³-16), (I-P15181, A-16,R²-12,R³-17), (I-P15182,A-16,R²-12,R³-18), (I-P15183,A-16,R²-12,R³-19), (I-P15184, A-16,R²-12,R³-20), (I-P15185,A-16,R²-12,R³-21), (I-P15186,A-16,R²-12,R³-22), (I-P15187, A-16,R²-12,R³-23), (I-P15188,A-16,R²-12,R³-24), (I-P15189,A-16,R²-12,R³-25), (I-P15190, A-16,R²-12,R³-26), (I-P15191, A-16,R²-12,R³-27), (I-P15192,A-16,R²-12,R³-28), (I-P15193, A-16,R²-12,R³-29), (I-P15194,A-16,R²-12,R³-30), (I-P15195,A-16,R²-12,R³-31), (I-P15196, A-16,R²-12,R³-32), (I-P15197,A-16,R²-12,R³-33), (I-P15198,A-16,R²-12,R³-34), (I-P15199, A-16,R²-13,R³-1), (I-P15200,A-16,R²-13,R³-2), (I-P15201,A-16,R²-13,R³-3), (I-P15202, A-16,R²-13,R³-4), (I-P15203,A-16,R²-13,R³-5), (I-P15204,A-16,R²-13,R³-6), (I-P15205,A-16,R²-13,R³-7), (I-P15206,A-16,R²-13,R³-8), (I-P15207,A-16,R²-13,R³-9), (I-P15208, A-16,R²-13,R³-10), (I-P15209,A-16,R²-13,R³-11), (I-P15210,A-16,R²-13,R³-12), (I-P15211, A-16,R²-13,R³-13), (I-P15212, A-16,R²-13,R³-14), (I-P15213,A-16,R²-13,R³-15), (I-P15214, A-16,R²-13,R³-16), (I-P15215,A-16,R²-13,R³-17), (I-P15216,A-16,R²-13,R³-18), (I-P15217, A-16,R²-13,R³-19), (I-P15218,A-16,R²-13,R³-20), (I-P15219,A-16,R²-13,R³-21), (I-P15220,A-16,R²-13,R³-22), (I-P15221,A-16,R²-13,R³-23), (I-P15222,A-16,R²-13,R³-24), (I-P15223, A-16,R²-13,R³-25), (I-P15224,A-16,R²-13,R³-26), (I-P15225,A-16,R²-13,R³-27), (I-P15226, A-16,R²-13,R³-28), (I-P15227,A-16,R²-13,R³-29), (I-P15228,A-16,R²-13,R³-30), (I-P15229, A-16,R²-13,R³-31), (I-P15230,A-16,R²-13,R³-32), (I-P15231,A-16,R²-13,R³-33), (I-P15232, A-16,R²-13,R³-44), (I-P15233,A-16,R²-14,R³-1), (I-P15234,A-16,R²-14,R³-2), (I-P15235, A-16,R²-14,R³-3), (I-P15236,A-16,R²-14,R³-4), (I-P15237,A-16,R²-14,R³-5), (I-P15238, A-16,R²-14,R³-6), (I-P15239,A-16,R²-14,R³-7), (I-P15240, A-16,R²-14,R³-8), (I-P15241, A-16,R²-14,R³-9), (I-P15242, A-16,R²-14,R³-10), (I-P15243,A-16,R²-14,R³-11), (I-P15244, A-16,R²-14,R³-12), (I-P15245,A-16,R²-14,R³-13), (I-P15246,A-16,R²-14,R³-14), I-P15247, A-16,R²-14,R³-15), (I-P15248,A 16,R²-14,R³-16), (I-P15249,A-16,R²-14,R³-17), (I-P15250, A-16,R²-14,R³-18), (I-P15251,A-16,R²-14,R³-19), (I-P15252,A-16,R²-14,R³-20), (I-P15253, A-16,R²-14,R³-21), (I-P15254,A-16,R²-14,R³-22), (I-P15255,A-16,R²-14,R³-23), (I-P15256, A-16,R²-14,R³-24), (I-P15257,A-16,R²-14,R³-25), (I-P15258,A-16,R²-14,R³-26), (I-P15259,A-16,R²-14,R³-27), (I-P15260,A-16,R²-14,R³-28), (I-P15261,A-16,R²-14,R³-29), (I-P15262, A-16,R²-14,R³-30), (I-P15263,A-16,R²-14,R³-31), (I-P15264,A-16,R²-14,R³-32), (I-P15265, A-16,R²-14,R³-33), (I-P15266, A-16,R²-14,R³-34), (I-P15267,A-16,R²-15,R³-1), (I-P15268, A-16,R²-15,R³-2), (I-P15269,A-16,R²-15,R³-3), (I-P15270,A-16,R²-15,R³-4), (I-P15271, A-16,R²-15,R³-5), (I-P15272,A-16,R²-15,R³-6), (I-P15273,A-16,R²-15,R³-7), (I-P15274, A-16,R²-15,R³-8), (I-P15275,A-16,R²-15,R³-9), (I-P15276,A-16,R²-15,R³-10), (I-P15277, A-16,R²-15,R³-11), (I-P15278,A-16,R²-15,R³-12), (I-P15279,A-16,R²-15,R³-13), (I-P15280, A-16,R²-15,R³-14), (I-P15281,A-16,R²-15,R³-15), (I-P15282,A-16,R²-15,R³-16), (I-P15283, A-16,R²-15,R³-17), (I-P15284,A-16,R²-15,R³-18), (I-P15285,A-16,R²-15,R³-19), (I-P15286, A-16,R²-15,R³-20), (I-P15287, A-16,R²-15,R³-21), (I-P15288,A-16,R²-15,R³-22), (I-P15289, A-16,R²-15,R³-23), (I-P15290,A-16,R²-15,R³-24), (I-P15291,A-16,R²-15,R³-25), (I-P15292, A-16,R²-15,R³-26), (I-P15293,A-16,R²-15,R³-27), (I-P15294,A-16,R²-15,R³-28), (I-P15295, A-16,R²-15,R³-29), (I-P15296,A-16,R²-15,R³-30), (I-P15297,A-16,R²-15,R³-31), (I-P15298, A-16,R²-15,R³-32), (I-P15299,A-16,R²-15,R³-33), (I-P15300,A-16,R²-15,R³-34), (I-P15301, A-16,R²-15,R³-1), (I-P15302, A-16,R²-16,R³-2), (I-P15303,A-16,R²-16,R³-3), (I-P15304, A-16,R²-16,R³-4), (I-P15305,A-16,R²-16,R³-5), (I-P15306,A-16,R²-16,R³-6), (I-P15307, A-16,R²-16,R³-7), (I-P15308,A-16,R²-16,R³-8), (I-P15309,A-16,R²-16,R³-9), (I-P15310, A-16,R²-16,R³-10), (I-P15311,A-16,R²-16,R³-11), (I-P15312,A-16,R²-16,R³-12), (I-P15313, A-16,R²-16,R³-13), (I-P15314,A-16,R²-16,R³-14), (I-P15315,A-16,R²-16,R³-15), (I-P15316, A-16,R²-16,R³-16), (I-P15317,A-16,R²-16,R³-17), (I-P15318,A-16,R²-16,R³-19), (I-P15319, A-16,R²-16,R³-19), (I-P15320,A-16,R²-16,R³-20), (I-P153121,A-16,R²-16,R³-21), (I-P15322, A-16,R²-16,R³-22), (I-P15323,A-16,R²-16,R³-23), (I-P15324,A-16,R²-16,R³-24), (I-P15325, A-16,R²-16,R³-25), (I-P15326,A-16,R²-16,R³-26), (I-P15327,A-16,R²-16,R³-27), (I-P15328, A-16,R²-16,R³-28), (I-P15329,A-16,R²-16,R³-29), (I-P15330,A-16,R²-16,R³-30), (I-P15331, A-16,R²-16,R³-31), (I-P15332, A-16,R²-16,R³-32), (I-P15333,A-16,R²-16,R³-33), (I-P15334, A-16,R²-16,R³-34), (I-P15335,A-16,R²-17,R³-1), (I-P15336,A-16,R²-17,R³-2), (I-P15337, A-16,R²-17,R³-3), (I-P15338,A-16,R²-17,R³-4), (I-P15339,A-16,R²-17,R³-5), (I-P15340, A-16,R²-17,R³-6), (I-P15341,A-16,R²-17,R³-7), (I-P15342,A-16,R²-17,R³-8), (I-P15343, A-16,R²-17,R³-9), (I-P15344,A-16,R²-17,R³-10), (I-P15345,A-16,R²-17,R³-11), (I-P15346, A-16,R²-17,R³-12), (I-P15347,A-16,R²-17,R³-13), (I-P15348,A-16,R²-17,R³-14), (I-P15349, A-16,R²-17,R³-15), (I-P15350,A-16,R²-17,R³-16), (I-P15351, A-16,R²-17,R³-17), (I-P15352, A-16,R²-17,R³-18), (I-P15353,A-16,R²-17,R³-19), (I-P15354,A-16,R²-17,R³-20), (I-P15355, A-16,R²-17,R³-21), (I-P15356,A-16,R²-17,R³-22), (I-P15357,A-16,R²-17,R³-23), (I-P15358, A-16,R²-17,R³-24), (I-P15359,A-16,R²-17,R³-25), (I-P15360,A-16,R²-17,R³-26), (I-P15361, A-16,R²-17,R³-27), (I-P15362,A-16,R²-17,R³-28), (I-P15363,A-16,R²-17,R³-29), (I-P15364, A-16,R²-17,R³-30), (I-P15365,A-16,R²-17,R³-31), (I-P15366, A-16,R²-17,R³-32), (I-P15367, A-16,R²-17,R³-33), (I-P15368,A-16,R²-17,R³-34), (I-P15369,A-16,R²-18,R³-1), (I-P15370, A-16,R²-18,R³-2), (I-P15371,A-16,R²-18,R³-3), (I-P15372,A-16,R²-18,R³-4), (I-P15373, A-16,R²-18,R³-5), (I-P15374,A-16,R²-18,R³-6), (I-P15375,A-16,R²-18,R³-7), (I-P15376, A-16,R²-18,R³-8), (I-P15377,A-16,R²-18,R³-9), (I-P15378,A-16,R²-18,R³-10), (I-P15379, A-16,R²-18,R³-11), (I-P15380,A-16,R²-18,R³-12), (I-P15381,A-16,R²-18,R³-13), (I-P15382, A-16,R²-18,R³-14), (I-P15383,A-16,R²-18,R³-15), (I-P15384,A-16,R²-18,R³-16), (I-P15385, A-16,R²-18,R³-17), (I-P15386,A-16,R²-18,R³-18), (I-P15387,A-16,R²-18,R³-19), (I-P15388, A-16,R²-18,R³-20), (I-P15389,A-16,R²-18,R³-21), (I-P15390,A-16,R²-18, (I-P15391, A-16,$R^2$-18,$R^3$-23), (I-P15392,A-16,$R^2$-18,$R^3$-24), (I-P15393,A-16,$R^2$-18,$R^3$-25), (I-P15394, A-16, $R^2$-18,$R^3$-26), (I-P15395,A-16,$R^2$-18,$R^3$-27), (I-P15396,A-16,$R^2$-18,$R^3$-28), (I-P15397, A-16,$R^2$-18,$R^3$-29), (I-P15398, A-16,$R^2$-18,$R^3$-30), (I-P15399,A-16,$R^2$-18,$R^3$-31), (I-P15400, A-16,$R^2$-18,$R^3$-32), (I-P15401,A-16,$R^2$-18,$R^3$-33), (I-P15402,A-16,$R^2$-18,$R^3$-34), (I-P15403, A-16,$R^2$-19,$R^3$-1), (I-P15404,A-16,$R^2$-19,$R^3$-2), (I-P15405,A-16,$R^2$-19,$R^3$-3), (I-P15406, A-16,$R^2$-19,$R^3$-4), (I-P15407,A-16,$R^2$-19,$R^3$-5), (I-P15408,A-16,$R^2$-19,$R^3$-6), (I-P15409, A-16,$R^2$-19,$R^3$-7), (I-P15410,A-16,$R^2$-19,$R^3$-8), (I-P15411,A-16,$R^2$-19,$R^3$-9), (I-P15412, A-16,$R^2$-19,$R^3$-10), (I-P15413,A-16,$R^2$-19,$R^3$-11), (I-P15414,A-16,$R^2$-19,$R^3$-12), (I-P15415, A-16,$R^2$-19,$R^3$-13), (I-P15416,A-16,$R^2$-19,$R^3$-14), (I-P15417,A-16,$R^2$-19,$R^3$-15), (I-P15418, A-16,$R^2$-19,$R^3$-16), (I-P15419, A-16,$R^2$-19,$R^3$-17), (I-P15420,A-16,$R^2$-19,$R^3$-18), (I-P15421, A-16,$R^2$-19,$R^3$-19), (I-P15422,A-16,$R^2$-19,$R^3$-20), (I-P15423,A-16,$R^2$-19,$R^3$-21), (I-P15424, A-16,$R^2$-19,$R^3$-22), (I-P15425,A-16,$R^2$-19,$R^3$-23), (I-P15426,A-16,$R^2$-19,$R^3$-24), (I-P15427, A-16,$R^2$-19,$R^3$-25), (I-P15428,A-16,$R^2$-19,$R^3$-26), (I-P15429,A-16,$R^2$-19,$R^3$-27), (I-P15430, A-16,$R^2$-19,$R^3$-28), (I-P15431,A-16,$R^2$-19,$R^3$-29), (I-P15432,A-16,$R^2$-19,$R^3$-30), (I-P15433, A-16,$R^2$-19,$R^3$-31), (I-P15434,A-16,$R^2$-19,$R^3$-32), (I-P15435,A-16,$R^2$-19,$R^3$-33), (I-P15436, A-16,$R^2$-19,$R^3$-34), (I-P15437,A-16,$R^2$-20,$R^3$-1), (I-P15438,A-16,$R^2$-20,$R^3$-2), (I-P15439, A-16,$R^2$-20,$R^3$-3), (I-P15440,A-16,$R^2$-20,$R^3$-4), (I-P15441,A-16,$R^2$-20,$R^3$-5), (I-P15442, A-16,$R^2$-20,$R^3$-6), (I-P15443,A-16,$R^2$-20,$R^3$-7), (I-P15444,A-16,$R^2$-20,$R^3$-8), (I-P15445, A-16,$R^2$-20,$R^3$-9), (I-P15446,A-16,$R^2$-20,$R^3$-10), (I-P15447,A-16,$R^2$-20,$R^3$-11), (I-P15448, A-16,$R^2$-20,$R^3$-12), (I-P15449,A-16,$R^2$-20,$R^3$-13), (I-P15450,A-16,$R^2$-20,$R^3$-14), (I-P15451, A-16,$R^2$-20,$R^3$-15), (I-P15452,A-16,$R^2$-20,$R^3$-16), (I-P15453,A-16,$R^2$-20,$R^3$-17), (I-P15454, A-16,$R^2$-20,$R^3$-18), (I-P15455,A-16,$R^2$-20,$R^3$-19), (I-P15456,A-16,$R^2$-20,$R^3$-20), (I-P15457, A-16,$R^2$-20,$R^3$-21), (I-P15458,A-16,$R^2$-20,$R^3$-22), (I-P15459,A-16,$R^2$-20,$R^3$-23), (I-P15460, A-16,$R^2$-20,$R^3$-24), (I-P15461,A-16,$R^2$-20,$R^3$-25), (I-P15462,A-16,$R^2$-20,$R^3$-26), (I-P15463, A-16,$R^2$-20,$R^3$-27), (I-P15464, A-16,$R^2$-20,$R^3$-28), (I-P15465,A-16,$R^2$-20,$R^3$-29), (I-P15466, A-16,$R^2$-20,$R^3$-30), (I-P15467,A-16,$R^2$-20,$R^3$-31), (I-P15468,A-16,$R^2$-20,$R^3$-32), (I-P15469, A-16,$R^2$-20,$R^3$-33), (I-P15470,A-16,$R^2$-20,$R^3$-34), (I-P15471,A-16,$R^2$-21,$R^3$-1), (I-P15472, A-16,$R^2$-21,$R^3$-2), (I-P15473,A-16,$R^2$-21,$R^3$-3), (I-P15474,A-16,$R^2$-21,$R^3$-4), (I-P15475, A-16,$R^2$-21,$R^3$-5), (I-P15476,A-16,$R^2$-21,$R^3$-6), (I-P15477,A-16,$R^2$-21,$R^3$-7), (I-P15478,A-16,$R^2$-21,$R^3$-8), (I-P15479,A-16,$R^2$-21,$R^3$-9), (I-P15480,A-16,$R^2$-21,$R^3$-10), (I-P15481, A-16, $R^2$-21,$R^3$-11), (I-P15482,A-16,$R^2$-21,$R^3$-12), (I-P15483,A-16,$R^2$-21,$R^3$-13), (I-P15484, A-16,$R^2$-21,$R^3$-14), (I-P15485, A-16,$R^2$-21,$R^3$-15), (I-P15486,A-16,$R^2$-21,$R^3$-16), (I-P15487, A-16,$R^2$-21,$R^3$-17), (I-P15488,A-16,$R^2$-21,$R^3$-18), (I-P15489,A-16,$R^2$-21,$R^3$-19), (I-P15490, A-16,$R^2$-21, $R^3$-20), (I-P15491,A-16,$R^2$-21,$R^3$-21), (I-P15492,A-16,$R^2$-21,$R^3$-22), (I-P15493, A-16,$R^2$-21,$R^3$-23), (I-P15494,A-16, $R^2$-21,$R^3$-24), (I-P15495,A-16,$R^2$-21,$R^3$-25), (I-P15496, A-16,$R^2$-21,$R^3$-26), (I-P15497,A-16,$R^2$-21,$R^3$-27), (I-P15498,A-16,$R^2$-21,$R^3$-28), (I-P15499, A-16,$R^2$-21,$R^3$-29), (I-P15500,A-16,$R^2$-21,$R^3$-30), (I-P15501,A-16,$R^2$-21,$R^3$-31), (I-P15502, A-16,$R^2$-21,$R^3$-32), (I-P15503,A-16,$R^2$-21,$R^3$-33), (I-P15504,A-16,$R^2$-21,$R^3$-34), (I-P15505, A-16, $R^2$-22,$R^3$-1), (I-P15506,A-16,$R^2$-22,$R^3$-2), (I-P15507,A-16,$R^2$-22,$R^3$-3), (I-P15508, A-16,$R^2$-22,$R^3$-4), (I-P15509,A-16,$R^2$-22,$R^3$-5), (I-P15510,A-16,$R^2$-22,$R^3$-6), (I-P15511,A-16,$R^2$-22,$R^3$-7), (I-P15512,A-16,$R^2$-22,$R^3$-8), (I-P15513,A-16,$R^2$-22,$R^3$-9), (I-P15514, A-16,$R^2$-22,$R^3$-10), (I-P15515,A-16,$R^2$-22,$R^3$-11), (I-P15516,A-16,$R^2$-22,$R^3$-12), (I-P15517, A-16,$R^2$-22,$R^3$-13), (I-P15518,A-16,$R^2$-22,$R^3$-14), (I-P15519,A-16,$R^2$-22,$R^3$-15), (I-P15520, A-16,$R^2$-22,$R^3$-16), (I-P15521,A-16,$R^2$-22,$R^3$-17), (I-P15522,A-16,$R^2$-22,$R^3$-18), (I-P15523, A-16,$R^2$-22,$R^3$-19), (I-P15524,A-16,$R^2$-22,$R^3$-20), (I-P15525,A-16,$R^2$-22,$R^3$-21), (I-P15526, A-16,$R^2$-22,$R^3$-22), (I-P15527,A-16,$R^2$-22,$R^3$-23), (I-P15528,A-16,$R^2$-22,$R^3$-24), (I-P15529,A-16,$R^2$-22,$R^3$-25), (I-P15530, A-16,$R^2$-22,$R^3$-26), (I-P15531,A-16,$R^2$-22,$R^3$-27), (I-P15532, A-16,$R^2$-22,$R^3$-28), (I-P15533,A-16,$R^2$-22,$R^3$-29), (I-P15534,A-16,$R^2$-22,$R^3$-30), (I-P15535, A-16,$R^2$-22,$R^3$-31), (I-P15536,A-16,$R^2$-22,$R^3$-32), (I-P15537,A-16,$R^2$-22,$R^3$-33), (I-P15538, A-16,$R^2$-22,$R^3$-34), (I-P15539,A-16,$R^2$-23,$R^3$-1), (I-P15540,A-16,$R^2$-23,$R^3$-2), (I-P15541, A-16,$R^2$-23,$R^3$-3), (I-P15542,A-16,$R^2$-23,$R^3$-4), (I-P15543,A-16,$R^2$-23,$R^3$-5), (I-P15544, A-16,$R^2$-23,$R^3$-6), (I-P15545,A-16,$R^2$-23,$R^3$-7), (I-P15546,A-16,$R^2$-23,$R^3$-8), (I-P15547, A-16,$R^2$-23,$R^3$-9), (I-P15548,A-16,$R^2$-23,$R^3$-10), (I-P15549,A-16,$R^2$-23,$R^3$-11), (I-P15550, A-16,$R^2$-23,$R^3$-12), (I-P15551, A-16,$R^2$-23,$R^3$-13), (I-P15552,A-16,$R^2$-23,$R^3$-14), (I-P15553, A-16,$R^2$-23,$R^3$-15), (I-P15554,A-16,$R^2$-23,$R^3$-16), (I-P15555,A-16,$R^2$-23,$R^3$-17), (I-P15556, A-16,$R^2$-23, $R^3$-18), (I-P15557,A-16,$R^2$-23,$R^3$-19), (I-P15558,A-16,$R^2$-23,$R^3$-20), (I-P15559, A-16,$R^2$-23,$R^3$-21), (I-P15560,A-16, $R^2$-23,$R^3$-22), (I-P15561,A-16,$R^2$-23,$R^3$-23), (I-P15562, A-16,$R^2$-23,$R^3$-24), (I-P15563,A-16,$R^2$-23,$R^3$-25), (I-P15564,A-16,$R^2$-23,$R^3$-26), (I-P15565, A-16,$R^2$-23,$R^3$-27), (I-P15566,A-16,$R^2$-23,$R^3$-28), (I-P15567,A-16,$R^2$-23, $R^3$-29), (I-P15568, A-16,$R^2$-23,$R^3$-30), (I-P15569,A-16,$R^2$-23,$R^3$-31), (I-P15570,A-16,$R^2$-23,$R^3$-32), (I-P15571, A-16, $R^2$-23,$R^3$-33), (I-P15572,A-16,$R^2$-23,$R^3$-34), (I-P15573,A-16,$R^2$-24,$R^3$-1), (I-P15574, A-16,$R^2$-24,$R^3$-2), (I-P15575,A-16,$R^2$-24,$R^3$-3), (I-P15576,A-16,$R^2$-24,$R^3$-4), (I-P15577, A-16,$R^2$-24,$R^3$-5), (I-P15578,A-16,$R^2$-24,$R^3$-6), (I-P15579, A-16,$R^2$-24,$R^3$-7), (I-P15580,A-16,$R^2$-24,$R^3$-8), (I-P15581, A-16,$R^2$-24,$R^3$-9), (I-P15582,A-16,$R^2$-24,$R^3$-10), (I-P15583, A-16,$R^2$-24,$R^3$-11), (I-P15584,A-16,$R^2$-24,$R^3$-12), (I-P15585,A-16,$R^2$-24,$R^3$-13), (I-P15586, A-16,$R^2$-24, $R^3$-14), (I-P15587,A-16,$R^2$-24,$R^3$-15), (I-P15588,A-16,$R^2$-24,$R^3$-16), (I-P15589, A-16,$R^2$-24,$R^3$-17), (I-P15590,A-16, $R^2$-24,$R^3$-18), (I-P15591,A-16,$R^2$-24,$R^3$-19), (I-P15592, A-16,$R^2$-24,$R^3$-20), (I-P15593,A-16,$R^2$-24,$R^3$-21), (I-P15594,A-16,$R^2$-24,$R^3$-22), (I-P15595, A-16,$R^2$-24,$R^3$-23), (I-P15596,A-16,$R^2$-24,$R^3$-24), (I-P15597,A-16,$R^2$-24, $R^3$-25), (I-P15598, A-16,$R^2$-24,$R^3$-26), (I-P15599,A-16,$R^2$-24,$R^3$-27), (I-P15600,A-16,$R^2$-24,$R^3$-28), (I-P15601, A-16, $R^2$-24,$R^3$-29), (I-P15602,A-16,$R^2$-24,$R^3$-30), (I-P15603,A-16,$R^2$-24,$R^3$-31), (I-P15604, A-16,$R^2$-24,$R^3$-32), (I-P15605, A-16,$R^2$-24,$R^3$-33), (I-P15606,A-16,$R^2$-24,$R^3$-34), (I-P15607, A-16,$R^2$-25,$R^3$-1), (I-P15608,A-16,$R^2$-25,$R^3$-2), (I-P15609,A-16,$R^2$-25,$R^3$-3), (I-P15610, A-16,$R^2$-25,$R^3$-4), (I-P15611,A-16,$R^2$-25,$R^3$-4), (I-P15612,A-16,$R^2$-25,$R^3$-6), (I-P15613, A-16,$R^2$-25,$R^3$-7), (I-P15614,A-16,$R^2$-25,$R^3$-8), (I-P15615,A-16,$R^2$-25,$R^3$-9), (I-P15616, A-16,$R^2$-25,$R^3$-10), (I-P15617,A-16,$R^2$-25,$R^3$-11), (I-P15618,A-16,$R^2$-25,$R^3$-12), (I-P15619, A-16,$R^2$-25,$R^3$-13), (I-P15620,A-16,$R^2$-25,$R^3$-14), (I-P15621,A-16,$R^2$-25,$R^3$-15), (I-P15622, A-16,$R^2$-25,$R^3$-16), (I-P15623,A-16,$R^2$-25,$R^3$-17), (I-P15624,A-16,$R^2$-25,$R^3$-18), (I-P15625, A-16,$R^2$-25,$R^3$-19), (I-P15626, A-16,$R^2$-25,$R^3$-20), (I-P15627,A-16,$R^2$-25,$R^3$-21), (I-P15628, A-16,$R^2$-25,$R^3$-22), (I-P15629,A-16,$R^2$-25,$R^3$-23), (I-P15630,A-16,$R^2$-25,$R^3$-24), (I-P15631, A-16,$R^2$-25, $R^3$-25), (I-P15632,A-16,$R^2$-25,$R^3$-26), (I-P15633,A-16,$R^2$-25,$R^3$-27), (I-P15634, A-16,$R^2$-25,$R^3$-28), (I-P15635,A-16,$R^2$-25,$R^3$-29), (I-P15636, A-16,$R^2$-25,$R^3$-30), (I-P15637, A-16,$R^2$-25,$R^3$-31), (I-P15638,A-16,$R^2$-25,$R^3$-32), (I-P15639,A-16,$R^2$-25,$R^3$-33), (I-P15640, A-16,$R^2$-25,$R^3$-34), (I-P15641,A-16,$R^2$-26,$R^3$-1), (I-P15642,A-16,$R^2$-26,

R$^3$-2), (I-P15643, A-16,R$^2$-26,R$^3$-3), (I-P15644,A-16,R$^2$-26, R$^3$-4), (I-P15645,A-16,R$^2$-26,R$^3$-5), (I-P15646, A-16,R$^2$-26, R$^3$-6), (I-P15647,A-16,R$^2$-26,R$^3$-7), (I-P15648,A-16,R$^2$-26, R$^3$-8), (I-P15649, A-16,R$^2$-26,R$^3$-9), (I-P15650,A-16,R$^2$-26, R$^3$-10), (I-P15651,A-16,R$^2$-26,R$^3$-11), (I-P15652, A-16,R$^2$-26,R$^3$-12), (I-P15653,A-16,R$^2$-26,R$^3$-13), (I-P15654,A-16, R$^2$-26,R$^3$-14), (I-P15655, A-16,R$^2$-26,R$^3$-15), (I-P15656,A-16,R$^2$-26,R$^3$-16), (I-P15657,A-16,R$^2$-26,R$^3$-17), (I-P15658, A-16,R$^2$-26,R$^3$-18), (I-P15659,A-16,R$^2$-26,R$^3$-19), (I-P15660,A-16,R$^2$-26,R$^3$-20), (I-P15661, A-16,R$^2$-26,R$^3$-21), (I-P15662,A-16,R$^2$-26,R$^3$-22), (I-P15663,A-16,R$^2$-26, R$^3$-23), (I-P15664, A-16,R$^2$-26,R$^3$-24), (I-P15665,A-16,R$^2$-26,R$^3$-25), (I-P15666,A-16,R$^2$-26,R$^3$-26), (I-P15667, A-16, R$^2$-26,R$^3$-27), (I-P15668,A-16,R$^2$-26,R$^3$-28), (I-P15669,A-16,R$^2$-26,R$^3$-29), (I-P15670, A-16,R$^2$-26,R$^3$-30), (I-P15671, A-16,R$^2$-26,R$^3$-31), (I-P15672,A-16,R$^2$-26,R$^3$-32), (I-P15673, A-16,R$^2$-26,R$^3$-33), (I-P15674,A-16,R$^2$-26,R$^3$-34), (I-P15675,A-16,R$^2$-27,R$^3$-1), (I-P15676, A-16,R$^2$-27, R$^3$-2), (I-P15677,A-16,R$^2$-27,R$^3$-3), (I-P15678,A-16,R$^2$-27, R$^3$-4), (I-P15679, A-16,R$^2$-27,R$^3$-5), (I-P15680,A-16,R$^2$-27, R$^3$-6), (I-P15681,A-16,R$^2$-27,R$^3$-7), (I-P15682, A-16,R$^2$-27, R$^3$-8), (I-P15683,A-16,R$^2$-27,R$^3$-9), (I-P15684,A-16,R$^2$-27, R$^3$-10), (I-P15685, A-16,R$^2$-27,R$^3$-11), (I-P15686,A-16,R$^2$-27,R$^3$-12), (I-P15687,A-16,R$^2$-27,R$^3$-13), (I-P15688, A-16, R$^2$-27,R$^3$-14), (I-P15689,A-16,R$^2$-27,R$^3$-15), (I-P15690,A-16,R$^2$-27,R$^3$-16), (I-P15691, A-16,R$^2$-27,R$^3$-17), (I-P15692, A-16,R$^2$-27,R$^3$-18), (I-P15693,A-16,R$^2$-27,R$^3$-19), (I-P15694, A-16,R$^2$-27,R$^3$-20), (I-P15695,A-16,R$^2$-27,R$^3$-21), (I-P15696,A-16,R$^2$-27,R$^3$-22), (I-P15697, A-16,R$^2$-27, R$^3$-23), (I-P15698,A-16,R$^2$-27,R$^3$-24), (I-P15699,A-16,R$^2$-27,R$^3$-25), (I-P15700, A-16,R$^2$-27,R$^3$-26), (I-P15701,A-16, R$^2$-27,R$^3$-27), (I-P15702,A-16,R$^2$-27,R$^3$-28), (I-P15703, A-16,R$^2$-27,R$^3$-29), (I-P15704,A-16,R$^2$-27,R$^3$-30), (I-P15705,A-16,R$^2$-27,R$^3$-31), (I-P15706, A-16,R$^2$-27,R$^3$-32), (I-P15707,A-16,R$^2$-27,R$^3$-33), (I-P15708,A-16,R$^2$-27, R$^3$-34), (I-P15709, A-16,R$^2$-28,R$^3$-1), (I-P15710,A-16,R$^2$-28,R$^3$-2), (I-P15711,A-16,R$^2$-28,R$^3$-3), (I-P15712, A-16,R$^2$-28,R$^3$-4), (I-P15713,A-16,R$^2$-28,R$^3$-5), (I-P15714,A-16,R$^2$-28,R$^3$-6), (I-P15715, A-16,R$^2$-28,R$^3$-7), (I-P15716,A-16,R$^2$-28,R$^3$-8), (I-P15717,A-16,R$^2$-28,R$^3$-9), (I-P15718, A-16,R$^2$-28,R$^3$-10), (I-P15719,A-16,R$^2$-28,R$^3$-11), (I-P15720,A-16, R$^2$-28,R$^3$-12), (I-P15721, A-16,R$^2$-28,R$^3$-13), (I-P15722,A-16,R$^2$-28,R$^3$-14), (I-P15723,A-16,R$^2$-28,R$^3$-15), (I-P15724, A-16,R$^2$-28,R$^3$-16), (I-P15725,A-16,R$^2$-28,R$^3$-17), (I-P15726,A-16,R$^2$-28,R$^3$-18), (I-P15727, A-16,R$^2$-28,R$^3$-19), (I-P15728,A-16,R$^2$-28,R$^3$-20), (I-P15729,A-16,R$^2$-28, R$^3$-21), (I-P15730, A-16,R$^2$-28,R$^3$-22), (I-P15731,A-16,R$^2$-28,R$^3$-23), (I-P15732,A-16,R$^2$-28,R$^3$-24), (I-P15733, A-16, R$^2$-28,R$^3$-25), (I-P15734,A-16,R$^2$-28,R$^3$-26), (I-P15735,A-16,R$^2$-28,R$^3$-27), (I-P15736, A-16,R$^2$-28,R$^3$-28), (I-P15737, A-16,R$^2$-28,R$^3$-29), (I-P15738,A-16,R$^2$-28,R$^3$-30), (I-P15739, A-16,R$^2$-28,R$^3$-31), (I-P15740,A-16,R$^2$-28,R$^3$-32), (I-P15741,A-16,R$^2$-28,R$^3$-33), (I-P15742, A-16,R$^2$-28, R$^3$-34), (I-P15743,A-16,R$^2$-29,R$^3$-1), (I-P15744,A-16,R$^2$-29,R$^3$-2), (I-P15745, A-16,R$^2$-29,R$^3$-3), (I-P15746,A-16,R$^2$-29,R$^3$-4), (I-P15747,A-16,R$^2$-29,R$^3$-5), (I-P15748, A-16,R$^2$-29,R$^3$-6), (I-P15749,A-16,R$^2$-29,R$^3$-7), (I-P15750,A-16,R$^2$-29,R$^3$-8), (I-P15751, A-16,R$^2$-29,R$^3$-9), (I-P15752,A-16,R$^2$-29,R$^3$-10), (I-P15753,A-16,R$^2$-29,R$^3$-11), (I-P15754, A-16, R$^2$-29,R$^3$-12), (I-P15755,A-16,R$^2$-29,R$^3$-13), (I-P15756,A-16,R$^2$-29,R$^3$-14), (I-P15757, A-16,R$^2$-29,R$^3$-15), (I-P15758, A-16,R$^2$-29,R$^3$-16), (I-P15759,A-16,R$^2$-29,R$^3$-17), (I-P15760, A-16,R$^2$-29,R$^3$-18), (I-P15761,A-16,R$^2$-29,R$^3$-19), (I-P15762,A-16,R$^2$-29,R$^3$-20), (I-P15763, A-16,R$^2$-29, R$^3$-21), (I-P15764,A-16,R$^2$-29,R$^3$-22), (I-P15765,A-16,R$^2$-29,R$^3$-23), (I-P15766, A-16,R$^2$-29,R$^3$-24), (I-P15767,A-16, R$^2$-29,R$^3$-25), (I-P15768,A-16,R$^2$-29,R$^3$-26), (I-P15769, A-16,R$^2$-29,R$^3$-27), (I-P15770,A-16,R$^2$-29,R$^3$-28), (I-P15771,A-16,R$^2$-29,R$^3$-29), (I-P15772, A-16,R$^2$-29,R$^3$-30), (I-P15773,A-16,R$^2$-29,R$^3$-31), (I-P15774,A-16,R$^2$-29, R$^3$-32), (I-P15775, A-16,R$^2$-29,R$^3$-33), (I-P15776,A-16,R$^2$-29,R$^3$-34)

Test Example 1

Evaluation Method of llp-HSD1 Inhibitor (Evaluation of Compound Against Human 11β-HSD1)

After preincubating an inhibitor in a reaction solution consisting of 50 mM sodium phosphate buffer (pH 7.5), bovine serum albumin (1 mg/mL), NADPH (0.42 mg/mL), glucose-6-phosphate (1.26 mg/mL), glucose-6-phosphate dehydrogenase and an enzyme at room temperature for 30), (Inutes, cortisone (5 μM) was added as a substrate (total amount 10 μL). After reacting at 37° C. for 2 hours, an XL-665-labeled cortisol solution (5 μL), and a Cryptate-labeled anti-cortisol antibody solution (5 μL) were added. The reaction was performed at room temperature for 2 hours, and fluorescence intensity (HTRF method) was measured. A cortisol concentration was calculated from a standard curve prepared using a known concentration of cortisol for each assay.

Taking a concentration of cortisol generated in the absence of the inhibitor as a control value, 50% inhibitory concentration ($IC_{50}$ value) of the inhibitor against 11β-HSD1 was calculated from an inhibition curve plotting inhibition rate against the control value at each concentration of an inhibitor.

Test Example 2

Evaluation Method of 11β-HSD1 Inhibitor (Evaluation of Compound Against Mouse 11β-HSD1)

After preincubating an inhibitor in a reaction solution consisting of 50 mM sodium phosphate buffer (pH 7.5), bovine serum albumin (1 mg/mL), NADPH (0.42 mg/mL), glucose-6-phosphate (1.26 mg/mL), glucose-6-phosphate dehydrogenase, and an enzyme at room temperature for 30 minutes, 11-dehydrocorticosterone (2 μM) was added as a substrate (total amount 10 μL). After reacting at 37° C. for 2 hours, an XL-665-labeled cortisol solution (5 μL), and a Cryptate-labeled anti-cortisol antibody solution (5 μL) were added. The reaction was performed at room temperature for 2 hours, and fluorescence intensity (HTRF method) was measured.

A corticosterone concentration was calculated from a standard curve prepared using a known concentration of corticosterone for each assay.

Taking a concentration of corticosterone generated in the absence of the inhibitor as a control value, 50% inhibitory concentration ($IC_{50}$ value) of the inhibitor against 11β-HSD1 was calculated from an inhibition curve plotting inhibition rate against the control value at each concentration of the inhibitor.

Results of Test Examples 1 and 2 are shown below.
Compound 1-7: human $IC_{50}$=3.4 nM, mouse $IC_{50}$=0.41 nM
Compound 1-9: human $IC_{50}$=11 nM, mouse $IC_{50}$=1.7 nM
Compound 1-36: human $IC_{50}$=1.2 nM, mouse $IC_{50}$=1 nM
Compound 1-63: human $IC_{50}$=1.4 nM, mouse $IC_{50}$=0.21 nM
Compound 1-77: human $IC_{50}$=0.62 nM, mouse $IC_{50}$=0.23 nM
Compound 1-105: human $IC_{50}$=147.8 nM, mouse $IC_{50}$=3.6 nM Compound 1-121: human $IC_{50}$=154.3 nM, mouse $IC_{50}$=4.9 nM Compound 1-127: human $IC_{50}$=88.1 nM, mouse $IC_{50}$=3.0 nM Compound 1-128: human $IC_{50}$=62.4 nM, mouse $IC_{50}$=5.5 nM Compound 1-131: human $IC_{50}$=20.8 nM, mouse $IC_{50}$=1.4 nM Compound 1-133: human $IC_{50}$=75.6 nM, mouse $IC_{50}$=0.52 nM Compound 1-138: human $IC_{50}$=35.1 nM, mouse $IC_{50}$=0.28 nM Compound 1-139: human $IC_{50}$=64.4 nM, mouse $IC_{50}$=0.37 nM Test Example 3

Materials and Methods of Oral Absorption of 11β-HSD1 Inhibitor Against Diabetes (1) Animal: male C57BL/6J Jcl mice at the age of 6 weeks were purchased from CLEA Japan, Inc., and used for the experiment at the age of 7 weeks after preliminary rearing for 1 week.
(2) Rearing conditions: Mice were fed in the following environment: temperature 23±2° C., humidity 55±10%, in a cycle of 8:00 to 20:00 in light and 20:00 to 8:00 in dark. During preliminary rearing and experimental periods, the mice were allowed free access to solid feed (CE-2, CLEA Japan, Inc.) and sterilized tap water.
(3) Identification of individual and cage: Individual number was written with oil ink on the tail of a mouse to achieve identification. A cage was attached with a label describing a name of a study director, data of arrival, a strain, a sex, and a name of a supplier, and the mice were fed by 20), (Ice/cage during preliminary rearing. After start of the experiment, the mice were fed in 3), (Ice/cage.
(4) Setting of dose and grouping: The following groups were set according to dose amounts of oral or intravenous administration.

| Oral administration | 20 mg/kg (n = 3) |
| Intravenous administration | 5 mg/kg (n = 3) |

(5) Preparation of dosing liquid: A preparation method is shown below. A suspension was prepared using 0.5% methylcellulose (1500 cP) as a vehicle for oral administration. A solubilized solution was prepared using N,N-dimethylacetamide/polyethylene glycol 400(=1/2) as a vehicle for intravenous administration.
(6) Administration method: As to oral administration, the dosing suspension was administered compulsorily into the stomach using an oral sonde at 10 mL/kg. As to intravenous administration, the dosing solution was administered into caudal vein at 2.5 mL/kg using a glass syringe.
(7) Evaluation item: Blood was collected from heart by time-point blood sampling, and a drug concentration in plasma was measured by using HPLC or LC/MS/MS.
(8) Statistical analysis: As to a plasma concentration profile, an area under the plasma concentration-time curve (AUC) was calculated by using non-linear minimum program WinNonlin (registered trade name), and bioavailability was calculated from AUC values in the oral administration group and the intravenous administration group.

Evaluation Method of HSD1 Inhibitory Activity Using Excised Adipose Tissue

Male ob/ob mice at the age of 9-10 weeks were used for the experiment. A test compound 30-50 mg/kg was orally administered to an animal. Eight and 16 hours later, the visceral adipose tissue was excised under chloral hydrate anesthesia and HSD1 activity in adipose was measured. Taking HSD1 activity in adipose tissue of the animal to which 0.5% methyl cellulose solution was orally administered and similar treatment was given as a control value (100%), HSD1 inhibitory activity of test compound was measured.

Three times equivalent volume of phosphate buffered solution (50 mM sodium phosphate (pH 7.5), bovine serum albumin (1 mg/ml)) was added to about 200 mg of excised adipose tissue, and homogenate solution was prepared and used for the measurement of HSD1 enzyme activity. As to HSD1 enzyme activity measurement, 60 µL of reaction solution (50 mM sodium phosphate buffer (pH 7.5), bovine serum albumin (1 mg/mL), NADPH (0.42 mg/mL), glucose-6-phosphate (1.26 mg/mL), glucose-6-phosphate dehydrogenase) and 20 µL of adipose homogenate solution were mixed, and the reaction was initiated by adding 20 µL of 10 µM 11-DHC solution as a substrate. The reaction was performed at 37° C. for 60 minutes, and 200 µL of ethyl acetate was added to stop the reaction. After 10 µL of dexamethasone solution (20 pmol/µL) as an internal standard for analysis was added, the mixture was centrifuged (15000 rpm×3), (In, r.t.) and 150 µL of supernatant was collected. After the supernatant was dried under reduced pressure, the residue was dissolved to 60 µL of water-methanol solution ($H_2O$:methanol=45:55) and concentration of corticosterone was determined by using HPLC.

Corticosterone concentration was calculated from the calibration curve using dexamethasone as an internal standard.

The following Formulation Examples 1 to 8 are merely examples, and are not intended to limit the scope of the present invention. The term "active ingredient" means the present compound, pharmaceutically acceptable salt thereof, or hydrate thereof.

Formulation Example 1

A hard gelatin capsule is prepared by using the following ingredients:

| | Dose (mg/capsule) |
| --- | --- |
| Active ingredient | 250 |
| Starch (dry) | 200 |
| Magnesium stearate | 10 |
| Total | 460 mg |

Formulation Example 2

A tablet is prepared by using the following ingredients:

| | Dose (mg/tablet) |
| --- | --- |
| Active ingredient | 250 |
| Cellulose (microcrystal) | 400 |
| Silicon dioxide (fumed) | 10 |
| Stearic acid | 5 |
| Total | 665 mg |

The ingredients are mixed, and compressed to form tables each weighing 665 mg.

Formulation Example 3

An aerosol solution containing the following ingredients is prepared

|  | Weight |
| --- | --- |
| Active ingredient | 0.25 |
| Ethanol | 25.75 |
| Propellant 22 (chlorodifluoromethane) | 74.00 |
| Total | 100.00 |

The active ingredient and ethanol are mixed, and the mixture is added to part of propellant 22, cooled to −30° C., and transferred to a packing machine. Then, a necessary amount is supplied to a stainless steel container, and diluted with the remaining propellant. A bubble unit is attached to the container.

Formulation Example 4

A tablet containing 60 mg of the active ingredient is prepared in the following manner:

| Active ingredient | 60 mg |
| --- | --- |
| Starch | 45 mg |
| Microcrystalline cellulose | 35 mg |
| Polyvinylpyrrolidone (10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. An aqueous solution containing polyvinylpyrrolidone is mixed with obtained powder and then the mixture is passed through a No. 14 mesh U.S. sieve. Granules obtained in this manner are dried at 50° C. and passed through a No. 18 mesh U.S. sieve. The sodium carboxymethyl starch, magnesium stearate and talc that are passed through a No. 60 mesh U.S. sieve in advance, are added to the granules, mixed, and then compressed by a tableting machine to obtain tablets each weighing 150 mg.

Formulation Example 5

A capsule containing 80 mg of the active ingredient is prepared in the following manner:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, starch, cellulose, and magnesium stearate are mixed, and passed through a No. 45 mesh U.S. sieve, and filled into a hard gelatin capsule in 200 mg quantities.

Formulation Example 6

Suppository containing 225 mg of the active ingredient is prepared in the following manner:

| Active ingredient | 225 mg |
| --- | --- |
| Saturated fatty acid glyceride | 2000 mg |
| Total | 2225 mg |

The active ingredient is passed through a No. 60 mesh U.S. sieve, and suspended in saturated fatty acid glyceride that is melted by heating least necessarily in advance. Then, the resultant mixture is put into an apparent 2 g mold, and cooled.

Formulation Example 7

A suspension containing 50 mg of the active ingredient is prepared in the following manner:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Pigment | q.v. |
| Purified water to total | 5 mL |

The active ingredient is passed through a No. 45 mesh U.S. sieve, and mixed with sodium carboxymethyl cellulose and syrup to form a smooth paste. The benzoic acid solution and the flavor diluted with part of water are added, and stirred. Then a sufficient amount of water is added to achieve required volume.

Formulation Example 8

An intravenous formulation is prepared in the following manner:

| Active ingredient | 100 mg |
| --- | --- |
| Saturated fatty acid glyceride | 1000 mL |

The solution of the above ingredients is intravenously administered to a patient usually at a speed of 1 mL per minute.

INDUSTRIAL APPLICABILITY

As is apparent from the above test examples, the compounds according to the present invention show inhibitory activity to 11β-hydroxysteroid dehydrogenase type 1. Therefore, the compounds according to the present invention are very useful as therapeutic agents for diabetes.

The invention claimed is:
1. A compound represented by the Formula (I):

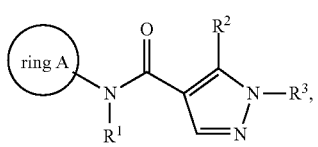

or its pharmaceutically acceptable salt,
wherein Ring A is a group represented by the formula:

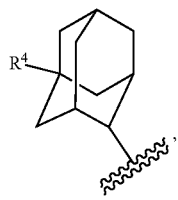

$R^1$ is hydrogen or optionally substituted alkyl,
$R^2$ is —$OR^5$, —$SR^5$, halogen, halogenated alkyl, halogenated alkoxy, hydroxy, cyano, nitro, carboxy, optionally substituted alkyl, optionally substituted alkenyl, optionally substituted alkynyl, optionally substituted aryl, optionally substituted cycloalkyl, optionally substituted cycloalkenyl, optionally substituted heteroaryl, optionally substituted heterocycle,
a group represented by the formula: —$NR^{5A}R^{6A}$,
wherein $R^{5A}$ and $R^{6A}$ are each independently hydrogen, hydroxy, alkoxy, optionally substituted alkyl, optionally substituted alkenyl, optionally substituted carbamoyl, optionally substituted aryl, optionally substituted cycloalkyl, optionally substituted cycloalkenyl, optionally substituted heteroaryl or optionally substituted heterocycle, or $R^{5A}$ and $R^{6A}$ taken together with the adjacent nitrogen atom to which they are attached may form an optionally substituted ring,
a group represented by the formula: —$S(=O)x-R^{7A}$,
wherein x is an integer of 1 or 2, $R^{7A}$ is optionally substituted alkyl, optionally substituted alkenyl, optionally substituted aryl, optionally substituted cycloalkyl, optionally substituted cycloalkenyl, optionally substituted heteroaryl or optionally substituted heterocycle,
a group represented by the formula: —$C(=O)NR^{5A}R^{6A}$
wherein $R^{5A}$ and $R^{6A}$ are as defined in the above, or
a group represented by the formula: —$(CR^{8A}R^{9A})y$-O—$(CR^{10A}R^{11A})z$-$CR^{12A}R^{13A}R^{14A}$,
wherein y and z are each independently integer of 0 to 5, $R^{8A}$, $R^{9A}$, $R^{10A}$, $R^{11A}$, $R^{12A}$, $R^{13A}$ and $R^{14A}$ are each independently hydrogen, hydroxy, halogen, halogenated alkyl, halogenated alkoxy, alkoxy, cyano, carboxy, optionally substituted alkyl, optionally substituted alkenyl, optionally substituted aryl, optionally substituted cycloalkyl, optionally substituted cycloalkenyl, optionally substituted heteroaryl or optionally substituted heterocycle,
$R^3$ is a group represented by the formula: —CH=CH—C($R^aR^b$)—$R^c$—$R^d$ or
a group represented by the formula: —$(CR^eR^f)_m$—C($R^aR^b$)—$R^c$—$R^d$, wherein $R^a$ and $R^b$ are each independently hydrogen, optionally substituted alkyl or halogen, or $R^a$ and $R^b$ taken together with the adjacent carbon atom to which they are attached may form an optionally substituted ring,
$R^c$ is —$(CH_2)_n$—, wherein n is an integer of 0 to 3,
$R^d$ is hydrogen, halogen, hydroxy, carboxy, cyano, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle,
a group represented by the formula: —C(=O)—$NR^gR^h$ or
a group represented by the formula: —$NR^iR^j$,
$R^e$ and $R^f$ are each independently hydrogen, halogen or optionally substituted alkyl, $R^g$ and $R^h$ are each independently hydrogen, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxy, optionally substituted carbamoyl or $R^g$ and $R^h$ taken together with the adjacent nitrogen atom to which they are attached may form an optionally substituted ring,
$R^i$ and $R^j$ are each independently hydrogen, carboxy, hydroxy, optionally substituted alkyl, optionally substituted alkenyl, optionally substituted alkynyl, optionally substituted cycloalkyl, optionally substituted cycloalkenyl, optionally substituted aryl, optionally substituted heteroaryl, optionally substituted heterocycle, optionally substituted acyl, optionally substituted carbamoyl, optionally substituted thiocarbamoyl, optionally substituted alkylsulfonyl, optionally substituted cycloalkylsulfonyl, optionally substituted arylsulfonyl, optionally substituted heteroarylsulfonyl, optionally substituted heterocyclesulfonyl, optionally substituted alkyloxycarbonyl, optionally substituted cycloalkyloxycarbonyl, optionally substituted aryloxycarbonyl, optionally substituted heteroaryloxycarbonyl, optionally substituted heterocycleoxycarbonyl, optionally substituted alkylcarbonyl, optionally substituted cycloalkylcarbonyl, optionally substituted arylcarbonyl, optionally substituted heteroarylcarbonyl, optionally substituted heterocyclecarbonyl, optionally substituted sulfamoyl or $R^i$ and $R^j$ taken together with the adjacent nitrogen atom to which they are attached may form an optionally substituted ring,
$R^4$ is optionally substituted alkyl, optionally substituted alkenyl, —$OR^6$, —$CONR^7R^8$, —$NR^9CONR^7R^8$, —$NR^9SO_2NR^7R^8$, —$(CR^{10}R^{11})pOH$, —$(CR^{10}R^{11})pOCONR^7R^8$, —$NR^9COR^{12}$, —$NR^9C(=O)OR^{12}$, —$(CR^{10}R^{11})pNR^9COR^{12}$, —$C(=O)NR^9OR^{12}$, —$CONR^9CONR^7R^8$, —CN, or —COOH,
$R^5$ is optionally substituted alkyl, optionally substituted alkenyl, optionally substituted cycloalkyl, optionally substituted aryl, optionally substituted heteroaryl or optionally substituted heterocycle,
$R^6$ is optionally substituted alkyl, optionally substituted alkenyl, optionally substituted cycloalkyl, optionally substituted aryl, optionally substituted heteroaryl, optionally substituted heterocycle, —$SO_2R^5$, —$SO_2NR^7R^8$ or —$CONR^7R^8$, $R^7$ and $R^8$ are each independently hydrogen, optionally substituted alkyl, optionally substituted cycloalkyl, optionally substituted aryl, optionally substituted heteroaryl, optionally substituted heterocycle or —SO$_2$R$^5$, or $R^7$ and $R^8$ taken together with the adjacent nitrogen atom to which they are attached may form an optionally substituted ring, $R^9$ is hydrogen or optionally substituted alkyl, $R^{10}$ and $R^{11}$ are each independently hydrogen, halogen or optionally substituted alkyl, $R^{12}$ is optionally substituted alkyl, optionally substituted cycloalkyl, optionally substituted aryl, optionally substituted heteroaryl or optionally substituted heterocycle, m and p are each independently integer of 1 to 3, provided that, when $R^2$ is halogen, halogenated alkyl, optionally substituted alkyl, optionally substituted heteroaryl, a group represented by the formula: —NR$^{5A}$R$^{6A}$, wherein $R^{5A}$ and $R^{6A}$ are as defined in the above or a group represented by the formula: —(CR$^{8A}$R$^{9A}$)y-O—(CR$^{10A}$R$^{11A}$)z-CR$^{12A}$R$^{13A}$R$^{14A}$, wherein $R^{8A}$ to $R^{14A}$, y and z are as defined in the above, $R^3$ is a group represented by the formula: —CH=CH—C(R$^a$R$^b$)—R$^c$—R$^d$, provided that the compounds shown as follows are excluded,

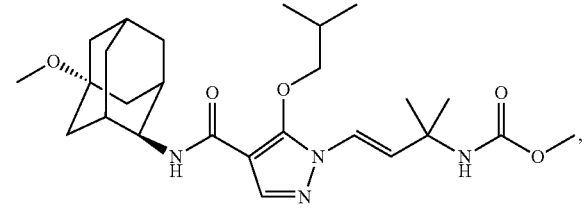

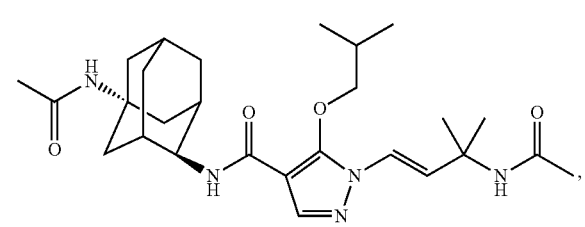

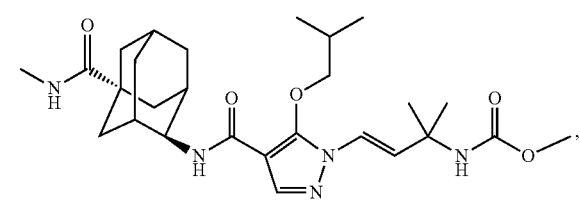

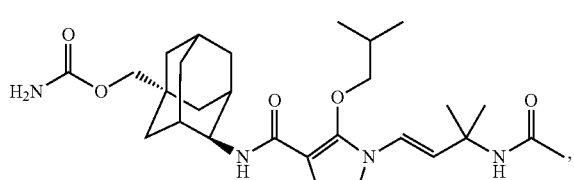

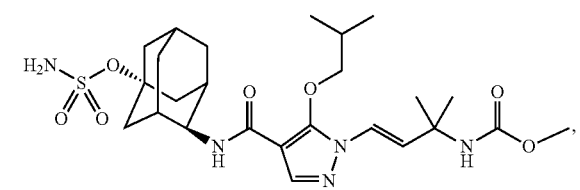

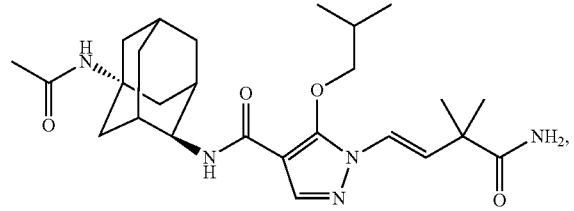

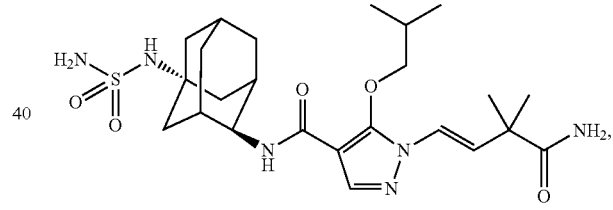

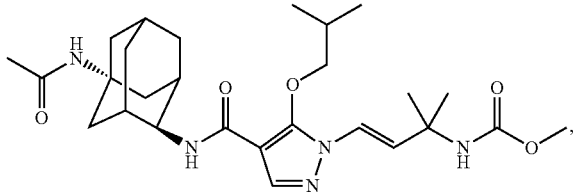

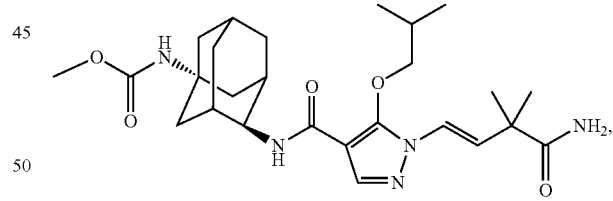

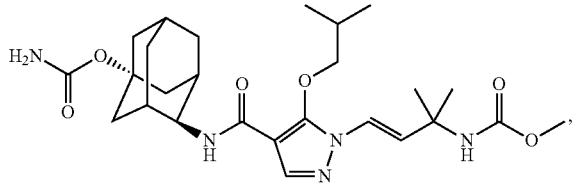

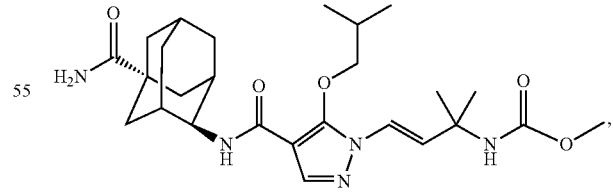

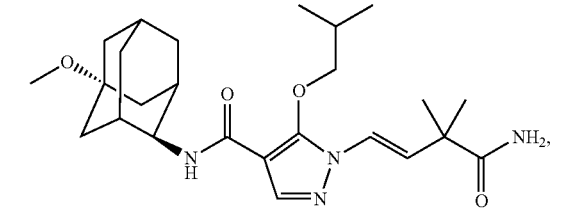

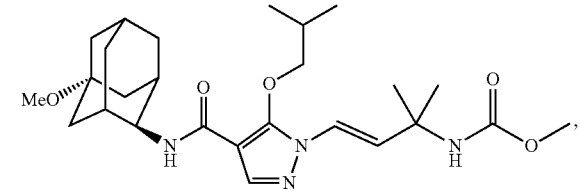

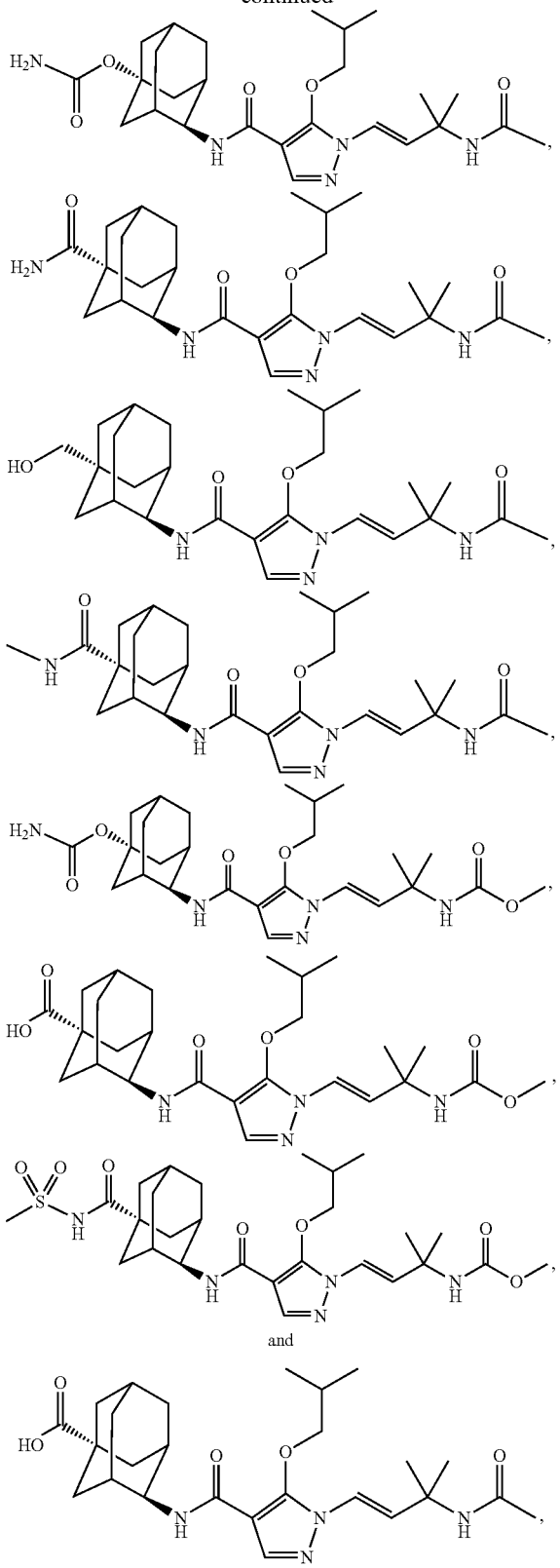

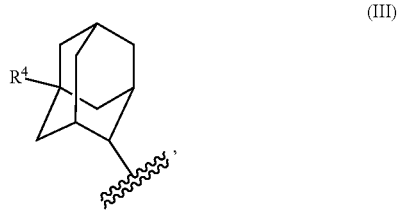

alkyl, optionally substituted alkenyl, optionally substituted cycloalkyl, optionally substituted aryl, optionally substituted heteroaryl, optionally substituted heterocycle or —CONR$^7$R$^8$.

4. The compound according to claim 1, or its pharmaceutically acceptable salt, wherein Ring A is a group represented by the formula (III):

wherein R$^6$ is optionally substituted alkyl, optionally substituted alkenyl, optionally substituted cycloalkyl, optionally substituted aryl, optionally substituted heteroaryl, optionally substituted heterocycle or —CONR$^7$R$^8$.

5. The compound according to claim 1, or its pharmaceutically acceptable salt, wherein R$^1$ is hydrogen.

6. The compound according to claim 1, or its pharmaceutically acceptable salt, wherein R$^2$ is —OR$^5$.

7. The compound according to claim 1, or its pharmaceutically acceptable salt, wherein R$^5$ is optionally substituted alkyl.

8. The compound according to claim 1, or its pharmaceutically acceptable salt, wherein R$^a$ and R$^b$ are each independently optionally substituted alkyl.

9. The compound according to claim 1, or its pharmaceutically acceptable salt, wherein R$^c$ is —(CH$_2$)$_n$—, wherein n is an integer of 0 or 1.

10. The compound according to claim 1, or its pharmaceutically acceptable salt, wherein R$^d$ is halogen, hydroxy, cyano, optionally substituted heteroaryl or optionally substituted heterocycle.

11. The compound according to claim 1, or its pharmaceutically acceptable salt, wherein R$^d$ is a group represented by the formula: —C(=O)—NR$^g$R$^h$, wherein R$^g$ and R$^h$ are each independently hydrogen, optionally substituted alkyl, optionally substituted alkyloxy or optionally substituted carbamoyl.

12. The compound according to claim 1, or its pharmaceutically acceptable salt, wherein R$^d$ is a group represented by the formula: —NR$^i$R$^j$, wherein R$^i$ and R$^j$ are each independently hydrogen, optionally substituted alkylsulfonyl, optionally substituted alkyloxycarbonyl, optionally substituted alkylcarbonyl or optionally substituted heterocyclecarbonyl.

13. The compound according to claim 1, or its pharmaceutically acceptable salt, wherein R$^4$ is —OR$^6$, —CONR$^7$R$^8$, —NR$^9$CONR$^7$R$^8$, —(CR$^{10}$R$^{11}$)$_p$OH, —(CR$^{10}$R$^{11}$)$_p$OCONR$^7$R$^8$, —NR$^9$COR$^{12}$, —NR$^9$C(=O)OR$^{12}$, —(CR$^{10}$R$^{11}$)$_p$NR$^9$COR$^{12}$, —C(=O)NR$^9$OR$^{12}$, —CONR$^9$CONR$^7$R$^8$ or —CN.

14. The compound according to claim 13, or its pharmaceutically acceptable salt, wherein R$^7$ and R$^8$ are each independently hydrogen or optionally substituted alkyl.

15. The compound according to claim 13, or its pharmaceutically acceptable salt, wherein R$^9$ is hydrogen.

16. The compound according to claim 13, or its pharmaceutically acceptable salt, wherein R$^{10}$ and R$^{11}$ are each hydrogen.

17. The compound according to claim 13, or its pharmaceutically acceptable salt, wherein $R^{12}$ is optionally substituted alkyl.
18. A compound defined below, or its pharmaceutically acceptable salt,
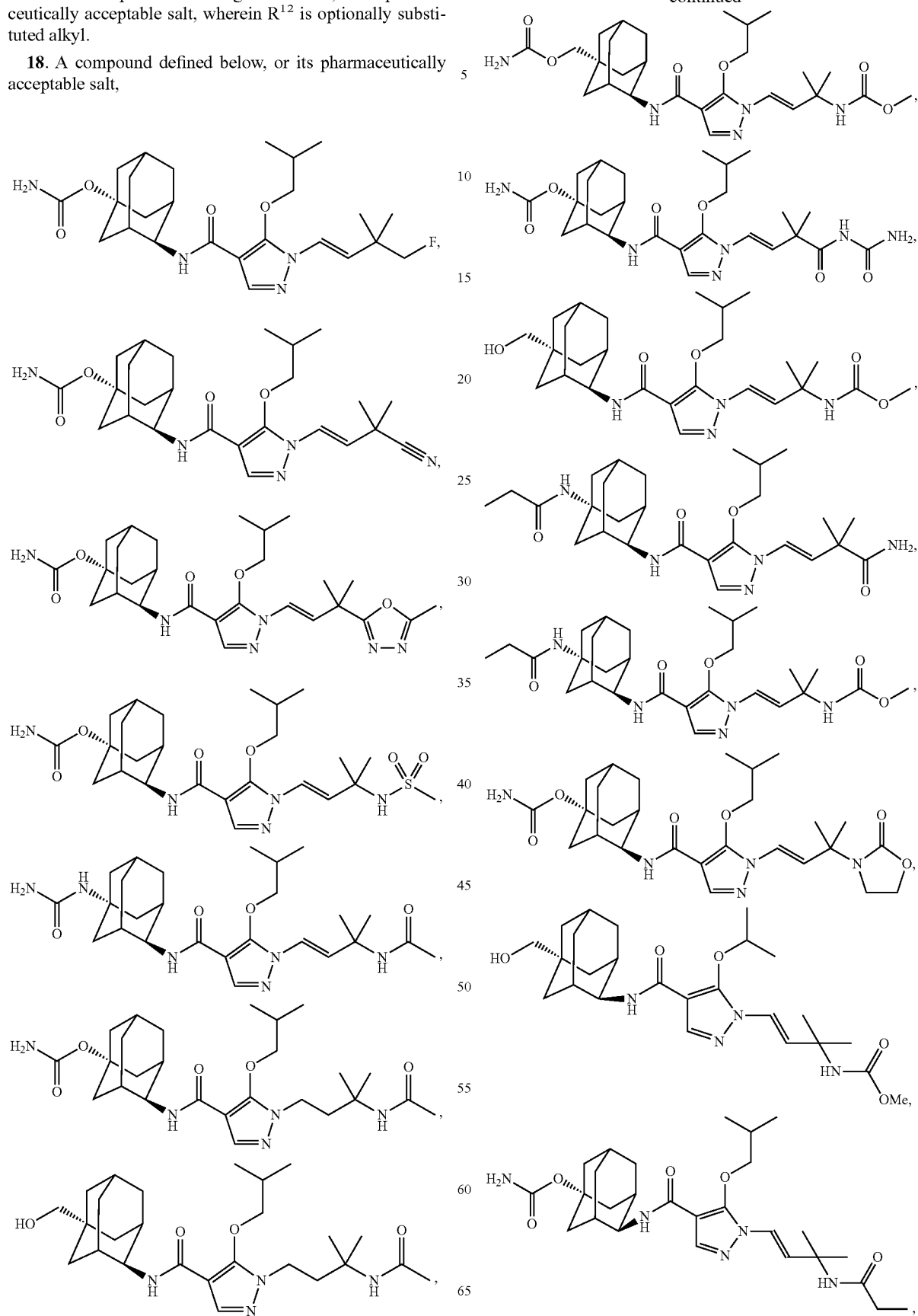

311
-continued
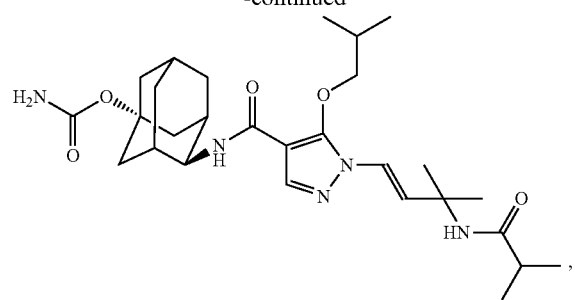
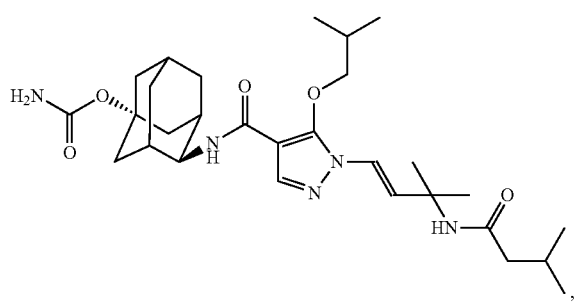
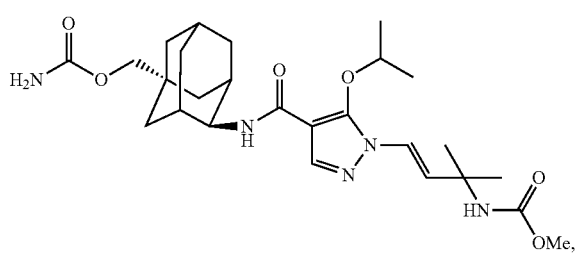
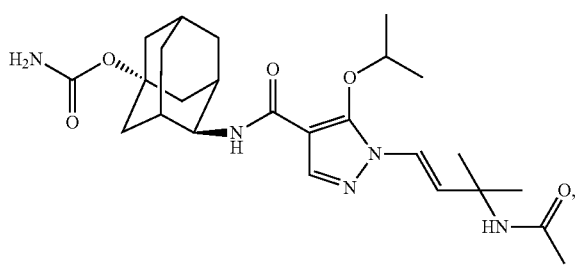
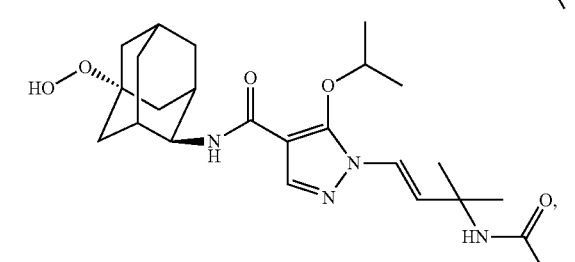
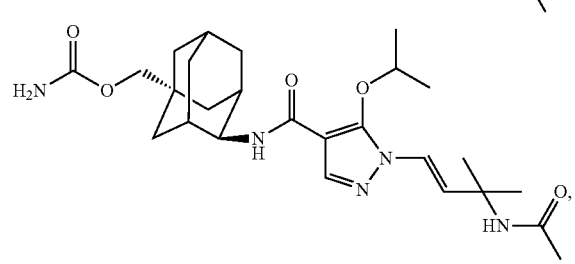
312
-continued
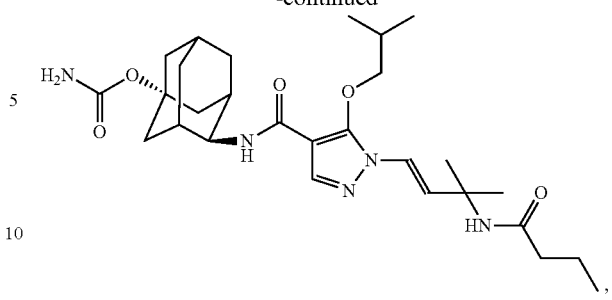
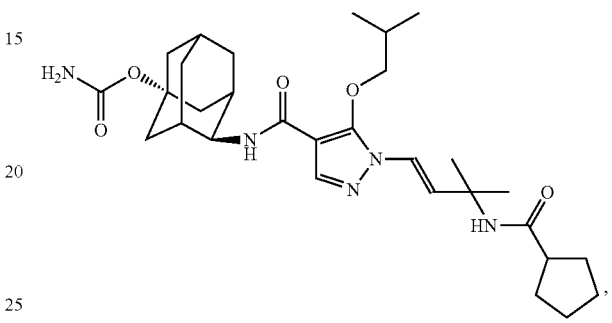
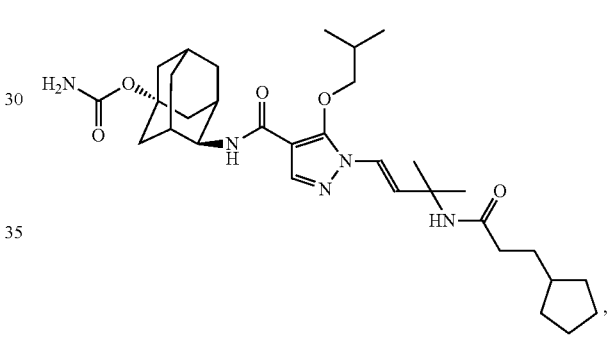
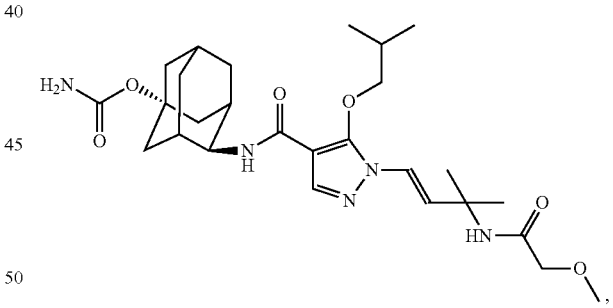
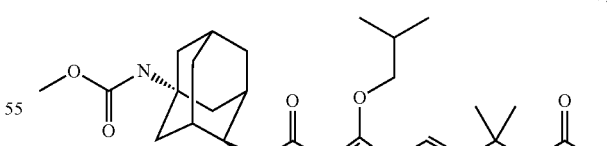
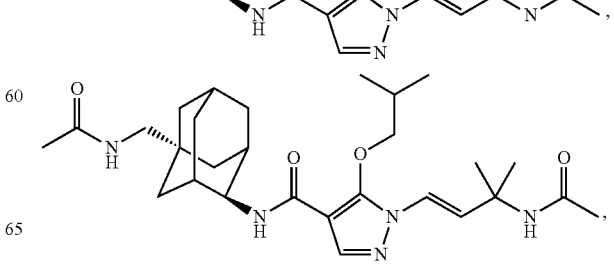

313
-continued
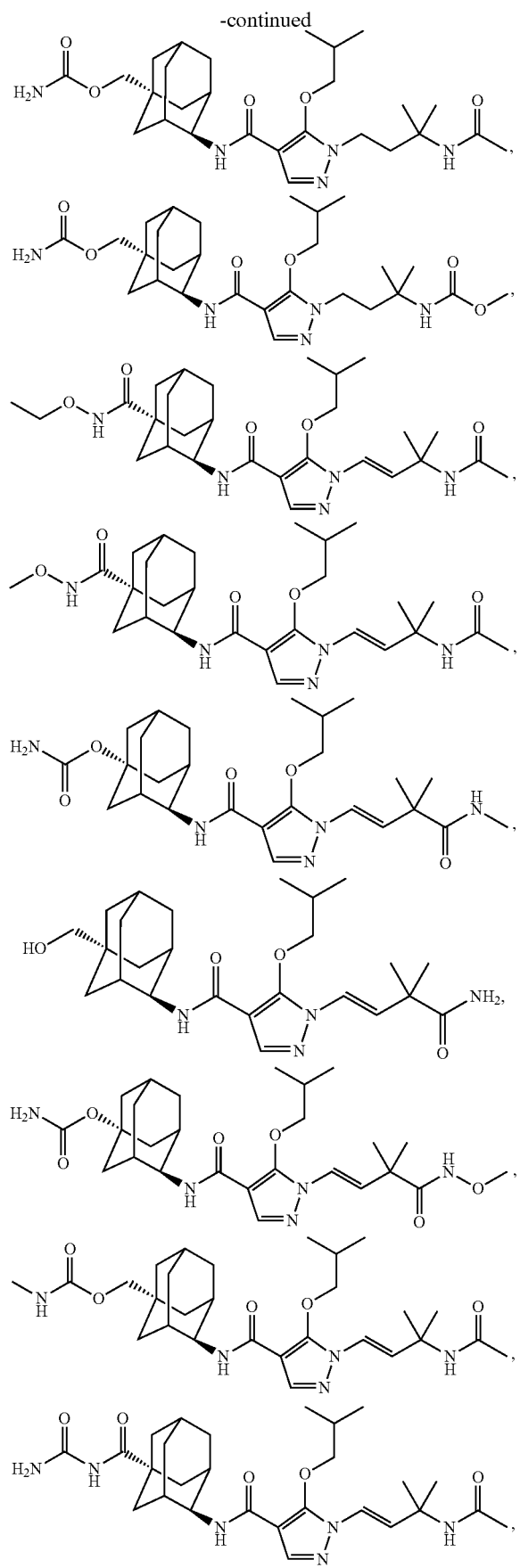
314
-continued
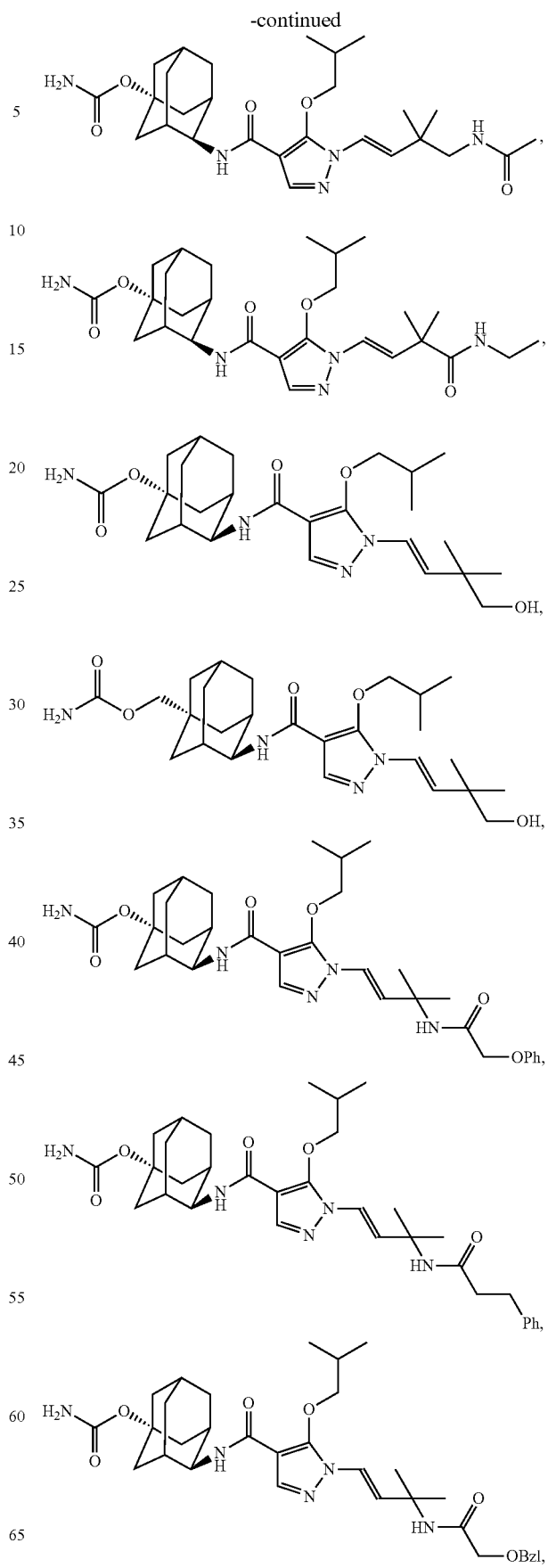

-continued

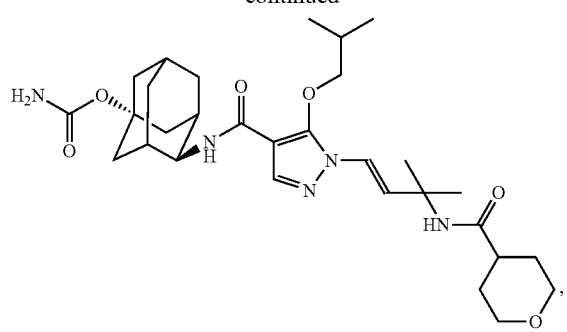

or

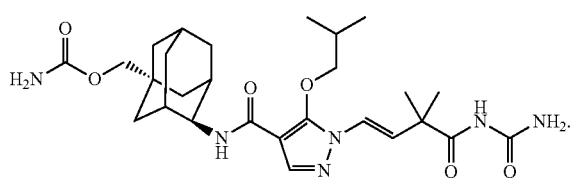

19. A pharmaceutical composition comprising a compound according to claim 1, or its pharmaceutically acceptable salt.

20. The pharmaceutical composition according to claim 19, further comprising a carrier, wherein the composition includes the compound or its pharmaceutically acceptable salt in an amount sufficient for the composition to have an 11β-hydroxysteroid dehydrogenase type 1 inhibitory activity.

21. A pharmaceutical composition comprising a compound according to claim 18, or its pharmaceutically acceptable salt.

22. A compound defined below, or its pharmaceutically acceptable salt:

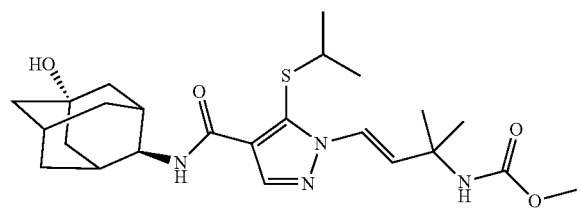 [SMILES: COC(=O)NC(C)(C)/C=C/n1ncc(C(=O)N[C@H]2C3CC4CC2C[C@](O)(C4)C3)c1SC(C)C]

23. A pharmaceutical composition comprising the compound according to claim 22, or its pharmaceutically acceptable salt.

24. The pharmaceutical composition of claim 23, further comprising a carrier, wherein the composition includes the compound or its pharmaceutically acceptable salt in an amount sufficient for the composition to have a 11β-hydroxysteroid dehydrogenase type 1 inhibitory activity.

25. A compound defined below, or its pharmaceutically acceptable salt:

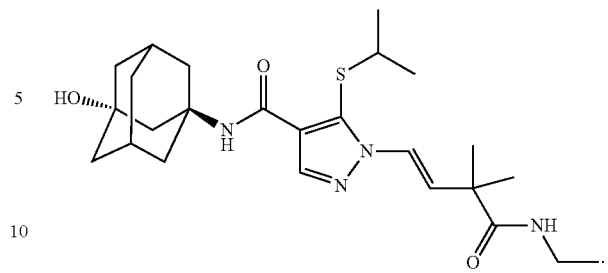

26. A pharmaceutical composition comprising the compound according to claim 25, or its pharmaceutically acceptable salt.

27. The pharmaceutical composition of claim 26, further comprising a carrier, wherein the composition includes the compound or its pharmaceutically acceptable salt in an amount sufficient for the composition to have a 11β-hydroxysteroid dehydrogenase type 1 inhibitory activity.

28. A compound defined below, or its pharmaceutically acceptable salt:

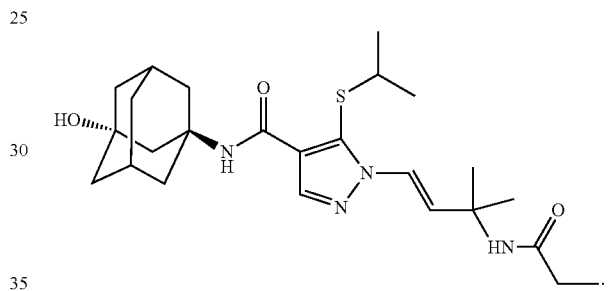

29. A pharmaceutical composition comprising the compound according to claim 28, or its pharmaceutically acceptable salt.

30. The pharmaceutical composition of claim 29, further comprising a carrier, wherein the composition includes the compound or its pharmaceutically acceptable salt in an amount sufficient for the composition to have a 11β-hydroxysteroid dehydrogenase type 1 inhibitory activity.

31. A compound defined below, or its pharmaceutically acceptable salt:

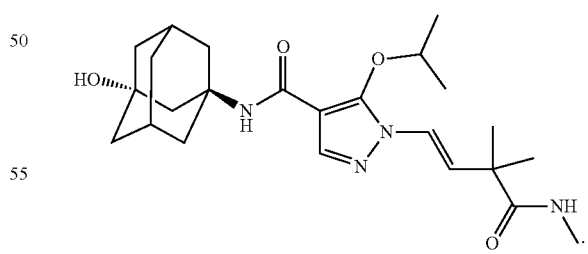

32. A pharmaceutical composition comprising the compound according to claim 31, or its pharmaceutically acceptable salt.

33. The pharmaceutical composition of claim 32, further comprising a carrier, wherein the composition includes the compound or its pharmaceutically acceptable salt in an amount sufficient for the composition to have a 11β-hydroxysteroid dehydrogenase type 1 inhibitory activity.

34. A compound defined below, or its pharmaceutically acceptable salt:

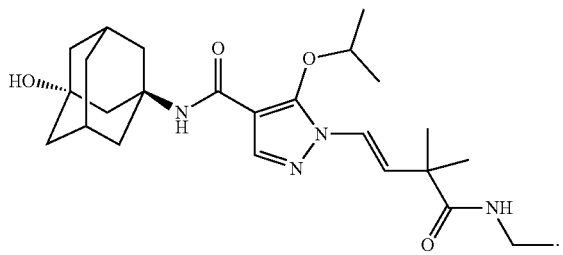

35. A pharmaceutical composition comprising the compound according to claim 34, or its pharmaceutically acceptable salt.

36. The pharmaceutical composition of claim 35, further comprising a carrier, wherein the composition includes the compound or its pharmaceutically acceptable salt in an amount sufficient for the composition to have a 11β-hydroxysteroid dehydrogenase type 1 inhibitory activity.

37. A compound defined below, or its pharmaceutically acceptable salt:

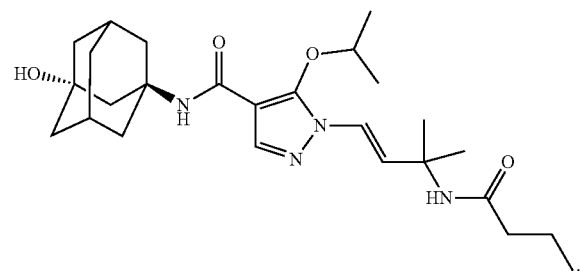 [SMILES: CCCC(=O)NC(C)(C)/C=C/n1ncc(C(=O)N[C@]23CC4CC(C[C@@](O)(C4)C2)C3)c1OC(C)C]

38. A pharmaceutical composition comprising the compound according to claim 37, or its pharmaceutically acceptable salt.

39. The pharmaceutical composition of claim 38, further comprising a carrier, wherein the composition includes the compound or its pharmaceutically acceptable salt in an amount sufficient for the composition to have a 11β-hydroxysteroid dehydrogenase type 1 inhibitory activity.

40. A compound according to claim 18, wherein the compound is as defined below, or its pharmaceutically acceptable salt:

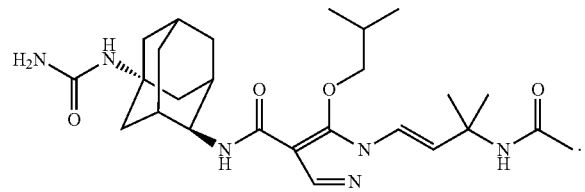 [SMILES: CC(=O)NC(C)(C)/C=C/N/C(OCC(C)C)=C(\C=N)C(=O)N[C@H]1C2CC3CC1C[C@](NC(N)=O)(C3)C2 ; "."]

41. A compound according to claim 18, wherein the compound is as defined below, or its pharmaceutically acceptable salt:

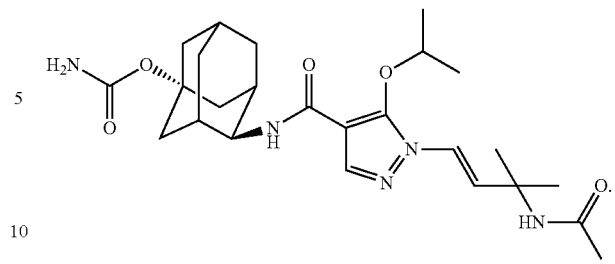

42. A compound according to claim 18, wherein the compound is as defined below, or its pharmaceutically acceptable salt:

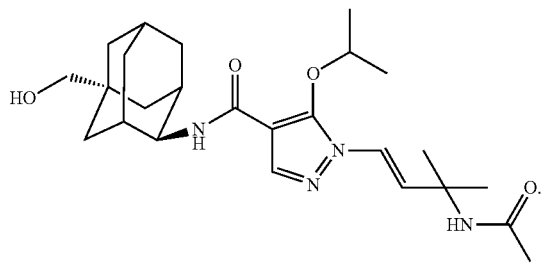

43. A compound according to claim 18, wherein the compound is as defined below, or its pharmaceutically acceptable salt:

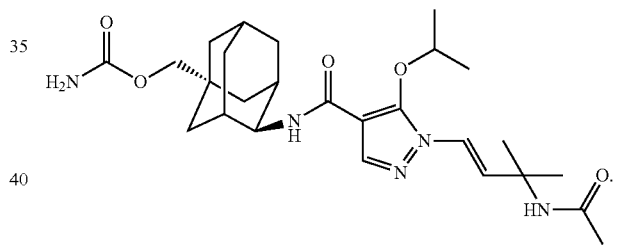

44. A compound according to claim 18, wherein the compound is as defined below, or its pharmaceutically acceptable salt:

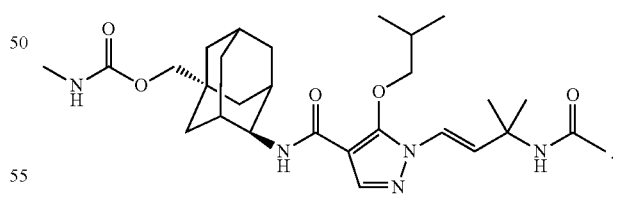

45. A method for treating diabetes, comprising administering a compound according to claim 1, or its pharmaceutically acceptable salt.

46. A method for treating diabetes, comprising administering a compound according to claim 18, or its pharmaceutically acceptable salt.

* * * * *